(12) United States Patent
Finlay et al.

(10) Patent No.: US 7,750,003 B2
(45) Date of Patent: Jul. 6, 2010

(54) COMPOUNDS-943

(75) Inventors: Maurice Raymond Verschoyle Finlay, Macclesfield (GB); Jeffrey Morris, Macclesfield (GB); Kurt Gordon Pike, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 458 days.

(21) Appl. No.: 11/844,092

(22) Filed: Aug. 23, 2007

(65) Prior Publication Data

US 2008/0171743 A1 Jul. 17, 2008

Related U.S. Application Data

(60) Provisional application No. 60/948,544, filed on Jul. 9, 2007.

(30) Foreign Application Priority Data

Aug. 24, 2006 (GB) ................. 0616747.2

(51) Int. Cl.
*A61K 31/535* (2006.01)
*C07D 413/04* (2006.01)

(52) U.S. Cl. .................... 514/235.8; 544/122

(58) Field of Classification Search ................. 544/122; 514/235.8

See application file for complete search history.

(56) References Cited

U.S. PATENT DOCUMENTS

| 5,250,530 | A | 10/1993 | Giencke et al. |
| 2002/0086858 | A1 | 7/2002 | Breu et al. |
| 2007/0049603 | A1 | 3/2007 | Miknis et al. |
| 2007/0299068 | A1 | 12/2007 | Karp et al. |

FOREIGN PATENT DOCUMENTS

| EP | 0407899 | 3/1995 |
| EP | 1277738 | 1/2003 |
| EP | 1911753 | 4/2008 |
| EP | 1970375 | 9/2008 |
| EP | 2003131 | 12/2008 |
| GB | 2431156 | 4/2007 |
| JP | 2007/091649 | 4/2007 |
| JP | 2007/119450 | 5/2007 |
| JP | 2007/246474 | 9/2007 |
| WO | WO 02/38551 | 5/2002 |
| WO | WO 2004/048365 | 6/2004 |
| WO | WO 2005/000404 | 1/2005 |
| WO | WO 2006/005915 | 1/2006 |
| WO | WO 2006/005918 | 1/2006 |
| WO | WO 2006/053227 | 5/2006 |
| WO | WO 2006/124662 | 11/2006 |
| WO | WO 2006/124874 | 11/2006 |
| WO | WO 2006/125554 | 11/2006 |
| WO | WO 2007/005673 | 1/2007 |
| WO | WO 2007/013691 | 2/2007 |
| WO | WO 2007/041130 | 4/2007 |
| WO | WO 2007/041358 | 4/2007 |
| WO | WO 2007/042806 | 4/2007 |
| WO | WO 2007/042810 | 4/2007 |
| WO | WO 2007/049041 | 5/2007 |
| WO | WO 2007/054831 | 5/2007 |
| WO | WO 2007/063868 | 6/2007 |
| WO | WO 2007/066099 | 6/2007 |
| WO | WO 2007/066102 | 6/2007 |
| WO | WO 2007/066103 | 6/2007 |
| WO | WO 2007/072163 | 6/2007 |
| WO | WO 2007/080382 | 7/2007 |
| WO | WO 2007/084413 | 7/2007 |
| WO | WO 2007/084786 | 7/2007 |
| WO | WO 2007/089768 | 8/2007 |
| WO | WO 2007/105023 | 9/2007 |
| WO | WO 2007/114323 | 10/2007 |
| WO | WO 2007/124288 | 11/2007 |
| WO | WO 2007/126043 | 11/2007 |
| WO | WO 2007/141571 | 12/2007 |
| WO | WO 2008/005538 | 1/2008 |
| WO | WO 2008/023159 | 2/2008 |
| WO | WO 2008/023180 | 2/2008 |
| WO | WO 2008/125833 | 10/2008 |

OTHER PUBLICATIONS

CAS Resgistry No. 633321-89-9, CHEMCATS Accession No. 2004:32970, Catalog Name: Ambinter Screening Library and Order No. 13995080, 2004.

Chandra et al. "Antileishmanial agents part-IV: synthesis and antileishmanial activity of novel terpenyl pyrimidines" Eur. J.Med. Chem 40:552-556 (2005).

Davey et al. "Design, synthesis, and activity of 2-imidazol-1-ylpyrimidine derived inducible nitric oxide synthase dimerization inhibitors" J.Med.Chem. 50:1146-1157 (2007).

Dotzauer et al. "2,4-Diamino-9H-pyrimido[4,5-b]indol-5-ols: Synthesis, in vitro cytotoxic activity, and QSAR investigations" Bioorganic & Medicinal Chemistry 14(21):7282-7292 (2006).

(Continued)

*Primary Examiner*—Rebecca L Anderson

(57) ABSTRACT

A compound of formula (I)

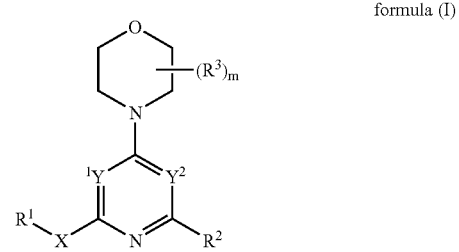

formula (I)

or a pharmaceutically acceptable salt thereof, processes for their preparation, pharmaceutical compositions containing them and their use in therapy, for example in the treatment of proliferative disease such as cancer and particularly in disease mediated by an mTOR kinase and/or one or more PI3K enzyme.

39 Claims, No Drawings

OTHER PUBLICATIONS

Katiyar et al. "Syntheses of 2,4,6-trisubstituted pyrimidine derivatives as a new class of antifilarial topoisomerase II inhibitors" Bioorganic & Medicinal Chemistry Letters 15(1):47-50 (2005).

Kumar et al. "A Novel and Convenient Synthesis of 2-Amino-4-(N-alkyl-N-arylamino)-pyrimidines using Polarized Ketene S,S- and S,N-Acetals" Synthesis 9:748-751 (1980).

Schmidt et al. "Neue synthase von pyrimidinderivaten" Chemische Berichte 98(2):346-351 (1965).

Spintzer et al. "Cyclization reactions of 2-acyl-1-chloro-enamines with thioamide functional compounds: Alternative access to the 1,3-thiazine and 1,3-oxazine series" Monatshefte Fur Chemie 118:1383-1394 (1987).

Suryawanshi et al. "Chemotherapy of leishmaniasis part-VIII: Synthesis and bioevaluation of novel chalcones" Eur. J.Med. Chem 42:1211-1217 (2007).

Wang et al. "Novel Vanilloid Receptor-1 Antagonists: 3. The identification of a second-generation clinical candidate with improved physiochemical and pharmacokinetic properties" J.Med.Chem. 50:3528-3539 (2007).

File CA PLUS, Accession No. 1967:421928, Minami et al "2(or 6)-Nitrofurylvinyl-4-substituted aminopyrimidines" (1967) [XP002505932].

CAS Registry No. 303147-15-1, Database Registry (Online), Chemical Abstracts Service, Columbus, Ohio, US, (Nov. 17, 2000) [XP002514456].

CAS Registry No. 303147-55-9, Database Registry (Online), Chemical Abstracts Service, Columbus, Ohio, US, (Nov. 17, 2000) [XP002514455].

CAS Registry No. 306980-67-6, Database Registry (Online), Chemical Abstracts Service, Columbus, Ohio, US, (Dec. 6, 2000) [XP002514454].

CAS Registry No. 320421-27-0, Database Registry (Online), Chemical Abstracts Service, Columbus, Ohio, US, (Feb. 6, 2001) [XP002514453].

CAS Registry No. 320421-35-0, Database Registry (Online), Chemical Abstracts Service, Columbus, Ohio, US, (Feb. 6, 2001) [XP002514452].

CAS Registry No. 338960-59-1, Database Registry (Online), Chemical Abstracts Service, Columbus, Ohio, US, (May 30, 2001) [XP002514451].

CAS Registry No. 338961-71-0, Database Registry (Online), Chemical Abstracts Service, Columbus, Ohio, US, (May 30, 2001) [XP002514450].

CAS Registry No. 338967-56-9, Database Registry (Online), Chemical Abstracts Service, Columbus, Ohio, US, (May 30, 2001) [XP002514449].

CAS Registry No. 338967-57-0, Database Registry (Online), Chemical Abstracts Service, Columbus, Ohio, US, (May 30, 2001) [XP002514448].

CAS Registry No. 338967-72-9, Database Registry (Online), Chemical Abstracts Service, Columbus, Ohio, US, (May 30, 2001) [XP002514447].

CAS Registry No. 339278-75-0, Database Registry (Online), Chemical Abstracts Service, Columbus, Ohio, US, (Jun. 4, 2001) [XP002514446].

CAS Registry No. 339278-82-9, Database Registry (Online), Chemical Abstracts Service, Columbus, Ohio, US, (Jun. 4, 2001) [XP002514445].

CAS Registry No. 339278-88-5, Database Registry (Online), Chemical Abstracts Service, Columbus, Ohio, US, (Jun. 4, 2001) [XP002514444].

CAS Registry No. 339278-90-9, Database Registry (Online), Chemical Abstracts Service, Columbus, Ohio, US, (Jun. 4, 2001) [XP002514443].

CAS Registry No. 339278-95-4, Database Registry (Online), Chemical Abstracts Service, Columbus, Ohio, US, (Jun. 4, 2001) [XP002514442].

CAS Registry No. 339278-96-5, Database Registry (Online), Chemical Abstracts Service, Columbus, Ohio, US, (Jun. 4, 2001) [XP002514441].

CAS Registry No. 477866-84-5, Database Registry (Online), Chemical Abstracts Service, Columbus, Ohio, US, (Dec. 31, 2002) [XP002514440].

CAS Registry No. 477866-88-9, Database Registry (Online), Chemical Abstracts Service, Columbus, Ohio, US, (Dec. 31, 2002) [XP002514439].

CAS Registry No. 477866-96-9, Database Registry (Online), Chemical Abstracts Service, Columbus, Ohio, US, (Dec. 31, 2002) [XP002514438].

CAS Registry No. 477867-03-1, Database Registry (Online), Chemical Abstracts Service, Columbus, Ohio, US, (Dec. 31, 2002) [XP002514437].

CAS Registry No. 477867-18-8, Database Registry (Online), Chemical Abstracts Service, Columbus, Ohio, US, (Dec. 31, 2002) [XP002514436].

CAS Registry No. 477886-32-1, Database Registry (Online), Chemical Abstracts Service, Columbus, Ohio, US, (Dec. 31, 2002) [XP002514434].

CAS Registry No. 477886-35-1, Database Registry (Online), Chemical Abstracts Service, Columbus, Ohio, US, (Dec. 31, 2002) [XP002514435].

CAS Registry No. 478031-34-4, Database Registry (Online), Chemical Abstracts Service, Columbus, Ohio, US, (Jan. 3, 2003) [XP002514433].

CAS Registry No. 478043-19-5, Database Registry (Online), Chemical Abstracts Service, Columbus, Ohio, US, (Jan. 3, 2003) [XP002514432].

Schmidt et al. "Neue synthase von pyrimidinderivaten" Chemische Berichte 98(2):346-351 (1965) (Translation enclosed).

Spitzner et al. "Cyclization reactions of 2-acyl-1-chloro-enamines with thioamide functional compounds: Alternative access to the 1,3-thiazine and 1,3-oxazine series" Monatshefte Fur Chemie 118:1383-1394 (1987) (Translation enclosed).

COMPOUNDS-943

This application claims the benefit under 35 U.S.C. §119 (a)-(d) of Application No GB0616747.2 filed on 24 Aug. 2006 and under 35 U.S.C. §119(e) of Application No. U.S. 60/948,544 filed on 9 Jul. 2007.

The present invention relates to morpholino pyrimidine derivatives, processes for their preparation, pharmaceutical compositions containing them and their use in therapy, for example in the treatment of proliferative disease such as cancer and particularly in disease mediated by an mTOR kinase and/or one or more PI3K enzyme.

It is now well understood that deregulation of oncogenes and tumour-suppressor genes contributes to the formation of malignant tumours, for example by way of increased cell proliferation or increased cell survival. It is also known that signalling pathways mediated by the PI3K/mTOR families have a central role in a number of cell processes including proliferation and survival, and deregulation of these pathways is a causative factor in a wide spectrum of human cancers and other diseases.

The mammalian target of the macrolide antibiotic Rapamycin (sirolimus) is the enzyme mTOR. This enzymes belongs to the phosphatidylinositol (PI) kinase-related kinase (PIKK) family of protein kinases, which also includes ATM, ATR, DNA-PK and hSMG-1. mTOR, like other PIKK family members, does not possess detectable lipid kinase activity, but instead functions as a serine/threonine kinase. Much of the knowledge of mTOR signalling is based upon the use of Rapamycin. Rapamycin first binds to the 12 kDa immunophilin FK506-binding protein (FKBP12) and this complex inhibits mTOR signalling (Tee and Blenis, Seminars in Cell and Developmental Biology, 2005, 16, 29-37). The mTOR protein consists of a catalytic kinase domain, an FKBP12-Rapamycin binding (FRB) domain, a putative repressor domain near the C-terminus and up to 20 tandemly-repeated HEAT motifs at the N-terminus, as well as FRAP-ATM-TRRAP (FAT) and FAT C-terminus domain (Huang and Houghton, Current Opinion in Pharmacology, 2003, 3, 371-377).

mTOR kinase is a key regulator of cell growth and has been shown to regulate a wide range of cellular functions including translation, transcription, mRNA turnover, protein stability, actin cytoskeleton reorganisation and autophagy (Jacinto and Hall, Nature Reviews Molecular and Cell Biology, 2005, 4, 117-126). mTOR kinase integrates signals from growth factors (such as insulin or insulin-like growth factor) and nutrients (such as amino acids and glucose) to regulate cell growth. mTOR kinase is activated by growth factors through the PI3K-Akt pathway. The most well characterised function of mTOR kinase in mammalian cells is regulation of translation through two pathways, namely activation of ribosomal S6K1 to enhance translation of mRNAs that bear a 5'-terminal oligopyrimidine tract (TOP) and suppression of 4E-BP1 to allow CAP-dependent mRNA translation.

Generally, investigators have explored the physiological and pathological roles of mTOR using inhibition with Rapamycin and related Rapamycin analogues based on their specificity for mTOR as an intracellular target. However, recent data suggests that Rapamycin displays variable inhibitory actions on mTOR signalling functions and suggest that direct inhibition of the mTOR kinase domain may display substantially broader anti-cancer activities than that achieved by Rapamycin (Edinger et al., Cancer Research, 2003, 63, 8451-8460). For this reason, potent and selective inhibitors of mTOR kinase activity would be useful to allow a more complete understanding of mTOR kinase function and to provide useful therapeutic agents.

There is now considerable evidence indicating that the pathways upstream of mTOR, such as the PI3K pathway, are frequently activated in cancer (Vivanco and Sawyers, Nature Reviews Cancer, 2002, 2, 489-501; Bjornsti and Houghton, Nature Reviews Cancer, 2004, 4, 335-348; Inoki et al., Nature Genetics, 2005, 37, 19-24). For example, components of the PI3K pathway that are mutated in different human tumours include activating mutations of growth factor receptors and the amplification and/or overexpression of PI3K and Akt.

In addition there is evidence that endothelial cell proliferation may also be dependent upon mTOR signalling. Endothelial cell proliferation is stimulated by vascular endothelial cell growth factor (VEGF) activation of the PI3K-Akt-mTOR signalling pathway (Dancey, Expert Opinion on Investigational Drugs, 2005, 14, 313-328). Moreover, mTOR kinase signalling is believed to partially control VEGF synthesis through effects on the expression of hypoxia-inducible factor-1α (HIF-1α) (Hudson et al., Molecular and Cellular Biology, 2002, 22, 7004-7014). Therefore, tumour angiogenesis may depend on mTOR kinase signalling in two ways, through hypoxia-induced synthesis of VEGF by tumour and stromal cells, and through VEGF stimulation of endothelial proliferation and survival through PI3K-Akt-mTOR signalling.

These findings suggest that pharmacological inhibitors of mTOR kinase should be of therapeutic value for treatment of the various forms of cancer comprising solid tumours such as carcinomas and sarcomas and the leukaemias and lymphoid malignancies. In particular, inhibitors of mTOR kinase should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

In addition to tumourigenesis, there is evidence that mTOR kinase plays a role in an array of hamartoma syndromes. Recent studies have shown that the tumour suppressor proteins such as TSC1, TSC2, PTEN and LKB1 tightly control mTOR kinase signalling. Loss of these tumour suppressor proteins leads to a range of hamartoma conditions as a result of elevated mTOR kinase signalling (Tee and Blenis, Seminars in Cell and Developmental Biology, 2005, 16, 29-37). Syndromes with an established molecular link to dysregulation of mTOR kinase include Peutz-Jeghers syndrome (PJS), Cowden disease, Bannayan-Riley-Ruvalcaba syndrome (BRRS), *Proteus* syndrome, Lhermitte-Duclos disease and Tuberous Sclerosis (TSC) (Inoki et al., Nature Genetics, 2005, 37, 19-24). Patients with these syndromes characteristically develop benign hamartomatous tumours in multiple organs.

Recent studies have revealed a role for mTOR kinase in other diseases (Easton & Houghton, Expert Opinion on Therapeutic Targets, 2004, 8, 551-564). Rapamycin has been demonstrated to be a potent immunosuppressant by inhibiting antigen-induced proliferation of T cells, B cells and antibody production (Sehgal, Transplantation Proceedings, 2003, 35, 7S-14S) and thus mTOR kinase inhibitors may also be useful immunosuppressives. Inhibition of the kinase activity of mTOR may also be useful in the prevention of restenosis, that is the control of undesired proliferation of normal cells in the vasculature in response to the introduction of stents in the treatment of vasculature disease (Morice et al., New England Journal of Medicine, 2002, 346, 1773-1780). Furthermore, the Rapamycin analogue, everolimus, can reduce the severity and incidence of cardiac allograft vasculopathy (Eisen et al., New England Journal of Medicine, 2003, 349, 847-858). Elevated mTOR kinase activity has been associated with cardiac hypertrophy, which is of clinical importance as a major risk factor for heart failure and is a consequence of increased cellular size of cardiomyocytes (Tee & Blenis, Seminars in Cell and Developmental Biology, 2005, 16, 29-37). Thus mTOR kinase inhibitors are expected to be of value in the prevention and treatment of a wide variety of diseases in addition to cancer.

It is also believed that a number of these morpholino pyrimidine derivatives may have inhibitory activity against the phosphatidylinositol (PI) 3-kinases family of kinases.

Phosphatidylinositol (PI) 3-kinases (PI3Ks) are ubiquitous lipid kinases that function both as signal transducers downstream of cell-surface receptors and in constitutive intracellular membrane and protein trafficking pathways. All PI3Ks are dual-specificity enzymes with a lipid kinase activity that phosphorylates phosphoinositides at the 3-hydroxy position, and a less well characterised protein kinase activity. The lipid products of PI3K-catalysed reactions comprising phosphatidylinositol 3,4,5-trisphosphate [PI(3,4,5)P$_3$], phosphatidylinositol 3,4-bisphosphate [PI(3,4)P$_2$] and phosphatidylinositol 3-monophosphate [PI(3)P] constitute second messengers in a variety of signal transduction pathways, including those essential to cell proliferation, adhesion, survival, cytoskeletal rearrangement and vesicle trafficking. PI(3)P is constitutively present in all cells and its levels do not change dramatically following agonist stimulation. Conversely, PI(3,4)P$_2$ and PI(3,4,5)P$_3$ are nominally absent in most cells but they rapidly accumulate on agonist stimulation.

The downstream effects of PI3K-produced 3-phosphoinositide second messengers are mediated by target molecules containing 3-phosphoinositide binding domains such as the pleckstrin homology (PH) domain and the recently identified FYVE and phox domains. Well-characterised protein targets for PI3K include PDK1 and protein kinase B (PKB). In addition, tyrosine kinases like Btk and Itk are dependent on PI3K activity.

The PI3K family of lipid kinases can be classified into three groups according to their physiological substrate specificity (Vanhaesebroeck et al., Trends in Biol. Sci., 1997, 22, 267). Class III PI3K enzymes phosphorylate PI alone. In contrast, Class II PI3K enzymes phosphorylate both PI and PI 4-phosphate [PI(4)P]. Class I PI3K enzymes phosphorylate PI, PI(4)P and PI 4,5-bisphosphate [PI(4,5)P$_2$], although only PI(4,5)P$_2$ is believed to be the physiological cellular substrate. Phosphorylation of PI(4,5)P$_2$ produces the lipid second messenger PI(3,4,5)P$_3$. More distantly related members of the lipid kinase superfamily are Class IV kinases such as mTOR (discussed above) and DNA-dependent kinase that phosphorylate serine/threonine residues within protein substrates. The most studied and understood of the PI3K lipid kinases are the Class I PI3K enzymes.

Class I PI3Ks are heterodimers consisting of a p110 catalytic subunit and a regulatory subunit. The family is further divided into Class Ia and Class Ib enzymes on the basis of regulatory partners and the mechanism of regulation. Class Ia enzymes consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI3Ks are generally activated in response to growth factor-stimulation of receptor tyrosine kinases via interaction of their regulatory subunit SH2 domains with specific phospho-tyrosine residues of activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor systems (GPCRs) and its expression appears to be limited to leukocytes and cardiomyocytes.

There is now considerable evidence indicating that Class Ia PI3K enzymes contribute to tumourigenesis in a wide variety of human cancers, either directly or indirectly (Vivanco and Sawyers, Nature Reviews Cancer, 2002, 2, 489-501). For example, the p110α subunit is amplified in some tumours such as those of the ovary (Shayesteh et al., Nature Genetics, 1999, 21, 99-102) and cervix (Ma et al., Oncogene, 2000, 19, 2739-2744). More recently, activating mutations within the catalytic site of the p110α catalytic subunit have been associated with various other tumours such as those of the colorectal region and of the breast and lung (Samuels et al., Science, 2004, 304, 554). Tumour-related mutations in the p85α regulatory subunit have also been identified in cancers such as those of the ovary and colon (Philp et al., Cancer Research, 2001, 61, 7426-7429). In addition to direct effects, it is believed that activation of Class Ia PI3Ks contributes to tumourigenic events that occur upstream in signalling pathways, for example by way of ligand-dependent or ligand-independent activation of receptor tyrosine kinases, GPCR systems or integrins (Vara et al., Cancer Treatment Reviews, 2004, 30, 193-204). Examples of such upstream signalling pathways include over-expression of the receptor tyrosine kinase erbB2 in a variety of tumours leading to activation of PI3K-mediated pathways (Harari et al., Oncogene, 2000, 19, 6102-6114) and over-expression of the ras oncogene (Kauffmann-Zeh et al., Nature, 1997, 385, 544-548). In addition, Class Ia PI3Ks may contribute indirectly to tumourigenesis caused by various downstream signalling events. For example, loss of the effect of the PTEN tumour-suppressor phosphatase that catalyses conversion of PI(3,4,5)P$_3$ back to PI(4,5)P$_2$ is associated with a very broad range of tumours via deregulation of PI3K-mediated production of PI(3,4,5)P$_3$ (Simpson and Parsons, Exp. Cell Res., 2001, 264, 29-41). Furthermore, augmentation of the effects of other PI3K-mediated signalling events is believed to contribute to a variety of cancers, for example by activation of Akt (Nicholson and Anderson, Cellular Signalling, 2002, 14, 381-395).

In addition to a role in mediating proliferative and survival signalling in tumour cells, there is evidence that Class Ia PI3K enzymes contribute to tumourigenesis in tumour-associated stromal cells. For example, PI3K signalling is known to play an important role in mediating angiogenic events in endothelial cells in response to pro-angiogenic factors such as VEGF (Abid et al., Arterioscler. Thromb. Vasc. Biol., 2004, 24, 294-300). As Class I PI3K enzymes are also involved in motility and migration (Sawyer, Expert Opinion Investig. Drugs, 2004, 13, 1-19), PI3K enzyme inhibitors should provide therapeutic benefit via inhibition of tumour cell invasion and metastasis. In addition, Class I PI3K enzymes play an important role in the regulation of immune cells contributing to pro-tumourigenic effects of inflammatory cells (Coussens and Werb, Nature, 2002, 420, 860-867).

These findings suggest that pharmacological inhibitors of Class I PI3K enzymes will be of therapeutic value for the treatment of various diseases including different forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

PI3Kγ, the Class Ib PI3K, is activated by GPCRs, as was finally demonstrated in mice lacking the enzyme. Thus, neutrophils and macrophages derived from PI3Kγ-deficient animals failed to produce $PI(3,4,5)P_3$ in response to stimulation with various chemotactic substances (such as IL-8, C5a, fMLP and MIP-1a), whereas signalling through protein tyrosine kinase-coupled receptors to Class Ia PI3Ks was intact (Hirsch et al., Science, 2000, 287 (5455), 1049-1053; Li et al., Science, 2002, 287 (5455), 1046-1049; Sasaki et al., Science 2002, 287 (5455), 1040-1046). Furthermore, $PI(3,4,5)P_3$-mediated phosphorylation of PKB was not initiated by these GPCR ligands in PI3Kγ-null cells. Taken together, the results demonstrated that, at least in resting haematopoietic cells, PI3Kγ is the sole PI3K isoform that is activated by GPCRs in vivo. When murine bone marrow-derived neutrophils and peritoneal macrophages from wild-type and PI3Kγ$^{-/-}$ mice were tested in vitro, a reduced, but not completely abrogated, performance in chemotaxis and adherence assays was observed. However, this translated into a drastic impairment of IL-8 driven neutrophil infiltration into tissues (Hirsch et al., Science, 2000, 287 (5455), 1049-1053). Recent data suggest that PI3Kγ is involved in the path finding process rather than in the generation of mechanical force for motility, as random migration was not impaired in cells that lacked PI3Kγ (Hannigan et al., Proc. Nat. Acad. of Sciences of U.S.A., 2002, 99 (6), 3603-8). Data linking PI3Kγ to respiratory disease pathology came with the demonstration that PI3Kγ has a central role in regulating endotoxin-induced lung infiltration and activation of neutrophils leading to acute lung injury (Yum et al., J. Immunology, 2001, 167 (11), 6601-8). The fact that although PI3Kγ is highly expressed in leucocytes, its loss seems not to interfere with haematopoiesis, and the fact that PI3Kγ-null mice are viable and fertile further implicates this PI3K isoform as a potential drug target. Work with knockout mice also established that PI3Kγ is an essential amplifier of mast cell activation (Laffargue et al., Immunity, 2002, 16 (3), 441-451).

Thus, in addition to tumourigenesis, there is evidence that Class I PI3K enzymes play a role in other diseases (Wymann et al., Trends in Pharmacological Science, 2003, 24, 366-376). Both Class Ia PI3K enzymes and the single Class Ib enzyme have important roles in cells of the immune system (Koyasu, Nature Immunology, 2003, 4, 313-319) and thus they are therapeutic targets for inflammatory and allergic indications. Recent reports demonstrate that mice deficient in PI3Kγ and PI3Kδ are viable, but have attenuated inflammatory and allergic responses (Ali et al., Nature, 2004, 431 (7011), 1007-11). Inhibition of PI3K is also useful to treat cardiovascular disease via anti-inflammatory effects or directly by affecting cardiac myocytes (Prasad et al., Trends in Cardiovascular Medicine, 2003, 13, 206-212). Thus, inhibitors of Class I PI3K enzymes are expected to be of value in the prevention and treatment of a wide variety of diseases in addition to cancer.

Several compounds that inhibit PI3Ks and phosphatidylinositol (PI) kinase-related kinase (PI3KKs) have been identified, including wortmannin and the quercetin derivative LY294002. These compounds are reasonably specific inhibitors of PI3Ks and PI3KKs over other kinases but they lack potency and display little selectivity within the PI3K families.

Accordingly, it would be desirable to provide further effective mTOR and/or PI3K inhibitors for use in the treatment of cancer, inflammatory or obstructive airways diseases, immune or cardiovascular diseases.

Morpholino pyrimidine derivatives and PI3K inhibitors are known in the art.

International Patent Application WO 2004/048365 discloses compounds that possess PI3K enzyme inhibitory activity and are useful in the treatment of cancer. These compounds are arylamino- and heteroarylamino-substituted pyrimidines which differ from the compounds of the present invention with respect to their arylamino- and heteroarylamino substituents. These substituents are not equivalent to the —$XR^1$ substituents of the present invention. Inhibitors of PI3K activity useful in the treatment of cancer are also disclosed in European Patent Application 1 277 738 which mentions 4-morpholino-substituted bicyclic heteroaryl compounds such as quinazoline and pyrido[3,2-d]pyrimidine derivatives and 4-morpholino-substituted tricyclic heteroaryl compounds but not monocyclic pyrimidine derivatives.

A number of compounds such as 4-morpholin-4-yl-6-(phenylsulfonylmethyl)-2-pyridin-4-yl-pyrimidine and 4-{6-[(phenylsulfonyl)methyl]-2-pyridin-2-ylpyrimidin-4-yl}morpholine have been registered in the Chemical Abstracts database but no utility has been indicated and there is no suggestion that these compounds have mTOR and/or PI3K inhibitory activity or useful therapeutic properties.

Surprisingly, we have found that certain morpholino pyrimidine derivatives possess useful therapeutic properties. Without wishing to be bound by theoretical constraints, it is believed that the therapeutic usefulness of the derivatives is derived from their inhibitory activity against mTOR kinase and/or one or more PI3K enzyme (such as the Class Ia enzyme and/or the Class Ib enzyme). Because signalling pathways mediated by the PI3K/mTOR families have a central role in a number of cell processes including proliferation and survival, and because deregulation of these pathways is a causative factor in a wide spectrum of human cancers and other diseases, it is expected that the derivatives will be therapeutically useful. In particular, it is expected that the derivatives will have anti-proliferative and/or apoptotic properties which means that they will be useful in the treatment of proliferative disease such as cancer. The compounds of the present invention may also be useful in inhibiting the uncontrolled cellular proliferation which arises from various non-malignant diseases such as inflammatory diseases, obstructive airways diseases, immune diseases or cardiovascular diseases.

Generally, the compounds of the present invention possess potent inhibitory activity against mTOR kinase but the compound may also possess potent inhibitory activity against one or more PI3K enzyme (such as the Class Ia enzyme and/or the Class Ib enzyme).

In accordance with an aspect of the present invention, there is provided a compound of formula (I)

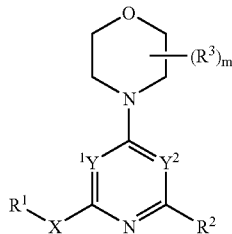

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided a compound of formula (I)

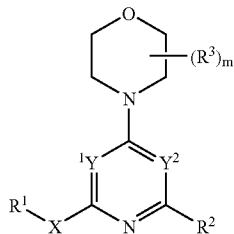

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided a compound of formula (I)

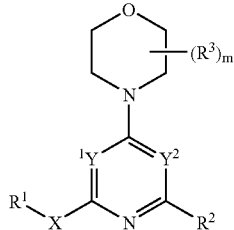

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

or $X-R^1$ is $-CR^6R^7OH$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl ($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl $C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided a compound of formula (I)

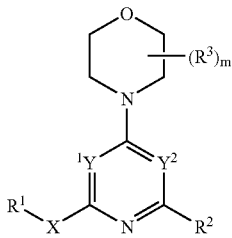

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7$C≡C—, —$NR^4CR^6R^7$—, —$OCR^6R^7$—, —$SCR^6R^7$—, —S(O)$CR^6R^7$—, —S(O)$_2CR^6R^7$—, —C(O)$NR^4CR^6R^7$—, —$NR^4$C(O)$NR^5CR^6R^7$—, —S(O)$_2NR^4CR^6R^7$—, —C(O)$NR^4$—, —$NR^4$C(O)—, —$NR^4$C(O)$NR^5$—, —S(O)$_2NR^4$— and —$NR^4$S(O)$_2$—;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —$OR^9$, —$SR^9$, —$SOR^9$, —$SO_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and —$NR^9SO_2R^{10}$;

or X—$R^1$ is —$CR^6R^7OH$;

$R^2$ is a group selected from $C_{1-6}$alkyl, carbocyclyl and heterocyclyl which group is substituted by —$NR^{17}CONR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;

each $R^3$, when present, is independently selected from halo, cyano, nitro, —$R^{13}$, —$OR^{13}$, —$SR^{13}$, —$SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$NR^{13}CO_2R^{14}$ and —$NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided the use of a compound of formula (I)

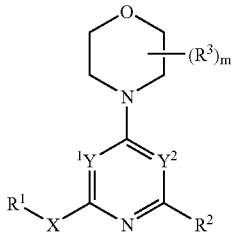

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl $C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with another aspect of the present invention, there is provided the use of a compound of formula (I)

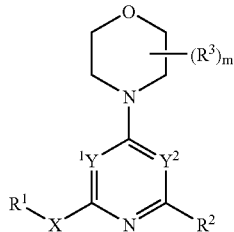

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with another aspect of the present invention, there is provided the use of a compound of formula (I)

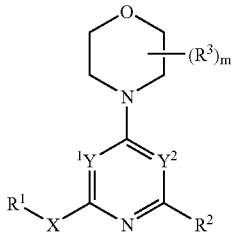

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $—CR^4{=}CR^5—$, $—CR^4{=}CR^5CR^6R^7—$, $—CR^6R^7CR^5{=}CR^4—$, $—C{\equiv}C—$, $—C{\equiv}CCR^6R^7—$, $—CR^6R^7C{\equiv}C—$, $—NR^4CR^6R^7—$, $—OCR^6R^7—$, $—SCR^6R^7—$, $—S(O)CR^6R^7—$, $—S(O)_2CR^6R^7—$, $—C(O)NR^4CR^6R^7—$, $—NR^4C(O)CR^6R^7—$, $—NR^4C(O)NR^5CR^6R^7—$, $—NR^4S(O)_2CR^6R^7—$, $—S(O)_2NR^4CR^6R^7—$, $—C(O)NR^4—$, $—NR^4C(O)—$, $—NR^4C(O)NR^5—$, $—S(O)_2NR^4—$ and $—NR^4S(O)_2—$;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $—R^9$, $—OR^9$, $—SR^9$, $—SOR^9$, $—SO_2R^9$, $—COR^9$, $—CO_2R^9$, $—CONR^9R^{10}$, $—NR^9R^{10}$, $—NR^9COR^{10}$, $—NR^9CO_2R^{10}$, $—NR^9CONR^{10}R^{15}$, $—NR^9COCONR^{10}R^{15}$ and $—NR^9SO_2R^{10}$;

or $X—R^1$ is $—CR^6R^7OH$;

$R^2$ is a group selected from $C_{1-6}$alkyl, carbocyclyl and heterocyclyl which group is substituted by $—NR^{17}CONR^{18}R^{19}$ and optionally substituted by one or more substituent group independently selected from halo, cyano, nitro, $—R^{11}$, $—OR^{11}$, $—SR^{11}$, $—SOR^{11}$, $—SO_2R^{11}$, $—COR^{11}$, $—CO_2R^{11}$, $—CONR^{11}R^{12}$, $—NR^{11}R^{12}$, $—NR^{11}COR^{12}$, and $—NR^{11}COCONR^{12}R^{16}$;

each $R^3$, when present, is independently selected from halo, cyano, nitro, $—R^{13}$, $—OR^{13}$, $—SR^{13}$, $—SOR^{13}$, $—SO_2R^{13}$, $—COR^{13}$, $—CO_2R^{13}$, $—CONR^{13}R^{14}$, $—NR^{13}R^{14}$, $—NR^{13}COR^{14}$, $—NR^{13}CO_2R^{14}$ and $—NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with another aspect of the present invention, there is provided the use of a compound of formula (I)

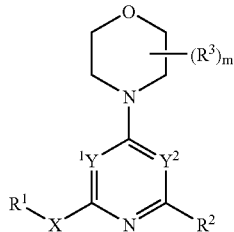

formula (I)

or a pharmaceutically acceptable salt; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7C$≡C—, —$NR^4CR^6R^7$—, —$OCR^6R^7$—, —$SCR^6R^7$—, —S(O)$CR^6R^7$—, —S(O)$_2CR^6R^7$—, —C(O)$NR^4CR^6R^7$—, —$NR^4$C(O)$NR^5CR^6R^7$—, —S(O)$_2NR^4CR^6R^7$—, —C(O)$NR^4$—, —$NR^4$C(O)—, —$NR^4$C(O)$NR^5$—, —S(O)$_2NR^4$— and —$NR^4$S(O)$_2$—;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, —$R^9$, —$OR^9$, —$SR^9$, —$SOR^9$, —$SO_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and —$NR^9SO_2R^{10}$;

or X—$R^1$ is —$CR^6R^7$OH $R^2$ is a group selected from $C_{1-6}$alkyl, carbocyclyl and heterocyclyl which group is substituted by —$NR^{17}CONR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;

each $R^3$, when present, is independently selected from halo, cyano, nitro, —$R^{13}$, —$OR^{13}$, —$SR^{13}$, —$SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$R^{13}CO_2R^{14}$ and —$NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy $C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with a further aspect of the present invention, there is also provided a compound of formula (I)

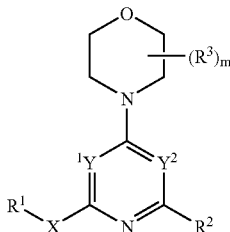

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-O_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $NR^9SO_2R^{10}$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-R^{13,31}SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In accordance with a further aspect of the present invention, there is also provided a compound of formula (I)

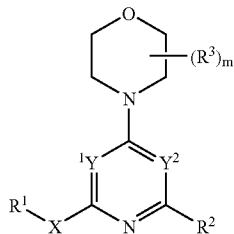

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7C$≡C—, —$NR^4CR^6R^7$—, —$OCR^6R^7$—, —$SCR^6R^7$—, —S(O)$CR^6R^7$—, —S(O)$_2CR^6R^7$—, —C(O)$NR^4CR^6R^7$—, —$NR^4C(O)CR^6R^7$—, —$NR^4C(O)NR^5CR^6R^7$—, —$NR^4S(O)_2CR^6R^7$—, —S(O)$_2NR^4CR^6R^7$—, —C(O)$NR^4$—, —$NR^4C(O)$—, —$NR^4C(O)NR^5$—, —(O)$_2NR^4$— and —$NR^4S(O)_2$—;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, —$R^9$, —$OR^9$, —$SR^9$, —$SOR^9$, —$O_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and $NR^9SO_2R^{10}$;

$R^2$ is a group selected from $C_{1-6}$alkyl, carbocyclyl and heterocyclyl which group is substituted by —$NR^{17}CONR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;

each $R^3$, when present, is independently selected from halo, cyano, nitro, —$R^{13}$, —$OR^{13}$, —$R^{13}$, $^{31}SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$NR^{13}CO2R^{14}$ and —$NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl $C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl) amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In accordance with a further aspect of the present invention, there is also provided a compound of formula (I)

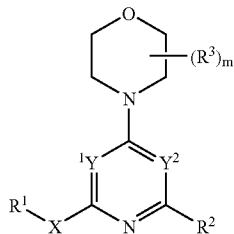

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-(O)_2NR^4-$ and $-NR^4S(O)_2-$;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-O_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $NR^9SO_2R^{10}$;

or $X-R^1$ is $-CR^6R^7OH$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-R^{13}$, $^{31}SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy $C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl $C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl) amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In accordance with a further aspect of the present invention, there is also provided a compound of formula (I)

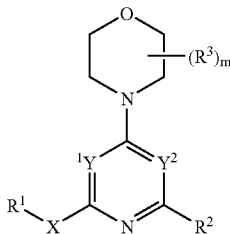

formula (I)

or a pharmaceutically acceptable salt thereof, wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)NR^5CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-O_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $NR^9SO_2R^{10}$;

or $X-R^1$ is $-CR^6R^7OH$;

$R^2$ is a group selected from $C_{1-6}$alkyl, carbocyclyl and heterocyclyl which group is substituted by $-NR^{17}CONR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-R^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention. Solvates and mixtures thereof also form an aspect of the present invention. For example, a suitable solvate of a compound of formula (I) is, for example, a hydrate such as a hemi-hydrate, a mono-hydrate, a di-hydrate or a tri-hydrate or an alternative quantity thereof.

The present invention relates to the compounds of formula (I) as herein defined as well as to salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to furmarate, methanesulfonate, hydrochloride, hydrobromide, citrate and maleate salts and salts formed with phosphoric and sulfuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl, 1,3-dioxolen-2-onylmethyl esters for example 5-methyl-1,3-dioxolen-2-onylmethyl, and $C_{1-6}$alkoxycarbonyloxyethyl esters for example 1-methoxycarbonyloxyethyl; and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example formyl, acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$alkylaminoethyl)-N—$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^{A}C(O)OC_{1-6}$alkyl-CO—, wherein $R^{A}$ is for example, benzyloxy-$C_{1-4}$alkyl, or phenyl. Suitable substituents on a phenyl group in such esters include, for example, 4-$C_{1-4}$piperazino-$C_{1-4}$alkyl, piperazino-$C_{1-4}$alkyl and morpholino-$C_{1-4}$alkyl.

The compounds of the formula (I) may be also be administered in the form of a prodrug which is broken down in the human or animal body to give a compound of the formula (I). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

In this specification the generic term "$C_{p-q}$alkyl" includes both straight-chain and branched-chain alkyl groups. However references to individual alkyl groups such as "propyl" are specific for the straight chain version only (i.e. n-propyl and isopropyl) and references to individual branched-chain alkyl groups such as "tert-butyl" are specific for the branched chain version only.

The prefix $C_{p-q}$ in $C_{p-q}$alkyl and other terms (where p and q are integers) indicates the range of carbon atoms that are present in the group, for example $C_{1-4}$alkyl includes $C_1$alkyl (methyl), $C_2$alkyl (ethyl), $C_3$alkyl (propyl as n-propyl and isopropyl) and $C_4$alkyl (n-butyl, sec-butyl, isobutyl and tert-butyl).

The term $C_{p-q}$alkoxy comprises —O—$C_{p-q}$alkyl groups.
The term $C_{p-q}$alkanoyl comprises —C(O)alkyl groups.
The term halo includes fluoro, chloro, bromo and iodo.

"Carbocyclyl" is a saturated, unsaturated or partially saturated monocyclic, bicyclic or tricyclic ring system containing from 3 to 14 ring atoms, wherein a ring $CH_2$ group may be replaced with a C=O group. "Carbocyclyl" includes "aryl", "$C_{p-q}$cycloalkyl" and "$C_{p-q}$cycloalkenyl".

"aryl" is an aromatic monocyclic, bicyclic or tricyclic carbocyclyl ring system.

"$C_{p-q}$cycloalkenyl" is an unsaturated or partially saturated monocyclic, bicyclic or tricyclic carbocyclyl ring system containing at least 1 C=C bond and wherein a ring $CH_2$ group may be replaced with a C=O group.

"$C_{p-q}$cycloalkyl" is a saturated monocyclic, bicyclic or tricyclic carbocyclyl ring system and wherein a ring $CH_2$ group may be replaced with a C=O group.

"Heterocyclyl" is a saturated, unsaturated or partially saturated monocyclic, bicyclic or tricyclic ring system containing from 3 to 14 ring atoms of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group. "Heterocyclyl" includes "heteroaryl", "cycloheteroalkyl" and "cycloheteroalkenyl".

"Heteroaryl" is an aromatic monocyclic, bicyclic or tricyclic heterocyclyl, particularly having 5 to 10 ring atoms, of which 1, 2, 3 or 4 ring atoms are chosen from nitrogen, sulfur or oxygen where a ring nitrogen or sulfur may be oxidised.

"Cycloheteroalkenyl" is an unsaturated or partially saturated monocyclic, bicyclic or tricyclic heterocyclyl ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

"Cycloheteroalkyl" is a saturated monocyclic, bicyclic or tricyclic heterocyclic ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

This specification may make use of composite terms to describe groups comprising more than one functionality. Unless otherwise described herein, such terms are to be interpreted as is understood in the art. For example carbocyclyl$C_{p-q}$alkyl comprises $C_{p-q}$alkyl substituted by carbocyclyl, heterocyclyl$C_{p-q}$alkyl comprises $C_{p-q}$alkyl substituted by heterocyclyl, and bis($C_{p-q}$alkyl)amino comprises amino substituted by 2 $C_{p-q}$alkyl groups which may be the same or different.

Halo$C_{p-q}$alkyl is a $C_{p-q}$alkyl group that is substituted by 1 or more halo substituents and particularly 1, 2 or 3 halo substituents. Similarly, other generic terms containing halo such as halo$C_{p-q}$alkoxy may contain 1 or more halo substituents and particularly 1, 2 or 3 halo substituents.

Hydroxy$C_{p-q}$alkyl is a $C_{p-q}$alkyl group that is substituted by 1 or more hydroxyl substituents and particularly by 1, 2 or 3 hydroxy substituents. Similarly other generic terms containing hydroxy such as hydroxy$C_{p-q}$alkoxy may contain 1 or more and particularly 1, 2 or 3 hydroxy substituents.

$C_{p-q}$alkoxy$C_{p-q}$alkyl is a $C_{p-q}$alkyl group that is substituted by 1 or more $C_{p-q}$alkoxy substituents and particularly 1, 2 or 3 $C_{p-q}$alkoxy substituents. Similarly other generic terms containing $C_{p-q}$alkoxy such as $C_{p-q}$alkoxy$C_{p-q}$alkoxy may contain 1 or more $C_{p-q}$alkoxy substituents and particularly 1, 2 or 3 $C_{p-q}$alkoxy substituents.

Where optional substituents are chosen from "1 or 2", from "1, 2, or 3" or from "1, 2, 3 or 4" groups or substituents it is to be understood that this definition includes all substituents being chosen from one of the specified groups i.e. all substitutents being the same or the substituents being chosen from two or more of the specified groups i.e. the substitutents not being the same.

"Proliferative disease(s)" includes malignant disease(s) such as cancer as well as non-malignant disease(s) such as inflammatory diseases, obstructive airways diseases, immune diseases or cardiovascular diseases.

Suitable values for any R group or any part or substitutent for such groups include:
for $C_{1-4}$alkyl: methyl, ethyl, propyl, butyl, 2-methylpropyl and tert-butyl;
for $C_{1-6}$alkyl: $C_{1-4}$alkyl, pentyl, 2,2-dimethylpropyl, 3-methylbutyl and hexyl;
for $C_{3-6}$cycloalkyl: cyclopropyl, cyclobutyl, cyclopentyl and cyclohexyl;
for $C_{3-6}$cycloalkyl$C_{1-4}$alkyl: cyclopropylmethyl, cyclopropylethyl, cyclobutylmethyl, cyclopentylmethyl and cyclohexylmethyl;
for aryl: phenyl and naphthyl;
for aryl$C_{1-4}$alkyl: benzyl, phenethyl, naphthylmethyl and naphthylethyl;
for carbocyclyl: aryl, cyclohexenyl and $C_{3-6}$cycloalkyl;
for halo: fluoro, chloro, bromo and iodo;
for $C_{1-4}$alkoxy: methoxy, ethoxy, propoxy and isopropoxy;
for $C_{1-6}$alkoxy: $C_{1-4}$alkoxy, pentyloxy, 1-ethylpropoxy and hexyloxy;
for $C_{1-6}$alkanoyl: acetyl, propanoyl and 2-methylpropanoyl;
for heteroaryl: pyridyl, imidazolyl, quinolinyl, cinnolyl, pyrimidinyl, thienyl, pyrrolyl, pyrazolyl, thiazolyl, thiadzolyl, triazolyl, oxazolyl, isoxazolyl, furanyl, pyridazinyl, pyrazinyl, indolyl, benzofuranyl, dibenzofuranyl and benzothienyl;
for heteroaryl$C_{1-4}$alkyl: pyrrolylmethyl, pyrrolylethyl, imidazolylmethyl, imidazolylethyl, pyrazolylmethyl, pyrazolylethyl, furanylmethyl, furanylethyl, thienylmethyl, theinylethyl, pyridylmethyl, pyridylethyl, pyrazinylmethyl, pyrazinylethyl, pyrimidinylmethyl, pyrimidinylethyl, pyrimidinylpropyl, pyrimidinylbutyl, imidazolylpropyl, imidazolylbutyl, quinolinylpropyl, 1,3,4-triazolylpropyl and oxazolylmethyl;
for heterocyclyl: heteroaryl, pyrrolidinyl, isoquinolinyl, quinoxalinyl, benzothiazolyl, benzoxazolyl, piperidinyl, piperazinyl, azetidinyl, morpholinyl, tetrahydroisoquinolinyl, tetrahydroquinolinyl, indolinyl, dihydro-2H-pyranyl and tetrahydrofuranyl.

It should be noted that examples given for terms used in the description are not limiting.

Particular values of m, X, $^1Y$ and $Y^2$, $R^1$, $R^2$ and $R^3$ are as follows. Such values may be used where appropriate, in connect with any aspect of the invention, or part thereof, and with any of the definitions, claims or embodiments defined herein.

m
In one aspect of the invention m is 0, 1, 2 or 3.
In another aspect m is 0, 1 or 2.
In a further aspect m is 0 or 1.
In yet another aspect m is 0 so that $R^3$ is absent.
In yet another aspect m is 1 and $R^3$ is methyl.

$^1Y$ and $Y^2$
In one aspect of the invention $^1Y$ is N and $Y^2$ is $CR^3$.
In another aspect $^1Y$ is N and $Y^2$ is CH.
In yet another aspect $^1Y$ is $CR^8$ and $Y^2$ is N.
In a further aspect $^1Y$ is CH or CF and $Y^2$ is N.
In yet a further aspect $^1Y$ is CH and $Y^2$ is N.

X
In one aspect of the invention X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$NR^4C(O)$—, —$C(O)NR^4$—, —$S(O)_2NR^4$— and —$NR^4S(O)_2$—.

In another aspect X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$, —$C(O)NR^4$— and —$NR^4C(O)$—.

In a further aspect X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4$—, and —$NR^4C(O)$—.

In a further aspect X is a linker group selected from —$NR^4CR^6R^7$—, —$OCR^6R^7$—, —$SCR^6R^7$—, —$S(O)CR^6R^7$— and —$S(O)_2CR^6R^7$—.

In yet another aspect X is a linker group selected from —$SCR^6R^7$—, —$S(O)CR^6R^7$— and —$S(O)_2CR^6R^7$—.

In another aspect X is a linker group selected from —$NR^4$—$CH_2$—, —$OCH_2$—, —$OCH(CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —$S(O)C(CH_3)_2$—, —$S(O)_2CH_2$—, —$S(O)_2CH(CH_3)$—, —$S(O)_2C(CH_3)_2$—, —$C(O)NR^4$— and —$NR^4C(O)$—.

In another aspect X is a linker group selected from —$NR^4$—$CH_2$—, —$OCH_2$—, —$SCH_2$—, —$S(O)CH_2$—, —$S(O)_2CH_2$—, —$C(O)NR^4$—, and —$NR^4C(O)$—.

In another aspect X is a linker group selected from —$NR^4$—$CH_2$—, —$OCH_2$—, —$OCH(CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —$S(O)C(CH_3)_2$—, —$S(O)_2CH_2$—, —$S(O)_2CH(CH_3)$— and —$S(O)_2C(CH_3)_2$—.

In another aspect X is a linker group selected from —$NR^4$—$CH_2$—, —$OCH_2$—, —$SCH_2$—, —$S(O)CH_2$— and —$S(O)_2CH_2$—.

In a further aspect X is a linker group selected from —NHCH$_2$—, —N(CH$_3$)CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)—, —S(O)$_2$C(CH$_3$)$_2$—, —C(O)NH—, —C(O)N(CH$_3$)—, —NHC(O)— and —N(CH$_3$)C(O)—.

In a further aspect X is a linker group selected from —NHCH$_2$—, —N(CH$_3$)CH$_2$—, —OCH$_2$—, —SCH$_2$—, —S(O)CH$_2$—, —S(O)$_2$CH$_2$—, —C(O)NH—, —C(O)N(CH$_3$)—, —NHC(O)— and —N(CH$_3$)C(O)—.

In yet a further aspect X is a linker group selected from —NHCH$_2$—, —N(CH$_3$)CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)— and —S(O)$_2$C(CH$_3$)$_2$—.

In yet a further aspect X is a linker group selected from —NHCH$_2$—, —N(CH$_3$)CH$_2$—, —OCH$_2$—, —SCH$_2$— and —S(O)$_2$CH$_2$—.

In another aspect X is —SCH$_2$— or —S(O)$_2$CH$_2$—.

In another aspect X is —SCH$_2$—, —SCH(CH$_3$)— or —SC(CH$_3$)$_2$—.

In another aspect X is —S(O)CH$_2$—, —S(O)CH(CH$_3$)— or —S(O)C(CH$_3$)$_2$—.

In another aspect X is —S(O)$_2$CH$_2$—, —S(O)$_2$CH(CH$_3$)— or —S(O)$_2$C(CH$_3$)$_2$—.

In another aspect X is —S(O)$_2$CH$_2$—.

In another aspect X is —S(O)$_2$C(CH$_3$)$_2$—.

$R^1$

In one aspect of the invention $R^1$ is a group selected from $C_{1-4}$alkyl, $C_{3-10}$cycloalkyl, aryl, $C_{3-10}$cycloalkyl$C_{1-4}$alkyl, aryl$C_{1-4}$alkyl, cycloheteroalkyl, heteroaryl, cycloheteroalkyl$C_{1-4}$alkyl, heteroaryl$C_{1-4}$alkyl, which group is optionally substituted by one or more substituent group selected from halo, cyano, nitro, $R^9$, —OR$^9$, —COR$^9$, —CONR$^9$R$^{10}$, —NR$^9$R$^{10}$ and —NR$^9$COR$^{10}$.

In another aspect, $R^1$ is a group selected from adamantyl, methyl, ethyl, propyl, butyl, isobutyl, tert-butyl, cyclopentyl, cyclohexyl, phenyl, benzyl, oxetanyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —OR$^9$, —COR$^9$, —CONR$^9$R$^{10}$, —NR$^9$R$^{10}$ and —NR$^9$COR$^{10}$.

In another aspect, $R^1$ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —OR$^9$, —COR$^9$, —CONR$^9$R$^{10}$, —NR$^9$R$^{10}$ and —NR$^9$COR$^{10}$.

In a further aspect, $R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NMe$_2$, —NHCOCH$_3$, —CONH$_2$ and —CONHCH$_3$.

In a further aspect, $R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$.

In another aspect $R^1$ is a group selected from methyl, ethyl, isopropyl, cyclopropyl, cyclohexyl, —CH$_2$CH$_2$OH, —CH$_2$CH$_2$NC(O)CH$_3$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrrolidin-3-yl, thiazol-2-yl, 4-methylthiazol-2-yl, and 3-methyl-1,3,4-thiadiazol-2-yl.

In yet another aspect $R^1$ is a group selected from methyl, isopropyl, cyclopropyl, cyclohexyl, —CH$_2$CH$_2$OH, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrrolidin-3-yl, thiazol-2-yl, 4-methylthiazol-2-yl, and 3-methyl-1,3,4-thiadiazol-2-yl.

In yet another aspect $R^1$ is a group selected from methyl, ethyl, isopropyl, tert-butyl, cyclopropyl, cyclopentyl, cyclohexyl, —CH$_2$CH$_2$OH, —CH$_2$CH$_2$OMe, —CH$_2$CH$_2$NMe$_2$, —CH$_2$CH$_2$NC(O)CH$_3$, —CH$_2$CONH$_2$, phenyl, 3,5-difluorophenyl, 4-fluorophenyl, 2-chlorophenyl, 4-chlorophenyl, 2-trifluoromethylphenyl, 2-methoxyphenyl, 2-methylphenyl, 4-acetamidophenyl, 4-aminophenyl, pyridin-4-yl, pyridin-2-yl, oxetan-3-yl, 2-oxopyrrolidin-3-yl, 1-methylimidazol-5-ylmethyl, 1-methylpyrrolidin-3-yl, thiazol-2-yl, 4-methylthiazol-2-yl, and 3-methyl-1,3,4-thiadiazol-2-yl.

In another aspect $R^1$ is methyl, ethyl, isopropyl, tert-butyl, 4-fluorophenyl, 3,5-difluorophenyl, pyridin-4-yl or cyclopropyl.

In another aspect $R^1$ is methyl, ethyl, isopropyl, tert-butyl, 4-fluorophenyl, pyridin-4-yl or cyclopropyl.

In another aspect $R^1$ is methyl or cyclopropyl.

In another aspect $R^1$ is methyl.

X—$R^1$

In one embodiment X—$R^1$ is —C(CH$_3$)$_2$OH or —CH$_2$OH.

In one embodiment X—$R^1$ is —CH$_2$OH.

$R^2$

In one aspect of the invention $R^2$ is selected from carbocyclyl or heterocyclyl which group is substituted by —NR$^{17}$CONR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from carbocyclyl or heterocyclyl which group is substituted by —NHCONR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from carbocyclyl or heterocyclyl which group is substituted by —NHCONHR$^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from 5 or 6 membered carbocyclyl or heterocyclyl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from 5 or 6 membered carbocyclyl or heterocyclyl which group is substituted by —$NHCONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from 5 or 6 membered carbocyclyl or heterocyclyl which group is substituted by —$NHCONHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from a 6 membered aryl and 5 or 6 membered heteroaryl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from a 6 membered aryl and 5 or 6 membered heteroaryl which group is substituted by —$NHCONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In one aspect of the invention $R^2$ is selected from a 6 membered aryl and 5 or 6 membered heteroaryl which group is substituted by —$NHCONHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NR^{17}CONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONHR^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is phenyl or pyridyl substituted by —$NR^{17}CONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is phenyl or pyridyl substituted by —$NHCONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is phenyl or pyridyl substituted by —$NHCONHR^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

In another aspect $R^2$ is phenyl or pyridyl optionally substituted by —$NR^{17}CONR^{18}R^{19}$.

In another aspect $R^2$ is phenyl or pyridyl optionally substituted by —$NHCONR^{18}R^{19}$.

In another aspect $R^2$ is phenyl or pyridyl optionally substituted by —$NHCONHR^{19}$.

In another aspect $R^2$ is

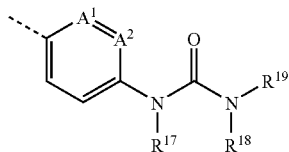

wherein $A^1$ and $A^2$ are selected from CH or N provided that at least one of $A^1$ or $A^2$ is CH.

In another aspect $R^2$ is

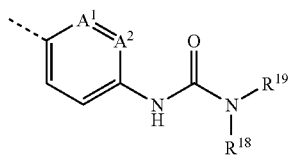

wherein $A^1$ and $A^2$ are selected from CH or N provided that at least one of $A^1$ or $A^2$ is CH.

In another aspect $R^2$ is

[chemical structure showing aryl ring with $A^1$, $A^2$ positions and NH-C(O)-NH-$R^{19}$ urea linkage]

wherein $A^1$ and $A^2$ are selected from CH or N provided that at least one of $A^1$ or $A^2$ is CH.

$R^4$

In one aspect of the invention $R^4$ is hydrogen or methyl.

In another aspect $R^4$ is hydrogen.

$R^4$ and $R^1$

In another aspect of the invention, when X is —NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —NR$^4$C(O)—, —NR$^4$C(O)NR$^5$— or —NR$^4$S(O)$_2$—, $R^1$ and $R^4$ together with the atom or atoms to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —NR$^4$C(O)—, —NR$^4$C(O)NR$^5$— or —NR$^4$S(O)$_2$—, $R^1$ and $R^4$ together with the atom or atoms to which they are attached form a 4-, 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —NR$^4$C(O)—, —NR$^4$C(O)NR$^5$— or —NR$^4$S(O)$_2$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl) amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —NR$^4$C(O)—, —NR$^4$C(O)NR$^5$— or —NR$^4$S(O)$_2$—, $R^1$ and $R^4$ together with the atom or atoms to which they are attached form a 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —NR$^4$C(O)—, —NR$^4$C(O)NR$^5$— or —NR$^4$S(O)$_2$—, $R^1$ and $R^4$ together with the atom or atoms to which they are attached form a piperidine, morpholine, azetidine, azepine, diazepane and thiomorpholine ring which ring is optionally substituted by one or more substituent groups selected from halo, hydroxy, oxo and $C_{1-6}$alkyl.

In another aspect of the invention, when X is —NR$^4$C(O)—$R^1$ and $R^4$ together with the atom or atoms to which they are attached form a piperidine, morpholine, azetidine, azepine, diazepane and thiomorpholine ring which ring is optionally substituted by one or more substituent groups selected from halo, hydroxy, oxo and $C_{1-6}$alkyl.

In another aspect of the invention, when X is —NR$^4$C(O)—$R^1$ and $R^4$ together with the atom or atoms to which they are attached form a 1-methyl-piperidine, 4-hydroxy-piperidine, morpholine, 3-methylmorpholine, 3-hydroxyazetidine, azepine, 1,4-diazepane and a thiomorpholine-1,1-dioxide ring.

$R^5$

In one aspect of the invention $R^5$ is hydrogen or methyl.

In another aspect $R^5$ is hydrogen.

In another aspect $R^5$ is methyl.

$R^6$

In one aspect of the invention $R^6$ is hydrogen or methyl.

In another aspect $R^6$ is hydrogen.

In another aspect $R^6$ is methyl.

$R^7$

In one aspect of the invention $R^7$ is hydrogen or methyl.

In another aspect $R^7$ is hydrogen.

In another aspect $R^7$ is methyl.

$R^8$

In one aspect of the invention $R^8$ is hydrogen or halo.

In another aspect $R^8$ is hydrogen or fluoro.

In a further aspect $R^8$ is hydrogen.

$R^9$

In one aspect of the invention $R^9$ is hydrogen or $C_{1-4}$alkyl optionally substituted by 1, 2 or 3 substituent groups selected from halo, cyano, nitro, hydroxy, $C_{1-4}$alkoxy, amino, $C_{1-4}$alkylamino and bis($C_{1-4}$alkyl)amino.

In another aspect $R^9$ is hydrogen or $C_{1-4}$alkyl optionally substituted by 1, 2 or 3 halo substituents.

In a further aspect $R^9$ is hydrogen, methyl or trifluoromethyl.

$R^{10}$

In one aspect of the invention $R^{10}$ is hydrogen.

$R^{11}$

In one aspect of the invention $R^{11}$ is hydrogen or a group selected from $C_{1-4}$alkyl, aryl and cycloheteroalkyl which group is optionally substituted by 1, 2 or 3 groups selected from halo, hydroxy and cyano.

In another aspect $R^{11}$ is hydrogen, methyl optionally substituted with hydroxy or cyano, phenyl or pyrrolidinyl.

In another aspect $R^{11}$ is hydrogen or methyl.

$R^{12}$

In one aspect of the invention $R^{12}$ is hydrogen or methyl.

$R^{17}$

In one aspect of the invention $R^{17}$ is hydrogen or a group selected from $C_{1-4}$alkyl, aryl and cycloheteroalkyl which group is optionally substituted by 1, 2 or 3 groups selected from halo, hydroxy and cyano.

In another aspect $R^{17}$ is hydrogen, methyl optionally substituted with hydroxy or cyano, phenyl or pyrrolidinyl.

In another aspect $R^{17}$ is hydrogen or methyl.

In another aspect $R^{17}$ is hydrogen.

$R^{18}$

In one aspect of the invention $R^{18}$ is hydrogen or methyl.

In one aspect of the invention $R^{18}$ is hydrogen $R^{19}$

In one aspect of the invention $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from $C_{1-6}$alkyl, $C_{3-6}$cycloakyl, phenyl, naphthyl, pyrrolyl, imidazolyl, isoxazolyl, pyrazolyl, furanyl, thienyl, pyridinyl, pyrimidinyl, pyridazinyl, azaindolyl, indolyl, quinolinyl, benzimidazolyl, benzofuranyl, dibenzofuranyl, benzothienyl, phenyl$C_{1-6}$alkyl, naphthyl$C_{1-6}$alkyl, pyrrolyl$C_{1-6}$alkyl, imidazolyl$C_{1-6}$alkyl, isoxazolyl$C_{1-6}$alkyl, pyrazolyl$C_{1-6}$alkyl, furanyl$C_{1-6}$alkyl, thienyl$C_{1-6}$alkyl, pyridinyl$C_{1-6}$alkyl, pyrimidinyl$C_{1-6}$alkyl, pyridazinyl$C_{1-6}$alkyl, azaindolyl$C_{1-6}$alkyl, indolyl$C_{1-6}$alkyl, quinolinyl$C_{1-6}$alkyl, benzimidazolyl$C_{1-6}$alkyl, benzofuranyl$C_{1-6}$alkyl, dibenzofuranyl$C_{1-6}$alkyl, benzothienyl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from $C_{1-6}$alkyl, $C_{3-6}$cycloakyl, phenyl, naphthyl, pyrrolyl, imidazolyl, isoxazolyl, pyrazolyl, furanyl, thienyl, pyridinyl, pyrimidinyl, pyridazinyl, azaindolyl, indolyl, quinolinyl, benzimidazolyl, benzofuranyl, dibenzofuranyl, benzothienyl, phenyl$C_{1-6}$alkyl, naphthyl$C_{1-6}$alkyl, pyrrolyl$C_{1-6}$alkyl, imidazolyl$C_{1-6}$alkyl, isoxazolyl$C_{1-6}$alkyl, pyrazolyl$C_{1-6}$alkyl, furanyl$C_{1-6}$alkyl, thienyl$C_{1-6}$alkyl, pyridinyl$C_{1-6}$alkyl, pyrimidinyl$C_{1-6}$alkyl, pyridazinyl$C_{1-6}$alkyl, azaindolyl$C_{1-6}$alkyl, indolyl$C_{1-6}$alkyl, quinolinyl$C_{1-6}$alkyl, benzimidazolyl$C_{1-6}$alkyl, benzofuranyl$C_{1-6}$alkyl, dibenzofuranyl$C_{1-6}$alkyl, benzothienyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino $C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyridin-2-yl, pyrimidin-2-yl, and 1H-pyrazol-3-yl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyrimidin-2-yl, and 1H-pyrazol-3-yl.

In another aspect of the invention $R^{19}$ is a group selected from methyl, ethyl, propyl, cyclopropyl, cyclobutyl, —CH$_2$CH$_2$OH, —CH$_2$CH$_2$NMe$_2$, —C(Me)$_2$CH$_2$OH and 1H-pyrazol-3-yl.

$R^{18}$ and $R^{19}$

In one aspect of the invention, $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention, $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention, $R^{18}$ and $R^{19}$ together with the nitrogen atom to which they are attached form a morpholine ring.

In one aspect of the invention there is provided a subset of compounds of formula (I), or a pharmaceutically acceptable salt thereof;

m is 0, 1 or 2;

$^1Y$ and $Y^2$ are independently N or $CR^8$ provided that one of $^1Y$ and $Y^2$ is N and the other is $CR^8$;

X is a linker group selected from —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)NR$^5$CR$^6$R$^7$—, —S(O)$_2$NR$^4$CR$^6$R$^7$—, —NR$^4$C(O)—, —S(O)$_2$NR$^4$— and —NR$^4$S(O)$_2$—;

$R^1$ is a group selected from $C_{1-6}$alkyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —OR$^9$, —COR$^9$, —CONR$^9$R$^{10}$, —NR$^9$R$^{10}$ and —NR$^9$COR$^{10}$;

or X—R$^1$ is —C(CH$_3$)$_2$OH or —CH$_2$OH;

$R^2$ is selected from aryl and heteroaryl which group is substituted by —NR$^{17}$CONR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$;

each $R^3$, when present, is methyl;

$R^4$ and $R^5$ are independently hydrogen or $C_{1-6}$alkyl;

or, when X is —NR$^4$CR$^6$R$^7$—, —NR$^4$C(O)NR$^5$CR$^6$R$^7$—, —NR$^4$C(O)— or —NR$^4$S(O)$_2$—, $R^1$ and $R^4$ together with the atom or atoms to which they are attached form a 4-, 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$, $R^{17}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention there is provided a subset of compounds of formula (I), or a pharmaceutically acceptable salt thereof;

m is 0, 1 or 2;

$^1Y$ and $Y^2$ are independently N or $CR^8$ provided that one of $^1Y$ and $Y^2$ is N and the other is $CR^8$;

X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$NR^4C(O)$—, —$S(O)_2NR^4$— and —$NR^4S(O)_2$—;

$R^1$ is a group selected from $C_{1-6}$alkyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —$OR^9$, —$COR^9$, —$CONR^9R^{10}$, —$NR^9R^{10}$ and —$NR^9COR^{10}$;

or X—$R^1$ is —$C(CH_3)_2OH$ or —$CH_2OH$;

$R^2$ is selected from aryl and heteroaryl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

each $R^3$, when present, is methyl;

$R^4$ and $R^5$ are independently hydrogen or $C_{1-6}$alkyl;

or, when X is —$NR^4CR^6R^7$—, —$NR^4C(O)NR^5CR^6R^7$—, —$NR^4C(O)$— or —$NR^4S(O)_2$—, $R^1$ and $R^4$ together with the atom or atoms to which they are attached form a 4-, 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$, $R^{17}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl $C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention there is provided a subset of compounds of formula (I), or a pharmaceutically acceptable salt thereof;

m is 0, 1 or 2;

$^1Y$ and $Y^2$ are independently N or $CR^8$ provided that one of $^1Y$ and $Y^2$ is N and the other is $CR^8$;

X is a linker group selected from —$NR^4$—$CH_2$—, —$OCH_2$—, —$OCH(CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —$S(O)C(CH_3)_2$—, —$S(O)_2CH_2$—, —$S(O)_2CH(CH_3)$—, —$S(O)_2C(CH_3)_2$—, —$C(O)NR^4$— and —$NR^4C(O)$—;

$R^1$ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —$OR^9$, —$COR^9$, —$CONR^9R^{10}$, —$NR^9R^{10}$ and —$NR^9COR^{10}$;

or X—$R^1$ is —$C(CH_3)_2OH$ or —$CH_2OH$;

$R^2$ is selected from 5 or 6 membered aryl and heteroaryl which group is substituted by —$NHCONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

each $R^3$, when present, is methyl;

$R^4$ is hydrogen or $C_{1-6}$alkyl;

or, when X is —$NR^4$—$CH_2$— or —$NR^4C(O)$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$ alkyl)amino;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (I), or a pharmaceutically acceptable salt thereof;

m is 0 or 1;

$^1Y$ is CH and $Y^2$ is N;

X is a linker group selected from —$S(O)_2CH_2$—, —$S(O)_2CH(CH_3)$— and —$S(O)_2C(CH_3)_2$—;

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NMe_2$, —$NHCOCH_3$, —$CONH_2$ and —$CONHCH_3$;

or —$XR^1$ is —$C(CH_3)_2OH$ or —$CH_2OH$;

$R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

$R^3$, when present, is methyl;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (I), or a pharmaceutically acceptable salt thereof;

m is 0 or 1;

$^1Y$ is CH and $Y^2$ is N;

X is a linker group selected from —$S(O)_2CH_2$—, —$S(O)_2CH(CH_3)$— and —$S(O)_2C(CH_3)_2$—;

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NHCOCH_3$, —$CONH_2$ and —$CONHCH_3$;

or —XR¹ is —C(CH$_3$)$_2$OH or —CH$_2$OH;

R² is selected from phenyl, pyrrolyl, imidazolyl, pyrazolyl, furanyl, thienyl, pyridinyl, pyrimidinyl, pyridazinyl and thiazolyl which group is substituted by —NHCONHR¹⁹ and optionally substituted by one or more substituent group independently selected from halo, cyano, nitro, —R¹¹, —OR¹¹, —COR¹¹, —CONR¹¹R¹², —NR¹¹R¹² ad —NR¹¹COR¹²;

R³, when present, is methyl;

R¹¹, R¹² and R¹⁸ are independently hydrogen or a group selected from C$_{1-6}$alkyl, carbocyclyl and heterocyclyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxy C$_{1-6}$alkyl, C$_{1-6}$alkoxyC$_{1-6}$alkoxy, amino, C$_{1-6}$alkylamino and bis(C$_{1-6}$alkyl)amino; and R¹⁹ is hydrogen or a group selected from C$_{1-6}$alkyl, C$_{3-6}$cycloakyl, aryl, heteroaryl, arylC$_{1-6}$alkyl and heteroarylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

¹Y is CH and Y² is N.

R¹ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NMe$_2$, —NHCOCH$_3$, —CONH$_2$ and —CONHCH$_3$;

R² is phenyl or pyridyl substituted by —NHCONHR¹⁹ and optionally substituted by one or more substituent group independently selected from fluoro, methyl, methoxy, hydroxymethyl, cyanomethyl, —CONH$_2$, —CONHCH$_3$ and —CON(CH$_3$)$_2$;

R³ is methyl; and

R¹⁹ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxy C$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

¹Y is CH and Y² is N.

R¹ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$;

R² is phenyl or pyridyl substituted by —NHCONHR¹⁹ and optionally substituted by one or more substituent group independently selected from fluoro, methyl, methoxy, hydroxymethyl, cyanomethyl, —CONH$_2$, —CONHCH$_3$ and —CON(CH$_3$)$_2$;

R³ is methyl; and

R¹⁹ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, C$_{1-6}$alkyl, C$_{1-6}$alkoxy, haloC$_{1-6}$ alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

¹Y is CH and Y² is N.

R¹ is a group selected from methyl, ethyl, isopropyl, tert-butyl, cyclopropyl, cyclopentyl, cyclohexyl, —CH$_2$CH$_2$OH, —CH$_2$CH$_2$OMe, —CH$_2$CH$_2$NMe$_2$, —CH$_2$CH$_2$NC(O)CH$_3$, —CH$_2$CONH$_2$, phenyl, 3,5-difluorophenyl, 4-fluorophenyl, 2-chlorophenyl, 4-chlorophenyl, 2-trifluoromethylphenyl, 2-methoxyphenyl, 2-methylphenyl, 4-acetamidophenyl, 4-aminophenyl, pyridin-4-yl, pyridin-2-yl, oxetan-3-yl, 2-oxopyrrolidin-3-yl, 1-methylimidazol-5-ylmethyl, 1-methylpyrrolidin-3-yl, thiazol-2-yl, 4-methylthiazol-2-yl, and 3-methyl-1,3,4-thiadiazol-2-yl;

R² is

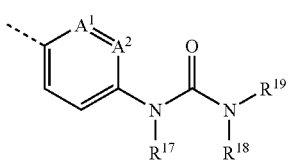

wherein $A^1$ and $A^2$ are selected from CH or N provided that at least one of $A^1$ or $A^2$ is CH;

$R^{17}$ is hydrogen;

$R^{18}$ is hydrogen;

$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyridin-2-yl, pyrimidin-2-yl, and 1H-pyrazol-3-yl;

and, $R^3$ is methyl.

In a further particular class of compound of formula (I), or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N.

$R^1$ is a group selected from methyl, isopropyl, cyclopropyl, cyclohexyl, —CH$_2$CH$_2$OH, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrrolidin-3-yl, thiazol-2-yl, 4-methylthiazol-2-yl, and 3-methyl-1,3,4-thiadiazol-2-yl;

$R^2$ is

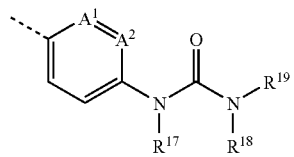

wherein $A^1$ and $A^2$ are selected from CH or N provided that at least one of $A^1$ or $A^2$ is CH;

$R^{17}$ is hydrogen;

$R^{18}$ is hydrogen;

$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyridin-2-yl, pyrimidin-2-yl, and 1H-pyrazol-3-yl;

and, $R^3$ is methyl.

In a further particular class of compound of formula (I), or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N.

$R^1$ is methyl or cyclopropyl;

$R^2$ is

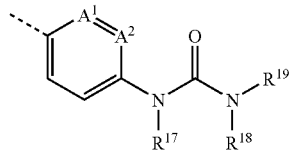

wherein $A^1$ and $A^2$ are selected from CH or N provided that at least one of $A^1$ or $A^2$ is CH;

$R^{17}$ is hydrogen;

$R^{18}$ is hydrogen;

$R^{19}$ is methyl, ethyl, propyl, cyclopropyl, cyclobutyl, —CH$_2$CH$_2$OH, —CH$_2$CH$_2$NMe$_2$, —C(Me)$_2$CH$_2$OH and 1H-pyrazol-3-yl;

and, $R^3$ is methyl.

In a further particular class of compound of formula (I), or a pharmaceutically acceptable salt thereof;

m is 1;

X is a —S(O)$_2$C(CH$_3$)$_2$— linker group;

$^1$Y is CH and Y$^2$ is N.

$R^1$ is ethyl, ethyl, isopropyl, tert-butyl, 4-fluorophenyl, pyridin-4-yl or cyclopropyl;

$R^2$ is

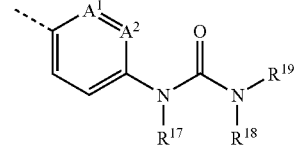

wherein $A^1$ and $A^2$ are selected from CH or N provided that at least one of $A^1$ or $A^2$ is CH;

$R^{17}$ is hydrogen;

$R^{18}$ is hydrogen;

$R^{19}$ is methyl, ethyl, propyl, cyclopropyl, cyclobutyl, —CH$_2$CH$_2$OH, —CH$_2$CH$_2$NMe$_2$, —C(Me)$_2$CH$_2$OH and 1H-pyrazol-3-yl;

and, $R^3$ is methyl.

In one aspect of the invention there is provided a subset of compounds of formula (I) wherein the compound of formula (I) is a compound of formula (Ia) or (Ib)

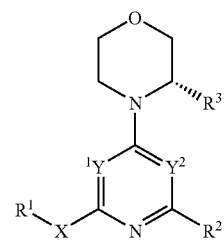

(Ia)

-continued

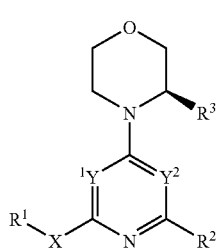

(Ib)

or a pharmaceutically acceptable salt thereof;

$^1Y$ and $Y^2$ are independently N or $CR^8$ provided that one of $^1Y$ and $Y^2$ is N and the other is $CR^8$;

X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$NR^4C(O)$—, —$S(O)_2NR^4$— and —$NR^4S(O)_2$—;

$R^1$ is a group selected from $C_{1-6}$alkyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —$OR^9$, —$COR^9$, —$CONR^9R^{10}$, —$NR^9R^{10}$ and —$NR^9COR^{10}$;

or X—$R^1$ is —$C(CH_3)_2OH$ or —$CH_2OH$;

$R^2$ is selected from aryl and heteroaryl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

$R^3$ is methyl;

$R^4$ and $R^5$ are independently hydrogen or $C_{1-6}$alkyl;

or, when X is —$NR^4CR^6R^7$—, —$NR^4C(O)NR^5CR^6R^7$—, —$NR^4C(O)$— or —$NR^4S(O)_2$—, $R^1$ and $R^4$ together with the atom or atoms to which they are attached form a 4-, 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy $C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$, $R^{17}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl $C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino $C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl ($C_{1-6}$alkyl)amino, carbamoyl, $C_{1-6}$alkylcarbamoyl and bis ($C_{1-6}$alkyl)carbamoyl.

In another aspect of the invention there is provided a subset of compounds of formula (I) wherein the compound of formula (I) is a compound of formula (Ia) or (Ib)

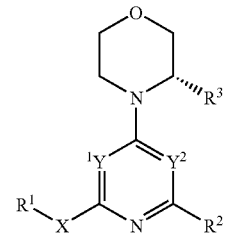

(Ia)

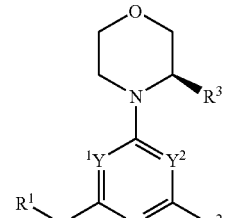

(Ib)

or a pharmaceutically acceptable salt thereof;

$^1Y$ and $Y^2$ are independently N or $CR^8$ provided that one of $^1Y$ and $Y^2$ is N and the other is $CR^8$;

X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$NR^4C(O)$—, —$S(O)_2NR^4$— and —$NR^4S(O)_2$—;

R¹ is a group selected from $C_{1-6}$alkyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, R⁹, —OR⁹, —COR⁹, —CONR⁹R¹⁰, —NR⁹R¹⁰ and —NR⁹COR¹⁰;

or X—R¹ is —C(CH₃)₂OH or —CH₂OH;

R² is selected from aryl and heteroaryl which group is substituted by —NR¹⁷CONR¹⁸R¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹²;

R³ is methyl;

R⁴ and R⁵ are independently hydrogen or $C_{1-6}$alkyl;

or, when X is —NR⁴CR⁶R⁷—, —NR⁴C(O)NR⁵CR⁶R⁷—, —NR⁴C(O)— or —NR⁴S(O)₂—, R¹ and R⁴ together with the atom or atoms to which they are attached form a 4-, 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

R⁶ and R⁷ are independently selected from hydrogen, halo, cyano, nitro and $C_{1-6}$alkyl;

R⁸ is selected from hydrogen, halo, cyano and $C_{1-6}$alkyl;

R⁹ and R¹⁰ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

R¹¹, R¹², R¹⁷ and R¹⁸ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and R¹⁹ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or R¹⁸ and R¹⁹ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention there is provided a subset of compounds of formula (I) wherein the compound of formula (I) is a compound of formula (Ia) or (Ib)

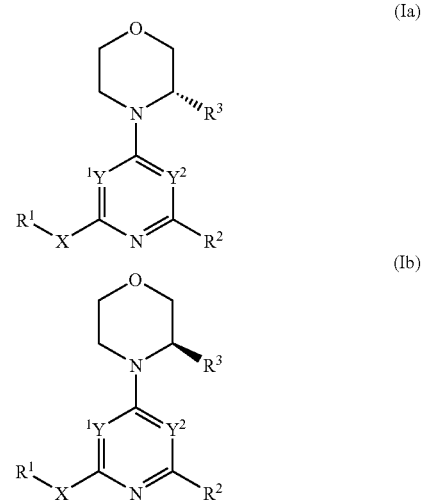

or a pharmaceutically acceptable salt thereof;

¹Y and Y² are independently N or CR⁸ provided that one of ¹Y and Y² is N and the other is CR⁸;

X is a linker group selected from —NR⁴—CH₂—, —OCH₂—, —OCH(CH₃)—, —OC(CH₃)₂—, —SCH₂—, —SCH(CH₃)—, —SC(CH₃)₂—, —S(O)CH₂—, —S(O)CH(CH₃)—, —S(O)C(CH₃)₂—, —S(O)₂CH₂—, —S(O)₂CH(CH₃)—, —S(O)₂C(CH₃)₂—, —C(O)NR⁴— and —NR⁴C(O)—;

R¹ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, R⁹, —OR⁹, —COR⁹, —CONR⁹R¹⁰, —NR⁹R¹⁰ and —NR⁹COR¹⁰;

or X—R¹ is —C(CH₃)₂OH or —CH₂OH;

R² is selected from 5 or 6 membered aryl and heteroaryl which group is substituted by —NHCONR¹⁸R¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹²;

R³ is methyl;

$R^4$ is hydrogen or $C_{1-6}$alkyl;

or, when X is —$NR^4$—$CH_2$— or —$NR^4C(O)$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy $C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl $C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (I), the compound of formula (I) is a compound of formula (Ia) or (Ib),

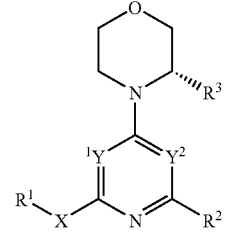

(Ia)

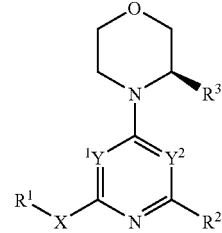

(Ib)

or a pharmaceutically acceptable salt thereof;

$Y^1$ is CH and $Y^2$ is N;

X is a linker group selected from —$S(O)_2CH_2$—, —$S(O)_2CH(CH_3)$— and —$S(O)_2C(CH_3)_2$—;

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NMe_2$, —$NHCOCH_3$, —$CONH_2$ and —$CONHCH_3$;

or —$XR^1$ is —$C(CH_3)_2OH$ or —$CH_2OH$;

$R^2$ is selected from phenyl, pyrrolyl, imidazolyl, pyrazolyl, furanyl, thienyl, pyridinyl, pyrimidinyl, pyridazinyl and thiazolyl which group is substituted by —$NHCONHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

$R^3$ is methyl;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy $C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl $C_{1-6}$alkyl which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (I), the compound of formula (I) is a compound of formula (Ia) or (Ib),

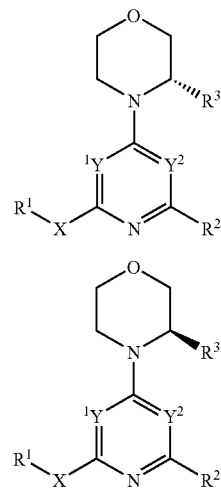

or a pharmaceutically acceptable salt thereof;
$Y^1$ is CH and $Y^2$ is N;
X is a linker group selected from —S(O)$_2$CH$_2$—, —S(O)$_2$CH(CH$_3$)— and —S(O)$_2$C(CH$_3$)$_2$—;
$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$; or —XR$^1$ is —C(CH$_3$)$_2$OH or —CH$_2$OH;
$R^2$ is selected from phenyl, pyrrolyl, imidazolyl, pyrazolyl, furanyl, thienyl, pyridinyl, pyrimidinyl, pyridazinyl and thiazolyl which group is substituted by —NHCONHR$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$;
$R^3$ is methyl;
$R^{11}$, $R^{12}$ and $R^{18}$ are independently hydrogen or a group selected from C$_{1-6}$alkyl, carbocyclyl and heterocyclyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino and bis(C$_{1-6}$alkyl)amino; and
$R^{19}$ is hydrogen or a group selected from C$_{1-6}$alkyl, C$_{3-6}$cycloakyl, aryl, heteroaryl, arylC$_{1-6}$alkyl and heteroaryl C$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), the compound of formula (I) is a compound of formula (Ia) or (Ib)

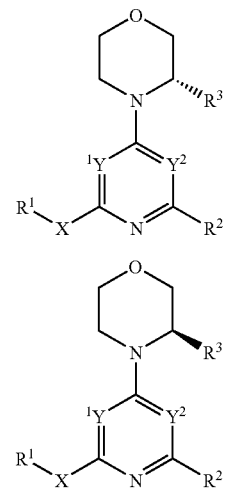

or a pharmaceutically acceptable salt thereof;
X is a linker group selected from —S(O)$_2$CH$_2$—, —S(O)$_2$CH(CH$_3$)— and —S(O)$_2$C(CH$_3$)$_2$—;
$Y^1$ is CH and $Y^2$ is N.
$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NMe$_2$, —NHCOCH$_3$, —CONH$_2$ and —CONHCH$_3$;
$R^2$ is phenyl or pyridyl substituted by —NHCONHR$^{19}$ and optionally substituted by one or more substituent group independently selected from fluoro, methyl, methoxy, hydroxymethyl, cyanomethyl, —CONH$_2$, —CONHCH$_3$ and —CON(CH$_3$)$_2$;
$R^3$ is methyl; and
$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxy C$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), the compound of formula (I) is a compound of formula (Ia) or (Ib)

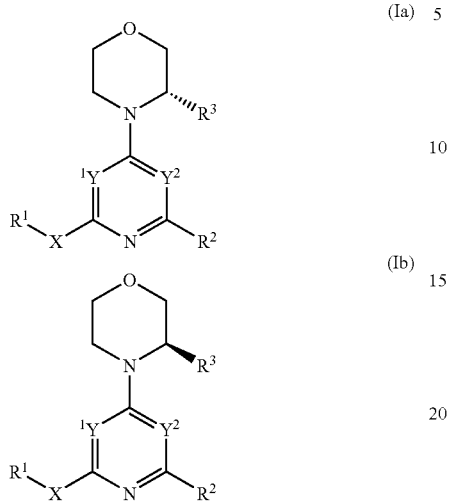

or a pharmaceutically acceptable salt thereof;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N.

R$^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$;

R$^2$ is phenyl or pyridyl substituted by —NHCONHR$^{19}$ and optionally substituted by one or more substituent group independently selected from fluoro, methyl, methoxy, hydroxymethyl, cyanomethyl, —CONH$_2$, —CONHCH$_3$ and —CON(CH$_3$)$_2$;

R$^3$ is methyl; and

R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (I), the compound of formula (I) is a compound of formula (Ia) or (Ib)

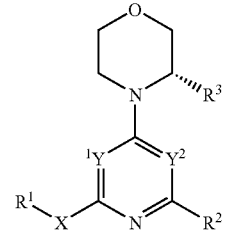

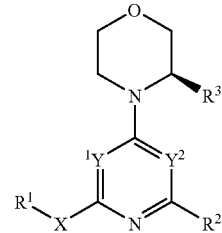

or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N.

R$^1$ is a group selected from methyl, ethyl, isopropyl, tert-butyl, cyclopropyl, cyclopentyl, cyclohexyl, —CH$_2$CH$_2$OH, —CH$_2$CH$_2$OMe, —CH$_2$CH$_2$NMe$_2$, —CH$_2$CH$_2$NC(O)CH$_3$, —CH$_2$CONH$_2$, phenyl, 3,5-difluorophenyl, 4-fluorophenyl, 2-chlorophenyl, 4-chlorophenyl, 2-trifluoromethylphenyl, 2-methoxyphenyl, 2-methylphenyl, 4-acetamidophenyl, 4-aminophenyl, pyridin-4-yl, pyridin-2-yl, oxetan-3-yl, 2-oxopyrrolidin-3-yl, 1-methylimidazol-5-ylmethyl, 1-methylpyrrolidin-3-yl, thiazol-2-yl, 4-methylthiazol-2-yl, and 3-methyl-1,3,4-thiadiazol-2-yl;

R$^2$ is

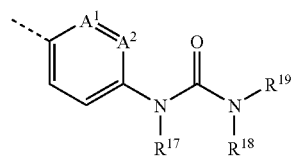

wherein A$^1$ and A$^2$ are selected from CH or N provided that at least one of A$^1$ or A$^2$ is CH;

R$^{17}$ is hydrogen;

R$^{18}$ is hydrogen; and

R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyridin-2-yl, pyrimidin-2-yl, and 1H-pyrazol-3-yl;

and, R$^3$ is methyl.

In a further particular class of compound of formula (I), the compound of formula (I) is a compound of formula (Ia) or (Ib)

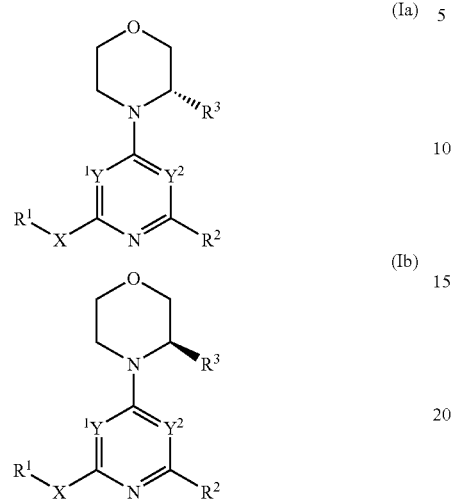

or a pharmaceutically acceptable salt thereof;
m is 1;
X is a linker group selected from —S(O)₂CH₂—, —S(O)₂CH(CH₃)— and —S(O)₂C(CH₃)₂—;
$^1$Y is CH and Y$^2$ is N.
R$^1$ is a group selected from methyl, isopropyl, cyclopropyl, cyclohexyl, —CH₂CH₂OH, —CH₂CH₂NC(O)CH₃, —CH₂CONH₂, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrrolidin-3-yl, thiazol-2-yl, 4-methylthiazol-2-yl, and 3-methyl-1,3,4-thiadiazol-2-yl;
R$^2$ is

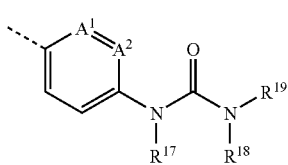

wherein A$^1$ and A$^2$ are selected from CH or N provided that at least one of A$^1$ or A$^2$ is CH;
R$^{17}$ is hydrogen;
R$^{18}$ is hydrogen; and
R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH₂(cyclopropyl), —CH₂CH₂NMe₂, —CH(CH₃)CH₂OH, —C(CH₃)₂CH₂OH, —CH₂CH₂OH, —CH₂CH₂CH₂OH, 4-methylphenyl, 4-chlorophenyl, 4-trifluoromethylphenyl, 4-fluorophenyl, 4-methoxyphenyl, 3,4-difluorophenyl, thien-2-yl, —CH₂(imidazol-2-yl), —CH₂(imidazol-3-yl), isoxazol-3-yl, 6-oxo-1H-pyridin-2-yl, 5-methylisoxazol-3-yl, 1-methylpyrazol-4-yl, —CH₂(1-methylpyrazol-4-yl), 6-methoxypyridin-3-yl, 5-fluoropyridin-2-yl, pyrimidin-2-yl, and 1H-pyrazol-3-yl;
and, R$^3$ is methyl.

In a further particular class of compound of formula (I), the compound of formula (I) is a compound of formula (Ia) or (Ib)

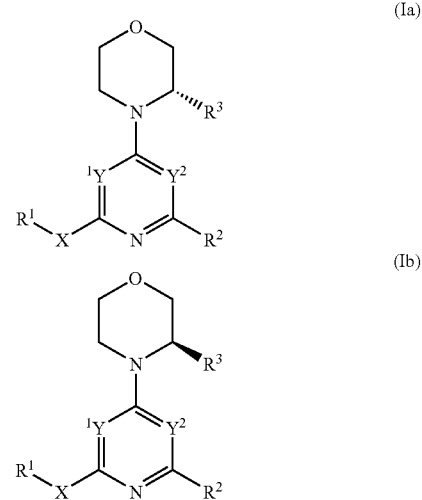

or a pharmaceutically acceptable salt thereof;
m is 1;
X is a linker group selected from —S(O)₂CH₂—, —S(O)₂CH(CH₃)— and —S(O)₂C(CH₃)₂—;
$^1$Y is CH and Y$^2$ is N.
R$^1$ is methyl or cyclopropyl;
R$^2$ is

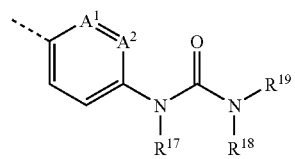

wherein A$^1$ and A$^2$ are selected from CH or N provided that at least one of A$^1$ or A$^2$ is CH;
R$^{17}$ is hydrogen;
R$^{18}$ is hydrogen; and
R$^{19}$ is hydrogen or a group selected from methyl, ethyl, propyl, cyclopropyl, cyclobutyl, —CH₂CH₂OH, —CH₂CH₂NMe₂, —C(Me)₂CH₂OH and 1H-pyrazol-3-yl;
and, R$^3$ is methyl.

In a further particular class of compound of formula (I), the compound of formula (I) is a compound of formula (Ia) or (Ib)

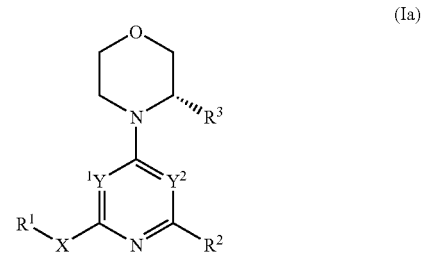

-continued

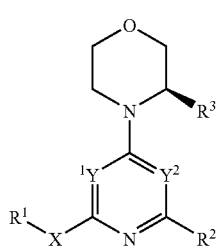
(Ib)

or a pharmaceutically acceptable salt thereof;
m is 1;
X is a —S(O)$_2$C(CH$_3$)$_2$— linker group;
$^1$Y is CH and Y$^2$ is N.
R$^1$ is methyl, ethyl, isopropyl, tert-butyl, 4-fluorophenyl, pyridin-4-yl or cyclopropyl;
R$^2$ is

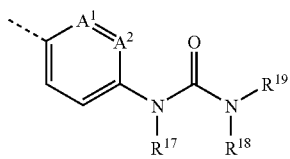

wherein A$^1$ and A$^2$ are selected from CH or N provided that at least one of A$^1$ or A$^2$ is CH;
R$^{17}$ is hydrogen;
R$^{18}$ is hydrogen; and
R$^{19}$ is hydrogen or a group selected from methyl, ethyl, propyl, cyclopropyl, cyclobutyl, —CH$_2$CH$_2$OH, —CH$_2$CH$_2$NMe$_2$, —C(Me)$_2$CH$_2$OH and 1H-pyrazol-3-yl;
and, R$^3$ is methyl.

Another aspect of the invention provides a compound, or a combination of compounds, selected from any one of the Examples or a pharmaceutically acceptable salt thereof.

The invention also provides processes for the preparation of a compound of formula (I) or a pharmaceutically acceptable salt thereof.

A compound of formula (I), wherein X=—S(O)$_2$CR$^6$R$^7$—, may be prepared by oxidising a compound of the formula (I), wherein X=SCR$^6$R$^7$—, for example by using Oxone® at room temperature in a mixed solvent system of water and ethanol

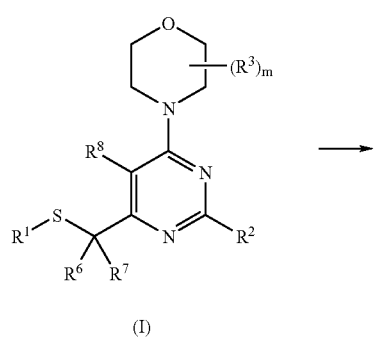
(I)

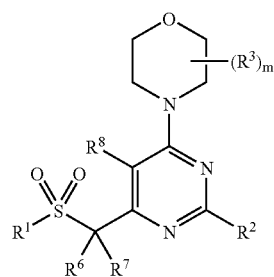
(I)

A compound of formula (I), wherein R$^1$X=R$^1$OCR$^6$R$^7$—, may be prepared by the reaction of a compound of formula (I), wherein R$^1$X=HOCR$^6$R$^7$—, with a compound of formula (II), wherein L$^1$ is a leaving group (such as halo, tosyl, mesyl etc.) optionally in the presence of a suitable base such as triethylamine and a solvent such as tetrahydrofuran or N,N-dimethylformamide.

$$R^1—L^1$$
(II)

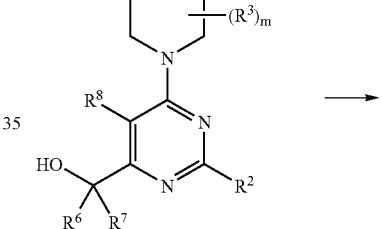
(I)

(I)

A compound of formula (I), wherein R$^1$X=R$^1$R$^4$NCR$^6$R$^7$—, may be prepared by the reaction of a compound of formula (I), wherein R$^1$X=HR$^4$NCR$^6$R$^7$—, with a compound of formula (II), wherein L$^1$ is a leaving group (such as halo, tosyl, mesyl etc.) optionally in the presence of a suitable base such as triethylamine and a solvent such as tetrahydrofuran or N,N-dimethylformamide; or by the reaction of a compound of formula (I), wherein R$^1$X=HR$^4$NCR$^6$R$^7$—, with a compound of formula (III) in the presence of a suitable reducing agent such as NaCNBH$_3$.

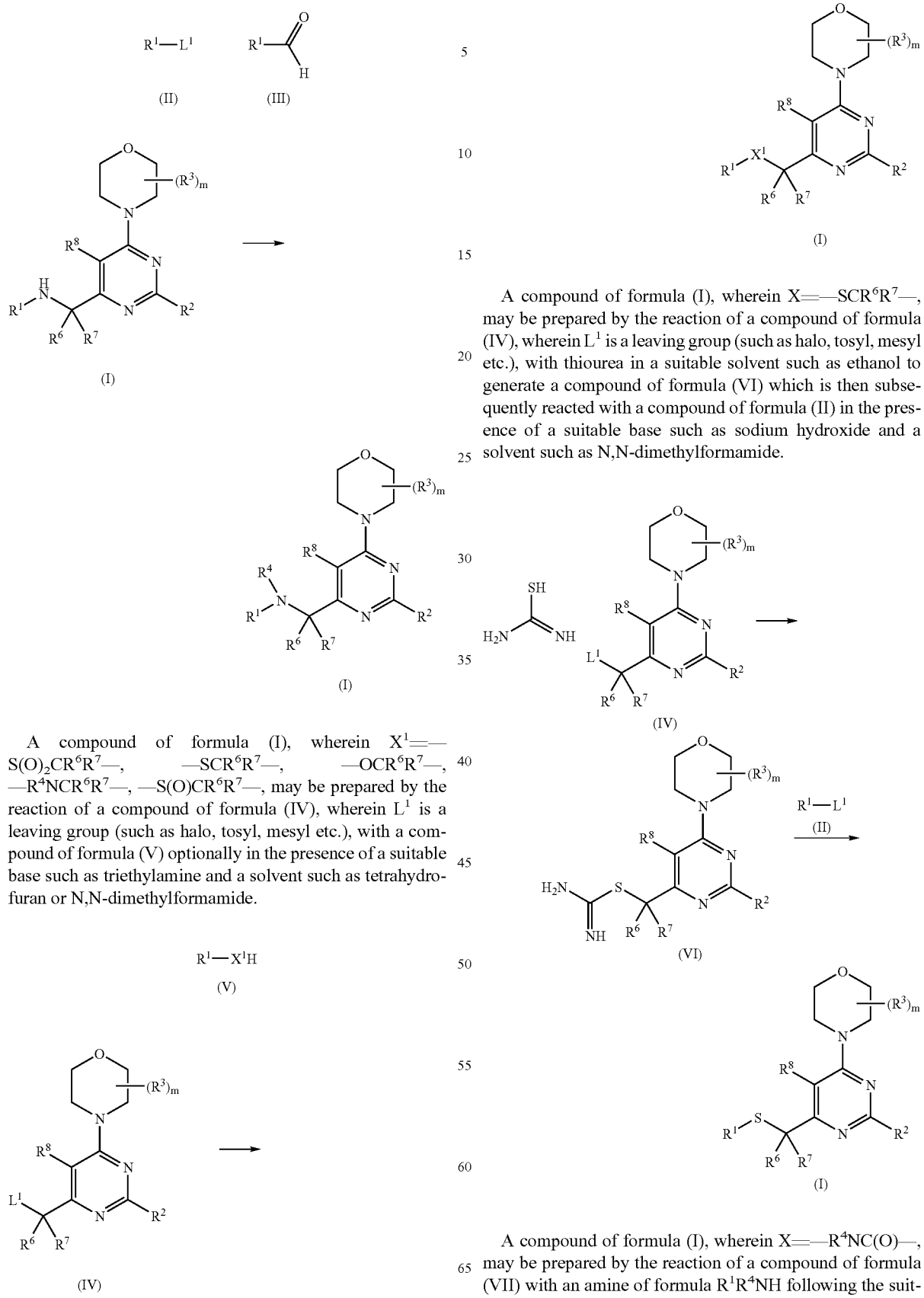

A compound of formula (I), wherein $X^1$=—S(O)$_2$CR$^6$R$^7$—, —SCR$^6$R$^7$—, —OCR$^6$R$^7$—, —R$^4$NCR$^6$R$^7$—, —S(O)CR$^6$R$^7$—, may be prepared by the reaction of a compound of formula (IV), wherein L$^1$ is a leaving group (such as halo, tosyl, mesyl etc.), with a compound of formula (V) optionally in the presence of a suitable base such as triethylamine and a solvent such as tetrahydrofuran or N,N-dimethylformamide.

A compound of formula (I), wherein X=—SCR$^6$R$^7$—, may be prepared by the reaction of a compound of formula (IV), wherein L$^1$ is a leaving group (such as halo, tosyl, mesyl etc.), with thiourea in a suitable solvent such as ethanol to generate a compound of formula (VI) which is then subsequently reacted with a compound of formula (II) in the presence of a suitable base such as sodium hydroxide and a solvent such as N,N-dimethylformamide.

A compound of formula (I), wherein X=—R$^4$NC(O)—, may be prepared by the reaction of a compound of formula (VII) with an amine of formula R$^1$R$^4$NH following the suitable activation of the carboxylic acid by methods known in the literature such as the use of a coupling agent such as HATU or the conversion to an acyl chloride.

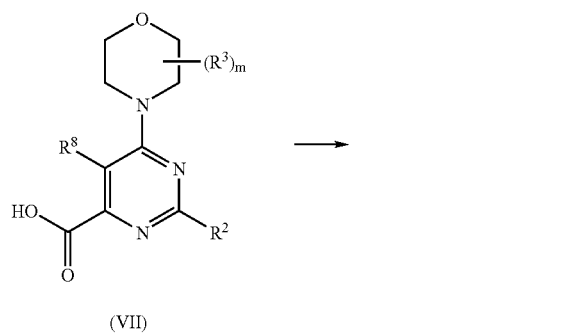

(VII)

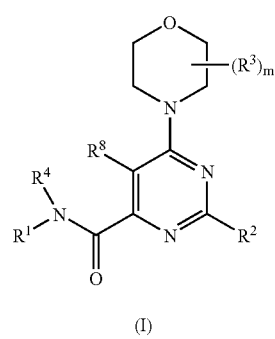

(I)

A compound of formula (I), wherein X= —S(O)$_2$CR$^6$R$^7$—, may be prepared by the sequential reaction of a compound of formula (I), wherein X= —S(O)$_2$CH$_2$—, with a compound of formula (VIII) followed by reaction with a compound of formula (IX), wherein L$^1$ is a leaving group (such as halo, tosyl, mesyl etc.), in the presence of a suitable base such as sodium hydride or potassium tert-butoxide in a suitable solvent such as tetrahydrofuran or N,N-dimethylformamide.

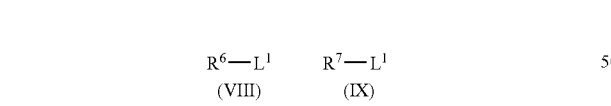

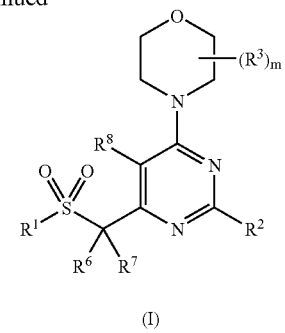

(I)

A compound of formula (I), wherein R$^1$X=HOCR$^6$R$^7$—, may be prepared by the reaction of a compound of formula (X), with suitable organometallic reagents of formula (XI) and formula (XII) such as the grignard reagent in a suitable solvent. Where R$^6$ and R$^7$ are different then it may be possible to use techniques known in the literature such the conversion of a compound of formula (X) to the Weinreb amide and reaction with an organometallic reagent of formula (XI) and then reaction with an organometallic reagent of formula (XII) in a subsequent step.

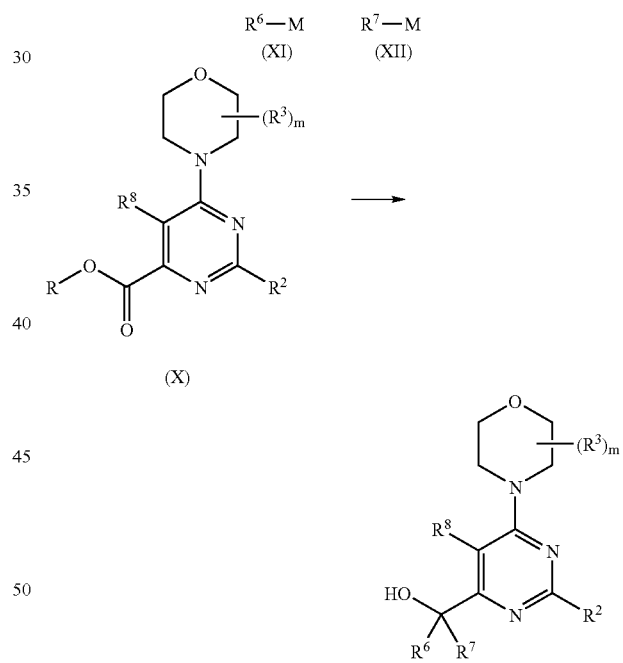

A compound of formula (I) may be prepared from a compound of formula (XIII), wherein L$^2$ is a leaving group (such as halo, tosyl, mesyl, —SMe, —S(O)$_2$Me etc.), with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (I) may be prepared from a compound of formula (XIII), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

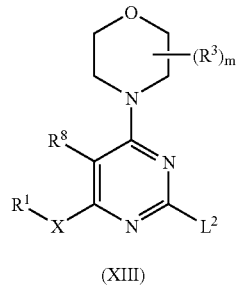

(XIII)

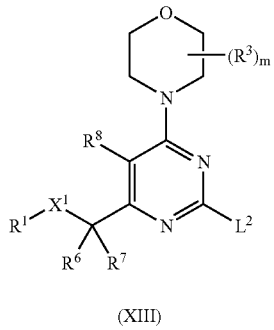

(XIII)

A compound of formula (XIII), wherein X=—SCR$^6$R$^7$—, may be prepared by the reaction of a compound of formula (XIV), wherein L$^1$ is a leaving group (such as halo, tosyl, mesyl etc.), with thiourea in a suitable solvent such as ethanol to generate a compound of formula (XV) which is then subsequently reacted with a compound of formula (II) in the presence of a suitable base such as sodium hydroxide and a solvent such as N,N-dimethylformamide.

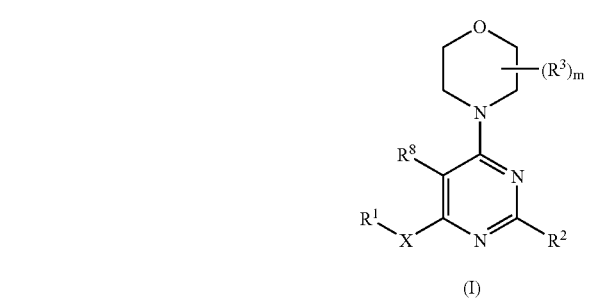

(I)

It will be appreciated that a compound of formula (XIII) may be transformed into another compound of formula (XIII) by techniques such as oxidation, alkylation, reductive amination etc., either listed above or otherwise known in the literature.

A compound of formula (XIII), wherein X$^1$=—S(O)$_2$CR$^6$R$^7$—, —SCR$^6$R$^7$—, —OCR$^6$R$^7$—, —R$^4$NCR$^6$R$^7$—, —S(O)CR$^6$R$^7$—, may be prepared by the reaction of a compound of formula (XIV), wherein L$^1$ is a leaving group (such as halo, tosyl, mesyl etc.), with a compound of formula (V) optionally in the presence of a suitable base such as triethylamine and a solvent such as tetrahydrofuran or N,N-dimethylformamide.

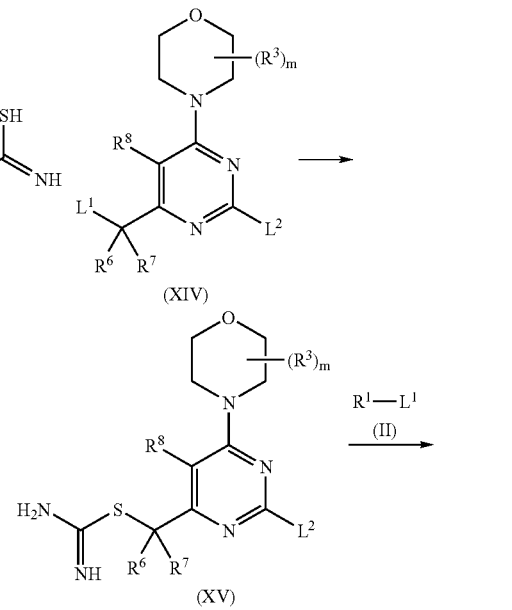

R$^1$—X$^1$H (V)

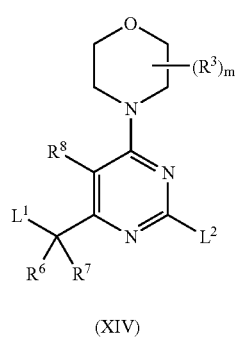

(XIV)

A compound of formula (XIII), wherein X=—R$^4$NC (O)—, may be prepared by the reaction of a compound of formula (XVI) with an amine of formula R$^1$R$^4$NH following the suitable activation of the carboxylic acid by methods known in the literature such as the use of a coupling agent such as HATU or the conversion to an acyl chloride.

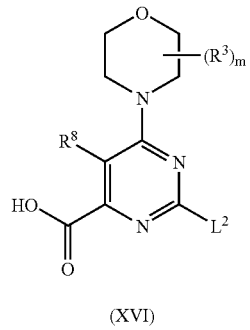

(XVI)

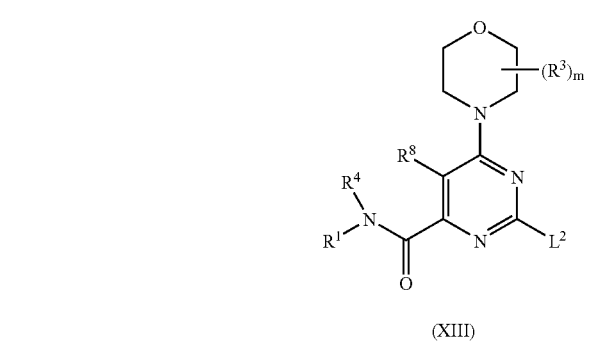

(XIII)

A compound of formula (XIII), wherein X=—S(O)$_2$CR$^6$R$^7$—, may be prepared by the sequential reaction of a compound of formula (XIII), wherein X=—S(O)$_2$CH$_2$—, with a compound of formula (VIII) followed by reaction with a compound of formula (IX), wherein L$^1$ is a leaving group (such as halo, tosyl, mesyl etc.), in the presence of a suitable base such as sodium hydride or potassium tert-butoxide in a suitable solvent such as tetrahydrofuran or N,N-dimethylformamide.

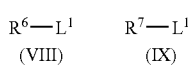

(VIII)  (IX)

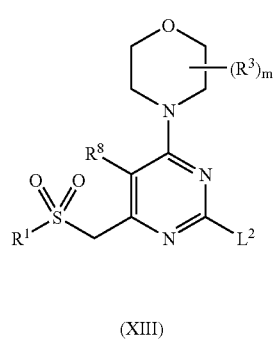

(XIII)

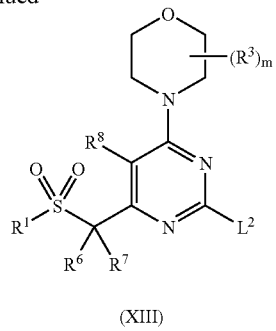

(XIII)

A compound of formula (XIII), wherein R$^1$X=HOCR$^6$R$^7$—, may be prepared by the reaction of a compound of formula (XVII), with suitable organometallic reagents of formula (XI) and formula (XII) such as the grignard reagent in a suitable solvent. Where R$^6$ and R$^7$ are different then it may be possible to use techniques known in the literature such the conversion of a compound of formula (XVII) to the Weinreb amide and reaction with an organometallic reagent of formula (XI) and then reaction with an organometallic reagent of formula (XII) in a subsequent step.

R$^6$—M  R$^7$—M
(XI)  (XII)

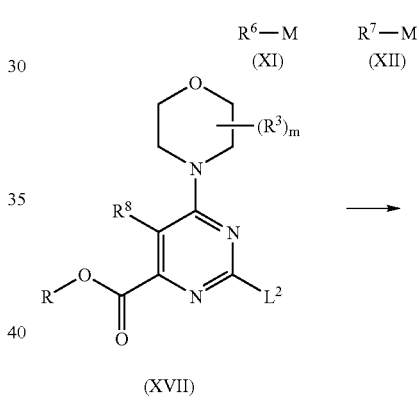

(XVII)

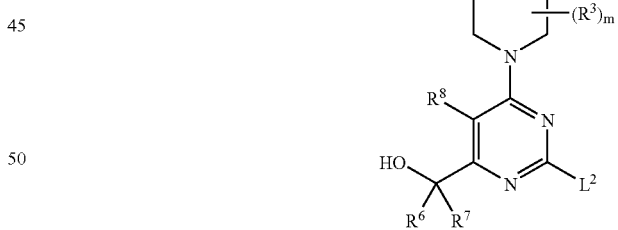

(XIII)

A compound of formula (IV) may be prepared from a compound of formula (XIV), wherein L$^2$ is a leaving group (such as halo, tosyl, mesyl, —SMe, —S(O)$_2$Me etc.) and L$^1$ is a leaving group (such as halo, tosyl, mesyl etc.), with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (IV) may be prepared from a compound of formula (XIV), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

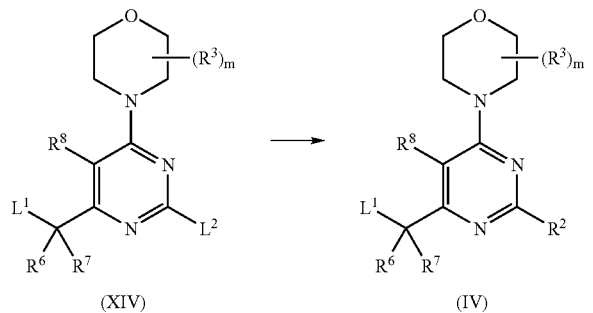

A compound of formula (X) may be prepared from a compound of formula (XVII), wherein L$^2$ is a leaving group (such as halo, tosyl, mesyl, —SMe, —S(O)$_2$Me etc.) and R is a hydrogen or C$_{1-4}$ alkyl group, with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (X) may be prepared from a compound of formula (XVII), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

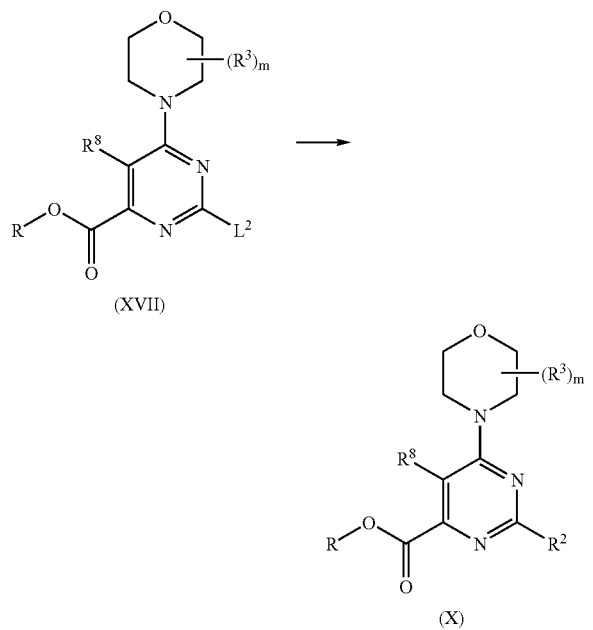

A compound of formula (XVIII) may be prepared from a compound of formula (XIX), wherein L$^2$ is a leaving group (such as halo, tosyl, mesyl, —SMe, —S(O)$_2$Me etc.), with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (XVIII) may be prepared from a compound of formula (XIX), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

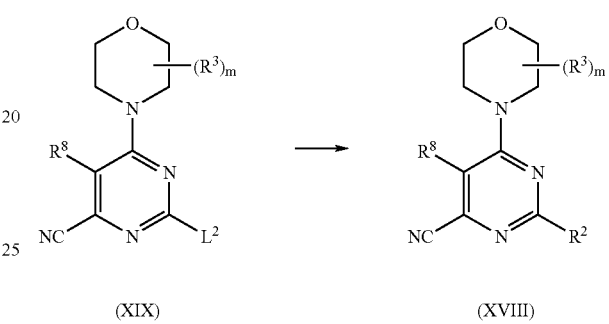

A compound of formula (XX) may be prepared from a compound of formula (XXI), wherein L$^2$ is a leaving group (such as halo, tosyl, mesyl, —SMe, —S(O)$_2$Me etc.), with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (XX) may be prepared from a compound of formula (XXI), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

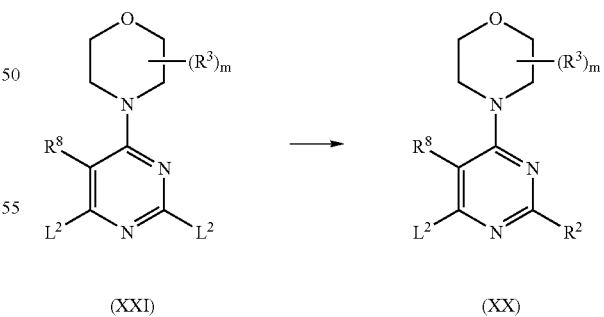

A compound of formula (I), wherein L$^1$ is a leaving group (such as halo, tosyl, mesyl etc.), may be prepared by the reaction of a compound of formula (XXII) with a compound of formula (XXIII) optionally in the presence of a suitable base such as triethylamine in a suitable solvent such as N,N-dimethylformamide.

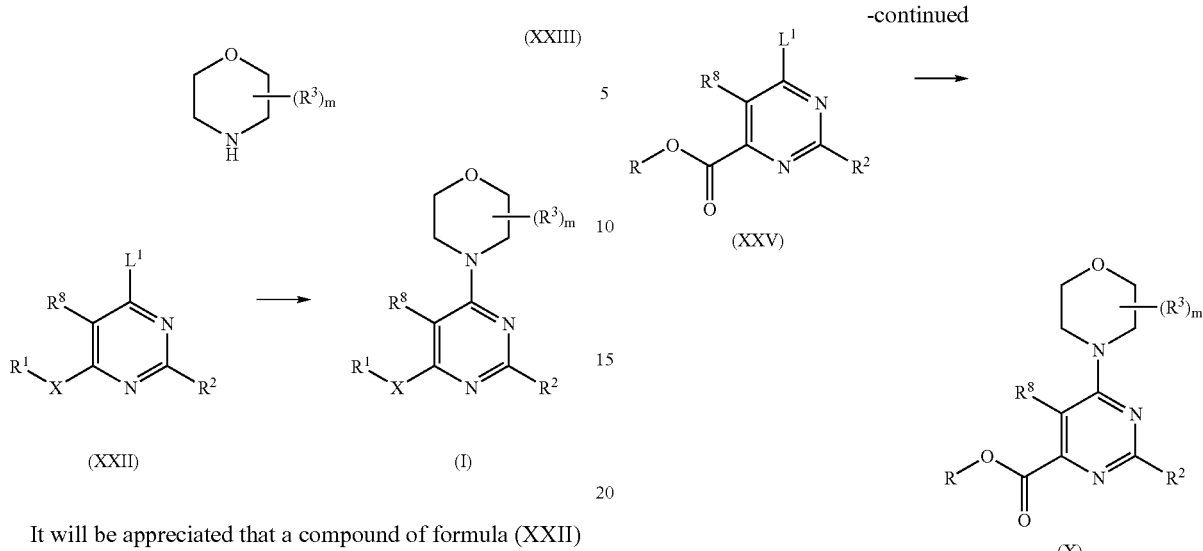

It will be appreciated that a compound of formula (XXII) may be transformed into another compound of formula (XXII) by techniques such as oxidation, alkylation, reductive amination etc., either listed above or otherwise known in the literature.

A compound of formula (IV), wherein $L^1$ is a leaving group (such as halo, tosyl, mesyl etc.), may be prepared by the reaction of a compound of formula (XXIV) with a compound of formula (XXIII) optionally in the presence of a suitable base such as triethylamine in a suitable solvent such as N,N-dimethylformamide.

A compound of formula (XVIII), wherein $L^1$ is a leaving group (such as halo, tosyl, mesyl etc.), may be prepared by the reaction of a compound of formula (XXVI) with a compound of formula (XXIII) optionally in the presence of a suitable base such as triethylamine in a suitable solvent such as N,N-dimethylformamide.

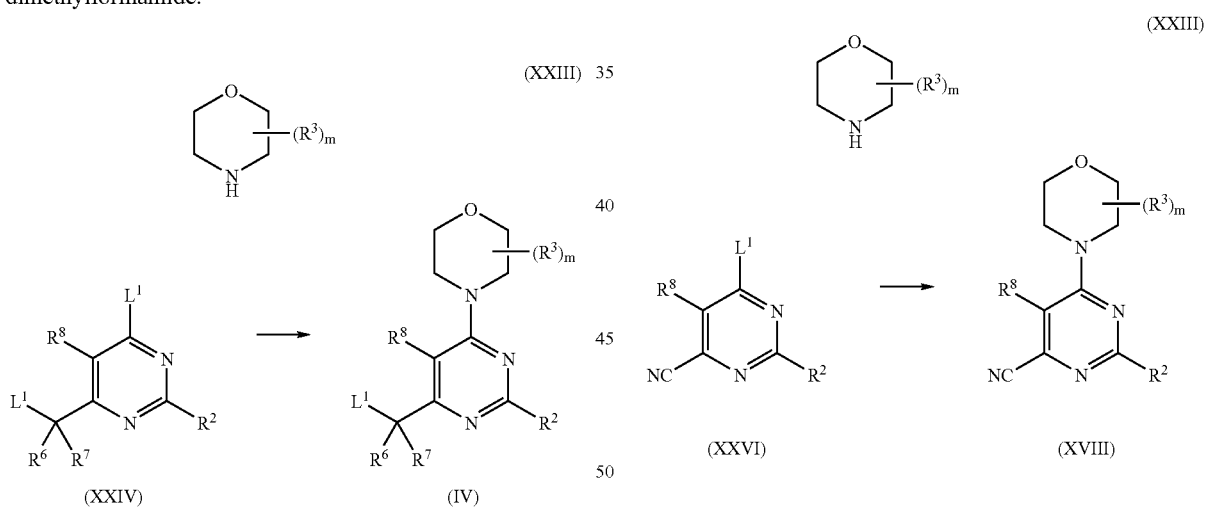

A compound of formula (X), wherein $L^1$ is a leaving group (such as halo, tosyl, mesyl etc.) and R is a hydrogen or a $C_{1-4}$ alkyl group, may be prepared by the reaction of a compound of formula (XXV) with a compound of formula (XXIII) optionally in the presence of a suitable base such as triethylamine in a suitable solvent such as N,N-dimethylformamide.

A compound of formula (XX), wherein $L^1$ is a leaving group (such as halo, tosyl, mesyl etc.) and $L^2$ is a leaving group (such as halo, tosyl, mesyl, —SMe, —S(O)$_2$Me etc.), may be prepared by the reaction of a compound of formula (XXVII) with a compound of formula (XXIII) optionally in the presence of a suitable base such as triethylamine in a suitable solvent such as N,N-dimethylformamide.

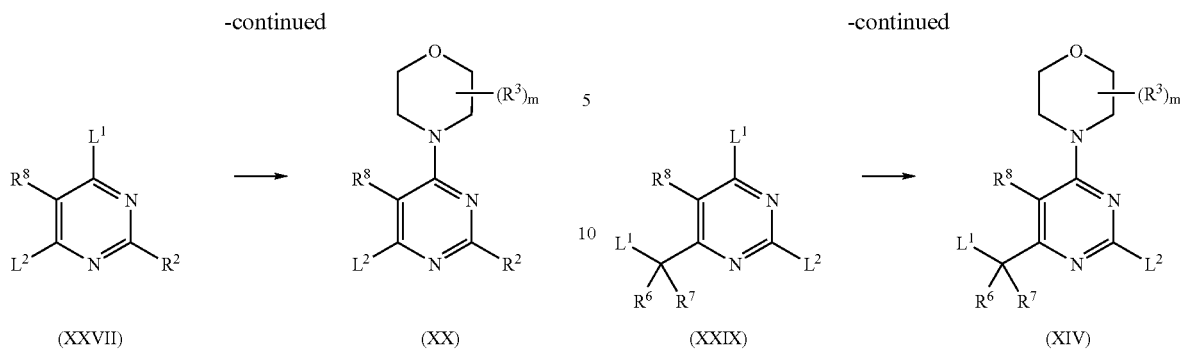

A compound of formula (XIII), wherein L¹ is a leaving group (such as halo, tosyl, mesyl etc.) and L² is a leaving group (such as halo, tosyl, mesyl, —SMe, —S(O)₂Me etc.), may be prepared by the reaction of a compound of formula (XXVIII) with a compound of formula (XXIII) optionally in the presence of a suitable base such as triethylamine in a suitable solvent such as N,N-dimethylformamide.

A compound of formula (XVII), wherein L¹ is a leaving group (such as halo, tosyl, mesyl etc.) and L² is a leaving group (such as halo, tosyl, mesyl, —SMe, —S(O)₂Me etc.) and R is a hydrogen or a $C_{1-4}$ alkyl group, may be prepared by the reaction of a compound of formula (XXX) with a compound of formula (XXIII) optionally in the presence of a suitable base such as triethylamine in a suitable solvent such as N,N-dimethylformamide.

It will be appreciated that a compound of formula (XIII) may be transformed into another compound of formula (XIII) by techniques such as oxidation, alkylation, reductive amination etc., either listed above or otherwise known in the literature.

A compound of formula (XIV), wherein L¹ is a leaving group (such as halo, tosyl, mesyl etc.) and L² is a leaving group (such as halo, tosyl, mesyl, —SMe, —S(O)₂Me etc.), may be prepared by the reaction of a compound of formula (XXIX) with a compound of formula (XXIII) optionally in the presence of a suitable base such as triethylamine in a suitable solvent such as N,N-dimethylformamide.

A compound of formula (XIX), wherein L¹ is a leaving group (such as halo, tosyl, mesyl etc.) and L² is a leaving group (such as halo, tosyl, mesyl, —SMe, —S(O)₂Me etc.), may be prepared by the reaction of a compound of formula (XXXI) with a compound of formula (XXIII) optionally in the presence of a suitable base such as triethylamine in a suitable solvent such as N,N-dimethylformamide.

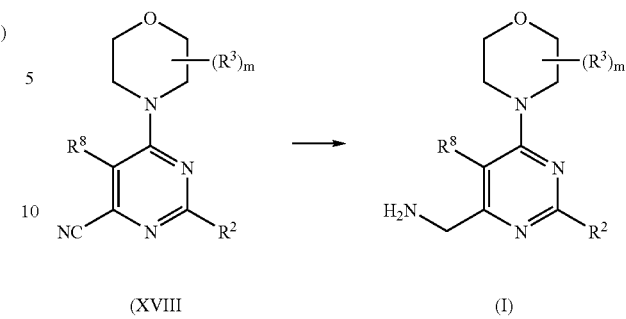

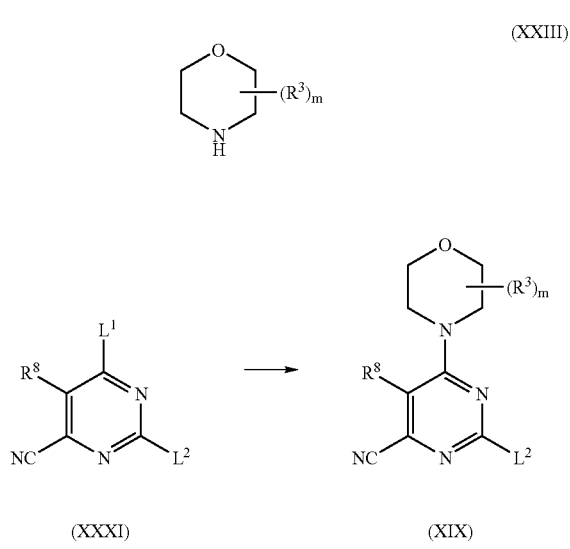

A compound of formula (XXI), wherein $L^1$ is a leaving group (such as halo, tosyl, mesyl etc.) and $L^2$ is a leaving group (such as halo, tosyl, mesyl, —SMe, —S(O)$_2$Me etc.), may be prepared by the reaction of a compound of formula (XXXII) with a compound of formula (XXIII) optionally in the presence of a suitable base such as triethylamine in a suitable solvent such as N,N-dimethylformamide.

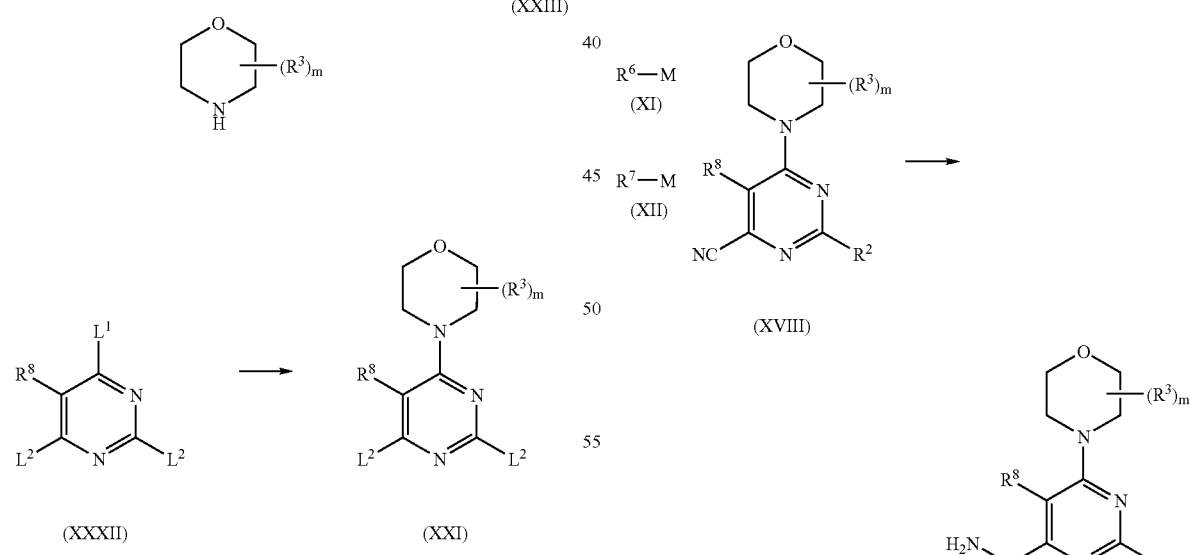

A compound of formula (I), wherein $R^1X$=H$_2$NCH$_2$—, may be prepared from a compound of formula (XVIII) by a reduction such as hydrogenation with hydrogen gas and a suitable catalyst such as Palladium on carbon in a suitable solvent such as ethanol.

A compound of formula (I), wherein $R^1X$=H$_2$NC(O)—, may be prepared from a compound of formula (XVIII) by hydrolysis with, for example, sodium hydroxide in a suitable solvent such as a water ethanol mix.

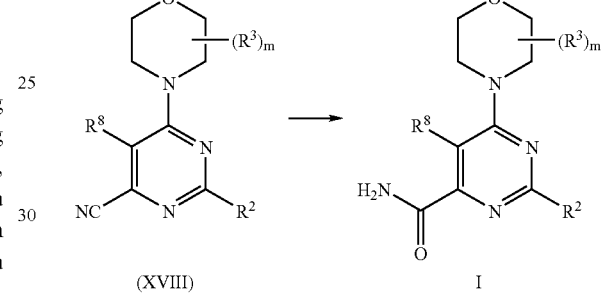

A compound of formula (I), wherein $R^1X$=H$_2$NCR$^6$R$^7$—, may be prepared from a compound of formula (XVIII) by reaction with organometallic reagents (XI) and (XII).

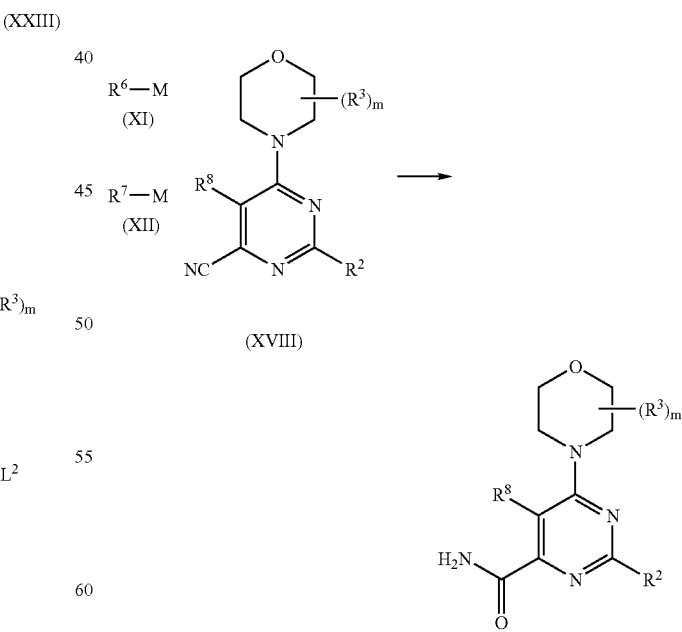

A compound of formula (XIII), wherein $R^1X$=H$_2$NCH$_2$—, may be prepared from a compound of formula (XIX) by a reduction such as hydrogenation with hydrogen gas and a suitable catalyst such as Palladium on carbon in a suitable solvent such as ethanol.

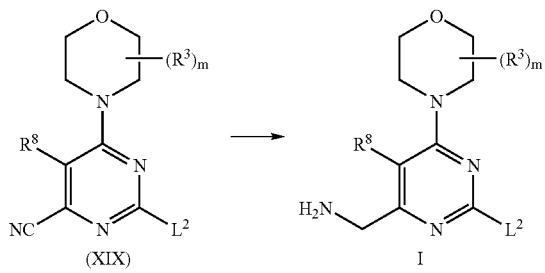

A compound of formula (XIII), wherein R¹X=H₂NC(O)—, may be prepared from a compound of formula (XIX) by hydrolysis with, for example, sodium hydroxide in a suitable solvent such as a water ethanol mix.

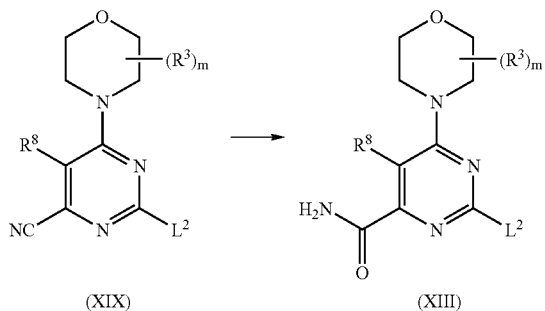

A compound of formula (XIII), wherein R¹X=H₂NCR⁶R⁷—, may be prepared from a compound of formula (XIX) by reaction with organometallic reagents (XI) and (XII).

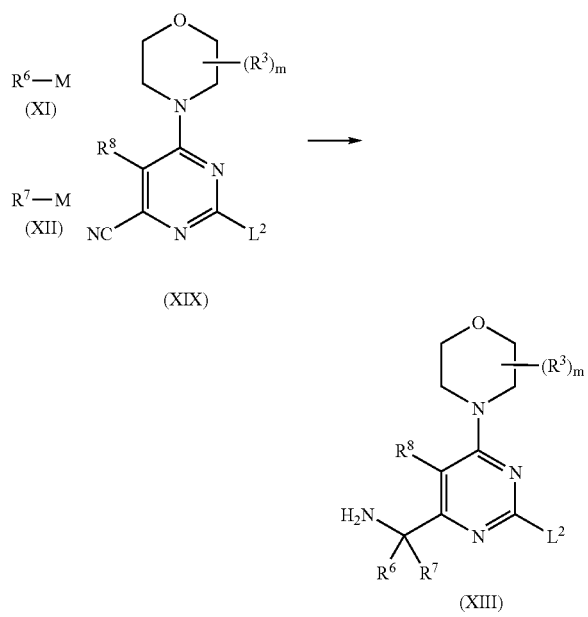

It will be appreciated that the R² group may be introduced at any stage initially as a carbocyclic or heterocyclic amine (optionally with the nitrogen protected, such protecting groups include but are not limited to nitro, tert-butoxy carbamate etc.) which can be transformed at a subsequent stage in the synthesis (after appropriate deprotection) to a urea by either direct reaction with an isocyanate (or otherwise activated group such as a phenoxy carbamate, etc.) or by activation of the amine (such as with phosgene or the formation of a phenoxy carbamate, etc.) and subsequent reaction with an appropriate amine, or other methods of forming a urea known in the literature.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of formula (I) my be converted into further compounds of formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel and these are provided as a further feature of the invention.

Biological Assays

The following assays can be used to measure the effects of the compounds of the present invention as mTOR kinase inhibitors, as PI3 kinase inhibitors, as inhibitors in vitro of the activation of PI3 kinase signalling pathways and as inhibitors in vitro of the proliferation of MDA-MB-468 human breast adenocarcinoma cells.

(a) In Vitro mTOR Kinase Assay

The assay used AlphaScreen technology (Gray et al., Analytical Biochemistry, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., Journal of Biochemistry, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulfate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one). A 30 µl mixture of recombinant purified mTOR enzyme, 1 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-$NH_2$; Bachem UK Ltd), ATP (20 µM) and a buffer solution [comprising Tris-HCl pH7.4 buffer (50 mM), EGTA (0.1 mM), bovine serum albumin (0.5 mg/mL), DTT (1.25 mM) and manganese chloride (10 mM)] was agitated at room temperature for 90 minutes.

Control wells that produced a maximum signal corresponding to maximum enzyme activity were created by using 5% DMSO instead of test compound. Control wells that produced a minimum signal corresponding to fully inhibited enzyme were created by adding EDTA (83 mM) instead of test compound. These assay solutions were incubated for 2 hours at room temperature.

Each reaction was stopped by the addition of 10 µl of a mixture of EDTA (50 mM), bovine serum albumin (BSA; 0.5 mg/mL) and Tris-HCl pH7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng; Perkin Elmer, Catalogue No. 6760002B and 6760137R respectively) were added and the assay plates were left for about 20 hours at room temperature in the dark. The resultant signals arising from laser light excitation at 680 nm were read using a Packard Envision instrument.

Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead: acceptor bead complex produces a signal that can be measured. Accordingly, the presence of mTOR kinase activity results in an assay signal. In the presence of an mTOR kinase inhibitor, signal strength is reduced.

mTOR enzyme inhibition for a given test compound was expressed as an $IC_{50}$ value.

(b) In Vitro PI3K Enzyme Assay

The assay used AlphaScreen technology (Gray et al., Analytical Biochemistry, 2003, 313: 234-245) to determine the ability of test compounds to inhibit phosphorylation by recombinant Type I PI3K enzymes of the lipid PI(4,5)P2.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ respectively) were sub-cloned into a pDEST10 vector (Invitrogen Limited, Fountain Drive, Paisley, UK). The vector is a Gateway-adapted version of Fastbac1 containing a 6-His epitope tag. A truncated form of Type Ib human PI3K p110γ isoform corresponding to amino acid residues 144-1102 (EMBL Accession No. X8336A) and the full length human p85α regulatory subunit (EMBL Accession No. HSP13KIN) were also sub-cloned into pFastBac1 vector containing a 6-His epitope tag. The Type Ia p110 constructs were co-expressed with the p85α regulatory subunit. Following expression in the baculovirus system using standard baculovirus expression techniques, expressed proteins were purified using the His epitope tag using standard purification techniques.

DNA corresponding to amino acids 263 to 380 of human general receptor for phosphoinositides (Grp1) PH domain was isolated from a cDNA library using standard molecular biology and PCR cloning techniques. The resultant DNA fragment was sub-cloned into a pGEX 4T1 *E. coli* expression vector containing a GST epitope tag (Amersham Pharmacia Biotech, Rainham, Essex, UK) as described by Gray et al., *Analytical Biochemistry* 2003, 313: 234-245). The GST-tagged Grp1 PH domain was expressed and purified using standard techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one, Brunel Way, Stonehouse, Gloucestershire, UK Catalogue No. 784075). A mixture of each selected recombinant purified PI3K enzyme (15 ng), DiC8-PI(4,5)$P_2$ substrate (40 µM; Cell Signals Inc., Kinnear Road, Columbus, USA, Catalogue No. 901), adenosine triphosphate (ATP; 4 µM) and a buffer solution [comprising Tris-HCl pH7.6 buffer (40 mM, 10 µl), 3-[(3-cholamidopropyl)dimethylammonio]-1-propane-sulfonate (CHAPS; 0.04%), dithiothreitol (DTT; 2 mM) and magnesium chloride (10 mM)] was agitated at room temperature for 20 minutes.

Control wells that produced a minimum signal corresponding to maximum enzyme activity were created by using 5% DMSO instead of test compound. Control wells that produced a maximum signal corresponding to fully inhibited enzyme were created by adding wortmannin (6 µM; Calbiochem/Merck Bioscience, Padge Road, Beeston, Nottingham, UK, Catalogue No. 681675) instead of test compound. These assay solutions were also agitated for 20 minutes at room temperature.

Each reaction was stopped by the addition of 10 µl of a mixture of EDTA (100 mM), bovine serum albumin (BSA, 0.045%) and Tris-HCl pH7.6 buffer (40 mM).

Biotinylated-DiC8-PI(3,4,5)P3 (50 nM; Cell Signals Inc., Catalogue No. 107), recombinant purified GST-Grp1 PH protein (2.5 nM) and AlphaScreen Anti-GST donor and acceptor beads (100 ng; Packard Bioscience Limited, Station Road, Pangbourne, Berkshire, UK, Catalogue No. 6760603M) were added and the assay plates were left for about 5 to 20 hours at room temperature in the dark. The resultant signals arising from laser light excitation at 680 nm were read using a Packard AlphaQuest instrument.

PI(3,4,5)P3 is formed in situ as a result of PI3K mediated phosphorylation of PI(4,5)P2. The GST-Grp1 PH domain protein that is associated with AlphaScreen Anti-GST donor beads forms a complex with the biotinylated PI(3,4,5)P3 that is associated with Alphascreen Streptavidn acceptor beads. The enymatically-produced PI(3,4,5)P3 competes with biotinylated PI(3,4,5)P3 for binding to the PH domain protein. Upon laser light excitation at 680 nm, the donor bead: acceptor bead complex produces a signal that can be measured. Accordingly, PI3K enzyme activity to form PI(3,4,5)P3 and subsequent competition with biotinylated PI(3,4,5)P3 results in a reduced signal. In the presence of a PI3K enzyme inhibitor, signal strength is recovered.

PI3K enzyme inhibition for a given test compound was expressed as an $IC_{50}$ value.

(c) In Vitro Phospho-Ser473 Akt Assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning.

A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in DMEM containing 10% heat-inactivated FCS and 1% L-glutamine.

For the assay, the cells were detached from the culture flask using 'Accutase' (Innovative Cell Technologies Inc., San Diego, Calif., USA; Catalogue No. AT104) using standard tissue culture methods and resuspended in media to give $1.7 \times 10^5$ cells per mL. Aliquots (90 µl) were seeded into each of the inner 60 wells of a black Packard 96 well plate (Perki-nElmer, Boston, Mass., USA; Catalogue No. 6005182) to give a density of 15000 cells per well. Aliquots (90 µl) of culture media were placed in the outer wells to prevent edge effects. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and serially diluted as required with growth media to give a range of concentrations that were 10-fold the required final test concentrations. Aliquots (10 µl) of each compound dilution were placed in a well (in triplicate) to give the final required concentrations. As a minimum response control, each plate contained wells having a final concentration of 100 µM LY294002 (Calbiochem, Beeston, UK, Catalogue No. 440202). As a maximum response control, wells contained 1% DMSO instead of test compound. Following incubation, the contents of the plates were fixed by treatment with a 1.6% aqueous formaldehyde solution (Sigma, Poole, Dorset, UK, Catalogue No. F1635) at room temperature for 1 hour.

All subsequent aspiration and wash steps were carried out using a Tecan 96 well plate washer (aspiration speed 10 mm/sec). The fixing solution was removed and the contents of the plates were washed with phosphate-buffered saline (PBS; 50 µl; Gibco, Catalogue No. 10010015). The contents of the plates were treated for 10 minutes at room temperature with an aliquot (50 µl) of a cell permeabilisation buffer consisting of a mixture of PBS and 0.5% Tween-20. The 'permeabilisation' buffer was removed and non-specific binding sites were blocked by treatment for 1 hour at room temperature of an aliquot (50 µl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at room temperature with rabbit anti phospho-Akt (Ser473) antibody solution (50 µl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at room temperature with Alexafluor488 labelled goat anti-rabbit IgG (50 µl per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 µl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

(d) In Vitro MDA-MB-468 human breast adenocarcinoma Proliferation Assay

This assay determines the ability of test compounds to inhibit cell proliferation as assessed using Cellomics Array-scan technology. A MDA-MB-468 human breast adenocarcinoma cell line (LGC Promochem, Catalogue No. HTB-132) was routinely maintained as described in Biological Assay (b) herein.

For the proliferation assay, the cells were detached from the culture flask using Accutase and seeded into the inner 60 wells of a black Packard 96 well plate at a density of 8000 cells per well in 100 µl of complete growth media. The outer wells contained 100 µl of sterile PBS. The cells were incubated overnight at 37° C. with 5% $CO_2$ to allow them to adhere.

On day 2, the cells were treated with test compounds and incubated for 48 hours at 37° C. with 5% $CO_2$. Test compounds were prepared as 10 mM stock solutions in DMSO and serially diluted as required with growth media to give a range of test concentrations. Aliquots (50 µl) of each compound dilution were placed in a well and the cells were incubated for 2 days at 37° C. with 5% $CO_2$. Each plate contained control wells without test compound.

On day 4, BrdU labelling reagent (Sigma, Catalogue No. B9285) at a final dilution of 1:1000 was added and the cells were incubated for 2 hours at 37° C. The medium was removed and the cells in each well were fixed by treatment with 100 µl of a mixture of ethanol and glacial acetic acid (90% ethanol, 5% glacial acetic acid and 5% water) for 30 minutes at room temperature. The cells in each well were washed twice with PBS (100 µl). Aqueous hydrochloric acid (2M, 100 µl) was added to each well. After 20 minutes at room temperature, the cells were washed twice with PBS. Hydrogen peroxide (3%, 50 µl; Sigma, Catalogue No. H1009) was added to each well. After 10 minutes at room temperature, the wells were washed again with PBS.

BrdU incorporation was detected by incubation for 1 hour at room temperature with mouse anti-BrdU antibody (50 µl; Caltag, Burlingame, Calif., US; Catalogue No. MD5200) that was diluted 1:40 in PBS containing 1% BSA and 0.05% Tween-20. Unbound antibody was removed with two washes of PBS. For visualisation of incorporated BrdU, the cells were treated for 1 hour at room temperature with PBS (50 µl) and 0.05% Tween-20 buffer containing a 1:1000 dilution of Alexa fluor 488-labelled goat anti-mouse IgG. For visualisation of the cell nucleus, a 1:1000 dilution of Hoechst stain (Molecular Probes, Catalogue No. H3570) was added. Each plate was washed in turn with PBS. Subsequently, PBS (100 µl) was added to each well and the plates were analysed using a Cellomics array scan to assess total cell number and number of BrdU positive cells.

Fluorescence dose response data obtained with each compound were analysed and the degree of inhibition of MDA-MB-468 cell growth was expressed as an $IC_{50}$ value.

Although the pharmacological properties of the compounds of formula (I) vary with structural change as expected, in general, it is believed that activity possessed by compounds of formula (I) may be demonstrated at the following concentrations or doses in one or more of the above tests (a) to (d):—

Test (a):—$IC_{50}$ versus mTOR kinase at less than 10 µM, in particular 0.001-0.5 µM for many compounds; for example 34b the IC50 was measured on two occasions, the values were 0.155 and 0.093 µM.

Test (b):—$IC_{50}$ versus p110γ Type Ib human PI3K at less than 10 µM, in particular 0.001-0.5 µM for many compounds; and $IC_{50}$ versus p110α Type Ia human PI3K at less than 10 µM, in particular 0.001-0.5 µM for many compounds;

for example 34b the IC50 was measured on two occasions, the values were 91.2 and 57.8 µM.

Test (c):—$IC_{50}$ versus Serine 473 in Akt at less than 10 µM, in particular 0.1-20 µM for many compounds); for example 34b the IC50 was measured on two occasions, the values were 1.361 and 0.654 µM.

Test (d):—$IC_{50}$ at less than 20 µM;

The compounds of the present invention are advantageous in that they possess pharmacological activity. In particular, the compounds of the present invention modulate (in particular, inhibit) mTOR kinase and/or phosphatidylinositol-3-kinase (PI3K) enzymes, such as the Class Ia PI3K enzymes (e.g. PI3Kalpha, PI3 Kbeta and PI3 Kdelta) and the Class Ib PI3K enzyme (PI3 Kgamma). More particularly compounds of the present invention modulate (in particular, inhibit) mTOR kinase. More particularly compounds of the present invention modulate (in particular, inhibit) one or more PI3K enzyme. The inhibitory properties of compounds of formula (I) may be demonstrated using the test procedures set out herein and in the experimental section. Accordingly, the compounds of formula (I) may be used in the treatment (therapeutic or prophylactic) of conditions/diseases in human and non-human animals which are mediated by mTOR kinase and/or one or more PI3K enzyme(s), and in particular by mTOR kinase.

The invention also provides a pharmaceutical composition comprising a compound of formula (I), or a pharmaceutically acceptable salt thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of formula I will naturally vary according to the nature and severity of the disease state, the age and sex of the animal or patient and the route of administration, according to well known principles of medicine.

In using a compound of formula (I) for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used.

Typically, unit dosage forms will contain about 10 mg to 0.5 g of a compound of this invention.

As stated herein, it is known that mTOR kinase and the PI3K enzymes have roles in tumourigenesis as well as numerous other diseases. We have found that the compounds of formula (I) possess potent anti-tumour activity which it is believed is obtained by way of inhibition of mTOR kinase and/or one or more of the PI3K enzymes.

Accordingly, the compounds of the present invention are of value as anti-tumour agents. Particularly, the compounds of the present invention are of value as anti-proliferative, apoptotic and/or anti-invasive agents in the containment and/or treatment of solid and/or liquid tumour disease. Particularly, the compounds of the present invention are expected to be useful in the prevention or treatment of those tumours which are sensitive to inhibition of mTOR and/or one or more of the PI3K enzymes such as the Class Ia PI3K enzymes and the Class Ib PI3K enzyme. Further, the compounds of the present invention are expected to be useful in the prevention or treatment of those tumours which are mediated alone or in part by mTOR and/or one or more of the PI3K enzymes such as the Class Ia PI3K enzymes and the Class Ib PI3K enzyme. The compounds may thus be used to produce an mTOR enzyme inhibitory effect in a warm-blooded animal in need of such treatment. Certain compounds may be used to produce an PI3K enzyme inhibitory effect in a warm-blooded animal in need of such treatment.

As stated herein, inhibitors of mTOR kinase and/or one or more PI3K enzymes should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

According to a further aspect of the invention there is provided a compound of formula (I), or a pharmaceutically acceptable salt thereof, as defined herein for use as a medicament in a warm-blooded animal such as man.

According to a further aspect of the invention, there is provided a compound of formula (I), or a pharmaceutically acceptable salt thereof, as defined herein for use in the production of an anti-proliferative effect in a warm-blooded animal such as man.

According to a further aspect of the invention, there is provided a compound of formula (I), or a pharmaceutically acceptable salt thereof, as defined herein for use in the production of an apoptotic effect in a warm-blooded animal such as man.

According to a further feature of the invention there is provided a compound of formula (I), or a pharmaceutically acceptable salt thereof, as defined herein for use in a warm-blooded animal such as man as an anti-invasive agent in the containment and/or treatment of proliferative disease such as cancer.

According to a further aspect of the invention there is provided the use of a compound of formula (I), or a pharmaceutically acceptable salt thereof, as defined herein for the production of an anti-proliferative effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an anti-proliferative effect in a warm-blooded animal such as man.

According to a further aspect of the invention, there is provided the use of a compound of formula (I), or a pharmaceutically acceptable salt thereof, as defined herein for the production of an apoptotic effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an apoptotic effect in a warm-blooded animal such as man.

According to a further feature of the invention there is provided the use of a compound of formula (I), or a pharmaceutically acceptable salt thereof, as defined herein in the manufacture of a medicament for use in a warm-blooded animal such as man as an anti-invasive agent in the containment and/or treatment of proliferative disease such as cancer.

According to a further feature of this aspect of the invention there is provided a method for producing an anti-proliferative effect in a warm-blooded animal, such as man, in need of such treatment which comprises administering to said animal an effective amount of a compound of formula (I), or a pharmaceutically acceptable salt thereof, as defined herein.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a compound of formula (I), or a pharmaceutically acceptable salt thereof, as defined herein.

According to a further aspect of the invention there is provided the use of a compound of formula (I), or a pharmaceutically acceptable salt thereof, as defined herein in the manufacture of a medicament for use in the prevention or treatment of proliferative disease such as cancer in a warm-blooded animal such as man.

According to a further feature of this aspect of the invention there is provided a method for the prevention or treatment of proliferative disease such as cancer in a warm-blooded animal, such as man, in need of such treatment which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided the use of a compound of formula (I), or a pharmaceutically acceptable salt thereof, as defined herein in the manufacture of a medicament for use in the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in providing a mTOR kinase inhibitory effect and/or a PI3K enzyme inhibitory effect (such as a Class Ia PI3K enzyme or Class Ib PI3K enzyme inhibitory effect).

According to a further feature of this aspect of the invention there is provided the use of a compound of formula (I), or a pharmaceutically acceptable salt thereof, as defined herein in the manufacture of a medicament for use in providing a mTOR kinase inhibitory effect and/or a PI3K enzyme inhibitory effect (such as a Class Ia PI3K enzyme or Class Ib PI3K enzyme inhibitory effect).

According to a further aspect of the invention there is also provided a method for providing a mTOR kinase inhibitory effect and/or a PI3K enzyme inhibitory effect (such as a Class Ia PI3K enzyme or Class Ib PI3K enzyme inhibitory effect) which comprises administering an effective amount of a compound of formula I, or a pharmaceutically acceptable salt thereof, as defined herein.

According to a further feature of the invention there is provided a compound of formula I, or a pharmaceutically acceptable salt thereof, as defined herein for use in the treatment of cancer, inflammatory diseases, obstructive airways diseases, immune diseases or cardiovascular diseases.

According to a further feature of the invention there is provided a compound of formula I, or a pharmaceutically acceptable salt thereof, as defined herein for use in the treatment of solid tumours such as carcinoma and sarcomas and the leukaemias and lymphoid malignancies.

According to a further feature of the invention there is provided a compound of formula I, or a pharmaceutically acceptable salt thereof, as defined herein for use in the treatment of cancer of the breast, colorectum, lung (including small cell lung cancer, non-small cell lung cancer and bronchioalveolar cancer) and prostate.

According to a further feature of the invention there is provided a compound of formula (I), or a pharmaceutically acceptable salt thereof, as defined herein for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided the use of a compound of formula (I), or a pharmaceutically acceptable salt thereof, as defined herein in the manufacture of a medicament for use in the treatment of cancer, inflammatory diseases, obstructive airways diseases, immune diseases or cardiovascular diseases.

According to a further feature of the invention there is provided the use of a compound of formula (I), or a pharmaceutically acceptable salt thereof, as defined herein in the manufacture of a medicament for use in the treatment of solid tumours such as carcinoma and sarcomas and the leukaemias and lymphoid malignancies.

According to a further feature of the invention there is provided the use of a compound of formula (I), or a pharmaceutically acceptable salt thereof, as defined herein in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a compound of formula (I), or a pharmaceutically acceptable salt thereof, as defined herein in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a compound of formula (I), or a pharmaceutically acceptable salt thereof, as defined herein.

According to a further feature of the invention there is provided a method for treating solid tumours such as carcinoma and sarcomas and the leukaemias and lymphoid malignancies in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a compound of formula (I), or a pharmaceutically acceptable salt thereof, as defined herein.

As stated herein, the in vivo effects of a compound of formula (I) may be exerted in part by one or more metabolites that are formed within the human or animal body after administration of a compound of formula (I).

The invention further relates to combination therapies wherein a compound of formula (I), or a pharmaceutically acceptable salt thereof, or a pharmaceutical composition or formulation comprising a compound of formula (I) is administered concurrently or sequentially or as a combined preparation with another treatment of use in the control of oncology disease.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment of cancer.

Suitable agents to be used in combination include:—
(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);
(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat and inhibitors of urokinase plasminogen activator receptor function);
(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;
(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];
(vi) vascular damaging agents such as combretastatin A4 and compounds disclosed in International Patent Applications WO 99/02166, WO 00/40529, WO 00/41669, WO 01/92224, WO 02/04434 and WO 02/08213;
(vii) antisense therapies, for example those which are directed to the targets listed above, such as ISIS 2503, an anti-ras antisense agent;
(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be further explained by reference to the following illustrative examples.

Unless stated otherwise, starting materials were commercially available. All solvents and commercial reagents were of laboratory grade and were used as received.

In the examples $^1$H NMR spectra were recorded on a Bruker DPX 300 (300 MHz), Bruker DRX 400 (400 MHz) instrument or a Bruker DRX 500 (500 MHz) instrument. The central peaks of chloroform-d ($\delta_H$ 7.27 ppm), dimethylsulfoxide-d$_6$ ($\delta_H$ 2.50 ppm) or acetone-d$_6$ ($\delta_H$ 2.05 ppm) were used as internal references. The following abbreviations have been used: s, singlet; d, doublet;

t, triplet; q, quartet; m, multiplet; br, broad.

Column chromatography was carried out using silica gel (0.04-0.063 mm, Merck). In general, a Kromasil KR-100-5-C18 reversed-phase column (250×20 mm, Akzo Nobel) was used for preparative HPLC with mixtures of acetonitrile and water [containing 0.1% trifluoroacetic acid (TFA)] used as the eluent at a flow rate of 10 mL/min.

The following methods were used for liquid chromatography (LC)/mass spectral (MS) analysis —

HPLC: Agilent 1100 or Waters Alliance HT (2790 & 2795)

Mass Spectrometer Waters ZQ ESCi

HPLC Column

The standard HPLC column used is the Phemonenex Gemini C18 5 μm, 50×2 mm.

Acidic HPLC Methods

The mobile phases used are: Mobile phase A: Water

Mobile Phase B: Acetonitrile

Mobile Phase C: 1% Formic Acid in 50:50 Water:MeCN (v/v)

Each method is followed by a rapid equilibration using a 5 mL flow rate for 0.45 min.

Four Generic HPLC Methods are Available:

5 Minute Monitor Acidic method

| Time/min | Mobile Phase A: | Mobile Phase B: | Mobile Phase C: | Curve | Flow Rate/mL/min |
|---|---|---|---|---|---|
| 0.00 | 95 | 0 | 5 | 1 | 1.1 |
| 4 | 0 | 95 | 5 | 6 | 1.1 |
| 4.5 | 0 | 95 | 5 | 6 | 1.1 |

Early Acidic method for early eluting compounds

| Time/min | Mobile Phase A: | Mobile Phase B: | Mobile Phase C: | Curve | Flow Rate/mL/min |
|---|---|---|---|---|---|
| 0.00 | 95 | 0 | 5 | 1 | 1.1 |
| 4 | 57.5 | 37.5 | 5 | 6 | 1.1 |
| 4.5 | 57.5 | 37.5 | 5 | 6 | 1.1 |

Mid Acidic method for middle eluting compounds

| Time/min | Mobile Phase A: | Mobile Phase B: | Mobile Phase C: | Curve | Flow Rate/mL/min |
|---|---|---|---|---|---|
| 0.00 | 95 | 0 | 5 | 1 | 1.1 |
| 0.01 | 67.5 | 27.5 | 5 | 6 | 1.1 |
| 4.5 | 27.5 | 67.5 | 5 | 6 | 1.1 |

Late Acidic method for late eluting compounds

| Time/min | Mobile Phase A: | Mobile Phase B: | Mobile Phase C: | Curve | Flow Rate/mL/min |
|---|---|---|---|---|---|
| 0.00 | 95 | 0 | 5 | 1 | 1.1 |
| 0.01 | 27.5 | 67.5 | 5 | 6 | 1.1 |
| 4.5 | 5 | 95 | 5 | 6 | 1.1 |

Basic HPLC Methods

In some instances the standard acidic methods may be unsuitable for either the compound ionisation or the chromatography separation required. In such cases four comparable Basic HPLC methods are available.

The mobile phases used are: Mobile phase A: Water
Mobile Phase B: Acetonitrile
Mobile Phase D: 0.1% 880 Ammonia in acetonitrile Each method is followed by a rapid equilibration using a 5 mL flow rate for 0.45 min.

Minute Monitor Basic method

| Time/min | Mobile Phase A: | Mobile Phase B: | Mobile Phase D: | Curve | Flow Rate/mL/min |
|---|---|---|---|---|---|
| 0.00 | 95 | 0 | 5 | 1 | 1.1 |
| 4 | 0 | 95 | 5 | 6 | 1.1 |
| 4.5 | 0 | 95 | 5 | 6 | 1.1 |

Early Basic method for early eluting compounds

| Time/min | Mobile Phase A: | Mobile Phase B: | Mobile Phase D: | Curve | Flow Rate/mL/min |
|---|---|---|---|---|---|
| 0.00 | 95 | 0 | 5 | 1 | 1.1 |
| 4 | 57.5 | 37.5 | 5 | 6 | 1.1 |
| 4.5 | 57.5 | 37.5 | 5 | 6 | 1.1 |

Mid Basic method for middle eluting compounds

| Time/min | Mobile Phase A: | Mobile Phase B: | Mobile Phase D: | Curve | Flow Rate/mL/min |
|---|---|---|---|---|---|
| 0.00 | 95 | 0 | 5 | 1 | 1.1 |
| 0.01 | 67.5 | 27.5 | 5 | 6 | 1.1 |
| 4.5 | 27.5 | 67.5 | 5 | 6 | 1.1 |

Late Basic method for late eluting compounds

| Time/min | Mobile Phase A: | Mobile Phase B: | Mobile Phase C: | Curve | Flow Rate/mL/min |
|---|---|---|---|---|---|
| 0.00 | 95 | 0 | 5 | 1 | 1.1 |
| 0.01 | 27.5 | 67.5 | 5 | 6 | 1.1 |
| 4.5 | 5 | 95 | 5 | 6 | 1.1 |

The following method was used for liquid chromatography (LC)/mass spectral (MS) analysis:—

Instrument: Agilent 1100; Column: Waters 'Symmetry' 2.1×30 mm; Mass Spectral analysis using chemical ionisation (APCI); Flow rate: 0.7 mL/min; Absorption Wavelength: 254 nm; Solvent A: water+0.1% TFA; Solvent B: acetonitrile+0.1% TFA; Solvent Gradient: 15-95% Solvent B for 2.7 minutes followed by 95% Solvent B for 0.3 minutes.

The following methods were used for LC analysis:—

Method A:—Instrument: Agilent 1100; Column: Kromasil C18 reversed-phase silica, 100×3 mm, 5 μm particle size; Solvent A: 0.1% TFA/water, Solvent B: 0.08% TFA/acetonitrile; Flow Rate: 1 mL/min; Solvent Gradient: 10-100% Solvent B for 20 minutes followed by 100% Solvent B for 1 minute; Absorption Wavelengths: 220, 254 and 280 nm. In general, the retention time of the product was noted.

Method B:—Instrument: Agilent 1100; Column: Waters 'Xterra' C8 reversed-phase silica, 100×3 mm, 5 μm particle size; Solvent A: 0.015M ammonia in water, Solvent B: acetonitrile; Flow Rate: 1 ml/min, Solvent Gradient: 10-100% Solvent B for 20 minutes followed by 100% Solvent B for 1 minute; Absorption Wavelength: 220, 254 and 280 nm. In general, the retention time of the product was noted.

The following abbreviations are used herein or within the following illustrative examples:—

| Abbr. | Meaning |
|---|---|
| HPLC | High Performance Liquid Chromatography |
| HBTU | O-(benzotriazol-1-yl)-N,N,N',N'-tetramethyluronium hexafluorophosphate; |
| HATU | O-(7-azabenzotriazol-1-yl)-N,N,N',N'-tetramethyluronium hexafluorophosphate; |
| HOBT | 1-hydroxybenzotriazole; |
| HOAT | 1-hydroxy-7-azabenzotriazole; |
| NMP | N-methylpyrrolidin-2-one; |
| DMSO | dimethylsulfoxide; |
| DMF | N,N-dimethylformamide; |
| DMA | N,N-dimethylacetamide; |
| THF | tetrahydrofuran; |
| DME | 1,2-dimethoxyethane; |
| DCCI | dicyclohexylcarbodiimide; |
| MeOH | methanol; |
| MeCN | acetonitrile; |
| DCM | dichloromethane; |
| DIPEA | N,N-diisopropylethylamine; |
| DBU | 1,8-diazabicyclo[5.4.0]undec-7-ene; |
| RT | room temperature (approximately 17 to 25° C.); |
| tR | retention time; |
| m/z | mass/charge ratio. |

The chemical names were generated by software which used the Lexichem Toolkit (v. 1.40) from OpenEye Scientific Software (www.eyesopen.com) to generate IUPAC conforming names.

EXAMPLE 1

1-Ethyl-3-[4-[4-[(3S)-3-methylmorpholin-4-yl]-6-(methylsulfonylmethyl)pyrimidin-2-yl]phenyl]urea

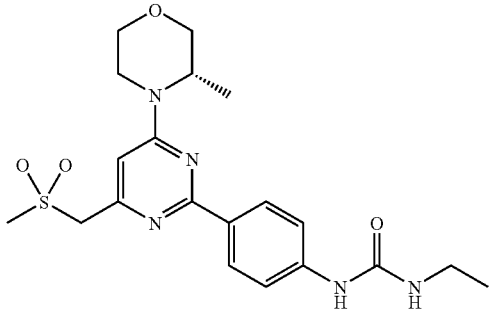

4-[4-[(3S)-3-Methylmorpholin-4-yl]-6-(methylsulfonylmethyl)pyrimidin-2-yl]aniline (100 mg, 0.28 mmol) was dissolved in dioxane (4 mL). Ethylisocyanate (0.109 mL, 1.38 mmol) was added and the reaction heated at 70° C. for 4 hours. Reaction was complete and was evaporated to dryness. The resultant oil was purified by chromatography, eluting with 10-50% ethyl acetate in isohexane, to give 3-ethyl-1-[4-[4-[(3S)-3-methylmorpholin-4-yl]-6-(methylsulfonylmethyl)pyrimidin-2-yl]phenyl]urea as a pale yellow oil (113 mg, 94%).

NMR Spectrum: $^1$H NMR (399.9 MHz, DMSO-$d_6$) δ 0.99 (t, 3H), 1.25 (d, 3H), 3.11 (q, 2H), 3.20 (s, 3H), 3.29 (m, 2H), 3.5 (m, 1H), 3.67 (m, 1H), 3.78 (m, 1H), 3.99 (m, 1H), 4.16 (m, 1H), 4.47 (s, 2H), 6.18 (t, 1H), 6.78 (s, 1H), 7.50 (d, 2H), 8.21 (d, 2H), 8.68 (s, 1H)

LCMS Spectrum: MH+ 434, retention time 1.37 min, Method 5 Min Acid

The compounds shown in table were prepared in an analogous manner to 3-ethyl-1-[4-[4-[(3S)-3-methylmorpholin-4-yl]-6-(methylsulfonylmethyl)pyrimidin-2-yl]phenyl]urea by reacting the appropriate isocyanate with the appropriate aniline.

| Example | Structure | NAME | LCMS MH+ | Retention time (min) | Notes |
|---|---|---|---|---|---|
| 1a | 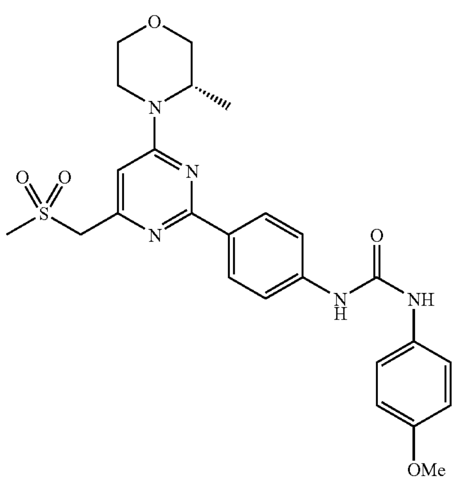 | 1-(4-methoxyphenyl)-3-[4-[4-[(3S)-3-methylmorpholin-4-yl]-6-(methylsulfonylmethyl)pyrimidin-2-yl]phenyl]urea | 512 | 2.19 | Purified by ethyl acetate slurry then chromatography |

-continued

| Example | Structure | NAME | LCMS MH+ | Retention time (min) | Notes |
|---|---|---|---|---|---|
| 1b | 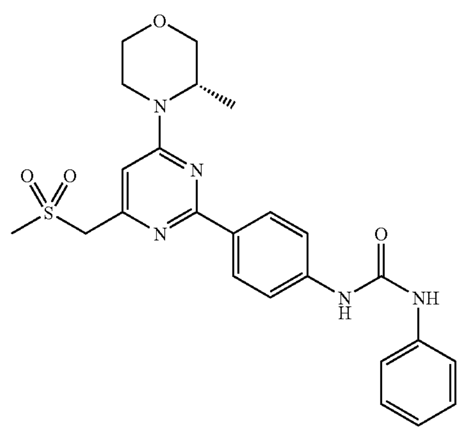 | 1-[4-[4-[(3S)-3-methylmorpholin-4-yl]-6-(methylsulfonyl-methyl)pyrimidin-2-yl]phenyl]-3-phenyl-urea | 482 | 2.26 | Chromatography eluted with 0-8% MeOH/DCM |
| 1c | 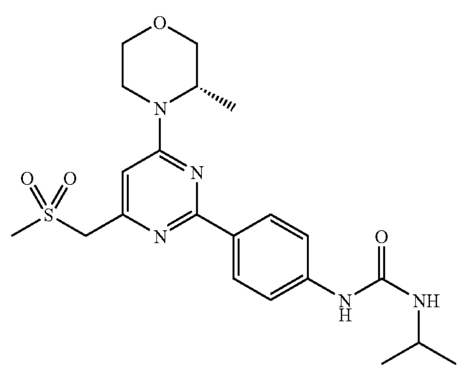 | 3-[4-[4-[(3S)-3-methylmorpholin-4-yl]-6-(methylsulfonyl-methyl)pyrimidin-2-yl]phenyl]-1-propan-2-yl-urea | 448 | 1.90 | Chromatography eluted with 0-8% MeOH/DCM |
| 1e | 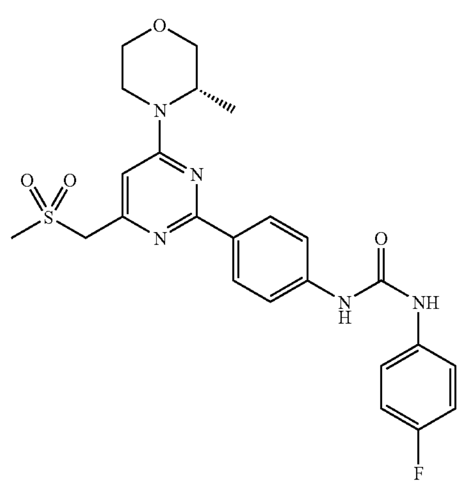 | 3-(4-fluorophenyl)-1-[4-[4-[(3S)-3-methylmorpholin-4-yl]-6-(methylsulfonyl-methyl)pyrimidin-2-yl]phenyl]urea | 500 | 2.05 | Triturated with ethyl acetate |

-continued

| Example | Structure | NAME | LCMS MH+ | Retention time (min) | Notes |
|---|---|---|---|---|---|
| 1f | 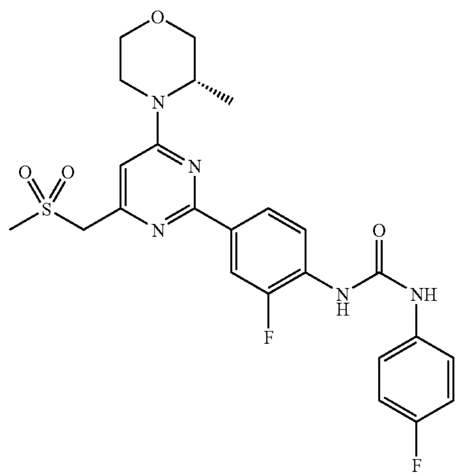 | 1-[2-fluoro-4-[4-[(3S)-3-methylmorpholin-4-yl]-6-(methylsulfonyl-methyl)pyrimidin-2-yl]phenyl]-3-(4-fluorophenyl)urea | 518 | 2.38 | Purified by reverse phase chromatography |
| 1g | 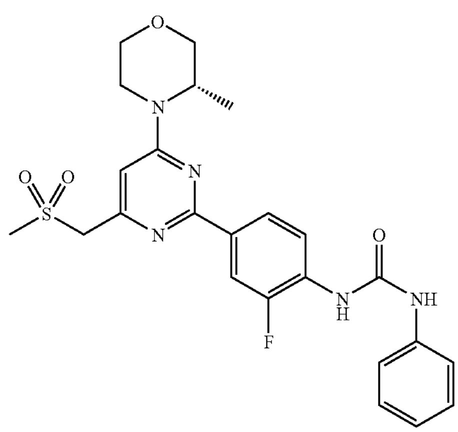 | 1-[2-fluoro-4-[4-[(3S)-3-methylmorpholin-4-yl]-6-(methylsulfonyl-methyl)pyrimidin-2-yl]phenyl]-3-phenyl-urea | 500 | 2.36 | Purified by reverse phase chromatography |
| 1h | 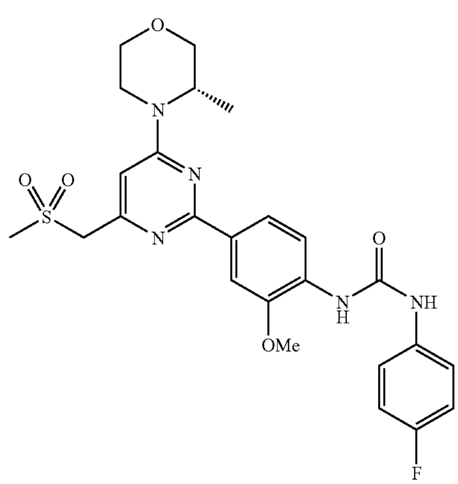 | 3-(4-fluorophenyl)-1-[2-methoxy-4-[4-[(3S)-3-methylmorpholin-4-yl]-6-(methylsulfonyl-methyl)pyrimidin-2-yl]phenyl]urea | 529 | 2.22 | Crystallised from NMP/water then triturated with EtOAc |

| Example | Structure | NAME | LCMS MH+ | Retention time (min) | Notes |
|---|---|---|---|---|---|
| 1i | 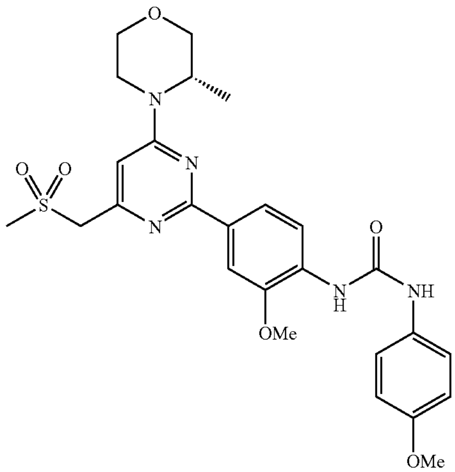 | 3-[2-methoxy-4-[4-[(3S)-3-methylmorpholin-4-yl]-6-(methylsulfonyl-methyl)pyrimidin-2-yl]phenyl]-1-(4-methoxyphenyl)urea | 542 | 2.06 | Crystallised from NMP/water then triturated with EtOAc |
| 1j | 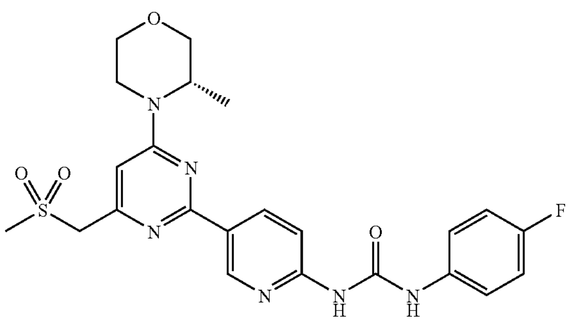 | 3-(4-fluorophenyl)-1-[5-[4-[(3S)-3-methylmorpholin-4-yl]-6-(methylsulfonyl-methyl)pyrimidin-2-yl]pyridin-2-yl]urea | 501 | 2.26 | Crystallised from dimethyl-formamide/water |
| 1k | 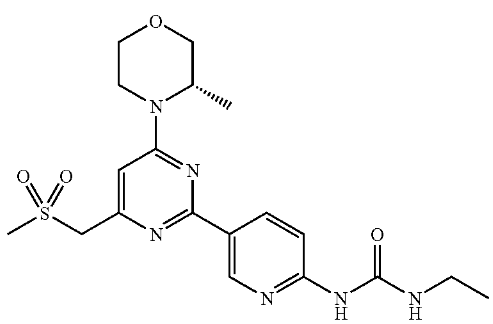 | 1-ethyl-3-[5-[4-[(3S)-3-methylmorpholin-4-yl]-6-(methylsulfonyl-methyl)pyrimidin-2-yl]pyridin-2-yl]urea | 435 | 1.51 | Purified by reverse phase chroma-tography |

Example 1a: $^1$H NMR (399.9 MHz, DMSO-d$_6$) δ 1.28 (d, 3H), 3.21 (s, 3H), 3.4 (m, 2H), 3.5 (m, 1H), 3.65 (m, 1H), 3.71 (s, 3H), 3.8 (d, 1H), 3.99 (m, 1H), 4.2 (m, 1H), 4.50 (s, 2H), 6.79 (s, 1H), 6.89 (d, 2H), 7.38 (d, 2H), 7.55 (d, 2H), 8.25 (d, 2H), 8.50 (s, 1H), 8.83 (s, 1H)

Example 1b: $^1$H NMR (399.9 MHz, DMSO-d$_6$) δ 1.25 (d, 3H), 3.21 (s, 2H), 3.28-3.38 (m, 2H), 3.35 (t, 1H), 3.67 (d, 1H), 3.69 (d, 1H), 4.18-4.22 (m, 1H), 4.50 (s, 3H), 6.79 (s, 1H), 7.00 (m, 1H), 7.31 (m, 2H) 7.47 (d, 2H), 7.59 (d, 2H), 8.27 (d, 2H), 8.71 (s, 1H), 8.91 (s, 1H)

Example 1c: $^1$H NMR (399.9 MHz, DMSO-d$_6$) δ 1.10 (d, 6H), 1.24 (d, 3H), 3.29 (s, 3H), 3.49 (m, 1H), 3.64-3.66 (m, 1H), 3.77 (m, 2H), 4.18-4.21 (m, 1H), 4.49 (s, 3H), 6.08 (d, 1H), 6.79, (s, 1H), 7.48 (d, 2H), 8.22 (d, 2H), 8.51 (s, 1H)

Example 1d: $^1$H NMR (399.9 MHz, DMSO-d$_6$) δ 1.25-1.27 (m, 3H), 3.22 (s, 3H), 3.35-3.36 (m, 1H), 3.41 (s, 1H), 3.51 (d, 2H), 3.65-3.68 (m, 1H), 3.79 (d, 1H), 3.98-4.02 (m, 1H), 4.18 (s, 1H), 4.50 (s, 2H), 6.80 (s, 1H), 7.12-7.16 (m, 2H), 7.47-7.50 (m, 2H), 7.57 (d, 2H), 8.27 (d, 2H), 8.75 (s, 1H), 8.92 (s, 1H)

Example 1e: $^1$H NMR (399.9 MHz, DMSO-d$_6$) δ 1.25-1.27 (m, 3H), 3.21 (s, 3H), 3.25 (t, 1H), 3.48-3.54 (m, 1H), 3.64-3.68 (m, 1H), 3.79 (d, 1H), 3.98-4.02 (m, 1H), 4.19 (s, 1H), 4.50 (m, 1H), 4.51 (s, 2H), 6.84 (s, 1H), 7.16 (d, 2H), 7.47-7.51 (m, 2H), 8.08-8.12 (m, 1H), 8.13-8.15 (m, 1H), 8.31 (t, 1H), 8.77 (d, 1H), 9.17 (s, 1H)

Example 1f: $^1$H NMR (399.9 MHz, DMSO-d$_6$) δ 1.26 (d, 3H), 3.21 (s, 3H), 3.24-3.26 (m, 1H), 3.52 (t, 1H), 3.66 (t, 1H), 3.79 (d, 1H), 3.99-4.02 (m, 2H), 4.18 (m, 1H), 4.52 (s, 3H), 6.84 (s, 1H), 7.02 (t, 1H), 7.30-7.34 (m, 2H), 7.48 (d, 2H), 8.08-8.15 (m, 2H), 8.34 (t, 1H), 8.79 (d, 1H), 9.15 (s, 1H)

Example 1g: $^1$H NMR (399.9 MHz, DMSO-d$_6$) δ 1.25-1.27 (m, 3H), 3.24 (s, 3H), 3.30 (m, 1H), 3.49-3.53 (m, 1H), 3.65-3.69 (m, 1H), 3.80 (d, 1H), 3.98 (s, 3H), 4.00 (m, 1H), 4.02 (m, 1H), 4.48 (m, 1H), 4.52 (s, 2H), 6.82 (s, 1H), 7.12-7.17 (m, 2H), 7.47-7.51 (m, 2H), 7.96 (s, 2H), 8.27 (s, 1H), 8.42 (s, 1H), 9.45 (d, 1H)

Example 1h: $^1$H NMR (399.9 MHz, DMSO-d$_6$) δ 1.26 (d, 3H), 3.24 (s, 3H), 3.30 (m, 1H), 3.49-3.55 (m, 1H), 3.65-3.69 (m, 1H), 3.74 (s, 3H), 3.80 (d, 1H), 3.97 (s, 3H), 4.00 (m, 1H), 4.02 (m, 1H), 4.18-4.22 (m, 1H), 4.47-4.49 (m, 1H), 4.52 (s, 2H), 6.81 (s, 1H), 6.88-6.91 (m, 2H, 7.36-7.40 (m, 2H), 7.95 (s, 2H), 8.28 (d, 1H), 8.36 (s, 1H), 9.23 (s, 1H)

Example 1i: $^1$H NMR (399.9 MHz, DMSO-d$_6$) δ1.27 (d, 3H), 3.21 (s, 3H), 3.25 (m, 1H), 3.48-3.55 (m, 1H), 3.65-3.69 (m, 1H), 3.79 (d, 1H), 3.98-4.02 (m, 1H), 4.20 (s, 1H), 4.52 (s, 3H), 6.87 (s, 1H), 7.14-7.21 (m, 2H), 7.56-7.60 (m, 2H), 7.61-7.64 (m, 1H), 8.57-8.59 (m, 1H), 9.21-9.21 (m, 1H), 9.70 (s, 1H), 10.52 (s, 1H)

Example 1j: $^1$H NMR (399.9 MHz, DMSO-d$_6$) δ1.12 (t, 3H), 1.25-1.26 (m, 3H), 3.20 (s, 3H), 3.22-3.24 (m, 2H), 3.26 (m, 1H), 3.47-3.54 (m, 1H), 3.64-3.67 (m, 1H), 3.78 (d, 1H), 3.97-4.01 (m, 1H), 4.18 (s, 1H), 4.50 (s, 3H), 6.84 (s, 1H), 7.48 (d, 1H), 8.10 (d, 1H), 8.48-8.51 (m, 1H), 9.11 (m, 1H), 9.41 (s, 1H)

Test (a): Example (1) 0.0062 μM; Example (1a) 0.062 μM; Example (1b) 0.013 μM; Example (1c) 0.078 μM; Example (1d) 0.042 μM; Example (1e) 0.32 μM; Example (1f) 0.36 μM; Example (1g) 0.96 μM; Example (1h) 1.2 μM; Example (1i) 0.55 μM; Example (1j) 0.043 μM.

The preparation of the anilines 4-[4-[(3S)-3-methylmorpholin-4-yl]-6-(methylsulfonylmethyl)pyrimidin-2-yl]aniline and 2-fluoro-4-[4-[(3S)-3-methylmorpholin-4-yl]-6-(methylsulfonylmethyl)pyrimidin-2-yl]aniline are described below.

4-[4-[(3S)-3-Methylmorpholin-4-yl]-6-(methylsulfonylmethyl)pyrimidin-2-yl]aniline

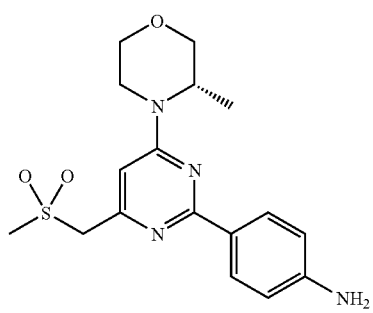

tert-Butyl N-[4-[4-[(3S)-3-methylmorpholin-4-yl]-6-(methylsulfonylmethyl)pyrimidin-2-yl]phenyl]carbamate (1.09 g, 2.35 mmol) was dissolved in methanol (5 mL) and 4M hydrogenchloride in dioxane (5 mL) was added. The solution was stirred at room temperature overnight, then the mixture evaporated to a dark brown oil and dissolved in ethyl acetate (10 mL). Water (5 mL) was added followed by the addition of sodium bicarbonate solution until neutral pH was achieved (~2 mL). The phases were separated and the organic phase washed with water (10 mL). The organic layer was dried over magnesium sulphate and evaporated to a pale yellow foam (805 mg).

NMR Spectrum: $^1$H NMR (399.9 MHz, DMSO-d$_6$) δ 1.23 (3H, d), 3.31 (3H, s), 3.5 (1H, m), 3.64 (1H, m), 3.78 (1H, m), 4.13 (1H, m), 4.49 (2H, m), 5.57 (2H, s), 6.61 (2H, d), 6.68 (1H, s), 8.08 (1H, d)

LCMS Spectrum: MH+ 363, retention time 1.02 min, Method 5 Min Acid tert-Butyl N-[4-[4-[(3S)-3-methylmorpholin-4-yl]-6-(methylsulfonylmethyl)pyrimidin-2-yl]phenyl]carbamate

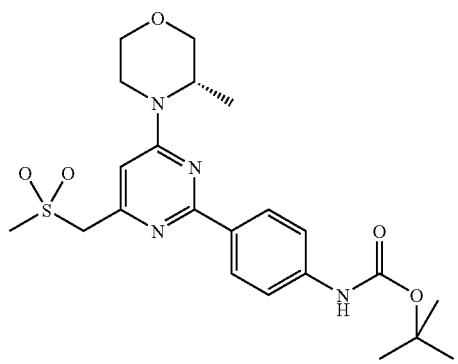

2-Chloro-4-[(3S)-3-methylmorpholin-4-yl]-6-(methylsulfonylmethyl)pyrimidine (1.0 g, 3.27 mmol) was dissolved in a solution of 18% DMF in a mixture of 7:3:2 DME:water:ethanol (7 mL). [4-[(2-Methylpropan-2-yl)oxycarbonylamino]phenyl]boronic acid (1.165 g, 4.91 mmol), 2M sodium carbonate solution (4 mL) and dichlorobis(triphenylphosphine) palladium catalyst (115 mg, 0.16 mmol) were then added to the solution and refluxed at 90° C. for 5 hours under nitrogen atmosphere. The reaction was allowed to cool to room temp then partitioned between ethyl acetate and water. The organics were dried over magnesium sulphate, filtered and concentrated to dryness. The crude oil was dissolved in dichloromethane and filtered to remove insoluble material. A beige solid precipitated from the filtrates and the filtrates were filtered again. The solid was analysed and found to be the excess boronic acid and the filtrates contained the product and some impurities. The filtrates were purified by chromatography on silica, eluting with 0-40% ethyl acetate in isohexane, to give the desired compound as an orange oil (530 mg).

LCMS Spectrum: MH+ 463, retention time 2.23 min, Method 5 Min Acid

2-Chloro-4-[(3S)-3-methylmorpholin-4-yl]-6-(methylsulfonylmethyl)pyrimidine

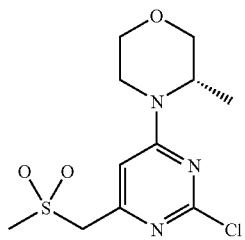

2,4-Dichloro-6-(methylsulfonylmethyl)pyrimidine (30 g, 0.13 mol) was dissolved in dichloromethane and stirred (under nitrogen) at −5° C. Triethylamine (17.4 mL, 0.13 mol) was added to give a clear brown solution. (3S)-3-Methylmorpholine was dissolved in dichloromethane and added dropwise keeping the reaction below −5° C. The cooling bath was then removed and the mixture stirred for 1 hour. The reaction mixture was heated at reflux for 2 hours, then the reaction mixture was washed with water, dried then evaporated. The crude material was purified by preparative HPLC to give the desired material as a solid (19.3 g).

NMR Spectrum: $^1$H NMR (400.13 MHz, DMSO-$d_6$) δ1.21-1.23 (m, 3H), 3.11 (s, 3H), 3.19-3.26 (m, 1H), 3.42-3.49 (m, 1H), 3.58-3.62 (1H, m), 3.73 (d, 1H), 3.92-3.96 (m, 2H), 4.27-4.31 (m, 1H), 4.45 (s, 2H), 6.92 (s, 1H)

LCMS Spectrum: MH+ 306, retention time 1.42 min, Method 5 Min Acid

2,4-Dichloro-6-(methylsulfonylmethyl)pyrimidine

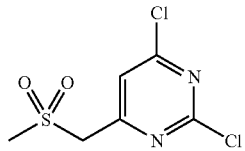

6-(Methylsulfonylmethyl)-1H-pyrimidine-2,4-dione (132 g, 0.65 mol) was added to phosphorus oxychloride (1.2 L) and the mixture heated to reflux for 16 hours, then cooled to room temperature. The excess phosphorus oxychloride was removed in vacuo, the residue azeotroped with toluene (2×500 mL) and dissolved in dichloromethane. This mixture was then poured slowly onto ice (4 L) and stirred for 20 minutes, then extracted with dichloromethane (3×1 L) (the insoluble black material was filtered off and discarded) and ethyl acetate (2×1 L). The extracts were combined, dried, then evaporated to leave the desired material as a dark brown solid (51 g). The material was used without further purification.

NMR Spectrum: $^1$H NMR (400.13 MHz, DMSO-$d_6$) δ3.13 (s, 3H), 4.79 (s, 2H), 7.87 (s, 1H)

LCMS Spectrum: MH+ 239, retention time 1.21 min, Method 5 Min Acid

6-(Methylsulfonylmethyl)-1H-pyrimidine-2,4-dione

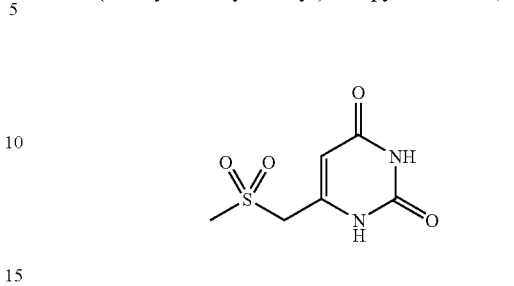

6-(Chloromethyl)-1H-pyrimidine-2,4-dione (175 g, 1.09 mol) was dissolved in DMF (2 L) and methanesulphinic acid sodium salt (133.5 g, 1.31 mol) was added. The reaction was heated to 125° C. for 2 hours then allowed to cool and the suspension filtered and concentrated in vacuo to give a yellow solid. The crude material was washed with water, filtered, then triturated with toluene. The solid was filtered then triturated with isohexane to leave the desired compound as a yellow solid (250 g). The material was used without further purification.

6-(Chloromethyl)-1H-pyrimidine-2,4-dione is a commercially available material.

2-Fluoro-4-[4-[(3S)-3-methylmorpholin-4-yl]-6-(methylsulfonylmethyl)pyrimidin-2-yl]aniline

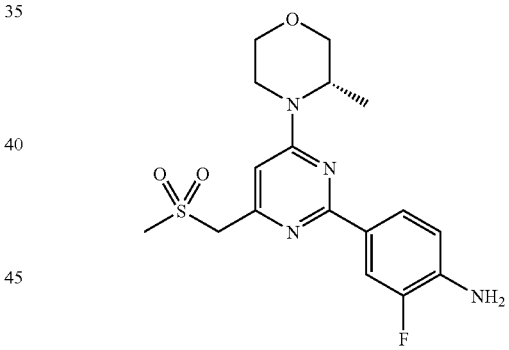

2-Chloro-4-[(3S)-3-methylmorpholin-4-yl]-6-(methylsulfonylmethyl)pyrimidine (860 mg) was dissolved in 18% DMF in 7:3:2 DME:water:ethanol (21 mL total solvent volume). 4-Pinacolato boron-2-fluoroaniline (1.005 g), 2M sodium carbonate (4 mL) and dichlorobis(triphenylphosphine) palladium (99 mg) was then added to the solution and heated under reflux at 90° C. for 5 hours under nitrogen atmosphere. The reaction was partitioned between DCM (50 mL) and water (50 mL). The organic extract was dried over magnesium sulphate, filtered and concentrated in vacuo. The brown oil was dissolved in dichloromethane, filtered to remove fine material and loaded onto a Companion for purification using a 0-50% ethyl acetate in isohexane gradient over 20 minutes. The purified product was obtained as a pale yellow oil.

LCMS Spectrum: MH+ 381, retention time 1.32 min, Method 5 Min Acid

5-[4-[(3S)-3-Methylmorpholin-4-yl]-6-(methylsulfonylmethyl)pyrimidin-2-yl]pyridin-2-amine

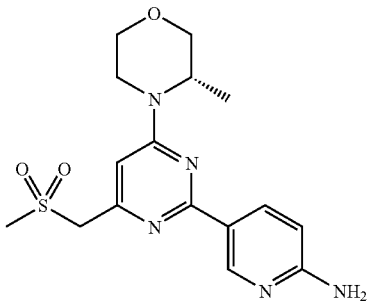

2-Chloro-4-[(3S)-3-methylmorpholin-4-yl]-6-(methylsulfonylmethyl)pyrimidine (363 mg, 1.19 mmol) was dissolved in a solution of 18% DMF in a mixture of 7:3:2 DME:water:ethanol (7 mL). 5-(4,4,5,5-Tetramethyl-1,3,2-dioxaborolan-2-yl)pyridin-2-amine (496 mg, 2.25 mmol), 2M sodium carbonate solution (2 mL) and dichlorobis(triphenylphosphine) palladium (42 mg) were added to the solution and it was heated under reflux at 90° C. for 90 minutes under nitrogen atmosphere. The reaction was partitioned between ethyl acetate (50 mL) and water (50 mL), the organics dried over magnesium sulphate, filtered and concentrated in vacuo to give the desired product as a yellow oil (410 mg) which was used without further purification.

LCMS Spectrum: MH+ 364, retention time 0.89 min, Method 5 Min Acid

2-Methoxy-4-[4-[(3S)-3-methylmorpholin-4-yl]-6-(methylsulfonylmethyl)pyrimidin-2-yl]aniline

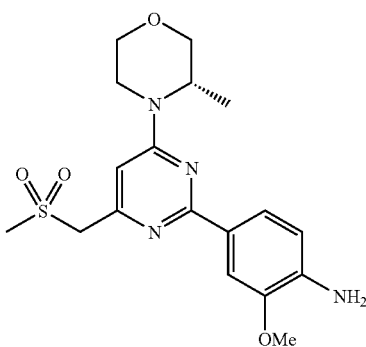

2-Chloro-4-[(3S)-3-methylmorpholin-4-yl]-6-(methylsulfonylmethyl)pyrimidine (700 mg, 2.29 mmol) was dissolved in a solution of 18% DMF in a mixture of 7:3:2 DME:water:ethanol (7 mL). (4-Amino-3-methoxy-phenyl)boronic acid (574 mg, 3.43 mmol), 2M sodium carbonate solution (4 mL) and dichlorobis(triphenylphosphine) palladium (81 mg) was then added to the solution and refluxed at 90° C. for 1 hour. The reaction was allowed to cool to room temp then partitioned between ethyl acetate (50 mL) and water (50 mL), the organics dried over magnesium sulphate, filtered and concentrated in vacuo. The residue was dissolved in dichloromethane and filtered to remove insoluble material. The filtrates were purified using a companion.

NMR Spectrum: $^1$H NMR (399.9 MHz, DMSO-d$_6$) δ1.24 (d, 3H), 3.17-3.21 (m, 1H), 3.23 (s, 3H), 3.47-3.54 (m, 1H), 3.64-3.67 (m, 1H), 3.78 (d, 1H), 3.83 (s, 3H), 3.97-4.01 (m, 1H), 4.16 (d, 1H), 4.46 (s, 3H), 5.23 (s, 2H), 6.68-6.70 (m, 1H), 6.69 (s, 1H), 7.77 (m, 1H), 7.97 (s, 1H)

LCMS Spectrum: MH+ 393, retention time 1.17 min, 5 min acid method

EXAMPLE 2

N-[4-[4-[(3S)-3-methylmorpholin-4-yl]-6-(methylsulfonylmethyl)pyrimidin-2-yl]phenyl]azetidine-1-carboxamide

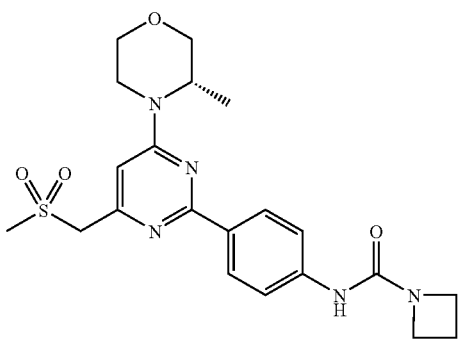

Phosgene 20% solution in toluene (0.245 ml, 0.50 mmol) was diluted with dichloromethane (0.5 mL). 4-[4-[(3S)-3-Methylmorpholin-4-yl]-6-(methylsulfonylmethyl)pyrimidin-2-yl]aniline (150 mg, 0.41 mmol) was dissolved in dichloromethane (2 mL) and pyridine (0.5 mL). This was added to the phosgene solution dropwise over 2 minutes. The reaction was stirred at room temp for 1 hour. Then azetidine (0.034 mL, 0.50 mmol) was added and the mixture stirred at room temp for 1 hour. The reaction was partioned between water and ethyl acetate (25 mL of each). The organic layer was dried over magnesium sulphate and evaporated to dryness. The yellow oil was purified by chromatography, eluting with 10-70% ethyl acetate in isohexane, to give the desired material as a yellow foam (50 mg, 25%).

NMR Spectrum: $^1$H NMR (399.9 MHz, DMSO-d$_6$) δ 1.25 (d, 3H), 2.16-2.24 (m, 2H), 3.19-3.23 (m, 4H), 3.47-3.54 (m, 1H), 3.64-3.68 (m, 1H), 3.79 (d, 1H), 3.99 (t, 5H), 4.17 (s, 1H), 4.49 (s, 3H), 6.79 (s, 1H), 7.62-7.64 (m, 2H), 8.20-8.23 (m, 2H), 8.57 (s, 1H)

LCMS Spectrum: MH+ 446, retention time 1.37 min, Method 5 Min Acid

The following compounds were prepared in an analogous manner to N-[4-[4-[(3S)-3-methylmorpholin-4-yl]-6-(methylsulfonylmethyl)pyrimidin-2-yl]phenyl]azetidine-1-carboxamide from 4-[4-[(3S)-3-methylmorpholin-4-yl]-6-(methylsulfonylmethyl)pyrimidin-2-yl]aniline and the appropriate amine.

| Example | Structure | NAME | LCMS MH+ | Retention time (min) | Notes |
|---|---|---|---|---|---|
| 2a | 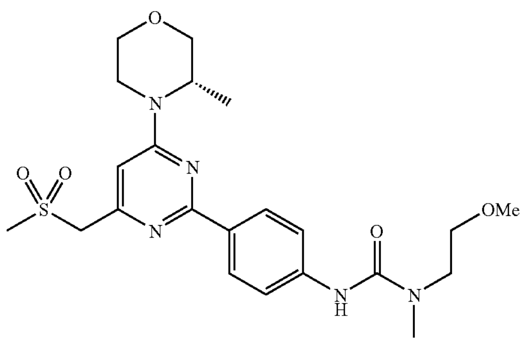 | 1-(2-methoxyethyl)-1-methyl-3-[4-[4-[(3S)-3-methylmorpholin-4-yl]-6-(methylsulfonylmethyl)pyrimidin-2-yl]phenyl]urea | 478 | 1.46 | N/a |
| 2b | 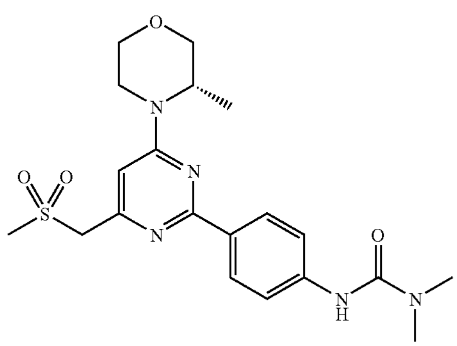 | 1,1-dimethyl-3-[4-[4-[(3S)-3-methylmorpholin-4-yl]-6-(methylsulfonylmethyl)pyrimidin-2-yl]phenyl]urea | 434 | 1.28 | Purified by reverse phase chromatography |
| 2c | 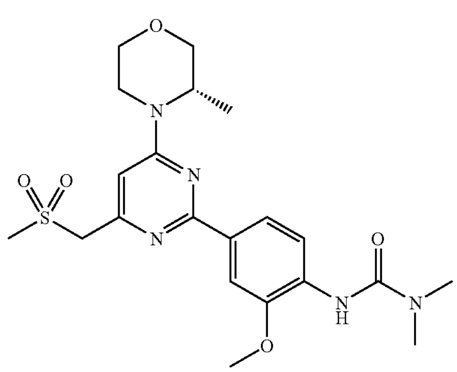 | 3-[2-methoxy-4-[4-[(3S)-3-methylmorpholin-4-yl]-6-(methylsulfonylmethyl)pyrimidin-2-yl]phenyl]-1,1-dimethyl-urea | 464 | 1.54 | Purified by reverse phase chromatography |
| 2d | 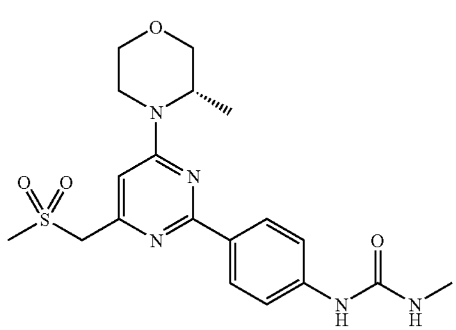 | 1-methyl-3-[4-[4-[(3S)-3-methylmorpholin-4-yl]-6-(methylsulfonylmethyl)pyrimidin-2-yl]phenyl]urea | 420 | 1.19 | Purified by reverse phase chromatography |

-continued

| Example | Structure | NAME | LCMS MH+ | Retention time (min) | Notes |
|---|---|---|---|---|---|
| 2e | 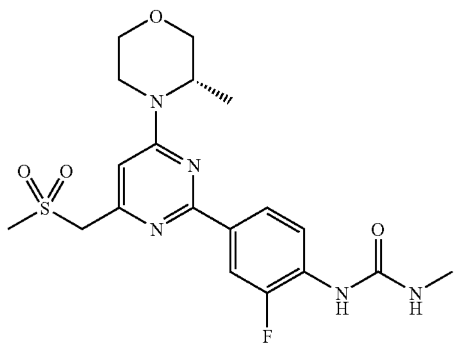 | 3-[2-fluoro-4-[4-[(3S)-3-methylmorpholin-4-yl]-6-(methylsulfonylmethyl)pyrimidin-2-yl]phenyl]-1-methyl-urea | 438 | 1.44 | Purified by reverse phase chromatography |
| 2f | 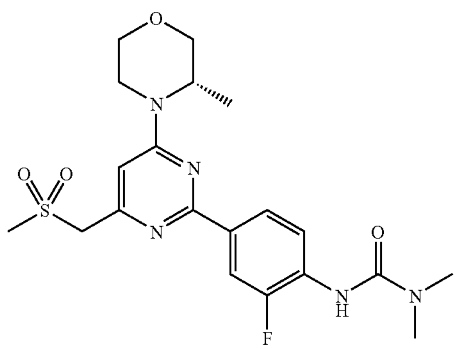 | 3-[2-fluoro-4-[4-[(3S)-3-methylmorpholin-4-yl]-6-(methylsulfonylmethyl)pyrimidin-2-yl]phenyl]-1,1-dimethyl-urea | 452 | 1.55 | Purified by reverse phase chromatography |

Example 2a: $^1$H NMR (399.9 MHz, DMSO-d$_6$) δ 1.25 (d, 3H), 3.00 (s, 3H), 3.21 (s, 3H), 3.23-3.27 (m, 2H), 3.45 (m, 2H), 3.51 (s, 4H), 3.53 (m, 1H), 3.64-3.68 (m, 1H), 3.79 (d, 1H), 3.98-4.02 (m, 1H), 4.17-4.21 (m, 1H), 4.50 (s, 3H), 6.79 (s, 1H), 7.58 (s, 2H), 8.21-8.23 (m, 2H), 8.47 (s, 1H)

Example 2b: $^1$H NMR (399.9 MHz, DMSO-d$_6$) δ1.24-1.26 (m, 3H), 2.96 (s, 6H), 3.21 (s, 3H), 3.25 (d, 1H), 3.48-3.54 (m, 1H), 3.64-3.68 (m, 1H), 3.79 (d, 1H), 3.98-4.02 (m, 1H), 4.19 (d, 1H), 4.49 (s, 3H), 6.79 (s, 1H), 7.58-7.62 (m, 2H), 8.20-8.23 (m, 2H), 8.50 (s, 1H)

Example 2c: $^1$H NMR (399.9 MHz, DMSO-d$_6$) δ1.25-1.27 (m, 3H), 2.97 (s, 6H), 3.18 (m, 1H), 3.23 (s, 3H), 3.48-3.55 (m, 1H), 3.65-3.69 (m, 1H), 3.79 (d, 1H), 3.93 (s, 3H), 3.98-4.02 (m, 1H), 4.20 (d, 1H), 4.47 (s, 1H), 4.51 (s, 2H), 6.82 (s, 1H), 7.52 (s, 1H), 7.91-7.94 (m, 2H), 8.00 (s, 1H)

Example 2d: $^1$H NMR (399.9 MHz, DMSO-d$_6$) δ1.25 (d, 3H), 2.66-2.67 (d, 3H), 3.21 (s, 3H), 3.23 (d, 1H), 3.47-3.54 (m, 1H), 3.64-3.68 (m, 1H), 3.79 (d, 1H), 3.97-4.01 (m, 1H), 4.18 (d, 1H), 4.48 (m, 1H), 4.49 (s, 2H), 6.08 (q, 1H), 6.78 (s, 1H), 7.49-7.53 (m, 2H), 8.20-8.22 (m, 2H), 8.76 (s, 1H)

Example 2e: $^1$H NMR (399.9 MHz, DMSO-d$_6$) δ1.24-1.26 (m, 3H), 2.69 (d, 3H), 3.23-3.24 (m, 1H), 3.26-3.27 (m, 1H), 3.20 (s, 3H), 3.47-3.54 (m, 1H), 3.64-3.67 (m, 1H), 3.79 (d, 1H), 3.97-4.01 (m, 1H), 4.16-4.20 (m, 1H), 4.50 (s, 2H), 6.57 (q, 1H), 6.82 (s, 1H), 8.02-8.09 (m, 1H), 8.05-8.07 (m, 1H), 8.29 (m, 1H), 8.55 (d, 1H)

Example 2f: $^1$H NMR (399.9 MHz, DMSO-d$_6$) δ1.25-1.27 (m, 3H), 2.96 (s, 6H), 3.20 (s, 3H), 3.48-3.55 (m, 1H), 3.64-3.68 (m, 1H), 3.79 (d, 1H), 3.98-4.02 (m, 1H), 4.21 (t, 1H), 4.40 (m, 1H), 4.51 (s, 2H), 6.85 (s, 1H), 7.68 (t, 1H), 8.02-8.11 (m, 2H), 8.15 (s, 1H)

Test (a): Example (2) 0.31 μM; Example (2a) 2.3 μM; Example (2b) 0.29 μM; Example (2c) 1.2 μM; Example (2d) 0.0068 μM; Example (2e) 0.038 μM; Example (2f) 1.7 μM.

EXAMPLE 3

1-[2-Methyl-4-[4-[(3S)-3-methylmorpholin-4-yl]-6-(methylsulfonylmethyl)pyrimidin-2-yl]phenyl]-3-phenyl-urea

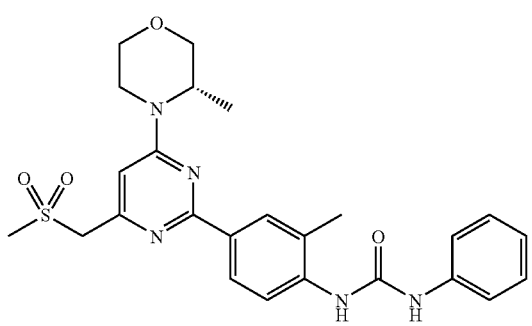

2-Methyl-4-[4-[(3S)-3-methylmorpholin-4-yl]-6-(methylsulfonylmethyl)pyrimidin-2-yl]aniline (130 mg, 0.34 mmol) was dissolved in 1,4-dioxane (4 mL). Phenylisocyanate (0.038 mL, 0.34 mmol) was added and the reaction heated at 75° C. for 3 hours. The reaction mixture was evaporated to dryness and the resultant residue triturated with ethyl acetate to give the desired compound as a cream solid (42 mg).

NMR Spectrum: $^1$H NMR (400.13 MHz, DMSO-d$_6$) δ 1.25 (s, 3H), 2.34 (s, 3H), 3.21 (s, 3H), 3.23-3.26 (m, 1H), 3.48-3.55 (m, 1H), 3.64-3.68 (m, 1H), 3.79 (d, 1H), 4.00 (d, 1H), 4.20 (d, 1H), 4.50 (s, 3H), 6.79 (s, 1H), 6.97-7.01 (m, 1H), 7.31 (d, 2H), 7.47-7.50 (m, 2H), 8.08 (s, 2H), 8.13 (d, 2H), 9.13 (s, 1H)

LCMS Spectrum: MH+ 496, retention time 2.08 minutes, Method 5 Min Acid

The following compound was prepared in an analogous fashion from the appropriate aniline and isocyanate.

| Example | Structure | NAME | LCMS MH+ | Retention time (min) | Notes |
|---|---|---|---|---|---|
| 3a | 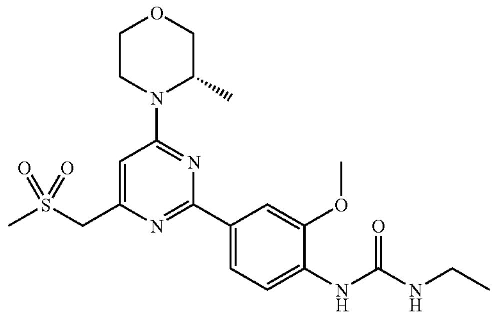 | 1-ethyl-3-[2-methoxy-4-[4-[(3S)-3-methylmorpholin-4-yl]-6-(methylsulfonylmethyl)pyrimidin-2-yl]phenyl]urea | 464 | 1.54 | Purified by reverse phase chromatography followed by normal phase chromatography |
| 3b | 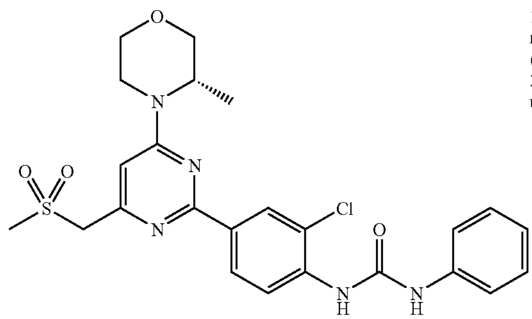 | 1-[2-Chloro-4-[4-[(3S)-3-methylmorpholin-4-yl]-6-(methylsulfonylmethyl)pyrimidin-2-yl]phenyl]-3-phenyl-urea | 515 | 2.51 | Purified on silica eluting with 0-4% methanol in DCM |
| 3c | 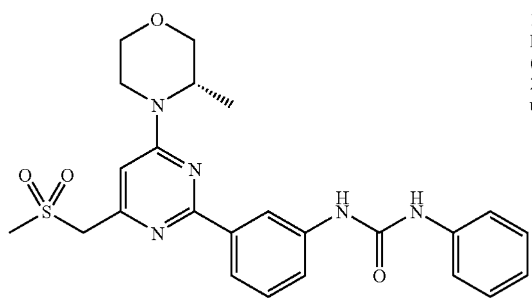 | 1-[3-[4-[(3S)-3-Methylmorpholin-4-yl]-6-(methylsulfonylmethyl)pyrimidin-2-yl]phenyl]-3-phenyl-urea | 481 | 2.30 | Purified by recrystallisation from DMF/water (twice) followed by trituration with acetonitrile |
| 3d | 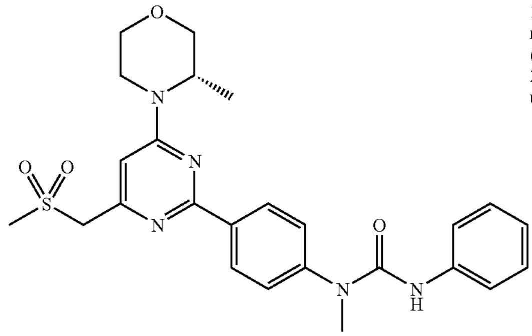 | 1-Methyl-1-[4-[4-[(3S)-3-methylmorpholin-4-yl]-6-(methylsulfonylmethyl)pyrimidin-2-yl]phenyl]-3-phenyl-urea | 496 | 2.18 | |

Example 3a: ¹H NMR (400.13 MHz, DMSO-d₆) δ1.07 (t, 3H), 1.25 (d, 3H), 3.09-3.14 (m, 2H), 3.19-3.24 (m, 1H), 3.25 (s, 3H), 3.47-3.54 (m, 1H), 3.64-3.68 (m, 1H), 3.78 (d, 1H), 3.92 (s, 3H), 3.97-4.01 (m, H), 4.17-4.20 (m, 1H), 4.50 (s, 3H), 6.78 (s, 1H), 6.95 (t, 1H), 7.87-7.90 (m, 2H), 8.06 (s, 1H), 8.21-8.24 (m, 1H)

Example 3b: ¹H NMR (400.13 MHz, DMSO-d₆) δ1.26 (d, 3H), 3.20 (s, 3H), 3.25 (d, 1H), 3.48-3.54 (m, 1H), 3.64-3.68 (m, 1H), 3.79 (d, 1H), 3.98-4.02 (m, 1H), 4.20 (d, 1H), 4.48 (m, 1H), 4.52 (s, 2H), 6.84 (s, 1H), 7.02 (t, 1H), 7.32 (d, 2H), 7.49 (d, 2H), 8.24-8.27 (m, 1H), 8.34 (d, 1H), 8.34-8.37 (m, 1H), 8.49 (s, 1H), 9.52 (s, 1H)

Example 3c: ¹H NMR (400.13 MHz, DMSO-d₆) δ1.27 (d, 3H), 3.23 (s, 3H), 3.26 (m, 1H), 3.49-3.56 (m, 1H), 3.65-3.69 (m, 1H), 3.80 (d, 1H), 3.99-4.03 (m, 1H), 4.20 (d, 1H), 4.53 (s, 3H), 6.87 (s, 1H), 6.98 (t, 1H), 7.29 (t, 2H), 7.40 (t, 1H), 7.47 (d, 2H), 7.71-7.74 (m, 1H), 7.95 (d, 1H), 8.31 (s, 1H), 8.65 (s, 1H), 8.82 (s, 1H)

Example 3d: ¹H NMR (400.13 MHz, DMSO-d₆) δ1.25 (d, 3H), 3.21 (s, 3H), 3.34 (s, 3H), 3.39 (m, 1H), 3.50 (d, 1H), 3.66 (d, 1H), 3.79 (d, 1H), 4.00 (d, 1H), 4.17 (d, 1H), 4.52 (s, 3H), 6.85 (s, 1H), 6.96 (t, 1H), 7.24 (t, 2H), 7.44 (m, 4H), 8.33 (s, 1H), 8.35 (s, 2H)

Test (a): Example (3) 1.5 μM; Example (3a) 0.1 μM; Example (3b) 0.44 μM; Example (3c) 3.3 μM; Example (3d) 2.9 μM.

The preparation of 2-methyl-4-[4-[(3S)-3-methylmorpholin-4-yl]-6-(methylsulfonylmethyl)pyrimidin-2-yl]aniline is described below.

2-Methyl-4-[4-[(3S)-3-methylmorpholin-4-yl]-6-(methylsulfonylmethyl)pyrimidin-2-yl]aniline

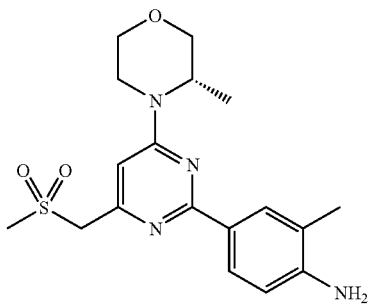

4-Bromo-2-methylaniline (1.00 g, 5.37 mmol), potassium acetate (1.59 g, 16.1 mmol) and 4,4,5,5-tetramethyl-2-(4,4,5,5-tetramethyl-1,3,2-dioxaborolan-2-yl)-1,3,2-dioxaborolane (1.64 g, 6.45 mmol) were dissolved in 1,4-dioxane (20 mL) and the solution degassed for 5 minutes. Dichlorobis(triphenylphosphine)palladium (264 mg, 0.32 mmol) was added and the reaction stirred at 90° C. for 4 hours. 2-Chloro-4-[(3S)-3-methylmorpholin-4-yl]-6-(methylsulfonylmethyl) pyrimidine (1.65 g, 5.37 mmol), ethanol (1.5 mL), 2M sodium carbonate aqueous solution (3 mL) and dichlorobis (triphenylphosphine)palladium (264 mg) were added. The reaction was maintained at 90° C. for 18 hours then allowed to cool to room temperature. Water (15 mL) and ethyl acetate (15 mL) were added and the mixture was filtered to remove the insoluble impurities. The phases were separated and the aqueous layer extracted with a second portion of ethyl acetate (15 mL). The combined organics were dried (MgSO₄) and concentrated in vacuo. The residue was chromatographed on silica, eluting with 0-3% methanol in DCM, to give the desired compound as a beige foam (290 mg).

NMR Spectrum: ¹H NMR (400.13 MHz, DMSO-d₆) δ1.22-1.24 (m, 3H), 3.16-3.19 (m, 1H), 3.20 (s, 3H), 3.46-3.52 (m, 1H), 3.62-3.66 (m, 1H), 3.77 (d, 1H), 3.90 (s, 1H), 3.96-4.00 (m, 1H), 4.14-4.18 (m, 1H), 4.43 (s, 2H), 4.45 (s, 1H), 5.32 (s, 2H), 6.63 (s, 1H), 6.66 (s, 1H), 7.91-7.94 (m, 2H)

LCMS Spectrum: MH+ 377, retention time 1.21 min, Method 5 Min Acid

The preparation of 2-chloro-4-[4-[(3S)-3-methylmorpholin-4-yl]-6-(methylsulfonylmethyl)pyrimidin-2-yl]aniline is described below.

2-Chloro-4-[4-[(3S)-3-methylmorpholin-4-yl]-6-(methylsulfonylmethyl)pyrimidin-2-yl]aniline

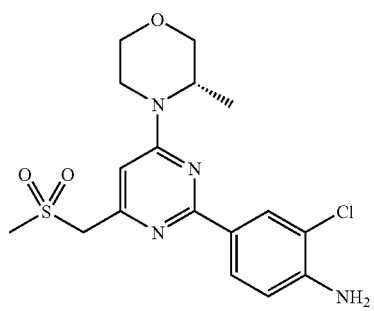

4-Bromo-2-chloroaniline (1.00 g, 4.84 mmol), potassium acetate (1.58 g, 14.5 mmol) and bis(pinacolato)diboron (1.64 g, 5.81 mmol) were dissolved in 1,4-dioxane (20 mL). The solution was degassed under nitrogen for 5 min. [1,1'-Bis(diphenylphosphino)ferrocene] (213 mg, 0.29 mmol) was added. The reaction was stirred at 90° C. for 4 hours. Ethanol (1.5 mL), 2-chloro-4-[(3S)-3-methylmorpholin-4-yl]-6-(methylsulfonylmethyl)pyrimidine (1.49 g, 4.84 mmol), 2M sodium carbonate solution (5.4 mL) and [1,1'-bis(diphenylphosphino)ferrocene] (213 mg) were added and heating was continued for 18 hours. The reaction was evaporated to dryness and the residue partitioned between water (15 mL) and ethyl acetate (15 mL). The mixture was filtered to remove the insoluble material, the phases were separated and the aqueous layer was washed with ethyl acetate (15 mL). The combined organics were dried over magnesium sulfate and evaporated to a yellow oil. The crude product was purified by chromatography on silica, eluting with a 0-4% methanol in DCM, to give the desired material as a cream foam (1.1 g).

NMR Spectrum: ¹H NMR (400.13 MHz, DMSO-d₆) δ1.22-1.24 (m, 3H), 3.18 (s, 3H), 3.19-3.21 (m, 1H), 3.45-3.52 (m, 1H), 3.62-3.65 (m, 1H), 3.77 (d, 1H), 3.96-4.00 (m, 1H), 4.13-4.17 (m, 1H), 4.46 (s, 3H), 5.82 (s, 2H), 6.72 (s, 1H), 6.85 (d, 1H), 8.00-8.03 (m, 1H), 8.14 (d, 1H)

LCMS Spectrum: MH+ 397, retention time 1.64 min, Method 5 Min Acid

The preparation of 3-[4-[(3S)-3-methylmorpholin-4-yl]-6-(methylsulfonylmethyl)pyrimidin-2-yl]aniline is described below.

3-[4-[(3S)-3-Methylmorpholin-4-yl]-6-(methylsulfonylmethyl)pyrimidin-2-yl]aniline

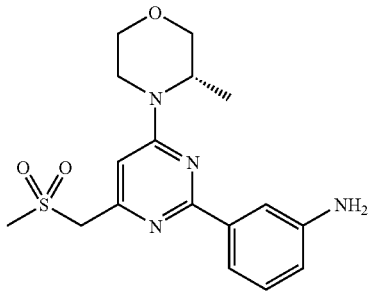

2-Chloro-4-[(3S)-3-methylmorpholin-4-yl]-6-(methylsulfonylmethyl)pyrimidine (1.50 g, 4.91 mmol) was dissolved in 18% DMF in 7:3:2 dimethoxyethane:water:ethanol (15 mL). (3-Aminophenyl)boronic acid (1.01 g, 7.36 mmol), 2M sodium carbonate (5 mL) and dichlorobis(triphenylphosphine) palladium (173 mg, 0.25 mmol) were added to the solution. The reaction was refluxed at 90° C. for 18 hours under a nitrogen atmosphere then the reaction allowed to cool and partitioned between ethyl acetate (50 mL) and water (50 mL). The organic layer was dried over magnesium sulphate, filtered and vacuumed to dryness. The resultant brown oil was dissolved in DCM and filtered to remove insoluble material then the filtrate chromatographed on silica, eluting with 0-4% methanol in DCM, to give the desired product as a yellow oil (1.61 g).

NMR Spectrum: $^1$H NMR (400.13 MHz, DMSO-$d_6$) δ1.24-1.26 (m, 3H), 2.90 (s, 3H), 3.19-3.26 (m, 1H), 3.47-3.54 (m, 1H), 3.64-3.68 (m, 1H), 3.77-3.80 (m, 1H), 3.99 (d, 1H), 4.17 (s, 1H), 4.49 (s, 3H), 6.67-6.70 (m, 1H), 6.81 (s, 1H), 7.11 (d, 1H), 7.50-7.52 (m, 1H), 7.57-7.58 (m, 1H), 7.96 (s, 1H)

LCMS Spectrum: MH+ 364, retention time 0.93 min, Method 5 Min Acid

The preparation of N-methyl-4-[4-[(3S)-3-methylmorpholin-4-yl]-6-(methylsulfonylmethyl)pyrimidin-2-yl]aniline is described below N-Methyl-4-[4-[(3S)-3-methylmorpholin-4-yl]-6-(methylsulfonylmethyl)pyrimidin-2-yl]aniline

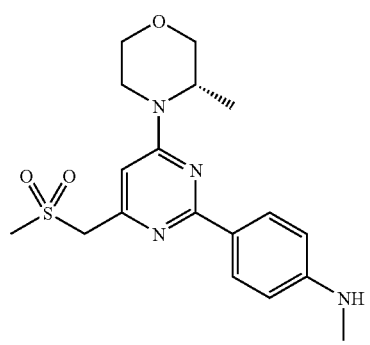

2-Chloro-4-[(3S)-3-methylmorpholin-4-yl]-6-(methylsulfonylmethyl)pyrimidine (1.01 g, 3.30 mmol) was dissolved in 18% DMF in 7:3:2 dimethoxy ethane:water:ethanol (7 mL). N-Methyl-4-(4,4,5,5-tetramethyl-1,3,2-dioxaborolan-2-yl)aniline (1.00 g, 4.29 mmol), 2M sodium carbonate solution (4 mL) and dichlorobis(triphenylphosphine) palladium (116 mg, 0.16 mmol) were added to the solution. The reaction was refluxed at 90° C. for 3 hours under nitrogen atmosphere then the mixture allowed to cool and partitioned ethyl acetate (30 mL) and water (30 mL). The organic layer was dried over magnesium sulphate, filtered and evaporated to dryness. The brown oil was dissolved in DCM and filtered to remove insoluble material then the filtrate chromatographed on silica, eluting with 0-4% methanol in DCM, to give the desired product as a yellow foam (1.12 g, 90%)

NMR Spectrum: $^1$H NMR (400.13 MHz, DMSO-$d_6$) δ1.23 (d, 3H), 2.74 (d, 3H), 3.06-3.17 (m, 1H), 3.21 (s, 3H), 3.46-3.52 (m, 1H), 3.62-3.66 (m, 1H), 3.77 (d, 1H), 3.96-4.00 (m, 1H), 4.14 (d, 1H), 4.44 (s, 2H), 4.46 (s, 1H), 6.14 (q, 1H), 6.57-6.61 (m, 2H), 6.67 (s, 1H), 8.10-8.13 (m, 2H)

LCMS Spectrum: MH+ 377, retention time 1.33 min, Method 5 Min Acid

EXAMPLE 4

1-Ethyl-3-[2-fluoro-4-[4-[(3S)-3-methylmorpholin-4-yl]-6-(methylsulfonylmethyl)pyrimidin-2-yl]phenyl]urea

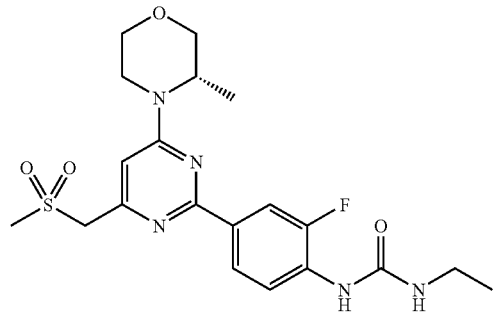

Bis(trichloromethyl) carbonate (44 mg, 0.16 mmol) was dissolved in DCM (0.25 mL) to give a colourless solution. 2-Fluoro-4-[4-[(3S)-3-methylmorpholin-4-yl]-6-(methylsulfonylmethyl)pyrimidin-2-yl]aniline (140 mg, 0.39 mmol) was dissolved in DCM (2.0 mL) and pyridine (0.2 mL). The resultant solution was added dropwise to the bis(trichloromethyl) carbonate solution at 0° C. and the mixture allowed to warm to room temperature then stirred for 10 minutes. Ethylamine (2M in THF, 0.5 mL, 1.0 mmol) was added and the mixture stirred at room temperature for 1 hour. Water (5 mL) was added and the aqueous layer was extracted with DCM (5 mL). The combined organic layers were dried ($MgSO_4$) and concentrated in vacuo. The crude oil was purified by prep HPLC to give the desired material as a white solid (149 mg, 84%).

NMR Spectrum: $^1$H NMR (400.13 MHz, DMSO-$d_6$) δ1.08 (t, 3H), 1.25 (d, 3H), 3.13-3.18 (m, 2H), 3.20 (s, 3H), 3.22-3.27 (m, 1H), 3.47-3.53 (m, 1H) 3.63-3.67 (m, 1H), 3.78 (d, 1H), 3.97-4.01 (m, 1H), 4.16-4.20 (m, 1H), 4.49 (m, 3H), 6.68 (t, 1H), 6.81 (s, 1H), 8.01-8.08 (m, 2H), 8.29 (t, 1H), 8.47 (d, 1H)

Mass Spectrum:

The following compounds were prepared in an analogous fashion using the appropriate aniline and amines.

| Example | Structure | NAME | LCMS MH+ | Retention time (min) |
|---|---|---|---|---|
| 4a | 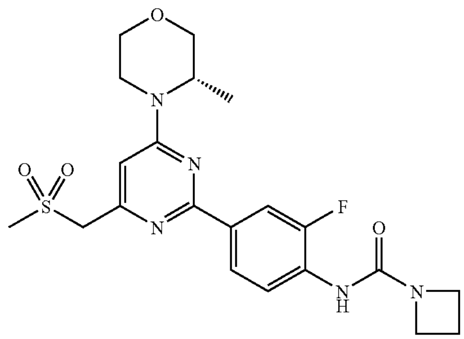 | N-[2-Fluoro-4-[4-[(3S)-3-methylmorpholin-4-yl]-6-(methylsulfonylmethyl)pyrimidin-2-yl]phenyl]azetidine-1-carboxamide | 463 | 1.61 |
| 4b | 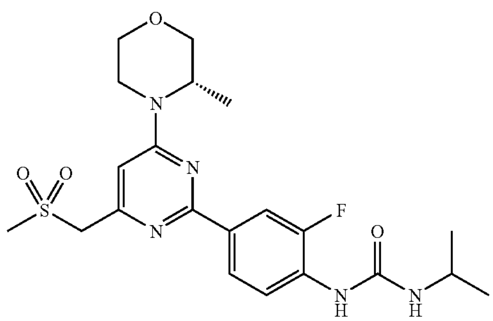 | 3-[2-fluoro-4-[4-[(3S)-3-methylmorpholin-4-yl]-6-(methylsulfonylmethyl)pyrimidin-2-yl]phenyl]-1-propan-2-yl-urea | 465 | 1.83 |
| 4c | 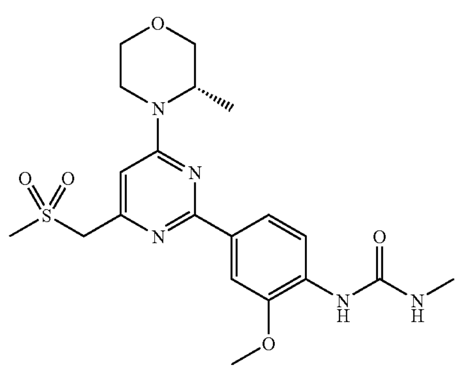 | 3-[2-methoxy-4-[4-[(3S)-3-methylmorpholin-4-yl]-6-(methylsulfonylmethyl)pyrimidin-2-yl]phenyl]-1-methyl-urea | 450 | 1.36 |
| 4d* | 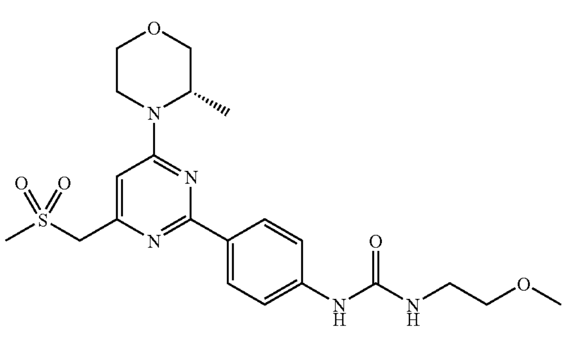 | 1-(2-methoxyethyl)-3-[4-[4-[(3S)-3-methylmorpholin-4-yl]-6-(methylsulfonylmethyl)pyrimidin-2-yl]phenyl]urea | 464 | 1.32 |

-continued

| Example | Structure | NAME | LCMS MH+ | Retention time (min) |
|---|---|---|---|---|
| 4e* | 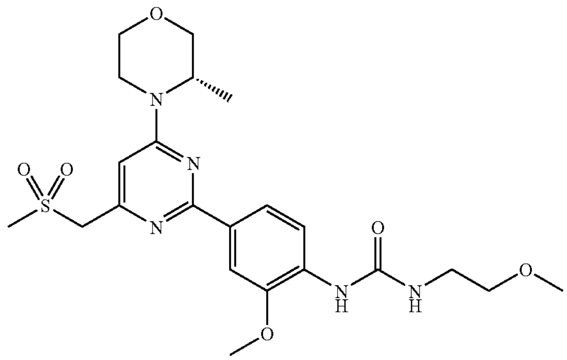 | 1-(2-methoxyethyl)-3-[2-methoxy-4-[4-[(3S)-3-methylmorpholin-4-yl]-6-(methylsulfonylmethyl)pyrimidin-2-yl]phenyl]urea | 440 | 1.47 |
| 4f* | 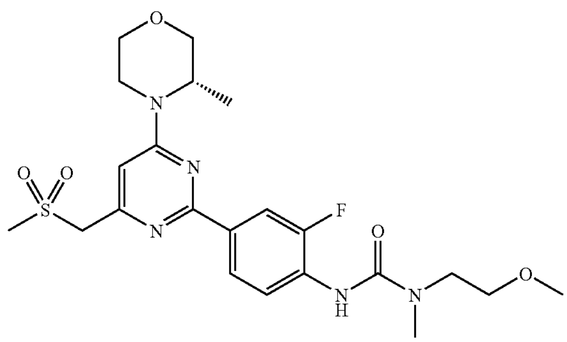 | 3-[2-Fluoro-4-[4-[(3S)-3-methylmorpholin-4-yl]-6-(methylsulfonylmethyl)pyrimidin-2-yl]phenyl]-1-(2-methoxyethyl)-1-methyl-urea | 495 | 1.74 |
| 4g* | 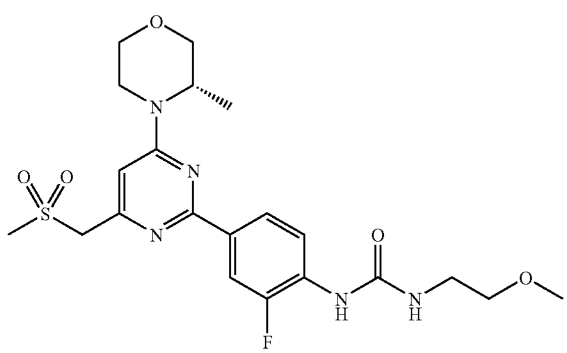 | 3-[2-fluoro-4-[4-[(3S)-3-methylmorpholin-4-yl]-6-(methylsulfonylmethyl)pyrimidin-2-yl]phenyl]-1-(2-methoxyethyl)urea | 482 | 1.87 |

*Chromatographed on silica, eluting with 0-5% methanol in DCM

Example 4a: $^1$H NMR (400.13 MHz, DMSO-$d_6$) δ1.25 (d, 3H), 2.16-2.24 (m, 2H), 3.20 (s, 3H), 3.23-3.26 (m, 1H), 3.47-3.54 (m, 1H), 3.63-3.67 (m, 1H), 3.78 (d, 1H), 4.00 (t, 5H), 4.19 (d, 1H), 4.50 (s, 3H), 6.84 (s, 1H), 7.83-7.87 (m, 1H, 8.04 (d, 1H6), 8.08-8.10 (m, 1H), 8.18 (s, 1H)

Example 4b: $^1$H NMR (400.13 MHz, DMSO-$d_6$) δ1.12 (d, 6H), 1.25 (d, 3H), 3.20 (s, 3H), 3.24 (d, 1H), 3.47-3.53 (m, 1H), 3.63-3.67 (m, 1H), 3.74-3.82 (m, 2H), 3.97-4.01 (m, 1H), 4.18 (d, 1H), 4.49 (s, 3H), 6.63 (d, 1H), 6.81 (s, 1H), 8.01-8.08 (m, 2H), 8.29 (t, 1H), 8.37 (d, 1H)

Example 4c: $^1$H NMR (399.9 MHz, DMSO-$d_6$) δ1.25-1.26 (m, 3H), 2.66-2.67 (m, 3H), 3.18 (d, 1H), 3.23 (s, 3H), 3.48-3.55 (m, 1H), 3.65-3.68 (m, 1H), 3.79 (d, 1H), 3.92 (s, 3H), 3.98-4.02 (m, 1H) 4.19 (s, 1H), 4.50 (s, 2H), 6.79 (s, H), 6.85 (d, 1H), 7.90 (s, 1H), 8.11 (s, 1H), 8.22-8.24 (m, 1H)

Example 4d: $^1$H NMR (400.13 MHz, DMSO-$d_6$) δ1.24 (d, 3H), 3.19-3.24 (m, 2H), 3.21 (s, 3H), 3.27 (s, 3H), 3.40 (t, 2H), 3.47-3.53 (m, 1H), 3.63-3.67 (m, 1H), 3.78 (d, 1H), 3.97-4.01 (m, 1H), 4.17 (s, 1H), 4.49 (s, 3H), 6.27 (t, 1H), 6.77 (s, 1H), 7.47-7.51 (m, 2H), 8.19-8.23 (m, 2H), 8.78 (s, 1H)

Example 4e: $^1$H NMR (399.9 MHz, DMSO-$d_6$) δ1.25-1.26 (m, 3H), 3.23 (s, 3H), 3.27 (s, 1H), 3.28-3.21 (m, 2H), 3.38-3.40 (m, 2H), 3.51 (d, 1H), 3.66 (d, 1H), 3.77 (s, 1H), 3.92 (s, 3H), 4.00 (d, 1H), 4.17-4.21 (m, 1H), 4.50 (s, 3H), 6.79 (s, 1H), 7.12 (s, 1H), 7.88-7.90 (m, 2H), 8.22-8.24 (m, 1H), 8.26 (1s, H)

Example 4f: $^1$H NMR (400.13 MHz, DMSO-$d_6$) δ1.24-1.26 (m, 3H), 2.97 (s, 3H), 3.20 (s, 3H), 3.23-3.26 (m, 1H), 3.47-3.56 (m, 5H), 3.64-3.67 (m, 1H), 3.78 (d, 1H), 3.97-4.01 (m, 1H), 4.17-4.21 (m, 1H), 4.50 (s, 3H), 6.84 (s, 1H), 7.82 (t, 1H), 8.02-8.10 (m, 2H), 8.41 (s, 1H)

Example 4g: $^1$H NMR (399.9 MHz, DMSO-$d_6$) δ1.25 (d, 3H), 3.20 (s, 3H), 3.23 (m, 1H), 3.29 (m, 2H), 3.30 (s, 3H), 3.41 (t, 2H), 3.51 (d, 1H), 3.65 (d, 1H), 3.78 (d, 1H), 3.97-4.01

(m, 1H), 4.19 (d, 1H), 4.50 (s, 3H), 6.82 (s, 1H), 6.87 (t, 1H), 8.02-8.09 (m, 2H), 8.29 (t, 1H), 8.63 (d, 1H)

Test (a): Example (4) 0.031 µM; Example (4a) 1 µM; Example (4b) 0.14 µM; Example (4c) 0.8 µM; Example (4d) 0.17 µM; Example (4e) 0.6 µM; Example (4f) 0.68 µM; Example (4g) 0.83 µM.

EXAMPLE 5

1-Ethyl-3-[4-[4-(hydroxymethyl)-6-[(3S)-3-methyl-morpholin-4-yl]pyrimidin-2-yl]phenyl]urea

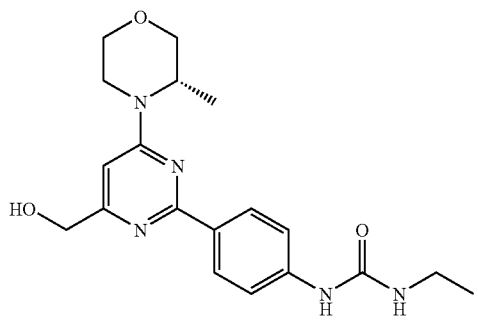

1-[4-[4-[(Dimethyl-tert-butyl-silyl)oxymethyl]-6-[(3S)-3-methylmorpholin-4-yl]pyrimidin-2-yl]phenyl]-3-ethyl-urea (104 mg) was dissolved in THF (10 mL) and TBAF (1.0 M solution, 0.22 mL) was added. The reaction was allowed to stir for 1 hour at room temperature and then passed down a SCX-2 column. The column was washed with methanol and the desired material eluted with 7N ammonia in methanol. The fractions were concentrated in vacuo to give the desired compound (76 mg) as a white solid.

NMR Spectrum: $^1$H NMR (399.9 MHz, DMSO-d$_6$) δ1.07 (3H, t), 1.23 (3H, d), 3.11-3.16 (2H, m), 3.19-3.23 (1H, m), 3.49 (1H, d), 3.62-3.66 (1H, m), 3.77 (1H, d), 3.95-3.99 (1H, m), 4.16 (1H, d), 4.45 (2H, d), 4.48 (1H, s), 5.38 (1H, s), 6.14 (1H, t), 6.66 (1H, s), 7.46 (2H, d), 8.19 (2H, d), 8.62 (1H, s)

Mass Spectrum; M+H$^+$ 372.

Test (a): 0.063 µM.

The preparation of 1-[4-[4-[(dimethyl-tert-butyl-silyl)oxymethyl]-6-[(3S)-3-methylmorpholin-4-yl]pyrimidin-2-yl]phenyl]-3-ethyl-urea is described below.

1-[4-[4-[(Dimethyl-tert-butyl-silyl)oxymethyl]-6-[(3S)-3-methylmorpholin-4-yl]pyrimidin-2-yl]phenyl]-3-ethyl-urea

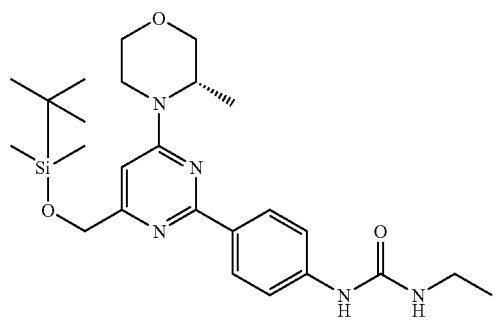

4-[4-[(Dimethyl-tert-butyl-silyl)oxymethyl]-6-[(3S)-3-methylmorpholin-4-yl]pyrimidin-2-yl]aniline (250 mg) was dissolved in 1,4-dioxane (4 mL) and ethyl isocyanate (0.144 mL) added. The reaction was heated to 120° C. for 1 hour in a microwave reactor. The reaction was concentrated in vacuo then the residue chromatographed on silica, eluting with 2.5% methanol in DCM, to give the desired compound (106 mg) as a white solid.

Mass Spectrum; M+H$^+$ 486.

4-[4-[(Dimethyl-tert-butyl-silyl)oxymethyl]-6-[(3S)-3-methylmorpholin-4-yl]pyrimidin-2-yl]aniline

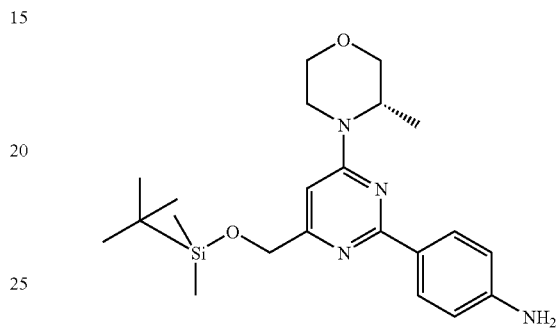

[2-(4-Aminophenyl)-6-[(3S)-3-methylmorpholin-4-yl]pyrimidin-4-yl]methanol (1.54 g) was dissolved in DCM (60 mL) and tert-butyldiemethylsilylchloride (928 mg) and imidozole added. The mixture was stirred at room temperature for 0.5 hours before being filtered and concentrated in vacuo. The residue was chromatographed on silica, eluting with 1% methanol in DCM, to give the desired compound (1.61 g) as a white solid.

NMR Spectrum: $^1$H NMR (399.9 MHz, DMSO-d$_6$) δ0.12-0.13 (6H, m), 0.94-0.95 (9H, m), 1.21 (3H, d), 3.13-3.20 (1H, m), 3.46-3.52 (1H, m), 3.62-3.66 (1H, m), 3.77 (1H, d), 3.96-3.99 (1H, m), 4.13 (1H, d), 4.37-4.39 (1H, m), 4.60 (2H, s), 5.48 (2H, d), 6.50 (1H, s), 6.57-6.59 (2H, m), 8.02-8.04 (2H, m)

Mass Spectrum; M+H$^+$ 415.

[2-(4-Aminophenyl)-6-[(3S)-3-methylmorpholin-4-yl]pyrimidin-4-yl]methanol

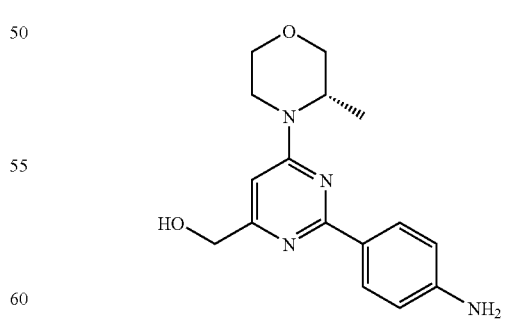

tert-Butyl N-[4-[4-(hydroxymethyl)-6-[(3S)-3-methyl-morpholin-4-yl]pyrimidin-2-yl]phenyl]carbamate (1.20 g) was dissolved in 4M hydrogen chloride in dioxane (5 mL) and dioxane (5 mL). The reaction was stirred for 18 hour then DCM (10 mL) added to help solubilise material. The reaction was stirred at 40° C. for a further 18 hours then evaporated to dryness. The solid was suspended in DCM (20 mL) and a mixture of a saturated aqueous solution of sodium hydrogen carbonate (6 mL) and water (4 mL) was added. The organics were separated, dried (MgSO₄) and concentrated in vacuo to give the desired compound (648 mg) as a pale yellow solid.

NMR Spectrum: $^1$H NMR (399.9 MHz, DMSO-$d_6$) δ1.21 (3H, d), 3.16 (1H, d), 3.48 (1H, d), 3.61-3.65 (1H, m), 3.75 (1H, d), 3.95 (1H, d), 4.13 (1H, d), 4.41 (2H, d), 4.45 (1H, s), 5.32 (1H, t), 5.47 (2H, s), 6.57-6.59 (3H, m), 8.02-8.04 (2H, m)

Mass Spectrum; M+H⁺ 301.

tert-Butyl N-[4-[4-(hydroxymethyl)-6-[(3S)-3-methylmorpholin-4-yl]pyrimidin-2-yl]phenyl]carbamate

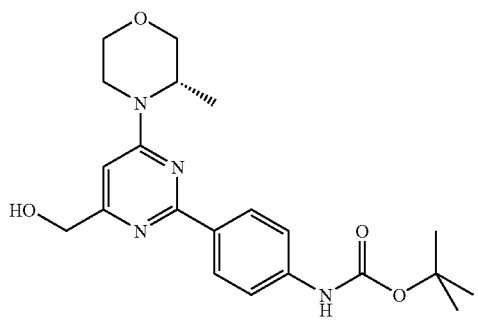

A mixture of [2-chloro-6-[(3S)-3-methylmorpholin-4-yl]pyrimidin-4-yl]methanol (2.44 g), (4-Boc-aminophenyl)boronic acid (4.76 g), 2M solution of sodium carbonate (10 mL) and a solvent mixture (18% DMF in 7:3:2 DME:Water:Ethanol) (35 mL) was degassed. Dichlorobis(triphenylphosphine)palladium (300 mg) was added and the reaction heated at 80° C. for 3 hour. The reaction was allowed to cool and concentrated in vacuo. The residue was partitioned between ethyl acetate (200 mL) and water (200 mL), the organics washed with brine (100 mL) and dried (MgSO₄). The crude material was chromatographed on silica, eluting with 2.5% methanol in DCM, to give the desired compound (4.00 g) as a white solid.

Mass Spectrum; M+H⁺ 401.

[2-Chloro-6-[(3S)-3-methylmorpholin-4-yl]pyrimidin-4-yl]methanol

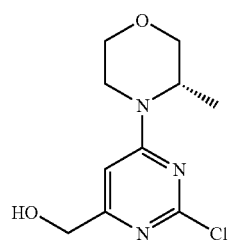

Methyl 2-chloro-6-[(3S)-3-methylmorpholin-4-yl]pyrimidine-4-carboxylate (3.15 g) was dissolved in dry THF (20 mL) and cooled to 0° C. under nitrogen. To this is added dropwise a solution of lithium borohydride (2.0M in THF, 6.09 mL). The solution was allowed to warm to room temperature and stirred for 1 hour. The reaction was quenched with water (20 mL) then evaporated to dryness. The residue was dissolved in ethyl acetate (150 mL) and washed with water (150 mL) followed by brine (50 mL). The organics were concentrated in vacuo to give to the desired compound (2.44 g) as white solid.

NMR Spectrum: $^1$H NMR (399.9 MHz, DMSO-$d_6$) δ1.20-1.21 (3H, m), 3.18-3.22 (1H, m), 3.40-3.47 (1H, m), 3.56-3.60 (1H, m), 3.71 (1H, d), 3.91-3.94 (1H, m), 3.98 (1H, d), 4.35 (3H, d), 5.51 (1H, t), 6.74 (1H, s)

Mass Spectrum; M+H⁺ 244.

Methyl 2-chloro-6-[(3S)-3-methylmorpholin-4-yl]pyrimidine-4-carboxylate

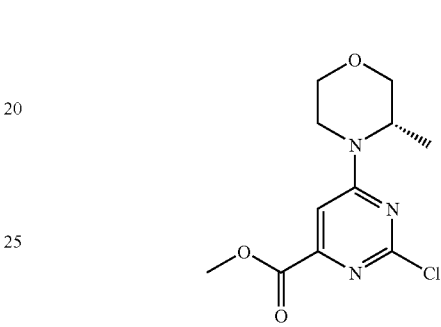

Methyl 2,6-dichloropyrimidine-4-carboxylate (5.00 g) was dissolved in DCM (120 mL). (3S)-3-Methylmorpholine (2.49 g) dissolved in triethylamine (3.70 mL) and DCM (10 mL) was added dropwise to the solution over 10 minutes. The reaction was left to stir at room temperature for 1 hour then the mixture concentrated in vacuo and dissolved in DCM (300 mL). The organics were washed with water (150 mL) and dried (MgSO₄). The crude material was chromatographed on silica, eluting with 2.5% methanol in DCM, to give the desired compound (3.15 g) as a white solid.

NMR Spectrum: $^1$H NMR (399.9 MHz, DMSO-$d_6$) δ1.22-1.24 (3H, m), 3.25 (1H, d), 3.41-3.48 (1H, m), 3.57-3.61 (1H, m), 3.71 (1H, d), 3.87 (3H, s), 3.91-3.95 (1H, m), 4.25 (1H, s), 4.45 (1H, s), 7.29 (1H, s)

Mass Spectrum; M+H⁺ 272.

EXAMPLE 6

1-[4-[4-(Hydroxymethyl)-6-[(3S)-3-methylmorpholin-4-yl]pyrimidin-2-yl]phenyl]-3-phenyl-urea

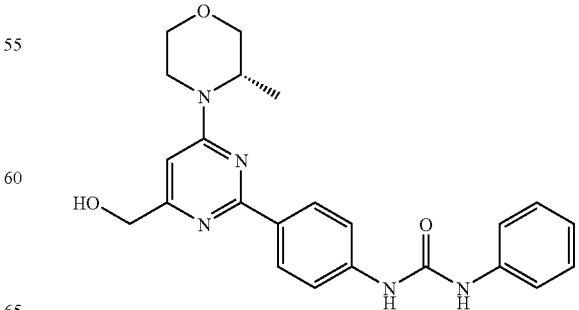

1-(4-Bromo-phenyl)-3-phenyl-urea (960 mg), potassium acetate (969 mg), bis(pinacolato)diboron (1.01 g) was dissolved in 1,4 dioxane (50 mL). The solution was degassed for 5 minutes then 1,1'-bis(diphenylphosphino)ferrocenedichloropalladium(II) dichloromethane adduct added (162 mg) and the reaction was heated to 80° C. for 3 hours. Further 1,1'-bis (diphenylphosphino)ferrocenedichloropalladium(II) dichloromethane adduct was added (162 mg) and the reaction stirred at 80° C. for another 3 hours. [2-Chloro-6-[(3S)-3-methylmorpholin-4-yl]pyrimidin-4-yl]methanol (803 mg), ethanol (3.75 mL), 2M sodium carbonate solution (6.9 mL) and 1,1'-bis(diphenylphosphino)ferrocenedichloropalladium (II) dichloromethane adduct (162 mg) were added and the heating was continued for 16 hours. More ethanol (5 mL) and 1,1'-bis(diphenylphosphino)ferrocenedichloropalladium(II) dichloromethane adduct (162 mg) were added and the reaction was allowed to stir for another 5 hours before being allowed to cool and neutralised with 2M hydrochloric acid. The reaction mixture was passed through three SCX-2 columns, each time loading the sample and washing with methanol, then removing the desired material with 7N ammonia in methanol. The solution was concentrated in vacuo, and the residue chromatographed on silica, eluting with 5% methanol in DCM, to give the desired material (398 mg) as a white solid.

NMR Spectrum: $^1$H NMR (DMSO-$d_6$) δ1.24 (3H, d), 3.20-3.24 (1H, m), 3.47-3.53 (1H, m), 3.63-3.67 (1H, m), 3.77 (1H, d), 3.96-4.00 (1H, m), 4.18 (1H, d), 4.47 (2H, d), 4.50 (1H, s), 5.39 (1H, t), 6.68 (1H, s), 6.97-7.01 (1H, m), 7.28-7.31 (1H, m), 7.30 (1H, s), 7.46-7.48 (2H, m), 7.52-7.56 (2H, m), 8.25-8.27 (2H, m), 8.68 (1H, s), 8.87 (1H, s)

Mass Spectrum; M+H$^+$ 419.

Test (a): 0.56 μM.

The preparation of [2-chloro-6-[(3S)-3-methylmorpholin-4-yl]pyrimidin-4-yl]methanol was described earlier.

EXAMPLE 7

3-[4-[4-(Methylsulfonylmethyl)-6-morpholin-4-yl-pyrimidin-2-yl]phenyl]-1-propan-2-yl-urea

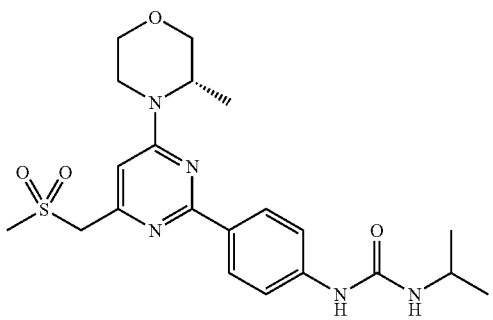

4-[4-(Methylsulfonylmethyl)-6-morpholin-4-yl-pyrimidin-2-yl]aniline (70 mg, 0.2 mmol) and isoproylisocyanate (0.1 mL, 1 mmol) were heated in dioxane (2 mL) at 70° C. for 4 hours. The reaction mixture was evaporated and the residue triturated with ethyl acetate. The suspension was filtered and the white solid washed with ethyl acetate and diethyl ether then dried under vacuum at 60° C. overnight to yield the title compound (38 mg).

LCMS Spectrum: MH+ 434, Retention Time 1.66 min, Method: Monitor Basic

NMR Spectrum: $^1$H NMR (399.9 MHz, DMSO-$d_6$) δ1.11 (d, 6H), 3.2 (s, 3H), 3.7 (m, 8H), 3.76 (m, 1H), 4.48 (s, 2H), 6.05 (d, 1H), 6.8 (s, 1H), 7.48 (d, 2H), 8.2 (d, 2H), 8.54 (s, 1H)

The following compounds were prepared in an analogous fashion from XXX using the appropriate isocyanate.

| Example | Structure | NAME | LCMS MH+ | Retention Time (min) |
|---|---|---|---|---|
| 7a | 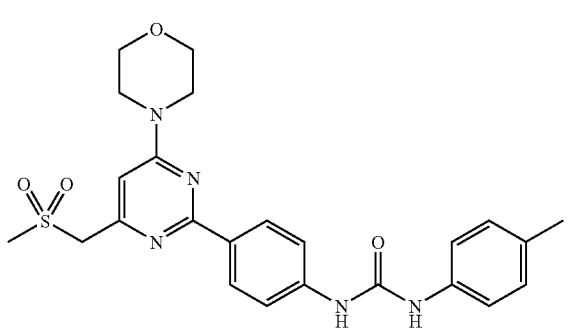 | 1-(4-methylphenyl)-3-[4-[4-(methylsulfonylmethyl)-6-morpholin-4-yl-pyrimidin-2-yl]phenyl]urea | 482.03 | 2.15 |

| Example | Structure | NAME | LCMS MH+ | Retention Time (min) |
|---|---|---|---|---|
| 7b | 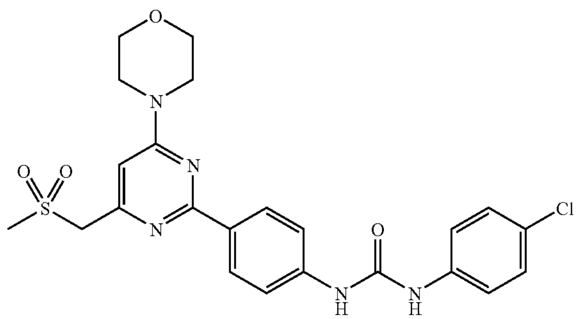 | 3-(4-chlorophenyl)-1-[4-[4-(methylsulfonylmethyl)-6-morpholin-4-yl-pyrimidin-2-yl]phenyl]urea | 501.95 | 2.26 |
| 7c | 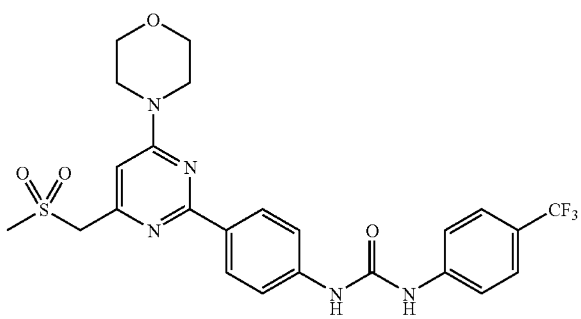 | 1-[4-[4-(methylsulfonylmethyl)-6-morpholin-4-yl-pyrimidin-2-yl]phenyl]-3-[4-(trifluoromethyl)phenyl]urea | 536.00 | 2.39 |
| 7d | 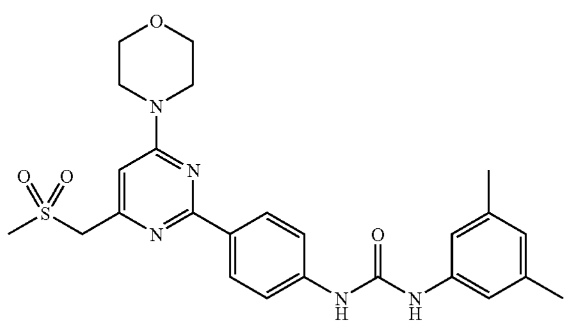 | 1-(3,5-dimethylphenyl)-3-[4-[4-(methylsulfonylmethyl)-6-morpholin-4-yl-pyrimidin-2-yl]phenyl]urea | 496.05 | 2.29 |
| 7e | 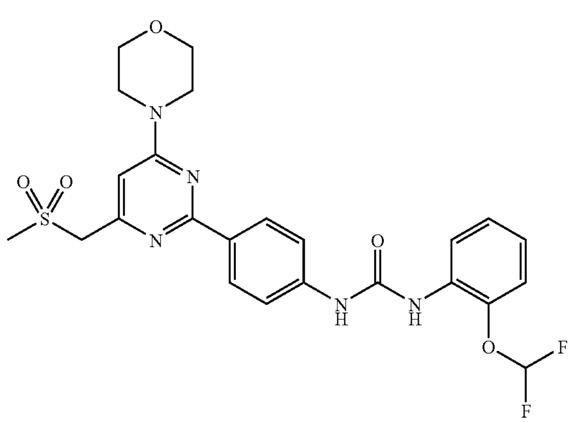 | 3-[2-(difluoromethoxy)phenyl]-1-[4-[4-(methylsulfonylmethyl)-6-morpholin-4-yl-pyrimidin-2-yl]phenyl]urea | 533.97 | 2.25 |

-continued

| Example | Structure | NAME | LCMS MH+ | Retention Time (min) |
|---|---|---|---|---|
| 7f | 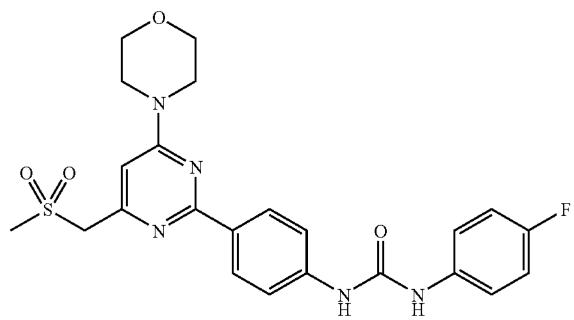 | 3-(4-fluorophenyl)-1-[4-[4-(methylsulfonylmethyl)-6-morpholin-4-yl-pyrimidin-2-yl]phenyl]urea | 485.97 | 2.07 |
| 7g | 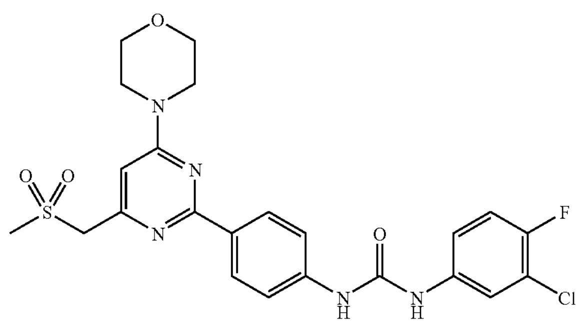 | 3-(3-chloro-4-fluoro-phenyl)-1-[4-[4-(methylsulfonylmethyl)-6-morpholin-4-yl-pyrimidin-2-yl]phenyl]urea | 519.96 | 2.29 |
| 7h* | 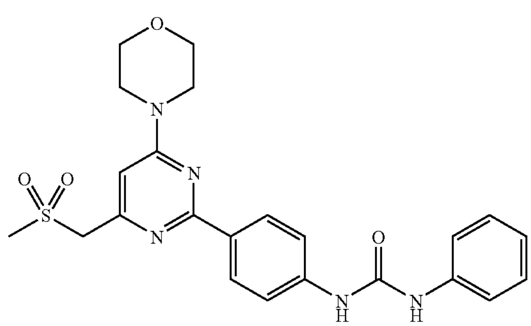 | 1-[4-[4-(methylsulfonylmethyl)-6-morpholin-4-yl-pyrimidin-2-yl]phenyl]-3-phenyl-urea | 468.56 | 3.00 |
| 7i* | 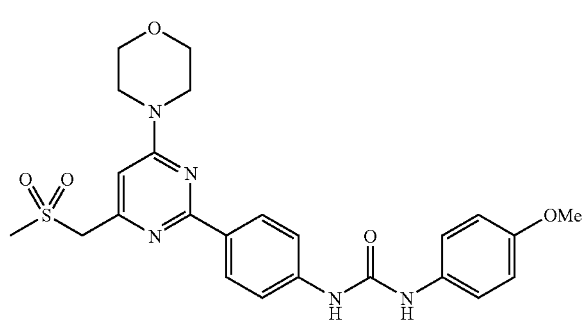 | 1-(4-methoxyphenyl)-3-[4-[4-(methylsulfonylmethyl)-6-morpholin-4-yl-pyrimidin-2-yl]phenyl]urea | 498.60 | 2.93 |

-continued

| Example | Structure | NAME | LCMS MH+ | Retention Time (min) |
|---|---|---|---|---|
| 7j* | 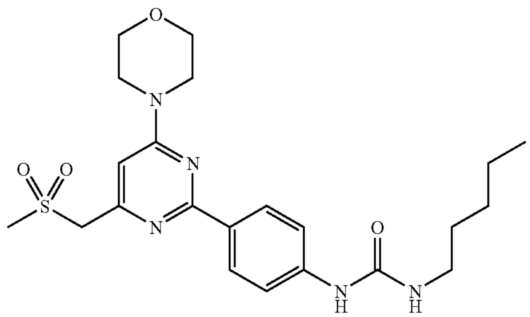 | 3-[4-[4-(methylsulfonylmethyl)-6-morpholin-4-yl-pyrimidin-2-yl]phenyl]-1-pentyl-urea | 462.64 | 3.02 |
| 7k* | 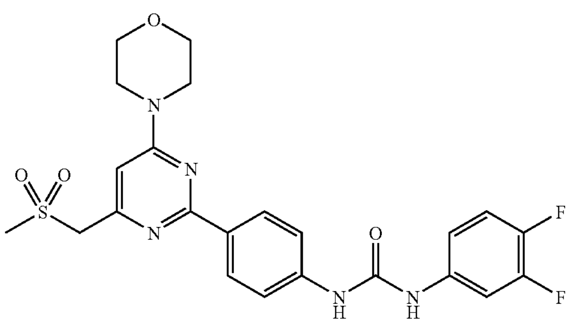 | 3-(3,4-difluorophenyl)-1-[4-[4-(methylsulfonylmethyl)-6-morpholin-4-yl-pyrimidin-2-yl]phenyl]urea | 504.59 | |
| 7l* | 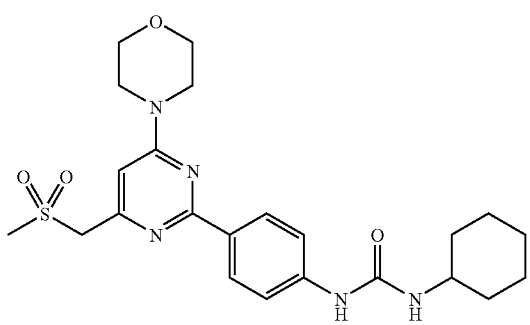 | 3-cyclohexyl-1-[4-[4-(methylsulfonylmethyl)-6-morpholin-4-yl-pyrimidin-2-yl]phenyl]urea | 474.63 | 3.02 |
| 7m* | 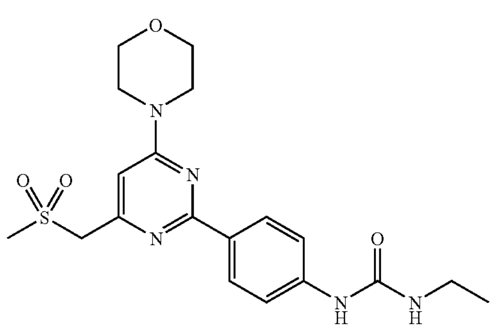 | 1-ethyl-3-[4-[4-(methylsulfonylmethyl)-6-morpholin-4-yl-pyrimidin-2-yl]phenyl]urea | 420.60 | 2.49 |

| Example | Structure | NAME | LCMS MH+ | Retention Time (min) |
|---|---|---|---|---|
| 7n* | 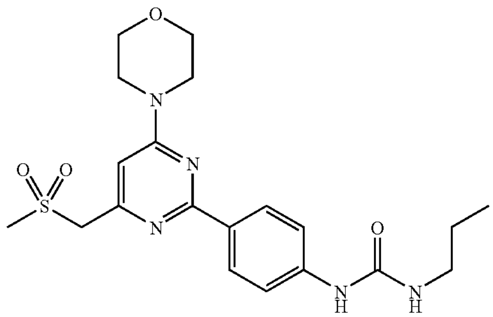 | 3-[4-[4-(methylsulfonylmethyl)-6-morpholin-4-yl-pyrimidin-2-yl]phenyl]-1-propyl-urea | 434.61 | 2.66 |
| 7o* | 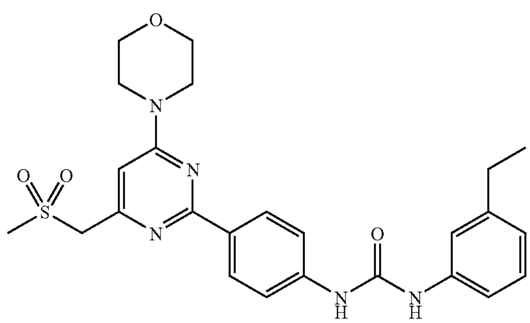 | 1-(3-ethylphenyl)-3-[4-[4-(methylsulfonylmethyl)-6-morpholin-4-yl-pyrimidin-2-yl]phenyl]urea | 496.62 | 3.29 |
| 7p* | 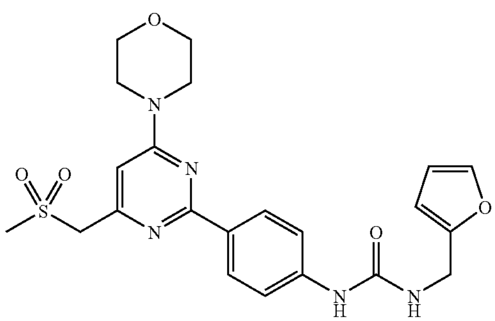 | 3-(2-furylmethyl)-1-[4-[4-(methylsulfonylmethyl)-6-morpholin-4-yl-pyrimidin-2-yl]phenyl]urea | 472.58 | 2.76 |
| 7q* | 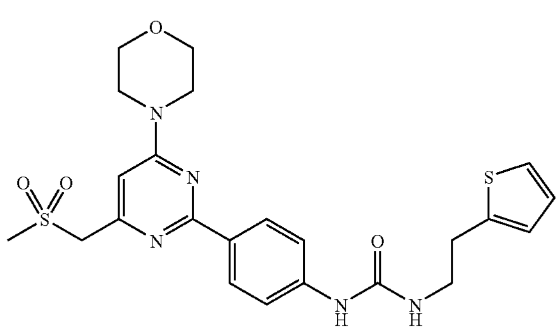 | 1-[4-[4-(methylsulfonylmethyl)-6-morpholin-4-yl-pyrimidin-2-yl]phenyl]-3-(2-thiophen-2-ylethyl)urea | 502.58 | 2.96 |

| Example | Structure | NAME | LCMS MH+ | Retention Time (min) |
|---|---|---|---|---|
| 7r* | (see structure) | 1-[4-[4-(methylsulfonylmethyl)-6-morpholin-4-yl-pyrimidin-2-yl]phenyl]-3-thiophen-2-yl-urea | 474.54 | 2.92 |

*Compounds were further purified by prep HPLC

Example 7a: $^1$H NMR (400.13 MHz, DMSO-$d_6$) δ2.25 (s, 3H), 3.21 (s, 3H), 3.71 (s, 8H), 4.49 (s, 2H), 6.83 (s, 1H), 7.09 (d, 2H), 7.34 (d, 2H), 7.56 (d, 2H), 8.26 (d, 2H), 8.6 (s, 1H), 8.88 (s, 1H)

Example 7b: $^1$H NMR (400.13 MHz, DMSO-$d_6$) δ3.22 (s, 3H), 3.70 (s, 8H), 4.49 (s, 2H), 6.84 (s, 1H), 7.34 (d, 2H), 7.50 (d, 2H), 7.56 (d, 2H), 8.28 (d, 2H), 8.84 (s, 1H), 8.95 (s, 1H)

Example 7c: $^1$H NMR (400.13 MHz, DMSO-$d_6$) δ3.21 (s, 3H), 3.72 (s, 8H), 4.49 (s, 2H), 6.84 (s, 1H), 7.59 (d, 2H), 7.65 (m, 4H), 8.3 (d, 2H), 9.40 (s, 1H), 9.13 (s, 1H)

Example 7d: $^1$H NMR (400.13 MHz, DMSO-$d_6$) δ2.23 (s, 6H), 3.21 (s, 3H), 3.72 (bs, 8H), 4.49 (s, 2H), 6.64 (s, 1H), 6.85 (s, 1H), 7.08 (s, 2H), 7.55 (d, 2H), 8.28 (d, 2H), 8.58 (s, 1H), 8.92 (s, 1H)

Example 7e: $^1$H NMR (400.13 MHz, DMSO-$d_6$) δ3.21 (s, 3H), 3.72 (s, 8H), 4.49 (s, 2H), 6.84 (s, 1H), 7.05 (m, 1H), 7.22 (m, 2H), 7.59 (d, 2H), 8.24 (d, 1H), 8.3 (d, 2H), 8.38 (s, 1H), 9.60 (s, 1H)

Example 7f: $^1$H NMR (400.13 MHz, DMSO-$d_6$) δ3.22 (s, 3H), 3.70 (bs, 8H), 4.49 (s, 2H), 6.84 (s, 1H), 7.12 (m, 2H), 7.48 (m, 2H), 7.55 (d, 2H), 8.26 (d, 2H), 8.73 (s, 1H), 8.90 (s, 1H)

Example 7g: $^1$H NMR (400.13 MHz, DMSO-$d_6$) δ3.21 (s, 3H), 3.72 (s, 8H), 4.49 (s, 2H), 6.84 (s, 1H), 7.34 (m, 2H), 7.56 (m, 2H), 7.8 (m, 1H), 8.28 (m, 2H), 8.95 (s, 1H), 9.05 (s, 1H)

Example 7i: $^1$H NMR (400.13 MHz, DMSO-$d_6$) δ3.22 (s, 3H), 3.70 (bs, 8H), 4.49 (s, 2H), 6.84 (s, 1H), 7.34 (d, 2H), 7.50 (d, 2H), 7.56 (d, 2H), 8.28 (d, 2H), 8.84 (s, 1H), 8.95 (s, 1H)

Example 7j: $^1$H NMR (400.13 MHz, DMSO-$d_6$) δ0.88 (m, 3H), 1.39 (m, 4H), 1.43 (m, 2H), 3.08 (m, 2H), 3.21 (s, 3H), 3.70 (bs, 8H), 4.47 (s, 2H), 6.2 (t, 1H), 6.81 (s, 1H), 7.49 (d, 2H), 8.20 (d, 2H), 8.66 (s, 1H)

Example 7m: $^1$H NMR (400.13 MHz, DMSO-$d_6$) δ1.05 (t, 3H), 3.12 (q, 2H), 3.21 (s, 3H), 3.7 (bs, 8H), 4.46 (s, 2H), 6.19 (t, 1H), 6.8 (s, 1H), 7.50 (d, 2H), 8.21 (d, 2H), 8.69 (s, 1H)

Example 7n: $^1$H NMR (400.13 MHz, DMSO-$d_6$) δ0.87 (m, 3H), 1.45 (m, 2H), 3.05 (m, 2H), 3.20 (s, 3H), 3.70 (bs, 8H), 4.45 (s, 2H), 6.14 (t, 1H), 6.81 (s, 1H), 7.49 (d, 2H), 8.20 (d, 2H), 8.69 (s, 1H)

Example 7o: $^1$H NMR (400.13 MHz, DMSO-$d_6$) δ1.19 (t, 3H), 2.55 (q, 2H), 3.21 (s, 3H), 3.70 (bs, 8H), 4.49 (s, 2H), 6.85 (m, 2H), 7.19 (t, 2H), 7.27 (d, 1H), 7.33 (s, 1H), 7.56 (d, 2H), 8.26 (d, 2H), 8.68 (s, 1H), 8.92 (s, 1H)

Example 7p: $^1$H NMR (400.13 MHz, DMSO-$d_6$) δ3.20 (s, 3H), 3.70 (bs, 8H), 4.31 (d, 1H), 4.47 (s, 2H), 6.28 (d, 1 h), 6.40 (d, 1H), 6.61 (t, 1H), 6.82 (s, 1H), 7.51 (d, 2H), 7.59 (s, 1H), 8.22 (d, 2H), 8.77 (s, 1H)

Example 7q: $^1$H NMR (400.13 MHz, DMSO-$d_6$) δ2.98 (t, 2H), 3.21 (s, 3H), 3.38 (m, 2H), 3.70 (bs, 8H), 4.47 (s, 2H), 6.29 (t, 1H), 6.81 (s, 1H), 6.93 (d, 1H), 6.97 (m, 1H), 7.36 (m, 1H), 7.50 (d, 2H), 8.21 (d, 2H), 8.80 (s, 1H)

Test (a): Example (7) 0.17 μM; Example (7a) 0.28 μM; Example (7b) 0.42 μM; Example (7c) 1.7 μM; Example (7d) 2.6 μM; Example (7e) 2.6 μM; Example (7f) 0.029 μM; Example (7g) 1.3 μM; Example (7h) 0.24 μM; Example (7I) 0.032 μM; Example (7j) 1.9 μM; Example (7k) 0.72 μM; Example (7l) 7 μM; Example (7m) 0.081 μM; Example (7n) 0.2 μM; Example (7o) 1.7 μM; Example (7p) 3.8 μM; Example (7q) 1.7 μM; Example (7r) 0.19 μM.

The preparation of 4-[4-(methylsulfonylmethyl)-6-morpholin-4-yl-pyrimidin-2-yl]aniline is described below:

4-[4-(Methylsulfonylmethyl)-6-morpholin-4-yl-pyrimidin-2-yl]aniline

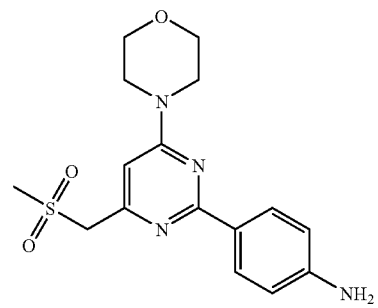

2-Methylsulfanyl-4-(methylsulfonylmethyl)-6-morpholin-4-yl-pyrimidine (1.00 g, 3.3 mmol), 4-aminophenylboronic acid (904 mg, 6.60 mmol), Copper(I)thiophene-2-carboxylate (1.64 g, 8.58 mmol), Pd(PPh$_3$)$_4$ (153 mg, 0.04 equiv., 0.13 mmol) were added to a microwave vessel and 1,4-Dioxane (20 mL) added. The system was degassed with N$_2$, sealed and heated in a microwave reactor at 130° C. for 1 hour. Upon cooling the reaction was poured into water and the resulting precipitate was collected by filtration and dried under vacuum to afford the title compound as an off-white solid. (988 mg)

LCMS Spectrum: MH+ 349.41, Retention Time 1.43 Method: Monitor Acid

NMR Spectrum: ¹H NMR (300.132 MHz, DMSO) 83.20 (3H, s), 3.61-3.83 (8H, m), 4.43 (2H, s), 5.57 (1H, s), 6.60 (2H, d), 6.70 (1H, s), 8.04 (2H, d)

2-Methylsulfanyl-4-(methylsulfonylmethyl)-6-morpholin-4-yl-pyrimidine

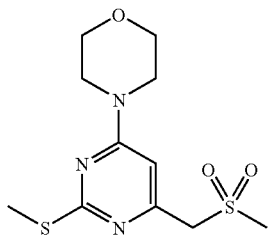

2-Methylsulfanyl-6-(methylsulfonylmethyl)pyrimidin-4-ol (15 g, 63.97 mmol) was heated at reflux in phosphorous oxychloride (100 ml) for approximately 1 hour. Phosphorous oxychloride was evaporated and the residue was neutralised with sodium hydroxide solution and extracted into ethyl acetate. The resultant mixture was then dried over magnesium sulfate, filtered and evaporated to dryness to afford the crude chloro product. This was then dissolved in DCM, morpholine (319 mmol, 28 ml) was added and the reaction stirred at room temperature. Upon completion the resulting precipitate was collected as a white solid. Concentration of the filtrate afforded more solid, giving a combined yield of 13.7 g.

NMR Spectrum: ¹H NMR (300.132 MHz, DMSO) 82.45 (s, 3H), 3.49-3.74 (m, 8H), 4.37 (s, 2H), 6.66 (s, 1H) ppm.

LCMS Spectrum: MH+ 304.50, Retention Time 1.49 min, Method: Monitor Basic

2-Methylsulfanyl-6-(methylsulfonylmethyl)pyrimidin-4-ol

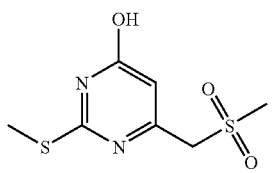

6-(Chloromethyl)-2-methylsulfanyl-pyrimidin-4-ol (19.07 g, 100 mmol) was suspended in acetonitrile (400 ml). To this stirring suspension was added methanesulphinic acid sodium salt (12.255 g, 120 mmol) and DMF (100 ml). The reaction was then heated to 100° C. to give a dark suspension and monitored by LCMS. Once complete, the solvents were removed and the resultant product added to 1:1 MeOH:DCM (200 ml) and acidified with acetic acid (10 ml). The resultant precipitate was collected, washed with water (200 ml) and MeOH (100 ml) and dried overnight in vacuo to afford the title compound as a white solid, 16.45 g.

NMR Spectrum: ¹H NMR (300.132 MHz, DMSO) 82.50 (s, 3H), 3.12 (s, 3H), 4.39 (s, 2H), 6.25 (s, 1H), 13.09 (s, 1H) ppm.

LCMS Spectrum: MH+ 235.2, Retention Time 0.5 minutes, Method: 5 min Early Base 6-(Chloromethyl)-2-methylsulfanyl-pyrimidin-4-ol

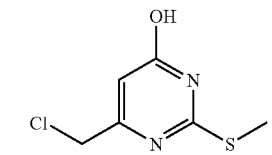

S-Methyl-2-thiopseudourea sulphate (20 g, 71.85 mmol), ethyl 4-chloroacetoacetate (10.755 ml, 79.04 mmol) and sodium carbonate (13.925 g, 107.78 mmol) were dissolved in water (100 ml) and stirred at room temperature overnight. The reaction was monitored by TLC, and once complete, the reaction precipitate was collected and the supernatant was neutralised with 6N hydrochloric acid to yield more reaction precipitate which was also collected. The accumulated precipitate was then washed with water (×3) and an off-white solid was obtained. This was dried in vacuo at 60° C. for 48 hours to yield the desired compound as a pale yellow/white solid, 43.2 g.

NMR Spectrum: ¹H NMR (300.132 MHz, CDCl₃) δ 2.59 (s, 3H), 4.35 (s, 2H), 6.41 (s, 1H), 12.70 (s, 1H) ppm Mass Spectrum: M⁺ 190

4-[4-(Methylsulfonylmethyl)-6-morpholin-4-yl-pyrimidin-2-yl]aniline can also be prepared from 2,4-dichloro-6-(methylsulfonylmethyl)pyrimidine as described below 4-[4-(Methylsulfonylmethyl)-6-morpholin-4-yl-pyrimidin-2-yl]aniline

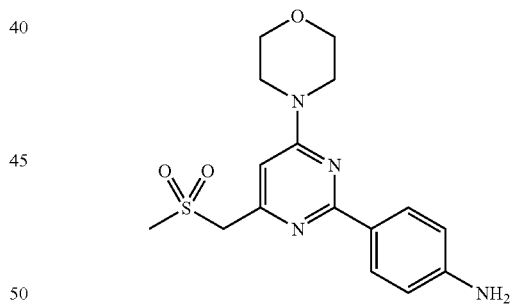

2-Chloro-4-(methylsulfonylmethyl)-6-morpholin-4-yl-pyrimidine (5 g, 17.1 mmol), was dissolved in a mixture of DMF:DME:water:ethanol (16.5 mL:41 mL:18 mL:12 mL). 4-(4,4,5,5-Tetramethyl-1,3,2-dioxaborolan-2-yl)aniline (5.62 g, 25.6 mmol), a 2M aqueous solution of sodium carbonate (25 mL), and dichlorobis(triphenylphosphine) palladium (600 mg) were added and the mixture refluxed for 5 hours under a nitrogen atmosphere. The mixture was cooled, diluted with water and extracted into DCM. The organic layer was dried over Na₂SO₄, filtered and evaporated. The crude material was dissolved in minimum of hot DCM then hexane added and the precipitate filtered to give the desired material (1.6 g).

LCMS Spectrum: MH+ 349, Retention time 1.48 min, Method: Monitor Base

NMR Spectrum ¹H NMR (400.13 MHz, DMSO-d₆) δ3.20 (3H, s), 3.67-3.72 (8H, m), 4.43 (2H, s), 5.55-5.56 (2H, m), 6.59 (2H, d), 6.70 (1H, s), 8.03 (2H, d)

2-Chloro-4-(methylsulfonylmethyl)-6-morpholin-4-yl-pyrimidine

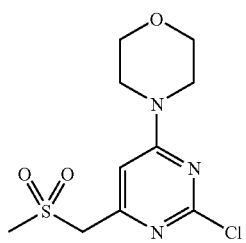

A suspension of 2,4-dichloro-6-(methylsulfonylmethyl) pyrimidine (10.56 g) in DCM (230 mL) was stirred magnetically (under nitrogen) and cooled to −5° C. Triethylamine (6.78 mL) was added followed by the dropwise addition of a solution of morpholine (3.85 mL) in DCM (30 mL) maintaining the reaction temperature below −5° C. The reaction was stirred at room temperature for 1 hour and then the organic mixture washed with water (300 mL). The organic phase was dried (MgSO4), filtered and evaporated to a brown solid which was chromatographed on silica, eluting with 50% ethyl acetate in DCM, to give the desired material (6.81 g) as a white solid.

NMR Spectrum: ¹H NMR (DMSO-d₆) δ3.12 (3H, s), 3.63 (4H, s), 3.68-3.70 (4H, m), 4.45 (2H, s), 6.96 (1H, s)

Mass Spectrum: MH+ 292.

EXAMPLE 8

3-Cyclopropyl-1-[4-[4-(methylsulfonylmethyl)-6-morpholin-4-yl-pyrimidin-2-yl]phenyl]urea

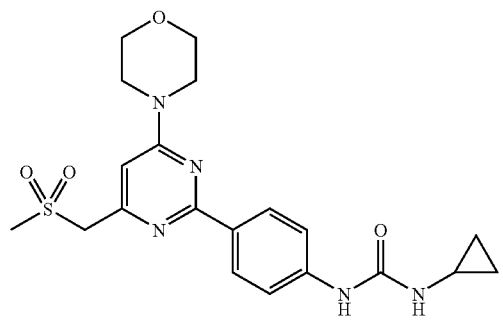

A mixture of phenyl N-[4-[4-(methylsulfonylmethyl)-6-morpholin-4-yl-pyrimidin-2-yl]phenyl]carbamate (94 mg, 0.2 mmol), cyclopropylamine (0.069 mL, 1 mmol), and triethylamine (0.090 mL, 0.65 mmol), in NMP (1-2 mL) was heated at 50-70° C. for 2 hours. The mixture was then purified directly using prep HPLC (monitor basic method) to give the desired material.

LCMS Spectrum: MH+ 432, Retention time 2.42 min, Method Basic

The following compounds were prepared in an analogous fashion from the required phenyl carbamate and the appropriate amine, using either NMP or DMF as the solvent.

| Example | Structure | NAME | LCMS MH+ | Retention Time (min) | Notes |
|---|---|---|---|---|---|
| 8a | 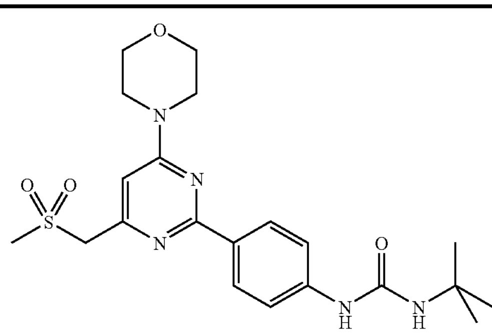 | 1-[4-[4-(methylsulfonylmethyl)-6-morpholin-4-yl-pyrimidin-2-yl]phenyl]-3-tert-butyl-urea | 448 | 2.82 | |
| 8b | 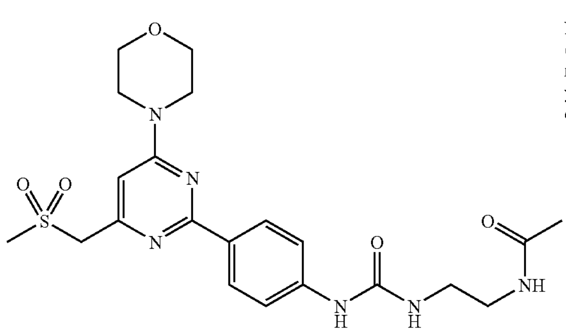 | N-[2-[[4-[4-(methylsulfonylmethyl)-6-morpholin-4-yl-pyrimidin-2-yl]phenyl]carbamoylamino]ethyl]acetamide | 478 | 2.24 | |

-continued

| Example | Structure | NAME | LCMS MH+ | Retention Time (min) | Notes |
|---|---|---|---|---|---|
| 8c | 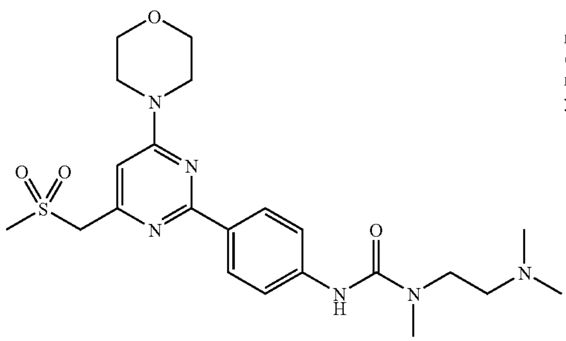 | 1-(2-dimethylaminoethyl)-1-methyl-3-[4-[4-(methylsulfonylmethyl)-6-morpholin-4-yl-pyrimidin-2-yl]phenyl]urea | 478 | 2.6 | |
| 8d | 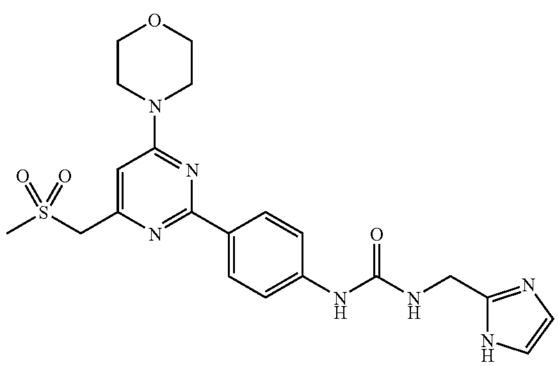 | 3-(1H-imidazol-2-ylmethyl)-1-[4-[4-(methylsulfonylmethyl)-6-morpholin-4-yl-pyrimidin-2-yl]phenyl]urea | 472 | 2.11 | |
| 8e | 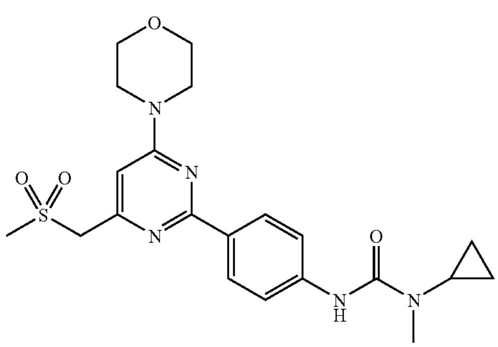 | 1-cyclopropyl-1-methyl-3-[4-[4-(methylsulfonylmethyl)-6-morpholin-4-yl-pyrimidin-2-yl]phenyl]urea | 446 | 2.45 | |
| 8f | 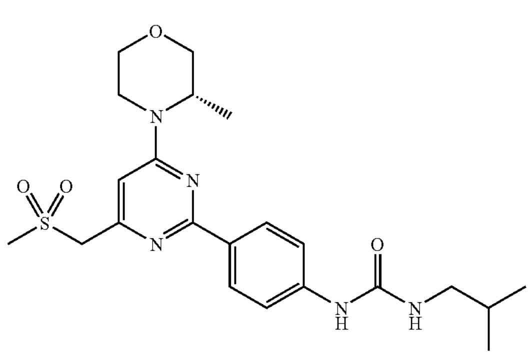 | 1-[4-[4-[(3S)-3-Methylmorpholin-4-yl]-6-(methylsulfonylmethyl)pyrimidin-2-yl]phenyl]-3-(2-methylpropyl)urea | 462 | 2.84 | |

| Example | Structure | NAME | LCMS MH+ | Retention Time (min) | Notes |
|---|---|---|---|---|---|
| 8g | 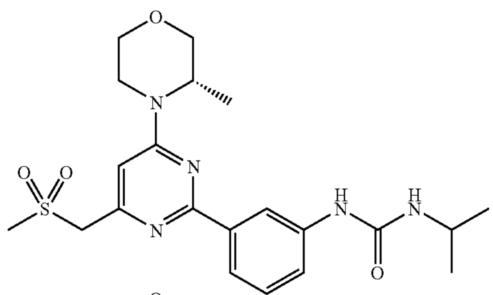 | 1-[3-[4-[(3S)-3-Methylmorpholin-4-yl]-6-(methylsulfonylmethyl)pyrimidin-2-yl]phenyl]-3-propan-2-yl-urea | 448 | 1.71 | Purified by trituration with methanol |
| 8h | 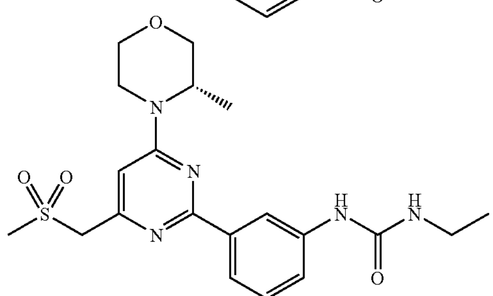 | 3-Ethyl-1-[3-[4-[(3S)-3-methylmorpholin-4-yl]-6-(methylsulfonylmethyl)pyrimidin-2-yl]phenyl]urea | 434 | 1.71 | Purified by recrystallisation from methanol |
| 8i | 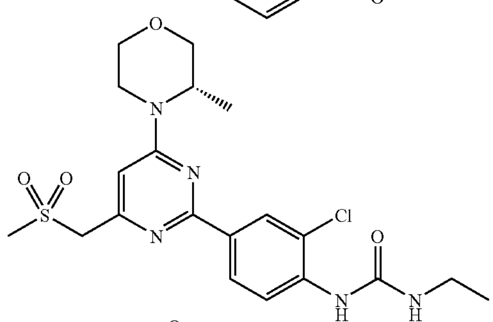 | 1-[2-Chloro-4-[4-[(3S)-3-methylmorpholin-4-yl]-6-(methylsulfonylmethyl)pyrimidin-2-yl]phenyl]-3-ethyl-urea | 468 | 1.78 | |
| 8j | 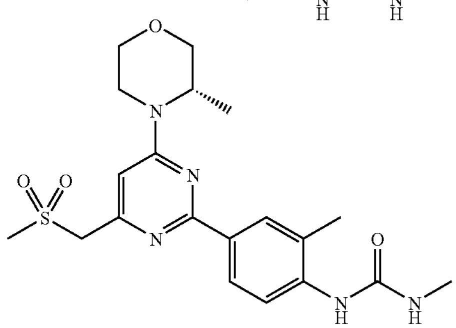 | 3-Methyl-1-[2-methyl-4-[4-[(3S)-3-methylmorpholin-4-yl]-6-(methylsulfonylmethyl)pyrimidin-2-yl]phenyl]urea | 434 | 1.28 | |

Example 8g: $^1$H NMR (400.13 MHz, DMSO-d$_6$) δ 1.11 (d, 6H), 1.26 (d, 3H), 3.23 (s, 3H), 3.25 (d, 1H), 3.48-3.55 (m, 1H), 3.65-3.68 (m, 1H), 3.76 (d, 1H), 3.80 (t, 1H), 3.98-4.02 (m, 1H), 4.18 (d, 1H), 4.48 (m, 1H), 4.52 (s, 2H), 5.98 (d, 1H), 6.85 (s, 1H), 7.32 (t, 1H), 7.65-7.68 (m, 1H), 7.86-7.88 (m, 1H), 8.20 (t, 1H), 8.43 (s, 1H)

Example 8h: $^1$H NMR (400.13 MHz, DMSO-d$_6$) δ 1.07 (t, 3H), 1.26 (d, 3H), 3.09-3.14 (m, 2H), 3.22 (s, 3H), 3.24 (m, 1H), 3.48-3.55 (m, 1H), 3.65-3.68 (m, 1H), 3.79 (d, 1H), 3.98-4.02 (m, 1H), 4.18 (s, 1H), 4.51 (s, 3H), 6.08 (t, 1H), 6.85 (s, 1H), 7.32 (t, 1H), 7.64-7.67 (m, 1H), 7.86-7.88 (m, 1H), 8.23 (s, 1H), 8.55 (s, 1H)

Example 8i: $^1$H NMR (400.13 MHz, DMSO-d$_6$) δ 1.09 (t, 3H), 1.25 (d, 3H), 3.15 (m, 2H), 3.19 (s, 3H), 3.20-3.26 (m, 1H), 3.47-3.53 (m, 1H), 3.63-3.67 (m, 1H), 3.78 (d, 1H), 3.97-4.01 (m, 1H), 4.18 (d, 1H), 4.46 (s, 1H), 4.50 (s, 2H), 6.82 (s, 1H), 7.13 (t, 1H), 8.14 (s, 1H), 8.17-8.20 (m, 1H), 8.28 (d, 1H), 8.33 (d, 1H)

Example 8j: $^1$H NMR (400.13 MHz, DMSO-d$_6$) δ 1.24 (d, 3H), 2.26 (s, 3H), 2.68 (d, 3H), 3.20 (s, 3H), 3.22-3.26 (m, 1H), 3.47-3.54 (m, 1H), 3.63-3.67 (m, 1H), 3.78 (d, 1H), 3.97-4.01 (m, 1H), 4.19 (d, 1H), 4.49 (s, 3H), 6.56 (q, 1H), 6.77 (s, 1H), 7.79 (s, 1H), 8.02 (s, 1H), 8.06-8.09 (m, 2H)

Test (a): Example (8) 0.031 μM; Example (8a) 0.47 μM; Example (8b) 0.42 μM; Example (8c) 2.2 μM; Example (8d) 0.57 μM; Example (8e) 0.28 μM; Example (8f) 0.3 μM; Example (8g) 0.96 μM; Example (8h) 0.92 μM; Example (8i) 1.4 μM; Example (8j) 0.16 μM.

The preparation of phenyl N-[4-[4-(methylsulfonylmethyl)-6-morpholin-4-yl-pyrimidin-2-yl]phenyl]carbamate is described below.

Phenyl N-[4-[4-(methylsulfonylmethyl)-6-morpholin-4-yl-pyrimidin-2-yl]phenyl]carbamate

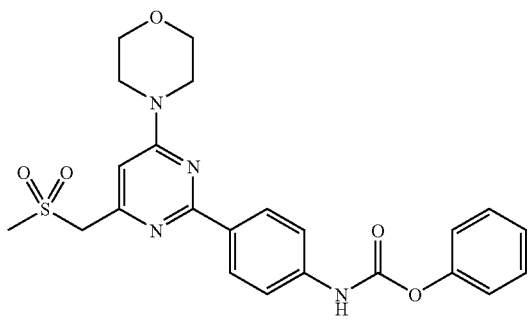

Phenyl chloroformate (1.33 mL, 10.6 mmol) was added at 0-5° C. to a mixture of sodium hydrogencarbonate (1.34 g, 15.9 mmol) and 4-[4-(methylsulfonylmethyl)-6-morpholin-4-yl-pyrimidin-2-yl]aniline (3.7 g, 10.6 mmol) in dioxane (150 mL). The reaction was stirred at RT for 3 hours, evaporated then dissolved in DCM. The organic mixture was washed with water, dried over $Na_2SO_4$, filtered and evaporated to a pale yellow foam which was triturated with hexane/ether then filtered yielding the desired material as a white solid (5.4 g).

LCMS Spectrum MH+ 470, Retention time 2.18 Method: Monitor base

NMR Spectrum $^1$H NMR (400.13 MHz, DMSO-$d_6$) δ3.22 (3H, s), 3.58 (4H, s), 3.73 (4H, s), 4.50 (2H, s), 6.88 (1H, s), 7.24-7.30 (3H, m), 7.43-7.47 (2H, m), 7.63 (2H, d), 8.30 (2H, d), 10.45 (1H, s).

The following phenyl carbamates were prepared in an analogous fashion from the appropriate aniline.

| Structure | NAME | LCMS MH+ | Retention Time (min) | NMR $^1$H NMR (400.13 MHz, DMSO-$d_6$) |
|---|---|---|---|---|
| 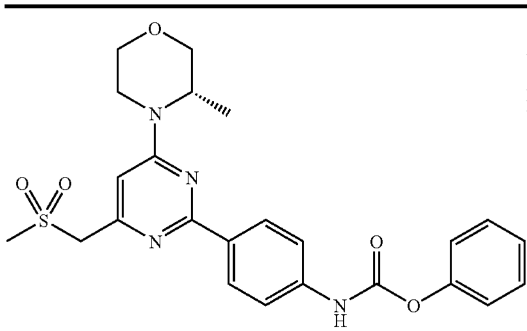 | Phenyl N-[4-[4-[(3S)-3-methylmorpholin-4-yl]-6-(methylsulfonylmethyl)pyrimidin-2-yl]phenyl]carbamate | 483 | 2.37 | |
| 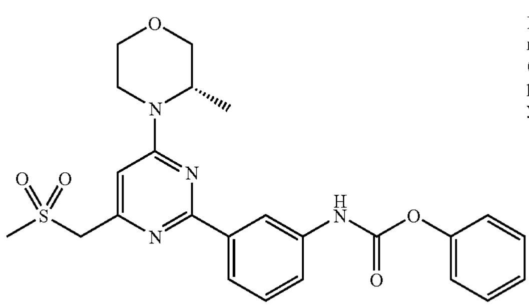 | Phenyl N-[3-[4-[(3S)-3-methylmorpholin-4-yl]-6-(methylsulfonylmethyl)pyrimidin-2-yl]phenyl]carbamate | 482 | 2.36 | δ1.26 (d, 3H), 3.23 (s, 3H), 3.21-3.29 (m, 1H), 3.49-3.54 (m, 1H), 3.58 (s, 1H), 3.64-3.68 (m, 1H), 3.79 (d, 1H), 3.98-4.06 (m, 1H), 4.19 (d, 1H), 4.53 (s, 2H), 6.87 (s, 1H), 7.23-7.31 (m, 2H), 7.42 (d, 1H), 7.44-7.47 (m, 2H), 7.61-7.66 (m, 1H), 7.71 (d, 1H), 8.02-8.05 (m, 1H), 8.50 (t, 1H), 10.36 (s, 1H) |
| 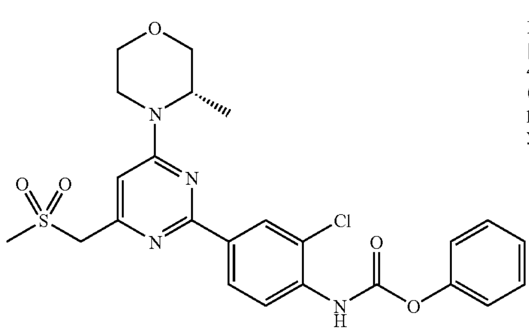 | Phenyl N-[2-chloro-4-[4-[(3S)-3-methylmorpholin-4-yl]-6-(methylsulfonylmethyl)pyrimidin-2-yl]phenyl]carbamate | 517 | 2.40 | δ1.26 (s, 3H), 3.20 (s, 3H), 3.24-3.25 (m, 1H), 3.48-3.54 (m, 1H), 3.64-3.68 (m, 1H), 3.79 (d, 1H), 3.98-4.02 (m, 1H), 4.18-4.23 (m, 1H), 4.51 (m, 1H), 4.55 (s, 2H), 6.90 (s, 1H), 7.14-7.18 (m, 1H), 7.24-7.28 (m, 2H), 7.42-7.45 (m, 2H), 7.84 (d, 1H), 8.29-8.31 (m, 1H), 8.39 (d, 1H), 9.83 (s, 1H) |

| Structure | NAME | LCMS MH+ | Retention Time (min) | NMR ¹H NMR (400.13 MHz, DMSO-$d_6$) |
|---|---|---|---|---|
| 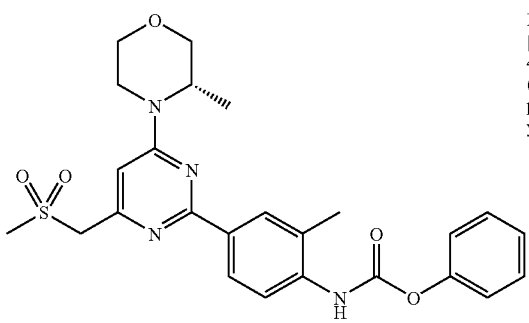 | Phenyl N-[2-methyl-4-[4-[(3S)-3-methylmorpholin-4-yl]-6-(methylsulfonylmethyl)pyrimidin-2-yl]phenyl]carbamate | 496 | 1.61 | |

The preparations of anilines required above were described earlier.

EXAMPLE 9

1-[4-[4-[(3S)-3-Methylmorpholin-4-yl]-6-(propan-2-ylsulfonylmethyl)pyrimidin-2-yl]phenyl]-3-phenyl-urea

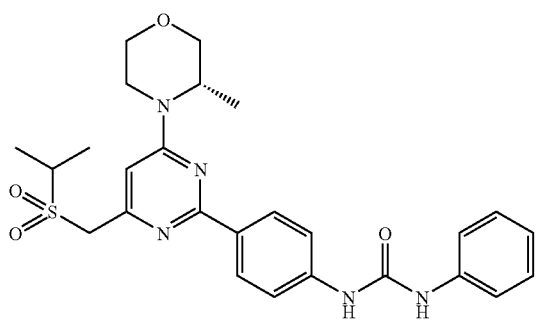

1-[4-[4-[(3S)-3-Methylmorpholin-4-yl]-6-(propan-2-yl-sulfanylmethyl)pyrimidin-2-yl]phenyl]-3-phenyl-urea (78 mg) was dissolved in 1,4-dioxane (6 mL) and water (1 mL). The solution was cooled to 0° C. and 3-chloroperoxybenzoic acid (75%) (34 mg) added followed immediately by sodium permanganate (40 mg). The reaction was allowed to stir at room temperature for 2 hours. The reaction was loaded onto a SCX-2 column, the column washed with methanol and the desired material eluted with 7N ammonia in methanol. The fractions were concentrated in vacuo to give the desired compound as a pale yellow solid (77 mg).

NMR Spectrum: ¹H NMR (399.9 MHz, DMSO-$d_6$) δ1.25 (3H, d), 1.31-1.38 (6H, m), 3.18-3.24 (1H, m), 3.48-3.58 (2H, m), 3.64-3.68 (1H, m), 3.79 (1H, d), 3.98-4.01 (1H, m), 4.18 (1H, d), 4.48 (3H, s), 6.79 (1H, s), 6.97-7.01 (1H, m), 7.28-7.31 (1H, m), 7.31 (1H, d), 7.46-7.49 (2H, m), 7.56-7.58 (2H, m), 8.25 (2H, d), 8.73 (1H, s), 8.92 (1H, s)

Mass Spectrum; M+H⁺ 510.

Test (a): 0.59 μM.

1-[4-[4-[(3S)-3-Methylmorpholin-4-yl]-6-(propan-2-ylsulfanylmethyl)pyrimidin-2-yl]phenyl]-3-phenyl-urea

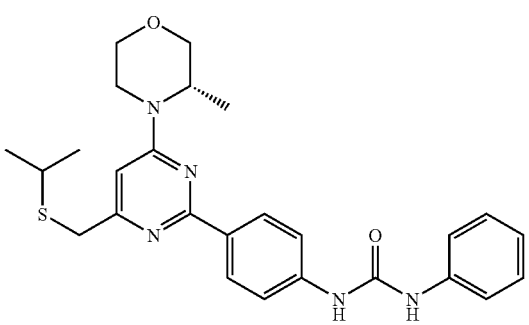

Isopropyl mercaptan (0.075 mL) was dissolved in acetonitrile (5 mL) and 1,8-diazabicyclo[5.4.0]undec-7-ene (0.12 mL). The reaction was allowed to stir at room temperature for 15 minutes then 1-[4-[4-[(3S)-3-methylmorpholin-4-yl]-6-(methylsulfonyloxymethyl)pyrimidin-2-yl]phenyl]-3-phenyl-urea (228 mg) in acetonitrile (5 mL) added. The reaction was stirred for 30 minutes then concentrated in vacuo. The residue was chromatographed on silica, eluting with 2.5% methanol in DCM, to give the desired compound (78 mg) as a gum.

Mass Spectrum; M+H⁺ 478.

1-[4-[4-[(3S)-3-Methylmorpholin-4-yl]-6-(methylsulfonyloxymethyl)pyrimidin-2-yl]phenyl]-3-phenyl-urea

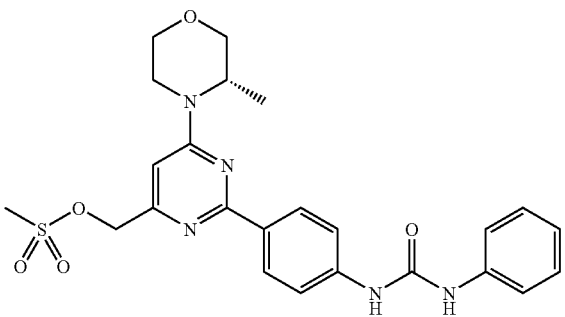

1-[4-[4-(Hydroxymethyl)-6-[(3S)-3-methylmorpholin-4-yl]pyrimidin-2-yl]phenyl]-3-phenyl-urea (388 mg) was dissolved in DCM (15 mL) and triethylamine (0.194 mL) and the solution was cooled to 0° C. Methanesulfonyl chloride (0.108 mL) was added and the reaction stirred for 90 mins at 0° C. The reaction mixture was concentrated in vacuo and partitioned between DCM (20 mL) and water (10 mL). The organic phase was washed with brine (10 mL), dried (MgSO$_4$) and concentrated in vacuo to give the desired compound (273 mg) as a solid.

The preparation of 1-[4-[4-(hydroxymethyl)-6-[(3S)-3-methylmorpholin-4-yl]pyrimidin-2-yl]phenyl]-3-phenyl-urea was described earlier.

EXAMPLE 10

3-[4-[4-(Hydroxymethyl)-6-[(3S)-3-methylmorpholin-4-yl]pyrimidin-2-yl]phenyl]-1,1-dimethyl-urea

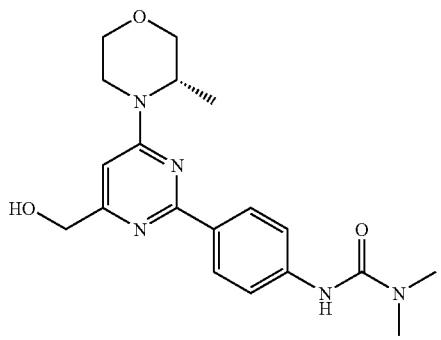

3-(4-Bromophenyl)-1,1-dimethyl-urea (825 mg), potassium acetate (998 mg), and bis(pinacolato)diboron (1.03 g) were dissolved in 1,4 dioxane (45 mL). The solution was degassed for 5 minutes then 1,1'-bis(diphenylphosphino)ferrocenedichloropalladium(II) dichloromethane adduct was added (167 mg) and the reaction was heated to 85° C. for 3 hours. [2-Chloro-6-[(3S)-3-methylmorpholin-4-yl]pyrimidin-4-yl]methanol (828 mg), ethanol (3.75 mL), 2M sodium carbonate solution (8.53 mL) and 1,1'-bis(diphenylphosphino)ferrocenedichloropalladium(II) dichloromethane adduct (167 mg) were added and the heating was continued for 16 hours. The reaction was cooled and evaporated to dryness and the residue partitioned between ethyl acetate (125 mL) and water (100 mL). The organics were dried over magnesium sulphate, filtered and concentrated in vacuo. The crude material was chromatographed on silica, eluting with 5% methanol in DCM, to give the desired material (737 mg) as a white solid.

NMR Spectrum: $^1$H NMR (DMSO-d$_6$) δ1.22-1.24 (3H, m), 2.95 (6H, s), 3.16-3.23 (1H, m), 3.46-3.53 (1H, m), 3.62-3.66 (1H, m), 3.77 (1H, d), 3.96-4.00 (1H, m), 4.18 (1H, d), 4.45-4.50 (3H, m), 5.38 (1H, t), 6.66 (1H, s), 7.55-7.59 (2H, m), 8.18-8.22 (2H, m), 8.45 (1H, s)

Mass Spectrum; M+H$^+$ 372.

Test (a): 19 µM.

The preparation of 3-(4-bromophenyl)-1,1-dimethyl-urea is described below.

3-(4-Bromophenyl)-1,1-dimethyl-urea

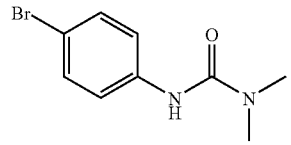

4-Bromophenyl isocyante (1.00 g) was dissolved in THF (30 mL). Dimethylamine (2.0M in THF, 2.78 mL) was added to the solution and the reaction stirred at RT for 2 hours. The reaction was filtered, concentrated in vacuo and the residue chromatographed on silica, eluting with 5% methanol in DCM, to give the desired material (830 mg) as a white solid.

NMR Spectrum: $^1$H NMR (DMSO-d$_6$) δ2.90 (6H, s), 7.37-7.40 (2H, m), 7.45-7.47 (2H, m), 8.37 (1H, s)

Mass Spectrum; M+H$^+$ 244.

EXAMPLE 11

N-[2-[[6-[(3S)-3-methylmorpholin-4-yl]-2-[4-(phenylcarbamoylamino)phenyl]pyrimidin-4-yl]methylsulfonyl]ethyl]acetamide

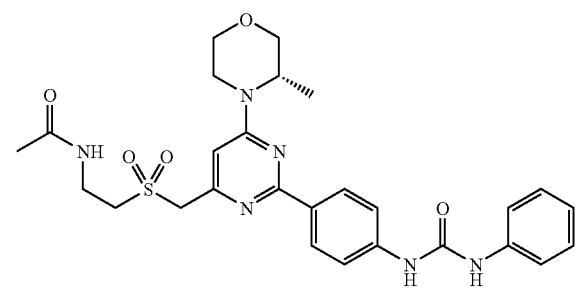

N-[2-[[6-[(3S)-3-Methylmorpholin-4-yl]-2-[4-(phenylcarbamoylamino)phenyl]pyrimidin-4-yl]methylsulfanyl]ethyl]acetamide (100 mg) was dissolved in 1,4-dioxane (6 mL) and water (1 mL). The solution was cooled to 0° C. and 3-chloroperbenzoic acid (75%) (40 mg) added followed immediately by sodium permanganate (47 mg). The reaction was allowed to stir at RT for 2 hours. Further 3-chloroperbenzoic acid (4 mg) and sodium permanganate (4 mg) were added and the reaction stirred for an extra hour. The reaction was loaded onto a SCX-2 column, washed with methanol and the desired material removed with 7N ammonia in methanol. The desired material was isolated as a white solid (102 mg).

NMR Spectrum: $^1$H NMR (DMSO-d$_6$) δ1.25 (3H, d), 1.84 (3H, s), 3.18-3.24 (1H, m), 3.48-3.54 (2H, m), 3.52 (1H, s), 3.58 (2H, q), 3.64-3.68 (1H, m), 3.79 (1H, d), 3.98-4.01 (1H, m), 4.18 (1H, d), 4.49 (1H, s), 4.53 (2H, s), 6.80 (1H, s), 6.99 (1H, t), 7.31 (2H, d), 7.46-7.49 (2H, m), 7.57 (2H, d), 8.16 (1H, t), 8.27 (2H, d), 8.70 (1H, s), 8.92 (1H, s)

Mass Spectrum; M+H$^+$ 553.

Test (a): 0.14 µM.

The preparation of N-[2-[[6-[(3S)-3-methylmorpholin-4-yl]-2-[4-(phenylcarbamoylamino)phenyl]pyrimidin-4-yl]methylsulfanyl]ethyl]acetamide is described below.

N-[2-[[6-[(3S)-3-Methylmorpholin-4-yl]-2-[4-(phenylcarbamoylamino)phenyl]pyrimidin-4-yl]methylsulfanyl]ethyl]acetamide

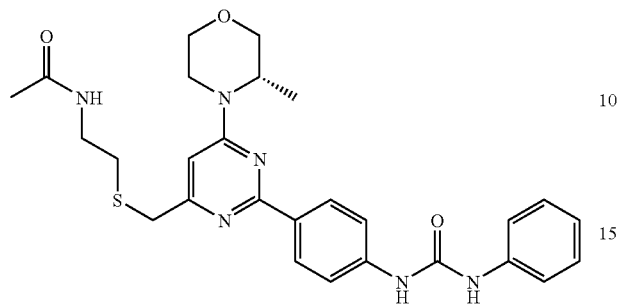

N-Acetylcysteamine (0.086 mL) was dissolved in acetonitrile (5 mL). DBU (0.120 mL) was then added to the solution and was allowed to stir at RT for 15 minutes. 1-[4-[4-[(3S)-3-Methylmorpholin-4-yl]-6-(methylsulfonyloxymethyl)pyrimidin-2-yl]phenyl]-3-phenyl-urea (228 mg) in acetonitrile (5 mL) was added to the reaction and stirred for 30 minutes. The reaction was concentrated in vacuo and the crude residue purified on silica, eluting with 5% methanol in DCM, to give the desired compound (100 mg) as a white solid.

Mass Spectrum; M+H$^+$ 521.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 12

1-[4-[4-(Benzenesulfonylmethyl)-6-[(3S)-3-methylmorpholin-4-yl]pyrimidin-2-yl]phenyl]-3-phenyl-urea

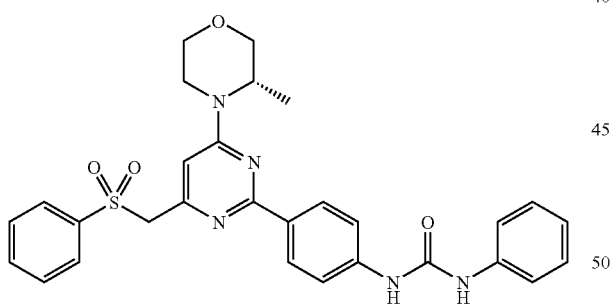

1-[4-[4-[(3S)-3-Methylmorpholin-4-yl]-6-(phenylsulfanylmethyl)pyrimidin-2-yl]phenyl]-3-phenyl-urea (62 mg) was dissolved in 1,4-dioxane (6 mL) and water (1 mL). The solution was cooled to 0° C. and 3-chloroperbenzoic acid (75%) (26 mg) was added followed immediately by sodium permanganate (30 mg). The reaction was allowed to stir at RT for 2 hours then further 3-chloroperbenzoic acid (4 mg) and sodium permanganate (4 mg) were added. The reaction was stirred for an extra 1 hour then the reaction was loaded onto a SCX-2 column, washed with methanol and the desired material removed with 7N ammonia in methanol. The desired material was isolated as a pale yellow solid (64 mg), NMR Spectrum: $^1$H NMR (DMSO-d$_6$) δ 1.20 (3H, d), 3.14-3.21 (1H, m), 3.45-3.52 (1H, m), 3.61-3.65 (1H, m), 3.77 (1H, d), 3.96-3.99 (1H, m), 4.10 (1H, d), 4.38 (1H, s), 4.71 (2H, s), 6.63 (1H, s), 6.99 (1H, m), 7.31 (2H, d), 7.46 (4H, t), 7.63 (2H, t), 7.73-7.78 (1H, m), 7.82 (1H, d), 7.82-7.84 (1H, m), 7.87 (2H, d), 8.69 (1H, s), 8.87 (1H, s).

Mass Spectrum; M+H$^+$ 544.

Test (a): 0.23 µM.

The preparation of 1-[4-[4-[(3S)-3-methylmorpholin-4-yl]-6-(phenylsulfanylmethyl)pyrimidin-2-yl]phenyl]-3-phenyl-urea is described below.

1-[4-[4-[(3S)-3-Methylmorpholin-4-yl]-6-(phenylsulfanylmethyl)pyrimidin-2-yl]phenyl]-3-phenyl-urea

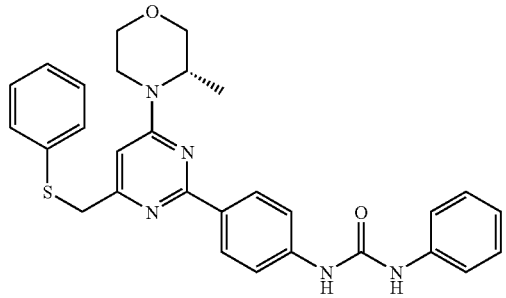

Thiophenol (0.029 mL) was dissolved in Acetonitrile (3 mL). DBU (0.043 mL) was then added to the solution and was allowed to stir at RT for 15 minutes. 1-[4-[4-[(3S)-3-Methylmorpholin-4-yl]-6-(methylsulfonyloxymethyl)pyrimidin-2-yl]phenyl]-3-phenyl-urea (80 mg) was added to the reaction and stirred for 30 minutes. The reaction was concentrated in vacuo and the residue chromatographed on silica, eluting with 5% methanol in DCM, to give the desired material (62 mg) as a white solid, Mass Spectrum; M+H$^+$ 512.

EXAMPLE 13

3-[4-[4-(Cyanomethylsulfonylmethyl)-6-[(3S)-3-methylmorpholin-4-yl]pyrimidin-2-yl]phenyl]-1,1-dimethyl-urea

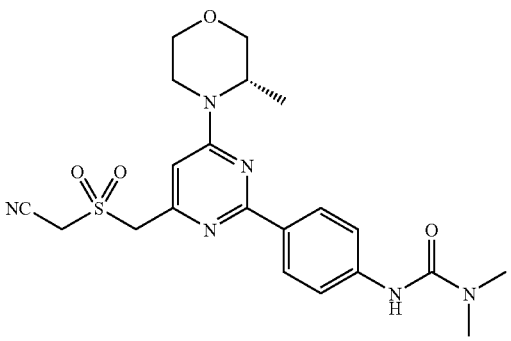

3-[4-[4-(Cyanomethylsulfanylmethyl)-6-[(3S)-3-methylmorpholin-4-yl]pyrimidin-2-yl]phenyl]-1,1-dimethyl-urea (162 mg) was dissolved in 1,4-dioxane (6 mL) and water (1 mL). The solution was cooled to 0° C. and 3-chloroperbenzoic acid (75%) (79 mg) was added followed immediately by sodium permanganate (92 mg). The reaction was allowed to stir at RT for 2 hours. Further 3-chloroperbenzoic acid (40 mg) and sodium permanganate (45 mg) were added and the reaction stirred for 1 hour then further 3-chloroperbenzoic acid (40 mg) and sodium permanganate (45 mg) added and the reaction stirred for 1 hour. The reaction was loaded onto a SCX-2 column, washed with methanol and the desired material removed with 7N ammonia in methanol. The desired material was isolated as a white solid (17 mg).

NMR Spectrum: $^1$H NMR (DMSO-$d_6$) δ1.25 (3H, d), 2.96 (6H, s), 3.18 (1H, d), 3.47-3.54 (1H, m), 3.64-3.67 (1H, m), 3.79 (1H, d), 3.98-4.01 (1H, m), 4.17 (1H, s), 4.46 (1H, d), 4.74 (2H, s), 5.10 (2H, d), 6.82 (1H, s), 7.59-7.61 (2H, m), 8.21-8.23 (2H, m), 8.49 (1H, s)

Mass Spectrum; M+H$^+$ 459.

Test (a): 2.1 µM.

The preparation of 3-[4-[4-(cyanomethylsulfanylmethyl)-6-[(3S)-3-methylmorpholin-4-yl]pyrimidin-2-yl]phenyl]-1,1-dimethyl-urea is described below.

3-[4-[4-(Cyanomethylsulfanylmethyl)-6-[(3S)-3-methylmorpholin-4-yl]pyrimidin-2-yl]phenyl]-1,1-dimethyl-urea

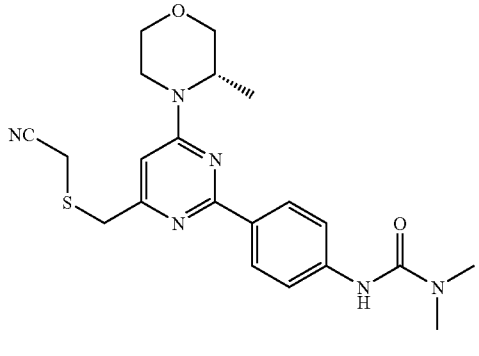

3-[4-[4-(Carbamimidoylsulfanylmethyl)-6-[(3S)-3-methylmorpholin-4-yl]pyrimidin-2-yl]phenyl]-1,1-dimethyl-urea (0.38 mmol) was dissolved in DMF (2 mL). This was treated with bromoacetonitrile (0.030 mL) and then the sodium hydroxide (61 mg) in water (1 mL) and stirred at RT for 15 minutes. The reaction mixture was concentrated in vacuo and the residue loaded onto a SCX-2 column, washed with methanol and the desired material removed with 7N ammonia in methanol. The desired material was isolated and used without further chromatography.

Mass Spectrum; M+H$^+$ 427.

3-[4-[4-(Carbamimidoylsulfanylmethyl)-6-[(3S)-3-methylmorpholin-4-yl]pyrimidin-2-yl]phenyl]-1,1-dimethyl-urea

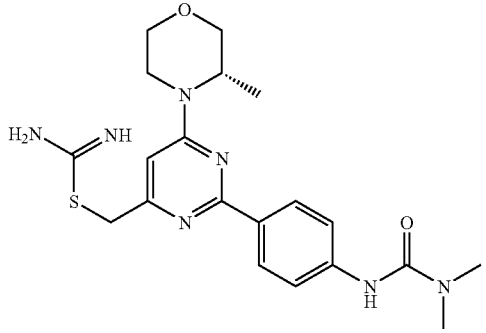

3-[4-[4-(Hydroxymethyl)-6-[(3S)-3-methylmorpholin-4-yl]pyrimidin-2-yl]phenyl]-1,1-dimethyl-urea (140 mg) was dissolved in DCM (5 mL) and triethylamine (0.079 mL) and the solution was cooled to 0° C. Methane sulfonyl chloride was added (0.044 mL) and the reaction was stirred for 15 minutes at RT. The solvent was removed under reduced pressure and replaced with ethanol (5 mL) then thiourea (32 mg) added. The reaction was then heated to 70° C. for 30 minutes then allowed to cool and concentrated in vacuo to give the desired material which was used without further purification.

Mass Spectrum; M+H$^+$ 430.

EXAMPLE 14

1,1-Dimethyl-3-[4-[4-[(3S)-3-methylmorpholin-4-yl]-6-(propan-2-ylsulfonylmethyl)pyrimidin-2-yl]phenyl]urea

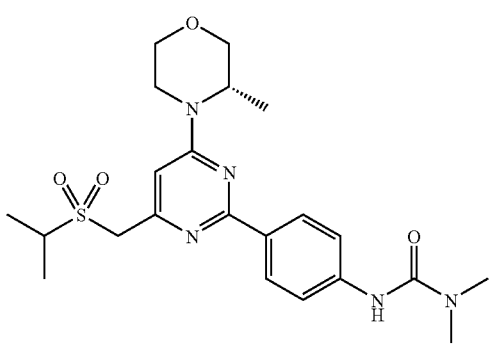

1,1-Dimethyl-3-[4-[4-[(3S)-3-methylmorpholin-4-yl]-6-(propan-2-ylsulfanylmethyl)pyrimidin-2-yl]phenyl]urea (163 mg) was dissolved in 1,4-dioxane (6 mL) and water (1 mL). The solution was cooled to 0° C. and 3-chloroperbenzoic acid (75%) (79 mg) was added followed immediately by sodium permanganate (92 mg). The reaction was allowed to stir at RT for 2 hours then further 3-chloroperbenzoic acid (20 mg) and sodium permanganate (25 mg) were added. The reaction was allowed to stir for 1 hour then loaded onto a SCX-2 column, washed with methanol and the desired material removed with 7N ammonia in methanol. The desired material (90 mg) was isolated as a white solid.

NMR Spectrum: $^1$H NMR (DMSO-$d_6$) δ1.25 (3H, d), 1.35-1.37 (6H, m), 2.95 (6H, s), 3.21-3.26 (2H, m), 3.47-3.54 (2H, m), 3.64-3.67 (1H, m), 3.78 (1H, d), 3.97-4.01 (1H, m), 4.24 (1H, m) 4.45-4.47 (2H, m), 6.78 (1H, s), 7.58-7.61 (2H, m), 8.17-8.20 (2H, m), 8.48 (1H, s)

Mass Spectrum; M+H$^+$ 462.

Test (a): 0.42 µM.

The preparation of 1,1-dimethyl-3-[4-[4-[(3S)-3-methylmorpholin-4-yl]-6-(propan-2-ylsulfanylmethyl)pyrimidin-2-yl]phenyl]urea is described below.

1,1-Dimethyl-3-[4-[4-[(3S)-3-methylmorpholin-4-yl]-6-(propan-2-ylsulfanylmethyl)pyrimidin-2-yl]phenyl]urea

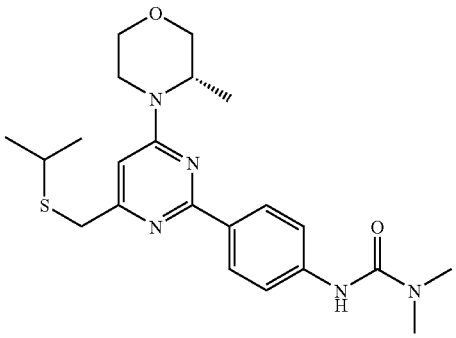

3-[4-[4-(Hydroxymethyl)-6-[(3S)-3-methylmorpholin-4-yl]pyrimidin-2-yl]phenyl]-1,1-dimethyl-urea (140 mg) was dissolved in DCM (5 mL) and triethylamine (0.079 mL) and the solution was cooled to 0° C. Methane sulfonyl chloride was added (0.044 mL) and the reaction was stirred for 15 minutes at RT before being concentrated in vacuo to give the mesylate which was used without further purification. Isopropyl mercaptan (0.062 mL) was dissolved in acetonitrile (5 mL). DBU (0.099 mL) was then added to the solution and was allowed to stir at RT for 5 minutes. The crude mesylate from above was suspended in acetonitrile (5 mL) and added to the thiol solution. The reaction was left to stir at RT for 1 hour then further DBU (0.099 mL) added and the reaction stirred at RT for 30 minutes. The reaction mixture was concentrated in vacuo to give the desired material which was used without further purification.

Mass Spectrum; M+H+ 430.

EXAMPLE 15

3-[4-[4-(Benzenesulfonylmethyl)-6-[(3S)-3-methylmorpholin-4-yl]pyrimidin-2-yl]phenyl]-1,1-dimethyl-urea

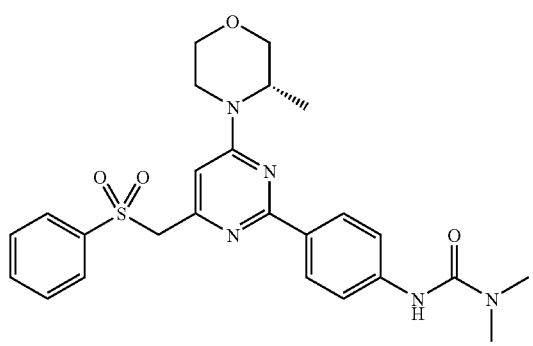

1,1-Dimethyl-3-[4-[4-[(3S)-3-methylmorpholin-4-yl]-6-(phenylsulfanylmethyl)pyrimidin-2-yl]phenyl]urea (158 mg) was dissolved in 1,4-dioxane (6 mL) and water (1 mL). The solution was cooled to 0° C. and 3-chloroperbenzoic acid (75%) (89 mg) was added followed immediately by sodium permanganate (96 mg). The reaction was allowed to stir at RT for 16 hours then further 3-chloroperbenzoic acid (20 mg) and sodium permanganate (25 mg) were added. The reaction was allowed to stir for 1 hour then loaded onto a SCX-2 column, washed with methanol and the desired material removed with 7N ammonia in methanol. The desired material was isolated as a white solid (90 mg).

NMR Spectrum: $^1$H NMR (DMSO-$d_6$) δ 1.20 (3H, d), 2.95 (6H, s), 3.13-3.20 (1H, m), 3.44-3.51 (1H, m), 3.61-3.65 (1H, m), 3.76 (1H, d), 3.95-3.99 (1H, m), 4.07 (1H, t), 4.36 (1H, s), 4.70 (2H, s), 6.62 (1H, s), 7.47-7.49 (2H, m), 7.62 (2H, t), 7.72-7.75 (1H, m), 7.79-7.84 (4H, m), 8.43 (1H, s)

Mass Spectrum; M+H+ 496.

Test (a): 1 µM.

The preparation of 1,1-dimethyl-3-[4-[4-[(3S)-3-methylmorpholin-4-yl]-6-(phenylsulfanylmethyl)pyrimidin-2-yl]phenyl]urea is described below.

1,1-Dimethyl-3-[4-[4-[(3S)-3-methylmorpholin-4-yl]-6-(phenylsulfanylmethyl)pyrimidin-2-yl]phenyl]urea

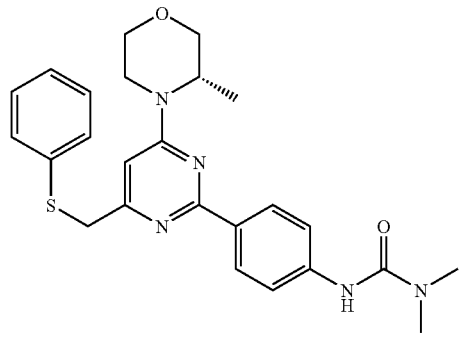

Thiophenol (0.062 mL) was dissolved in acetonitrile (5 mL). DBU (0.141 mL) was then added to the solution and was allowed to stir at RT for 5 minutes. 1,1-Dimethyl-3-[4-[4-[(3S)-3-methylmorpholin-4-yl]-6-(methylsulfonyloxymethyl)pyrimidin-2-yl]phenyl]urea (154 mg) was suspended in acetonitrile (5 mL) and added to the thiol. The reaction was left to stir at RT of 1 hour then concentrated in vacuo to give the desired material which was used without further purification.

Mass Spectrum; M+H+ 464.

1,1-Dimethyl-3-[4-[4-[(3S)-3-methylmorpholin-4-yl]-6-(methylsulfonyloxymethyl)pyrimidin-2-yl]phenyl]urea

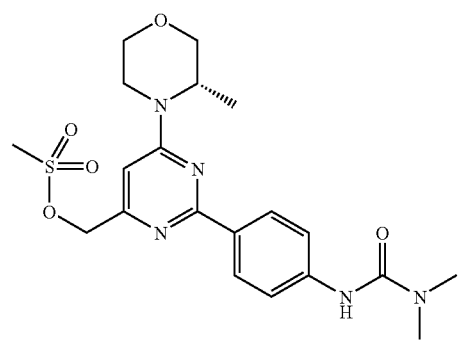

3-[4-[4-(Hydroxymethyl)-6-[(3S)-3-methylmorpholin-4-yl]pyrimidin-2-yl]phenyl]-1,1-dimethyl-urea (384 mg) was dissolved in DCM (12 mL) and triethylamine (0.216 mL) and the solution was cooled to 0° C. Methane sulfonyl chloride was added (0.121 mL) and the reaction was stirred for 15 minutes at RT before being concentrated in vacuo to give the desired material.

Mass Spectrum; M+H+ 450.

EXAMPLE 16

N-[2-[[2-[4-(Dimethylcarbamoylamino)phenyl]-6-[(3S)-3-methylmorpholin-4-yl]pyrimidin-4-yl]methylsulfonyl]ethyl]acetamide

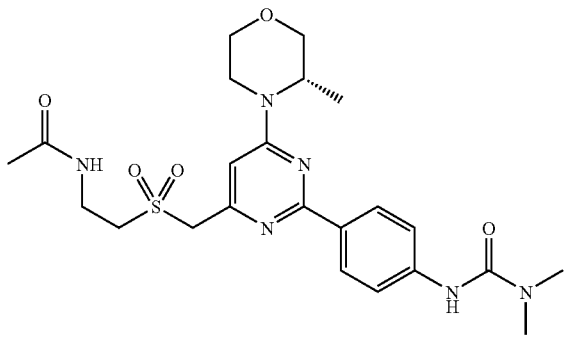

N-[2-[[2-[4-(Dimethylcarbamoylamino)phenyl]-6-[(3S)-3-methylmorpholin-4-yl]pyrimidin-4-yl]methylsulfanyl]ethyl]acetamide (158 mg) was dissolved in 1,4-dioxane (6 mL) and water (1 mL). The solution was cooled to 0° C. and 3-chloroperbenzoic acid (75%) (116 mg) was added followed immediately by sodium permanganate (134 mg). The reaction was allowed to stir at RT for 1 hour then loaded onto a SCX-2 column, washed with methanol and the desired material removed with 7N ammonia in methanol. The desired material (84 mg) was isolated as a white solid.

NMR Spectrum: $^1$H NMR (DMSO-$d_6$) δ1.25 (3H, d), 1.83 (3H, s), 2.96 (6H, s), 3.20-3.25 (1H, m), 3.47-3.50 (1H, m), 3.52 (2H, d), 3.57 (2H, q), 3.63-3.67 (1H, m), 3.78 (1H, d), 3.97-4.01 (1H, m), 4.18 (1H, d), 4.51 (3H, m), 6.78 (1H, s), 7.58-7.61 (2H, m), 8.16-8.19 (1H, m), 8.19-8.22 (2H, m), 8.49 (1H, s)

Mass Spectrum; M+H+ 505.

Test (a): 4 μM.

The preparation of N-[2-[[2-[4-(Dimethylcarbamoylamino)phenyl]-6-[(3S)-3-methylmorpholin-4-yl]pyrimidin-4-yl]methylsulfanyl]ethyl]acetamide is described below.

N-[2-[[2-[4-(Dimethylcarbamoylamino)phenyl]-6-[(3S)-3-methylmorpholin-4-yl]pyrimidin-4-yl]methylsulfanyl]ethyl]acetamide

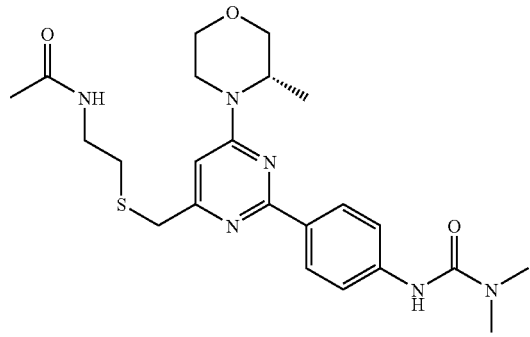

N-Acetylcysteamine (0.064 mL) was dissolved in acetonitrile (5 mL). DBU (0.141 mL) was then added to the solution and was allowed to stir at RT for 5 minutes. 1,1-Dimethyl-3-[4-[4-[(3S)-3-methylmorpholin-4-yl]-6-(methylsulfony- loxymethyl)pyrimidin-2-yl]phenyl]urea (154 mg) was suspended in acetonitrile (5 mL) and added to the thiol. The reaction was left to stir at RT of 1 hour then concentrated in vacuo to give the desired material.

Mass Spectrum; M+H+ 473.

EXAMPLE 17

2-[[2-[4-(Dimethylcarbamoylamino)phenyl]-6-[(3S)-3-methylmorpholin-4-yl]pyrimidin-4-yl]methylsulfonyl]acetamide

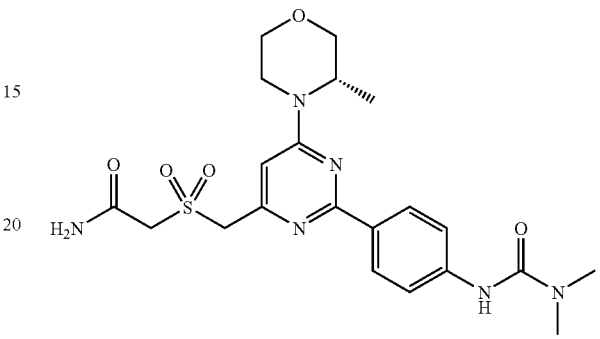

2-[[2-[4-(Dimethylcarbamoylamino)phenyl]-6-[(3S)-3-methylmorpholin-4-yl]pyrimidin-4-yl]methylsulfanyl]acetamide (158 mg) was dissolved in 1,4-dioxane (6 mL) and water (1 mL). The solution was cooled to 0° C. and 3-chloroperbenzoic acid (75%) (123 mg) was added followed immediately by sodium permanganate (143 mg). The reaction was allowed to stir at RT for 1 hour then loaded onto a SCX-2 column, washed with methanol and the desired material removed with 7N ammonia in methanol. The desired material (55 mg) was isolated as a white solid.

NMR Spectrum: $^1$H NMR (DMSO-$d_6$) δ1.25 (3H, d), 2.96 (6H, s), 3.22-3.26 (1H, m), 3.47-3.53 (1H, m), 3.63-3.67 (1H, m), 3.78 (1H, d), 3.97-4.01 (1H, m), 4.18 (1H, d), 4.27 (2H, s), 4.47 (1H, s), 4.67 (2H, s), 6.77 (1H, s), 7.53 (1H, s), 7.58-7.61 (2H, m), 7.79 (1H, s), 8.17-8.21 (2H, m), 8.49 (1H, s)

Mass Spectrum; M+H+ 477.

Test (a): 1.1 μM.

The preparation of 2-[[2-[4-(dimethylcarbamoylamino)phenyl]-6-[(3S)-3-methylmorpholin-4-yl]pyrimidin-4-yl]methylsulfanyl]acetamide is described below.

2-[[2-[4-(Dimethylcarbamoylamino)phenyl]-6-[(3S)-3-methylmorpholin-4-yl]pyrimidin-4-yl]methylsulfanyl]acetamide

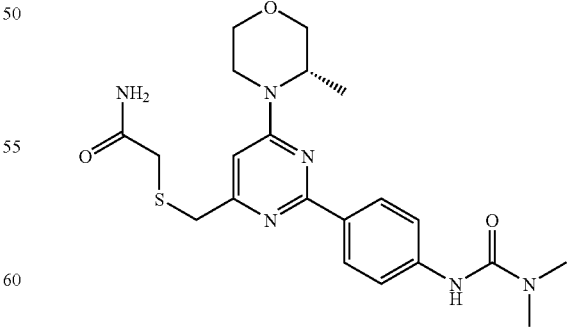

Dimethyl-3-[4-[4-[(3S)-3-methylmorpholin-4-yl]-6-(methylsulfonyloxymethyl)pyrimidin-2-yl]phenyl]urea (154 mg) was dissolved in ethanol (5 mL) and thiourea (29 mg) was added. The reaction was then heated to 70° C. for 30

EXAMPLE 18

1-[4-[4-(Hydroxymethyl)-6-[(3S)-3-methylmorpholin-4-yl]pyrimidin-2-yl]phenyl]-3-methyl-urea

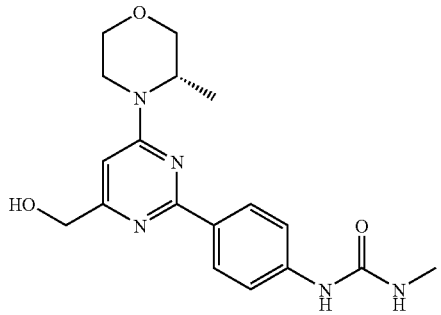

1-(4-Bromophenyl)-3-methyl-urea (2.50 g), potassium acetate (3.21 g), and bis(pinacolato)diboron (3.33 g) were dissolved in 1,4 dioxane (120 mL). The solution was degassed for 5 minutes then 1,1'-bis(diphenylphosphino)ferrocenedichloropalladium(II) dichloromethane adduct was added (535 mg) and the reaction was heated to 90° C. for 3 hours. Further 1,1'-bis(diphenylphosphino)ferrocenedichloropalladium(II) dichloromethane adduct (250 mg) was added and heating continued for 1 hour. Further 1,1'-bis(diphenylphosphino)ferrocenedichloropalladium(II) dichloromethane adduct (250 mg) was added and heating continued for a further 1 hour. [2-Chloro-6-[(3S)-3-methylmorpholin-4-yl]pyrimidin-4-yl]methanol (2.66 mg), ethanol (9.5 mL), 2M sodium carbonate solution (27.3 mL) and 1,1'-bis(diphenylphosphino)ferrocenedichloropalladium(II) dichloromethane adduct (535 mg) were added and the heating was continued for 16 hours. The reaction was cooled and evaporated to dryness then the residue partitioned between ethyl acetate (250 mL) and water (100 mL). The organics were dried over magnesium sulphate, filtered and concentrated in vacuo. The crude material was chromatographed on silica, eluting with 5% methanol in DCM, to give the desired material (1.25 g) as a brown solid.

NMR Spectrum: $^1$H NMR (DMSO-d$_6$) δ1.23 (3H, d), 2.66 (3H, d), 3.18-3.23 (1H, m), 3.46-3.52 (1H, m), 3.62-3.66 (1H, m), 3.76 (1H, d), 3.96-3.99 (1H, m), 4.16 (1H, d), 4.45 (2H, d), 4.49 (1H, d), 5.38 (1H, t), 6.05 (1H, q), 6.66 (1H, s), 7.46-7.48 (2H, m), 8.18-8.21 (2H, m), 8.69 (1H, s)

Mass Spectrum; M+H$^+$ 358.

Test (a): 0.12 µM.

The preparation of 1-(4-bromophenyl)-3-methyl-urea is described below.

1-(4-Bromophenyl)-3-methyl-urea

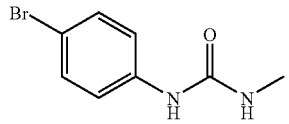

4-Bromophenyl isocyante (2.50 g) was dissolved in THF (75 mL). Methylamine (2.0M in THF, 75 mL) was added to the solution and stirred at RT for 1 hour. The reaction was filtered and vacuumed to dryness. The crude material was chromatographed on silica, eluting with 5% methanol in DCM, to give the desired material (2.65 g) as a white solid.

NMR Spectrum: $^1$H NMR (DMSO-d$_6$) δ2.64 (3H, d), 6.03 (1H, d), 7.37 (4H, s), 8.61 (1H, s)

Mass Spectrum; M+H$^+$ 229.

EXAMPLE 19

1-[4-[4-(Cyclohexylsulfonylmethyl)-6-[(3S)-3-methylmorpholin-4-yl]pyrimidin-2-yl]phenyl]-3-methyl-urea

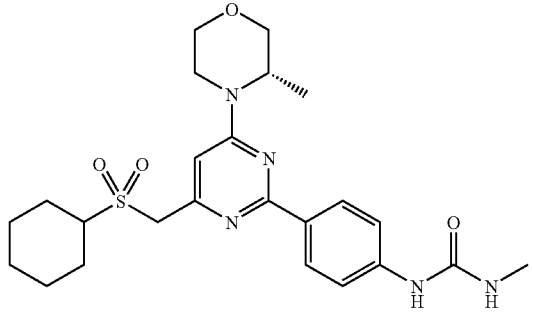

1-[4-[4-(Cyclohexylsulfanylmethyl)-6-[(3S)-3-methylmorpholin-4-yl]pyrimidin-2-yl]phenyl]-3-methyl-urea (0.35 mmol) was dissolved in 1,4-dioxane (5 mL) and water (1 mL). 3-chloroperbenzoic acid (75%) (121 mg) was added to the solution followed immediately by sodium permanganate (140 mg) and the reactions stirred at RT for 1 hour. Further 3-chloroperbenzoic acid (75%) (121 mg) and sodium permanganate (140 mg) were added and the reactions allowed to stir at RT for 1 hour. Further 3-chloroperbenzoic acid (75%) (121 mg) and sodium permanganate (140 mg) were added and the reactions allowed to stir at RT for another 1 hour then loaded onto a SCX-3 column. The column was washed with methanol and the desired material removed with 7N ammonia in methanol. The crude material was purified by prep-HPLC (basic) to give the desired material (74 mg) as a white solid.

NMR Spectrum: $^1$H NMR (DMSO-d$_6$) δ1.18-1.32 (7H, m), 1.42 (1H, d), 1.48 (1H, d), 1.68 (1H, d), 1.89 (2H, d), 2.25 (3H, d), 2.32-2.34 (1H, m), 2.66 (3H, d), 3.46-3.53 (1H, m), 3.63-3.67 (1H, m), 3.78 (1H, d), 3.97-4.01 (1H, m), 4.17 (1H, d), 4.43 (3H, s), 6.08 (1H, t), 6.77 (1H, s), 7.50-7.52 (2H, m), 8.19-8.21 (2H, m)

Mass Spectrum; M+H$^+$ 488.

--- minutes before being concentrated in vacuo. The residue was dissolved in DMF (2 mL) and treated with 2-bromoacetamide (52 mg) followed by sodium hydroxide (55 mg) in water (1 mL) and stirred at RT for 30 minutes. The reaction mixture was concentrated in vacuo then loaded onto a SCX-2 column, washed with methanol and the desired material removed with 7N ammonia in methanol. The desired material was used without further purification.

Mass Spectrum; M+H$^+$ 445.

The following compounds were prepared in an analogous fashion from the appropriate sulfides.

| Example | Structure | NAME | LCMS MH+ |
|---|---|---|---|
| 19a | 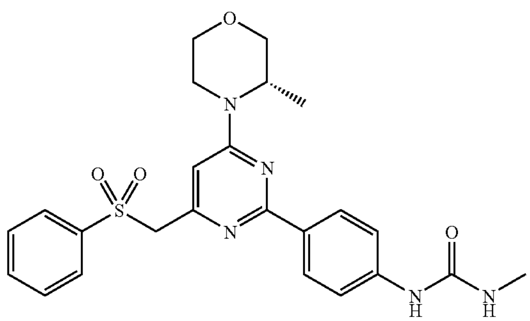 | 1-[4-[4-(benzenesulfonylmethyl)-6-[(3S)-3-methylmorpholin-4-yl]pyrimidin-2-yl]phenyl]-3-methyl-urea | 482 |
| 19b | 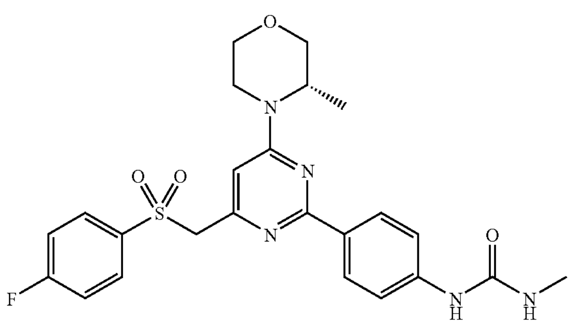 | 1-[4-[4-[(4-fluorophenyl)sulfonylmethyl]-6-[(3S)-3-methylmorpholin-4-yl]pyrimidin-2-yl]phenyl]-3-methyl urea | 500 |
| 19c | 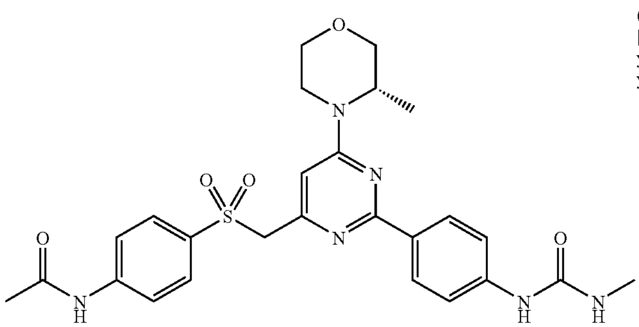 | N-[4-[[2-[4-(methylcarbamoylamino)phenyl]-6-[(3S)-3-methylmorpholin-4-yl]pyrimidin-4-yl]methylsulfonyl]phenyl]acetamide | 539 |
| 19d | 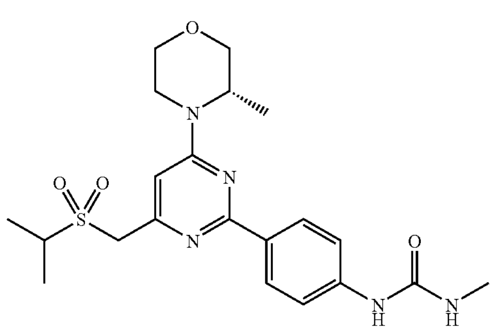 | 3-methyl-1-[4-[4-[(3S)-3-methylmorpholin-4-yl]-6-(propan-2-ylsulfonylmethyl)pyrimidin-2-yl]phenyl]urea | 448 |

| Example | Structure | NAME | LCMS MH+ |
|---|---|---|---|
| 19e | 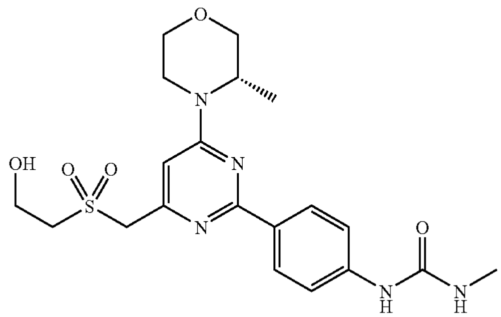 | 1-[4-[4-(2-hydroxyethylsulfonylmethyl)-6-[(3S)-3-methylmorpholin-4-yl]pyrimidin-2-yl]phenyl]-3-methyl-urea | 450 |
| 19f | 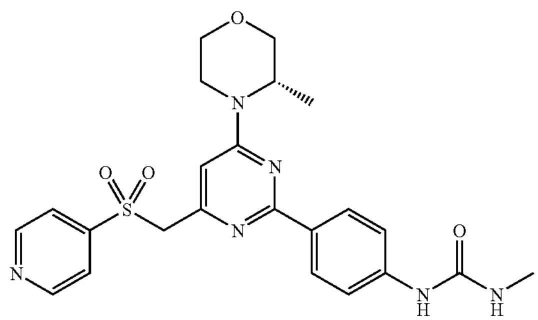 | 3-methyl-1-[4-[4-[(3S)-3-methylmorpholin-4-yl]-6-(pyridin-4-ylsulfonylmethyl)pyrimidin-2-yl]phenyl]urea | 483 |

Example 19a: $^1$H NMR (DMSO-$d_6$) δ1.18 (3H, d), 2.66 (3H, q), 3.11-3.19 (1H, m), 3.43-3.50 (1H, m), 3.60-3.63 (1H, m), 3.75 (1H, d), 3.94-3.98 (1H, m), 4.08 (1H, d), 4.35 (1H, s), 4.69 (2H, s), 6.04 (1H, q), 6.59 (1H, s), 7.36-7.38 (2H, m), 7.61 (2H, t), 7.71-7.75 (1H, m), 7.79-7.81 (3H, m), 7.82 (1H, s), 8.69 (1H, s)

Example 19b: $^1$H NMR (DMSO-$d_6$) δ1.20 (3H, d), 2.66 (3H, d), 3.14-3.21 (1H, m), 3.45-3.51 (1H, m), 3.61-3.65 (1H, m), 3.76 (1H, d), 3.95-3.99 (1H, m), 4.11 (1H, d), 4.37 (1H, s), 4.71 (2H, s), 6.04 (1H, q), 6.64 (1H, s), 7.37-7.41 (2H, m), 7.43-7.48 (2H, m), 7.77-7.80 (2H, m), 7.85-7.89 (2H, m), 8.71 (1H, s)

Example 19c: $^1$H NMR (DMSO-$d_6$) δ1.18 (3H, d), 2.13 (3H, s), 2.60-2.61 (3H, m), 2.67 (3H, q), 2.68 (1H, s), 3.44-3.49 (1H, m), 4.08 (1H, d), 4.35 (1H, s), 4.60 (2H, s), 6.05 (1H, q), 6.54 (1H, s), 7.37-7.39 (2H, m), 7.70 (2H, d), 7.77 (2H, d), 7.82 (2H, d), 8.68 (1H, s), 10.37 (1H, s)

Example 19d: $^1$H NMR (DMSO-$d_6$) δ1.24 (3H, d), 1.35-1.37 (7H, m), 2.66-2.69 (3H, m), 3.21-3.25 (1H, m), 3.47-3.54 (2H, m), 3.63-3.67 (1H, m), 3.78 (1H, d), 3.97-4.01 (1H, m), 4.46 (3H, s), 6.08 (1H, q), 6.77 (1H, s), 7.49-7.51 (2H, m), 8.17-8.19 (2H, m), 8.73 (1H, s)

Example 19e: $^1$H NMR (DMSO-$d_6$) δ1.24 (3H, d), 2.66 (2H, s), 2.68 (2H, q), 3.21-3.26 (1H, m), 3.51 (3H, t), 3.63-3.67 (1H, m), 3.78 (1H, d), 3.89-3.94 (2H, m), 3.97-4.01 (1H, m), 4.50 (3H, s), 5.18 (1H, t), 6.07 (1H, d), 6.76 (1H, s), 7.49-7.51 (2H, m), 8.20-8.22 (2H, m), 8.74 (1H, s)

Example 19f: $^1$H NMR (DMSO-$d_6$) δ1.20-1.25 (3H, m), 2.66 (3H, t), 3.15-3.21 (1H, m), 3.45-3.51 (1H, m), 3.61-3.65 (1H, m), 3.77 (1H, t), 3.95-3.99 (1H, m), 4.11 (1H, d), 4.39 (1H, s), 4.87 (2H, s), 6.05 (1H, q), 6.71 (1H, s), 7.35-7.37 (2H, m), 7.64-7.66 (2H, m), 7.81-7.82 (2H, m), 8.70 (1H, d), 8.90 (1H, d), 8.91 (1H, s)

Test (a): Example (19) 0.25 μM; Example (19a) 0.0047 μM; Example (19b) 0.033 μM; Example (19c) 0.022 μM; Example (19d) 0.066 μM; Example (19e) 0.011 μM; Example (19f) 0.027 μM.

The preparation of 1-[4-[4-(cyclohexylsulfanylmethyl)-6-[(3S)-3-methylmorpholin-4-yl]pyrimidin-2-yl]phenyl]-3-methyl-urea is described below.

1-[4-[4-(Cyclohexylsulfanylmethyl)-6-[(3S)-3-methylmorpholin-4-yl]pyrimidin-2-yl]phenyl]-3-methyl-urea

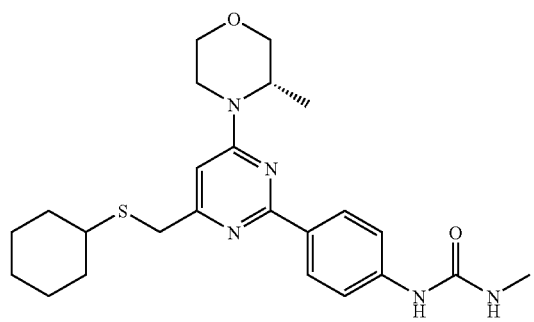

Cyclohexanethiol (0.61 mmol) was dissolved in acetonitrile (4 mL). DBU (0.050 mL) was then added and the solution allowed to stir at RT for 5 minutes. 3-Methyl-1-[4-[4-[(3S)-3-methylmorpholin-4-yl]-6-(methylsulfonyloxymethyl)pyrimidin-2-yl]phenyl]urea (151 mg) dissolved in acetonitrile (2 mL) and DBU (0.054 mL) was added and the reactions stirred at RT for 2 hours. The reaction mixture was concentrated in vacuo to give the desired material which was used without further purification.

The following sulfides were made in an analogous manner from 3-methyl-1-[4-[4-[(3S)-3-methylmorpholin-4-yl]-6-(methylsulfonyloxymethyl)pyrimidin-2-yl]phenyl]urea and the appropriate thiol.

| Structure | NAME |
|---|---|
| 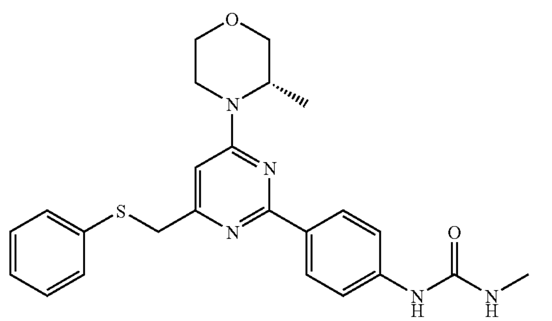 | 3-methyl-1-[4-[4-[(3S)-3-methylmorpholin-4-yl]-6-(phenylsulfanylmethyl)pyrimidin-2-yl]phenyl]urea |
| 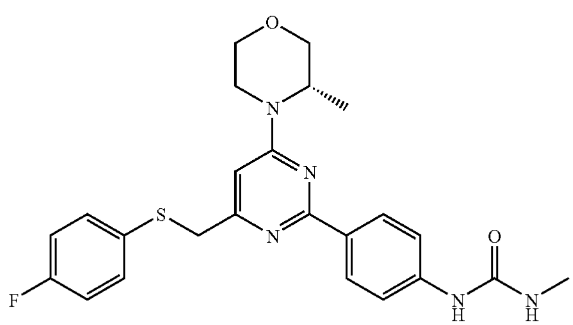 | 1-[4-[4-[(4-fluorophenyl)sulfanylmethyl]-6-[(3S)-3-methylmorpholin-4-yl]pyrimidin-2-yl]phenyl]-3-methyl-urea |
| 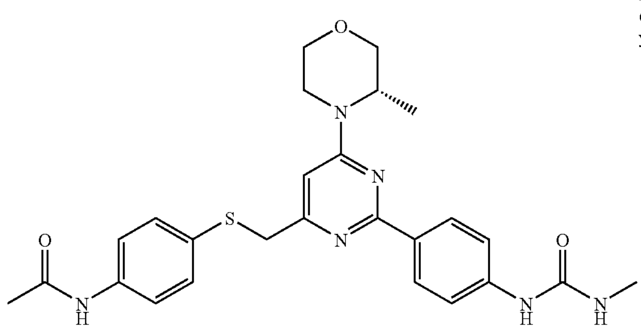 | N-[4-[[2-[4-(methylcarbamoylamino)phenyl]-6-[(3S)-3-methylmorpholin-4-yl]pyrimidin-4-yl]methylsulfanyl]phenyl]acetamide |
| 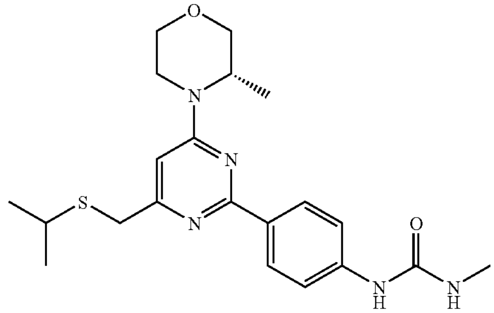 | 3-methyl-1-[4-[4-[(3S)-3-methylmorpholin-4-yl]-6-(propan-2-ylsulfanylmethyl)pyrimidin-2-yl]phenyl]urea |

-continued

| Structure | NAME |
|---|---|
| 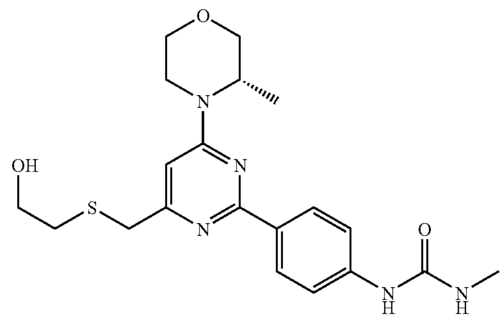 | 1-[4-[4-(2-hydroxyethylsulfanylmethyl)-6-[(3S)-3-methylmorpholin-4-yl]pyrimidin-2-yl]phenyl]-3-methyl-urea |
| 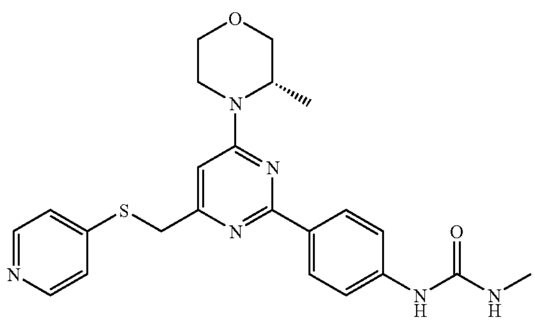 | 3-methyl-1-[4-[4-[(3S)-3-methylmorpholin-4-yl]-6-(pyridin-4-ylsulfanylmethyl)pyrimidin-2-yl]phenyl]urea |

The preparation of 3-methyl-1-[4-[4-[(3S)-3-methylmorpholin-4-yl]-6-(methylsulfonyloxymethyl)pyrimidin-2-yl]phenyl]urea is described below.

3-Methyl-1-[4-[4-[(3S)-3-methylmorpholin-4-yl]-6-(methylsulfonyloxymethyl)pyrimidin-2-yl]phenyl]urea

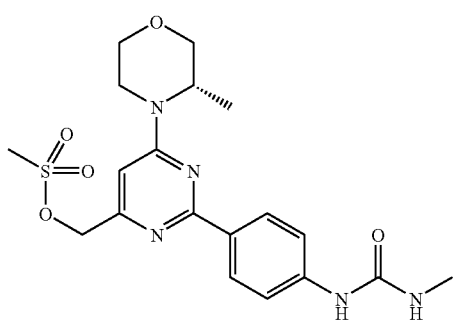

1-[4-[4-(Hydroxymethyl)-6-[(3S)-3-methylmorpholin-4-yl]pyrimidin-2-yl]phenyl]-3-methyl-urea (1.24 g) was partially dissolved in DCM (30 mL) and triethylamine (0.724 mL) and the solution was cooled to 0° C. Methane sulfonyl chloride was added (0.405 mL) and the reaction was stirred for 15 minutes at RT then concentrated in vacuo to give the desired material.

Mass Spectrum; M+H$^+$ 436.

EXAMPLE 20

3-[4-[4-(Benzenesulfonylmethyl)-6-morpholin-4-yl-pyrimidin-2-yl]phenyl]-1-methyl-urea

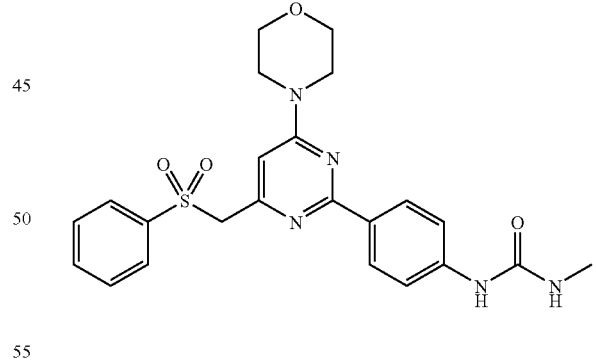

Phenyl (4-{4-morpholin-4-yl-6-[(phenylsulfonyl)methyl]pyrimidin-2-yl}phenyl)carbamate (250 mg, 0.45 mmol) was dissolved in DMF (5 mL). Triethylamine (0.188 mL, 1.35 mmol) was added followed by methylamine (2M in THF, 1.1 mL) and the solution heated at 50° C. for 1 hour. The reaction was cooled to room temperature and concentrated in vacuo. The resultant oil was purified by chromatography on silica, eluting with 0-5% methanol in DCM to give the desired material as a white solid (120 mg).

NMR Spectrum: ¹H NMR (400.13 MHz, DMSO-d$_6$) δ2.66 (d, 3H), 3.63 (m, 4H), 3.70 (m, 4H), 4.69 (s, 2H), 6.05 (m, 1H), 6.65 (s, 1H), 7.38 (d, 2H), 7.63 (t, 2H), 7.74 (d, 1H), 7.80 (m, 3H), 8.69 (s, 1H)

LCMS Spectrum: MH+ 468, retention time 1.76 min, Method 5 Min Base

The compounds shown in table were prepared in an analogous manner N'-(4-{4-morpholin-4-yl-6-[(phenylsulfonyl)methyl]pyrimidin-2-yl}phenyl)urea by reacting the appropriate amine with the appropriate carbamate and purification by either chromatography on silica or by preparative HPLC.

| Example | Structure | NAME | LCMS MH+ | Retention time (min) |
|---|---|---|---|---|
| 20a | 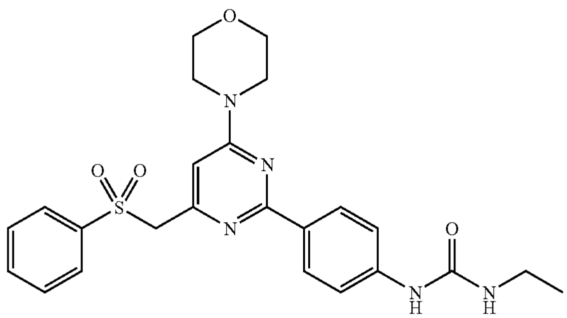 | 3-[4-[4-(benzenesulfonylmethyl)-6-morpholin-4-yl-pyrimidin-2-yl]phenyl]-1-ethyl-urea | 482 | 1.98 |
| 20b | 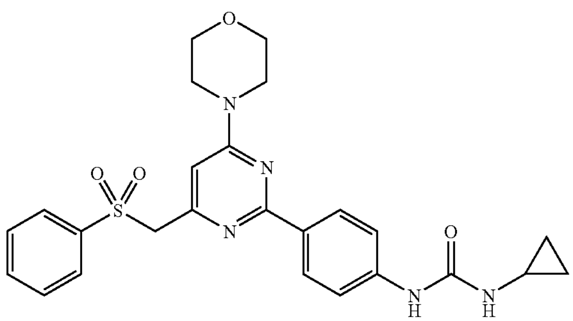 | 1-[4-[4-(benzenesulfonylmethyl)-6-morpholin-4-yl-pyrimidin-2-yl]phenyl]-3-cyclopropyl-urea | 494 | 1.92 |
| 20c | 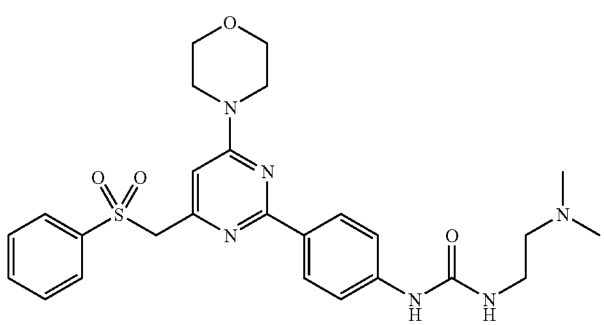 | 3-[4-[4-(benzenesulfonylmethyl)-6-morpholin-4-yl-pyrimidin-2-yl]phenyl]-1-(2-dimethylaminoethyl)urea | 525 | 1.98 |
| 20d | 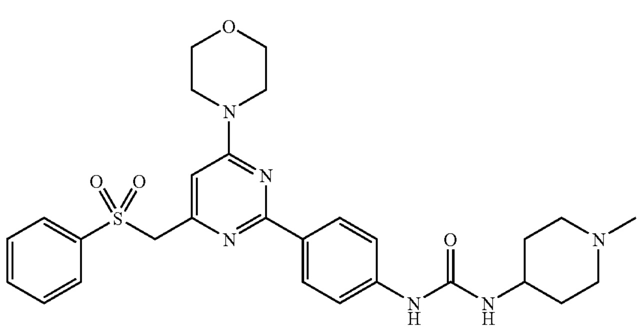 | 3-[4-[4-(benzenesulfonylmethyl)-6-morpholin-4-yl-pyrimidin-2-yl]phenyl]-1-(1-methyl-4-piperidyl)urea | 551 | 1.93 |

| Example | Structure | NAME | LCMS MH+ | Retention time (min) |
|---|---|---|---|---|
| 20e | 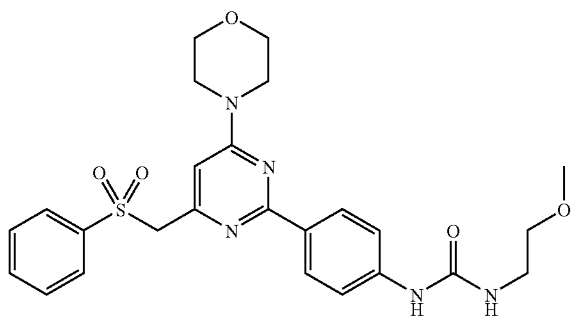 | 3-[4-[4-(benzenesulfonylmethyl)-6-morpholin-4-yl-pyrimidin-2-yl]phenyl]-1-(2-methoxyethyl)urea | 512 | 1.77 |
| 20f | 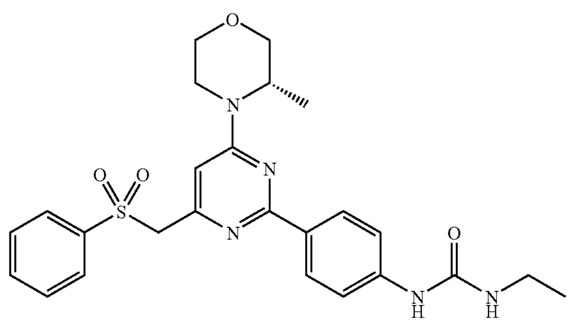 | 3-[4-[4-(benzenesulfonylmethyl)-6-[(3S)-3-methylmorpholin-4-yl]pyrimidin-2-yl]phenyl]-1-ethyl-urea | 496 | 2.06 |
| 20g | 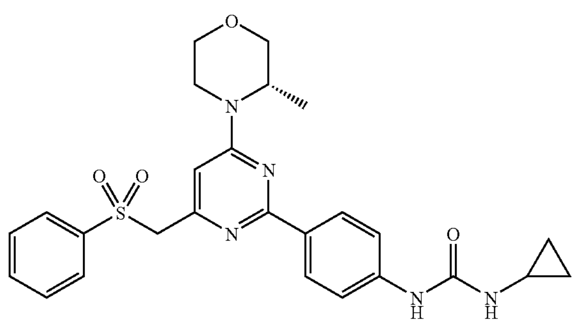 | 1-[4-[4-(benzenesulfonylmethyl)-6-[(3S)-3-methylmorpholin-4-yl]pyrimidin-2-yl]phenyl]-3-cyclopropyl-urea | 508 | 2.08 |
| 20h | 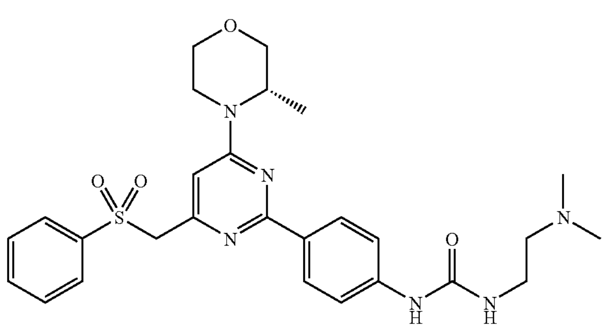 | 1-[4-[4-(benzenesulfonylmethyl)-6-[(3S)-3-methylmorpholin-4-yl]pyrimidin-2-yl]phenyl]-3-(2-dimethylaminoethyl)urea | 539 | 1.94 |

-continued

| Example | Structure | NAME | LCMS MH+ | Retention time (min) |
|---|---|---|---|---|
| 20i | 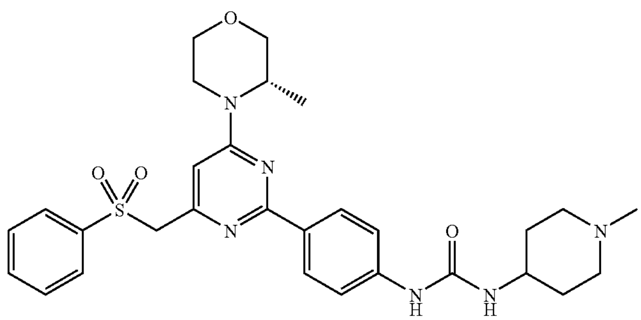 | 1-[4-[4-(benzenesulfonylmethyl)-6-[(3S)-3-methylmorpholin-4-yl]pyrimidin-2-yl]phenyl]-3-(1-methyl-4-piperidyl)urea | 565 | 1.94 |
| 20j | 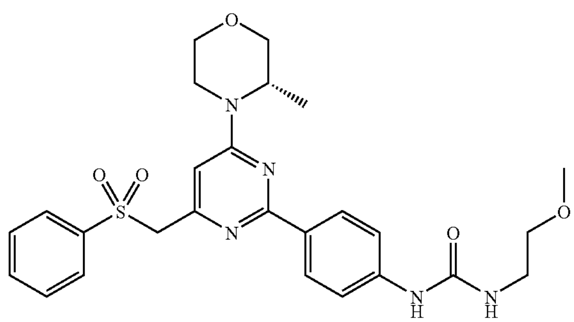 | 1-[4-[4-(benzenesulfonylmethyl)-6-[(3S)-3-methylmorpholin-4-yl]pyrimidin-2-yl]phenyl]-3-(2-methoxyethyl)urea | 526 | 1.98 |
| 20k | 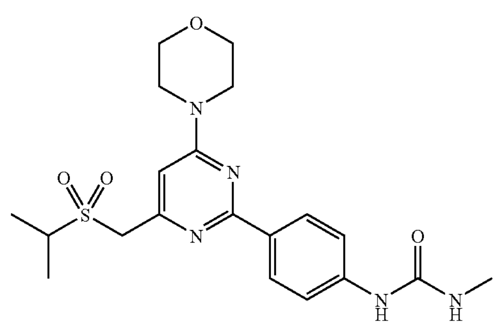 | 3-methyl-1-[4-[4-morpholin-4-yl-6-(propan-2-ylsulfonylmethyl)pyrimidin-2-yl]phenyl]urea | 434 | 1.47 |
| 20l | 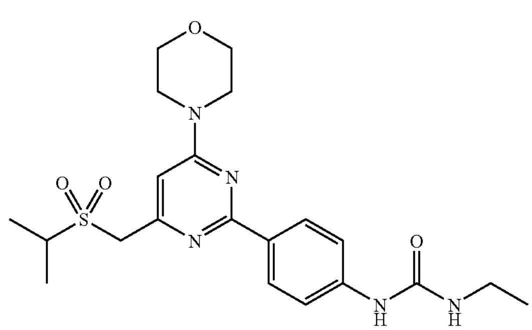 | 1-ethyl-3-[4-[4-morpholin-4-yl-6-(propan-2-ylsulfonylmethyl)pyrimidin-2-yl]phenyl]urea | 448 | 1.61 |

-continued

| Example | Structure | NAME | LCMS MH+ | Retention time (min) |
|---|---|---|---|---|
| 20m | 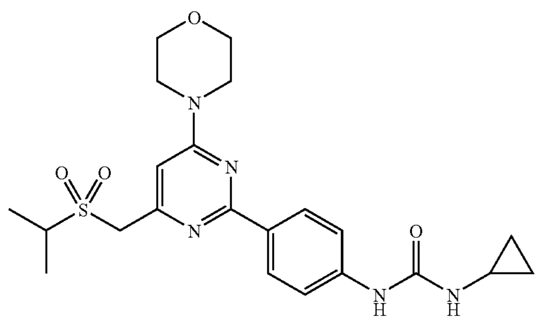 | 3-cyclopropyl-1-[4-[4-morpholin-4-yl-6-(propan-2-ylsulfonylmethyl)pyrimidin-2-yl]phenyl]urea | 460 | 1.63 |
| 20n | 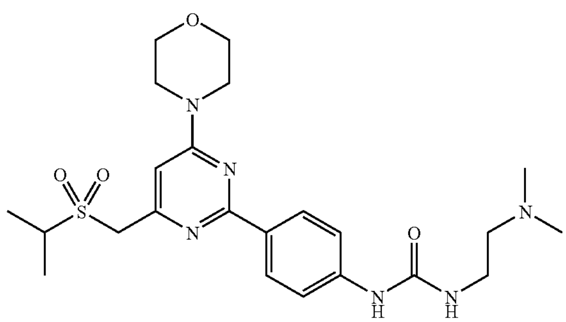 | 3-(2-dimethylaminoethyl)-1-[4-[4-morpholin-4-yl-6-(propan-2-ylsulfonylmethyl)pyrimidin-2-yl]phenyl]urea | 491 | 1.59 |
| 20o | 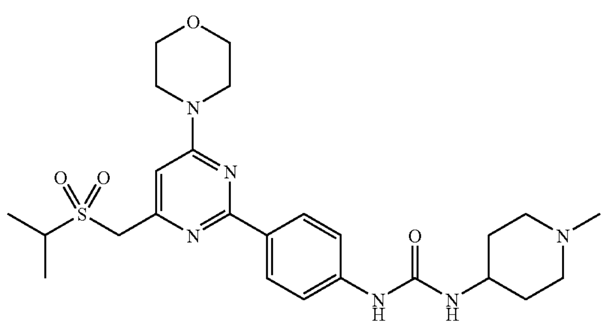 | 3-(1-methyl-4-pipendyl)-1-[4-[4-morpholin-4-yl-6-(propan-2-ylsulfonylmethyl)pyrimidin-2-yl]phenyl]urea | 517 | 1.61 |
| 20p | 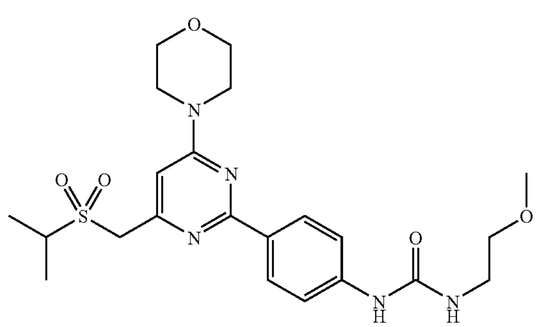 | 3-(2-methoxyethyl)-1-[4-[4-morpholin-4-yl-6-(propan-2-ylsulfonylmethyl)pyrimidin-2-yl]phenyl]urea | 478 | 1.53 |

-continued

| Example | Structure | NAME | LCMS MH+ | Retention time (min) |
|---|---|---|---|---|
| 20q | 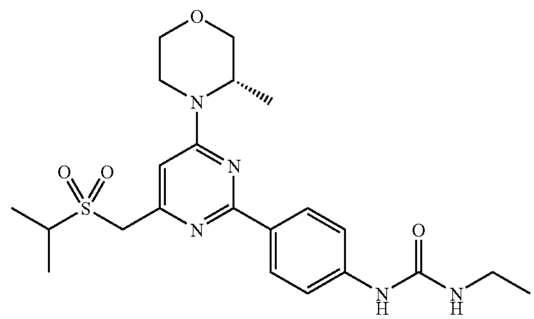 | 1-ethyl-3-[4-[4-[(3S)-3-methylmorpholin-4-yl]-6-(propan-2-ylsulfonylmethyl)pyrimidin-2-yl]phenyl]urea | 462 | 1.75 |
| 20r | 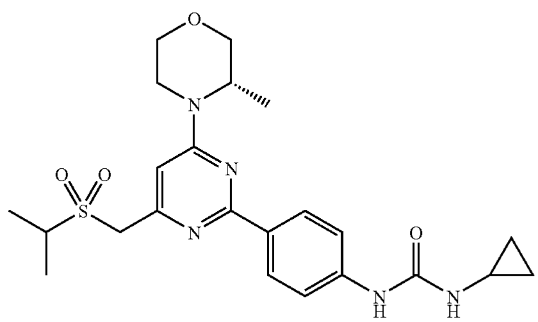 | 3-cyclopropyl-1-[4-[4-[(3S)-3-methylmorpholin-4-yl]-6-(propan-2-ylsulfonylmethyl)pyrimidin-2-yl]phenyl]urea | 474 | 1.77 |
| 20s | 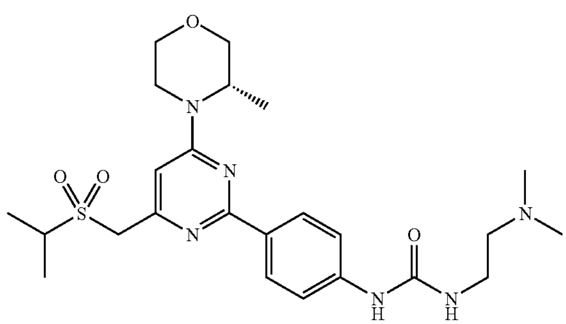 | 3-(2-dimethylaminoethyl)-1-[4-[4-[(3S)-3-methylmorpholin-4-yl]-6-(propan-2-ylsulfonylmethyl)pyrimidin-2-yl]phenyl]urea | 505 | 1.76 |
| 20t | 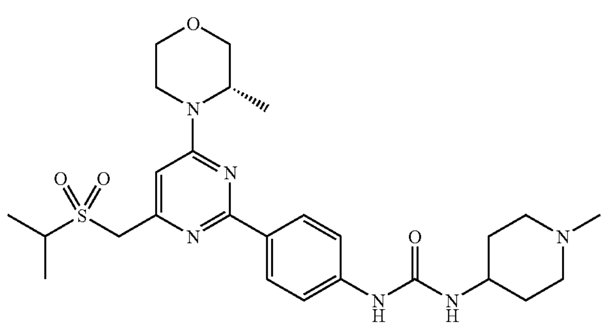 | 1-[4-[4-[(3S)-3-methylmorpholin-4-yl]-6-(propan-2-ylsulfonylmethyl)pyrimidin-2-yl]phenyl]-3-(1-methyl-4-piperidyl)urea | 531 | 1.77 |

| Example | Structure | NAME | LCMS MH+ | Retention time (min) |
|---|---|---|---|---|
| 20u | 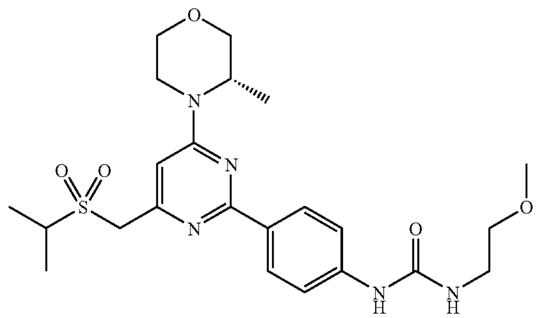 | 3-(2-methoxyethyl)-1-[4-[4-[(3S)-3-methylmorpholin-4-yl]-6-(propan-2-ylsulfonylmethyl)pyrimidin-2-yl]phenyl]urea | 492 | 1.67 |

Example 20a: $^1$H NMR (400.13 MHz, DMSO-d$_6$) δ1.00 (t, 3H), 3.05 (m, 2H), 3.56 (s, 4H), 3.63 (m, 4H), 4.62 (s, 2H), 6.07 (t, 1H), 6.59 (s, 1H), 7.30 (d, 2H), 7.55 (t, 2H), 7.71 (m, 5H), 8.54 (s, 1H)

Example 20b: $^1$H NMR (400.13 MHz, DMSO-d$_6$) δ0.42 (m, 2H), 0.65 (m, 2H), 2.55 (m, 1H), 3.64 (m, 4H), 3.71 (m, 4H), 4.69 (s, 2H), 6.41 (d, 1H), 6.66 (s, 1H), 7.38 (d, 2H), 7.63 (t, 2H), 7.75 (m, 1H), 7.81 (m, 4H), 8.49 (s, 1H)

Example 20c: $^1$H NMR (400.13 MHz, DMSO-d$_6$) δ2.20 (s, 6H), 2.38 (t, 2H), 3.20 (m, 2H), 3.63 (s, 4H), 3.70 (s, 4H), 4.69 (s, 2H), 6.17 (s, 1H), 6.65 (s, 1H), 7.37 (d, 2H), 7.62 (t, 2H), 7.75 (t, 1H), 7.81 (t, 4H), 8.87 (s, 1H)

Example 20d: $^1$H NMR (400.13 MHz, DMSO-d$_6$) δ1.49 (m, 2H), 1.86 (m, 2H), 2.32 (s, 3H), 2.84 (m, 2H), 3.54 (m, 2H), 3.63 (s, 4H), 3.70 (m, 4H), 4.69 (s, 2H), 6.46 (d, 1H), 6.65 (s, 1H), 7.35 (d, 2H), 7.63 (t, 2H), 7.74 (t, 2H), 7.81 (m, 3H), 8.76 (s, 1H)

Example 20e: $^1$H NMR (400.13 MHz, DMSO-d$_6$) δ3.27 (m, 2H), 3.29 (s, 3H), 3.40 (t, 2H), 3.63 (s, 4H), 3.71 (m, 4H), 4.69 (s, 2H), 6.25 (t, 1H), 6.66 (s, 1H), 7.35 (d, 2H), 7.62 (t, 1H), 7.75 (m, 2H), 7.81 (m, 4H), 8.73 (s, 1H)

Example 20f: $^1$H NMR (400.13 MHz, DMSO-d$_6$) δ1.15 (t, 3H), 1.25 (d, 3H), 3.12 (m, 3H), 3.47 (t, 1H), 3.62 (d, 1H), 3.76 (d, 1H), 3.96 (d, 1H), 4.08 (d, 1H), 4.36 (s, 1H), 4.70 (s, 2H), 6.14 (t, 1H), 6.60 (s, 1H), 7.38 (d, 2H), 7.62 (t, 2H), 7.74 (t, 1H), 7.81 (m, 4H), 8.62 (s, 1H)

Example 20g: $^1$H NMR (400.13 MHz, DMSO-d$_6$) δ0.42 (m, 2H), 0.65 (m, 2H), 1.20 (d, 3H), 2.55 (m, 1H), 3.16 (m, 1H), 3.47 (m, 1H), 3.62 (m, 1H), 3.75 (d, 1H), 3.97 (m, 1H), 4.09 (d, 1H), 4.36 (s, 1H), 4.70 (s, 2H), 6.42 (d, 1H), 6.60 (s, 1H), 7.39 (d, 2H), 7.63 (t, 2H), 7.75 (t, 1H), 7.82 (m, 4H), 8.49 (s, 1H)

Example 20h: $^1$H NMR (400.13 MHz, DMSO-d$_6$) δ1.19 (d, 3H), 2.23 (s, 6H), 2.40 (t, 2H), 3.21 (m, 1H), 3.47 (m, 1H), 3.62 (m, 1H), 3.75 (d, 1H), 3.96 (m, 1H), 4.08 (d, 1H), 4.36 (s, 1H), 4.70 (s, 2H), 6.21 (t, 1H), 6.60 (s, 1H), 7.40 (d, 2H), 7.62 (t, 2H), 7.75 (t, 1H), 7.82 (m, 3H), 7.96 (s, 1H), 8.90 (s, 1H)

Example 20i: $^1$H NMR (400.13 MHz, DMSO-d$_6$) δ1.19 (d, 3H), 1.40 (m, 2H), 1.79 (m, 2H), 2.02 (t, 2H), 2.16 (s, 3H), 2.64 (m, 2H), 3.16 (m, 1H), 3.47 (m, 2H), 3.62 (m, 1H), 3.75 (d, 1H), 3.96 (m, 1H), 4.08 (d, 1H), 4.35 (s, 1H), 4.69 (s, 2H), 6.16 (d, 1H), 6.60 (s, 1H), 7.35 (d, 2H), 7.65 (t, 2H), 7.74 (t, 1H), 7.81 (m, 4H), 8.52 (s, 1H)

Example 20j: $^1$H NMR (400.13 MHz, DMSO-d$_6$) δ1.20 (d, 3H), 3.15 (t, 1H), 3.29 (m, 5H), 3.40 (t, 2H), 3.47 (t, 1H), 3.62 (d, 1H), 3.75 (d, 1H), 3.96 (d, 1H), 4.08 (d, 1H), 4.36 (s, 1H), 4.70 (s, 2H), 6.25 (t, 1H), 6.60 (s, 1H), 7.37 (d, 2H), 7.62 (t, 2H), 7.74 (t, 1H), 7.82 (d, 4H), 8.73 (s, 1H)

Example 20k: $^1$H NMR (400.13 MHz, DMSO-d$_6$) δ1.36 (d, 6H), 2.66 (s, 3H), 3.51 (m, 1H), 3.72 (s, 8H), 4.47 (s, 2H), 6.09 (s, 1H), 6.83 (s, 1H), 7.51 (d, 2H), 8.18 (d, 2H), 8.76 (s, 1H)

Example 20l: $^1$H NMR (400.13 MHz, DMSO-d$_6$) δ1.07 (t, 3H), 1.35 (d, 6H), 3.12 (m, 2H), 3.51 (m, 1H), 3.72 (s, 8H), 4.47 (s, 2H), 6.18 (s, 1H), 6.83 (s, 1H), 7.51 (d, 2H), 8.18 (d, 2H), 8.68 (s, 1H)

Example 20m: $^1$H NMR (400.13 MHz, DMSO-d$_6$) δ0.42 (m, 2H), 0.65 (m, 2H), 1.38 (d, 6H), 2.56 (m, 1H), 3.51 (m, 1H), 3.72 (s, 8H), 4.46 (s, 2H), 6.45 (s, 1H), 6.82 (s, 1H), 7.51 (d, 2H), 8.19 (d, 2H), 8.55 (s, 1H)

Example 20n: $^1$H NMR (400.13 MHz, DMSO-d$_6$) δ1.36 (d, 6H), 2.85 (d, 6H), 3.20 (m, 2H), 3.46 (m, 2H), 3.51 (m, 1H), 3.72 (s, 8H), 4.46 (s, 2H), 6.56 (t, 1H), 6.83 (s, 1H), 7.55 (d, 2H), 8.21 (d, 2H), 9.10 (s, 1H)

Example 20o: $^1$H NMR (400.13 MHz, DMSO-d$_6$) δ1.36 (d, 6H), 1.57 (m, 2H), 1.97 (d, 2H), 2.59 (s, 1H), 2.78 (s, 2H), 3.16 (d, 2H), 3.29 (s, 3H), 3.50 (m, 1H), 3.72 (s, 8H), 4.46 (s, 2H), 6.44 (d, 1H), 6.81 (s, 1H), 7.49 (d, 2H), 8.20 (d, 2H), 8.65 (s, 1H)

Example 20p: $^1$H NMR (400.13 MHz, DMSO-d$_6$) δ1.38 (d, 6H), 3.28 (m, 2H), 3.29 (s, 3H), 3.40 (t, 2H), 3.51 (m, 1H), 3.72 (s, 8H), 4.46 (s, 2H), 6.28 (t, 1H), 6.81 (s, 1H), 7.49 (d, 2H), 8.20 (d, 2H), 8.77 (s, 1H)

Example 20q: $^1$H NMR (400.13 MHz, DMSO-d$_6$) δ1.07 (t, 3H), 1.24 (d, 3H), 1.36 (m, 6H), 3.13 (m, 2H), 3.23 (m, 1H), 3.51 (m, 2H), 3.65 (m, 1H), 3.72 (d, 1H), 3.99 (m, 1H), 4.17 (d, 1H), 4.46 (s, 3H), 6.17 (t, 1H), 6.77 (s, 1H), 7.50 (d, 2H), 8.18 (d, 2H), 8.65 (s, 1H)

Example 20r: $^1$H NMR (400.13 MHz, DMSO-d$_6$) δ0.42 (m, 2H), 0.65 (m, 2H), 1.25 (d, 3H), 1.37 (d, 6H), 2.57 (m, 2H), 3.23 (m, 1H), 3.50 (m, 1H), 3.65 (m, 1H), 3.78 (d, 1H), 3.99 (m, 1H), 4.17 (d, 1H), 4.46 (s, 2H), 6.44 (d, 1H), 6.77 (s, 1H), 7.51 (d, 2H), 8.19 (d, 2H), 8.53 (s, 1H)

Example 20s: $^1$H NMR (400.13 MHz, DMSO-d$_6$) δ1.22 (d, 3H), 1.36 (m, 6H), 2.18 (s, 6H), 2.34 (t, 2H), 3.21 (m, 2H), 3.50 (m, 2H), 3.65 (m, 1H), 3.76 (d, 1H), 3.99 (m, 1H), 4.06 (q, 2H), 4.17 (d, 1H), 4.46 (s, 2H), 6.17 (t, 1H), 6.77 (s, 1H), 7.49 (d, 2H), 8.18 (d, 2H), 8.89 (s, 1H)

Example 20t: $^1$H NMR (400.13 MHz, DMSO-d$_6$) δ1.22 (d, 3H), 1.36 (m, 6H), 1.42 (m, 2H), 1.80 (m, 2H), 2.03 (t, 2H), 2.17 (s, 3H), 2.65 (d, 2H), 3.18 (d, 1H), 3.23 (m, 1H), 3.50 (m, 2H), 3.65 (m, 1H), 3.76 (d, 1H), 3.98 (m, 1H), 4.06 (m, 1H), 4.17 (d, 1H), 4.46 (s, 2H), 6.19 (d, 1H), 6.77 (s, 1H), 7.48 (d, 2H), 8.18 (d, 2H), 8.56 (s, 1H)

Example 20u: $^1$H NMR (400.13 MHz, DMSO-d$_6$) δ1.24 (d, 4H), 1.36 (m, 6H), 3.18 (d, 3H), 3.24 (m, 2H), 3.40 (t, 2H), 3.50 (m, 2H), 3.65 (m, 1H), 3.78 (d, 1H), 3.99 (m, 1H), 4.06 (m, 1H), 4.17 (d, 1H), 4.46 (s, 2H), 6.28 (t, 1H), 6.77 (s, 1H), 7.49 (d, 2H), 8.19 (d, 2H), 8.77 (s, 1H)

Test (a): Example (20) 0.043 µM; Example (20a) 0.15 µM; Example (20b) 0.17 µM; Example (20c) 1 µM; Example (20d) 1.6 µM; Example (20e) 2.1 µM; Example (20f) 0.035 µM; Example (20g) 0.039 µM; Example (20h) 0.44 µM; Example (20i) 0.7 µM; Example (20j) 0.75 µM; Example (20k) 0.036 µM; Example (20l) 0.074 µM; Example (20m) 0.081 µM; Example (20n) 0.86 µM; Example (20o) 1.3 µM; Example (20p) 0.91 µM; Example (20q) 0.039 µM; Example (20r) 0.094 µM; Example (20s) 0.62 µM; Example (20t) 0.6 µM; Example (20u) 0.27 µM.

The preparations of the carbamates phenyl (4-{4-morpholin-4-yl-6-[(phenylsulfonyl)methyl]pyrimidin-2-yl}phenyl)carbamate, phenyl (4-{4-[(3S)-3-methylmorpholin-4-yl]-6-[(phenylsulfonyl)methyl]pyrimidin-2-yl}phenyl)carbamate, phenyl (4-{4-[(isopropylsulfonyl)methyl]-6-morpholin-4-ylpyrimidin-2-yl}phenyl)carbamate, phenyl (4-{4-[(isopropylsulfonyl)methyl]-6-[(3S)-3-methylmorpholin-4-yl]pyrimidin-2-yl}phenyl)carbamate are described below.

Phenyl (4-{4-morpholin-4-yl-6-[(phenylsulfonyl)methyl]pyrimidin-2-yl}phenyl)carbamate

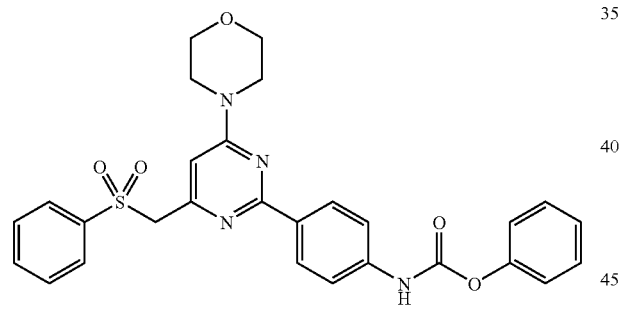

(4-{4-Morpholin-4-yl-6-[(phenylsulfonyl)methyl]pyrimidin-2-yl}phenyl)amine (1 g, 2.44 mmol) was dissolved in dioxane (10 mL). Sodium bicarbonate (307 mg, 3.65 mmol) was added, followed by phenyl chloroformate (0.307 mL, 2.44 mmol) and the reaction stirred at room temperature for 2 hours. The solvent was removed in vacuo, and the resultant oil partitioned between 10 mL DCM and 10 mL water. The organic phase was dried over magnesium sulphate, filtered and concentrated in vacuo. The cream solid obtained was chromatographed on silica, eluting with 0-50% ethyl acetate in DCM, to give the desired material as a white solid (790 mg).

NMR Spectrum: $^1$H NMR (400.13 MHz, DMSO-d$_6$) δ3.64 (s, 4H), 3.70 (m, 4H), 4.71 (s, 2H), 6.70 (s, 1H), 7.27 (m, 3H), 7.45 (t, 2H), 7.51 (d, 2H), 7.62 (t, 2H), 7.74 (m, 1H), 7.85 (m, 4H), 10.38 (s, 1H)

LCMS Spectrum: MH+ 531, retention time 2.61 min, Method 5 Min Base (4-{4-Morpholin-4-yl-6-[(phenylsulfonyl)methyl] pyrimidin-2-yl}phenyl)amine

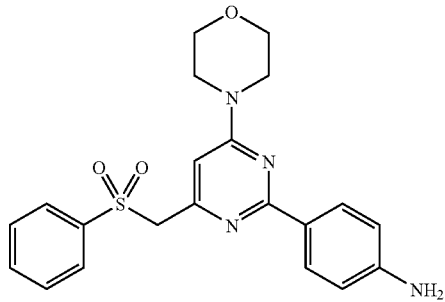

4-{2-Chloro-6-[(phenylsulfonyl)methyl]pyrimidin-4-yl}morpholine (3.3 g, 9.33 mmol) was dissolved in a solution of 18% DMF in a mixture of 7:3:2 dimethoxyethane:water:ethanol (36 mL). [4-(4,4,5,5-Tetramethyl-1,3,2-dioxaborolan-2-yl)phenyl]amine (3.07 g, 13.99 mmol), 2M sodium carbonate solution (12 mL) and dichlorobis(triphenylphosphine) palladium catalyst (328 mg, 0.47 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The crude oil was dissolved in DCM and filtered to remove insoluble material. A beige solid precipitated from the filtrates and the filtrates were filtered again. The solid was analysed and found to be the desired material (2.2 g).

NMR Spectrum: $^1$H NMR (400.13 MHz, DMSO-d$_6$) δ3.60 (m, 4H), 3.69 (m, 4H), 4.64 (s, 2H), 5.50 (s, 2H), 6.48 (d, 2H), 6.54 (s, 1H), 7.63 (m, 4H), 7.74 (t, 1H), 7.82 (m, 2H)

LCMS Spectrum: MH+ 411, retention time 1.70 min, Method 5 Min Base

4-{2-Chloro-6-[(phenylsulfonyl)methyl]pyrimidin-4-yl}morpholine

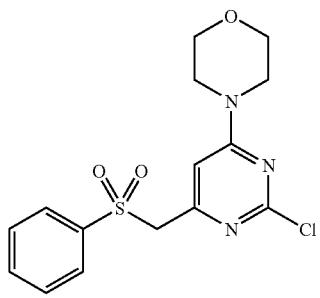

2,4-dichloro-6-[(phenylsulfonyl)methyl]pyrimidine (6 g, 19.8 mmol) was dissolved in DCM (50 mL) and stirred (under nitrogen) at −5° C. Triethylamine (3.06 mL, 21.8 mmol) was added to give a clear brown solution. Morpholine (1.65 mL, 19.8 mmol) was dissolved in DCM and added dropwise keeping the reaction below −5° C. The cooling bath was then removed and the reaction mixture stirred at room temperature for 1 hour. The reaction mixture was then washed with water (50 mL), dried over magnesium sulphate, filtered and concentrated in vacuo. The crude material was chromatographed on silica, eluting with 0-50% ethyl acetate in DCM to give the desired material as a white solid (4 g).

NMR Spectrum: $^1$H NMR (400.13 MHz, DMSO-$d_6$) δ 3.53 (s, 4H), 3.65 (t, 4H), 4.61 (s, 2H), 6.71 (s, 1H), 7.64 (t, 2H), 7.77 (m, 3H)

LCMS Spectrum: MH+ 354, retention time 1.50 min, Method 5 Min Base 2,4-dichloro-6-[(phenylsulfonyl)methyl]pyrimidine

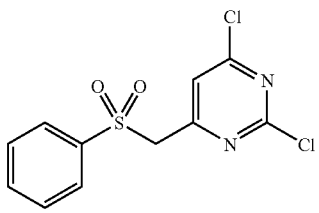

6-[(Phenylsulfonyl)methyl]pyrimidine-2,4(1H,3H)-dione (13.3 g, 49 mmol) was added to phosphorus oxychloride (100 mL) and the mixture heated to reflux for 16 hours. The reaction was then cooled to room temperature and the excess phosphorus oxychloride was removed in vacuo. The residue was azeotroped with toluene (2×100 mL) and dissolved in DCM. This mixture was then poured slowly onto ice (1 L) and stirred for 20 minutes, then extracted with DCM (3×500 mL) The extracts were combined, dried over magnesium sulphate, then concentrated in vacuo to give the desired material as a brown solid (12 g). The material was used without further purification.

NMR Spectrum: $^1$H NMR (400.13 MHz, DMSO-$d_6$) δ 4.97 (s, 2H), 7.65 (t, 2H), 7.72 (s, 1H), 7.79 (m, 3H)

LCMS Spectrum: M–H 301, retention time 2.08 min, Method 5 Min Basic

6-[(Phenylsulfonyl)methyl]pyrimidine-2,4(1H,3H)-dione

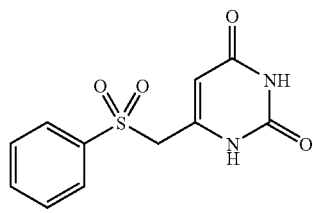

6-(Chloromethyl)-1H-pyrimidine-2,4-dione (8 g, 50 mmol) was dissolved in DMF (200 mL) and benzenesulphinic acid sodium salt (9.8 g, 60 mmol) was added. The reaction was heated to 125° C. for 2 hours then allowed to cool and the suspension filtered and concentrated in vacuo to give a yellow solid. The crude material was washed with water (100 mL), filtered, then triturated with acetonitrile to give the desired material as a cream solid (13.2 g). The material was used without further purification.

NMR Spectrum: $^1$H NMR (400.13 MHz, DMSO-$d_6$) δ 4.46 (s, 2H), 7.69 (t, 2H), 7.81 (m, 1H), 7.87 (m, 3H), 10.85 (s, 1H), 11.11 (s, 1H)

6-(Chloromethyl)-1H-pyrimidine-2,4-dione is a commercially available material.

Phenyl (4-{4-[(3S)-3-methylmorpholin-4-yl]-6-[(phenylsulfonyl)methyl]pyrimidin-2-yl}phenyl)carbamate

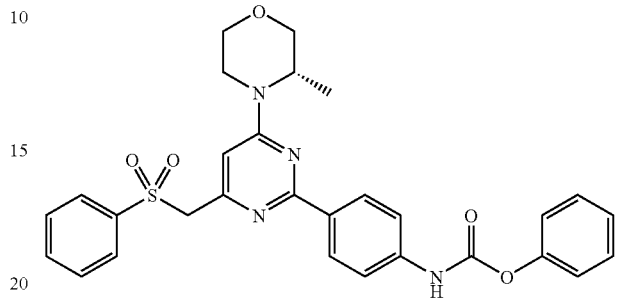

(4-{4-[(3S)-3-Methylmorpholin-4-yl]-6-[(phenylsulfonyl)methyl]pyrimidin-2-yl}phenyl)amine (2 g, 4.71 mmol) was dissolved in dioxane (20 mL). Sodium bicarbonate (594 mg, 7.07 mmol) was added, followed by phenyl chloroformate (0.593 mL, 4.71 mmol) and the reaction stirred at room temperature for 2 hours. The solvent was removed in vacuo, and the resultant oil partitioned between 20 mL DCM and 20 mL water. The organic phase was dried over magnesium sulphate, filtered and concentrated in vacuo. The cream solid obtained was chromatographed on silica, eluting with 0-50% ethyl acetate in DCM, to give the desired material as a white solid (1.1 g).

NMR Spectrum: $^1$H NMR (400.13 MHz, DMSO-$d_6$) δ 1.20 (d, 3H), 3.17 (m, 1H), 3.48 (m, 1H), 3.63 (m, 1H), 3.76 (d, 1H), 3.97 (m, 1H), 4.11 (d, 1H), 4.37 (s, 1H), 4.72 (s, 2H), 6.65 (s, 1H), 7.27 (m, 3H), 7.45 (t, 2H), 7.51 (d, 2H), 7.62 (t, 2H), 7.74 (t, 1H), 7.82 (d, 2H), 7.90 (d, 2H), 10.38 (s, 1H)

LCMS Spectrum: MH+ 545, retention time 2.7 min, Method 5 Min Base (4-{4-[(3S)-3-Methylmorpholin-4-yl]-6-[(phenylsulfonyl)methyl]pyrimidin-2-yl}phenyl)amine

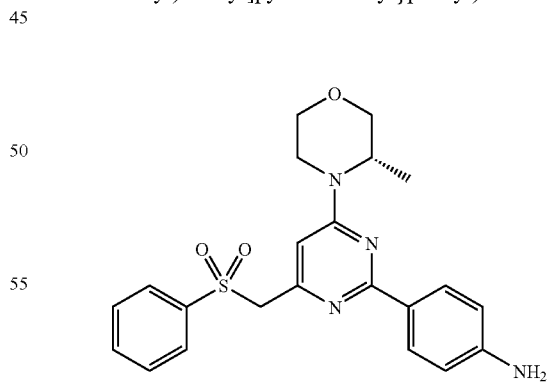

Tert-butyl (4-{4-[(3S)-3-methylmorpholin-4-yl]-6-[(phenylsulfonyl)methyl]pyrimidin-2-yl}phenyl)carbamate (3.1 g, 5.91 mmol) was dissolved in DCM (20 mL) and trifluoroacetic acid (10 mL) was added. The reaction mixture was stirred at room temperature for 2 hours then diluted with DCM (20 mL) and washed with saturated aqueous sodium bicarbonate (20 mL). Organic phase collected, dried over magnesium sulphate, filtered and concentrated in vacuo to give the desired material as a beige solid (2.5 g).

NMR Spectrum: ¹H NMR (400.13 MHz, DMSO-$d_6$) δ1.22 (d, 3H), 3.24 (m, 1H), 3.47 (m, 1H), 3.62 (m, 1H), 3.78 (d, 1H), 3.98 (m, 1H), 4.14 (s, 1H), 4.37 (s, 1H), 4.75 (s, 2H), 6.56 (s, 1H), 6.67 (d, 3H), 7.65 (m, 2H), 7.78 (m, 3H), 7.84 (m, 3H)

LCMS Spectrum: MH+ 425, retention time 2.03 min, Method 5 Min Base

Tert-butyl (4-{4-[(3S)-3-methylmorpholin-4-yl]-6-[(phenylsulfonyl)methyl]pyrimidin-2-yl}phenyl)carbamate

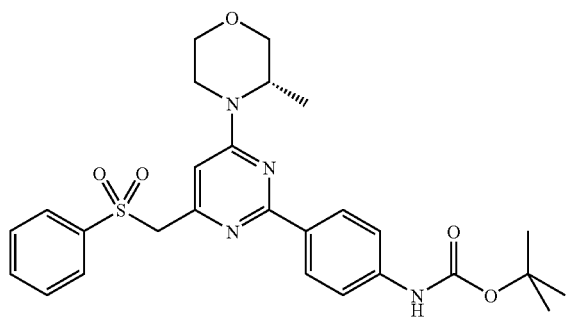

(3S)-4-{2-Chloro-6-[(phenylsulfonyl)methyl]pyrimidin-4-yl}-3-methylmorpholine (3.2 g, 8.70 mmol) was dissolved in a solution of 18% DMF in a mixture of 7:3:2 dimethoxyethane:water:ethanol (36 mL). Tert-butyl [4-(4,4,5,5-tetramethyl-1,3,2-dioxaborolan-2-yl)phenyl]carbamate (4.16 g, 13.05 mmol), 2M sodium carbonate solution (8 mL) and dichlorobis(triphenylphosphine) palladium catalyst (306 mg, 0.43 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The crude solid was chromatographed on silica, eluting with 0-30% ethyl acetate in DCM to give the desired material as a beige solid (3.1 g).

NMR Spectrum: ¹H NMR (400.13 MHz, DMSO-$d_6$) δ1.19 (d, 3H), 1.49 (s, 9H), 3.16 (m, 1H), 3.47 (m, 1H), 3.62 (m, 1H), 3.75 (d, 1H), 3.97 (m, 1H), 4.10 (d, 1H), 4.35 (s, 1H), 4.70 (s, 2H), 6.62 (s, 1H), 7.44 (d, 2H), 7.63 (d, 2H), 7.74 (m, 1H), 7.82 (m, 4H), 9.49 (s, 1H)

LCMS Spectrum: MH+ 525, retention time 2.80 min, Method 5 Min Base (3S)-4-{2-chloro-6-[(phenylsulfonyl)methyl]pyrimidin-4-yl}-3-methylmorpholine

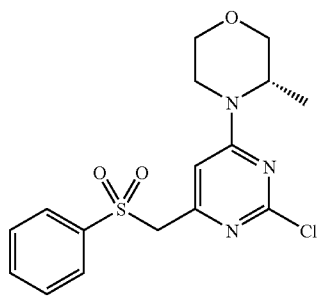

2,4-dichloro-6-[(phenylsulfonyl)methyl]pyrimidine (2.8 g, 9.24 mmol) was dissolved in DCM (20 mL) and stirred (under nitrogen) at −5° C. Triethylamine (1.42 mL, 10.17 mmol) was added to give a clear brown solution. (3S)-3-methylmorpholine (935 mg, 9.24 mmol) was dissolved in DCM and added dropwise keeping the reaction below −5° C. The cooling bath was then removed and the reaction mixture stirred at room temperature for 1 hour. The reaction mixture was then washed with water (50 mL), dried over magnesium sulphate, filtered and concentrated in vacuo. The crude material was chromatographed on silica, eluting with 0-50% ethyl acetate in DCM to give the desired material as a white solid (2.6 g).

NMR Spectrum: ¹H NMR (400.13 MHz, DMSO-$d_6$) δ1.15 (d, 3H), 3.15 (m, 1H), 3.42 (m, 1H), 3.56 (m, 1H), 3.72 (d, 1H), 3.92 (m, 2H), 4.15 (s, 1H), 4.62 (s, 2H), 6.66 (s, 1H), 7.74 (t, 1H), 7.76 (t, 1H), 7.78 (d, 1H), 7.80 (m, 2H)

LCMS Spectrum: MH+ 368, retention time 1.95 min, Method 5 Min Base

Phenyl (4-{4-[(isopropylsulfonyl)methyl]-6-morpholin-4-ylpyrimidin-2-yl}phenyl)carbamate

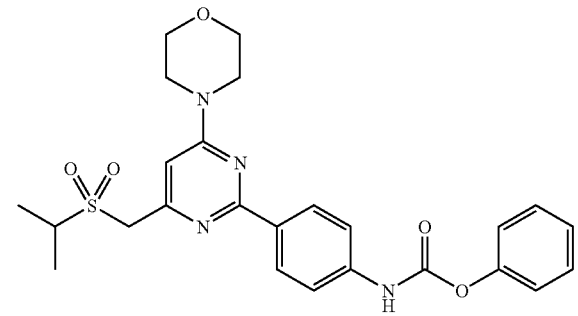

(4-{4-[(Isopropylsulfonyl)methyl]-6-morpholin-4-ylpyrimidin-2-yl}phenyl)amine (1.5 g, 3.98 mmol) was dissolved in dioxane (10 mL). Sodium bicarbonate (503 mg, 5.98 mmol) was added, followed by phenyl chloroformate (0.502 mL, 3.98 mmol) and the reaction stirred at room temperature for 2 hours. The solvent was removed in vacuo, and the resultant oil partitioned between 10 mL DCM and 10 mL water. The organic phase was dried over magnesium sulphate, filtered and concentrated in vacuo. The cream solid obtained was chromatographed on silica, eluting with 0-50% ethyl acetate in DCM, to give the desired material as a white solid (1.5 g).

NMR Spectrum: ¹H NMR (400.13 MHz, DMSO-$d_6$) δ1.30 (d, 6H), 3.45 (m, 1H), 3.65 (s, 8H), 4.40 (s, 2H), 6.78 (s, 1H), 7.20 (m, 3H), 7.38 (t, 2H), 7.56 (d, 2H), 8.22 (d, 2H), 10.37 (s, 1H)

LCMS Spectrum: MH+ 497, retention time 2.54 min, Method 5 Min Base

(4-{4-[(Isopropylsulfonyl)methyl]-6-morpholin-4-ylpyrimidin-2-yl}phenyl)amine

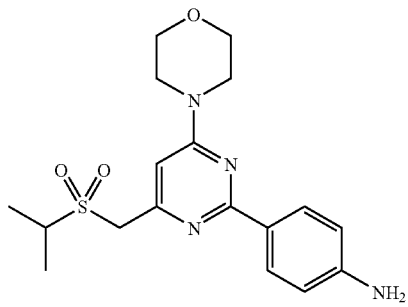

Tert-butyl (4-{4-[(isopropylsulfonyl)methyl]-6-morpholin-4-ylpyrimidin-2-yl}phenyl)carbamate (2.7 g, 5.67 mmol) was dissolved in DCM (20 mL) and trifluoroacetic acid (10 mL) was added. The reaction mixture was stirred at room temperature for 2 hours then diluted with DCM (20 mL) and washed with saturated aqueous sodium bicarbonate (20 mL). Organic phase collected, dried over magnesium sulphate, filtered and concentrated in vacuo to give the desired material as a cream solid (2.1 g).

NMR Spectrum: $^1$H NMR (400.13 MHz, DMSO-$d_6$) δ1.35 (d, 6H), 3.50 (m, 1H), 3.67 (m, 4H), 3.72 (m, 4H), 4.41 (s, 2H), 5.57 (s, 2H), 6.60 (d, 2H), 6.70 (s, 1H), 8.03 (d, 2H)

LCMS Spectrum: MH+ 377, retention time 1.61 min, Method 5 Min Base

Tert-butyl (4-{4-[(isopropylsulfonyl)methyl]-6-morpholin-4-ylpyrimidin-2-yl}phenyl)carbamate

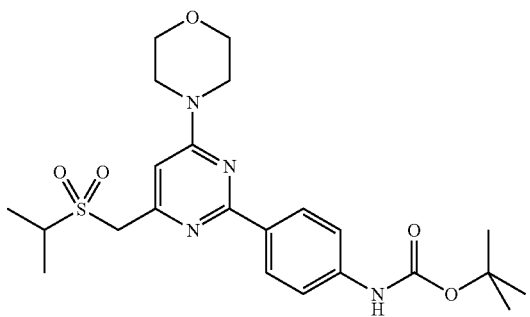

4-{2-Chloro-6-[(isopropylsulfonyl)methyl]pyrimidin-4-yl}morpholine (1.5 g, 4.69 mmol) was dissolved in a solution of 18% DMF in a mixture of 7:3:2 dimethoxyethane:water:ethanol (36 mL). {4-[(Tert-butoxycarbonyl)amino]phenyl}boronic acid (1.67 g, 7.04 mmol), 2M sodium carbonate solution (12 mL) and dichlorobis(triphenylphosphine) palladium catalyst (165 mg, 0.23 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The crude oil was dissolved in DCM and filtered to remove insoluble material. A brown solid precipitated from the filtrates and the filtrates were filtered again. The solid was analysed and found to be the desired material (1.9 g).

NMR Spectrum: $^1$H NMR (400.13 MHz, DMSO-$d_6$) δ1.36 (d, 6H), 1.50 (s, 9H), 3.52 (m, 1H), 3.72 (s, 8H), 4.46 (s, 2H), 6.83 (s, 1H), 7.57 (d, 2H), 8.22 (d, 2H), 9.56 (s, 1H)

LCMS Spectrum: MH+ 477, retention time 2.50 min, Method 5 Min Base

4-{2-Chloro-6-[(phenylsulfonyl)methyl]pyrimidin-4-yl}morpholine

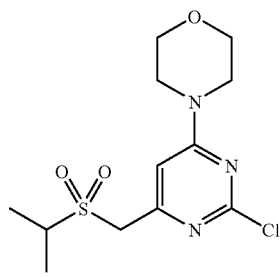

2,4-Dichloro-6-[(isopropylsulfonyl)methyl]pyrimidine (2.65 g, 9.85 mmol) was dissolved in DCM (50 mL) and stirred (under nitrogen) at −5° C. Triethylamine (1.5 mL, 10.84 mmol) was added to give a clear brown solution. Morpholine (0.86 mL, 9.85 mmol) was dissolved in DCM and added dropwise keeping the reaction below −5° C. The cooling bath was then removed and the reaction mixture stirred at room temperature for 1 hour. The reaction mixture was then washed with water (50 mL), dried over magnesium sulphate, filtered and concentrated in vacuo. The crude material was chromatographed on silica, eluting with 0-50% ethyl acetate in DCM to give the desired material (2.5 g).

NMR Spectrum: $^1$H NMR (400.13 MHz, DMSO-$d_6$) δ1.30 (d, 6H), 3.42 (m, 1H), 3.62 (s, 4H), 3.68 (m, 4H), 4.42 (s, 2H), 6.95 (s, 1H)

LCMS Spectrum: MH+ 320, retention time 1.51 min, Method 5 Min Base

2,4-Dichloro-6-[(isopropylsulfonyl)methyl]pyrimidine

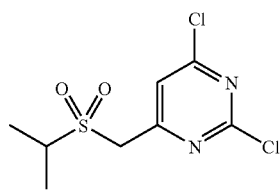

2,4-Dichloro-6-[(isopropylthio)methyl]pyrimidine (6.2 g, 26.16 mmol) was dissolved in DCM (100 mL) and 3,5-dichlorobenzenecarboperoxoic acid (13.5 g, 78.4 mmol) was added portionwise over 10 minutes. The reaction was stirred at room temperature for 4 hours. The reaction mixture was then washed with saturated aqueous sodium bicarbonate (50 mL), dried over magnesium sulphate, filtered and concentrated in vacuo to give a cream solid. Purification by normal phase chromatography, eluting with 0-50% ethyl acetate in iso-hexane gave the desired material as a cream solid (5.3 g).

NMR Spectrum: $^1$H NMR (400.13 MHz, DMSO-$d_6$) δ1.25 (d, 6H), 3.43 (m, 1H), 4.77 (s, 2H), 7.87 (s, 1H)

LCMS Spectrum: M–H 267, retention time 1.64 min, Method 5 Min Basic

2,4-Dichloro-6-[(isopropylthio)methyl]pyrimidine

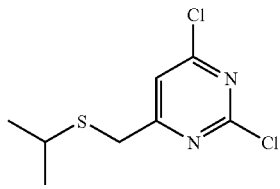

6-[(Isopropylthio)methyl]pyrimidine-2,4(1H,3H)-dione (8 g, 40 mmol) was added to phosphorus oxychloride (100 mL) and the mixture heated to reflux for 16 hours. The reaction was then cooled to room temperature and the excess phosphorus oxychloride was removed in vacuo. The residue was azeotroped with toluene (2×100 mL) and dissolved in DCM. This mixture was then poured slowly onto ice (1 L) and stirred for 20 minutes, then extracted with DCM (3×500 mL) The extracts were combined, dried over magnesium sulphate, then concentrated in vacuo to give the desired material as a brown oil (6.5 g). The material was used without further purification.

NMR Spectrum: $^1$H NMR (400.13 MHz, DMSO-$d_6$) δ 1.21 (d, 6H), 2.96 (m, 1H), 3.85 (s, 2H), 7.82 (s, 1H)

LCMS Spectrum: Retention time 2.51 min, Method 5 Min Basic

6-[(Isopropylthio)methyl]pyrimidine-2,4(1H,3H)-dione

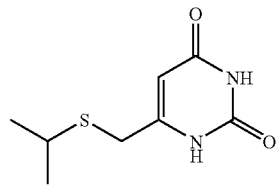

6-(Chloromethyl)-1H-pyrimidine-2,4-dione (8 g, 50 mmol) was dissolved in acetonitrile (200 mL) and 1,8-Diazabicyclo[5.4.0]undec-7-ene (13 mL, 87.19 mmol) was added and the reaction stirred at room temperature for 15 minutes. Isopropyl mercaptan (8.1 mL, 87.19 mmol) was then added and the reaction stirred at room temperature for a further 2 hours. Solvent removed in vacuo and the resulting brown oil was dissolved in DCM and washed with water. Organic phase dried over magnesium sulphate, filtered and concentrated in vacuo. The resulting oil was chromatographed on silica, eluting with 0-10% methanol in DCM to give the desired material as a white solid (8 g).

NMR Spectrum: $^1$H NMR (400.13 MHz, DMSO-$d_6$) δ 1.21 (d, 6H), 2.90 (m, 1H), 3.42 (s, 2H), 5.49 (s, 1H), 10.82 (s, 1H), 10.94 (s, 1H)

LCMS Spectrum: M–H 199, retention time 0.63 min, Method 5 Min Basic 6-(Chloromethyl)-1H-pyrimidine-2,4-dione is a commercially available material.

Phenyl (4-{4-[(isopropylsulfonyl)methyl]-6-[(3S)-3-methylmorpholin-4-yl]pyrimidin-2-yl}phenyl)carbamate

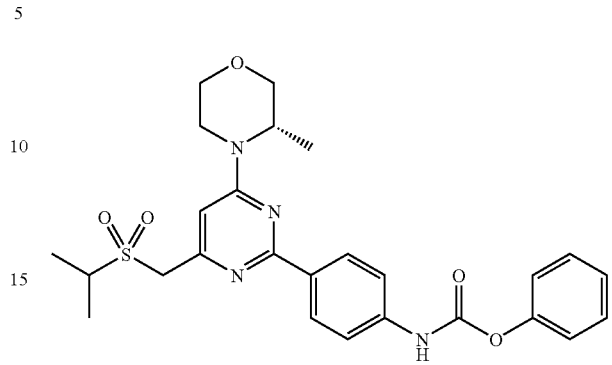

(4-{4-[(Isopropylsulfonyl)methyl]-6-[(3S)-3-methylmorpholin-4-yl]pyrimidin-2-yl}phenyl)amine (1.5 g, 3.84 mmol) was dissolved in dioxane (10 mL). Sodium bicarbonate (485 mg, 5.76 mmol) was added, followed by phenyl chloroformate (0.484 mL, 3.84 mmol) and the reaction stirred at room temperature for 2 hours. The solvent was removed in vacuo, and the resultant oil partitioned between 10 mL DCM and 10 mL water. The organic phase was dried over magnesium sulphate, filtered and concentrated in vacuo. The cream solid obtained was chromatographed on silica, eluting with 0-50% ethyl acetate in DCM, to give the desired material as a white solid (1.8 g).

NMR Spectrum: $^1$H NMR (400.13 MHz, DMSO-$d_6$) δ 1.18 (d, 3H), 1.30 (m, 6H), 3.17 (m, 2H), 3.44 (m, 2H), 3.58 (m, 1H), 3.70 (d, 1H), 3.92 (m, 1H), 4.12 (d, 1H), 4.41 (s, 2H), 6.74 (s, 1H), 7.20 (m, 3H), 7.38 (t, 2H), 7.56 (d, 2H), 8.22 (d, 2H), 10.37 (s, 1H)

LCMS Spectrum: MH+ 511, retention time 2.67 min, Method 5 Min Base

(4-{4-[(Isopropylsulfonyl)methyl]-6-[(3S)-3-methylmorpholin-4-yl]pyrimidin-2-yl}phenyl)amine

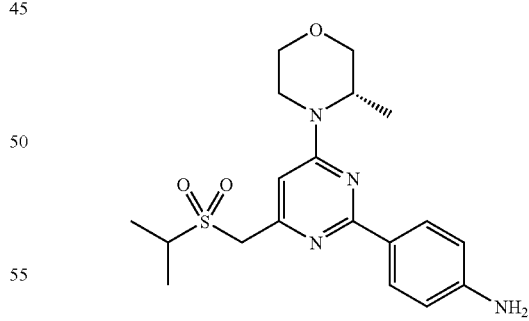

Tert-butyl (4-{4-[(isopropylsulfonyl)methyl]-6-[(3S)-3-methylmorpholin-4-yl]pyrimidin-2-yl}phenyl)carbamate (3.2 g, 6.52 mmol) was dissolved in DCM (20 mL) and trifluoroacetic acid (10 mL) was added. The reaction mixture was stirred at room temperature for 2 hours then diluted with DCM (20 mL) and washed with saturated aqueous sodium bicarbonate (20 mL). Organic phase collected, dried over magnesium sulphate, filtered and concentrated in vacuo to give the desired material as a cream solid (2.4 g).

NMR Spectrum: ¹H NMR (400.13 MHz, DMSO-d₆) δ 1.22 (d, 3H), 1.35 (m, 6H), 3.19 (m, 1H), 3.49 (m, 2H), 3.64 (m, 1H), 3.77 (d, 1H), 3.97 (m, 1H), 4.14 (d, 1H), 4.41 (s, 2H), 4.45 (m, 1H), 5.56 (s, 2H), 6.60 (d, 2H), 6.66 (s, 1H), 8.02 (d, 2H)

LCMS Spectrum: MH+ 391, retention time 1.84 min, Method 5 Min Base

Tert-butyl (4-{4-[(isopropylsulfonyl)methyl]-6-[(3S)-3-methylmorpholin-4-yl]pyrimidin-2-yl}phenyl)carbamate

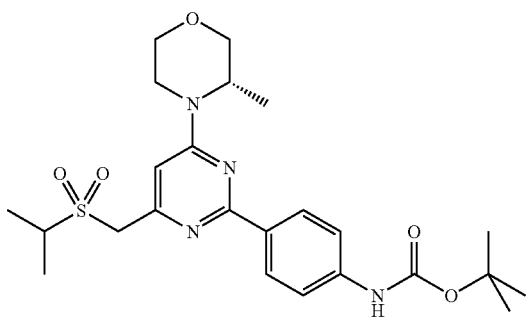

(3S)-4-{2-Chloro-6-[(isopropylsulfonyl)methyl]pyrimidin-4-yl}-3-methylmorpholine (2.0 g, 5.99 mmol) was dissolved in a solution of 18% DMF in a mixture of 7:3:2 dimethoxyethane:water:ethanol (16 mL). {4-[(Tert-butoxycarbonyl)amino]phenyl}boronic acid (2.13 g, 8.99 mmol), 2M sodium carbonate solution (8 mL) and dichlorobis(triphenylphosphine) palladium catalyst (211 mg, 0.30 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The cream solid obtained was chromatographed on silica, eluting with 0-50% ethyl acetate in DCM, to give the desired material as a brown solid (3.2 g).

NMR Spectrum: ¹H NMR (400.13 MHz, DMSO-d₆) δ 1.36 (m, 6H), 1.50 (s, 9H), 3.24 (m, 4H), 3.51 (m, 2H), 3.65 (m, 1H), 3.78 (d, 1H), 3.99 (m, 1H), 4.18 (d, 1H), 4.47 (s, 2H), 6.79 (s, 1H), 7.57 (d, 2H), 8.21 (d, 2H), 9.55 (s, 1H)

LCMS Spectrum: MH+ 491, retention time 2.67 min, Method 5 Min Base (3S)-4-{2-Chloro-6-[(isopropylsulfonyl)methyl]pyrimidin-4-yl}-3-methylmorpholine

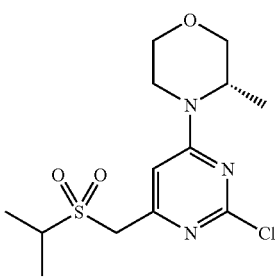

2,4-Dichloro-6-[(isopropylsulfonyl)methyl]pyrimidine (2.65 g, 9.85 mmol) was dissolved in DCM (50 mL) and stirred (under nitrogen) at −5° C. Triethylamine (1.5 mL, 10.84 mmol) was added to give a clear brown solution. 3S-3-Methyl morpholine (997 mg, 9.85 mmol) was dissolved in DCM and added dropwise keeping the reaction below −5° C. The cooling bath was then removed and the reaction mixture stirred at room temperature for 1 hour. The reaction mixture was then washed with water (50 mL), dried over magnesium sulphate, filtered and concentrated in vacuo. The crude material was chromatographed on silica, eluting with 0-50% ethyl acetate in DCM to give the desired material as a white solid (2 g).

NMR Spectrum: ¹H NMR (400.13 MHz, DMSO-d₆) δ 1.22 (d, 3H), 1.31 (d, 6H), 3.22 (m, 1H), 3.43 (m, 2H), 3.60 (m, 1H), 3.74 (d, 1H), 3.98 (m, 1H), 4.30 (s, 1H), 4.43 (s, 2H), 6.91 (s, 1H)

LCMS Spectrum: MH+ 332, retention time 1.70 min, Method 5 Min Base

EXAMPLE 21

3-Methyl-1-[4-[4-(2-methylsulfonylpropan-2-yl)-6-morpholin-4-yl-pyrimidin-2-yl]phenyl]urea

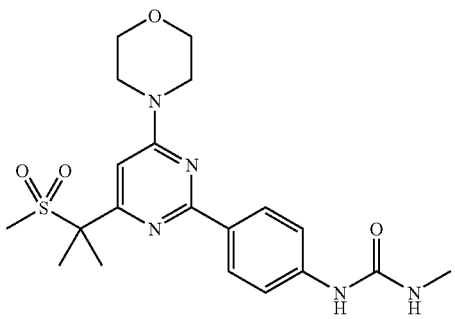

Phenyl (4-{4-[1-methyl-1-(methylsulfonyl)ethyl]-6-morpholin-4-ylpyrimidin-2-yl}phenyl)carbamate (116 mg, 0.22 mmol) was dissolved in DMF (3 mL). Triethylamine (0.098 mL, 0.7 mmol) was added followed by methylamine (2M in THF, 0.6 mL, 1.17 mmol). The mixture was stirred at 50° C. for 1 hour. The reaction was concentrated and purified by preparative HPLC to give the desired material as a white solid (54 mg).

NMR Spectrum: ¹H NMR (400.13 MHz, DMSO-d₆) δ 1.77 (s, 6H), 2.66 (d, 3H), 3.04 (s, 3H), 3.73 (s, 8H), 6.06 (m, 1H), 6.79 (s, 1H), 7.51 (d, 2H), 8.24 (d, 2H), 8.74 (s, 1H)

LCMS Spectrum: MH+ 434, retention time 1.64 min, Method 5 Min Base

The following compounds were prepared in analogous fashion from either phenyl (4-{4-[1-methyl-1-(methylsulfonyl)ethyl]-6-morpholin-4-ylpyrimidin-2-yl}phenyl)carbamate or phenyl (4-{4-[1-methyl-1-(methylsulfonyl)ethyl]-6-[(3S)-3-methylmorpholin-4-yl]pyrimidin-2-yl}phenyl)carbamate and the appropriate amine.

| Example | Structure | NAME | LCMS MH+ | Retention time (min) |
|---|---|---|---|---|
| 21a | 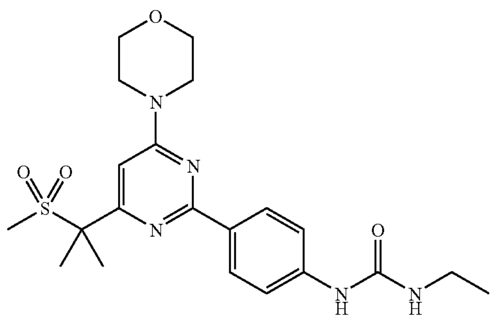 | 1-ethyl-3-[4-[4-(2-methylsulfonylpropan-2-yl)-6-morpholin-4-yl-pyrimidin-2-yl]phenyl]urea | 448 | 1.78 |
| 21b | 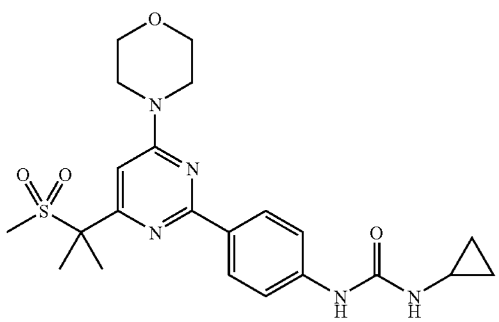 | 3-cyclopropyl-1-[4-[4-(2-methylsulfonylpropan-2-yl)-6-morpholin-4-yl-pyrimidin-2-yl]phenyl]urea | 460 | 1.91 |
| 21c | 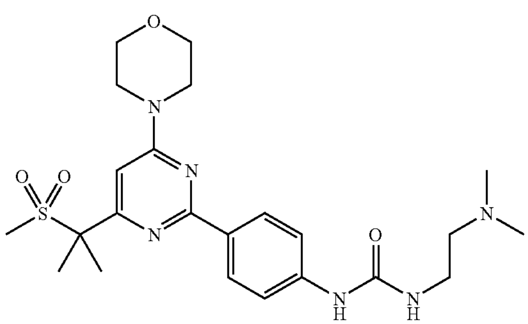 | 3-(2-dimethylaminoethyl)-1-[4-[4-(2-methylsulfonylpropan-2-yl)-6-morpholin-4-yl-pyrimidin-2-yl]phenyl]urea | 491 | 1.71 |
| 21d | 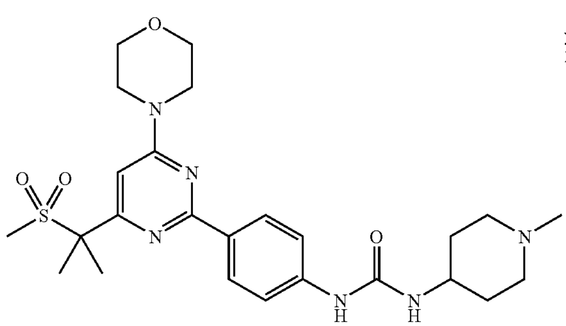 | 3-(1-methyl-4-piperidyl)-1-[4-[4-(2-methylsulfonylpropan-2-yl)-6-morpholin-4-yl-pyrimidin-2-yl]phenyl]urea | 517 | 1.75 |

-continued

| Example | Structure | NAME | LCMS MH+ | Retention time (min) |
|---|---|---|---|---|
| 21e | 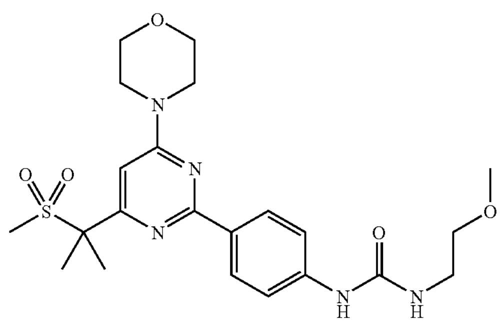 | 3-(2-methoxyethyl)-1-[4-[4-(2-methylsulfonylpropan-2-yl)-6-morpholin-4-yl-pyrimidin-2-yl]phenyl]urea | 478 | 1.72 |
| 21f | 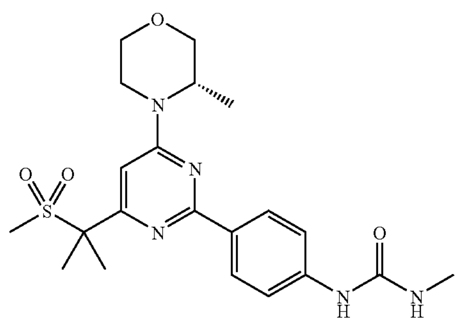 | 3-methyl-1-[4-[4-[(3S)-3-methylmorpholin-4-yl]-6-(2-methylsulfonylpropan-2-yl)pyrimidin-2-yl]phenyl]urea | 448 | 1.76 |
| 21g | 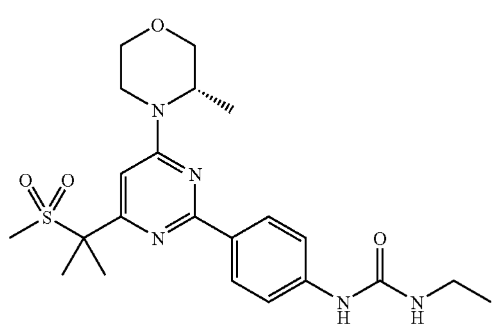 | 1-ethyl-3-[4-[4-[(3S)-3-methylmorpholin-4-yl]-6-(2-methylsulfonylpropan-2-yl)pyrimidin-2-yl]phenyl]urea | 462 | 1.92 |
| 21h | 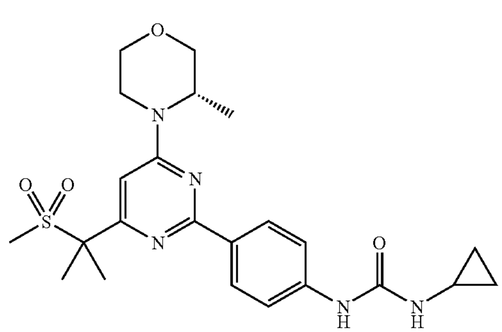 | 3-cyclopropyl-1-[4-[4-[(3S)-3-methylmorpholin-4-yl]-6-(2-methylsulfonylpropan-2-yl)pyrimidin-2-yl]phenyl]urea | 474 | 1.93 |

| Example | Structure | NAME | LCMS MH+ | Retention time (min) |
|---|---|---|---|---|
| 21i | 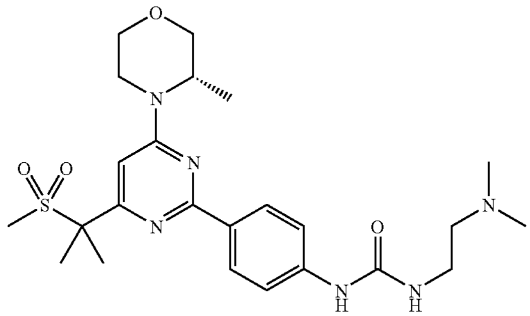 | 3-(2-dimethylaminoethyl)-1-[4-[4-[(3S)-3-methylmorpholin-4-yl]-6-(2-methylsulfonylpropan-2-yl)pyrimidin-2-yl]phenyl]urea | 505 | 1.83 |
| 21j | 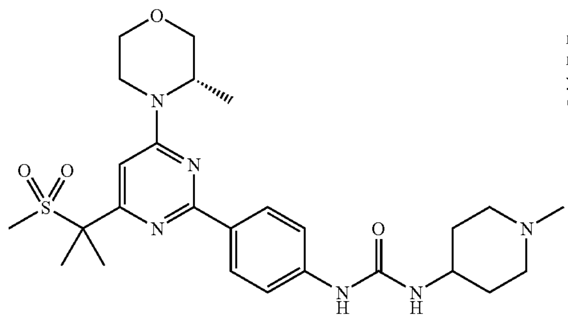 | 1-[4-[4-[(3S)-3-methylmorpholin-4-yl]-6-(2-methylsulfonylpropan-2-yl)pyrimidin-2-yl]phenyl]-3-(1-methyl-4-piperidyl)urea | 531 | 1.86 |
| 21k | 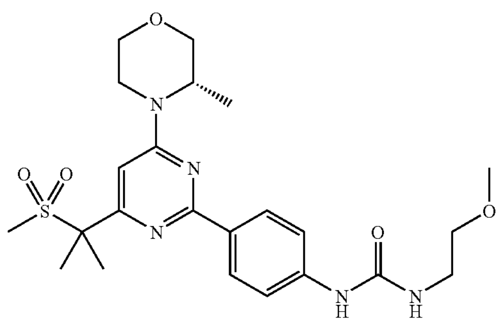 | 3-(2-methoxyethyl)-1-[4-[4-[(3S)-3-methylmorpholin-4-yl]-6-(2-methylsulfonylpropan-2-l)pyrimidin-2-yl]phenyl]urea | 492 | 1.84 |

Example 21a: $^1$H NMR (400.13 MHz, DMSO-d$_6$) δ1.07 (t, 3H), 1.77 (s, 6H), 3.04 (s, 3H), 3.13 (m, 2H), 3.73 (s, 8H), 6.15 (t, 1H), 6.79 (s, 1H), 7.50 (d, 2H), 8.24 (d, 2H), 8.66 (s, 1H)

Example 21b: $^1$H NMR (400.13 MHz, DMSO-d$_6$) δ0.42 (m, 2H), 0.65 (m, 2H), 1.77 (s, 6H), 2.57 (m, 1H), 3.04 (s, 3H), 3.73 (s, 8H), 6.43 (d, 1H), 6.79 (s, 1H), 7.51 (d, 2H), 8.24 (d, 2H), 8.54 (s, 1H)

Example 21c: $^1$H NMR (400.13 MHz, DMSO-d$_6$) δ1.77 (s, 6H), 2.18 (s, 6H), 2.34 (t, 2H), 3.04 (s, 3H), 3.19 (m, 2H), 3.73 (s, 8H), 6.15 (t, 1H), 6.79 (s, 1H), 7.49 (d, 2H), 8.24 (d, 2H), 8.90 (s, 1H)

Example 21d: $^1$H NMR (400.13 MHz, DMSO-d$_6$) δ1.40 (m, 2H), 1.77 (s, 6H), 2.03 (m, 2H), 2.17 (s, 3H), 2.45 (m, 2H), 2.67 (m, 2H), 3.04 (s, 3H), 3.47 (m, 1H), 3.73 (s, 8H), 6.18 (d, 1H), 6.79 (s, 1H), 7.48 (d, 2H), 8.24 (d, 2H), 8.57 (s, 1H)

Example 21e: $^1$H NMR (400.13 MHz, DMSO-d$_6$) δ1.77 (s, 6H), 3.04 (s, 3H), 3.27 (m, 2H), 3.29 (s, 3H), 3.40 (t, 2H), 3.73 (s, 8H), 6.26 (t, 1H), 6.79 (s, 1H), 7.49 (d, 2H), 8.24 (d, 2H), 8.79 (s, 1H)

Example 21f: $^1$H NMR (400.13 MHz, DMSO-d$_6$) δ1.16 (d, 3H), 1.70 (s, 6H), 2.59 (d, 3H), 2.96 (s, 3H), 3.16 (m, 1H), 3.43 (m, 1H), 3.58 (m, 1H), 3.70 (d, 1H), 3.91 (m, 1H), 4.16 (d, 1H), 4.53 (s, 1H), 5.99 (m, 1H), 6.66 (s, 1H), 7.44 (d, 2H), 8.16 (d, 2H), 8.67 (s, 1H)

Example 21g: $^1$H NMR (400.13 MHz, DMSO-d$_6$) δ1.00 (t, 3H), 1.16 (d, 3H), 1.70 (d, 6H), 2.96 (s, 3H), 3.06 (m, 2H), 3.16 (m, 1H), 3.43 (m, 1H), 3.58 (m, 1H), 3.70 (d, 1H), 3.91 (m, 1H), 4.16 (d, 1H), 4.52 (s, 1H), 6.09 (t, 1H), 6.67 (s, 1H), 7.43 (d, 2H), 8.16 (d, 2H), 8.59 (s, 1H)

Example 21h: $^1$H NMR (400.13 MHz, DMSO-d$_6$) δ0.42 (m, 2H), 0.65 (m, 2H), 1.23 (d, 3H), 1.78 (d, 6H), 2.56 (m, 1H), 3.03 (s, 3H), 3.23 (m, 1H), 3.50 (m, 1H), 3.65 (m, 1H), 3.78 (d, 1H), 3.98 (m, 1H), 4.23 (d, 1H), 4.60 (s, 1H), 6.43 (d, 1H), 6.74 (s, 1H), 7.51 (d, 2H), 8.24 (d, 2H), 8.54 (s, 1H)

Example 21i: $^1$H NMR (400.13 MHz, DMSO-d$_6$) δ1.23 (d, 3H), 1.77 (d, 6H), 2.18 (s, 6H), 2.34 (t, 2H), 3.03 (s, 3H), 3.19 (m, 3H), 3.49 (m, 1H), 3.65 (m, 1H), 3.77 (d, 1H), 3.98 (m, 1H), 4.23 (d, 1H), 4.59 (s, 1H), 6.16 (t, 1H), 6.73 (s, 1H), 7.49 (d, 2H), 8.23 (d, 2H), 8.90 (s, 1H)

Example 21j: $^1$H NMR (400.13 MHz, DMSO-d$_6$) δ1.24 (s, 3H), 1.41 (m, 2H), 1.78 (d, 6H), 1.81 (m, 2H), 2.02 (t, 2H), 2.16 (s, 3H), 2.64 (m, 2H), 3.03 (s, 3H), 3.22 (m, 1H), 3.50 (m, 2H), 3.65 (m, 1H), 3.78 (d, 1H), 3.98 (m, 1H), 4.23 (d, 1H), 4.61 (s, 1H), 6.18 (d, 1H), 6.74 (s, 1H), 7.48 (d, 2H), 8.23 (d, 2H), 8.57 (s, 1H)

Example 21k: $^1$H NMR (400.13 MHz, DMSO-d$_6$) δ1.23 (d, 3H), 1.77 (d, 6H), 3.03 (s, 3H), 3.21 (m, 2H), 3.27 (m, 1H), 3.40 (t, 2H), 3.48 (m, 2H), 3.65 (m, 1H), 3.72 (d, 1H), 3.97 (m, 1H), 4.23 (d, 1H), 4.60 (s, 1H), 6.26 (t, 1H), 6.74 (s, 1H), 6.86 (s, 1H), 7.49 (d, 2H), 8.24 (d, 2H), 8.78 (s, 1H) Test (a): Example (21) 0.05 μM; Example (21a) 0.73 μM; Example (21b) 0.36 μM; Example (21c) 0.48 μM; Example (21d) 0.27 μM; Example (21e) 1 μM; Example (21f) 0.017 μM; Example (21g) 0.02 μM; Example (21h) 0.028 μM; Example (21i) 0.076 μM; Example (21j) 0.51 μM; Example (21k) 0.31 μM.

The preparations of phenyl (4-{4-[1-methyl-1-(methylsulfonyl)ethyl]-6-morpholin-4-ylpyrimidin-2-yl}phenyl)carbamate and phenyl (4-{4-[1-methyl-1-(methylsulfonyl)ethyl]-6-[(3S)-3-methylmorpholin-4-yl]pyrimidin-2-yl}phenyl)carbamate are described below.

Phenyl (4-{4-[1-methyl-1-(methylsulfonyl)ethyl]-6-morpholin-4-ylpyrimidin-2-yl}phenyl)carbamate

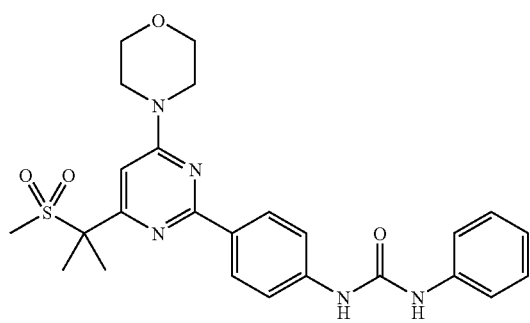

(4-{4-[1-Methyl-1-(methylsulfonyl)ethyl]-6-morpholin-4-ylpyrimidin-2-yl}phenyl)amine (1.5 g, 3.98 mmol) was dissolved in dioxane (15 mL). Sodium bicarbonate (503 mg, 5.98 mmol) was added, followed by phenyl chloroformate (0.502 mL, 3.98 mmol) and the reaction stirred at room temperature for 2 hours. The solvent was removed in vacuo, and the resultant oil partitioned between 20 mL DCM and 20 mL water. The organic phase was dried over magnesium sulphate, filtered and concentrated in vacuo. The cream solid obtained was chromatographed on silica, eluting with 0-50% ethyl acetate in DCM, to give the desired material as a white solid (700 mg).

NMR Spectrum: $^1$H NMR (400.13 MHz, DMSO-d$_6$) δ1.20 (d, 3H), 3.17 (m, 1H), 3.48 (m, 1H), 3.63 (m, 1H), 3.76 (d, 1H), 3.97 (m, 1H), 4.11 (d, 1H), 4.37 (s, 1H), 4.72 (s, 2H), 6.65 (s, 1H), 7.27 (m, 3H), 7.45 (t, 2H), 7.51 (d, 2H), 7.62 (t, 2H), 7.74 (t, 1H), 7.82 (d, 2H), 7.90 (d, 2H), 10.38 (s, 1H)

LCMS Spectrum: MH+ 545, retention time 2.7 min, Method 5 Min Base (4-{4-[1-Methyl-1-(methylsulfonyl)ethyl]-6-morpholin-4-ylpyrimidin-2-yl}phenyl)amine

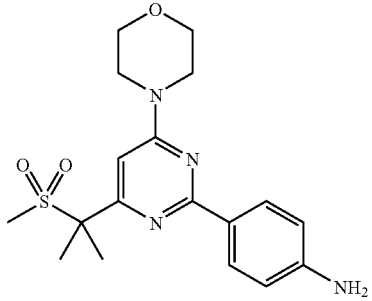

Tert-butyl (4-{4-[1-methyl-1-(methylsulfonyl)ethyl]-6-morpholin-4-ylpyrimidin-2-yl}phenyl)carbamate (2.6 g, 5.46 mmol) was dissolved in DCM (20 mL) and trifluoroacetic acid (10 mL) was added. The reaction mixture was stirred at room temperature for 2 hours then diluted with DCM (20 mL) and washed with saturated aqueous sodium bicarbonate (20 mL). Organic phase collected, dried over magnesium sulphate, filtered and concentrated in vacuo to give the desired material as a cream solid (2.1 g).

NMR Spectrum: $^1$H NMR (400.13 MHz, DMSO-d$_6$) δ1.75 (s, 6H), 3.03 (s, 3H), 3.71 (s, 8H), 5.56 (s, 2H), 6.61 (d, 2H), 6.69 (s, 1H), 8.07 (d, 2H)

LCMS Spectrum: MH+ 377, retention time 1.84 min, Method 5 Min Base

Tert-butyl (4-{4-[1-methyl-1-(methylsulfonyl)ethyl]-6-morpholin-4-ylpyrimidin-2-yl}phenyl)carbamate

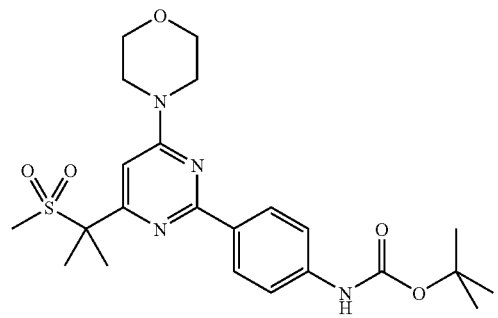

(3S)-4-{2-Chloro-6-[1-methyl-1-(methylsulfonyl)ethyl]pyrimidin-4-yl}-3-methylmorpholine (1.75 g, 5.47 mmol) was dissolved in a solution of 18% DMF in a mixture of 7:3:2 dimethoxyethane:water:ethanol (18 mL). Tert-butyl [4-(4,4,5,5-tetramethyl-1,3,2-dioxaborolan-2-yl)phenyl]carbamate (2.62 g, 8.2 mmol), 2M sodium carbonate solution (8 mL) and dichlorobis(triphenylphosphine) palladium catalyst (192 mg, 0.27 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The crude solid was chromatographed on silica, eluting with 0-30% ethyl acetate in DCM to give the desired material as a white solid (2.6 g).

NMR Spectrum: $^1$H NMR (400.13 MHz, DMSO-d$_6$) δ1.50 (s, 9H), 1.77 (s, 6H), 3.04 (s, 3H), 3.73 (s, 8H), 6.80 (s, 1H), 7.57 (d, 2H), 8.26 (d, 2H), 9.54 (s, 1H)

LCMS Spectrum: MH+ 477, retention time 2.66 min, Method 5 Min Base

4-{2-Chloro-6-[1-methyl-1-(methylsulfonyl)ethyl]pyrimidin-4-yl}morpholine

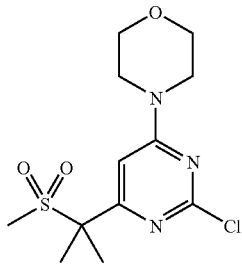

4-{2-Chloro-6-[(methylsulfonyl)methyl]pyrimidin-4-yl}morpholine (2.9 g, 9.94 mmol) was dissolved in DMF (20 mL) and the reaction cooled to −5° C. Sodium t-butoxide (956 mg, 9.94 mmol) was added to the reaction, followed by iodomethane (0.6 mL, 9.94 mmol), maintaining the temperature at −5° C. A second equivalent of sodium t-butoxide (956 mg, 9.94 mmol) and iodomethane (0.6 mL, 9.94 mmol) were then added and the reaction stirred at −5° C. for 1 hour, then at room temperature for 4 hours. DCM (20 mL) was added and the reaction washed with 2M aqueous HCl (20 mL). The organic phase was dried over magnesium sulphate, filtered and concentrated in vacuo. The crude solid was chromatographed on silica, eluting with 0-50% ethyl acetate in DCM to give the desired material as a white solid (1.7 g).

NMR Spectrum: $^1$H NMR (400.13 MHz, DMSO-$d_6$) δ1.68 (s, 6H), 2.99 (s, 3H), 3.67 (s, 8H), 6.91 (s, 1H)

LCMS Spectrum: MH+ 320, retention time 1.67 min, Method 5 Min Base

Phenyl (4-{4-[1-methyl-1-(methylsulfonyl)ethyl]-6-[(3S)-3-methylmorpholin-4-yl]pyrimidin-2-yl}phenyl)carbamate

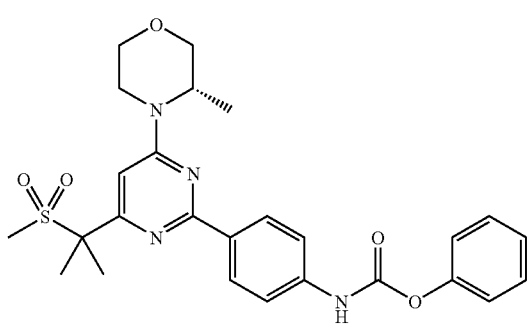

(4-{4-[1-Methyl-1-(methylsulfonyl)ethyl]-6-[(3S)-3-methylmorpholin-4-yl]pyrimidin-2-yl}phenyl)amine (3.6 g, 8.77 mmol) was dissolved in dioxane (20 mL). Sodium bicarbonate (1.1 g, 13.15 mmol) was added, followed by phenyl chloroformate (1.1 mL, 8.77 mmol) and the reaction stirred at room temperature for 2 hours. The solvent was removed in vacuo, and the resultant oil partitioned between 20 mL DCM and 20 mL water. The organic phase was dried over magnesium sulphate, filtered and concentrated in vacuo. The cream solid obtained was chromatographed on silica, eluting with 0-50% ethyl acetate in DCM, to give the desired material as a white solid (2 g).

NMR Spectrum: $^1$H NMR (400.13 MHz, DMSO-$d_6$) δ1.24 (d, 3H), 1.78 (d, 6H), 3.04 (s, 3H), 3.24 (m, 1H), 3.51 (m, 1H), 3.65 (m, 1H), 3.78 (d, 1H), 3.96 (m, 1H), 4.25 (d, 1H), 4.61 (s, 1H), 6.77 (s, 1H), 7.27 (m, 3H), 7.45 (m, 2H), 7.64 (d, 2H), 8.34 (d, 2H), 10.43 (s, 1H)

LCMS Spectrum: MH+ 511, retention time 2.7 min, Method 5 Min Base

(4-{4-[1-Methyl-1-(methylsulfonyl)ethyl]-6-[(3S)-3-methylmorpholin-4-yl]pyrimidin-2-yl}phenyl)amine

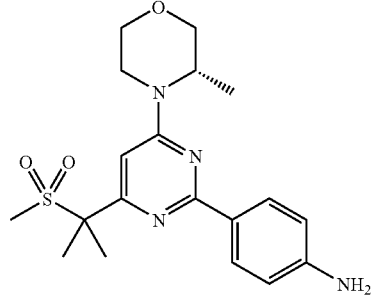

(3S)-4-{2-Chloro-6-[1-methyl-1-(methylsulfonyl)ethyl]pyrimidin-4-yl}-3-methylmorpholine (2.2 g, 6.59 mmol) was dissolved in a solution of 18% DMF in a mixture of 7:3:2 dimethoxyethane:water:ethanol (18 mL). [4-(4,4,5,5-Tetramethyl-1,3,2-dioxaborolan-2-yl)phenyl]amine (2.17 g, 9.89 mmol), 2M sodium carbonate solution (8 mL) and dichlorobis(triphenylphosphine) palladium catalyst (232 mg, 0.33 mmol) were then added and the reaction refluxed at 90° C. for 2 hours under a nitrogen atmosphere. The reaction was allowed to cool to room temp then partitioned between ethyl acetate (20 mL) and water (20 mL). The organics were dried over magnesium sulphate, filtered and concentrated in vacuo. The crude solid was chromatographed on silica, eluting with 0-10% methanol in DCM to give the desired material as a brown oil (3.6 g).

LCMS Spectrum: MH+ 389, retention time 1.00 min, Method 5 Min Base

(3S)-4-{2-Chloro-6-[1-methyl-1-(methylsulfonyl)ethyl]pyrimidin-4-yl}-3-methylmorpholine

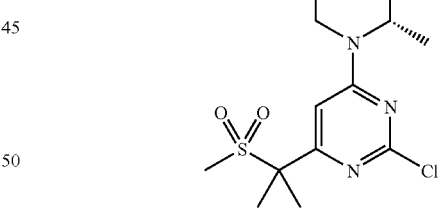

(3S)-4-{2-Chloro-6-[(methylsulfonyl)methyl]pyrimidin-4-yl}-3-methylmorpholine (2.1 g, 6.87 mmol) was dissolved in DMF (20 mL) and the reaction cooled to −5° C. Sodium t-butoxide (650 mg, 6.87 mmol) was added to the reaction, followed by iodomethane (0.4 mL, 6.87 mmol), maintaining the temperature at −5° C. A second equivalent of sodium t-butoxide (650 mg, 6.87 mmol) and iodomethane (0.4 mL, 6.87 mmol) were then added and the reaction stirred at −5° C. for 1 hour, then at room temperature for 4 hours. DCM (20 mL) was added and the reaction washed with 2M aqueous hydrochloric acid (20 mL). The organic phase was dried over magnesium sulphate, filtered and concentrated in vacuo. The crude solid was chromatographed on silica, eluting with 0-50% ethyl acetate in DCM to give the desired material (2.2 g).

NMR Spectrum: $^1$H NMR (400.13 MHz, DMSO-d$_6$) δ 1.21 (d, 3H), 1.68 (s, 6H), 2.74 (s, 3H), 3.21 (m, 1H), 3.45 (m, 1H), 3.59 (m, 1H), 3.73 (d, 1H), 3.94 (m, 1H), 4.07 (d, 1H), 4.45 (s, 1H), 6.86 (s, 1H)

LCMS Spectrum: MH+ 334, retention time 1.85 min, Method 5 Min Base

EXAMPLE 22

1-[4-[4-[(3S)-3-Methylmorpholin-4-yl]-6-(methylsulfonylmethyl)pyrimidin-2-yl]phenyl]-3-(1,2-oxazol-3-yl)urea

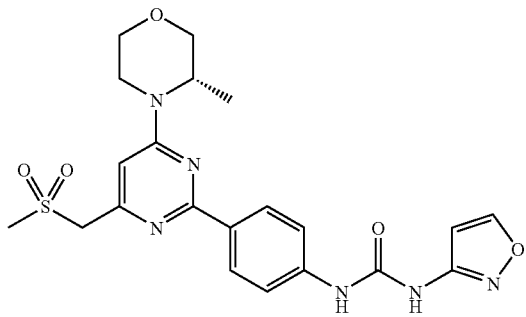

Phenyl N-[4-[4-[(3S)-3-methylmorpholin-4-yl]-6-(methylsulfonylmethyl)pyrimidin-2-yl]phenyl]carbamate (170 mg, 0.35 mmol) was dissolved in DMF (1.5 mL). Triethylamine (0.147 mL, 1.06 mmol) was added. 1,2-oxazol-3-amine (198 mg, 2.35 mmol) was added and the reaction stirred at 60° C. for 2 hours. The reaction was evaporated to dryness and purified by reverse phase chromatography to give the desired material as a white solid (81 mg).

NMR Spectrum: $^1$H NMR (400.13 MHz, DMSO-d$_6$) δ 1.24-1.26 (3H, m), 3.21 (3H, s), 3.23-3.26 (1H, m), 3.47-3.54 (1H, m), 3.64-3.68 (1H, m), 3.79 (1H, d), 3.98-4.01 (1H, m), 4.17-4.20 (1H, m), 4.50 (3H, s), 6.81 (1H, s), 6.87 (1H, d), 7.58 (2H, d), 8.29 (2H, d), 8.75 (1H, d), 9.07 (1H, s), 9.62 (1H, s)

LCMS Spectrum: MH+ 473, Retention Time 1.63 min, Method Monitor Acid

The following compounds were prepared in an analogous manner from phenyl N-[4-[4-[(3S)-3-methylmorpholin-4-yl]-6-(methylsulfonylmethyl)pyrimidin-2-yl]phenyl]carbamate and the appropriate amine.

| Example | Structure | NAME | LCMS MH+ | Retention Time (min) |
|---|---|---|---|---|
| 22a | 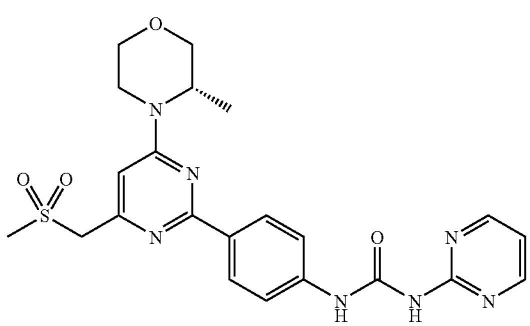 | 1-[4-[4-[(3S)-3-methylmorpholin-4-yl]-6-(methylsulfonylmethyl)pyrimidin-2-yl]phenyl]-3-pyrimidin-2-yl-urea | 484 | 1.60 |
| 22b | 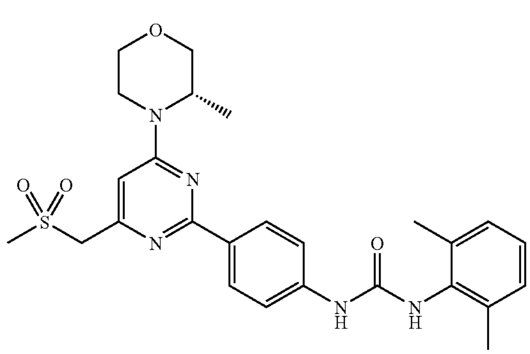 | 1-(2,6-dimethylphenyl)-3-[4-[4-[(3S)-3-methylmorpholin-4-yl]-6-(methylsulfonylmethyl)pyrimidin-2-yl]phenyl]urea | 510 | 1.98 |

-continued

| Example | Structure | NAME | LCMS MH+ | Retention Time (min) |
|---|---|---|---|---|
| 22c | 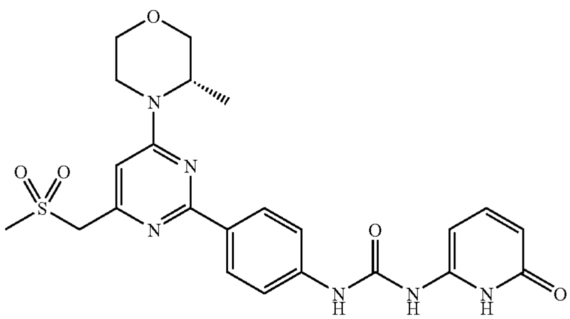 | 1-[4-[4-[(3S)-3-methylmorpholin-4-yl]-6-(methylsulfonylmethyl)pyrimidin-2-yl]phenyl]-3-(6-oxo-1H-pyridin-2-yl)urea | 499 | 1.35 |
| 22d | 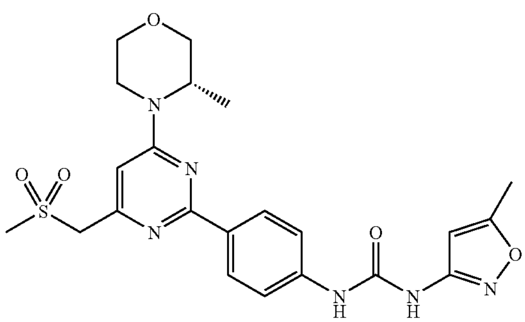 | 3-[4-[4-[(3S)-3-methylmorpholin-4-yl]-6-(methylsulfonylmethyl)pyrimidin-2-yl]phenyl]-1-(5-methyl-1,2-oxazol-3-yl)urea | 487 | 1.72 |
| 22e | 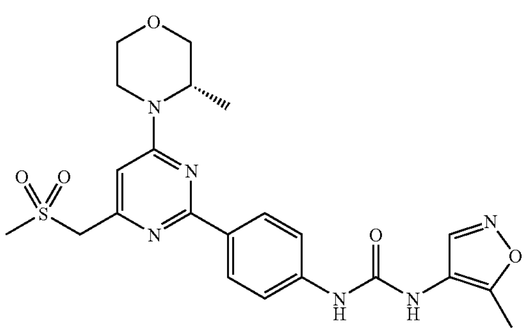 | 3-[4-[4-[(3S)-3-methylmorpholin-4-yl]-6-(methylsulfonylmethyl)pyrimidin-2-yl]phenyl]-1-(5-methyl-1,2-oxazol-4-yl)urea | 487 | 1.46 |
| 22f | 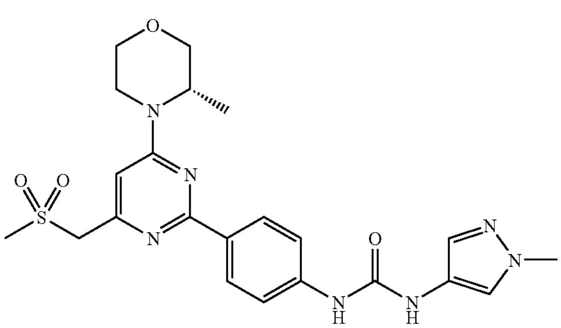 | 1-[4-[4-[(3S)-3-methylmorpholin-4-yl]-6-(methylsulfonylmethyl)pyrimidin-2-yl]phenyl]-3-(1-methylpyrazol-4-yl)urea | 486 | 1.27 |

| Example | Structure | NAME | LCMS MH+ | Retention Time (min) |
|---|---|---|---|---|
| 22g | 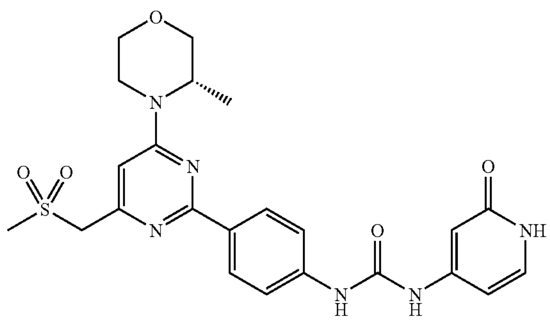 | 1-[4-[4-[(3S)-3-methylmorpholin-4-yl]-6-(methylsulfonylmethyl)pyrimidin-2-yl]phenyl]-3-(2-oxo-1H-pyridin-4-yl)urea | 499 | 1.21 |
| 22h | 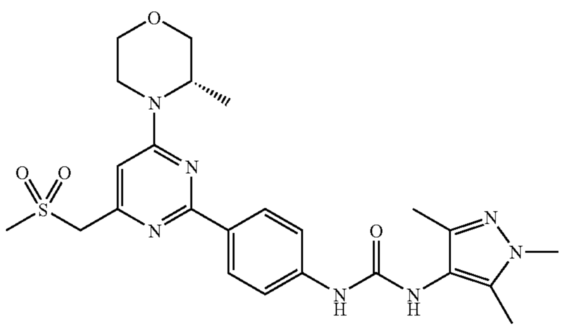 | 3-[4-[4-[(3S)-3-methylmorpholin-4-yl]-6-(methylsulfonylmethyl)pyrimidin-2-yl]phenyl]-1-(1,3,5-trimethylpyrazol-4-yl)urea | 514 | 1.29 |
| 22i | 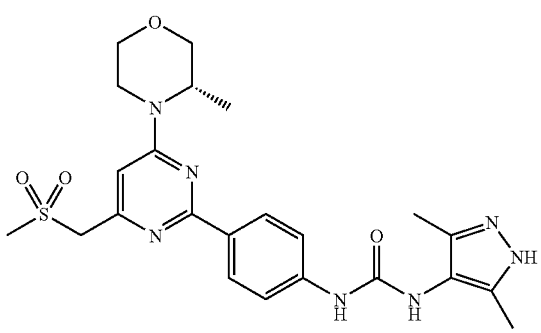 | 1-(3,5-dimethyl-1H-pyrazol-4-yl)-3-[4-[4-[(3S)-3-methylmorpholin-4-yl]-6-(methylsulfonylmethyl)pyrimidin-2-yl]phenyl]urea | 500 | 1.21 |

Example 22a: $^1$H NMR (400.13 MHz, DMSO-d$_6$) δ 1.26 (3H, d), 3.22 (3H, s), 3.24-3.26 (1H, m), 3.48-3.55 (1H, m), 3.65-3.68 (1H, m), 3.79 (1H, d), 3.98-4.02 (1H, m), 4.20 (1H, d), 4.51 (3H, s), 6.82 (1H, s), 7.16 (1H, t), 7.71-7.73 (2H, m), 8.30-8.33 (2H, m), 8.70 (2H, d), 10.21 (1H, s), 11.63 (1H, s)

Example 22b: $^1$H NMR (400.13 MHz, DMSO-d$_6$) δ 1.24-1.26 (3H, m), 2.23 (6H, s), 3.21 (3H, s), 3.23 (1H, d), 3.47-3.54 (1H, m), 3.64-3.67 (1H, m), 3.78 (1H, d), 3.97-4.01 (1H, m), 4.17-4.20 (1H, m), 4.49 (3H, s), 6.79 (1H, s), 7.08 (3H, d), 7.55-7.59 (2H, m), 7.78 (1H, s), 8.23-8.27 (2H, m), 9.00 (1H, s)

Example 22c: $^1$H NMR (400.13 MHz, DMSO-d$_6$) δ 1.26 (3H, d), 3.22 (3H, s), 3.24 (1H, d), 3.48-3.55 (1H, m), 3.64-3.68 (1H, m), 3.79 (1H, d), 3.98-4.02 (1H, m), 4.19 (1H, d), 4.51 (3H, s), 6.24 (1H, d), 6.81 (1H, s), 7.56 (1H, t), 7.70 (2H, d), 8.28-8.30 (2H, m), 9.28 (1H, s)

Example 22d: $^1$H NMR (400.13 MHz, DMSO-d$_6$) δ 1.25 (3H, d), 2.38 (3H, d), 3.21 (3H, s), 3.23 (1H, m), 3.47-3.54 (1H, m), 3.64-3.68 (1H, m), 3.79 (1H, d), 3.97-4.01 (1H, m), 4.18 (1H, d), 4.50 (3H, s), 6.57 (1H, d), 6.81 (1H, s), 7.56 (2H, d), 8.27-8.29 (2H, m), 9.05 (1H, d), 9.46 (1H, s)

Example 22e: $^1$H NMR (400.13 MHz, DMSO-d$_6$) δ 1.25 (3H, d), 2.37 (3H, s), 3.21 (3H, s), 3.22-3.26 (1H, m), 3.47-

3.54 (1H, m), 3.64-3.67 (1H, m), 3.78 (1H, d), 3.97-4.01 (1H, m), 4.18 (1H, s), 4.49 (3H, s), 6.80 (1H, s), 7.55-7.58 (2H, m), 8.18 (1H, s), 8.25-8.27 (2H, m), 8.67 (1H, d), 8.99 (1H, s)

Example 22f: $^1$H NMR (400.13 MHz, DMSO-$d_6$) δ 1.25 (3H, d), 3.21 (3H, s), 3.22-3.26 (1H, m), 3.47-3.54 (1H, m), 3.64-3.67 (1H, m), 3.77-3.30 (1H, m) 3.79 (3H, s), 3.97-4.01 (1H, m), 4.18 (1H, s), 4.49 (3H, s), 6.79 (1H, s), 7.38 (1H, d), 7.53-7.57 (2H, m), 7.76 (1H, s), 8.23-8.26 (2H, m), 8.39 (1H, s), 8.84 (1H, s)

Example 22g: $^1$H NMR (400.13 MHz, DMSO-$d_6$) δ 1.25 (3H, d), 3.21 (3H, s), 3.23-3.26 (1H, m), 3.47-3.54 (1H, m), 3.64-3.68 (1H, m), 3.78 (1H, d), 3.97-4.01 (1H, m), 4.18 (1H, d), 4.50 (3H, s), 6.25-6.27 (1H, m), 6.46 (1H, d), 6.81 (1H, s), 7.25 (1H, d), 7.55-7.57 (2H, m), 8.27-8.29 (2H, m), 8.92 (1H, s), 9.05 (1H, s), 11.04 (1H, s)

Example 22h: $^1$H NMR (400.13 MHz, DMSO-$d_6$) δ 1.25 (3H, d), 2.01 (3H, s), 2.10 (3H, s), 3.21 (3H, s), 3.25 (1H, d), 3.47-3.54 (1H, m), 3.64 (3H, s), 3.66-3.70 (1H, m), 3.78 (1H, d), 3.97-4.01 (1H, m), 4.18 (1H, d), 4.49 (3H, s), 6.78 (1H, s), 7.48 (1H, s), 7.53-7.57 (2H, m), 8.22-8.24 (2H, m), 8.80 (1H, s)

Example 22i: $^1$H NMR (400.13 MHz, DMSO-$d_6$) δ 1.25 (3H, d), 2.03 (3H, s), 2.09 (3H, s), 3.21 (3H, s), 3.25 (1H, d), 3.47-3.54 (1H, m), 3.63-3.67 (1H, m), 3.78 (1H, d), 3.97-4.01 (1H, m), 4.18 (1H, d), 4.49 (3H, s), 6.78 (1H, s), 7.44 (1H, s), 7.55 (2H, d), 8.23 (2H, d), 8.81 (1H, s), 12.04 (1H, s)

Test (a): Example (22a) 0.06 μM; Example (22b) 1.6 μM; Example (22d) 0.0048 μM; Example (22e) 0.56 μM; Example (22f) 0.091 μM; Example (22g) 0.0045 μM; Example (22h) 1.5 μM; Example (22i) 4.3 μM.

Test (c): Example (22c) 0.21 μM.

The preparation of phenyl N-[4-[4-[(3S)-3-methylmorpholin-4-yl]-6-(methylsulfonylmethyl)pyrimidin-2-yl]phenyl]carbamate was described earlier

EXAMPLE 23

3-Methyl-1-[1-[4-[(3S)-3-methylmorpholin-4-yl]-6-(methylsulfonylmethyl)pyrimidin-2-yl]-4-piperidyl]urea

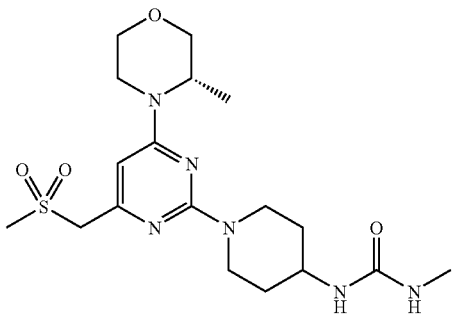

Phenyl N-[1-[4-[(3S)-3-methylmorpholin-4-yl]-6-(methylsulfonylmethyl)pyrimidin-2-yl]-4-piperidyl]carbamate (220 mg, 0.45 mmol) was dissolved in DMF (3 mL). Triethylamine (0.188 mL, 1.35 mmol) was added, followed by 2M methylamine in THF (1.2 mL, 2.25 mmol). The mixture was stirred at 50° C. for 3 hours. The reaction mixture was evaporated to dryness and purified by normal phase chromatography using a 0-6% methanol in DCM gradient to give an oil which upon trituration with diethyl ether gave the desired material as a white solid (153 mg).

NMR Spectrum: $^1$H NMR (400.13 MHz, DMSO-$d_6$) δ 1.17 (3H, d), 1.20-1.27 (2H, m), 1.77 (2H, d), 2.54 (3H, d), 2.99 (2H, d), 3.08 (1H, d), 3.12 (3H, s), 3.37-3.40 (1H, m), 3.43 (1H, d), 3.57 (1H, d), 3.71 (1H, d), 3.91 (1H, d), 3.94 (1H, d), 4.23 (2H, s), 4.26 (1H, d), 4.42 (2H, d), 5.57 (1H, q), 5.83 (1H, d), 6.14 (1H, s)

LCMS Spectrum: MH+ 427, Retention Time 0.85 min, Method 5 Minute Acid

The following compound was prepared in an analogous from phenyl N-[1-[4-[(3S)-3-methylmorpholin-4-yl]-6-(methylsulfonylmethyl)pyrimidin-2-yl]-4-piperidyl]carbamate and the appropriate amine.

| Example | Structure | NAME | LCMS MH+ | Retention Time (min) | Notes |
|---|---|---|---|---|---|
| 23a | 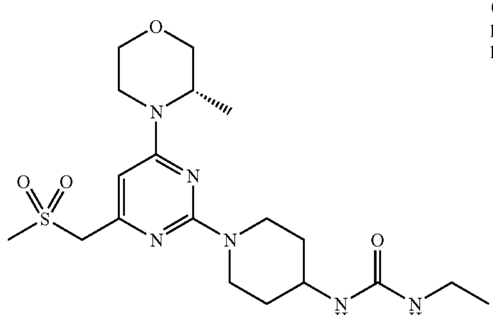 | 1-ethyl-3-[1-[4-[(3S)-3-methylmorpholin-4-yl]-6-(methylsulfonylmethyl)pyrimidin-2-yl]-4-piperidyl]urea | 441 | 1.03 | Purified by reverse phase chromatography |

Example 23a: ¹H NMR (400.13 MHz, DMSO-d₆) δ 0.98 (3H, t), 1.13-1.18 (3H, m), 1.20-1.26 (2H, m), 1.77 (2H, d), 2.97-3.03 (4H, m), 3.05-3.10 (1H, m), 3.12 (3H, s), 3.38-3.45 (1H, m), 3.55-3.59 (1H, m), 3.63 (1H, t), 3.71 (1H, d), 3.92 (1H, d), 3.92 (1H, d), 4.23 (2H, s), 4.27 (1H, m), 4.41 (2H, d), 5.64 (1H, t), 5.77 (1H, d), 6.14 (1H, s)

Test (a): Example (23) 5.6 μM; Example (23a) 3.7 μM.

The preparation of phenyl N-[1-[4-[(3S)-3-methylmorpholin-4-yl]-6-(methylsulfonylmethyl)pyrimidin-2-yl]-4-piperidyl]carbamate is described below.

Phenyl N-[1-[4-[(3S)-3-methylmorpholin-4-yl]-6-(methylsulfonylmethyl)pyrimidin-2-yl]-4-piperidyl] carbamate

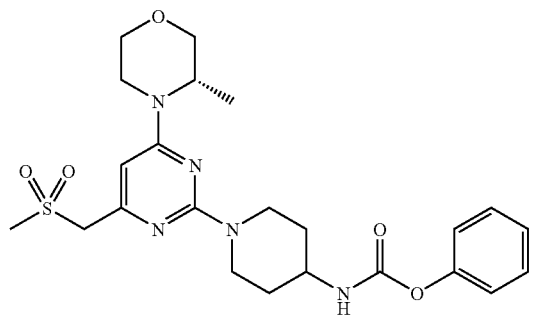

1-[4-[(3S)-3-methylmorpholin-4-yl]-6-(methylsulfonylmethyl)pyrimidin-2-yl]piperidin-4-amine (500 mg, 1.35 mmol) was dissolved in dioxane (10 mL). Sodium bicarbonate (171 mg, 1.50 mmol) was added. Then phenyl chloroformate (0.171 mL, 1.35 mmol) was added dropwise over 2 minutes. The slurry was stirred at RT for 3 hours. Phenyl chloroformate (0.021 mL, 0.27 mmol) and sodium bicarbonate (21 mg, 0.12 mmol) were added. Stirring at room temp was continued for 1 hour and the reaction mixture evaporated to dryness and partitioned between water (10 mL) and ethyl acetate (10 mL). The water was extracted with a second portion of ethyl acetate (10 mL). The combined organics were dried over magnesium sulfate and evaporated to give the desired material as a foam (701 mg).

NMR Spectrum: ¹H NMR (400.13 MHz, DMSO-d₆) δ 1.18 (3H, d), 1.34-1.44 (2H, m), 1.86 (2H, d), 2.99 (2H, d), 3.11 (1H, d), 3.13 (3H, s), 3.40-3.46 (1H, m), 3.60 (2H, d), 3.72 (2H, d), 3.91-3.96 (2H, m), 4.25 (2H, s), 4.28 (1H, m), 4.52 (2H, d), 6.16 (1H, s), 7.10 (2H, d), 7.20 (1H, t), 7.38 (2H, t), 7.76 (1H, d)

LCMS Spectrum: MH+ 490, Retention Time 1.58 min, Method Monitor Acid

1-[4-[(3S)-3-Methylmorpholin-4-yl]-6-(methylsulfonylmethyl)pyrimidin-2-yl]piperidin-4-amine

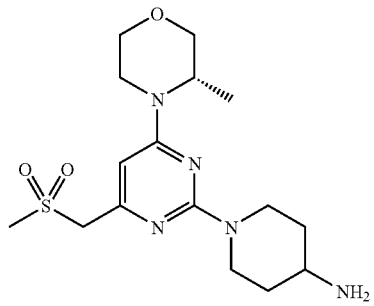

tert-Butyl N-[1-[4-[(3S)-3-methylmorpholin-4-yl]-6-(methylsulfonylmethyl)pyrimidin-2-yl]-4-piperidyl]carbamate (1.30 g, 2.77 mmol) was dissolved in methanol (10 mL). 4M Hydrochloric acid in dioxane (10 mL) was added. The reaction was stirred at RT for 3 hours. Saturated aqueous sodium bicarbonate was added until pH7 was reached and the organic solvents were removed in vacuo. Water (20 mL) was added and the product was extracted into ethyl acetate (50 mL). The aqueous layer was extracted with a second portion of ethyl acetate (25 mL). The combined organics were evaporated to give the desired material as a yellow foam (1.05 g).

NMR Spectrum: ¹H NMR (400.13 MHz, DMSO-d₆) δ 1.17 (3H, d), 1.69-1.73 (2H, m), 2.75-2.80 (1H, m), 2.87-2.94 (2H, m), 3.07 (1H, d), 3.11 (1H, m), 3.12 (3H, s), 3.39-3.45 (1H, m), 3.55-3.62 (1H, m), 3.69-3.73 (1H, m), 3.90-3.94 (2H, m), 4.22 (2H, s), 4.26 (1H, s), 4.43 (1H, s), 4.46 (1H, d), 6.12 (1H, s)

LCMS Spectrum: MH+ 370, Retention Time 0.48 min, Method Monitor Acid tert-Butyl N-[1-[4-[(3S)-3-methylmorpholin-4-yl]-6-(methylsulfonylmethyl)pyrimidin-2-yl]-4-piperidyl] carbamate

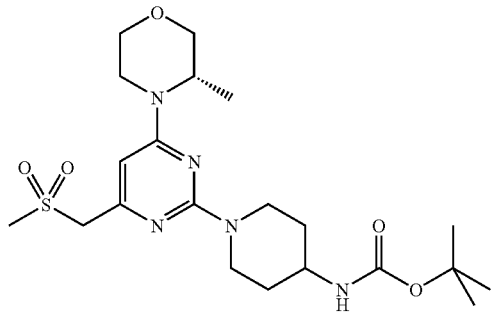

2-Chloro-4-[(3S)-3-methylmorpholin-4-yl]-6-(methylsulfonylmethyl)pyrimidine (1.00 g, 3.27 mmol), potassium carbonate (498 mg, 3.60 mmol) and tert-butyl N-(4-piperidyl)carbamate (721 mg, 3.60 mmol). Acetonitrile (10 mL) was added and the mixture was heated under reflux for 4 hours. The acetonitrile was evaporated off to leave a white solid which was partitioned between water (40 mL) and ethyl acetate (60 mL). The phases were separated and the aqueous layer was extracted with a second portion of ethyl acetate (40 mL). The combined organics were evaporated to dryness to give the desired material as a cream solid (1.32 g).

NMR Spectrum: ¹H NMR (400.13 MHz, DMSO-d₆) δ1.16-1.18 (3H, m), 1.23-1.31 (2H, m), 1.39 (9H, s), 1.74 (2H, d), 2.91 (2H, t), 3.06-3.09 (1H, m), 3.11 (3H, s), 3.39-3.44 (1H, m), 3.49 (1H, s), 3.55-3.59 (1H, m), 3.71 (1H, d), 3.90 (1H, d), 3.94 (1H, d), 4.23 (2H, s), 4.26 (1H, d), 4.50 (2H, d), 6.14 (1H, s), 6.78 (1H, d)

LCMS Spectrum: MH+ 470, Retention Time 1.39 min, Method Monitor Acid

The preparation of 2-Chloro-4-[(3S)-3-methylmorpholin-4-yl]-6-(methylsulfonylmethyl)pyrimidine was described earlier.

EXAMPLE 24

1-[4-[4-[(3S)-3-Methylmorpholin-4-yl]-6-(methyl-sulfonylmethyl)pyrimidin-2-yl]phenyl]-3-(2-pyridin-2-ylethyl)urea

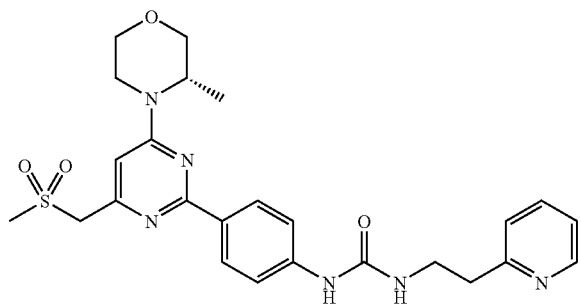

Phenyl N-[4-[4-[(3S)-3-methylmorpholin-4-yl]-6-(methylsulfonylmethyl)pyrimidin-2-yl]phenyl]carbamate (242 mg, 0.50 mmol) was dissolved in DMF (1.5 mL). Triethylamine (0.209 mL, 1.50 mmol) was added. 2-Pyridin-2-ylethanamine (306 mg, 2.50 mmol) was added. The reaction was stirred at 40° C. for 2 hours. The reaction mixture was purified by reverse phase chromatography to give the desired material as a white solid (239 mg).

NMR Spectrum: $^1$H NMR (400.13 MHz, DMSO-$d_6$) δ 1.24 (3H, d), 2.94 (2H, t), 3.21 (3H, s), 3.22-3.26 (1H, m), 3.48 (1H, d), 3.50-3.54 (2H, m), 3.63-3.67 (1H, m), 3.78 (1H, d), 3.97-4.00 (1H, m), 4.17 (1H, d), 4.48 (3H, s), 6.26 (1H, t), 6.77 (1H, s), 7.22-7.26 (1H, m), 7.30 (1H, d), 7.47-7.51 (2H, m), 7.71-7.75 (1H, m), 8.19-8.22 (2H, m), 8.52-8.54 (1H, m), 8.77 (1H, s)

LCMS Spectrum: MH+ 511, Retention Time 1.67 min, Method 5 Minute Basic

The following compounds were prepared in an analogous manner from the appropriate carbamate and the appropriate amine.

| Example | Structure | NAME | LCMS MH+ | Retention Time (min) |
|---|---|---|---|---|
| 24a | 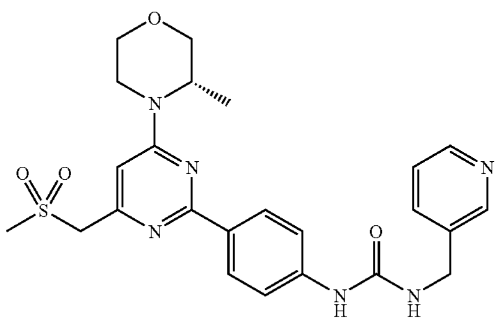 | 1-[4-[4-[(3S)-3-methylmorpholin-4-yl]-6-(methylsulfonylmethyl)pyrimidin-2-yl]phenyl]-3-(pyridin-3-ylmethyl)urea | 497 | 1.56 |
| 24b | 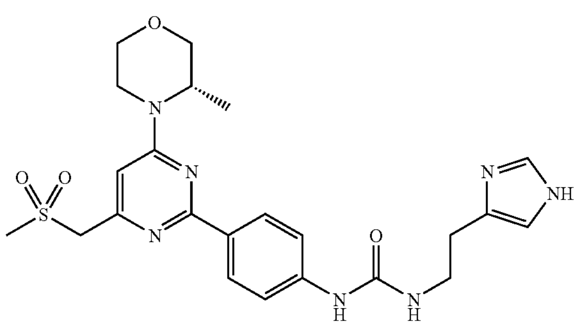 | 3-[2-(1H-imidazol-4-yl)ethyl]-1-[4-[4-[(3S)-3-methylmorpholin-4-yl]-6-(methylsulfonylmethyl)pyrimidin-2-yl]phenyl]urea | 500 | 1.42 |
| 24c | 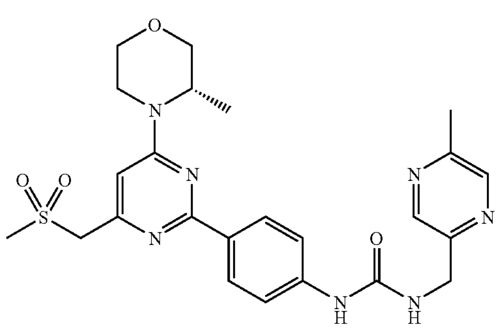 | 3-[4-[4-[(3S)-3-methylmorpholin-4-yl]-6-(methylsulfonylmethyl)pyrimidin-2-yl]phenyl]-1-[(5-methylpyrazin-2-yl)methyl]urea | 512 | 1.52 |

-continued

| Example | Structure | NAME | LCMS MH+ | Retention Time (min) |
|---|---|---|---|---|
| 24d | 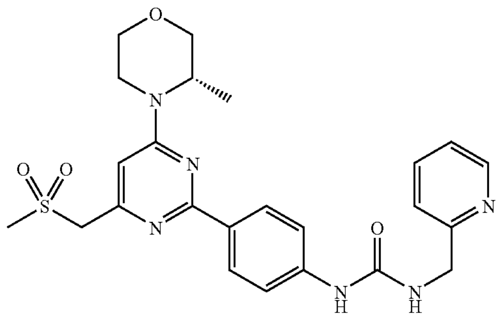 | 1-[4-[4-[(3S)-3-methylmorpholin-4-yl]-6-(methylsulfonylmethyl)pyrimidin-2-yl]phenyl]-3-(pyridin-2-ylmethyl)urea | 497 | 1.62 |
| 24e | 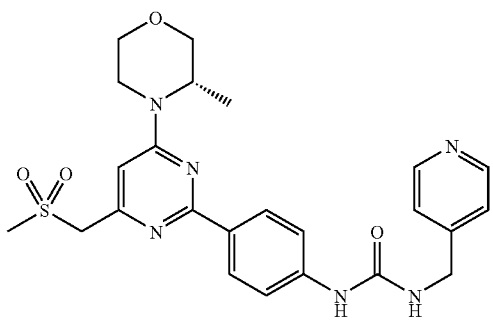 | 1-[4-[4-[(3S)-3-methylmorpholin-4-yl]-6-(methylsulfonylmethyl)pyrimidin-2-yl]phenyl]-3-(pyridin-4-ylmethyl)urea | 497 | 1.55 |
| 24f | 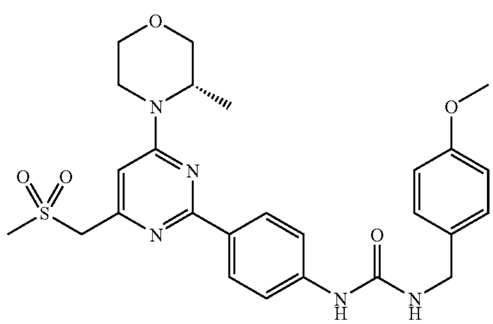 | 3-[(4-methoxyphenyl)methyl]-1-[4-[4-[(3S)-3-methylmorpholin-4-yl]-6-(methylsulfonylmethyl)pyrimidin-2-yl]phenyl]urea | 526 | 2.04 |
| 24g | 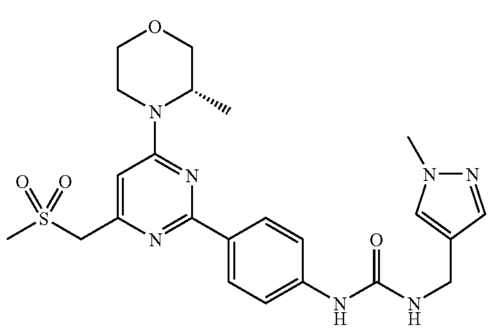 | 1-[4-[4-[(3S)-3-methylmorpholin-4-yl]-6-(methylsulfonylmethyl)pyrimidin-2-yl]phenyl]-3-[(1-methylpyrazol-4-yl)methyl]urea | 500 | 1.50 |

-continued

| Example | Structure | NAME | LCMS MH+ | Retention Time (min) |
|---|---|---|---|---|
| 24h | 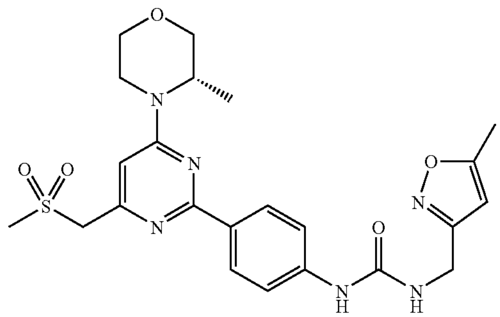 | 3-[4-[4-[(3S)-3-methylmorpholin-4-yl]-6-(methylsulfonylmethyl)pyrimidin-2-yl]phenyl]-1-[(5-methyl-1,2-oxazol-3-yl)methyl]urea | 501 | 1.73 |
| 24i | 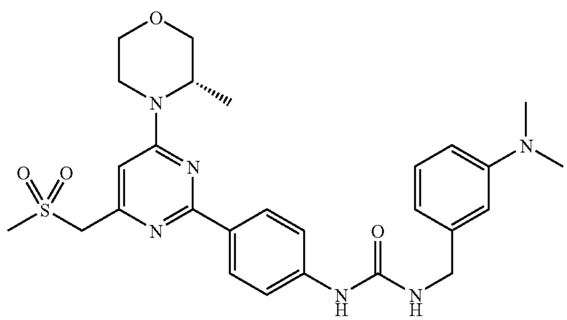 | 3-[(3-dimethylaminophenyl)methyl]-1-[4-[4-[(3S)-3-methylmorpholin-4-yl]-6-(methylsulfonylmethyl)pyrimidin-2-yl]phenyl]urea | 539 | 2.15 |
| 24j | 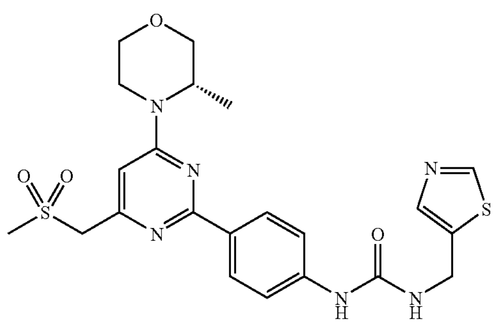 | 1-[4-[4-[(3S)-3-methylmorpholin-4-yl]-6-(methylsulfonylmethyl)pyrimidin-2-yl]phenyl]-3-(1,3-thiazol-5-ylmethyl)urea | 503 | 1.58 |
| 24k | 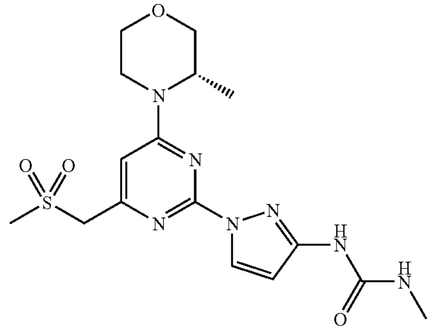 | 3-methyl-1-[1-[4-[(3S)-3-methylmorpholin-4-yl]-6-(methylsulfonylmethyl)pyrimidin-2-yl]pyrazol-3-yl]urea | 410 | 2.18 |

-continued

| Example | Structure | NAME | LCMS MH+ | Retention Time (min) |
|---|---|---|---|---|
| 24l | 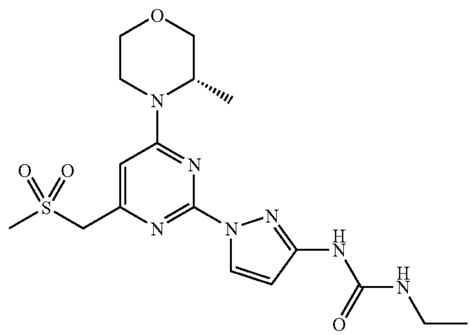 | 1-ethyl-3-[1-[4-[(3S)-3-methylmorpholin-4-yl]-6-(methylsulfonylmethyl)pyrimidin-2-yl]pyrazol-3-yl]urea | 424 | 2.29 |
| 24m | 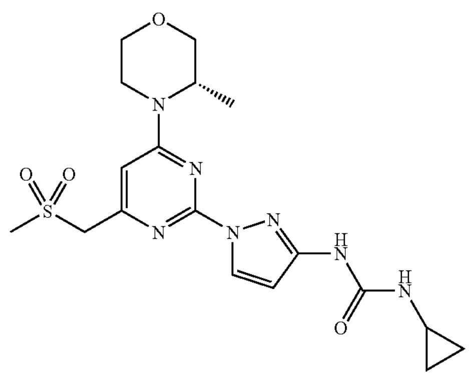 | 3-cyclopropyl-1-[1-[4-[(3S)-3-methylmorpholin-4-yl]-6-(methylsulfonylmethyl)pyrimidin-2-yl]pyrazol-3-yl]urea | 436 | 2.30 |
| 24n | 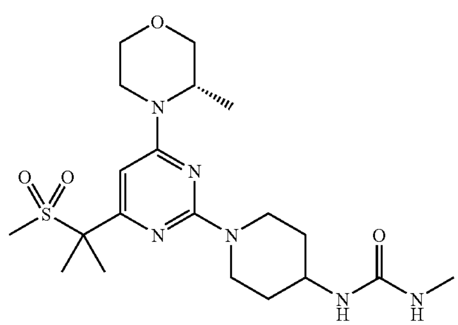 | 3-methyl-1-[1-[4-[(3S)-3-methylmorpholin-4-yl]-6-(2-methylsulfonylpropan-2-yl)pyrimidin-2-yl]-4-piperidyl]urea | 455 | 1.63 |
| 24o | 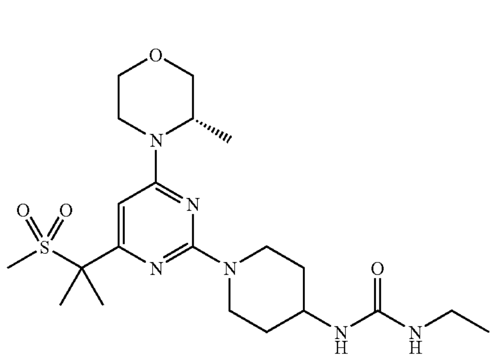 | 1-ethyl-3-[1-[4-[(3S)-3-methylmorpholin-4-yl]-6-(2-methylsulfonylpropan-2-yl)pyrimidin-2-yl]-4-piperidyl]urea | 469 | 1.76 |

-continued

| Example | Structure | NAME | LCMS MH+ | Retention Time (min) |
|---|---|---|---|---|
| 24p | 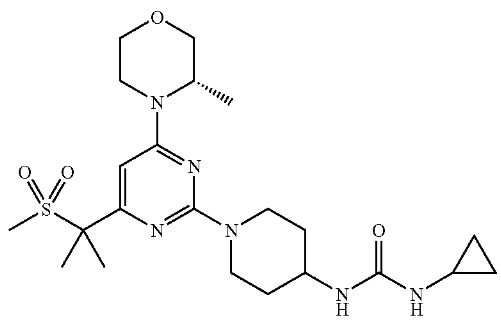 | 3-cyclopropyl-1-[1-[4-[(3S)-3-methylmorpholin-4-yl]-6-(2-methylsulfonylpropan-2-yl)pyrimidin-2-yl]-4-piperidyl]urea | 481 | 1.80 |
| 24q | 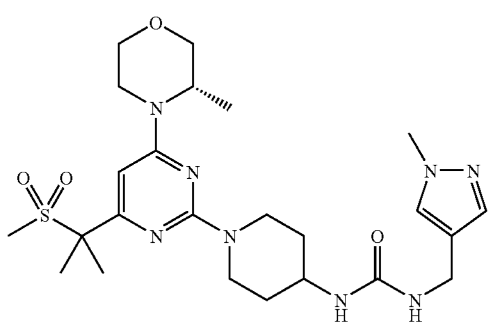 | 1-[1-[4-[(3S)-3-methylmorpholin-4-yl]-6-(2-methylsulfonylpropan-2-yl)pyrimidin-2-yl]-4-piperidyl]-3-[(1-methylpyrazol-4-yl)methyl]urea | 535 | 1.69 |
| 24r | 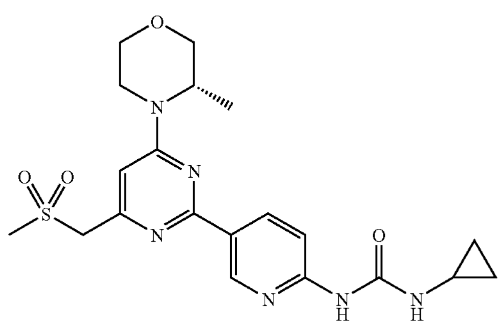 | 3-cyclopropyl-1-[5-[4-[(3S)-3-methylmorpholin-4-yl]-6-(methylsulfonylmethyl)pyrimidin-2-yl]pyridin-2-yl]urea | 446 | 1.56 |
| 24s | 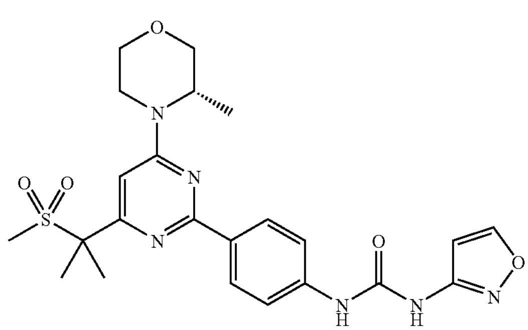 | 1-[4-[4-[(3S)-3-methylmorpholin-4-yl]-6-(2-methylsulfonylpropan-2-yl)pyrimidin-2-yl]phenyl]-3-(1,2-oxazol-3-yl)urea | 501 | 1.64 |

-continued

| Example | Structure | NAME | LCMS MH+ | Retention Time (min) |
|---|---|---|---|---|
| 24t | 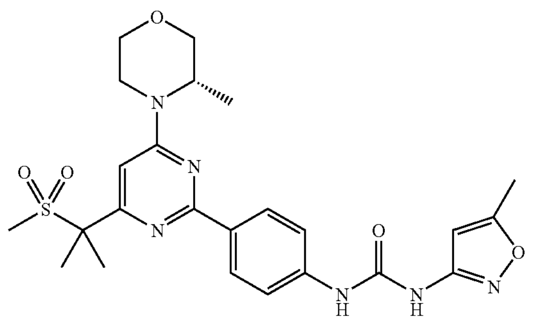 | 3-[4-[4-[(3S)-3-methylmorpholin-4-yl]-6-(2-methylsulfonylpropan-2-yl)pyrimidin-2-yl]phenyl]-1-(5-methyl-1,2-oxazol-3-yl)urea | 515 | 2.22 |
| 24u | 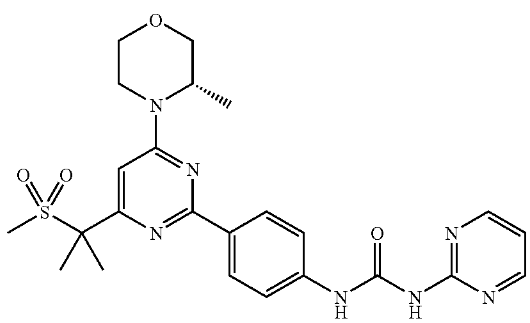 | 1-[4-[4-[(3S)-3-methylmorpholin-4-yl]-6-(2-methylsulfonylpropan-2-yl)pyrimidin-2-yl]phenyl]-3-pyrimidin-2-yl-urea | 512 | 2.10 |
| 24v | 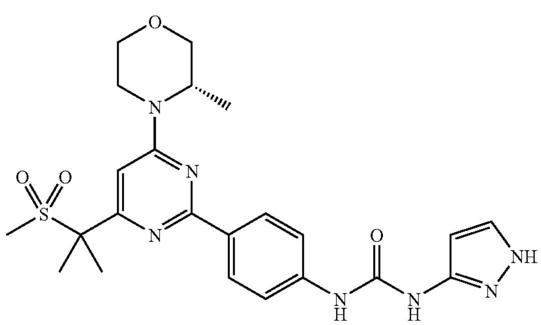 | 1-[4-[4-[(3S)-3-methylmorpholin-4-yl]-6-(2-methylsulfonylpropan-2-yl)pyrimidin-2-yl]phenyl]-3-(1H-pyrazol-3-yl)urea | 500 | 2.05 |
| 24w | 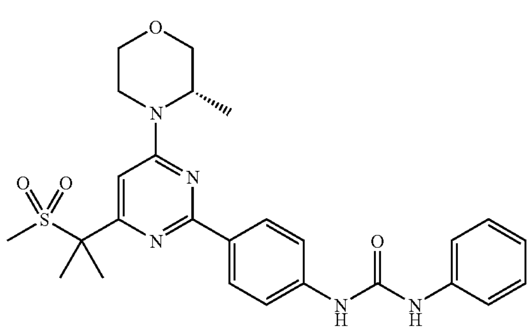 | 1-[4-[4-[(3S)-3-methylmorpholin-4-yl]-6-(2-methylsulfonylpropan-2-yl)pyrimidin-2-yl]phenyl]-3-phenyl-urea | 510 | 2.40 |

| Example | Structure | NAME | LCMS MH+ | Retention Time (min) |
|---|---|---|---|---|
| 24x | 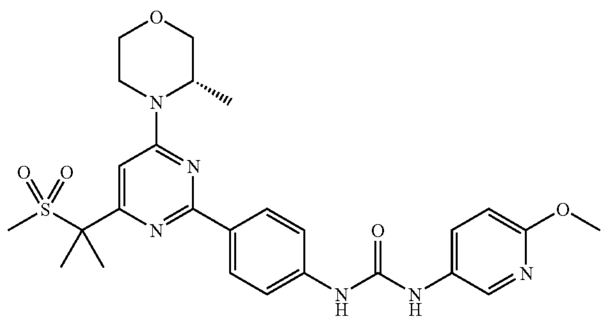 | 3-(6-methoxypyridin-3-yl)-1-[4-[4-[(3S)-3-methylmorpholin-4-yl]-6-(2-methylsulfonylpropan-2-yl)pyrimidin-2-yl]phenyl]urea | 541 | 2.14 |
| 24y | 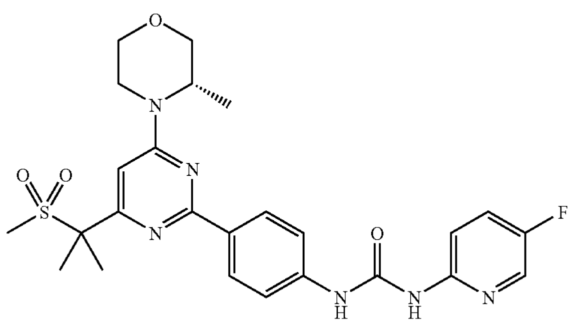 | 3-(5-fluoropyridin-2-yl)-1-[4-[4-[(3S)-3-methylmorpholin-4-yl]-6-(2-methylsulfonylpropan-2-yl)pyrimidin-2-yl]phenyl]urea | 529 | 2.39 |
| 24z | 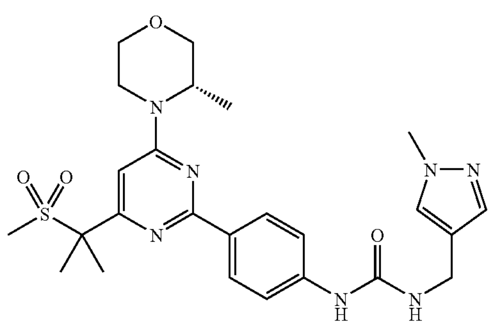 | 1-[5-[4-[(3S)-3-methylmorpholin-4-yl]-6-(2-methylsulfonylpropan-2-yl)pyrimidin-2-yl]pyrimidin-2-yl]-3-[(1-methylpyrazol-4-yl)methyl]urea | 530 | 1.68 |
| 24aa | 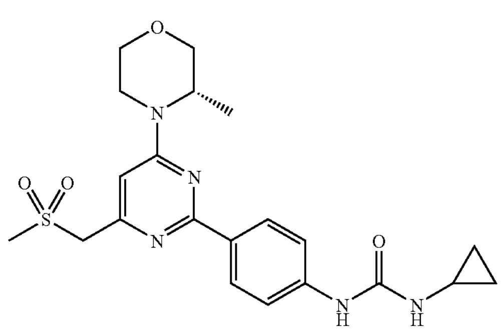 | 3-cyclopropyl-1-[4-[4-[(3S)-3-methylmorpholin-4-yl]-6-(methylsulfonylmethyl)pyrimidin-2-yl]phenyl]urea | 446 | 1.38 |

-continued

| Example | Structure | NAME | LCMS MH+ | Retention Time (min) |
|---|---|---|---|---|
| 24ab | 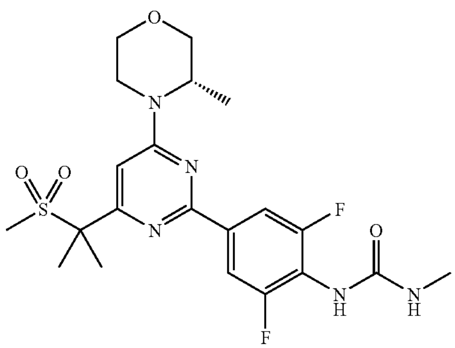 | 1-[2,6-difluoro-4-[4-[(3S)-3-methylmorpholin-4-yl]-6-(2-methylsulfonylpropan-2-yl)pyrimidin-2-yl]phenyl]-3-methyl-urea | 484 | 2.44 |
| 24ac | 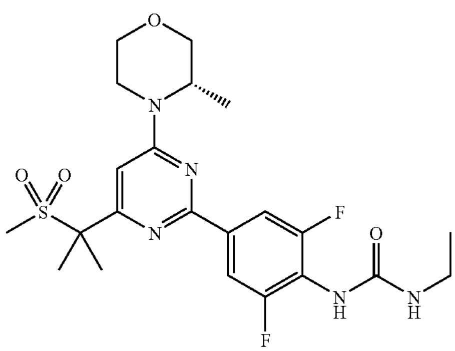 | 3-[2,6-difluoro-4-[4-[(3S)-3-methylmorpholin-4-yl]-6-(2-methylsulfonylpropan-2-yl)pyrimidin-2-yl]phenyl]-1-ethyl-urea | 498 | 2.56 |
| 24ad | 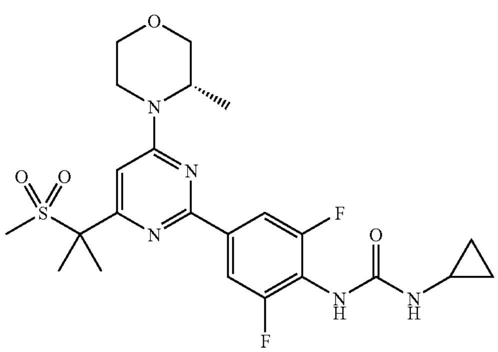 | 3-cyclopropyl-1-[2,6-difluoro-4-[4-[(3S)-3-methylmorpholin-4-yl]-6-(2-methylsulfonylpropan-2-yl)pyrimidin-2-yl]phenyl]urea | 510 | 2.58 |
| 24ae | 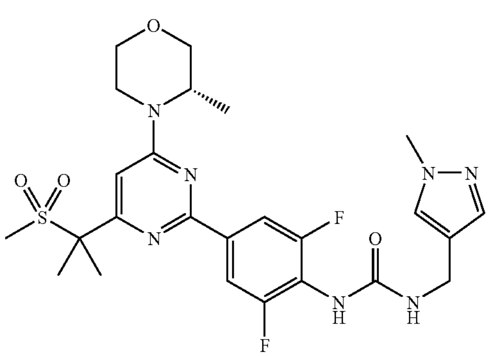 | 1-[2,6-difluoro-4-[4-[(3S)-3-methylmorpholin-4-yl]-6-(2-methylsulfonylpropan-2-yl)pyrimidin-2-yl]phenyl]-3-[(1-methylpyrazol-4-yl)methyl]urea | 564 | 2.46 |

-continued

| Example | Structure | NAME | LCMS MH+ | Retention Time (min) |
|---|---|---|---|---|
| 24af | 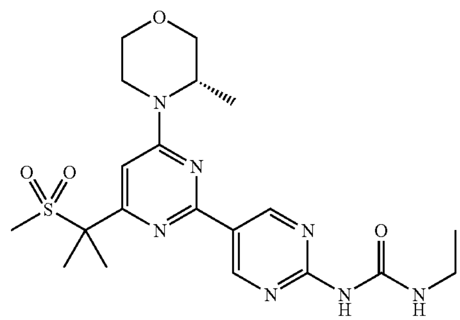 | 1-ethyl-3-[5-[4-[(3S)-3-methylmorpholin-4-yl]-6-(2-methylsulfonylpropan-2-yl)pyrimidin-2-yl]pyrimidin-2-yl]urea | 464 | 1.86 |
| 24ag | 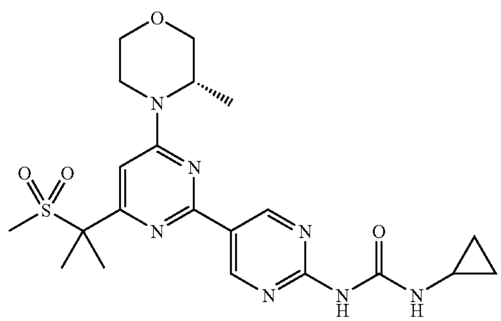 | 3-cyclopropyl-1-[5-[4-[(3S)-3-methylmorpholin-4-yl]-6-(2-methylsulfonylpropan-2-yl)pyrimidin-2-yl]pyrimidin-2-yl]urea | 476 | 1.88 |
| 24ah | 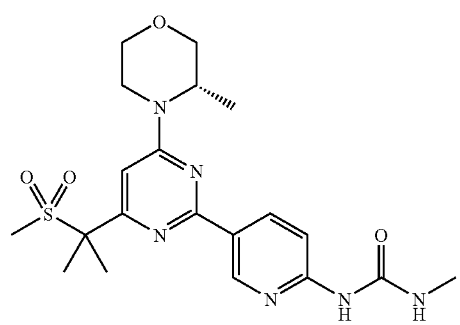 | 3-methyl-1-[5-[4-[(3S)-3-methylmorpholin-4-yl]-6-(2-methylsulfonylpropan-2-yl)pyrimidin-2-yl]pyridin-2-yl]urea | 449 | 1.77 |
| 24ai | 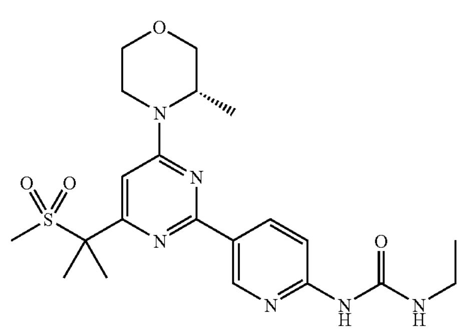 | 1-ethyl-3-[5-[4-[(3S)-3-methylmorpholin-4-yl]-6-(2-methylsulfonylpropan-2-yl)pyrimidin-2-yl]pyridin-2-yl]urea | 463 | 1.92 |

-continued

| Example | Structure | NAME | LCMS MH+ | Retention Time (min) |
|---------|-----------|------|----------|----------------------|
| 24aj | 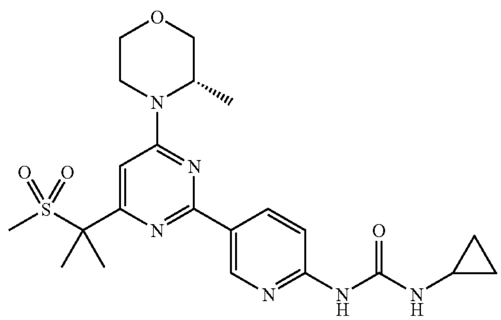 | 3-cyclopropyl-1-[5-[4-[(3S)-3-methylmorpholin-4-yl]-6-(2-methylsulfonylpropan-2-yl)pyrimidin-2-yl]pyridin-2-yl]urea | 475 | 1.95 |
| 24ak | 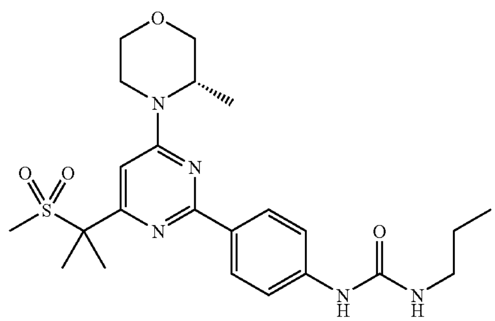 | 3-[4-[4-[(3S)-3-methylmorpholin-4-yl]-6-(2-methylsulfonylpropan-2-yl)pyrimidin-2-yl]phenyl]-1-propyl-urea | 476 | 1.92 |
| 24al | 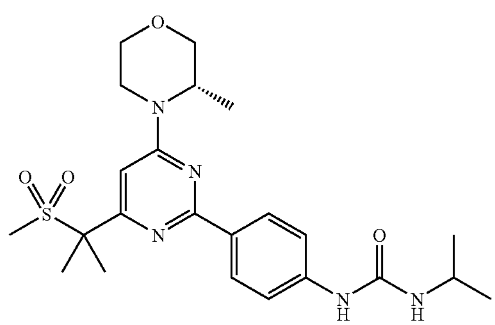 | 1-[4-[4-[(3S)-3-methylmorpholin-4-yl]-6-(2-methylsulfonylpropan-2-yl)pyrimidin-2-yl]phenyl]-3-propan-2-yl-urea | 476 | 2.08 |
| 24am | 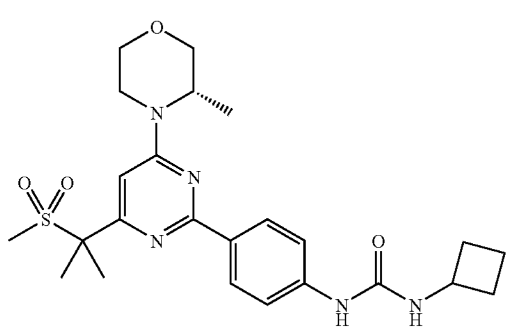 | 3-cyclobutyl-1-[4-[4-[(3S)-3-methylmorpholin-4-yl]-6-(2-methylsulfonylpropan-2-yl)pyrimidin-2-yl]phenyl]urea | 488 | 2.15 |

-continued

| Example | Structure | NAME | LCMS MH+ | Retention Time (min) |
|---|---|---|---|---|
| 24an | 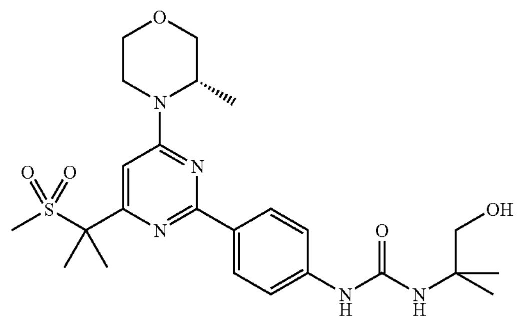 | 3-(1-hydroxy-2-methyl-propan-2-yl)-1-[4-[4-[(3S)-3-methylmorpholin-4-yl]-6-(2-methylsulfonylpropan-2-yl)pyrimidin-2-yl]phenyl]urea | 506 | 1.88 |
| 24ao | 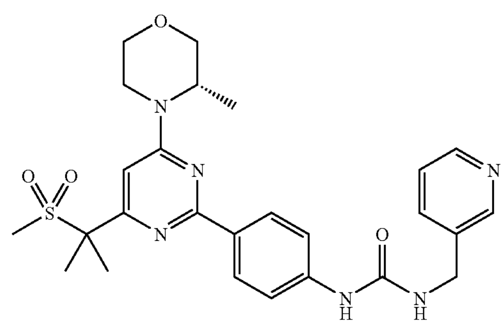 | 1-[4-[4-[(3S)-3-methylmorpholin-4-yl]-6-(2-methylsulfonylpropan-2-yl)pyrimidin-2-yl]phenyl]-3-(pyridin-3-ylmethyl)urea | 525 | 1.83 |
| 24ap | 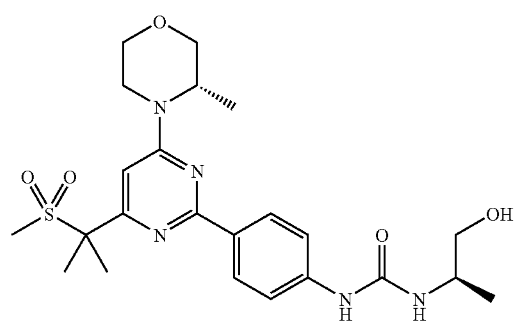 | 3-[(2R)-1-hydroxypropan-2-yl]-1-[4-[4-[(3S)-3-methylmorpholin-4-yl]-6-(2-methylsulfonylpropan-2-yl)pyrimidin-2-yl]phenyl]urea | 492 | 1.71 |
| 24aq | 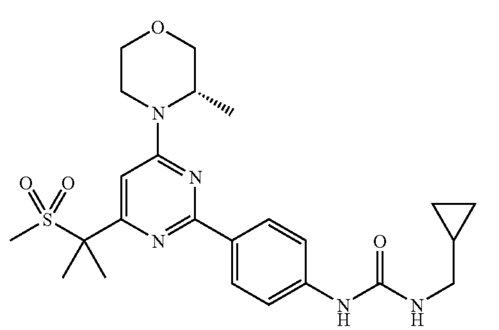 | 3-(cyclopropylmethyl)-1-[4-[4-[(3S)-3-methylmorpholin-4-yl]-6-(2-methylsulfonylpropan-2-yl)pyrimidin-2-yl]phenyl]urea | 488 | 2.14 |

-continued

| Example | Structure | NAME | LCMS MH+ | Retention Time (min) |
|---|---|---|---|---|
| 24ar | 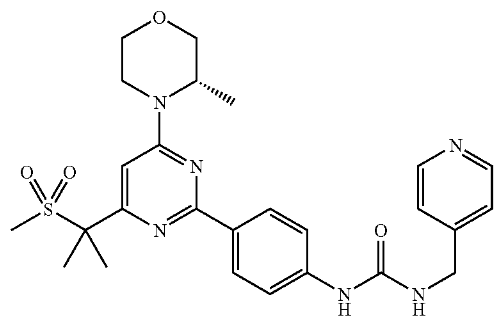 | 1-[4-[4-[(3S)-3-methylmorpholin-4-yl]-6-(2-methylsulfonylpropan-2-yl)pyrimidin-2-yl]phenyl]-3-(pyridin-4-ylmethyl)urea | 525 | 1.81 |
| 24as | 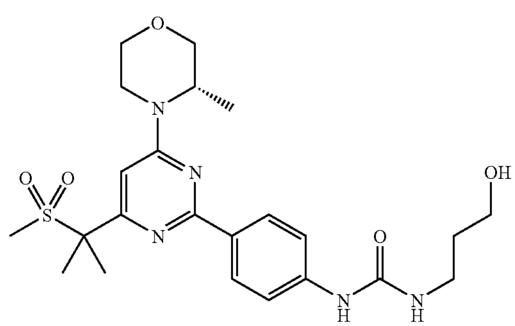 | 3-(3-hydroxypropyl)-1-[4-[4-[(3S)-3-methylmorpholin-4-yl]-6-(2-methylsulfonylpropan-2-yl)pyrimidin-2-yl]phenyl]urea | 492 | 1.66 |
| 24at | 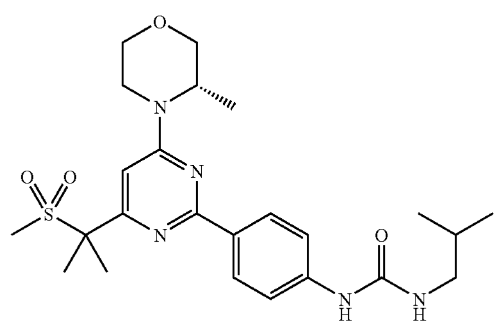 | 1-[4-[4-[(3S)-3-methylmorpholin-4-yl]-6-(2-methylsulfonylpropan-2-yl)pyrimidin-2-yl]phenyl]-3-(2-methylpropyl)urea | 490 | 2.24 |
| 24au | 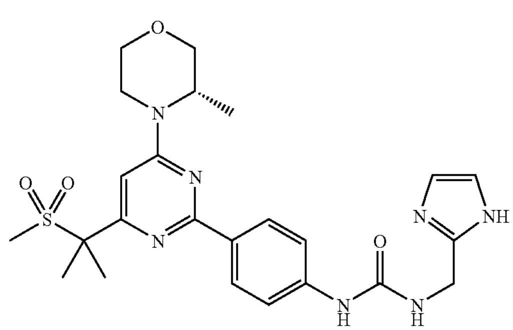 | 3-(1H-imidazol-2-ylmethyl)-1-[4-[4-[(3S)-3-methylmorpholin-4-yl]-6-(2-methylsulfonylpropan-2-yl)pyrimidin-2-yl]phenyl]urea | 514 | 1.76 |

-continued

| Example | Structure | NAME | LCMS MH+ | Retention Time (min) |
|---|---|---|---|---|
| 24av | 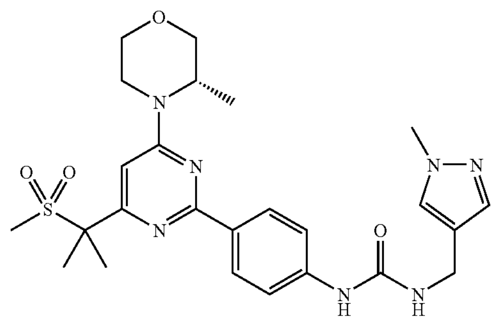 | 1-[4-[4-[(3S)-3-methylmorpholin-4-yl]-6-(2-methylsulfonylpropan-2-yl)pyrimidin-2-yl]phenyl]-3-[(1-methylpyrazol-4-yl)methyl]urea | 528 | 1.93 |
| 24aw | 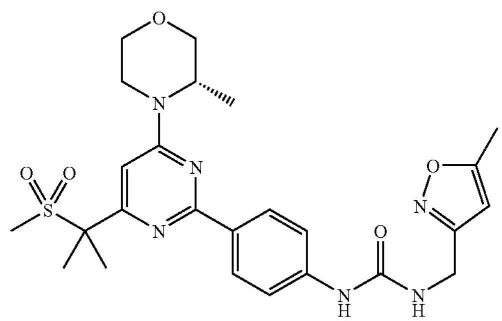 | 3-[4-[4-[(3S)-3-methylmorpholin-4-yl]-6-(2-methylsulfonylpropan-2-yl)pyrimidin-2-yl]phenyl]-1-[(5-methyl-1,2-oxazol-3-yl)methyl]urea | 529 | 2.01 |
| 24ax | 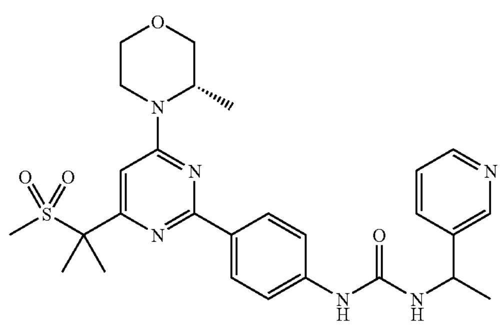 | 1-[4-[4-[(3S)-3-methylmorpholin-4-yl]-6-(2-methylsulfonylpropan-2-yl)pyrimidin-2-yl]phenyl]-3-(1-pyridin-3-ylethyl)urea | 539 | 1.91 |
| 24ay | 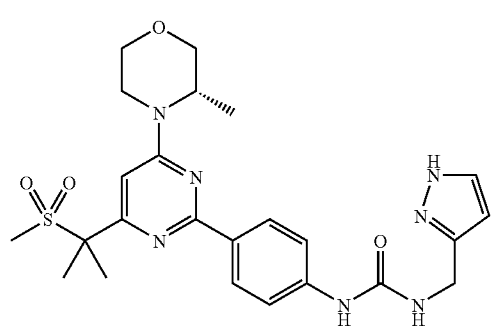 | 1-[4-[4-[(3S)-3-methylmorpholin-4-yl]-6-(2-methylsulfonylpropan-2-yl)pyrimidin-2-yl]phenyl]-3-(1H-pyrazol-3-ylmethyl)urea | 514 | 1.75 |

-continued

| Example | Structure | NAME | LCMS MH+ | Retention Time (min) |
|---|---|---|---|---|
| 24az | 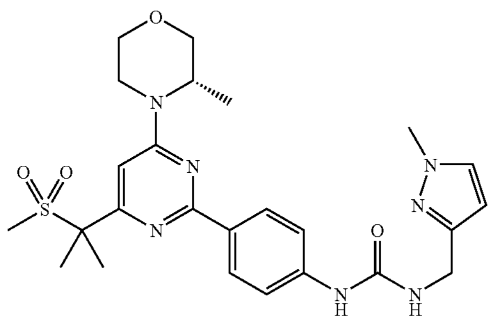 | 1-[4-[4-[(3S)-3-methylmorpholin-4-yl]-6-(2-methylsulfonylpropan-2-yl)pyrimidin-2-yl]phenyl]-3-[(1-methylpyrazol-3-yl)methyl]urea | 528 | 1.84 |
| 24ba | 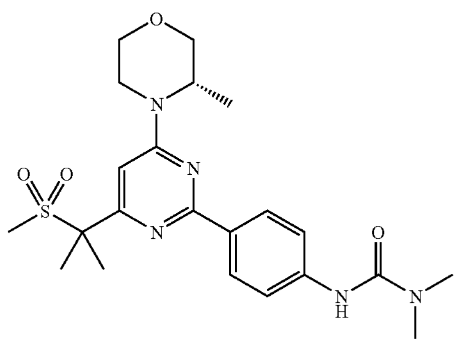 | 1,1-dimethyl-3-[4-[4-[(3S)-3-methylmorpholin-4-yl]-6-(2-methylsulfonylpropan-2-yl)pyrimidin-2-yl]phenyl]urea | 462 | 1.87 |
| 24bb | 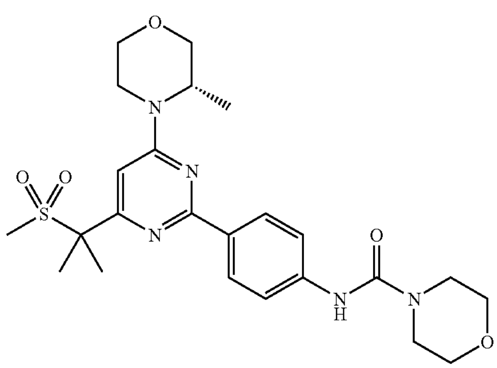 | N-[4-[4-[(3S)-3-methylmorpholin-4-yl]-6-(2-methylsulfonylpropan-2-yl)pyrimidin-2-yl]phenyl]morpholine-4-carboxamide | 504 | 1.84 |
| 24bc | 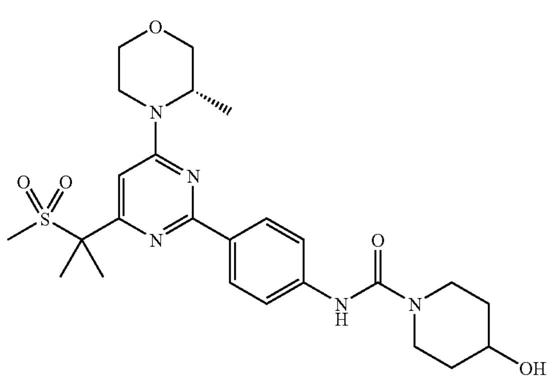 | 4-hydroxy-N-[4-[4-[(3S)-3-methylmorpholin-4-yl]-6-(2-methylsulfonylpropan-2-yl)pyrimidin-2-yl]phenyl]piperidine-1-carboxamide | 518 | 1.68 |

-continued

| Example | NAME | LCMS MH+ | Retention Time (min) |
|---|---|---|---|
| 24bd | 3-hydroxy-N-[4-[4-[(3S)-3-methylmorpholin-4-yl]-6-(2-methylsulfonylpropan-2-yl)pyrimidin-2-yl]phenyl]piperidine-1-carboxamide | 518 | 1.75 |
| 24be | N-[4-[4-[(3S)-3-methylmorpholin-4-yl]-6-(2-methylsulfonylpropan-2-yl)pyrimidin-2-yl]phenyl]azetidine-1-carboxamide | 474 | 1.91 |
| 24bf | 3-hydroxy-N-[4-[4-[(3S)-3-methylmorpholin-4-yl]-6-(2-methylsulfonylpropan-2-yl)pyrimidin-2-yl]phenyl]azetidine-1-carboxamide | 490 | 1.62 |
| 24bg | 1-cyclopropyl-1-methyl-3-[4-[4-[(3S)-3-methylmorpholin-4-yl]-6-(2-methylsulfonylpropan-2-yl)pyrimidin-2-yl]phenyl]urea | 488 | 2.18 |

| Example | Structure | NAME | LCMS MH+ | Retention Time (min) |
|---|---|---|---|---|
| 24bh | 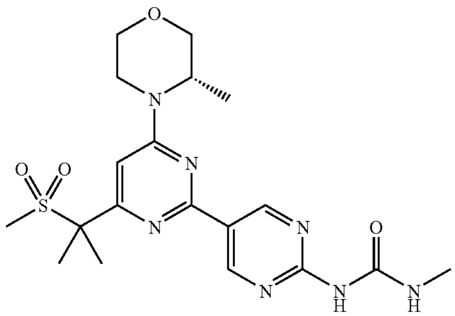 | 3-methyl-1-[5-[4-[(3S)-3-methylmorpholin-4-yl]-6-(2-methylsulfonylpropan-2-yl)pyrimidin-2-yl]pyrimidin-2-yl]urea | 450 | 1.70 |
| 24bi | 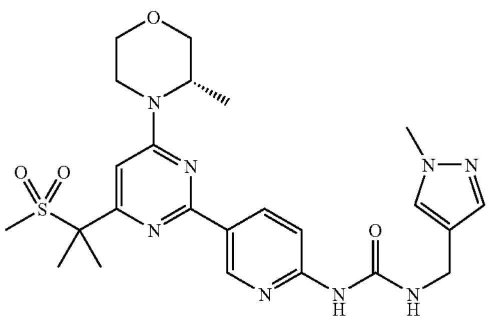 | 1-[5-[4-[(3S)-3-methylmorpholin-4-yl]-6-(2-methylsulfonylpropan-2-yl)pyrimidin-2-yl]pyridin-2-yl]-3-[(1-methylpyrazol-4-yl)methyl]urea | 529 | 1.75 |
| 24bj | 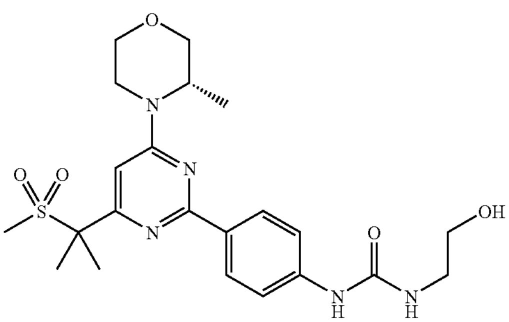 | 3-(2-hydroxyethyl)-1-[4-[4-[(3S)-3-methylmorpholin-4-yl]-6-(2-methylsulfonylpropan-2-yl)pyrimidin-2-yl]phenyl]urea | 478 | 1.61 |

Example 24a: $^1$H NMR (400.13 MHz, DMSO-d$_6$) δ 1.24 (3H, d), 3.21 (3H, s), 3.22-3.26 (1H, m), 3.47-3.53 (1H, m), 3.63-3.67 (1H, m), 3.78 (1H, d), 3.97-4.01 (1H, m), 4.17 (1H, d), 4.35 (2H, d), 4.48 (3H, s), 6.77 (1H, t), 6.78 (1H, s), 7.35-7.38 (1H, m), 7.52 (2H, d), 7.71-7.74 (1H, m), 8.22 (2H, d), 8.46-8.47 (1H, m), 8.55 (1H, d), 8.88 (1H, s)

Example 24b: $^1$H NMR (400.13 MHz, DMSO-d$_6$) δ 1.24 (3H, d), 2.67 (2H, t), 3.21 (3H, s), 3.24 (1H, d), 3.34-3.39 (2H, m), 3.47-3.53 (1H, m), 3.63-3.67 (1H, m), 3.78 (1H, d), 3.97-4.00 (1H, m), 4.17 (1H, d), 4.48 (3H, s), 6.23 (1H, t), 6.77 (1H, s), 6.83 (1H, s), 7.49-7.51 (2H, m), 7.55 (1H, d), 8.21 (2H, s), 8.79 (1H, s), 11.81 (1H, s)

Example 24c: $^1$H NMR (400.13 MHz, DMSO-d$_6$) δ 1.24 (3H, d), 2.48 (3H, s), 3.21 (3H, s), 3.22-3.26 (1H, m), 3.47-3.53 (1H, m), 3.63-3.67 (1H, m), 3.78 (1H, d), 3.97-4.00 (1H, m), 4.17 (1H, d), 4.45 (2H, d), 4.49 (3H, s), 6.78 (1H, s), 6.85 (1H, t), 7.50-7.53 (2H, m), 8.21-8.23 (2H, m), 8.49-8.51 (2H, m), 9.01 (1H, s)

Example 24d: $^1$H NMR (400.13 MHz, DMSO-d$_6$) δ 1.24 (3H, d), 3.21 (3H, s), 3.25 (1H, d), 3.47-3.53 (1H, m), 3.63-3.67 (1H, m), 3.78 (1H, d), 3.97-4.01 (1H, m), 4.17 (1H, d), 4.44 (2H, d), 4.49 (3H, s), 6.78 (1H, s), 6.84 (1H, t), 7.27-7.30 (1H, m), 7.37 (1H, d), 7.51-7.55 (2H, m), 7.76-7.80 (1H, m), 8.22 (2H, d), 8.53-8.55 (1H, m), 9.04 (1H, s)

Example 24e: $^1$H NMR (400.13 MHz, DMSO-d$_6$) δ 1.24 (3H, d), 3.21 (3H, s), 3.23-3.26 (1H, m), 3.50-3.53 (1H, m), 3.63-3.67 (1H, m), 3.78 (1H, d), 3.97 (1H, d), 4.00-4.19 (1H, m), 4.36 (2H, d), 4.48 (2H, s), 4.49 (1H, s), 6.78 (1H, s), 6.81 (1H, t), 7.30-7.31 (2H, m), 7.51-7.55 (2H, m), 8.21-8.24 (2H, m), 8.51-8.52 (2H, m), 8.96 (1H, s)

Example 24f: $^1$H NMR (400.13 MHz, DMSO-d$_6$) δ 1.24 (3H, d), 3.21 (3H, s), 3.24 (1H, d), 3.47-3.53 (1H, m), 3.63-3.67 (1H, m), 3.74 (3H, s), 3.78 (1H, d), 3.97-4.01 (1H, m), 4.17 (1H, d), 4.25 (2H, d), 4.48-4.48 (2H, m), 6.59 (1H, t), 6.78 (1H, s), 6.89-6.92 (2H, m), 7.23-7.26 (2H, m), 7.50-7.52 (2H, m), 8.20-8.23 (2H, m), 8.76 (1H, s)

Example 24g: $^1$H NMR (400.13 MHz, DMSO-d$_6$) δ 1.24 (3H, d), 3.24 (1H, d), 3.47-3.53 (1H, m), 3.63-3.67 (1H, m), 3.76 (1H, s), 3.79 (3H, s), 3.97-4.01 (1H, m), 4.13 (2H, d), 4.19 (1H, d), 4.48 (2H, s), 4.49 (1H, s), 6.42 (1H, t), 6.77 (1H, s), 7.35 (1H, s), 7.49-7.51 (2H, m), 7.59 (1H, s), 8.20-8.22 (2H, m), 8.69 (1H, s)

Example 24h: $^1$H NMR (400.13 MHz, DMSO-d$_6$) δ 1.24 (3H, d), 2.38 (3H, s), 3.25 (1H, d), 3.48-3.53 (1H, m), 3.63-

3.67 (1H, m), 3.78 (1H, d), 3.97-4.01 (1H, m), 4.17 (1H, d), 4.32 (2H, d), 4.48 (2H, s), 4.49 (1H, s), 6.16 (1H, d), 6.71 (1H, t), 6.78 (1H, s), 7.50-7.53 (2H, m), 8.21-8.24 (2H, m), 8.91 (1H, s)

Example 24i: $^1$H NMR (400.13 MHz, DMSO-$d_6$) δ 1.24 (3H, d), 2.88 (6H, s), 3.21 (3H, s), 3.25 (1H, d), 3.50-3.53 (1H, m), 3.63-3.67 (1H, m), 3.78 (1H, d), 3.97-4.01 (1H, m), 4.17 (1H, d), 4.25 (2H, d), 4.48 (1H, d), 4.49 (2H, s), 6.59 (2H, t), 6.63 (1H, d), 6.68 (1H, d), 6.78 (1H, s), 7.14 (1H, t), 7.51 (2H, d), 8.22 (2H, d), 8.77 (1H, s)

Example 24j: $^1$H NMR (400.13 MHz, DMSO-$d_6$) δ 1.24 (3H, d), 3.21 (3H, d), 3.23-3.26 (1H, m), 3.47-3.53 (1H, m), 3.63-3.67 (1H, m), 3.78 (1H, d), 3.97-4.01 (1H, m), 4.17 (1H, s), 4.49 (1H, d), 4.49 (2H, s), 4.54 (2H, d), 6.78 (1H, s), 6.80 (1H, t), 7.50-7.54 (2H, m), 7.79 (1H, d), 8.21-8.24 (2H, m), 8.87 (1H, s), 8.97 (1H, d)

Example 24k: $^1$H NMR (400.13 MHz, DMSO-$d_6$) δ 1.25 (3H, d), 2.69 (3H, d), 3.19 (1H, d), 3.25 (3H, s), 3.48 (1H, d), 3.63 (1H, d), 3.77 (1H, d), 3.96-3.99 (1H, m), 4.12 (1H, s), 4.44 (1H, m), 4.48 (2H, s), 6.49 (1H, d), 6.72 (1H, s), 6.78 (1H, s), 8.44 (1H, d), 9.30 (1H, s)

Example 24l: $^1$H NMR (400.13 MHz, DMSO-$d_6$) δ 1.08 (3H, t), 1.25 (3H, d), 3.12-3.19 (2H, m), 3.23 (3H, s), 3.24 (1H, m), 3.45-3.52 (1H, m), 3.62-3.65 (1H, m), 3.76 (1H, d), 3.95-3.99 (1H, m), 4.12 (1H, s), 4.45 (1H, m), 4.48 (2H, s), 6.46 (1H, d), 6.78 (1H, s), 6.89 (1H, s), 8.44 (1H, d), 9.22 (1H, s)

Example 24m: $^1$H NMR (400.13 MHz, DMSO-$d_6$) δ 0.39-0.43 (2H, m), 0.64-0.69 (2H, m), 1.25 (3H, d), 2.56-2.60 (1H, m), 3.22 (3H, s), 3.25 (1H, m), 3.45-3.52 (1H, m), 3.62-3.66 (1H, m), 3.77 (1H, d), 3.95-3.99 (1H, m), 4.12 (1H, s), 4.45 (1H, s), 4.48 (2H, s), 6.47 (1H, d), 6.78 (1H, s), 7.09 (1H, s), 8.44 (1H, d), 9.16 (1H, s)

Example 24n: $^1$H NMR (400.13 MHz, DMSO-$d_6$) δ 1.16 (3H, d), 1.18-1.24 (2H, m), 1.64 (6H, s), 1.77 (2H, d), 2.54 (3H, d), 2.98 (3H, s), 3.02 (2H, t), 3.08-3.12 (1H, m), 3.39-3.45 (1H, m), 3.55-3.60 (1H, m), 3.62-3.66 (1H, m), 3.69-3.74 (1H, m), 3.90-3.93 (1H, m), 3.98 (1H, d), 4.36 (1H, d), 4.42 (2H, d), 5.57 (1H, q), 5.82 (1H, s), 6.14 (1H, s)

Example 24o: $^1$H NMR (400.13 MHz, DMSO-$d_6$) δ 0.98 (3H, t), 1.15 (3H, t), 1.20-1.27 (2H, m), 1.64 (6H, s), 1.77 (2H, d), 2.98 (4H, s), 3.00-3.02 (2H, m), 3.05 (1H, d), 3.08-3.12 (1H, m), 3.39-3.45 (1H, m), 3.55-3.60 (1H, m), 3.64 (1H, d), 3.71 (1H, d), 3.90-3.93 (1H, m), 3.99 (1H, d), 4.36 (1H, d), 4.42 (2H, d), 5.64 (1H, t), 5.76 (1H, d), 6.14 (1H, s)

Example 24p: $^1$H NMR (400.13 MHz, DMSO-$d_6$) δ 0.29-0.33 (2H, m), 0.53-0.57 (2H, m), 1.16 (3H, d), 1.31 (2H, m), 1.64 (6H, s), 1.76 (2H, d), 2.09 (3H, s), 2.37-2.43 (1H, m), 2.75 (1H, s), 2.98 (3H, s), 2.96-3.01 (1H, m), 3.05-3.12 (1H, m), 3.39-3.45 (1H, m), 3.55-3.59 (1H, m), 3.66 (1H, t), 3.71 (1H, d), 3.90-3.93 (1H, m), 3.99 (1H, d), 4.36 (1H, d), 4.44 (2H, d), 5.72 (1H, d), 5.97 (1H, d), 6.14 (1H, s)

Example 24q: $^1$H NMR (400.13 MHz, DMSO-$d_6$) δ 1.16 (3H, d), 1.18-1.27 (2H, m), 1.64 (6H, s), 1.78 (2H, d), 2.98 (3H, s), 3.00 (1H, d), 3.03 (1H, d), 3.08-3.12 (1H, m), 3.39-3.45 (1H, m), 3.58 (1H, d), 3.65 (1H, t), 3.71 (1H, t), 3.78 (3H, s), 3.89-3.93 (1H, m), 4.00 (3H, d), 4.35 (1H, s), 4.41 (2H, d), 5.82 (1H, d), 5.89 (1H, t), 6.14 (1H, s), 7.28 (1H, s), 7.51 (1H, s)

Example 24r: $^1$H NMR (400.13 MHz, DMSO-$d_6$) δ 0.47-0.50 (2H, m), 0.66-0.71 (2H, m), 1.25 (3H, d), 2.61-2.67 (1H, m), 3.47-3.53 (1H, m), 3.63-3.67 (1H, m), 3.77 (1H, d), 3.96-4.00 (1H, m), 4.19 (1H, d), 4.49 (3H, d), 6.83 (1H, s), 7.54 (1H, d), 8.10 (1H, d), 8.48-8.51 (1H, m), 9.09 (1H, d), 9.32 (1H, s)

Example 24s: $^1$H NMR (400.13 MHz, DMSO-$d_6$) δ 1.24 (3H, d), 1.78 (6H, s), 3.04 (3H, s), 3.19-3.25 (1H, m), 3.47-3.54 (1H, m), 3.64-3.67 (1H, m), 3.78 (1H, d), 3.97-4.01 (1H, m), 4.25 (1H, d), 4.61 (1H, s), 6.77 (1H, s), 6.87 (1H, d), 7.58 (2H, d), 8.31 (2H, d), 8.75 (1H, d), 9.07 (1H, s), 9.61 (1H, s)

Example 24t: $^1$H NMR (400.13 MHz, DMSO-$d_6$) δ 1.24 (3H, d), 1.78 (6H, d), 2.38 (3H, d), 3.04 (3H, s), 3.19-3.25 (1H, m), 3.47-3.54 (1H, m), 3.64-3.67 (1H, m), 3.78 (1H, d), 3.97-4.01 (1H, m), 4.24 (1H, d), 4.61 (1H, s), 6.57 (1H, d), 6.77 (1H, s), 7.55-7.58 (2H, m), 8.31 (2H, d), 9.05 (1H, s), 9.46 (1H, s)

Example 24u: $^1$H NMR (400.13 MHz, DMSO-$d_6$) δ 1.24 (3H, d), 1.78 (6H, d), 3.04 (3H, s), 3.19-3.25 (1H, m), 3.47-3.53 (1H, m), 3.64-3.67 (1H, m), 3.78 (1H, d), 3.83 (3H, s), 3.97-4.00 (1H, m), 4.24 (1H, d), 4.61 (1H, s), 6.76 (1H, s), 6.80 (1H, d), 7.57 (2H, d), 7.83-7.86 (1H, m), 8.21 (1H, d), 8.29 (2H, d), 8.62 (1H, s), 8.97 (1H, s)

Example 24v: $^1$H NMR (400.13 MHz, DMSO-$d_6$) δ 1.25 (3H, d), 1.79 (6H, d), 3.04 (3H, s), 3.19-3.26 (1H, m), 3.47-3.54 (1H, m), 3.64-3.67 (1H, m), 3.78 (1H, d), 3.97-4.00 (1H, m), 4.25 (1H, d), 4.63 (1H, s), 5.42 (1H, s), 5.90 (1H, d), 6.78 (1H, s), 7.84 (2H, d), 8.06 (1H, d), 8.34 (2H, d), 9.84 (1H, s)

Example 24w: $^1$H NMR (400.13 MHz, DMSO-$d_6$) δ 1.25 (3H, d), 1.78 (6H, d), 3.04 (3H, s), 3.20-3.25 (1H, m), 3.47-3.54 (1H, m), 3.64-3.67 (1H, m), 3.78 (1H, d), 3.97-4.01 (1H, m), 4.24 (1H, d), 4.61 (1H, s), 6.76 (1H, s), 6.99 (1H, t), 7.30 (2H, d), 7.47 (2H, d), 7.57 (2H, d), 8.30 (2H, d), 8.71 (1H, s), 8.91 (1H, s)

Example 24x: $^1$H NMR (400.13 MHz, DMSO-$d_6$) δ 1.25 (3H, d), 1.78 (6H, d), 3.04 (3H, s), 3.20-3.25 (1H, m), 3.27 (3H, s), 3.47-3.54 (1H, m), 3.64-3.67 (1H, m), 3.78 (1H, d), 3.97-4.01 (1H, m), 4.24 (1H, d), 4.61 (1H, s), 6.76 (1H, s), 6.99 (1H, t), 7.30 (2H, d), 7.47 (2H, d), 7.57 (2H, d), 8.30 (2H, d), 8.71 (1H, s), 8.91 (1H, s)

Example 24y: $^1$H NMR (400.13 MHz, DMSO-$d_6$) δ 1.25 (3H, d), 1.78 (6H, d), 3.04 (3H, s), 3.19-3.26 (1H, m), 3.48-3.54 (1H, m), 3.64-3.68 (1H, m), 3.78 (1H, d), 3.97-4.01 (1H, m), 4.25 (1H, d), 4.62 (1H, s), 6.77 (1H, s), 7.61 (2H, d), 7.71-7.76 (1H, m), 7.78-7.82 (1H, m), 8.29 (2H, d), 8.32 (1H, d), 9.38 (1H, s), 9.87 (1H, s)

Example 24z: $^1$H NMR (400.13 MHz, DMSO-$d_6$) δ 1.24 (3H, d), 1.77 (6H, s), 3.00 (3H, s), 3.02-3.23 (1H, m), 3.46-3.51 (1H, m), 3.64 (1H, d), 3.76 (1H, d), 3.80 (3H, s), 3.95-3.98 (1H, m), 4.28 (1H, m), 4.29 (2H, d), 4.63 (1H, s), 6.83 (1H, s), 7.39 (1H, s), 7.63 (1H, s), 9.25 (1H, t), 9.36 (2H, s), 10.09 (1H, s)

Example 24aa: $^1$H NMR (399.9 MHz, DMSO-$d_6$) δ 0.41-0.45 (2H, m), 0.63-0.68 (2H, m), 1.25 (3H, d), 2.53-2.59 (1H, m), 3.21 (3H, s), 3.25 (1H, m), 3.47-3.54 (1H, m), 3.64-3.68 (1H, m), 3.78 (1H, d), 3.97-4.01 (1H, m), 4.18 (1H, d), 4.49 (3H, s), 6.44 (1H, d), 6.78 (1H, s), 7.52 (2H, d), 8.22 (2H, d), 8.55 (1H, s)

Example 24ab: $^1$H NMR (399.9 MHz, DMSO-$d_6$) δ 1.25 (3H, d), 1.79 (6H, d), 2.66 (3H, d), 3.02 (3H, s), 3.20-3.27 (1H, m), 3.47-3.54 (1H, m), 3.64-3.67 (1H, m), 3.78 (1H, d), 3.97-4.01 (1H, m), 4.27 (1H, d), 4.63 (1H, s), 6.27 (1H, q), 6.86 (1H, s), 7.95-8.01 (2H, m), 8.14 (1H, s)

Example 24ac: $^1$H NMR (399.9 MHz, DMSO-$d_6$) δ 1.07 (3H, t), 1.25 (3H, d), 1.79 (6H, d), 3.01 (3H, s), 3.09-3.15 (2H, m), 3.20-3.27 (1H, m), 3.47-3.54 (1H, m), 3.64-3.67 (1H, m), 3.78 (1H, d), 3.97-4.01 (1H, m), 4.27 (1H, d), 4.63 (1H, s), 6.36 (1H, t), 6.85 (1H, s), 7.95-8.01 (2H, m), 8.05 (1H, s)

Example 24ad: $^1$H NMR (399.9 MHz, DMSO-$d_6$) δ 0.43-0.47 (2H, m), 0.63-0.67 (2H, m), 1.25 (3H, d), 1.79 (6H, d), 2.53-2.58 (1H, m), 3.02 (3H, s), 3.20-3.27 (1H, m), 3.47-3.54 (1H, m), 3.64-3.67 (1H, m), 3.78 (1H, d), 3.97-4.01 (1H, m), 4.27 (1H, d), 4.63 (1H, s), 6.66 (1H, d), 6.86 (1H, s), 7.97 (2H, d), 8.00 (1H, s)

Example 24ae: $^1$H NMR (399.9 MHz, DMSO-d$_6$) δ 1.25 (3H, d), 1.79 (6H, d), 3.02 (3H, s), 3.20-3.27 (1H, m), 3.47-3.54 (1H, m), 3.64-3.67 (1H, m), 3.78 (1H, d), 3.81 (3H, s), 3.97-4.01 (1H, m), 4.12 (2H, d), 4.27 (1H, d), 4.63 (1H, s), 6.63 (1H, t), 6.86 (1H, s), 7.35 (1H, d), 7.58 (1H, s), 7.97-8.01 (2H, m), 8.09 (1H, s)

Example 24af: $^1$H NMR (399.9 MHz, DMSO-d$_6$) δ 1.15 (3H, t), 1.25 (3H, d), 1.78 (6H, d), 3.02 (3H, s), 3.20-3.24 (1H, m), 3.27-3.29 (2H, m), 3.47-3.53 (1H, m), 3.63-3.67 (1H, m), 3.77 (1H, d), 3.96-4.00 (1H, m), 4.28 (1H, d), 4.64 (1H, s), 6.84 (1H, s), 9.06 (1H, t), 9.39 (2H, s), 10.01 (1H, s)

Example 24ag: $^1$H NMR (399.9 MHz, DMSO-d$_6$) δ 0.54-0.57 (2H, m), 0.70-0.74 (2H, m), 1.25 (3H, d), 1.78 (3H, s), 1.78 (3H, s), 2.68-2.73 (1H, m), 3.02 (3H, s), 3.19-3.27 (1H, m), 3.46-3.53 (1H, m), 3.63-3.66 (1H, m), 3.77 (1H, d), 3.96-4.00 (1H, m), 4.28 (1H, d), 4.63 (1H, s), 6.84 (1H, s), 9.13 (1H, d), 9.38 (2H, s), 10.07 (1H, s)

Example 24ah: $^1$H NMR (399.9 MHz, DMSO-d$_6$) δ 1.24 (3H, d), 1.78 (3H, s), 1.78 (3H, s), 2.76 (3H, d), 3.03 (3H, s), 3.20-3.26 (1H, m), 3.47-3.54 (1H, m), 3.63-3.67 (1H, m), 3.77 (1H, d), 3.96-4.00 (1H, m), 4.25 (1H, d), 4.62 (1H, s), 6.80 (1H, s), 7.42-7.45 (1H, m), 8.15 (1H, d), 8.52-8.55 (1H, m), 9.14 (1H, d), 9.48 (1H, s)

Example 24ai: $^1$H NMR (399.9 MHz, DMSO-d$_6$) δ 1.12 (3H, t), 1.24 (3H, d), 1.78 (3H, s), 1.78 (3H, s), 3.02 (3H, s), 3.19-3.23 (2H, m), 3.24-3.26 (1H, m), 3.47-3.54 (1H, m), 3.63-3.67 (1H, m), 3.77 (1H, d), 3.96-4.00 (1H, m), 4.25 (1H, d), 4.61 (1H, s), 6.80 (1H, s), 7.46-7.49 (1H, m), 8.17 (1H, t), 8.52-8.55 (1H, m), 9.14 (1H, d), 9.40 (1H, s)

Example 24aj: $^1$H NMR (399.9 MHz, DMSO-d$_6$) δ 0.47-0.51 (2H, m), 0.67-0.71 (2H, m), 1.24 (3H, d), 1.78 (3H, s), 1.78 (3H, s), 2.61-2.67 (1H, m), 3.02 (3H, s), 3.19-3.26 (1H, m), 3.47-3.53 (1H, m), 3.63-3.67 (1H, m), 3.77 (1H, d), 3.96-4.00 (1H, m), 4.26 (1H, d), 4.62 (1H, s), 6.80 (1H, s), 7.53 (1H, d), 8.16 (1H, s), 8.53-8.56 (1H, m), 9.13 (1H, d), 9.33 (1H, s)

Example 24ak: $^1$H NMR (399.9 MHz, DMSO-d$_6$) δ 0.90 (3H, t), 1.24 (3H, d), 1.42-1.49 (2H, m), 1.78 (6H, d), 3.04 (3H, s), 3.18-3.25 (1H, m), 3.47-3.54 (1H, m), 3.63-3.67 (1H, m), 3.78 (1H, d), 3.97-4.00 (1H, m), 4.24 (1H, d), 4.61 (1H, d), 6.21 (1H, t), 6.74 (1H, s), 7.49-7.52 (2H, m), 8.23-8.25 (2H, m), 8.66 (1H, s))

Example 24al: $^1$H NMR (399.9 MHz, DMSO-d$_6$) δ 1.12 (6H, d), 1.24 (3H, d), 1.77 (3H, s), 1.78 (3H, s), 3.04 (3H, s), 3.21-3.24 (1H, m), 3.48-3.53 (1H, m), 3.63-3.67 (1H, m), 3.76-3.81 (2H, m), 3.97-4.00 (1H, m), 4.24 (1H, d), 4.60 (1H, d), 6.07 (1H, d), 6.74 (1H, s), 7.47-7.51 (2H, m), 8.23 (2H, d), 8.55 (1H, s)

Example 24am: $^1$H NMR (399.9 MHz, DMSO-d$_6$) δ 1.24 (3H, d), 1.59-1.66 (2H, m), 1.78 (6H, d), 1.84-1.89 (2H, m), 2.19-2.25 (2H, m), 3.04 (3H, s), 3.21-3.25 (1H, m), 3.48-3.53 (1H, m), 3.63-3.67 (1H, m), 3.78 (1H, d), 3.97-4.00 (1H, m), 4.15 (1H, q), 4.23 (1H, d), 4.60 (1H, d), 6.47 (1H, d), 6.74 (1H, s), 7.49 (2H, d), 8.24 (2H, d), 8.58 (1H, s)

Example 24an: $^1$H NMR (399.9 MHz, DMSO-d$_6$) δ 1.24 (3H, d), 1.25-1.25 (5H, m), 1.78 (6H, s), 3.04 (3H, s), 3.19-3.24 (1H, m), 3.40 (2H, d), 3.50 (1H, m), 3.63-3.67 (1H, m), 3.78 (1H, d), 3.97-4.01 (1H, m), 4.24 (1H, d), 4.59 (1H, s), 4.96 (1H, t), 6.01 (1H, s), 6.74 (1H, s), 7.46 (2H, d), 8.23 (2H, d), 8.74 (1H, s)

Example 24ao: $^1$H NMR (399.9 MHz, DMSO-d$_6$) δ 1.24 (3H, d), 1.78 (6H, d), 3.04 (3H, s), 3.19-3.25 (1H, m), 3.47-3.54 (1H, m), 3.63-3.67 (1H, m), 3.78 (1H, d), 3.97-4.00 (1H, m), 4.24 (1H, d), 4.36 (2H, d), 4.60 (1H, d), 6.75 (1H, s), 6.78 (1H, t), 7.36-7.39 (1H, m), 7.53 (2H, d), 7.72-7.75 (1H, m), 8.25 (2H, d), 8.46-8.48 (1H, m), 8.55 (1H, d), 8.88 (1H, s)

Example 24ap: $^1$H NMR (399.9 MHz, DMSO-d$_6$) δ 1.09 (3H, d), 1.24 (3H, d), 1.77 (3H, s), 1.78 (3H, s), 3.04 (3H, s), 3.19-3.25 (1H, m), 3.34-3.42 (2H, m), 3.47-3.54 (1H, m), 3.65 (1H, d), 3.70-3.74 (1H, m), 3.78 (1H, d), 3.97-4.00 (1H, m), 4.24 (1H, d), 4.60 (1H, s), 4.79 (1H, t), 6.10 (1H, d), 6.74 (1H, s), 7.49 (2H, d), 8.24 (2H, d), 8.73 (1H, s)

Example 24aq: $^1$H NMR (399.9 MHz, DMSO-d$_6$) δ 0.18-0.22 (2H, m), 0.42-0.47 (2H, m), 0.94-0.98 (1H, m), 1.24 (3H, d), 1.77 (3H, s), 1.78 (3H, s), 3.00 (2H, t), 3.04 (3H, s), 3.18-3.25 (1H, m), 3.47-3.54 (1H, m), 3.63-3.67 (1H, m), 3.78 (1H, d), 3.97-4.00 (1H, m), 4.24 (1H, d), 4.60 (1H, s), 6.27 (1H, t), 6.74 (1H, s), 7.50 (2H, d), 8.24 (2H, d), 8.70 (1H, s)

Example 24ar: $^1$H NMR (400.13 MHz, DMSO-d$_6$) δ 1.23 (3H, d), 1.76 (3H, s), 1.77 (3H, s), 3.04 (3H, s), 3.20-3.24 (1H, m), 3.46-3.52 (1H, m), 3.62-3.66 (1H, m), 3.77 (1H, d), 3.96-4.00 (1H, m), 4.24 (1H, d), 4.36 (2H, d), 4.60 (1H, s), 6.74 (1H, s), 6.83 (1H, t), 7.30-7.31 (2H, m), 7.51-7.55 (2H, m), 8.23-8.26 (2H, m), 8.51-8.52 (2H, m), 9.01 (1H, s)

Example 24as: $^1$H NMR (400.13 MHz, DMSO-d$_6$) δ 1.23 (3H, d), 1.56-1.62 (2H, m), 1.76 (3H, s), 1.77 (3H, s), 3.04 (3H, s), 3.14-3.19 (2H, m), 3.20-3.24 (1H, m), 3.44-3.47 (2H, m), 3.49-3.52 (1H, m), 3.62-3.66 (1H, m), 3.77 (1H, d), 3.96-4.00 (1H, m), 4.22 (1H, s), 4.52 (1H, t), 4.59 (1H, s), 6.22 (1H, t), 6.74 (1H, s), 7.48-7.51 (2H, m), 8.23 (2H, d), 8.75 (1H, s)

Example 24at: $^1$H NMR (400.13 MHz, DMSO-d$_6$) δ 0.88 (6H, d), 1.22 (3H, t), 1.66-1.73 (1H, m), 1.74-1.76 (3H, m), 1.77 (3H, s), 2.94 (2H, t), 3.04 (3H, s), 3.20-3.24 (1H, m), 3.46-3.53 (1H, m), 3.62-3.66 (1H, m), 3.77 (1H, d), 3.96-4.00 (1H, m), 4.22 (1H, s), 4.60 (1H, s), 6.26 (1H, t), 6.74 (1H, s), 7.48-7.51 (2H, m), 8.23 (2H, d), 8.68 (1H, s)

Example 24au: $^1$H NMR (400.13 MHz, DMSO-d$_6$) δ 1.23 (3H, d), 1.76 (3H, s), 1.77 (3H, s), 3.04 (3H, s), 3.17-3.24 (1H, m), 3.46-3.53 (1H, m), 3.62-3.66 (1H, m), 3.77 (1H, d), 3.96-4.00 (1H, m), 4.24 (1H, d), 4.32 (2H, d), 4.60 (1H, s), 6.64 (1H, t), 6.74 (1H, s), 6.83 (1H, s), 7.04 (1H, s), 7.50-7.53 (2H, m), 8.22-8.26 (2H, m), 8.96 (1H, s), 11.87 (1H, s)

Example 24av: $^1$H NMR (400.13 MHz, DMSO-d$_6$) δ 1.23 (3H, d), 1.76 (3H, s), 1.77 (3H, s), 3.04 (3H, s), 3.17-3.24 (1H, m), 3.46-3.53 (1H, m), 3.62-3.66 (1H, m), 3.76 (1H, s), 3.79 (3H, s), 3.96-4.00 (1H, m), 4.12 (2H, d), 4.23 (1H, d), 4.60 (1H, s), 6.44 (1H, t), 6.74 (1H, s), 7.35 (1H, s), 7.50 (2H, d), 7.60 (1H, s), 8.24 (2H, d), 8.74 (1H, s)

Example 24aw: $^1$H NMR (400.13 MHz, DMSO-d$_6$) δ 1.23 (3H, d), 1.76 (3H, s), 1.77 (3H, s), 2.38 (3H, d), 3.04 (3H, s), 3.17-3.24 (1H, m), 3.46-3.53 (1H, m), 3.62-3.66 (1H, m), 3.77 (1H, d), 3.96-4.00 (1H, m), 4.24 (1H, d), 4.32 (2H, d), 4.60 (1H, s), 6.16 (1H, t), 6.71 (1H, s), 6.74 (1H, s), 7.52 (2H, d), 8.25 (2H, d), 8.96 (1H, s)

Example 24ax: ¹H NMR (400.13 MHz, DMSO-d₆) δ 1.22 (3H, d), 1.44 (3H, d), 1.76 (3H, s), 1.76 (3H, s), 3.03 (3H, s), 3.19-3.24 (1H, m), 3.45-3.52 (1H, m), 3.62-3.65 (1H, m), 3.77 (1H, d), 3.95-3.99 (1H, m), 4.23 (1H, d), 4.59 (1H, s), 4.88 (1H, t), 6.74 (1H, s), 6.81 (1H, d), 7.36-7.39 (1H, m), 7.48 (2H, d), 7.75-7.78 (1H, m), 8.23 (2H, d), 8.45-8.47 (1H, m), 8.59 (1H, d), 8.71 (1H, s)

Example 24ay: ¹H NMR (400.13 MHz, DMSO-d₆) δ 1.23 (3H, d), 1.76 (3H, s), 1.77 (3H, s), 3.04 (3H, s), 3.17-3.24 (1H, m), 3.46-3.53 (1H, m), 3.62-3.66 (1H, m), 3.77 (1H, d), 3.96-4.00 (1H, m), 4.22-4.33 (1H, m), 4.28 (2H, d), 4.60 (1H, s), 6.18 (1H, s), 6.52 (1H, s), 6.74 (1H, s), 7.51 (2H, d), 7.67 (1H, s), 8.25 (2H, d), 8.84 (1H, s), 12.64 (1H, s)

Example 24az: ¹H NMR (400.13 MHz, DMSO-d₆) δ 1.24-1.76 (5H, m), 1.77 (3H, s), 3.20 (1H, d), 3.47-3.53 (1H, m), 3.62-3.66 (1H, m), 3.76-3.80 (4H, m), 3.96-4.00 (1H, m), 4.23 (2H, d), 4.25 (1H, s), 4.60 (1H, s), 6.14 (1H, d), 6.52 (1H, t), 6.74 (1H, s), 7.51 (2H, d), 7.61 (1H, d), 8.24 (2H, d), 8.84 (1H, s)

Example 24ba: ¹H NMR (400.13 MHz, DMSO-d₆) δ 1.23 (3H, d), 1.77 (3H, s), 1.77 (3H, s), 2.95 (6H, s), 3.04 (3H, s), 3.20-3.24 (1H, m), 3.49 (1H, d), 3.62-3.66 (1H, m), 3.77 (1H, d), 3.96-4.00 (1H, m), 4.23 (1H, s), 4.60 (1H, s), 6.75 (1H, s), 7.59 (2H, d), 8.23 (2H, d), 8.52 (1H, s)

Example 24bb: ¹H NMR (400.13 MHz, DMSO-d₆) δ 1.23 (3H, d), 1.77 (3H, s), 1.77 (3H, s), 3.04 (3H, s), 3.17-3.24 (1H, m), 3.45 (4H, t), 3.49-3.52 (1H, m), 3.61-3.63 (4H, m), 3.65 (1H, s), 3.77 (1H, d), 3.96-4.00 (1H, m), 4.25 (1H, d), 4.60 (1H, s), 6.75 (1H, s), 7.59 (2H, d), 8.25 (2H, d), 8.77 (1H, s)

Example 24bc: ¹H NMR (400.13 MHz, DMSO-d₆) δ 1.23 (3H, d), 1.29-1.38 (2H, m), 1.75-1.77 (2H, m), 1.77 (3H, s), 1.77 (3H, s), 3.04 (4H, s), 3.07-3.11 (2H, m), 3.16-3.24 (1H, m), 3.46-3.53 (1H, m), 3.62-3.66 (1H, m), 3.67-3.70 (1H, m), 3.77 (1H, d), 3.85 (2H, q), 3.96-4.00 (1H, m), 4.24 (1H, d), 4.60 (1H, s), 4.74 (1H, d), 6.74 (1H, s), 7.58 (2H, d), 8.23 (2H, d), 8.72 (1H, s)

Example 24bd: ¹H NMR (400.13 MHz, DMSO-d₆) δ 1.23 (3H, d), 1.33-1.41 (2H, m), 1.69-1.73 (1H, m), 1.77 (3H, s), 1.77 (3H, s), 1.85-1.88 (1H, m), 2.74-2.79 (1H, m), 2.91-2.97 (1H, m), 3.04 (3H, s), 3.17-3.24 (1H, m), 3.45-3.53 (2H, m), 3.62-3.66 (1H, m), 3.76 (1H, s), 3.79 (1H, t), 3.93-4.00 (2H, m), 4.24 (1H, d), 4.60 (1H, s), 4.88 (1H, d), 6.74 (1H, s), 7.57-7.59 (2H, m), 8.21-8.24 (2H, m), 8.69 (1H, s)

Example 24be: ¹H NMR (400.13 MHz, DMSO-d₆) δ 1.22 (3H, t), 1.76 (3H, s), 1.77 (3H, s), 2.15-2.23 (2H, m), 3.04 (3H, s), 3.18-3.24 (1H, m), 3.46-3.52 (1H, m), 3.62-3.66 (1H, m), 3.77 (1H, d), 3.98 (5H, t), 4.22 (1H, s), 4.60 (1H, s), 6.74 (1H, s), 7.62 (2H, d), 8.22-8.25 (2H, m), 8.59 (1H, s)

Example 24bf: ¹H NMR (400.13 MHz, DMSO-d₆) δ 1.23 (3H, d), 1.76 (3H, s), 1.77 (3H, s), 3.04 (3H, s), 3.16-3.24 (1H, m), 3.46-3.53 (1H, m), 3.62-3.66 (1H, m), 3.71-3.75 (2H, m), 3.77 (1H, d), 3.96-4.00 (1H, m), 4.14-4.18 (2H, m), 4.24 (1H, d), 4.41-4.46 (1H, m), 4.60 (1H, s), 5.66 (1H, d), 6.74 (1H, s), 7.62 (2H, d), 8.22-8.25 (2H, m), 8.64 (1H, s)

Example 24bg: ¹H NMR (400.13 MHz, DMSO-d₆) δ 0.68-0.72 (2H, m), 0.90 (2H, d), 1.23 (3H, d), 1.77 (3H, s), 1.78 (3H, s), 2.70-2.74 (1H, m), 2.87 (1H, d), 3.04 (3H, s), 3.17-3.24 (1H, m), 3.46-3.53 (1H, m), 3.63-3.66 (1H, m), 3.77 (1H, d), 3.96-4.00 (1H, m), 4.25 (1H, d), 4.59 (1H, s), 6.75 (1H, s), 7.63-7.66 (2H, m), 8.24 (2H, d), 8.43 (1H, s)

Example 24bh: ¹H NMR (400.13 MHz, DMSO-d6) δ 1.23 (3H, d), 1.77 (3H, s), 1.77 (3H, s), 2.80 (3H, d), 3.02 (3H, s), 3.18-3.26 (1H, m), 3.46-3.52 (1H, m), 3.62-3.65 (1H, m), 3.77 (1H, d), 3.95-3.99 (1H, m), 4.27 (1H, d), 4.63 (1H, s), 6.84 (1H, s), 8.98 (1H, d), 9.37 (2H, s), 10.11 (1H, s)

Example 24bi: ¹H NMR (400.13 MHz, DMSO-d6) δ 1.24 (3H, d), 1.78 (6H, d), 3.02 (3H, s), 3.18-3.26 (1H, m), 3.46-3.53 (1H, m), 3.63-3.66 (1H, m), 3.77 (1H, d), 3.80 (3H, s), 3.96-4.00 (1H, m), 4.24 (2H, d), 4.27 (1H, m), 4.61 (1H, s), 6.79 (1H, s), 7.38 (1H, s), 7.49-7.52 (1H, m), 7.62 (1H, s), 8.36 (1H, s), 8.53-8.56 (1H, m), 9.12 (1H, d), 9.45 (1H, s).

Example 24bj: ¹H NMR (400.13 MHz, DMSO-d6) δ 1.23 (3H, d), 1.77 (6H, d), 3.03 (3H, s), 3.17 (2H, q), 3.23 (1H, d), 3.46 (2H, q), 3.49-3.53 (1H, m), 3.63-3.66 (1H, m), 3.77 (1H, d), 3.96-4.00 (1H, m), 4.23 (1H, d), 4.60 (1H, d), 4.73 (1H, t), 6.25 (1H, t), 6.74 (1H, s), 7.50 (2H, d), 8.24 (2H, d), 8.81 (1H, s)

Test (a): Example (24) 0.34 μM; Example (24a) 0.082 μM; Example (24b) 0.038 μM; Example (24c) 0.56 μM; Example (24d) 4.4 μM; Example (24e) 0.81 μM; Example (24f) 4.5 μM; Example (24g) 0.31 μM; Example (24h) 4.4 μM; Example (24i) 0.33 μM; Example (24j) 0.22 μM; Example (24k) 0.18 μM; Example (24l) 0.84 μM; Example (24m) 0.65 μM; Example (24n) 3.2 μM; Example (24o) 3.4 μM; Example (24p) 0.89 μM; Example (24q) 5.8 μM; Example (24r) 0.34 μM; Example (24s) 0.0047 μM; Example (24t) 0.012 μM; Example (24u) 0.12 μM; Example (24v) 0.055 μM; Example (24w) 0.034 μM; Example (24x) 0.1 μM; Example (24y) 2.2 μM; Example (24z) 0.37 μM; Example (24aa) 0.11 μM; Example (24ab) 0.042 μM; Example (24ac) 0.048 μM; Example (24ad) 0.51 μM; Example (24ae) 0.24 μM; Example (24bh) 0.012 μM; Example (24bi) 0.43 μM; Example (24bj) δ 0.051 μM.

Test (c): Example (24af) 1.4 μM; Example (24ag) 0.32 μM; Example (24ah) 0.51 μM; Example (24ai) 0.26 μM; Example (24aj) 0.45 μM; Example (24ak) 0.21 μM; Example (24al) 0.038 μM; Example (24 μm) 0.21 μM; Example (24an) 1.8 μM; Example (24ao) 0.24 μM; Example (24ap) 0.077 μM; Example (24aq) 2 μM; Example (24ar) 0.049 μM; Example (24 as) 0.22 μM; Example (24 at) 0.089 μM; Example (24au) 2.4 μM; Example (24av) 4.9 μM; Example (24aw) 3.4 μM; Example (24ax) 0.64 μM; Example (24ay) 7.9 μM; Example (24az) 5.6 μM; Example (24ba) 5.1 μM; Example (24bb) 7.8 μM; Example (24bc) 0.69 μM; Example (24bd) 3.2 μM; Example (24be) 4.9 μM; Example (24bf) 6.7 μM; Example (24bg) 2.4 μM.

The preparation of phenyl N-[4-[4-[(3S)-3-methylmorpholin-4-yl]-6-(methylsulfonylmethyl)pyrimidin-2-yl]phenyl]carbamate and phenyl (4-{4-[1-methyl-1-(methylsulfonyl)ethyl]-6-[(3S)-3-methylmorpholin-4-yl]pyrimidin-2-yl}phenyl)carbamate is described earlier.

The following carbamates were prepared from the appropriate amine or aniline in an analogous fashion to phenyl N-[1-[4-[(3S)-3-methylmorpholin-4-yl]-6-(methylsulfonylmethyl)pyrimidin-2-yl]-4-piperidyl]carbamate, described earlier.

| Structure | NAME | LCMS MH+ | Retention Time (min) | Notes |
|---|---|---|---|---|
| 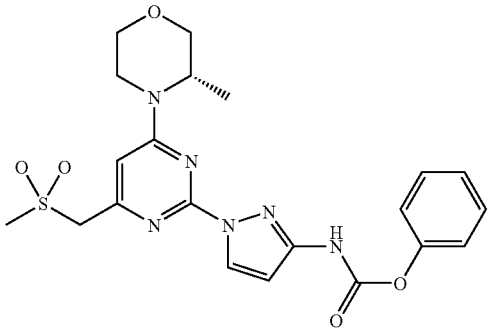 | phenyl N-[1-[4-[(3S)-3-methylmorpholin-4-yl]-6-(2-methylsulfonylmethyl)pyrimidin-2-yl]pyrazol-3-yl]carbamate | 495 | 2.09 | Purified by chromatography using 0-55% ethyl acetate in isohexane |
| 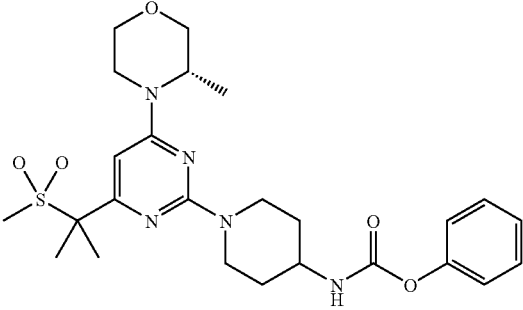 | phenyl N-[1-[4-[(3S)-3-methylmorpholin-4-yl]-6-(2-methylsulfonylpropan-2-yl)pyrimidin-2-yl]-4-piperidyl]carbamate | 518 | 2.34 | |
| 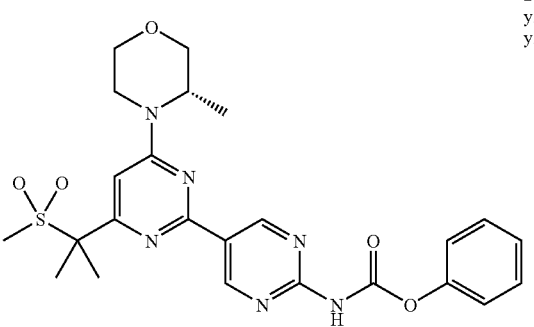 | phenyl N-[5-[4-[(3S)-3-methylmorpholin-4-yl]-6-(2-methylsulfonylpropan-2-yl)pyrimidin-2-yl]pyrimidin-2-yl]carbamate | 513 | 2.21 | Purified by chromatography using 0-3% methanol in DCM |

| Structure | NAME | LCMS MH+ | Retention Time (min) | Notes |
|---|---|---|---|---|
| 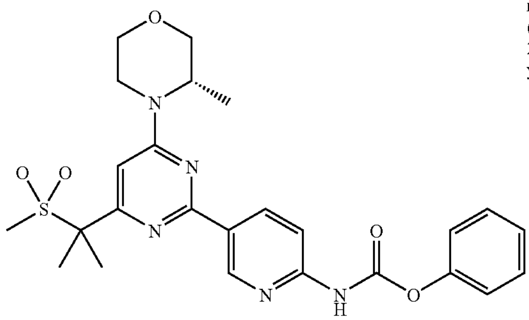 | phenyl N-[5-[4-[(3S)-3-methylmorpholin-4-yl]-6-(2-methylsulfonylpropan-2-yl)pyrimidin-2-yl]pyridin-2-yl]carbamate | 512 | 2.60 | Purified by chromatography using 0-3% methanol in DCM |
| 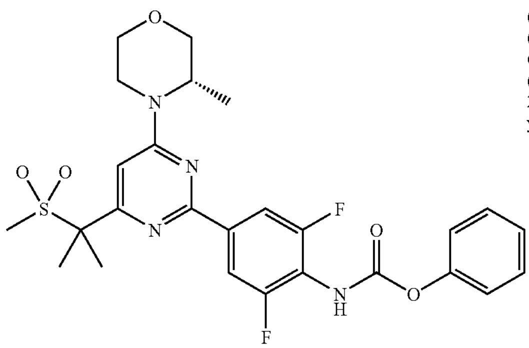 | (S)-phenyl 2,6-difluoro-4-(4-(3-methylmorpholino)-6-(2-(methylsulfonyl)propan-2-yl)pyrimidin-2-yl)phenylcarbamate | 547 | 2.67 | |

(S)-Phenyl 2,6-difluoro-4-(4-(3-methylmorpholino)-6-(2-(methylsulfonyl)propan-2-yl)pyrimidin-2-yl)phenylcarbamate: $^1$H NMR (400.13 MHz, DMSO-d6) δ 1.25 (3H, d), 1.79 (6H, d), 3.00 (3H, s), 3.20-3.27 (1H, m), 3.47-3.55 (1H, m), 3.58 (15H, s), 3.65 (1H, d), 3.75 (1H, d), 3.97-4.01 (1H, m), 4.28 (1H, d), 4.63 (1H, s), 6.88 (1H, s), 7.21 (2H, d), 7.27 (1H, t), 7.44 (2H, t), 8.08 (2H, d), 9.96 (1H, s)

The preparation of 1-[4-[(3S)-3-methylmorpholin-4-yl]-6-(methylsulfonylmethyl)pyrimidin-2-yl]pyrazol-3-amine is described below.

1-[4-[(3S)-3-Methylmorpholin-4-yl]-6-(methylsulfonylmethyl)pyrimidin-2-yl]pyrazol-3-amine

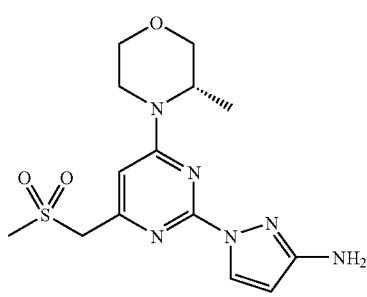

2-Chloro-4-[(3S)-3-methylmorpholin-4-yl]-6-(methylsulfonylmethyl)pyrimidine (1.00 g), 1H-pyrazol-3-amine (300 mg) and potassium carbonate (498 mg) were dissolved in butyronitrile (20 mL). The mixture was heated at reflux for 24 hours. The reaction was diluted with ethyl acetate (20 mL) and washed with water (20 mL). The water was extracted with ethyl acetate (20 mL). The combined organic extracts were dried over magnesium sulfate and evaporated. The crude product was purified by chromatography on silica, eluting with 0-5% methanol in DCM to give the desired material (635 mg).

NMR Spectrum: $^1$H NMR (400.13 MHz, DMSO-d$_6$) δ 1.23 (3H, d), 3.20 (3H, s), 3.24 (1H, m), 3.43-3.50 (1H, m), 3.60-3.64 (1H, m), 3.75 (1H, d), 3.94-3.98 (1H, m), 4.06-4.12 (1H, m), 4.43 (1H, s), 4.43 (2H, s), 5.25 (2H, s), 5.75 (1H, s), 5.80 (1H, d), 6.66 (1H, s), 8.26 (1H, d)

LCMS Spectrum: MH+ 490, Retention Time 1.58 min, Method Monitor Acid

1-[4-[(3S)-3-methylmorpholin-4-yl]-6-(2-methylsulfonylpropan-2-yl)pyrimidin-2-yl]piperidin-4-amine was prepared from (3S)-4-{2-Chloro-6-[1-methyl-1-(methylsulfonyl)ethyl]pyrimidin-4-yl}-3-methylmorpholine and tert-butyl N-(4-piperidyl)carbamate in an analogous two step procedure to 1-[4-[(3S)-3-methylmorpholin-4-yl]-6-(methylsulfonylmethyl)pyrimidin-2-yl]piperidin-4-amine.

| Structure | NAME | LCMS MH+ | Retention Time (min) |
|---|---|---|---|
| 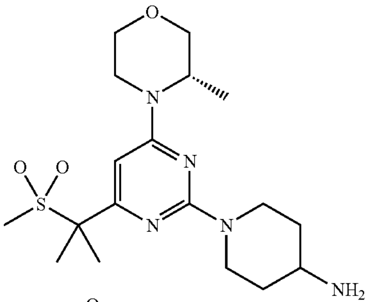 | 1-[4-[(3S)-3-methylmorpholin-4-yl]-6-(2-methylsulfonylpropan-2-yl)pyrimidin-2-yl]piperidin-4-amine | 398 | 0.94 |
| 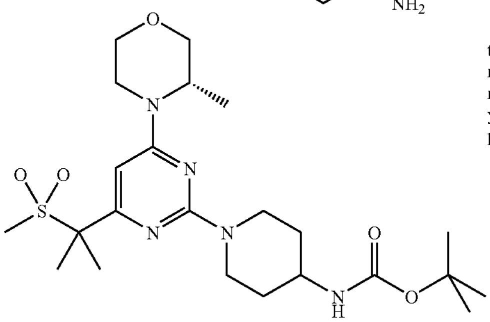 | tert-butyl N-[1-[4-[(3S)-3-methylmorpholin-4-yl]-6-(2-methylsulfonylpropan-2-yl)pyrimidin-2-yl]-4-piperidyl]carbamate | 498 | 2.43 |

1-[4-[(3S)-3-methylmorpholin-4-yl]-6-(2-methylsulfonylpropan-2-yl)pyrimidin-2-yl]piperidin-4-amine: $^1$H NMR (400.13 MHz, DMSO-d6) δ 1.27 (3H, d), 1.75 (6H, s), 1.83-1.87 (2H, m), 2.88 (1H, d), 2.91 (5H, s), 2.94 (1H, d), 3.17-3.25 (1H, m), 3.50-3.57 (1H, m), 3.68 (1H, d), 3.70 (2H, s), 3.75-3.77 (1H, m), 3.92 (1H, s), 3.95-3.99 (2H, m), 4.30 (1H, d), 4.61 (2H, d), 6.06 (1H, s)

tert-butyl N-[1-[4-[(3S)-3-methylmorpholin-4-yl]-6-(2-methylsulfonylpropan-2-yl)pyrimidin-2-yl]-4-piperidyl]carbamate: $^1$H NMR (400.13 MHz, DMSO-d6) δ 1.25 (5H, d), 1.27 (2H, d), 1.30-1.35 (2H, m), 1.45 (9H, s), 1.54 (6H, s), 1.98 (2H, d), 2.04 (4H, s), 2.90 (3H, s), 2.95-3.01 (2H, m), 3.17-3.24 (1H, m), 3.50-3.57 (1H, m), 3.66-3.70 (2H, m), 3.76 (1H, d), 3.95-3.99 (2H, m), 4.29 (1H, d), 4.56 (2H, d), 6.07 (1H, s)

The preparation of (3S)-4-{2-chloro-6-[1-methyl-1-(methylsulfonyl)ethyl]pyrimidin-4-yl}-3-methylmorpholine was described earlier.

5-[4-[(3S)-3-Methylmorpholin-4-yl]-6-(2-methylsulfonylpropan-2-yl)pyrimidin-2-yl]pyrimidin-2-amine and 5-[4-[(3S)-3-methylmorpholin-4-yl]-6-(2-methylsulfonylpropan-2-yl)pyrimidin-2-yl]pyridin-2-amine were prepared from (3S)-4-{2-chloro-6-[1-methyl-1-(methylsulfonyl)ethyl]pyrimidin-4-yl}-3-methylmorpholine in an analogous fashion to (4-{4-[1-Methyl-1-(methylsulfonyl)ethyl]-6-[(3S)-3-methylmorpholin-4-yl]pyrimidin-2-yl}phenyl)amine, described earlier.

| Structure | NAME | LCMS MH+ | Retention Time (min) |
|---|---|---|---|
| 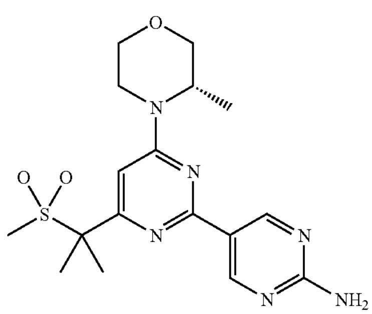 | 5-[4-[(3S)-3-methylmorpholin-4-yl]-6-(2-methylsulfonylpropan-2-yl)pyrimidin-2-yl]pyrimidin-2-amine | 393 | 1.57 |

| Structure | NAME | LCMS MH+ | Retention Time (min) |
|---|---|---|---|
| 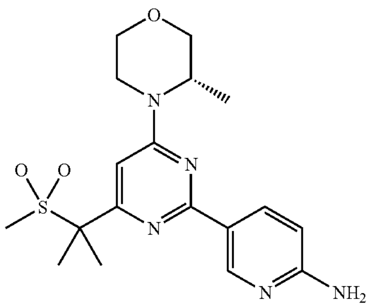 | 5-[4-[(3S)-3-methylmorpholin-4-yl]-6-(2-methylsulfonylpropan-2-yl)pyrimidin-2-yl]pyridin-2-amine | 392 | 1.16 |

5-[4-[(3S)-3-methylmorpholin-4-yl]-6-(2-methylsulfonylpropan-2-yl)pyrimidin-2-yl]pyrimidin-2-amine: $^1$H NMR (400.13 MHz, DMSO-d6) δ 1.23 (3H, d), 1.75-1.76 (6H, m), 3.00 (3H, s), 3.16-3.23 (1H, m), 3.45-3.52 (1H, m), 3.61-3.65 (1H, m), 3.76 (1H, d), 3.95-3.99 (1H, m), 4.22 (1H, d), 4.57 (1H, s), 6.74 (1H, s), 7.11 (2H, s), 9.09 (2H, s)

5-[4-[(3S)-3-methylmorpholin-4-yl]-6-(2-methylsulfonylpropan-2-yl)pyrimidin-2-yl]pyridin-2-amine: $^1$H NMR (400.13 MHz, CDCl$_3$) δ 1.33 (3H, d), 1.86 (6H, s), 2.93 (3H, s), 3.31-3.35 (1H, m), 3.56-3.62 (1H, m), 3.72-3.75 (1H, m), 3.82 (1H, d), 4.02-4.05 (1H, m), 4.12 (1H, d), 4.48-4.50 (1H, m), 4.83 (2H, s), 6.52-6.55 (1H, m), 6.59 (1H, s), 8.35-8.38 (1H, m), 9.08-9.09 (1H, m)

The preparation of 2,6-difluoro-4-[4-[(3S)-3-methylmorpholin-4-yl]-6-(2-methylsulfonylpropan-2-yl)pyrimidin-2-yl]aniline is described below.

2,6-Difluoro-4-[4-[(3S)-3-methylmorpholin-4-yl]-6-(2-methylsulfonylpropan-2-yl)pyrimidin-2-yl]aniline

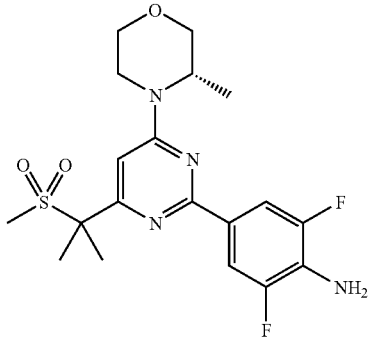

4-Bromo-2,6-difluoro-aniline (400 mg, 1.92 mmol), potassium acetate (566 mg, 5.77 mmol) and 4,4,5,5-tetramethyl-2-(4,4,5,5-tetramethyl-1,3,2-dioxaborolan-2-yl)-1,3,2-dioxaborolane (587 mg, 2.31 mmol) were dissolved in 1,4 dioxane (5 mL). The solution was degassed for 10 minutes then 1,1'-bis(diphenylphosphino)ferrocenedichloropalladium was added (95 mg, 0.12 mmol) and the reaction was stirred at 90° C. for 3 hours. (3S)-4-{2-Chloro-6-[1-methyl-1-(methylsulfonyl)ethyl]pyrimidin-4-yl}-3-methylmorpholine (450 mg, 1.35 mmol), ethanol (1 mL), 2M sodium carbonate (1 mL) and 1,1'-bis(diphenylphosphino)ferrocenedichloropalladium (95 mg, 0.12 mmol) were added and the heating was continued for 18 hours. The reaction was allowed to cool to RT then water (50 mL) added, followed by ethyl acetate (50 mL). The undissolved solid was removed by filtration. The phases were separated and the aqueous phase was extracted with a second portion of ethyl acetate (30 mL). The combined organics were dried over magnesium sulfate, filtered and evaporated to dryness. The crude product was dissolved in DCM (25 mL), filtered to remove the insoluble material and the filtrate purified by chromatography on silica, eluting with 0-35% ethyl acetate in isohexane, to give the desired material as an off-white solid (402 mg).

NMR Spectrum: $^1$H NMR (400.13 MHz, DMSO-d$_6$) δ 1.23 (3H, d), 1.76 (6H, d), 3.00 (3H, s), 3.17-3.24 (1H, m), 3.45-3.51 (1H, m), 3.62-3.65 (1H, m), 3.76 (1H, d), 3.95-3.99 (1H, m), 4.22 (1H, d), 4.57 (1H, s), 5.70 (2H, d), 6.73 (1H, s), 7.83-7.85 (2H, m)

LCMS Spectrum: MH+ 427, Retention Time 2.35 min, Method Monitor Acid

The preparation of phenyl N-[5-[4-[(3S)-3-methylmorpholin-4-yl]-6-(methylsulfonylmethyl)pyrimidin-2-yl]pyridin-2-yl]carbamate is described below.

Phenyl N-[5-[4-[(3S)-3-methylmorpholin-4-yl]-6-(methylsulfonylmethyl)pyrimidin-2-yl]pyridin-2-yl] carbamate

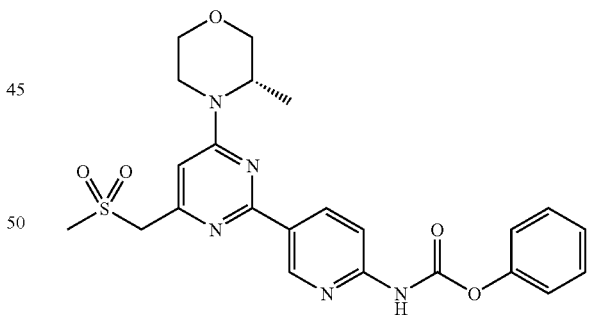

5-[4-[(3S)-3-Methylmorpholin-4-yl]-6-(methylsulfonylmethyl)pyrimidin-2-yl]pyridin-2-amine (770 mg, 2.12 mmol) was dissolved in dioxane (10 mL) and sodium bicarbonate (267 mg, 3.18 mmol) was added to give a thin yellow slurry. Phenyl chloroformate (0.267 mL, 2.12 mmol) was added dropwise over 10 minutes, controlling the exotherm using a water bath and the mixture was stirred at RT for 16 hours. Further sodium bicarbonate (267 mg, 3.18 mmol) and phenyl chloroformate (0.267 mL, 2.12 mmol) were added and the mixture was stirred at RT for 2 hours. Again phenyl chloroformate (0.267 mL, 2.12 mmol) was added and the mixture was stirred at RT for 1 hour then heated to 35° C. for 16 hours. The reaction was evaporated to dryness and the residue was partitioned between water (15 mL) and ethyl acetate (20 mL). The white solid was filtered off and washed with water (5 mL), DCM (5 mL) and methanol (5 mL). The solid was dried under vacuum at 40° C. for 5 hours to give the product as a white solid (117 mg).

LCMS Spectrum: MH+ 484, retention time 2.32 min, Method Monitor Acid

The preparation of 5-[4-[(3S)-3-methylmorpholin-4-yl]-6-(methylsulfonylmethyl)pyrimidin-2-yl]pyridin-2-amine was described earlier.

EXAMPLE 25

1-[1-[4-[(3S)-3-Methylmorpholin-4-yl]-6-(methylsulfonylmethyl)pyrimidin-2-yl]pyrazol-3-yl]-3-phenyl-urea

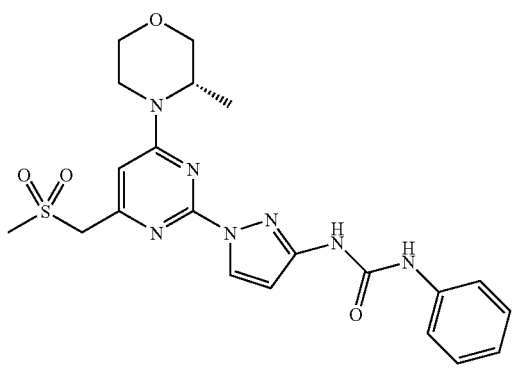

1-[4-[(3S)-3-methylmorpholin-4-yl]-6-(methylsulfonylmethyl)pyrimidin-2-yl]pyrazol-3-amine (90 mg, 0.26 mmol) was dissolved in dioxane (4 mL). Phenyl isocyanate (0.024 mL, 0.22 mmol) was added to the resultant solution. The mixture was heated at 80° C. for 2 hours.

The solid was filtered off and washed with diethyl ether (5 mL) to give the desired material as a white solid (66 mg).

NMR Spectrum: $^1$H NMR (400.13 MHz, DMSO-$d_6$) δ 1.26 (3H, d), 3.23 (3H, s), 3.40 (1H, m), 3.47-3.54 (1H, m), 3.63-3.67 (1H, m), 3.78 (1H, d), 3.98 (1H, d), 4.14 (1H, s), 4.47 (1H, m), 4.51 (2H, d), 6.60 (1H, d), 6.81 (1H, s), 7.01 (1H, t), 7.29-7.33 (2H, m), 7.47 (2H, d), 8.51 (1H, d), 9.18 (1H, s), 9.50 (1H, s)

LCMS Spectrum: MH+ 472, Retention Time 1.86 min, Method 5 Minute Acid

The following compounds were prepared in an analogous manner from 1-[4-[(3S)-3-methylmorpholin-4-yl]-6-(methylsulfonylmethyl)pyrimidin-2-yl]pyrazol-3-amine and the appropriate isocyanate.

| Example | Structure | NAME | LCMS MH+ | Retention Time (min) |
|---|---|---|---|---|
| 25a | 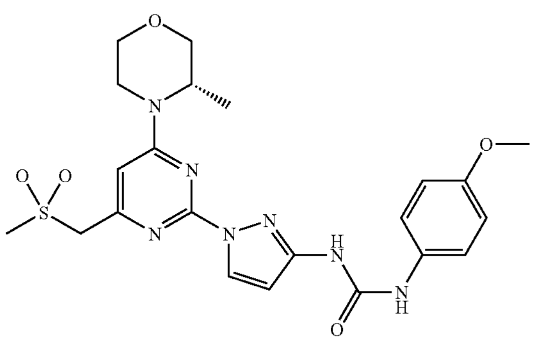 | 3-(4-methoxyphenyl)-1-[1-[4-[(3S)-3-methylmorpholin-4-yl]-6-(methylsulfonylmethyl)pyrimidin-2-yl]pyrazol-3-yl]urea | 502 | 1.98 |
| 25b | 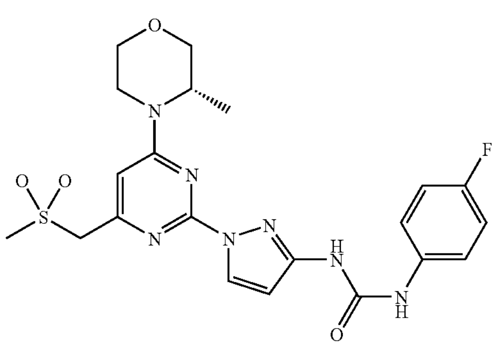 | 3-(4-fluorophenyl)-1-[1-[4-[(3S)-3-methylmorpholin-4-yl]-6-(methylsulfonylmethyl)pyrimidin-2-yl]pyrazol-3-yl]urea | 512 | 2.06 |

Example 25a: ¹H NMR (400.13 MHz, DMSO-d$_6$) δ 1.26 (3H, d), 3.47-3.53 (1H, m), 3.56 (1H, d), 3.63-3.67 (1H, m), 3.73 (3H, s), 3.78 (1H, d), 3.96-4.00 (1H, m), 4.14 (1H, s), 4.47 (1H, m), 4.50 (2H, s), 6.57 (1H, d), 6.81 (1H, s), 6.87-6.91 (2H, m), 7.35-7.39 (2H, m), 8.50 (1H, d), 9.04 (1H, s), 9.42 (1H, s)

Example 25b: ¹H NMR (400.13 MHz, DMSO-d$_6$) δ 1.26 (3H, d), 3.26 (1H, m), 3.46-3.53 (1H, m), 3.58 (3H, s), 3.63-3.67 (1H, m), 3.78 (1H, d), 3.96-4.00 (1H, m), 4.14 (1H, s), 4.46 (1H, m), 4.50 (2H, s), 6.59 (1H, d), 6.81 (1H, s), 7.13-7.18 (2H, m), 7.45-7.50 (2H, m), 8.51 (1H, d), 9.17 (1H, s), 9.51 (1H, s)

Test (a): Example (25) 1.9 μM; Example (25a) 4.4 μM; Example (25b) 4.4 μM.

EXAMPLE 26

N-Methyl-2-[[2-[4-(methylcarbamoylamino)phenyl]-6-[(3S)-3-methylmorpholin-4-yl]pyrimidin-4-yl]methylsulfonyl]acetamide

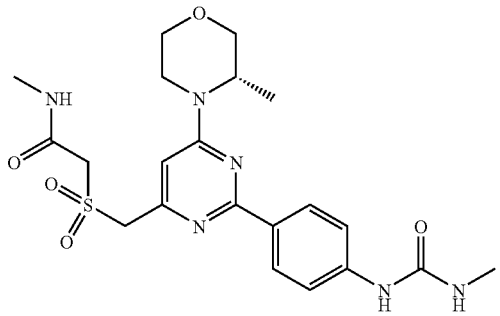

N-Methyl-2-[[2-[4-(methylcarbamoylamino)phenyl]-6-[(3S)-3-methylmorpholin-4-yl]pyrimidin-4-yl]methylsulfanyl]acetamide (0.35 mmol) was dissolved in 1,4-Dioxane (5 mL) and water (1 mL). m-CPBA (75%) (121 mg) followed immediately by sodium permanganate (140 mg) were added to the solution and the reaction stirred at RT for 1 h. Further m-CPBA (75%) (121 mg) followed immediately by sodium permanganate (140 mg) were added to the solution and stirred at RT for 1 h. Again further m-CPBA (75%) (121 mg) followed immediately by sodium permanganate (140 mg) were added and the reaction stirred at RT for 1 h. The reaction was loaded onto a SCX-3 (10 g) column, which was washed with methanol and the product eluted with 7N ammonia in methanol. The material was further purified by prep-HPLC (basic) to give the desired material (30 mg) as a white solid.

NMR Spectrum: ¹H NMR (400.13 MHz, DMSO-d$_6$) δ 1.23-1.25 (3H, m), 2.66-2.70 (3H, m), 2.68 (1H, d), 3.21-3.26 (1H, m), 3.46-3.53 (3H, m), 3.63-3.67 (1H, m), 3.78 (1H, d), 3.97-4.00 (1H, m), 4.17 (1H, d), 4.29 (2H, s), 4.47 (1H, s), 4.67 (2H, s), 6.07 (1H, q), 6.76 (1H, s), 7.48-7.52 (2H, m), 8.17-8.20 (2H, m), 8.31 (1H, t), 8.74 (1H, s)

Mass Spectrum; M+H⁺ 477.

The following compounds were prepared in an analogous fashion from the appropriate sulphides.

| Example | Structure | NAME | LCMS MH+ |
|---|---|---|---|
| 26a | 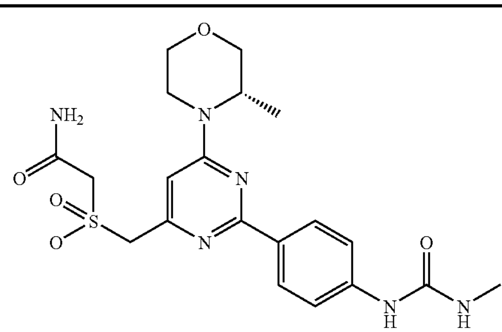 | 2-[[2-[4-(methylcarbamoylamino)phenyl]-6-[(3S)-3-methylmorpholin-4-yl]pyrimidin-4-yl]methylsulfonyl]acetamide | 463 |
| 26b | 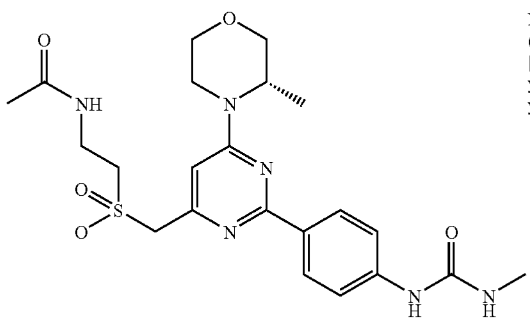 | N-[2-[[2-[4-(methylcarbamoylamino)phenyl]-6-[(3S)-3-methylmorpholin-4-yl]pyrimidin-4-yl]methylsulfonyl]ethyl]acetamide | 491 |

Example 26a: ¹H NMR (400.13 MHz, DMSO-d$_6$) δ 1.24 (3H, d), 2.66 (3H, d), 3.18-3.26 (1H, m), 3.47-3.53 (1H, m), 3.63-3.67 (1H, m), 3.77 (1H, d), 3.97-4.00 (1H, m), 4.17 (1H, d), 4.27 (2H, s), 4.48 (1H, s), 4.66 (2H, s), 6.07 (1H, q), 6.76 (1H, s), 7.48-7.52 (3H, m), 7.79 (1H, s), 8.17-8.21 (2H, m), 8.74 (1H, s)

Example 26b: ¹H NMR (400.13 MHz, DMSO-d$_6$) δ 1.24 (3H, d), 1.83 (3H, s), 2.66 (2H, s), 2.68 (2H, q), 3.21-3.26 (1H, m), 3.47-3.53 (2H, m), 3.52 (1H, s), 3.57 (2H, q), 3.63-3.67 (1H, m), 3.78 (1H, d), 3.97-4.01 (1H, m), 4.17 (1H, d), 4.51 (2H, s), 6.06 (1H, q), 6.77 (1H, s), 7.48-7.52 (2H, m), 8.14-8.21 (3H, m), 8.74 (1H, s)

Test (a): Example (26) 0.029 µM; Example (26a) 0.037 µM; Example (26b) 0.041 µM.

The preparation of N-methyl-2-[[2-[4-(methylcarbamoylamino)phenyl]-6-[(3S)-3-methylmorpholin-4-yl]pyrimidin-4-yl]methylsulfanyl]acetamide is described below.

N-Methyl-2-[[2-[4-(methylcarbamoylamino)phenyl]-6-[(3S)-3-methylmorpholin-4-yl]pyrimidin-4-yl]methylsulfanyl]acetamide

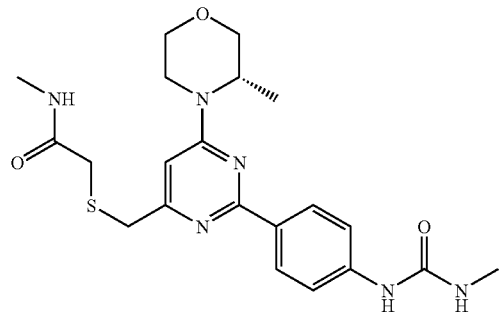

N-Methyl-2-sulfanyl-acetamide (0.61 mmol) was dissolved in Acetonitrile (4 mL). DBU (0.050 mL) was then added to the solution and stirred at RT for 5 min. A solution of 3-methyl-1-[4-[4-[(3S)-3-methylmorpholin-4-yl]-6-(methylsulfonyloxymethyl)pyrimidin-2-yl]phenyl]urea (151 mg) in acetonitrile (2 mL) and DBU (0.054 mL) were added and the reaction stirred at RT for 2 h before being concentrated in vacuo and used immediately in the subsequent step.

The following sulphides were made in an analogous fashion.

| Structure | NAME |
|---|---|
| 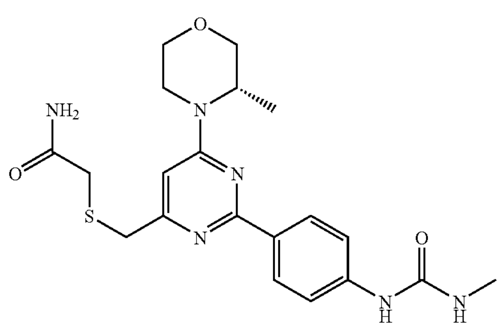 | 2-[[2-[4-(methylcarbamoylamino)phenyl]-6-[(3S)-3-methylmorpholin-4-yl]pyrimidin-4-yl]methylsulfanyl]acetamide |
| 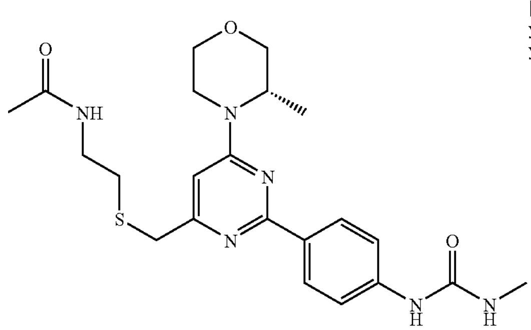 | N-[2-[[2-[4-(methylcarbamoylamino)phenyl]-6-[(3S)-3-methylmorpholin-4-yl]pyrimidin-4-yl]methylsulfanyl]ethyl]acetamide |

The preparation of 3-methyl-1-[4-[4-[(3S)-3-methylmorpholin-4-yl]-6-(methylsulfonyloxymethyl)pyrimidin-2-yl]phenyl]urea was described earlier.

EXAMPLE 27

1-[4-[4-[(3S)-3-Methylmorpholin-4-yl]-6-(morpholin-4-ylmethyl)pyrimidin-2-yl]phenyl]-3-phenyl-urea

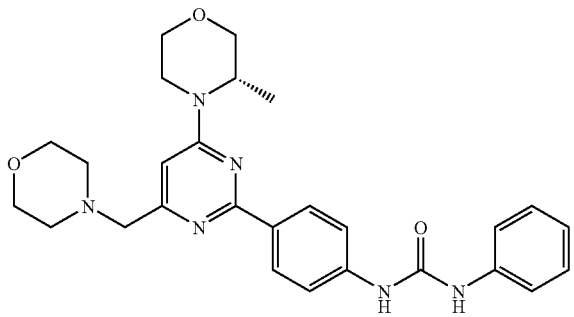

1-[4-[4-(Hydroxymethyl)-6-[(3S)-3-methylmorpholin-4-yl]pyrimidin-2-yl]phenyl]-3-phenyl-urea (90 mg) was dissolved in DCM (5 mL) and triethylamine (0.045 mL) and the solution cooled to 0° C. Methane sulfonyl chloride (0.026 mL) was added and the reaction stirred for 1 h at RT. Morpholine (0.2 mL) was added and the reaction was left at RT for 72 hours before being concentrated in vacuo and purified by prep-HPLC (basic) to give the desired compound (64 mg) as a white solid.

NMR Spectrum: $^1$H NMR (400.13 MHz, DMSO-$d_6$) δ 1.21 (3H, d), 3.17 (4H, t), 3.46-3.52 (4H, m), 3.63 (4H, d), 3.65 (1H, s), 3.76 (1H, d), 3.95-3.98 (1H, m), 4.14 (1H, d), 4.49 (1H, s), 6.64 (1H, s), 6.97 (1H, t), 7.29 (2H, d), 7.45 (2H, d), 7.53 (2H, d), 8.25 (2H, d), 8.68 (1H, s), 8.87 (1H, s).

Mass Spectrum; M+H$^+$ 489.

Test (a): 0.19 μM.

The preparation of 1-[4-[4-(hydroxymethyl)-6-[(3S)-3-methylmorpholin-4-yl]pyrimidin-2-yl]phenyl]-3-phenyl-urea was described earlier.

EXAMPLE 28

1-[4-[4-[(3S)-3-Methylmorpholin-4-yl]-6-(phenoxymethyl)pyrimidin-2-yl]phenyl]-3-phenyl-urea

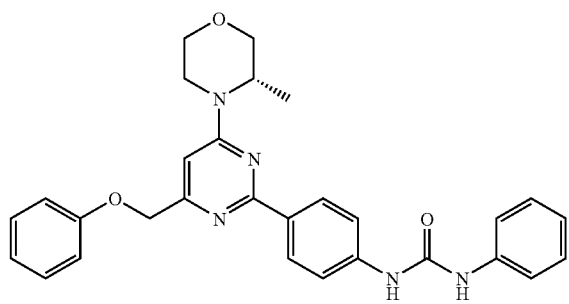

1-[4-[4-[(3S)-3-Methylmorpholin-4-yl]-6-(methylsulfonyloxymethyl)pyrimidin-2-yl]phenyl]-3-phenyl-urea was dissolved in DCM (5 mL), phenol (41 mg) added and the reaction left to stir at RT for 1 h. DBU (0.2 mL) was added and the mixture left to stir for 18 hours before being concentrated in vacuo and purified by prep-HPLC (basic) to give the desired material (26 mg) as a white solid.

NMR Spectrum: $^1$H NMR (400.13 MHz, DMSO-$d_6$) δ 1.19-1.21 (3H, m), 3.18 (1H, s), 3.47-3.52 (1H, m), 3.62-3.66 (1H, m), 3.76 (1H, d), 3.95-3.99 (1H, m), 4.16 (1H, s), 4.51 (1H, s), 5.08 (2H, s), 6.72 (1H, s), 6.96-7.01 (2H, m), 7.07-7.10 (2H, m), 7.28-7.35 (4H, m), 7.48 (2H, d), 7.57 (2H, d), 8.28 (2H, d), 8.75 (1H, s), 8.95 (1H, s)

Mass Spectrum; M+H$^+$ 496.

Test (a): 4.7 μM.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 29

1-[4-[4-[(3S)-3-Methylmorpholin-4-yl]-6-[(2-oxopyrrolidin-3-yl)sulfonylmethyl]pyrimidin-2-yl]phenyl]-3-phenyl-urea

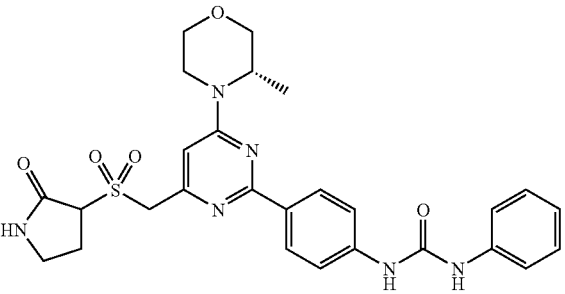

1-[4-[4-[(3S)-3-Methylmorpholin-4-yl]-6-[(2-oxopyrrolidin-3-yl)sulfanylmethyl]pyrimidin-2-yl]phenyl]-3-phenyl-urea (0.26 mmol) was dissolved in 1,4-Dioxane (5 mL) and water (1 mL). m-CPBA (75%) (113 mg) followed immediately by sodium permanganate (125 mg) was added to the solution and left to stir at RT for 1 h. The reaction was loaded onto a SCX-2 (10 g) column, which was washed with methanol and the product eluted with 7N ammonia in methanol. The material was further purified by prep-HPLC (basic) to give the desired material (18 mg) as a white solid.

NMR Spectrum: $^1$H NMR (400.13 MHz, DMSO-$d_6$) δ 1.25 (3H, d), 2.32-2.34 (1H, m), 2.47 (1H, d), 3.24 (2H, t), 3.34 (2H, d), 3.51 (1H, t), 3.66 (1H, d), 3.78 (1H, d), 3.97-4.01 (1H, m), 4.49 (1H, s), 4.58-4.63 (2H, m), 5.01 (1H, d), 6.79 (1H, s), 6.97-7.01 (1H, m), 7.28-7.32 (1H, m), 7.30 (1H, s), 7.46-7.48 (2H, m), 7.56-7.58 (2H, m), 8.24-8.27 (2H, m), 8.38 (1H, s), 8.72 (1H, s), 8.92 (1H, s)

Mass Spectrum; M+H$^+$ 551.

Test (a): 0.56 μM.

The preparation of 1-[4-[4-[(3S)-3-methylmorpholin-4-yl]-6-[(2-oxopyrrolidin-3-yl)sulfanylmethyl]pyrimidin-2-yl]phenyl]-3-phenyl-urea is described below.

273

1-[4-[4-[(3S)-3-Methylmorpholin-4-yl]-6-[(2-oxopy-rrolidin-3-yl)sulfanylmethyl]pyrimidin-2-yl]phenyl]-3-phenyl-urea

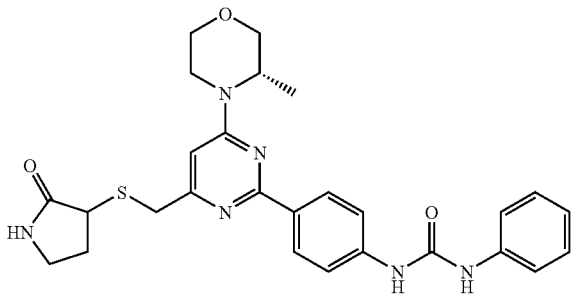

1-[4-[4-(Carbamimidoylsulfanylmethyl)-6-[(3S)-3-methylmorpholin-4-yl]pyrimidin-2-yl]phenyl]-3-phenyl-urea (125 mg) was dissolved in DMF (3 mL). The solution was then treated with 3-bromo-pyrrolidin-2-one (48 mg) followed by sodium hydroxide (42 mg) in water (1 mL), heated to 40° C. and left to stir for 24 h. The reaction was diluted in a little methanol and loaded onto a SCX-2 column (20 g), which was washed with methanol and the desired product eluted with 7N ammonia in methanol to give the desired material which was used without further characterisation.

1-[4-[4-(Carbamimidoylsulfanylmethyl)-6-[(3S)-3-methylmorpholin-4-yl]pyrimidin-2-yl]phenyl]-3-phenyl-urea

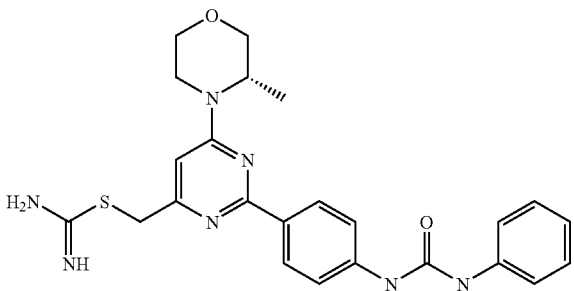

274

1-[4-[4-[(3S)-3-Methylmorpholin-4-yl]-6-(methylsulfo-nyloxymethyl)pyrimidin-2-yl]phenyl]-3-phenyl-urea (865 mg) was dissolved in ethanol (30 mL) and thiourea (146 mg) added. The reaction was then heated to 70° C. for 30 min then allowed to cool and concentrated in vacuo to give the desired material which was used without further characterisation.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 30

1-[4-[4-(Anilinomethyl)-6-[(3S)-3-methylmorpholin-4-yl]pyrimidin-2-yl]phenyl]-3-phenyl-urea

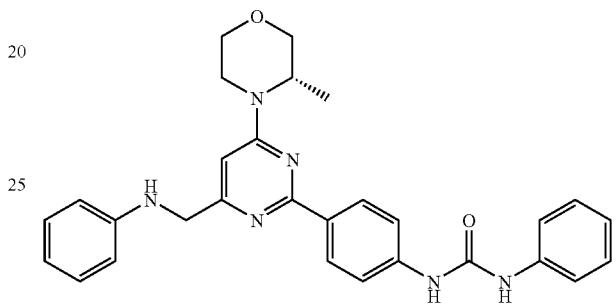

1-[4-[4-[(3S)-3-Methylmorpholin-4-yl]-6-(methylsulfo-nyloxymethyl)pyrimidin-2-yl]phenyl]-3-phenyl-urea (105 mg, 0.21 mmol) dissolved in a solution of DCM (5 mL) was added to aniline (0.097 mL, 1.06 mmol) and stirred at RT for 18 h. The mixture was vacuumed to dryness and purified by prep-HPLC (basic) to give the desired material (41 mg) as a white solid.

NMR Spectrum: $^1$H NMR (400.13 MHz, DMSO-$d_6$) δ 1.15 (3H, d), 3.12-3.18 (1H, m), 3.43-3.50 (1H, m), 3.59-3.63 (1H, m), 3.74 (1H, d), 3.93-3.97 (1H, m), 4.10 (1H, d), 4.24 (2H, d), 4.39 (1H, s), 6.20 (1H, t), 6.55 (1H, d), 6.60 (1H, s), 6.63 (1H, d), 6.65 (1H, s), 6.97-7.01 (1H, m), 7.06-7.10 (2H, m), 7.28-7.32 (1H, m), 7.30 (1H, s), 7.46-7.49 (2H, m), 7.55-7.57 (2H, m), 8.29-8.31 (2H, m), 8.69 (1H, s), 8.88 (1H, s).

Mass Spectrum; M+H$^+$ 495.

The following compounds were prepared in an analogous fashion.

| Example | Structure | NAME | LCMS MH+ |
|---|---|---|---|
| 30a | 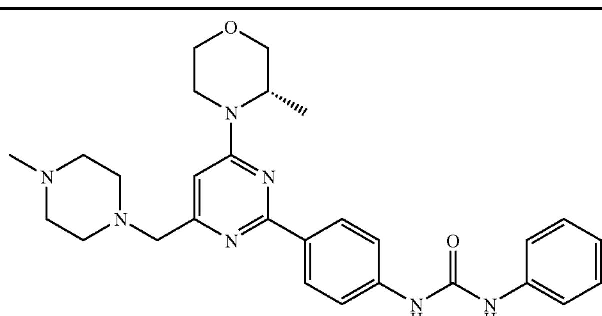 | 1-[4-[4-[(3S)-3-methylmorpholin-4-yl]-6-[(4-methylpiperazin-1-yl)methyl]pyrimidin-2-yl]phenyl]-3-phenyl-urea | 502 |

| Example | Structure | NAME | LCMS MH+ |
|---|---|---|---|
| 30b | 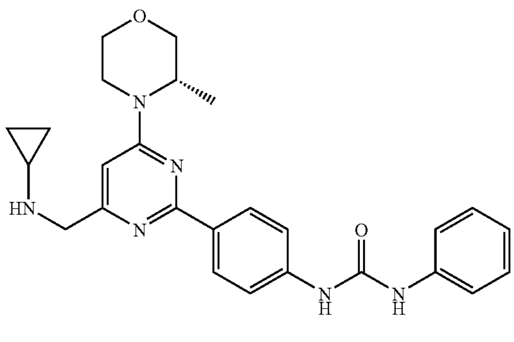 | 1-[4-[4-[(cyclopropylamino)methyl]-6-[(3S)-3-methylmorpholin-4-yl]pyrimidin-2-yl]phenyl]-3-phenyl-urea | 459 |
| 30c | 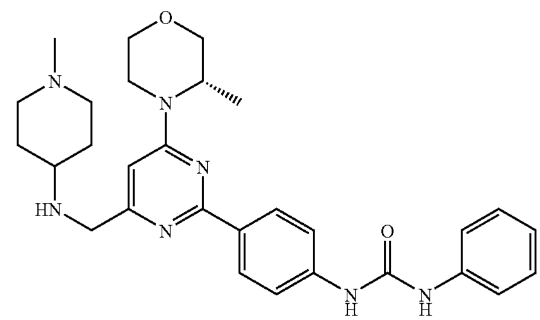 | 1-[4-[4-[(3S)-3-methylmorpholin-4-yl]-6-[[(1-methyl-4-piperidyl)amino]methyl]pyrimidin-2-yl]phenyl]-3-phenyl-urea | 516 |
| 30d | 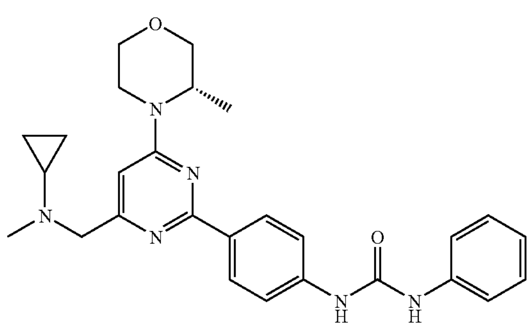 | 1-[4-[4-[(cyclopropyl-methyl-amino)methyl]-6-[(3S)-3-methylmorpholin-4-yl]pyrimidin-2-yl]phenyl]-3-phenyl-urea | 473 |

Example 30a: ¹H NMR (400.13 MHz, DMSO-d₆) δ 1.22 (3H, d), 2.22 (3H, s), 2.44 (2H, d), 2.53 (2H, d), 2.56 (2H, s), 2.60-2.61 (1H, m), 2.67-2.69 (1H, m), 3.15-3.23 (1H, m), 3.46-3.54 (3H, m), 3.63-3.67 (1H, m), 3.77 (1H, d), 3.96-4.00 (1H, m), 4.15 (1H, d), 4.47-4.49 (1H, m), 6.63 (1H, s), 6.97-7.01 (1H, m), 7.28-7.32 (1H, m), 7.30 (1H, s), 7.46-7.48 (2H, m), 7.53-7.56 (2H, m), 8.25-8.27 (2H, m), 8.69 (1H, s), 8.88 (1H, s)

Example 30b: ¹H NMR (400.13 MHz, DMSO-d₆) δ 0.30-0.31 (2H, m), 0.37-0.40 (2H, m), 1.23 (3H, d), 2.14-2.19 (1H, m), 3.15-3.23 (1H, m), 3.46-3.53 (1H, m), 3.63-3.66 (1H, m), 3.72 (2H, s), 3.77 (1H, d), 3.96-4.00 (1H, m), 4.17 (1H, d), 4.51 (1H, m), 6.67 (1H, s), 6.99-7.01 (1H, m), 7.28-7.32 (2H, m), 7.46-7.48 (2H, m), 7.53-7.56 (2H, m), 8.28 (2H, d), 8.69 (1H, s), 8.87 (1H, s)

Example 30d: ¹H NMR (400.13 MHz, DMSO-d₆) δ 0.40-0.41 (2H, t), 0.45-0.49 (2H, m), 1.21 (3H, d), 1.90-1.95 (1H, m), 2.34 (3H, s), 3.14-3.21 (1H, m), 3.46-3.53 (1H, m), 3.63 (3H, t), 3.76 (1H, d), 3.95-3.99 (1H, m), 4.13 (1H, d), 4.49 (1H, s), 6.54 (1H, s), 6.97-7.01 (1H, m), 7.28-7.32 (1H, m), 7.30 (1H, s), 7.46-7.48 (2H, m), 7.54-7.56 (2H, m) 8.26-8.2 (2H, m) 8.69 (1H, s) 8.87 (1H, s)

Test (a): Example (30) 0.9 μM; Example (30a) 0.12 μM; Example (30b) 0.18 μM; Example (30c) 1.1 μM; Example (30d) 0.28 μM.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 31

1-[4-[4-[(3S)-3-Methylmorpholin-4-yl]-6-[(1-methyl-4-piperidyl)oxymethyl]pyrimidin-2-yl]phenyl]-3-phenyl-urea

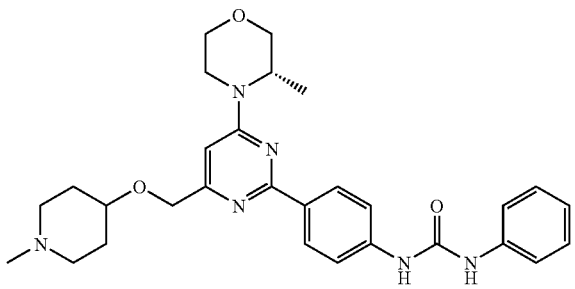

1-[4-[4-[(3S)-3-Methylmorpholin-4-yl]-6-(methylsulfonyloxymethyl)pyrimidin-2-yl]phenyl]-3-phenyl-urea (105 mg) dissolved in a solution of DCM (5 mL) and triethylamine (0.045 mL) was added to 4-hydroxy-1-methylpiperidine (5 equivalents). DBU (0.158 mL) was added and stirred at RT for 18 h. The mixture was vacuumed to dryness and purified by prep-HPLC (basic) to give the desired material (64 mg) as a white solid.

Mass Spectrum; M+H⁺ 517.

Test (a): 0.35 μM.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 32

1-[4-[4-(Methoxymethyl)-6-[(3S)-3-methylmorpholin-4-yl]pyrimidin-2-yl]phenyl]-3-phenyl-urea

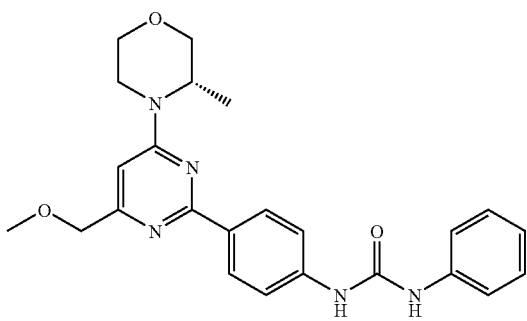

1-[4-[4-[(3S)-3-Methylmorpholin-4-yl]-6-(methylsulfonyloxymethyl)pyrimidin-2-yl]phenyl]-3-phenyl-urea (90 mg) dissolved in a solution of DCM (5 mL) and triethylamine (0.045 mL). Sodium methoxide (33% in methanol) (0.073 mL) was added to the reaction and the mixture stirred at RT for 18 h before being quenched with water and partitioned. The organic phase was dried over magnesium sulphate and evaporated to give a gum which was purified by prep-HPLC (basic) to give the desired compound (32 mg) as a white solid.

NMR Spectrum: ¹H NMR (400.13 MHz, DMSO-d₆) δ 1.23 (3H, d), 3.34 (1H, d), 3.43 (3H, s), 3.49 (1H, t), 3.63-3.66 (1H, m), 3.76 (1H, d), 3.97 (1H, d), 4.19 (1H, d), 4.41 (2H, s), 4.51 (1H, d), 6.59 (1H, s), 6.99 (1H, t), 7.30 (2H, t), 7.46-7.48 (2H, m), 7.55 (2H, d), 8.26 (2H, d), 8.69 (1H, s), 8.88 (1H, s)

Mass Spectrum; M+H⁺ 434.

Test (a): 0.0062 μM.

The preparation of 1-[4-[4-[(3S)-3-methylmorpholin-4-yl]-6-(methylsulfonyloxymethyl)pyrimidin-2-yl]phenyl]-3-phenyl-urea was described earlier.

EXAMPLE 33

3-Methyl-1-[4-[4-[(1-methylimidazol-2-yl)sulfonylmethyl]-6-[(3S)-3-methylmorpholin-4-yl]pyrimidin-2-yl]phenyl]urea

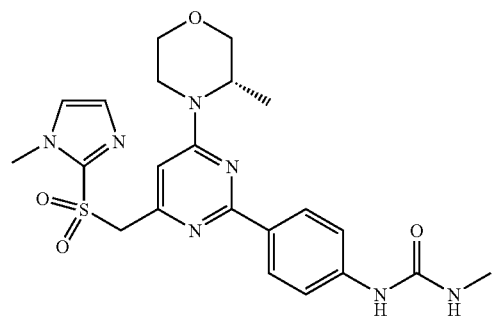

3-Methyl-1-[4-[4-[(1-methylimidazol-2-yl)sulfanylmethyl]-6-[(3S)-3-methylmorpholin-4-yl]pyrimidin-2-yl]phenyl]urea (0.23 mmol) was dissolved in 1,4-Dioxane (4 mL) and water (1 mL). m-CPBA (75%) (80 mg), followed immediately by sodium permanganate (92 mg), was added to the solution. The reaction was allowed to stir at RT for 18 h then loaded onto a SCX-2 (10 g) column, which was washed with methanol and the product eluted with 7N ammonia in methanol. The reaction was vacuumed to dryness and purified by prep-HPLC (basic) to give the desired material (37 mg) as a white solid.

NMR Spectrum: ¹H NMR (400.13 MHz, DMSO-d₆) δ 1.17-1.22 (3H, m), 2.66 (3H, d), 2.68 (1H, t), 3.14-3.22 (1H, m), 3.45-3.49 (1H, m), 3.62 (3H, s), 3.77 (1H, d), 3.96-3.99 (1H, m), 4.09-4.12 (1H, m), 4.41 (1H, s), 4.75 (2H, s), 6.07 (1H, q), 6.61 (1H, s), 7.20 (1H, d), 7.43-7.47 (2H, m), 7.43-7.49 (1H, m), 7.95-7.97 (2H, m), 8.72 (1H, s)

Mass Spectrum; M+H⁺ 486.

The following compounds were prepared in an analogous fashion from the appropriate sulphides.

| Example | Structure | NAME | LCMS MH+ |
|---------|-----------|------|----------|
| 33a | 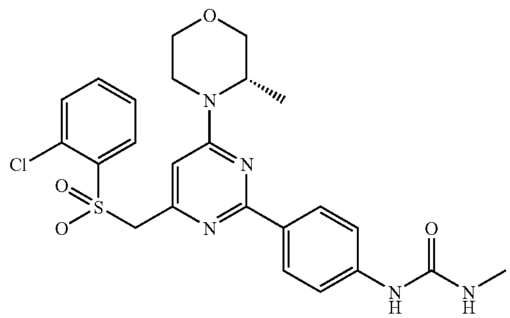 | 1-[4-[4-[(2-chlorophenyl)sulfonylmethyl]-6-[(3S)-3-methylmorpholin-4-yl]pyrimidin-2-yl]phenyl]-3-methyl-urea | 516 |
| 33b | 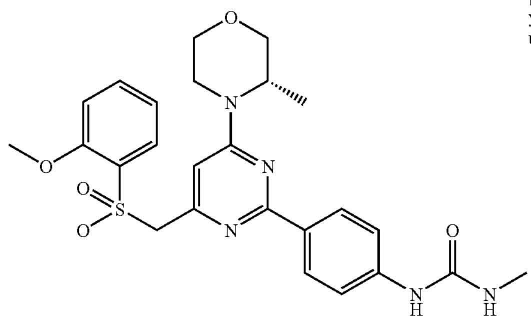 | 1-[4-[4-[(2-methoxyphenyl)sulfonylmethyl]-6-[(3S)-3-methylmorpholin-4-yl]pyrimidin-2-yl]phenyl]-3-methyl-urea | 512 |
| 33c | 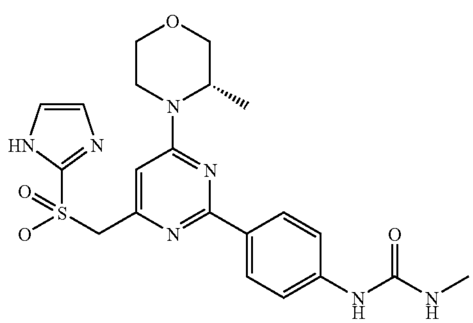 | 1-[4-[4-(1H-imidazol-2-ylsulfonylmethyl)-6-[(3S)-3-methylmorpholin-4-yl]pyrimidin-2-yl]phenyl]-3-methyl-urea | 472 |
| 33d | 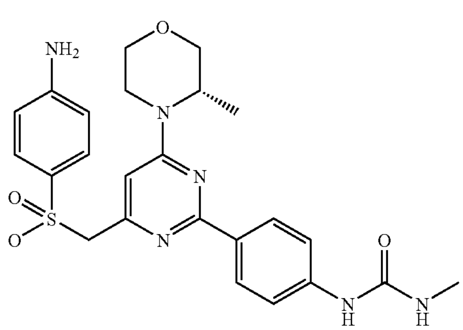 | 1-[4-[4-[(4-aminophenyl)sulfonylmethyl]-6-[(3S)-3-methylmorpholin-4-yl]pyrimidin-2-yl]phenyl]-3-methyl-urea | 497 |

| Example | Structure | NAME | LCMS MH+ |
|---|---|---|---|
| 33e | 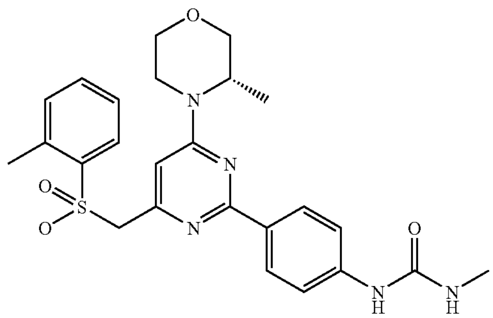 | 3-methyl-1-[4-[4-[(3S)-3-methylmorpholin-4-yl]-6-[(2-methylphenyl)sulfonylmethyl]pyrimidin-2-yl]phenyl]urea | 496 |
| 33f | 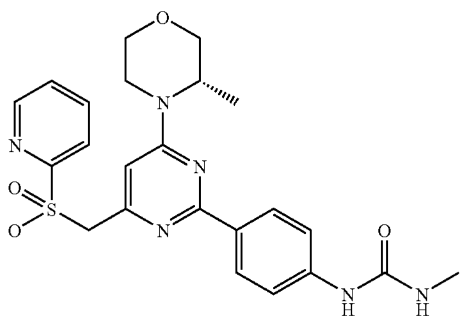 | 3-methyl-1-[4-[4-[(3S)-3-methylmorpholin-4-yl]-6-(pyridin-2-ylsulfonylmethyl)pyrimidin-2-yl]phenyl]urea | 483 |
| 33g | 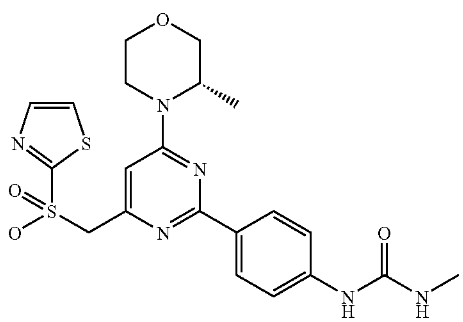 | 3-methyl-1-[4-[4-[(3S)-3-methylmorpholin-4-yl]-6-(1,3-thiazol-2-ylsulfonylmethyl)pyrimidin-2-yl]phenyl]urea | 489 |
| 33h | 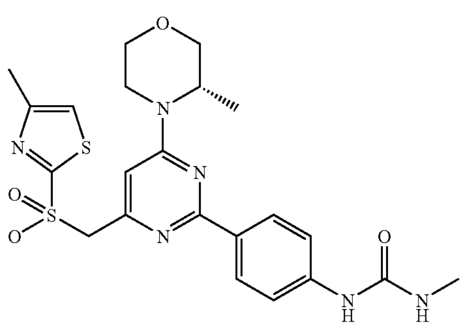 | 3-methyl-1-[4-[4-[(3S)-3-methylmorpholin-4-yl]-6-[(4-methyl-1,3-thiazol-2-yl)sulfonylmethyl]pyrimidin-2-yl]phenyl]urea | 503 |

Example 33a: $^1$H NMR (400.13 MHz, DMSO-$d_6$) δ 1.22 (3H, q), 2.65-2.68 (3H, m), 2.68 (1H, d), 3.17 (1H, d), 3.44-3.51 (1H, m), 3.61-3.65 (1H, m), 3.76 (1H, d), 3.95-3.99 (1H, m), 4.09 (1H, t), 4.88 (2H, s), 6.05 (1H, q), 6.71 (1H, s), 7.33-7.35 (2H, m), 7.44-7.48 (1H, m), 7.65-7.69 (1H, m), 7.67 (1H, s), 7.71-7.77 (2H, m), 7.83-7.85 (1H, m), 8.68 (1H, s).

Example 33b: $^1$H NMR (400.13 MHz, DMSO-$d_6$) δ 1.18 (3H, d), 2.66-2.69 (3H, m), 3.12-3.21 (1H, m), 3.43-3.50 (1H, m), 3.59-3.63 (1H, m), 3.75 (1H, d), 3.94-3.98 (1H, m), 4.05 (4H, m), 4.37 (1H, s), 4.70-4.77 (2H, m), 6.04 (1H, q), 6.61 (1H, s), 7.01-7.05 (1H, m), 7.34-7.36 (2H, m), 7.39 (1H, d), 7.54-7.57 (1H, m), 7.67-7.74 (3H, m), 8.67 (1H, s).

Example 33c: $^1$H NMR (400.13 MHz, DMSO-$d_6$) δ 1.20 (3H, d), 2.66 (3H, d), 3.12-3.20 (1H, m), 3.43-3.50 (1H, m), 3.60-3.63 (1H, m), 3.76 (1H, d), 3.95-3.99 (1H, m), 4.08 (1H, d), 4.36 (1H, s), 4.71 (2H, s), 6.06 (1H, q), 6.47 (1H, s), 7.34 (2H, s), 7.42-7.44 (2H, m), 7.95-7.97 (2H, m), 8.70 (1H, s), 13.52 (1H, s)

Example 33d: $^1$H NMR (400.13 MHz, DMSO-d$_6$) δ 1.19 (3H, d), 2.66-2.69 (3H, m), 3.12-3.21 (1H, m), 3.44-3.48 (1H, m), 3.60-3.64 (1H, m), 3.75 (1H, d), 3.94-3.98 (1H, m), 4.05 (1H, t), 4.33 (1H, s), 4.44 (2H, s), 6.06 (1H, t), 6.12 (2H, d), 6.41 (1H, s), 6.58-6.62 (2H, m), 7.34-7.38 (2H, m), 7.42-7.46 (2H, m), 7.99-8.01 (2H, m), 8.70 (1H, s)

Example 33e: $^1$H NMR (400.13 MHz, DMSO-d$_6$) δ 1.19 (3H, d), 2.67 (6H, m), 3.14-3.18 (1H, m), 3.44-3.50 (1H, m), 3.60-3.64 (1H, m), 3.76 (1H, d), 3.94-3.98 (1H, m), 4.06 (1H, q), 4.37 (1H, s), 4.66 (2H, s), 6.05 (1H, d), 6.60 (1H, s), 7.34 (1H, d), 7.36-7.38 (2H, m), 7.47 (1H, d), 7.56-7.60 (1H, m), 7.66-7.68 (1H, m), 7.77-7.80 (2H, m), 8.69 (1H, s)

Example 33f: $^1$H NMR (400.13 MHz, DMSO-d$_6$) δ 1.20 (3H, d), 2.65-2.68 (3H, m), 3.16-3.21 (1H, m), 3.44-3.51 (1H, m), 3.60-3.64 (1H, m), 3.76 (1H, d), 3.95-3.99 (1H, m), 4.11 (1H, d), 4.38 (1H, s), 4.80-4.88 (2H, m), 6.04 (1H, q), 6.68 (1H, s), 7.34-7.36 (2H, m), 7.64-7.67 (2H, m), 7.78-7.81 (1H, m), 7.88-7.90 (1H, m), 8.07-8.12 (1H, m), 8.69 (1H, s), 8.92-8.94 (1H, m)

Example 33g: $^1$H NMR (400.13 MHz, DMSO-d$_6$) δ 1.21 (3H, d), 2.67 (3H, q), 3.16-3.21 (1H, m), 3.45-3.52 (1H, m), 3.62-3.65 (1H, m), 3.77 (1H, d), 3.96-3.99 (1H, m), 4.40 (2H, s), 4.91 (2H, d), 6.06 (1H, d), 6.70 (1H, s), 7.40-7.42 (2H, m), 7.84 (2H, d), 8.27-8.29 (2H, m), 8.71 (1H, s).

Example 33h: $^1$H NMR (400.13 MHz, DMSO-d$_6$) δ 1.21-1.27 (3H, m), 2.52-2.61 (3H, m), 2.66-2.69 (3H, m), 3.15-3.22 (1H, m), 3.45-3.52 (1H, m), 3.62-3.66 (1H, m), 3.77 (1H, d), 3.96-4.00 (1H, m), 4.13 (1H, d), 4.40 (1H, s), 4.87 (2H, d), 6.05 (1H, q), 6.70 (1H, s), 7.41-7.43 (2H, m), 7.82 (1H, S)

Test (a): Example (33) 0.84 μM; Example (33a) 0.06 μM; Example (33b) 0.066 μM; Example (33c) 0.0014 μM; Example (33d) 0.00031 μM; Example (33e) 0.088 μM; Example (33f) 0.27 μM; Example (33g) 0.021 μM; Example (33h) 0.048 μM.

The preparation of 3-methyl-1-[4-[4-[(1-methylimidazol-2-yl)sulfanylmethyl]-6-[(3S)-3-methylmorpholin-4-yl]pyrimidin-2-yl]phenyl]urea is described below.

3-Methyl-1-[4-[4-[(1-methylimidazol-2-yl)sulfanylmethyl]-6-[(3S)-3-methylmorpholin-4-yl]pyrimidin-2-yl]phenyl]urea

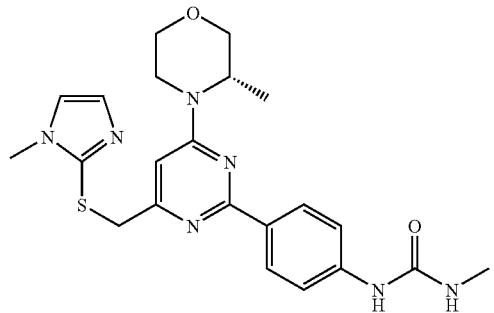

1-Methylimidazole-2-thiol (0.23 mmol) was dissolved in acetonitrile (2 mL), DBU (0.035 mL) added and the reaction allowed to stir at RT for 5 min. A solution of 3-methyl-1-[4-[4-[(3S)-3-methylmorpholin-4-yl]-6-(methylsulfonyloxymethyl)pyrimidin-2-yl]phenyl]urea (100 mg) in acetonitrile (2 mL) and DBU (0.034 mL) were added and the mixture left to stir at RT of 18 h, before being concentrated in vacuo to give the desired material. The material was used without further purification.

The following sulphides were prepared in an analogous fashion.

| Structure | NAME |
|---|---|
| 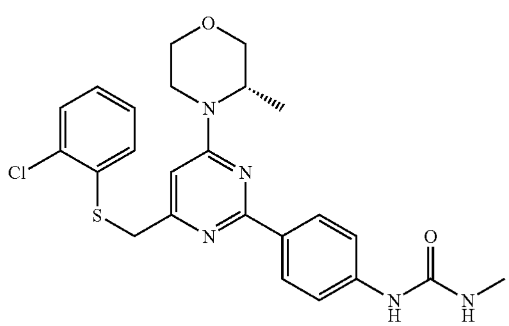 | 1-[4-[4-[(2-chlorophenyl)sulfanylmethyl]-6-[(3S)-3-methylmorpholin-4-yl]pyrimidin-2-yl]phenyl]-3-methyl-urea |
| 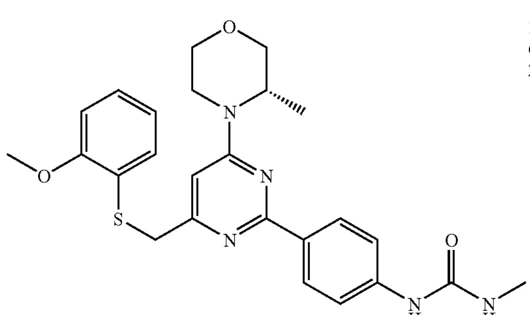 | 1-[4-[4-[(2-methoxyphenyl)sulfanylmethyl]-6-[(3S)-3-methylmorpholin-4-yl]pyrimidin-2-yl]phenyl]-3-methyl-urea |

| Structure | NAME |
|---|---|
| 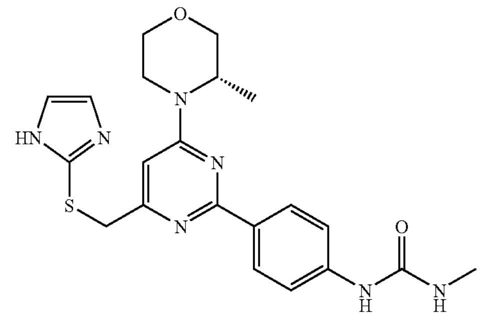 | 1-[4-[4-(1H-imidazol-2-ylsulfanylmethyl)-6-[(3S)-3-methylmorpholin-4-yl]pyrimidin-2-yl]phenyl]-3-methyl-urea |
| 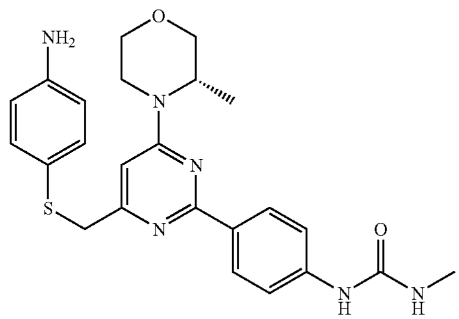 | 1-[4-[4-[(4-aminophenyl)sulfanylmethyl]-6-[(3S)-3-methylmorpholin-4-yl]pyrimidin-2-yl]phenyl]-3-methyl-urea |
| 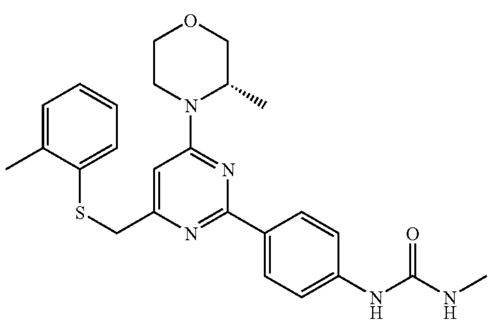 | 3-methyl-1-[4-[4-[(3S)-3-methylmorpholin-4-yl]-6-[(2-methylphenyl)sulfanylmethyl]pyrimidin-2-yl]phenyl]urea |
| 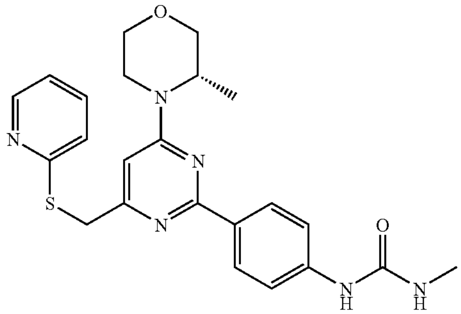 | 3-methyl-1-[4-[4-[(3S)-3-methylmorpholin-4-yl]-6-(pyridin-2-ylsulfanylmethyl)pyrimidin-2-yl]phenyl]urea |

| Structure | NAME |
|---|---|
| 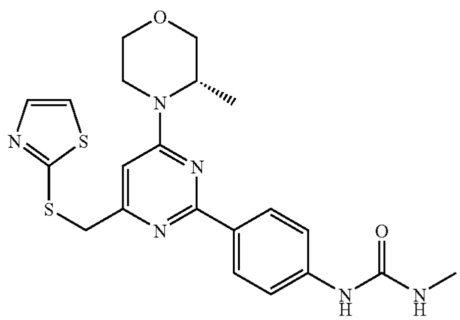 | 3-methyl-1-[4-[4-[(3S)-3-methylmorpholin-4-yl]-6-(1,3-thiazol-2-ylsulfanylmethyl)pyrimidin-2-yl]phenyl]urea |
| 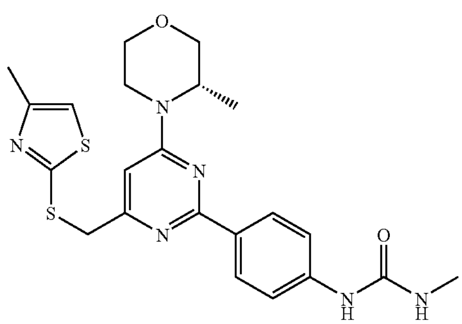 | 3-methyl-1-[4-[4-[(3S)-3-methylmorpholin-4-yl]-6-[(4-methyl-1,3-thiazol-2-yl)sulfanylmethyl]pyrimidin-2-yl]phenyl]urea |

The preparation of 3-methyl-1-[4-[4-[(3S)-3-methylmorpholin-4-yl]-6-(methylsulfonyloxymethyl)pyrimidin-2-yl]phenyl]urea was described earlier.

EXAMPLE 34

[4-[4-(Methylsulfonylmethyl)-6-morpholin-4-yl-pyrimidin-2-yl]phenyl]urea

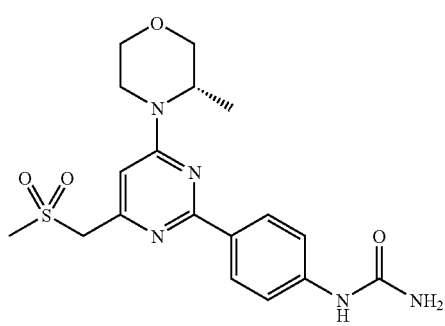

Phenyl N-[4-[4-(methylsulfonylmethyl)-6-morpholin-4-yl-pyrimidin-2-yl]phenyl]carbamate (110 mg) was dissolved in DMF (2 mL) and triethylamine (0.098 mL) added. 2-Aminopyrimidine (108 mg) was added and the reaction stirred at 40° C. for 2 hours. The crude mixture was purified by prep-HPLC (basic), however, only [4-[4-(Methylsulfonylmethyl)-6-morpholin-4-yl-pyrimidin-2-yl]phenyl]urea was isolated from the mixture (8 mg).

NMR Spectrum: $^1$H NMR (400.13 MHz, DMSO-$d_6$) δ 3.21 (3H, s), 3.71-3.72 (8H, m), 4.48 (2H, s), 5.91 (2H, s), 6.81 (1H, s), 7.49-7.51 (2H, m), 8.20-8.23 (2H, m), 8.76 (1H, s)

Mass Spectrum; M+H$^+$ 392.

The following compounds were prepared in an analogous procedure.

| Example | Structure | NAME | LCMS MH+ |
|---|---|---|---|
| 34a | 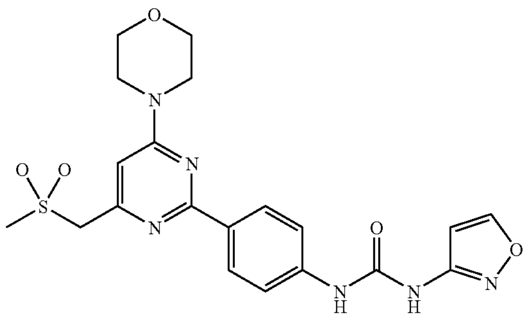 | 1-[4-[4-(methylsulfonylmethyl)-6-morpholin-4-yl-pyrimidin-2-yl]phenyl]-3-(1,2-oxazol-3-yl)urea | 458 |
| 34b | 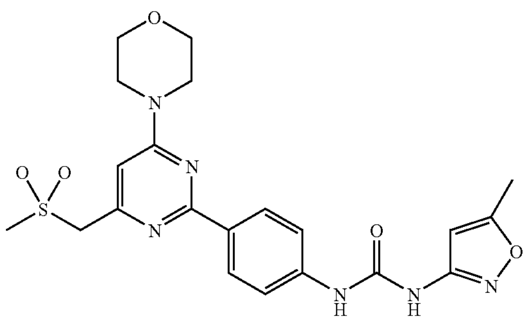 | 1-(5-methyl-1,2-oxazol-3-yl)-3-[4-[4-(methylsulfonylmethyl)-6-morpholin-4-yl-pyrimidin-2-yl]phenyl]urea | 472 |
| 34c | 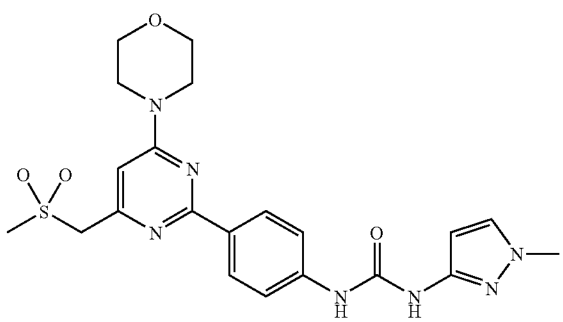 | 1-(1-methylpyrazol-3-yl)-3-[4-[4-(methylsulfonylmethyl)-6-morpholin-4-yl-pyrimidin-2-yl]phenyl]urea | 471 |

Example 34a: $^1$H NMR (400.13 MHz, DMSO-$d_6$) δ 3.21 (3H, s), 3.73 (8H, s), 4.50 (2H, s), 6.85-6.87 (2H, m), 7.56-7.59 (2H, m), 8.28-8.31 (2H, m), 8.75 (1H, d), 9.07 (1H, s), 9.62 (1H, s)

Example 34b: $^1$H NMR (400.13 MHz, DMSO-$d_6$) δ 3.15-3.25 (3H, s), 3.21-3.26 (3H, S), 3.73 (8H, s), 4.49 (2H, s), 6.56 (1H, s), 6.85 (1H, s), 7.55-7.57 (2H, m), 8.28-8.30 (2H, m), 9.05 (1H, s), 9.47 (1H, s)

Example 34c: $^1$H NMR (400.13 MHz, DMSO-$d_6$) δ 3.21 (3H, s), 3.72 (3H, s), 3.74 (8H, s), 4.49 (2H, s), 6.25 (1H, d), 6.84 (1H, s), 7.54-7.56 (2H, m), 7.57 (1H, d), 8.26-8.28 (2H, m), 8.93 (1H, s), 9.18 (1H, s).

Test (a): Example (34) 0.21 μM; Example (34a) 0.042 μM; Example (34b) 0.12 μM; Example (34c) 0.72 μM.

The preparation of phenyl N-[4-[4-(methylsulfonylmethyl)-6-morpholin-4-yl-pyrimidin-2-yl]phenyl]carbamate was described earlier.

EXAMPLE 35

3-(1-Hydroxypropan-2-yl)-1-[4-[4-[(3S)-3-methylmorpholin-4-yl]-6-(methylsulfonylmethyl)pyrimidin-2-yl]phenyl]urea

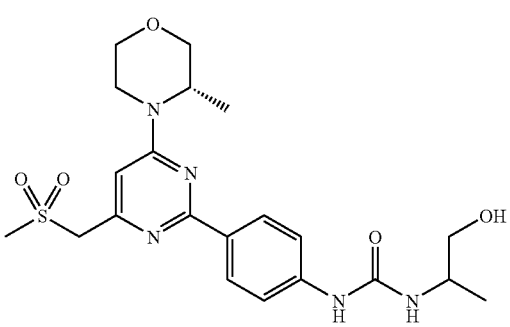

A solution of phenyl N-[4-[4-[(3S)-3-methylmorpholin-4-yl]-6-(methylsulfonylmethyl)pyrimidin-2-yl]phenyl]carbamate (110 mg, 0.23 mmol) and triethylamine (0.079 mL, 0.68 mmol) in DMF (2 mL) was added to 2-aminopropan-1-ol (1.14 mmol). The reaction was stirred at 40° C. for 2 hours then purified by prep-HPLC (basic) to give the desired material as a solid (22 mg).

NMR Spectrum: $^1$H NMR (400.13 MHz, DMSO-d$_6$) δ 1.09 (3H, d), 1.24 (3H, d), 3.21 (3H, s), 3.37-3.43 (2H, m), 3.47-3.53 (2H, m), 3.63-3.67 (1H, m), 3.72 (1H, d), 3.78 (1H, d), 3.97-4.01 (1H, m), 4.15-4.19 (1H, m), 4.48 (3H, s), 4.78 (1H, t), 6.09-6.11 (1H, m), 6.77 (1H, s), 7.47-7.49 (2H, m), 8.20-8.22 (2H, m), 8.71 (1H, s)

Mass Spectrum; M+H$^+$ 463.

The following compounds were prepared in an analogous fashion

| Example | Structure | NAME | LCMS MH+ |
|---|---|---|---|
| 35a | 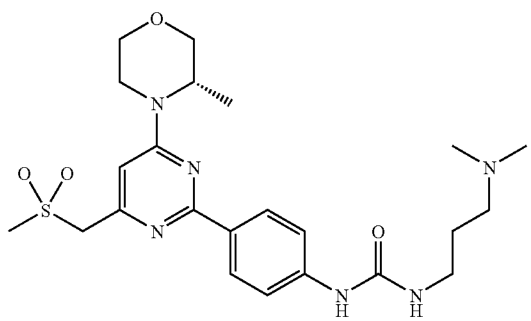 | 3-(3-dimethylaminopropyl)-1-[4-[4-[(3S)-3-methylmorpholin-4-yl]-6-(methylsulfonylmethyl)pyrimidin-2-yl]phenyl]urea | 491 |
| 35b | 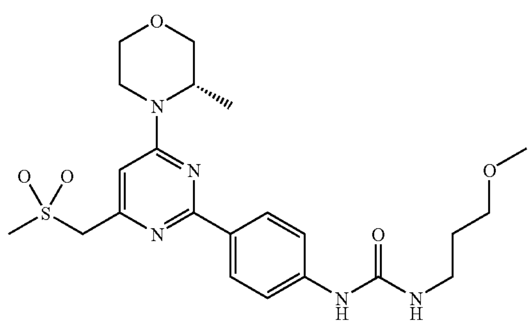 | 3-(3-methoxypropyl)-1-[4-[4-[(3S)-3-methylmorpholin-4-yl]-6-(methylsulfonylmethyl)pyrimidin-2-yl]phenyl]urea | 478 |
| 35c | 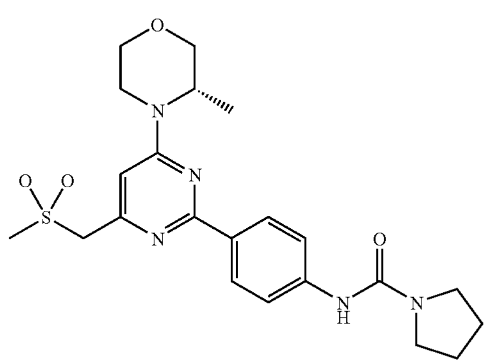 | N-[4-[4-[(3S)-3-methylmorpholin-4-yl]-6-(methylsulfonylmethyl)pyrimidin-2-yl]phenyl]pyrrolidine-1-carboxamide | 460 |

-continued

| Example | Structure | NAME | LCMS MH+ |
|---|---|---|---|
| 35d | 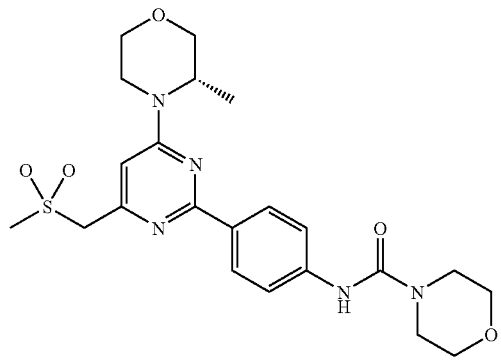 | N-[4-[4-[(3S)-3-methylmorpholin-4-yl]-6-(methylsulfonylmethyl)pyrimidin-2-yl]phenyl]morpholine-4-carboxamide | 476 |
| 35e | 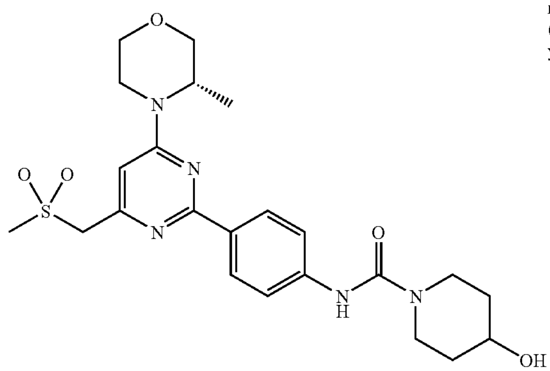 | 4-hydroxy-N-[4-[4-[(3S)-3-methylmorpholin-4-yl]-6-(methylsulfonylmethyl)pyrimidin-2-yl]phenyl]piperidine-1-carboxamide | 490 |
| 35f | 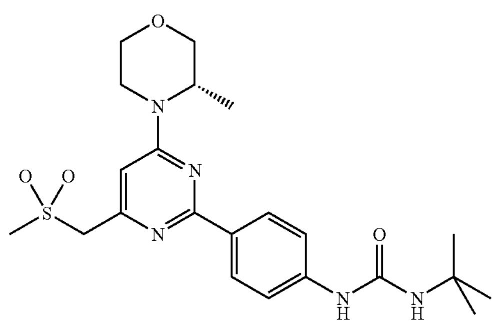 | 1-[4-[4-[(3S)-3-methylmorpholin-4-yl]-6-(methylsulfonylmethyl)pyrimidin-2-yl]phenyl]-3-tert-butyl-urea | 462 |
| 35g | 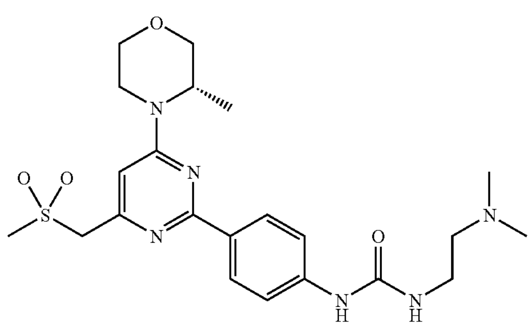 | 3-(2-dimethylaminoethyl)-1-[4-[4-[(3S)-3-methylmorpholin-4-yl]-6-(methylsulfonylmethyl)pyrimidin-2-yl]phenyl]urea | 477 |

-continued

| Example | Structure | NAME | LCMS MH+ |
|---------|-----------|------|----------|
| 35h | 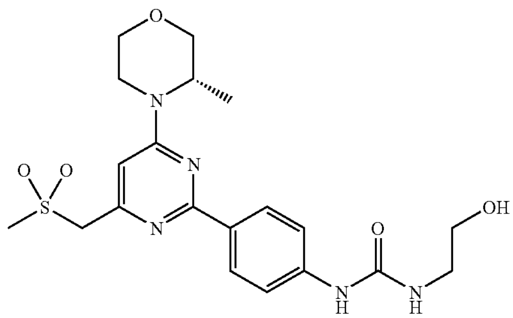 | 3-(2-hydroxyethyl)-1-[4-[4-[(3S)-3-methylmorpholin-4-yl]-6-(methylsulfonylmethyl)pyrimidin-2-yl]phenyl]urea | 450 |
| 35i | 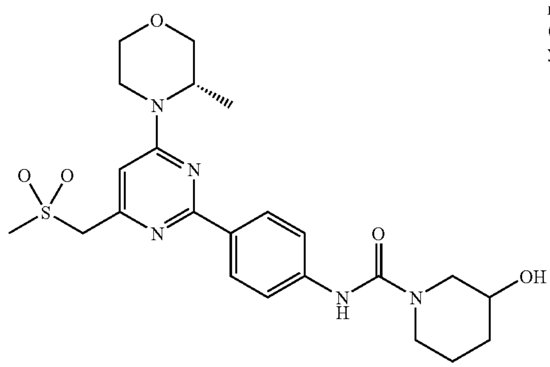 | 3-hydroxy-N-[4-[4-[(3S)-3-methylmorpholin-4-yl]-6-(methylsulfonylmethyl)pyrimidin-2-yl]phenyl]piperidine-1-carboxamide | 490 |
| 35j | 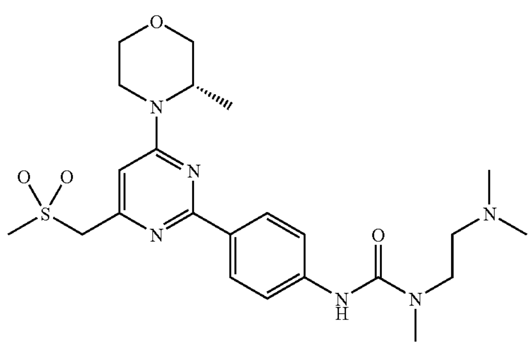 | 1-(2-dimethylaminoethyl)-1-methyl-3-[4-[4-[(3S)-3-methylmorpholin-4-yl]-6-(methylsulfonylmethyl)pyrimidin-2-yl]phenyl]urea | 491 |
| 35k | 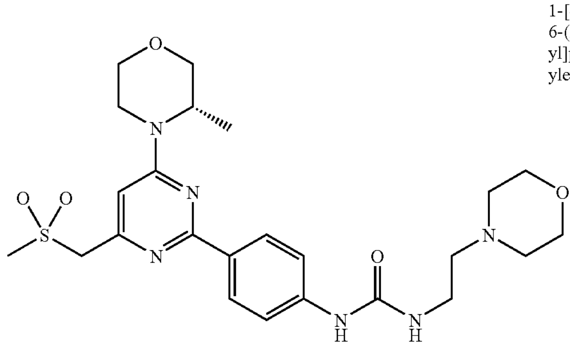 | 1-[4-[4-[(3S)-3-methylmorpholin-4-yl]-6-(methylsulfonylmethyl)pyrimidin-2-yl]phenyl]-3-(2-morpholin-4-ylethyl)urea | 486 |

-continued

| Example | Structure | NAME | LCMS MH+ |
|---|---|---|---|
| 35l | 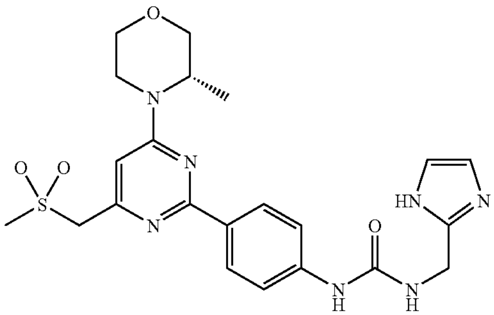 | 3-(1H-imidazol-2-ylmethyl)-1-[4-[4-[(3S)-3-methylmorpholin-4-yl]-6-(methylsulfonylmethyl)pyrimidin-2-yl]phenyl]urea | 460 |
| 35m | 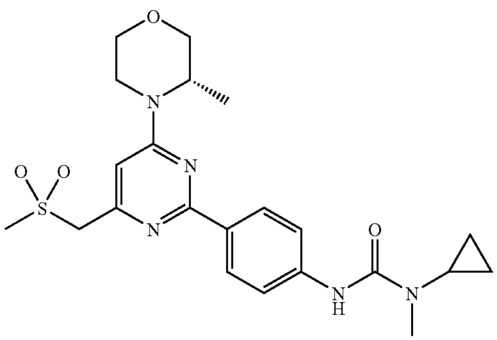 | 1-cyclopropyl-1-methyl-3-[4-[4-[(3S)-3-methylmorpholin-4-yl]-6-(methylsulfonylmethyl)pyrimidin-2-yl]phenyl]urea | 460 |
| 35n | 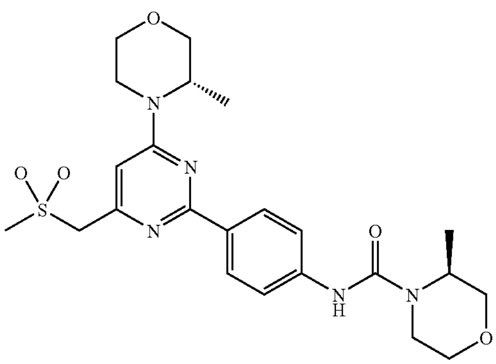 | (3S)-3-methyl-N-[4-[4-[(3S)-3-methylmorpholin-4-yl]-6-(methylsulfonylmethyl)pyrimidin-2-yl]phenyl]morpholine-4-carboxamide | 490 |

Example 35a: $^1$H NMR (400.13 MHz, DMSO-$d_6$) δ 1.24 (3H, d), 1.54-1.62 (2H, m), 2.10-2.14 (6H, s), 2.23 (2H, d), 2.32-2.34 (1H, m), 2.44-2.47 (1H, m), 3.07-3.15 (2H, m), 3.21 (3H, s), 3.63-3.67 (1H, m), 3.78 (1H, d), 3.97-4.01 (1H, m), 4.17 (1H, d), 4.48 (3H, s), 6.32 (1H, t), 6.77 (1H, s), 7.48-7.52 (2H, m), 8.19-8.21 (2H, m), 8.79 (1H, s)

Example 35b: $^1$H NMR (400.13 MHz, DMSO-$d_6$) δ 1.24 (3H, d), 1.68 (2H, t), 3.15 (2H, d), 3.21 (3H, s), 3.25 (4H, s), 3.38 (2H, t), 3.50 (1H, d), 3.67 (1H, d), 3.76-3.79 (1H, m), 4.01 (1H, m), 4.17 (1H, d), 4.48 (3H, s), 6.21 (1H, s), 6.77 (1H, s), 7.48-7.51 (2H, m), 8.19-8.22 (2H, m), 8.70 (1H, s)

Example 35c: $^1$H NMR (400.13 MHz, DMSO-$d_6$) δ 1.25 (3H, d), 1.85-1.88 (4H, m), 3.21 (3H, s), 3.40 (5H, m), 3.47-3.54 (1H, m), 3.64-3.67 (1H, m), 3.78 (1H, d), 3.97-4.01 (1H, m), 4.18 (1H, d), 4.48 (3H, s), 6.78 (1H, s), 7.63-7.66 (2H, m), 8.19-8.22 (2H, m), 8.31 (1H, s)

Example 35d: $^1$H NMR (400.13 MHz, DMSO-$d_6$) δ δ 1.25 (3H, d), 3.21 (3H, s), 3.33-3.34 (1H, m), 3.46 (5H, t), 3.61-3.63 (4H, m), 3.64-3.67 (1H, m), 3.78 (1H, d), 3.97-4.01 (1H, m), 4.19 (1H, d), 4.49 (3H, s), 6.79 (1H, s), 7.57-7.61 (2H, m), 8.21-8.23 (2H, m), 8.74 (1H, s)

Example 35e: $^1$H NMR (400.13 MHz, DMSO-$d_6$) δ 1.19-1.30 (4H, m), 1.31-1.39 (1H, m), 1.67 (2H, d), 1.71-1.72 (1H, m), 1.74-1.78 (2H, m), 3.09-3.12 (1H, m), 3.22 (3H, d), 3.48 (1H, d), 3.63-3.67 (1H, m), 3.78 (1H, d), 3.84 (1H, d), 3.83-3.88 (1H, m), 3.97-4.01 (1H, m), 4.19 (1H, d), 4.48-4.51 (3H, m), 4.69 (1H, s), 6.76 (1H, t), 7.57-7.59 (2H, m), 8.19-8.22 (2H, m), 8.69 (1H, s)

Example 35f: $^1$H NMR (400.13 MHz, DMSO-$d_6$) δ 1.24 (3H, d), 1.31 (9, s), 3.20 (3H, s), 3.22 (1H, d), 3.47-3.53 (1H, m), 3.63-3.67 (1H, m), 3.78 (1H, d), 3.97-4.01 (1H, m), 4.17 (1H, d), 4.48 (3H, s), 6.06 (1H, s), 6.77 (1H, s), 7.43-7.47 (2H, m), 8.19-8.21 (2H, m), 8.48 (1H, s)

Example 35g: $^1$H NMR (400.13 MHz, DMSO-$d_6$) δ 1.24 (3H, d), 2.18 (6H, s), 2.34 (2 h t), 3.17-3.25 (5H, m), 3.47-3.53 (1H, m), 3.63-3.67 (1H, m), 3.78 (1H, d), 3.97-4.01 (1H, m), 4.17 (1H, d), 4.48 (3H, s), 6.16 (1H, t), 6.77 (1H, s), 7.47-7.51 (2H, m), 8.19-8.22 (2H, m), 8.89 (1H, s)

Example 35h: ¹H NMR (400.13 MHz, DMSO-d₆) δ 1.24 (3H d), 3.21 (5H, t), 3.46 (3H, t), 3.52 (1H, d), 3.63-3.67 (1H, m), 3.78 (1H, d), 3.97-4.01 (1H, m), 4.15-4.19 (1H, m), 4.48 (3H, s), 4.73 (1H, s), 6.26 (1H, t), 6.77 (1H, s), 7.48-7.50 (2H, m), 8.21 (2H, d), 8.82 (1H, s)

Example 35i: ¹H NMR (400.13 MHz, DMSO-d₆) δ 1.25 (3H, d), 1.38 (2H, d), 1.70 (1H, d), 1.89 (1H, s), 2.74-2.78 (1H, m), 2.96 (1H, s), 3.20 (3H, s), 3.47-3.50 (1H, m), 3.51 (1H, s), 3.66-3.67 (1H, m), 3.77-3.80 (2H, m), 3.98 (2H, d), 4.17 (1H, d), 4.48 (3H, s), 4.83 (1H, d), 6.78 (1H, s), 7.57-7.59 (2H, m), 8.19-8.21 (2H, m), 8.66 (1H, s)

Example 35j: ¹H NMR (400.13 MHz, DMSO-d₆) δ 1.25 (3H, d), 2.26 (6H, s), 2.67-2.69 (2H, m), 2.95 (3H, s), 3.21 (3H, s), 3.40 (3H, t), 3.47-3.54 (1H, m), 3.64-3.67 (1H, m), 3.78 (1H, d), 3.97-4.01 (1H, m), 4.18 (1H, d), 4.49 (3H, s), 6.78 (1H, s), 7.50-7.53 (2H, m), 8.20-8.23 (2H, m), 9.51 (1H, s)

Example 35k: ¹H NMR (400.13 MHz, DMSO-d₆) δ 1.24 (3H, d), 2.39 (2H, d), 2.41 (4H, d), 3.21 (3H, s), 3.24 (2H, t), 3.47-3.53 (1H, m), 3.58-3.63 (5H, m), 3.67 (1H, d), 3.78 (1H, d), 3.97-4.01 (1H, m), 4.17 (1H, d), 4.48 (3H, s), 6.17 (1H, t), 6.77 (1H, s), 7.49-7.51 (2H, m), 8.21 (2H, d), 8.88 (1H, s)

Example 35l: ¹H NMR (400.13 MHz, DMSO-d₆) δ 1.25 (3H, d), 3.19-3.23 (3H, m), 3.26 (1H, s), 3.63-3.67 (1H, m), 3.78 (1H, d), 3.97-4.01 (1H, m), 4.16-4.19 (1H, m), 4.32 (2H, d), 4.48 (3H, s), 6.63 (1H, t), 6.78 (1H, s), 6.93 (2H, s), 7.51-7.53 (2H, m), 8.22 (2H, d), 8.93 (1H, s), 11.84 (1H, s)

Example 35m: ¹H NMR (400.13 MHz, DMSO-d₆) δ 0.69-0.73 (2H, m), 0.88-0.93 (2H, m), 1.25 (3H, d), 2.70-2.76 (1H, m), 2.88 (3H, s), 3.21 (3H, s), 3.22-3.25 (1H, m), 3.47-3.54 (1H, m), 3.64-3.67 (1H, m), 3.78 (1H, d), 3.97-4.01 (1H, m), 4.19 (1H, d), 4.49 (3H, s), 6.79 (1H, s), 7.62-7.65 (2H, m), 8.21-8.23 (2H, m), 8.39 (1H, s)

Example 35n: ¹H NMR (400.13 MHz, DMSO-d₆) δ 1.21 (3H, d), 1.25 (3H, d), 3.15-3.23 (1H, m), 3.20 (3H, s), 3.36-3.42 (2H, m), 3.50 (1H, d), 3.53-3.57 (1H, m), 3.64-3.68 (2H, m), 3.75 (1H, s), 3.78 (2H, d), 3.85-3.88 (1H, m), 3.97-4.01 (1H, m), 4.20 (2H, d), 4.49 (3H, s), 6.79 (1H, s), 7.58-7.61 (2H, m), 8.21-8.23 (2H, m), 8.65 (1H, s).

Test (a): Example (35) 0.064 µM; Example (35a) 6.4 µM; Example (35b) 0.42 µM; Example (35c) 3.4 µM; Example (35d) 3.2 µM; Example (35e) 2.5 µM; Example (35f) 0.82 µM; Example (35g) 0.66 µM; Example (35h) 0.024 µM; Example (35i) 0.77 µM; Example (35j) 3.6 µM; Example (35k) 1.2 µM; Example (35l) 0.47 µM; Example (35m) 2 µM; Example (35n) 1.1 µM.

The preparation of phenyl N-[4-[4-[(3S)-3-methylmorpholin-4-yl]-6-(methylsulfonylmethyl)pyrimidin-2-yl]phenyl]carbamate was described earlier

EXAMPLE 36

3-Cyclopropyl-1-[4-[4-[(3S)-3-methylmorpholine-4-carbonyl]-6-[(3S)-3-methylmorpholin-4-yl]pyrimidin-2-yl]phenyl]urea

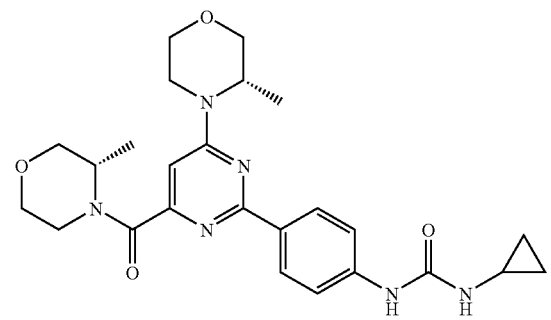

2-[4-(Cyclopropylcarbamoylamino)phenyl]-6-[(3S)-3-methylmorpholin-4-yl]pyrimidine-4-carboxylic acid (95 mg) was dissolved in DMF (3 mL) and (3S)-3-methylmorpholine added. DIPEA (0.125 mL) and HATU (137 mg) were added and the reactions stirred at RT for 3 h before being concentrated in vacuo and partitioned between DCM (25 mL) and water (25 mL). The organic layer was dried over magnesium sulphate, filtered and evaporated to dryness to give the desired material as a solid (88 mg).

NMR Spectrum: ¹H NMR (400.13 MHz, DMSO-d₆) δ 0.40-0.44 (2H, m), 0.63-0.67 (2H, m), 1.24 (6H, m), 2.52-2.61 (1H, m), 3.23-3.29 (2H, m) 3.41-3.42 (1H, m), 3.46-3.47 (1H, m), 3.50-3.55 (2H, m), 3.60 (2H, d), 3.70-3.81 (2H, m), 3.97 (2H, d), 4.17 (1H, s), 4.53 (1H, s), 6.43 (1H, s), 6.74 (1H, d), 7.51 (2H, d), 8.20 (2H, t), 8.54 (1H, s)

Mass Spectrum; M+H⁺ 480.

The following samples were prepared in an analogous fashion

| Example | Structure | NAME | LCMS MH+ |
|---|---|---|---|
| 36a | 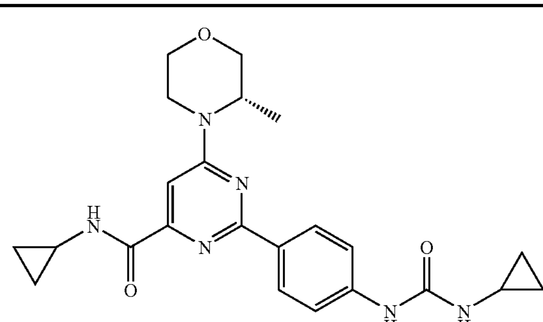 | N-cyclopropyl-2-[4-(cyclopropylcarbamoylamino)phenyl]-6-[(3S)-3-methylmorpholin-4-yl]pyrimidine-4-carboxamide | 436 |

-continued

| Example | Structure | NAME | LCMS MH+ |
|---|---|---|---|
| 36b | 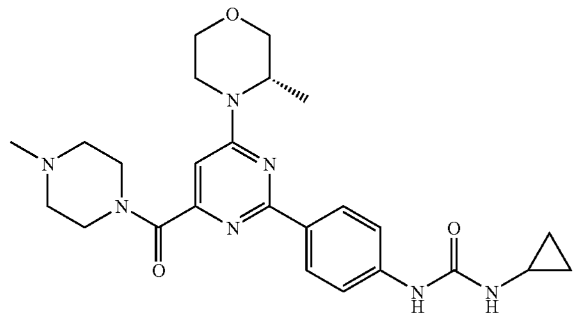 | 3-cyclopropyl-1-[4-[4-[(3S)-3-methylmorpholin-4-yl]-6-(4-methylpiperazine-1-carbonyl)pyrimidin-2-yl]phenyl]urea | 479 |

Example 36a: $^1$H NMR (400.13 MHz, DMSO-$d_6$) δ 0.39-0.44 (2H, m), 0.56-0.61 (2H, m), 0.65-0.68 (2H, m), 0.74-0.76 (2H, m), 1.24 (3H, d), 2.52-2.59 (1H, m), 2.53-2.61 (1H, m), 3.25 (1H, s), 3.50 (1H, d), 3.63-3.67 (1H, m), 3.77 (1H, d), 3.96-4.00 (1H, m), 4.25 (1H, s), 4.53 (1H, s), 6.42-6.43 (1H, m), 7.12 (1H, d), 7.51 (2H, d), 8.38-8.41 (2H, m), 8.56 (1H, s), 8.69 (1H, d).

Example 36b: $^1$H NMR (400.13 MHz, DMSO-$d_6$) δ 0.40-0.44 (2H, m), 0.63-0.67 (2H, m), 1.24 (3H, d), 2.25-2.26 (3H, m), 2.40-2.48 (2H, m), 2.43-2.48 (2H, m), 2.52-2.61 (1H, m), 3.18-3.25 (1H, m), 3.46-3.52 (3H, m), 3.62-3.66 (3H, m), 3.76 (1H, d), 3.95-3.99 (1H, m), 4.22 (1H, d), 4.55 (1H, s), 6.44 (1H, d), 6.73 (1H, s), 7.50-7.52 (2H, m), 8.18-8.20 (2H, m), 8.54 (1H, s).

Test (a): Example (36) 0.062 µM; Example (36a) 2.9 µM; Example (36b) 0.18 µM.

The preparation of 2-[4-(cyclopropylcarbamoylamino)phenyl]-6-[(3S)-3-methylmorpholin-4-yl]pyrimidine-4-carboxylic acid is described below.

2-[4-(Cyclopropylcarbamoylamino)phenyl]-6-[(3S)-3-methylmorpholin-4-yl]pyrimidine-4-carboxylic acid

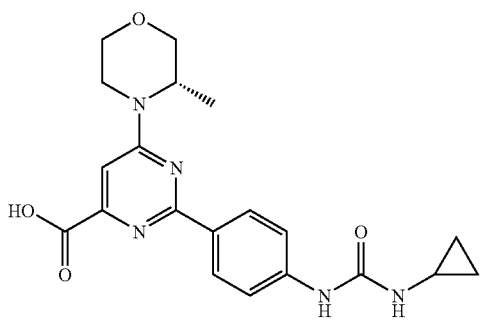

Methyl 2-[4-(cyclopropylcarbamoylamino)phenyl]-6-[(3S)-3-methylmorpholin-4-yl]pyrimidine-4-carboxylate (350 mg) was dissolved in water (15 mL) containing sodium hydroxide (67 mg) and the reaction was allowed to stir at RT for 1 h. A further 2 equivalents of sodium hydroxide were added along with THF (3 mL). The reaction was stirred for another 1 h then the THF removed under reduced pressure and the aqueous solution partitioned with ethyl acetate (15 mL). The aqueous layer was acidified with concentrated hydrochloric acid and the precipitate was filtered and dried in a vac-oven at 50° C. for 18 h to give the desired material (350 mg) as a white solid.

NMR Spectrum: $^1$H NMR (400.13 MHz, DMSO-$d_6$) δ 0.40-0.44 (2H, m), 0.60-0.64 (2H, m), 1.22 (3H, d), 2.52-2.58 (1H, m), 3.17-3.21 (1H, m), 3.46-3.53 (1H, m), 3.63-3.66 (1H, m), 3.75 (1H, d), 3.95-3.99 (1H, m), 4.14-4.17 (1H, m), 4.48 (1H, d), 6.92 (1H, s), 7.28 (1H, s), 7.56 (2H, d), 8.22 (2H, d), 9.41 (1H, s)

Mass Spectrum; M+H$^+$ 398.

Methyl 2-[4-(cyclopropylcarbamoylamino)phenyl]-6-[(3S)-3-methylmorpholin-4-yl]pyrimidine-4-carboxylate

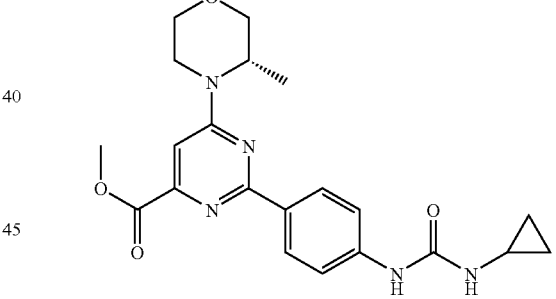

Methyl 6-[(3S)-3-methylmorpholin-4-yl]-2-[4-(phenoxycarbonylamino)phenyl]pyrimidine-4-carboxylate (547 mg) was dissolved in DMF (8 mL) and triethylamine (0.59 mL) followed by cyclopropylamine (0.491 mL) added. The reaction was stirred at 40° C. for 2 hours then the mixture was vacuumed to dryness and partitioned between DCM (50 mL) and water (50 mL). The organic layer was dried over magnesium sulphate and vacuumed to dryness then chromatographed on silica, eluting with 5% methanol in DCM, to give the desired material (351 mg) as a white solid.

NMR Spectrum: $^1$H NMR (400.13 MHz, DMSO-$d_6$) δ 0.41-0.44 (2H, m), 0.63-0.68 (2H, m), 1.25 (3H, d), 2.52-2.58 (1H, m), 2.67-2.69 (1H, m), 3.47-3.53 (1H, m), 3.63-3.67 (1H, m), 3.76 (1H, d), 3.91 (3H, s), 3.96-4.00 (1H, m), 4.23-4.27 (1H, m), 4.58 (1H, s), 6.43 (1H, d), 7.14 (1H, s), 7.51-7.53 (2H, m), 8.22-8.25 (2H, m), 8.56 (1H, s)

Mass Spectrum; M+H$^+$ 412.

Methyl 6-[(3S)-3-methylmorpholin-4-yl]-2-[4-(phenoxycarbonylamino)phenyl]pyrimidine-4-carboxylate

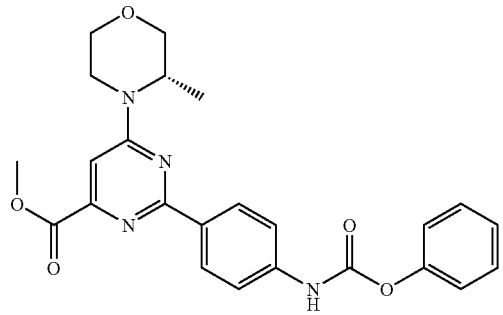

Methyl 2-(4-aminophenyl)-6-[(3S)-3-methylmorpholin-4-yl]pyrimidine-4-carboxylate (400 mg) was dissolved in dioxane (10 mL) and sodium bicarbonate (154 mg) and phenylchloroformate (0.154 mL) added dropwise. The mixture was stirred at RT for 16 hours then the dioxane removed under reduced pressure and the residue partitioned between water (50 mL) and ethyl acetate (50 mL). The organic layer was dried over magnesium sulphate, filtered and evaporated to give the desired material as a brown foam (624 mg).

NMR Spectrum: $^1$H NMR (400.13 MHz, DMSO-$d_6$) δ 1.26 (3H, d), 3.11 (1H, s), 3.47-3.54 (1H, m), 3.58 (1H, s), 3.63-3.67 (1H, m), 3.73 (1H, d), 3.91 (3H, s), 3.96-4.00 (1H, m), 4.27 (1H, s), 6.73-6.78 (1H, m), 7.14-7.20 (1H, m), 7.24-7.30 (2H, m), 7.43-7.48 (2H, m), 7.64-7.66 (2H, m), 8.32-8.34 (2H, m), 10.46 (1H, s)

Mass Spectrum; M+H$^+$ 449.

Methyl 2-(4-aminophenyl)-6-[(3S)-3-methylmorpholin-4-yl]pyrimidine-4-carboxylate

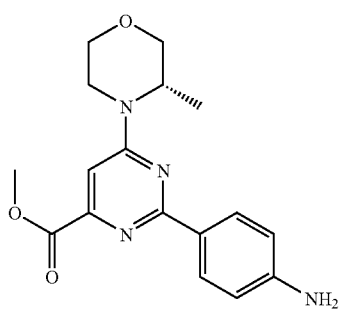

2-(4-Aminophenyl)-6-[(3S)-3-methylmorpholin-4-yl]pyrimidine-4-carboxylic acid (1.15 g) was dissolved in methanol (15 mL), sulfuric acid (0.01 mL) was added and the reaction was heated at 80° C. for 24 h. A small quantity of activated molecular sieve 4A was added to the reaction and stirred for 2 h. The reaction was filtered, vacuumed to dryness then suspended in ethyl acetate (250 mL) and washed once with a saturated solution of sodium bicarbonate (250 mL). The organic layer was filtered, dried over magnesium sulphate and vacuumed to dryness to give the desired material as a brown solid (405 mg).

NMR Spectrum: $^1$H NMR (400.13 MHz, DMSO-$d_6$) δ 1.23 (3H, d), 3.08 (1H, s), 3.45-3.52 (1H, m), 3.62-3.66 (1H, m), 3.75 (1H, d), 3.89 (3H, s), 3.97 (1H, d), 4.21 (1H, d), 4.55 (1H, s), 5.59 (2H, d), 6.59-6.63 (2H, m), 7.04 (1H, s), 8.06-8.08 (2H, m)

Mass Spectrum; M+H$^+$ 329.

2-(4-Aminophenyl)-6-[(3S)-3-methylmorpholin-4-yl]pyrimidine-4-carboxylic acid

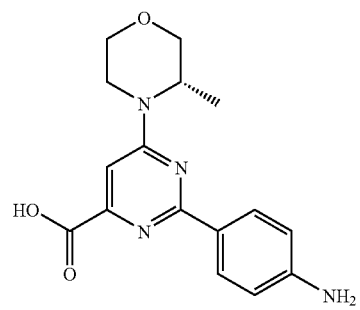

Methyl 2-chloro-6-[(3S)-3-methylmorpholin-4-yl]pyrimidine-4-carboxylate (1.00 g) was dissolved in an 18% DMF in a mixture of 7:3:2 DME:water:ethanol (10 mL). (4-Aminophenyl)boronic acid pinacol ester (1.21 g) and 2M sodium carbonate (5 mL) was then added and the solution and degassed for 5 min. Dichlorobis(triphenylphosphine) palladium catalyst (130 mg) was added and the reaction refluxed at 90° C. for 18 h under nitrogen atmosphere. The reaction was allowed to cool, concentrated in vacuo, and the residue partitioned between ethyl acetate (100 mL) and water (100 mL). The aqueous phase was filtered and the volume reduced in vacuo. The resultant solution was acidified with concentrated hydrochloric acid and vacuumed to dryness give the desired material.

Mass Spectrum; M+H$^+$ 315.

The preparation of methyl 2-chloro-6-[(3S)-3-methylmorpholin-4-yl]pyrimidine-4-carboxylate was described earlier.

EXAMPLE 37

3-Cyclopropyl-1-[4-[4-(2-hydroxypropan-2-yl)-6-[(3S)-3-methylmorpholin-4-yl]pyrimidin-2-yl]phenyl]urea

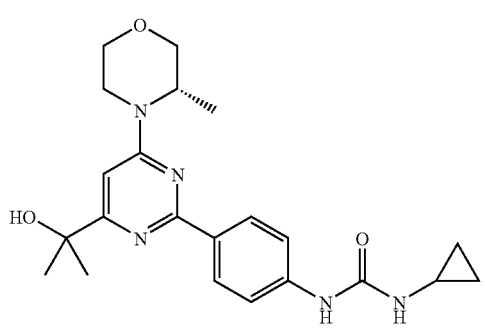

2-[2-Chloro-6-[(3S)-3-methylmorpholin-4-yl]pyrimidin-4-yl]propan-2-ol (70 mg) was dissolved in an 18% DMF in a mixture of 7:3:2 DME:water:ethanol (4 mL) and 4-(3-cyclopropylureido)phenylboronic acid (98 mg) and 2M sodium carbonate (1 mL) added. Dichlorobis(triphenylphosphine) palladium catalyst (10 mg) was added and the solution heated in a microwave reactor at 100° C. for 0.5 h. The mixture was acidified with concentrated hydrochloric acid and loaded directly onto a SCX-2 column (10 g), column washed with methanol then product eluted with 7N ammonia in methanol, to give the desired material (55 mg) as a white solid.

NMR Spectrum: $^1$H NMR (400.13 MHz, DMSO-d$_6$) δ 0.41-0.44 (2H, m), 0.62-0.67 (2H, m), 1.23 (3H, d), 1.45 (6H, s), 2.54 (1H, t), 3.19-3.23 (1H, m), 3.46-3.52 (1H, m), 3.62-3.66 (1H, m), 3.77 (1H, d), 3.96 (1H, d), 4.14-4.17 (1H, m), 4.50 (1H, s), 5.17 (1H, s), 6.41 (1H, d), 6.80 (1H, s), 7.48 (2H, d), 8.23 (2H, d), 8.50 (1H, s)

Mass Spectrum; M+H$^+$ 412.

Test (a): 0.051 µM.

The preparation of 2-[2-chloro-6-[(3S)-3-methylmorpholin-4-yl]pyrimidin-4-yl]propan-2-ol is described below.

2-[2-Chloro-6-[(3S)-3-methylmorpholin-4-yl]pyrimidin-4-yl]propan-2-ol

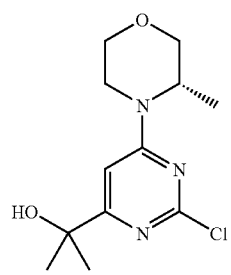

Methyl 2-chloro-6-[(3S)-3-methylmorpholin-4-yl]pyrimidine-4-carboxylate (300 mg) was dissolved in dry THF and cooled to −78° C. Methylmagnesium bromide (3.0M in diethyl ether, 0.74 mL) was added dropwise over 2 min then the reaction allowed to stir at −78° C. for 20 min before allowing to warm to RT. The reaction was stirred for a further 20 min and then quenched with water (2 mL). The reaction was reduced to dryness and partitioned between ethyl acetate (50 mL) and water (50 mL) and the organic layer dried over magnesium sulphate and vacuumed to dryness to the desired material as a white solid (291 mg).

NMR Spectrum: (400.13 MHz, DMSO-d$_6$) δ 1.16-1.23 (3H, m), 1.36 (6H, s), 3.15-3.23 (1H, m), 3.40-3.47 (1H, m), 3.56-3.60 (1H, m), 3.71 (1H, d), 3.91-3.94 (2H, m), 4.34 (1H, s), 5.28 (1H, s), 6.87 (1H, s).

Mass Spectrum; M+H$^+$ 272.

The preparation of methyl 2-chloro-6-[(3S)-3-methylmorpholin-4-yl]pyrimidine-4-carboxylate was described earlier.

EXAMPLE 38

1-[4-[4-(2-Hydroxypropan-2-yl)-6-[(3S)-3-methylmorpholin-4-yl]pyrimidin-2-yl]phenyl]-3-[(1-methylpyrazol-4-yl)methyl]urea

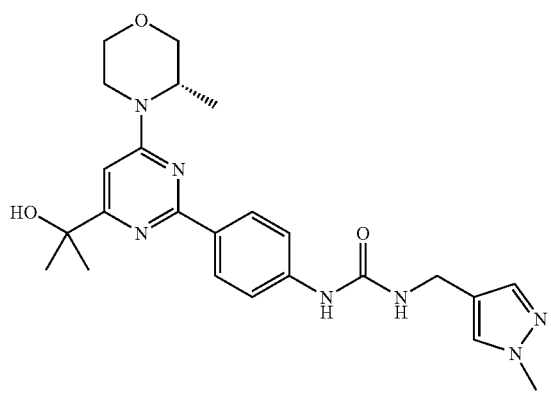

2-[2-Chloro-6-[(3S)-3-methylmorpholin-4-yl]pyrimidin-4-yl]propan-2-ol (70 mg) was dissolved in an 18% DMF in a mixture of 7:3:2 DME:water:ethanol (4 mL). 3-[(1-Methylpyrazol-4-yl)methyl]-1-[4-(4,4,5,5-tetramethyl-1,3,2-dioxaborolan-2-yl)phenyl]urea (115 mg) and 2M sodium carbonate (1 mL) were added. Dichlorobis(triphenylphosphine) palladium catalyst (10 mg) was added and the solution heated in a microwave reactor at 100° C. for 0.5 h. The mixture was acidified with concentrated hydrochloric acid and loaded directly onto a SCX-2 column (10 g), column washed with methanol then product eluted with 7N ammonia in methanol, to give the desired material (55 mg) as a white solid.

NMR Spectrum: $^1$H NMR (400.13 MHz, DMSO-d$_6$) δ 1.23 (3H, d), 1.45 (6H, s), 3.16-3.23 (1H, m), 3.46-3.52 (1H, m), 3.62-3.66 (1H, m), 3.78-3.80 (1H, m), 3.75-3.81 (3H, s), 3.96-3.99 (1H, m), 4.13 (3H, d), 4.49-4.52 (1H, m), 5.17 (1H, s), 6.39 (1H, t), 6.80 (1H, s), 7.35 (1H, s), 7.47-7.49 (2H, m), 7.59 (1H, s), 8.22-8.24 (2H, m), 8.65 (1H, s)

Mass Spectrum; M+H$^+$ 466.

Test (a): 1.3 µM.

The preparation of 2-[2-chloro-6-[(3S)-3-methylmorpholin-4-yl]pyrimidin-4-yl]propan-2-ol was described earlier.

The preparation of 3-[(1-methylpyrazol-4-yl)methyl]-1-[4-(4,4,5,5-tetramethyl-1,3,2-dioxaborolan-2-yl)phenyl]urea is described below.

3-[(1-Methylpyrazol-4-yl)methyl]-1-[4-(4,4,5,5-tetramethyl-1,3,2-dioxaborolan-2-yl)phenyl]urea

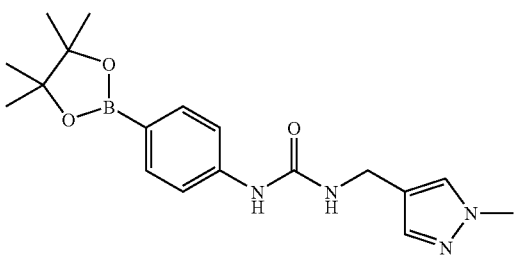

(4-Aminophenyl)boronic acid pinacol ester (200 mg) was dissolved in dry THF (5 mL) and sodium bicarbonate (116 mg) added followed by the dropwise addition of phenylchloroformate (0.115 mL). The mixture was stirred at RT for 1 hour. (1-Methylpyrazol-4-yl)methanamine (102 mg) was added and the reaction left to stir at RT for 2 h before being heated to 40° C. for 16 h. The mixture was concentrated in vacuo and the residue partitioned between DCM (25 mL) and water (25 mL). The organics were dried over magnesium sulphate, filtered and vacuumed to dryness. The material was chromatographed on silica, eluting with ethyl acetate, to give the desired material (232 mg) as a white solid.

NMR Spectrum: $^1$H NMR (400.13 MHz, DMSO-$d_6$) δ 1.28 (12H, s), 3.79 (3H, s), 4.11 (2H, d), 6.39 (1H, t), 7.34 (1H, s), 7.39-7.41 (2H, m), 7.52-7.54 (2H, m), 7.59 (1H, s), 8.56 (1H, s)

Mass Spectrum; M+H$^+$ 357.

EXAMPLE 39

1-[4-[4-(Hydroxymethyl)-6-[(3S)-3-methylmorpholin-4-yl]pyrimidin-2-yl]phenyl]-3-(1,2-oxazol-3-yl)urea

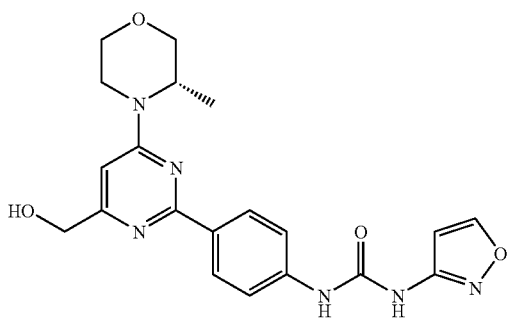

[2-Chloro-6-[(3S)-3-methylmorpholin-4-yl]pyrimidin-4-yl]methanol (500 mg) was dissolved in an 18% DMF in a mixture of 7:3:2 DME:water:ethanol (10 mL). 3-(1,2-Oxazol-3-yl)-1-[4-(4,4,5,5-tetramethyl-1,3,2-dioxaborolan-2-yl)phenyl]urea (811 mg) and 2M aqueous sodium carbonate solution (4 mL) were then added to the solution and the resultant mixture degassed for 5 min. Dichlorobis(triphenylphosphine) palladium catalyst (73 mg) was added and the solution refluxed at 90° C. for 7 h under nitrogen atmosphere. The reaction was allowed to cool then neutralised with concentrated hydrochloric acid and loaded directly onto a SCX-2 column (50 g), the column was washed with methanol and the product eluted with 7N ammonia in methanol. The material was further purified by chromatography on silica, eluting with 5% methanol in DCM, to give the desired material (318 mg) as a white solid.

NMR Spectrum: $^1$H NMR (400.13 MHz, DMSO-$d_6$) δ 1.24 (3H, d), 3.20-3.24 (1H, m), 3.47-3.53 (1H, m), 3.63-3.67 (1H, m), 3.77 (1H, d), 3.96-4.00 (1H, m), 4.16-4.19 (1H, m), 4.47 (2H, d), 4.50 (1H, s), 5.40 (1H, t), 6.69 (1H, s), 6.87 (1H, d), 7.53-7.56 (2H, m), 8.27-8.29 (2H, m), 8.75-8.75 (1H, m), 9.03 (1H, d), 9.60 (1H, s)

Mass Spectrum; M+H$^+$ 411.

Test (a): 0.075 μM.

The preparation of [2-chloro-6-[(3S)-3-methylmorpholin-4-yl]pyrimidin-4-yl]methanol has been described earlier.

The preparation of 3-(1,2-oxazol-3-yl)-1-[4-(4,4,5,5-tetramethyl-1,3,2-dioxaborolan-2-yl)phenyl]urea is described below.

3-(1,2-Oxazol-3-yl)-1-[4-(4,4,5,5-tetramethyl-1,3,2-dioxaborolan-2-yl)phenyl]urea

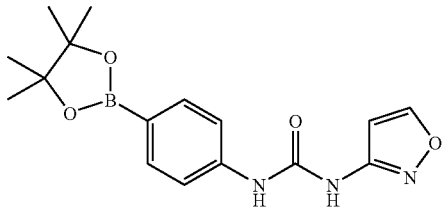

(4-Aminophenyl)boronic acid pinacol ester (1 g) was dissolved in dry THF (30 mL), sodium bicarbonate (576 mg) added followed by the dropwise addition of phenylchloroformate (0.575 mL). The mixture was stirred at RT for 1 hour then. 3-aminoisoxazole (0.506 mL) added and the reaction left to stir at 40° C. for 16 h. More 3-aminoisoxazole (0.506 mL) and sodium bicarbonate (576 mg) were added and the reaction heated to 75° C. for 8 h. before the mixture was concentrated in vacuo and partitioned between DCM (50 mL) and water (50 mL). The organic layer was dried over magnesium sulphate, filtered and vacuumed to dryness. The residue was chromatographed on silica, eluting with ethyl acetate, to give the desired compound (1.05 g) as a white solid.

NMR Spectrum: $^1$H NMR (400.13 MHz, DMSO-$d_6$) δ 1.29 (12 h, s), 5.89 (1H, d), 6.86 (1H, d), 7.47-7.49 (2H, m), 7.61-7.63 (2H, m), 8.32 (1H, t), 8.75 (1H, d)

Mass Spectrum; M+H$^+$ 330.

EXAMPLE 40

N-[2-[[6-[(3S)-3-methylmorpholin-4-yl]-2-[4-(1,2-oxazol-3-ylcarbamoylamino)phenyl]pyrimidin-4-yl]methylsulfonyl]ethyl]acetamide

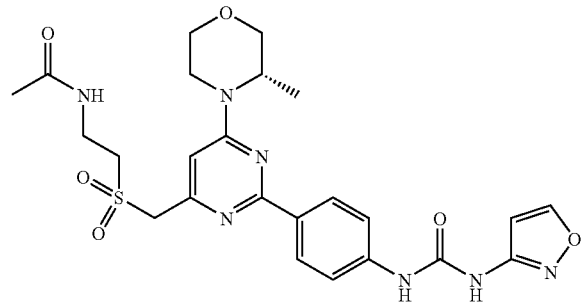

1-[4-[4-[(3S)-3-Methylmorpholin-4-yl]-6-(methylsulfonyloxymethyl)pyrimidin-2-Y$^3$]phenyl]-3-(1,2-oxazol-3-yl)urea (89 mg, 0.18 mmol) was partially dissolved in acetonitrile (4 mL) and N-(2-sulfanylethyl)acetamide (0.034 mL, 0.32 mmol) added. DBU (0.055 mL, 0.36 mmol) was added and the reaction stirred at RT for 6 h before being vacuumed to dryness. The material was dissolved in 1,4-Dioxane (2 mL) and a solution of m-CPBA (75%) (158 mg) in 1,4 Dioxane (2 mL), followed immediately by a solution of sodium permanganate (175 mg) in water (1 mL), added. The reaction was allowed to stir at RT for 1 h then loaded onto a SCX-2 (10 g) column, the column was washed with methanol and the product eluted with 7N ammonia in methanol. The material was further purified by prep-HPLC (basic) to give the desired material as a solid (13 mg).

NMR Spectrum: $^1$H NMR (399.9 MHz, DMSO-$d_6$) δ 1.26 (3H, d), 1.84 (3H, s), 3.24 (1H, d), 3.52 (2H, t), 3.54 (1H, s), 3.58 (2H, t), 3.65-3.68 (1H, m), 3.79 (1H, d), 3.98-4.02 (1H, m), 4.20 (1H, s), 4.54 (3H, m), 6.82 (1H, s), 6.88 (1H, d), 7.56-7.59 (2H, m), 8.16-8.17 (1H, m), 8.28-8.31 (2H, m), 8.76-8.77 (1H, m), 9.09 (1H, d), 9.62 (1H, s)

Mass Spectrum; M+H$^+$ 544.

The following compounds was prepared in an analogous fashion from 1-[4-[4-[(3S)-3-methylmorpholin-4-yl]-6-(methylsulfonyloxymethyl)pyrimidin-2-yl]phenyl]-3-(1,2-oxazol-3-yl)urea and the appropriate thiol.

1-[4-[4-(Hydroxymethyl)-6-[(3S)-3-methylmorpholin-4-yl]pyrimidin-2-yl]phenyl]-3-(1,2-oxazol-3-yl)urea (300 mg) was partially dissolved in DCM (10 mL) and triethylamine (0.153 mL) and the solution was cooled to 0° C. Methane sulfonyl chloride was added (0.086 mL) and the reaction was stirred for 45 mins at RT. The reaction was then washed with water (2 mL) and dried over magnesium sulphate. The solution was vacuumed to dryness to give the desired material as a yellow solid.

Mass Spectrum; M+H$^+$ 489.

| Example | Structure | NAME | LCMS MH+ |
|---|---|---|---|
| 40a | 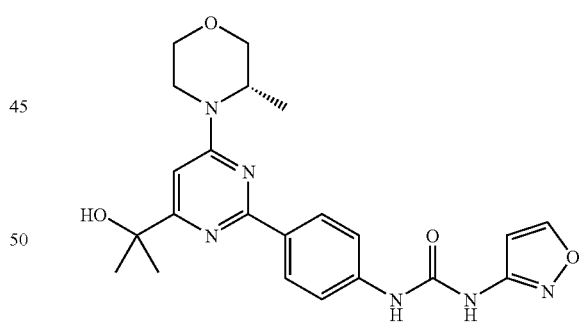 | 1-[4-[4-(2-hydroxyethylsulfonylmethyl)-6-[(3S)-3-methylmorpholin-4-yl]pyrimidin-2-yl]phenyl]-3-(1,2-oxazol-3-yl)urea | 503 |

Example 40a: $^1$H NMR (399.9 MHz, DMSO-$d_6$) δ 1.26 (3H, d), 3.24 (1H, d), 3.53 (3H, t), 3.65-3.68 (1H, m), 3.79 (1H, d), 3.93 (2H, q), 3.98-4.02 (1H, m), 4.20 (1H, s), 4.51 (3H, d), 5.20 (1H, t), 6.80 (1H, s), 6.88-6.88 (1H, m), 7.58 (2H, d), 8.29-8.31 (2H, m), 8.76 (1H, s), 9.09 (1H, d), 9.64 (1H, s).

Test (c): Example (40) 0.1 μM; Example (40a) 0.055 μM.

The preparation of 1-[4-[4-[(3S)-3-methylmorpholin-4-yl]-6-(methylsulfonyloxymethyl)pyrimidin-2-yl]phenyl]-3-(1,2-oxazol-3-yl)urea is described below.

1-[4-[4-[(3S)-3-Methylmorpholin-4-yl]-6-(methylsulfonyloxymethyl)pyrimidin-2-yl]phenyl]-3-(1,2-oxazol-3-yl)urea

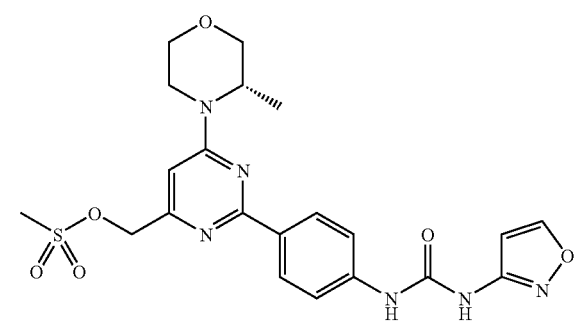

EXAMPLE 41

1-[4-[4-(2-Hydroxypropan-2-yl)-6-[(3S)-3-methylmorpholin-4-yl]pyrimidin-2-yl]phenyl]-3-(1,2-oxazol-3-yl)urea 2-[2-Chloro-6-[(3S)-3-methylmorpholin-4-yl]pyrimidin-4-yl]propan-2-ol (160 mg, 0.59 mmol) was added to 3-(1,2-oxazol-3-yl)-1-[4-(4,4,5,5-tetramethyl-1,3,2-dioxaborolan-2-yl)phenyl]urea (242 mg) and Dichlorobis (triphenylphosphine) palladium catalyst (21 mg) in an 18% DMF in a mixture of 7:3:2 DME:water:ethanol (6 mL). The reaction was heated to 100° C. for 30 minutes in the microwave reactor and cooled to RT. The reaction mixture was acidified with 2M hydrochloric acid and the crude material loaded onto a SCX (10 g) column, the desired material was eluted with 7N ammonia in methanol. The material was further purified by preparative HPLC using decreasingly polar mixtures of water (containing 1% NH3) and MeCN as eluents, to give the desired material (52 mg) as a white solid.

NMR Spectrum: $^1$H NMR (399.9 MHz, DMSO-d$_6$) δ 1.24 (3H, d), 1.47 (6H, s), 3.18-3.25 (1H, m), 3.47-3.54 (1H, m), 3.64-3.67 (1H, m), 3.78 (1H, d), 3.97-4.01 (1H, m), 4.16-4.19 (1H, m), 4.51-4.53 (1H, m), 5.20 (1H, s), 6.84 (1H, s), 6.88 (1H, d), 7.55-7.57 (2H, m), 8.30-8.32 (2H, m), 8.76 (1H, d), 9.06 (1H, s), 9.61 (1H, s)

Mass Spectrum: M+H$^+$ 439.4

Test (c): 0.047 μM.

The preparation of both 2-[2-chloro-6-[(3S)-3-methylmorpholin-4-yl]pyrimidin-4-yl]propan-2-ol and 3-(1,2-oxazol-3-yl)-1-[4-(4,4,5,5-tetramethyl-1,3,2-dioxaborolan-2-yl)phenyl]urea were described earlier.

EXAMPLE 42

3-Cyclopropyl-1-[4-[4-(hydroxymethyl)-6-[(3S)-3-methylmorpholin-4-yl]pyrimidin-2-yl]phenyl]urea

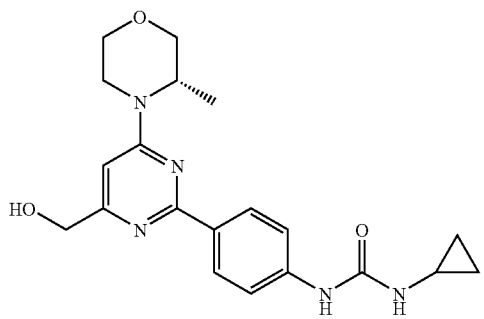

[2-Chloro-6-[(3S)-3-methylmorpholin-4-yl]pyrimidin-4-yl]methanol (3.30 g) was dissolved in an 18% DMF in a mixture of 7:3:2 DME:water:ethanol (50 mL). 4-(3-cyclopropylureido)phenylboronic acid (4.92 g) and 2M sodium carbonate (5 mL) were then added and the solution degassed for 5 min. Dichlorobis(triphenylphosphine) palladium catalyst (476 mg) was then added to the solution and refluxed at 90° C. for 7 h under a nitrogen atmosphere. The reaction was allowed to cool, evaporated, and the residue partitioned between DCM (200 mL) and water (200 mL). The organic layer was dried over magnesium sulphate, evaporated, and purified by chromatography on silica, eluting with 5% methanol in DCM, to give the desired material (4.33 g) as a yellow solid.

NMR Spectrum: $^1$H NMR (400.13 MHz, DMSO-d$_6$) δ 0.40-0.44 (2H, m), 0.62-0.67 (2H, m), 1.23 (3H, d), 2.54-2.58 (1H, m), 3.17-3.22 (1H, m), 3.46-3.52 (1H, m), 3.62-3.66 (1H, m), 3.77 (1H, d), 3.96-3.99 (1H, m), 4.15-4.18 (1H, m), 4.45 (2H, d), 4.49 (1H, d), 5.38 (1H, t), 6.41 (1H, d), 6.66 (1H, s), 7.46-7.50 (2H, m), 8.18-8.22 (2H, m), 8.49 (1H, s), Mass Spectrum; M+H$^+$ 384.

Test (a): 0.19 μM.

The preparation of [2-chloro-6-[(3S)-3-methylmorpholin-4-yl]pyrimidin-4-yl]methanol has been described earlier.

EXAMPLE 43

3-Cyclopropyl-1-[4-[4-[(3S)-3-methylmorpholin-4-yl]-6-(pyridin-4-ylsulfonylmethyl)pyrimidin-2-yl]phenyl]urea

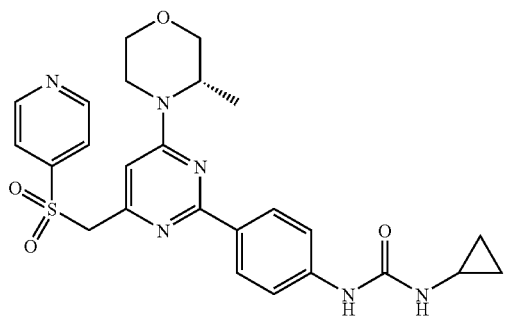

3-Cyclopropyl-1-[4-[4-[(3S)-3-methylmorpholin-4-yl]-6-(methylsulfonyloxymethyl)pyrimidin-2-yl]phenyl]urea (100 mg, 0.24 mmol) was partially dissolved in acetonitrile (4 mL) and pyridine-4-thiol (0.38 mmol) added. The reaction was stirred for 1 h at RT then DBU (0.065 mL, 0.43 mmol) added and the reaction stirred at RT for 18 h. The reaction was evaporated to dryness and dissolved in 1,4-Dioxane (2 mL). A solution of m-CPBA (75%) (94 mg) in 1,4 Dioxane (2 mL), followed immediately by a solution of sodium permanganate (104 mg) in water (1 mL), was added to the reaction and allowed to stir at RT for 1 h. A further solution of m-CPBA (75%) (94 mg) in 1,4 Dioxane (1 mL), followed immediately by a solution of sodium permanganate (104 mg) in water (0.5 mL), was added and reaction stirred at RT for 1 h. The reaction mixture was loaded onto a SCX-2 (10 g) column, the column was washed with methanol and the product eluted with 7N ammonia in methanol. The material was further purified by prep-HPLC (basic) to give the desired material as a solid (10 mg).

NMR Spectrum: $^1$H NMR (400.13 MHz, DMSO-d$_6$) δ 0.40-0.44 (2H, m), 0.63-0.67 (2H, m), 1.21 (3H, d), 2.58-2.61 (1H, m), 3.15-3.25 (1H, m), 3.45-3.52 (1H, m), 3.61-3.65 (1H, m), 3.77 (1H, d), 3.96-3.99 (1H, m), 4.10-4.14 (1H, m), 4.38 (1H, s), 4.86 (2H, t), 6.41-6.42 (1H, m), 6.71 (1H, s), 7.37 (2H, d), 7.66 (2H, d), 7.81-7.82 (2H, m), 8.50 (1H, s), 8.90-8.91 (2H, m)

Mass Spectrum; M+H$^+$ 509.

The following compounds were prepared in an analogous fashion using the appropriate thiol.

| Example | Structure | NAME | LCMS MH+ |
|---|---|---|---|
| 43a | 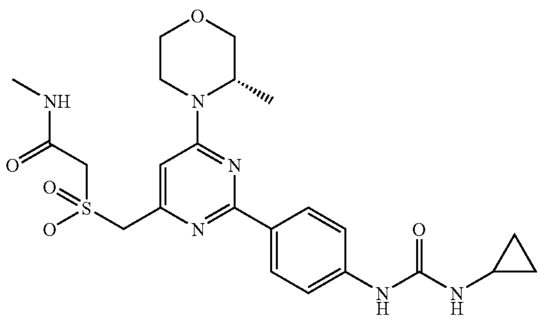 | 2-[[2-[4-(cyclopropylcarbamoylamino)phenyl]-6-[(3S)-3-methylmorpholin-4-yl]pyrimidin-4-yl]methylsulfonyl]-N-methyl-acetamide | 503 |
| 43b | 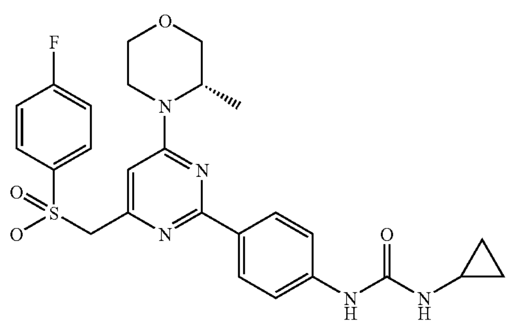 | 3-cyclopropyl-1-[4-[4-[(4-fluorophenyl)sulfonylmethyl]-6-[(3S)-3-methylmorpholin-4-yl]pyrimidin-2-yl]phenyl]urea | 526 |
| 43c | 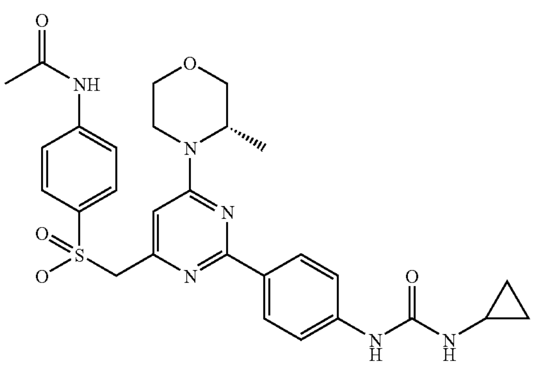 | N-[4-[[2-[4-(cyclopropylcarbamoylamino)phenyl]-6-[(3S)-3-methylmorpholin-4-yl]pyrimidin-4-yl]methylsulfonyl]phenyl]acetamide | 565 |
| 43d | 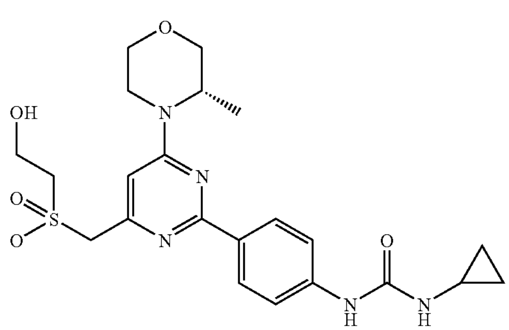 | 3-cyclopropyl-1-[4-[4-(2-hydroxyethylsulfonylmethyl)-6-[(3S)-3-methylmorpholin-4-yl]pyrimidin-2-yl]phenyl]urea | 476 |

-continued

| Example | Structure | NAME | LCMS MH+ |
|---|---|---|---|
| 43e | 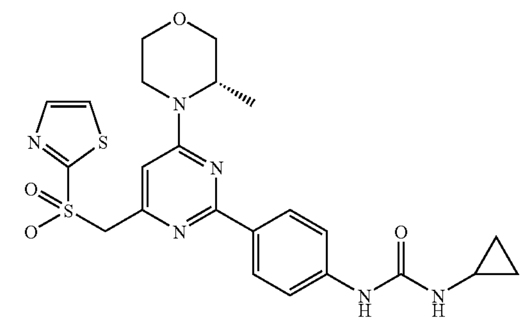 | 3-cyclopropyl-1-[4-[4-[(3S)-3-methylmorpholin-4-yl]-6-(1,3-thiazol-2-ylsulfonylmethyl)pyrimidin-2-yl]phenyl]urea | 515 |
| 43f | 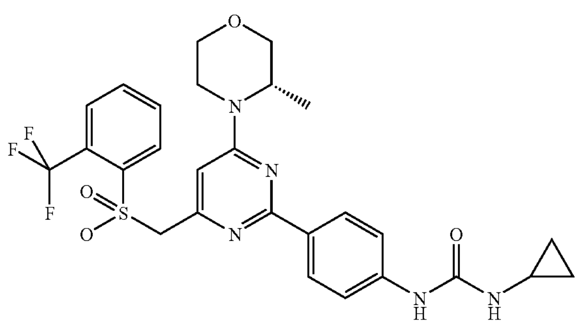 | 3-cyclopropyl-1-[4-[4-[(3S)-3-methylmorpholin-4-yl]-6-[[2-(trifluoromethyl)phenyl]sulfonylmethyl]pyrimidin-2-yl]phenyl]urea | 576 |
| 43g | 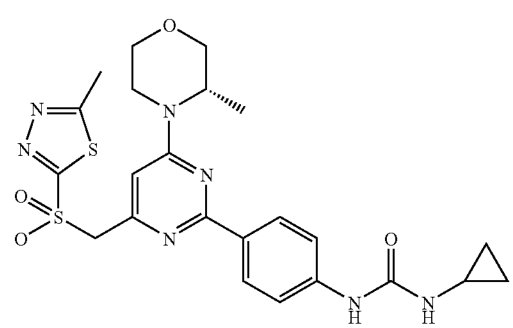 | 3-cyclopropyl-1-[4-[4-[(3S)-3-methylmorpholin-4-yl]-6-[(5-methyl-1,3,4-thiadiazol-2-yl)sulfonylmethyl]pyrimidin-2-yl]phenyl]urea | 530 |
| 43h | 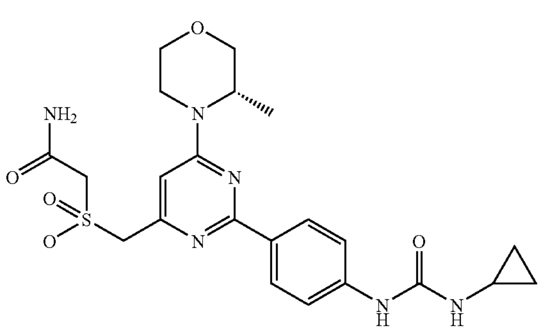 | 2-[[2-[4-(cyclopropylcarbamoylamino)phenyl]-6-[(3S)-3-methylmorpholin-4-yl]pyrimidin-4-yl]methylsulfonyl]acetamide | 489 |

-continued

| Example | Structure | NAME | LCMS MH+ |
|---|---|---|---|
| 43i | 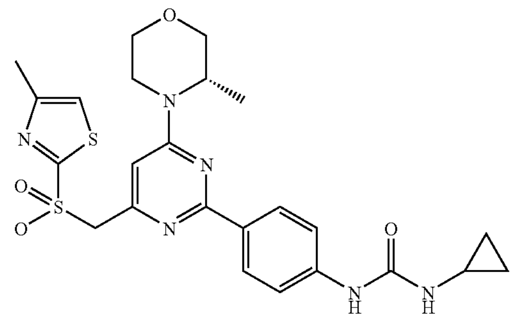 | 3-cyclopropyl-1-[4-[4-[(3S)-3-methylmorpholin-4-yl]-6-[(4-methyl-1,3-thiazol-2-yl)sulfonylmethyl]pyrimidin-2-yl]phenyl]urea | 529 |
| 43j | 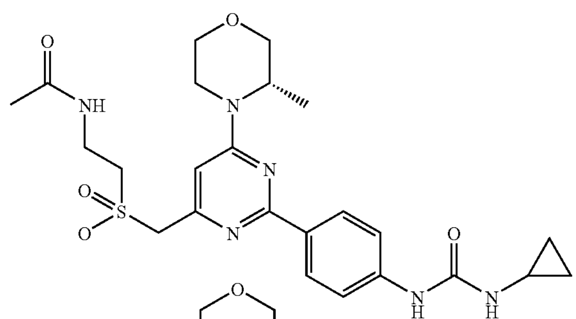 | N-[2-[[2-[4-(cyclopropylcarbamoylamino)phenyl]-6-[(3S)-3-methylmorpholin-4-yl]pyrimidin-4-yl]methylsulfonyl]ethyl]acetamide | 517 |
| 43k | 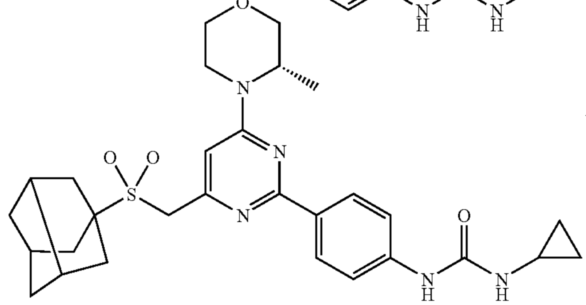 | 1-[4-[4-(1-adamantylsulfonylmethyl)-6-[(3S)-3-methylmorpholin-4-yl]pyrimidin-2-yl]phenyl]-3-cyclopropyl-urea | 598 |

Example 43a: $^1$H NMR (400.13 MHz, DMSO-d$_6$) δ 0.40-0.44 (2H, m), 0.63-0.67 (2H, m), 1.23-1.25 (3H, m), 2.57-2.60 (1H, m), 2.67-2.70 (3H, m), 3.19-3.25 (1H, m), 3.47-3.53 (1H, m), 3.63-3.67 (1H, m), 3.78 (1H, d), 3.97-4.01 (1H, m), 4.15-4.19 (1H, m), 4.29 (2H, s), 4.48 (1H, s), 4.67 (2H, s), 6.43-6.44 (1H, m), 6.77 (1H, s), 7.50 (2H, d), 8.19 (2H, d), 8.31 (1H, t), 8.54 (1H, s)

Example 43b: $^1$H NMR (400.13 MHz, DMSO-d$_6$) δ 0.40-0.44 (2H, m), 0.63-0.67 (2H, m), 1.20 (3H, d), 2.52-2.60 (1H, m), 3.15-3.20 (1H, m), 3.45-3.51 (1H, m), 3.61-3.65 (1H, m), 3.76 (1H, d), 3.95-3.99 (1H, m), 4.10-4.13 (1H, m), 4.38 (1H, s), 4.71 (2H, s), 6.40 (1H, d), 6.65 (1H, s), 7.38-7.41 (2H, m), 7.43-7.48 (2H, m), 7.79 (2H, d), 7.85-7.89 (2H, m), 8.51 (1H, s)

Example 43c: $^1$H NMR (400.13 MHz, DMSO-d$_6$) δ 0.40-0.44 (2H, m), 0.63-0.67 (2H, m), 1.19 (3H, d), 2.13 (3H, s), 2.53-2.61 (1H, m), 3.15-3.20 (1H, m), 3.43-3.50 (1H, m), 3.60-3.63 (1H, m), 3.75 (1H, d), 3.94-3.98 (1H, m), 4.09 (1H, s), 4.34 (1H, s), 4.60 (2H, s), 6.41-6.42 (1H, m), 6.55 (1H, s), 7.39 (2H, d), 7.70 (2H, d), 7.77 (2H, d), 7.83 (2H, d), 8.48 (1H, s), 10.37 (1H, s)

Example 43d: $^1$H NMR (400.13 MHz, DMSO-d$_6$) δ 0.40-0.44 (2H, m), 0.63-0.67 (2H, m), 1.24 (3H, d), 2.59-2.61 (1H, m), 3.15-3.20 (1H, m), 3.51 (3H, t), 3.63-3.67 (1H, m), 3.78 (1H, d), 3.92 (2H, q), 3.97-4.01 (1H, m), 4.16-4.19 (1H, m), 4.50 (3H, s), 5.18 (1H, t), 6.44 (1H, d), 6.76 (1H, s), 7.50-7.52 (2H, m), 8.21-8.23 (2H, m), 8.54 (1H, s)

Example 43e: $^1$H NMR (400.13 MHz, DMSO-d$_6$) δ 0.40-0.44 (2H, m), 0.63-0.67 (2H, m), 1.20 (3H, d), 2.52-2.61 (1H, m), 3.15-3.20 (1H, m), 3.45-3.52 (1H, m), 3.62-3.65 (1H, m), 3.77 (1H, d), 3.96-3.99 (1H, m), 4.12 (1H, d), 4.40 (2H, s), 4.90-4.91 (1H, m), 6.42 (1H, d), 6.71 (1H, s), 7.40-7.43 (2H, m), 7.84 (2H, d), 8.27-8.29 (2H, m), 8.50 (1H, s)

Example 43f: $^1$H NMR (400.13 MHz, DMSO-d$_6$) δ 0.40-0.44 (2H, m), 0.63-0.67 (2H, m), 1.20-1.22 (3H, m), 2.53 (1H, m), 3.17 (1H, d), 3.49 (1H, d), 3.62-3.66 (1H, m), 3.77 (1H, d), 3.95-3.99 (1H, m), 4.12 (1H, d), 4.40 (1H, s), 4.74-4.75 (2H, m), 6.42-6.42 (1H, m), 6.70 (1H, s), 7.37 (2H, d), 7.72 (2H, d), 7.80 (1H, d), 7.90 (2H, t), 8.08 (1H, d), 8.48 (1H, s)

Example 43g: $^1$H NMR (400.13 MHz, DMSO-d$_6$) δ 0.42 (2H, d), 0.63-0.67 (2H, m), 1.23 (3H, d), 2.53 (1H, d), 2.80 (3H, s), 3.20 (1H, d), 3.48 (1H, d), 3.62-3.66 (1H, m), 3.77 (1H, d), 4.12 (1H, d), 4.40 (2H, s), 5.04 (2H, t), 6.44 (1H, s), 6.80 (1H, s), 7.43 (2H, d), 7.79 (2H, d), 8.53 (1H, s)

Example 43i: $^1$H NMR (400.13 MHz, DMSO-d$_6$) δ 0.40-0.44 (2H, m), 0.63-0.67 (2H, m), 1.21 (3H, d), 2.60-2.61 (1H, m), 3.20 (1H, m), 3.34-3.39 (3H, m), 3.45-3.52 (1H, m), 3.62-3.66 (1H, m), 3.77 (1H, d), 3.96-4.00 (1H, m), 4.12 (1H, d), 4.41 (1H, s), 4.86-4.87 (2H, m), 6.41-6.42 (1H, m), 6.71 (1H, s), 7.41-7.44 (2H, m), 7.82 (1H, d), 7.87 (2H, d), 8.51 (1H, s)

Example 43j: $^1$H NMR (400.13 MHz, DMSO-$d_6$) δ 0.40-0.44 (2H, m), 0.63-0.67 (2H, m), 1.24 (3H, t), 1.83 (3H, s), 2.52-2.60 (1H, m), 3.19-3.25 (1H, m), 3.47-3.50 (2H, m), 3.52 (2H, d), 3.56 (2H, d), 3.63-3.67 (1H, m), 3.78 (1H, d), 3.97-4.01 (1H, m), 4.12 (1H, d), 4.50 (2H, d), 6.43 (1H, d), 6.78 (1H, s), 7.50 (2H, d), 8.19-8.22 (2H, m), 8.54 (1H, s), 9.00 (1H, s)

Example 43k: $^1$H NMR (400.13 MHz, DMSO-$d_6$) δ 0.40-0.44 (2H, m), 0.63-0.67 (2H, m), 1.24 (3H, d), 1.67 (6H, d), 2.03 (6H, s), 2.12 (3H, s), 2.53-2.60 (1H, m), 3.20-3.24 (1H, m), 3.47-3.51 (1H, m), 3.64-3.67 (1H, m), 3.78 (1H, d), 3.97-4.01 (1H, m), 4.12 (1H, d), 4.39-4.45 (3H, m), 6.43 (1H, d), 6.73 (1H, s), 7.49-7.51 (2H, m), 8.22 (2H, d), 8.53 (1H, s)

Test (a): Example (43) 0.076 μM; Example (43a) 0.087 μM; Example (43b) 0.15 μM; Example (43c) 0.013 μM; Example (43d) 0.011 μM; Example (43e) 0.13 μM; Example (43f) 0.11 μM; Example (43h) 0.0071 μM; Example (43i) 0.058 μM; Example (43j) 1.8 μM.

Test (c): Example (43g) 1.9 μM; Example (43k) 2.9 μM

The preparation of 3-cyclopropyl-1-[4-[4-[(3S)-3-methylmorpholin-4-yl]-6-(methylsulfonyloxymethyl)pyrimidin-2-yl]phenyl]urea is described below.

3-Cyclopropyl-1-[4-[4-[(3S)-3-methylmorpholin-4-yl]-6-(methylsulfonyloxymethyl)pyrimidin-2-yl]phenyl]urea

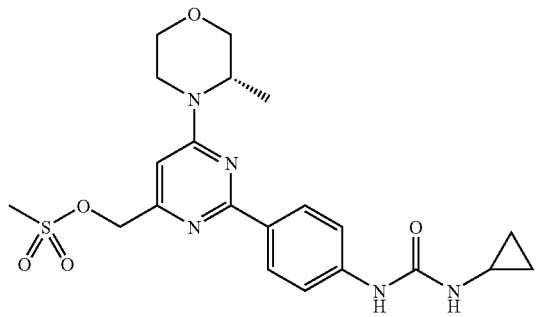

3-Cyclopropyl-1-[4-[4-(hydroxymethyl)-6-[(3S)-3-methylmorpholin-4-yl]pyrimidin-2-yl]phenyl]urea (1.83 g) was partially dissolved in DCM (50 mL) and triethylamine (1 mL) and the solution was cooled to 0° C. Methane sulfonyl chloride was added (0.56 mL) and the reaction was stirred for 45 mins at RT. The reaction was then washed with water (10 mL) and the organics dried over magnesium sulphate. The solution was vacuumed to dryness to give the desired material as a yellow solid.

Mass Spectrum; M+H$^+$ 462.

EXAMPLE 44

3-Cyclopropyl-1-[4-[4-(3-hydroxypropylsulfonylmethyl)-6-[(3S)-3-methylmorpholin-4-yl]pyrimidin-2-yl]phenyl]urea

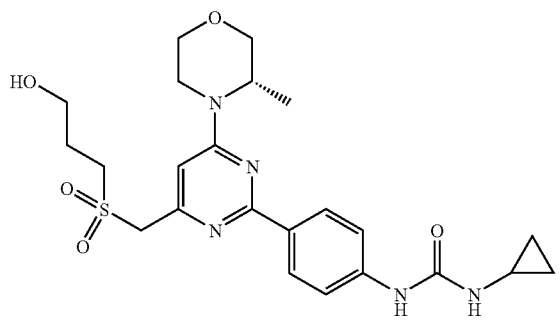

Sodium permanganate monohydrate (38 mg, 0.24 mmol) was added to m-CPBA (33.2 mg, 0.19 mmol) and 3-cyclopropyl-1-[4-[4-(3-hydroxypropylsulfanylmethyl)-6-[(3S)-3-methylmorpholin-4-yl]pyrimidin-2-yl]phenyl]urea (44 mg, 0.10 mmol) in Dioxane (2 mL) and Water (1 mL) at 20° C. The resulting solution was stirred at 20° C. for 45 minutes and the mixture loaded onto a SCX-3 (5 g) column, the desired product was eluted from the column using 7M ammonia in methanol. The material was further purified by preparative HPLC using decreasingly polar mixtures of water (containing 1% NH3) and acetonitrile as eluents, to give the desired material (19 mg) as a white solid.

NMR Spectrum: $^1$H NMR (400.13 MHz, DMSO-$d_6$) δ 0.40-0.44 (2H, m), 0.63-0.67 (2H, m), 1.24 (3H, d), 1.92-1.99 (2H, m), 2.53-2.60 (1H, m), 3.18-3.26 (1H, m), 3.39 (2H, q), 3.47-3.50 (1H, m), 3.55 (2H, q), 3.63-3.67 (1H, m), 3.78 (1H, d), 3.97-4.01 (1H, m), 4.16-4.19 (1H, m), 4.46 (3H, s), 4.72 (1H, t), 6.43 (1H, d), 6.78 (1H, s), 7.49-7.51 (2H, m), 8.20-8.23 (2H, m), 8.53 (1H, s)

Mass Spectrum; M+H$^+$ 490

Test (a): 1.8 μM.

The preparation of 3-cyclopropyl-1-[4-[4-(3-hydroxypropylsulfanylmethyl)-6-[(3S)-3-methylmorpholin-4-yl]pyrimidin-2-yl]phenyl]urea is described below.

3-Cyclopropyl-1-[4-[4-(3-hydroxypropylsulfanylmethyl)-6-[(3S)-3-methylmorpholin-4-yl]pyrimidin-2-yl]phenyl]urea

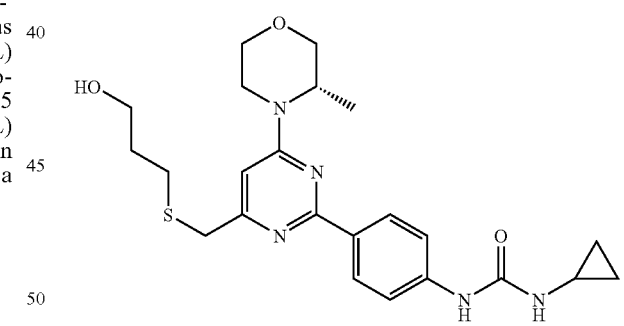

3-Cyclopropyl-1-[4-[4-[(3S)-3-methylmorpholin-4-yl]-6-(methylsulfonyloxymethyl)pyrimidin-2-yl]phenyl]urea (100 mg) was partially dissolved in acetonitrile (4 mL) and added to 3-sulfanylpropan-1-ol (0.38 mmol). The reactions was stirred for 1 h at RT. DBU (0.065 uL) was added to the reaction and the mixture left to stir at RT for 18 h. The mixture was concentrated in vacuo and purified by prep-HPLC (basic) to give the desired material (44 mg) as a white solid.

Mass Spectrum; M+H$^+$ 458.

The preparation of 3-cyclopropyl-1-[4-[4-[(3S)-3-methylmorpholin-4-yl]-6-(methylsulfonyloxymethyl)pyrimidin-2-yl]phenyl]urea was described earlier.

EXAMPLE 45

1-(2-Hydroxyethyl)-1-methyl-3-[4-[4-(methylsulfonylmethyl)-6-morpholin-4-yl-pyrimidin-2-yl]phenyl]urea

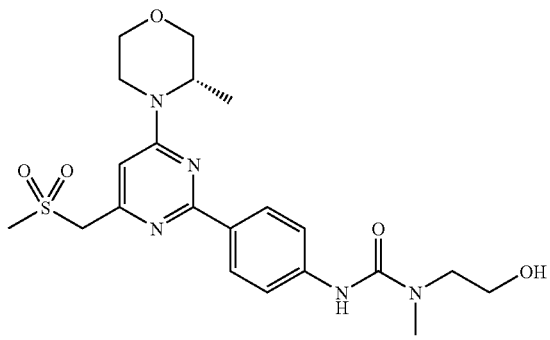

A solution of phenyl N-[4-[4-(methylsulfonylmethyl)-6-morpholin-4-yl-pyrimidin-2-yl]phenyl]carbamate (94 mg, 2 mmol) and triethylamine (0.09 mL, 9.2 mmol) in NMP (1 mL) was added to 2-methylaminoethanol (10 mmol). The mixture was heated at 70° C. for 2 hours and the reaction purified by prep HPLC, to give the desired compound.

LCMS Spectrum: MH+ 450, Retention Time 2.07 min.

The following compounds were made in an analogous fashion from either phenyl N-[4-[4-(methylsulfonylmethyl)-6-morpholin-4-yl-pyrimidin-2-yl]phenyl]carbamate or phenyl N-[4-[4-[(3S)-3-methylmorpholin-4-yl]-6-(methylsulfonylmethyl)pyrimidin-2-yl]phenyl]carbamate and the appropriate amine.

| Example | Structure | NAME | LCMS MH+ | Retention Time (min) |
|---|---|---|---|---|
| 45a | 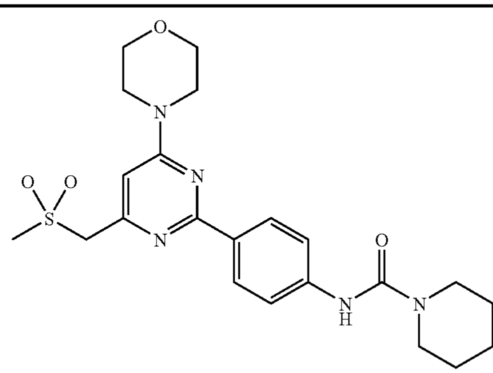 | N-[4-[4-(methylsulfonylmethyl)-6-morpholin-4-yl-pyrimidin-2-yl]phenyl]piperidine-1-carboxamide | 460 | 2.74 |
| 45b | 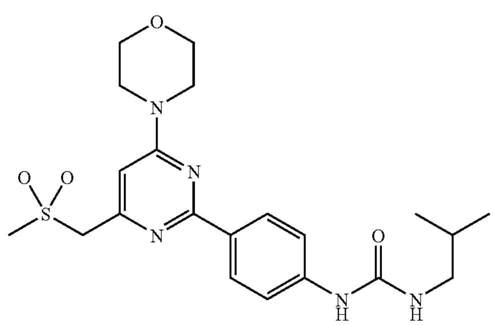 | 1-(2-methylpropyl)-3-[4-[4-(methylsulfonylmethyl)-6-morpholin-4-yl-pyrimidin-2-yl]phenyl]urea | 448 | 2.76 |
| 45c | 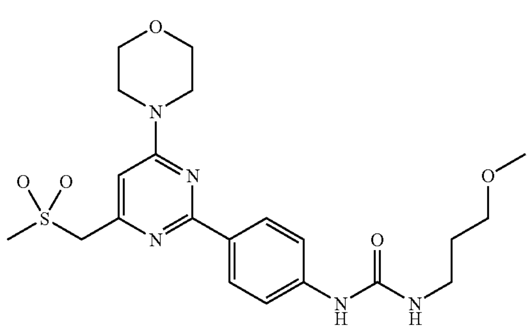 | 1-(3-methoxypropyl)-3-[4-[4-(methylsulfonylmethyl)-6-morpholin-4-yl-pyrimidin-2-yl]phenyl]urea | 464 | 2.46 |

-continued

| Example | Structure | NAME | LCMS MH+ | Retention Time (min) |
|---|---|---|---|---|
| 45d | 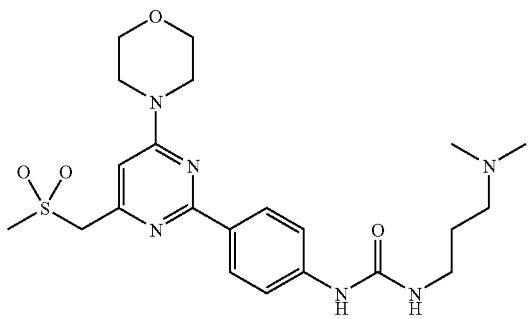 | 1-(4-dimethylaminobutyl)-3-[4-[4-(methylsulfonylmethyl)-6-morpholin-4-yl-pyrimidin-2-yl]phenyl]urea | 491 | 2.8 |
| 45e | 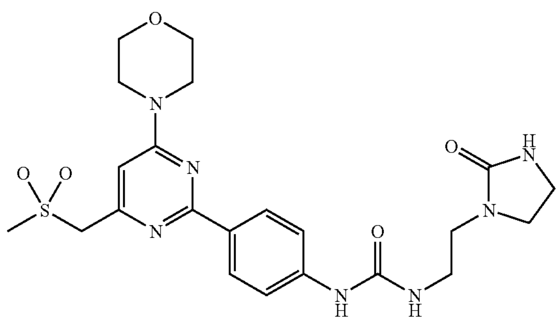 | 1-[4-[4-(methylsulfonylmethyl)-6-morpholin-4-yl-pyrimidin-2-yl]phenyl]-3-[2-(2-oxoimidazolidin-1-yl)ethyl]urea | 504 | 2.27 |
| 45f | 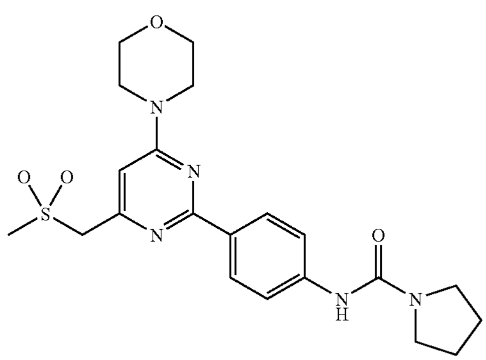 | N-[4-[4-(methylsulfonylmethyl)-6-morpholin-4-yl-pyrimidin-2-yl]phenyl]pyrrolidine-1-carboxamide | 446 | 2.56 |
| 45g | 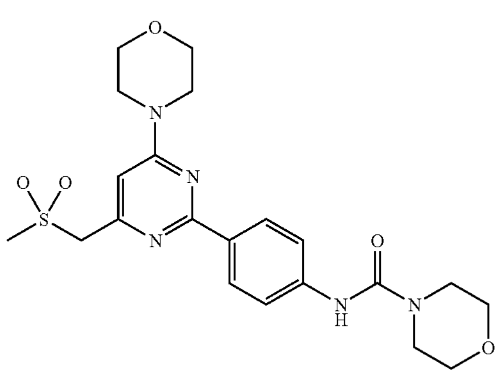 | N-[4-[4-(methylsulfonylmethyl)-6-morpholin-4-yl-pyrimidin-2-yl]phenyl]morpholine-4-carboxamide | 462 | 2.4 |

-continued

| Example | Structure | NAME | LCMS MH+ | Retention Time (min) |
| --- | --- | --- | --- | --- |
| 45h | 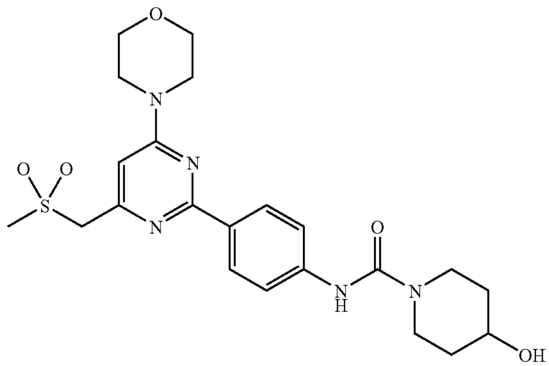 | 4-hydroxy-N-[4-[4-(methylsulfonylmethyl)-6-morpholin-4-yl-pyrimidin-2-yl]phenyl]piperidine-1-carboxamide | 476 | 2.28 |
| 45i | 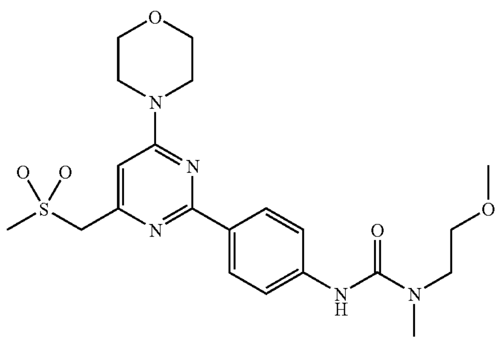 | 1-(1-methoxypropan-2-yl)-3-[4-[4-(methylsulfonylmethyl)-6-morpholin-4-yl-pyrimidin-2-yl]phenyl]urea | 464 | 2.51 |
| 45j | 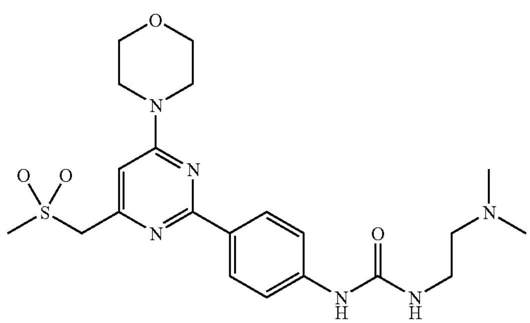 | 1-(2-dimethylaminoethyl)-3-[4-[4-(methylsulfonylmethyl)-6-morpholin-4-yl-pyrimidin-2-yl]phenyl]urea | 463 | 2.52 |
| 45k | 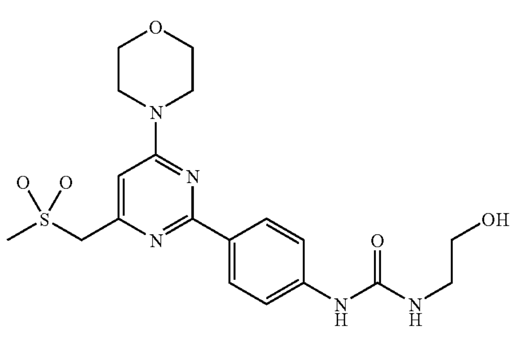 | 3-(2-hydroxyethyl)-1-[4-[4-(methylsulfonylmethyl)-6-morpholin-4-yl-pyrimidin-2-yl]phenyl]urea | 436 | 2.21 |

-continued

| Example | Structure | NAME | LCMS MH+ | Retention Time (min) |
|---|---|---|---|---|
| 45l | 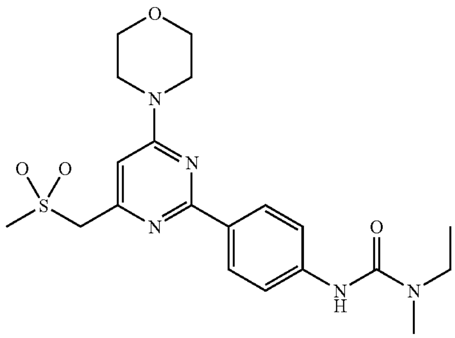 | 1-ethyl-1-methyl-3-[4-[4-(methylsulfonylmethyl)-6-morpholin-4-yl-pyrimidin-2-yl]phenyl]urea | 434 | 2.54 |
| 45m | 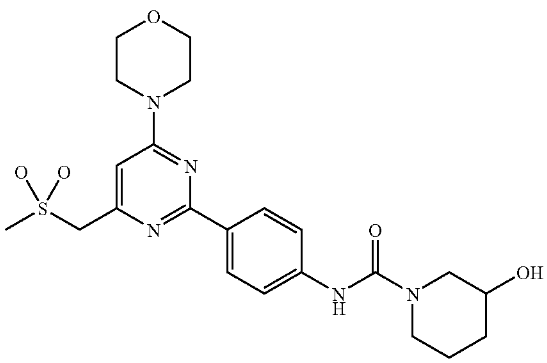 | 3-hydroxy-N-[4-[4-(methylsulfonylmethyl)-6-morpholin-4-yl-pyrimidin-2-yl]phenyl]piperidine-1-carboxamide | 476 | 2.35 |
| 45n | 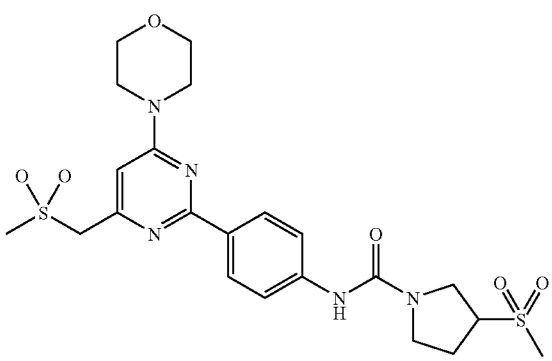 | 3-methylsulfonyl-N-[4-[4-(methylsulfonylmethyl)-6-morpholin-4-yl-pyrimidin-2-yl]phenyl]pyrrolidine-1-carboxamide | 524 | 2.34 |
| 45o | 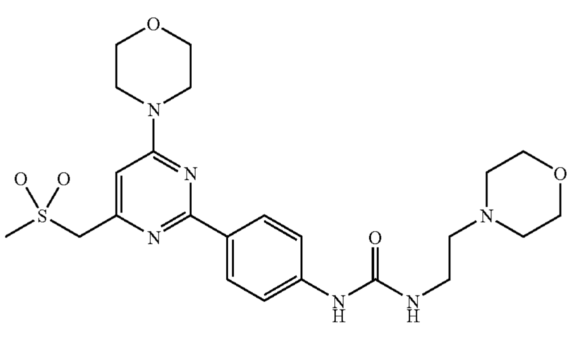 | 1-[4-[4-(methylsulfonylmethyl)-6-morpholin-4-yl-pyrimidin-2-yl]phenyl]-3-(2-morpholin-4-ylethyl)urea | 505 | 2.14 |

-continued

| Example | Structure | NAME | LCMS MH+ | Retention Time (min) |
|---|---|---|---|---|
| 45p | 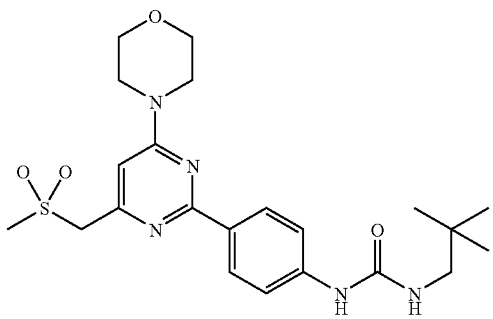 | 1-(2,2-dimethylpropyl)-3-[4-[4-(methylsulfonylmethyl)-6-morpholin-4-yl-pyrimidin-2-yl]phenyl]urea | 462 | 2.68 |
| 45q | 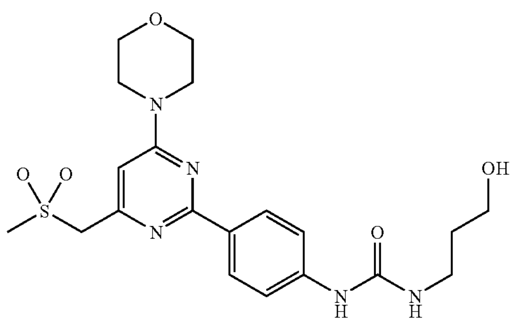 | 3-(3-hydroxypropyl)-1-[4-[4-(methylsulfonylmethyl)-6-morpholin-4-yl-pyrimidin-2-yl]phenyl]urea | 450 | 2.05 |
| 45r | 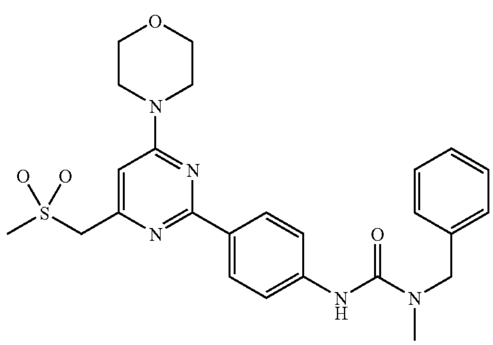 | 1-benzyl-1-methyl-3-[4-[4-(methylsulfonylmethyl)-6-morpholin-4-yl-pyrimidin-2-yl]phenyl]urea | 496 | 2.74 |
| 45s | 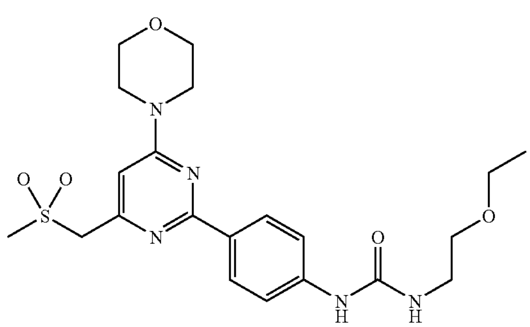 | 1-(2-ethoxyethyl)-3-[4-[4-(methylsulfonylmethyl)-6-morpholin-4-yl-pyrimidin-2-yl]phenyl]urea | 464 | 2.29 |

-continued

| Example | Structure | NAME | LCMS MH+ | Retention Time (min) |
|---|---|---|---|---|
| 45t | 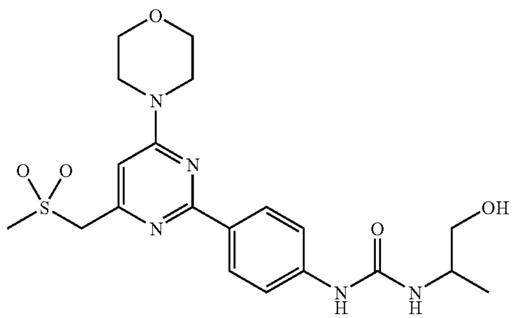 | 1-(1-hydroxypropan-2-yl)-3-[4-[4-(methylsulfonylmethyl)-6-morpholin-4-yl-pyrimidin-2-yl]phenyl]urea | 450 | 2.09 |
| 45u | 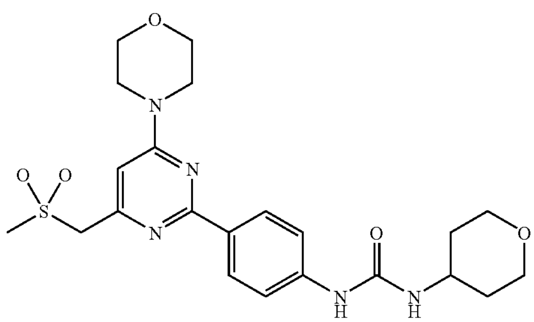 | 1-[4-[4-(methylsulfonylmethyl)-6-morpholin-4-yl-pyrimidin-2-yl]phenyl]-3-(oxan-4-yl)urea | 476 | 2.21 |
| 45v | 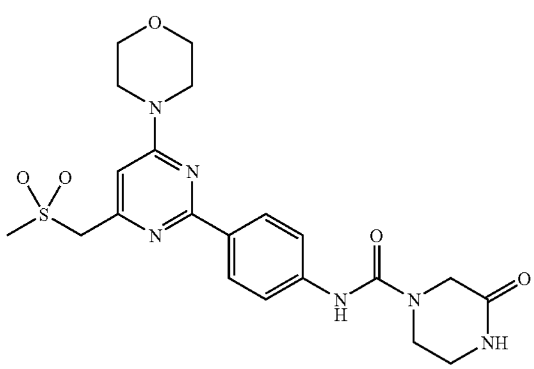 | [4-[4-(methylsulfonylmethyl)-6-morpholin-4-yl-pyrimidin-2-yl]phenyl]-3-oxo-piperazine-1-carboxamide | 475 | 2.00 |
| 45w | 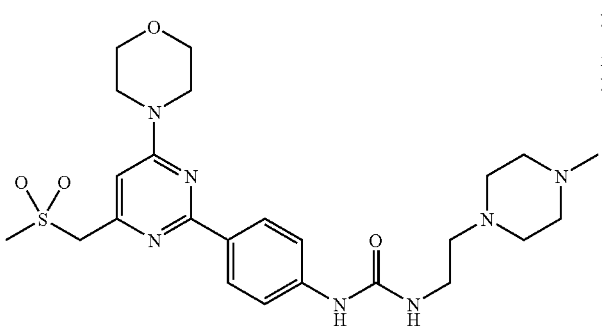 | 1-[2-(4-methylpiperazin-1-yl)ethyl]-3-[4-[4-(methylsulfonylmethyl)-6-morpholin-4-yl-pyrimidin-2-yl]phenyl]urea | 518 | 2.11 |

-continued

| Example | Structure | NAME | LCMS MH+ | Retention Time (min) |
|---|---|---|---|---|
| 45x | 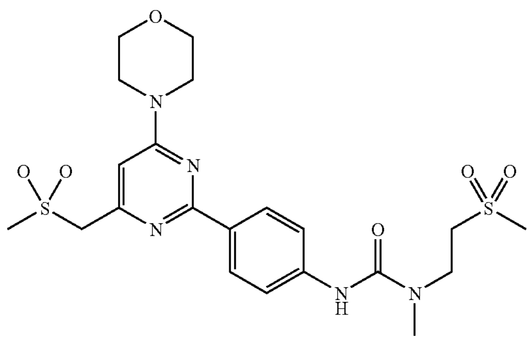 | 1-methyl-1-(2-methylsulfonylethyl)-3-[4-[4-(methylsulfonylmethyl)-6-morpholin-4-yl-pyrimidin-2-yl]phenyl]urea | 512 | 2.14 |
| 45y | 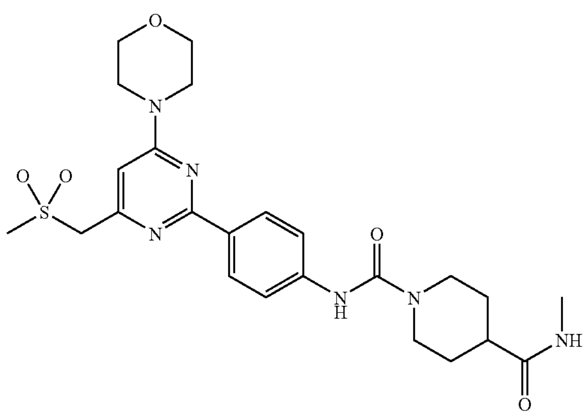 | N'-methyl-N-[4-[4-(methylsulfonylmethyl)-6-morpholin-4-yl-pyrimidin-2-yl]phenyl]piperidine-1,4-dicarboxamide | 516 | 2.07 |
| 45z | 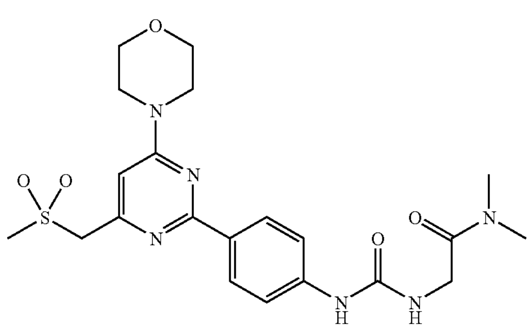 | N,N-dimethyl-2-[[4-[4-(methylsulfonylmethyl)-6-morpholin-4-yl-pyrimidin-2-yl]phenyl]carbamoylamino]acetamide | 477 | 2.11 |

| Example | Structure | NAME | LCMS MH+ | Retention Time (min) |
|---|---|---|---|---|
| 45aa | 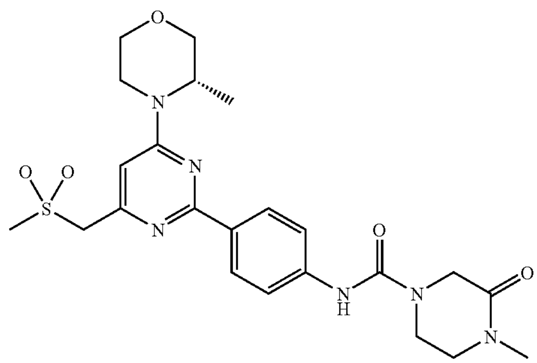 | 4-methyl-N-[4-[4-[(3S)-3-methylmorpholin-4-yl]-6-(methylsulfonylmethyl)pyrimidin-2-yl]phenyl]-3-oxo-piperazine-1-carboxamide | 489 | 1.23 |
| 45ab | 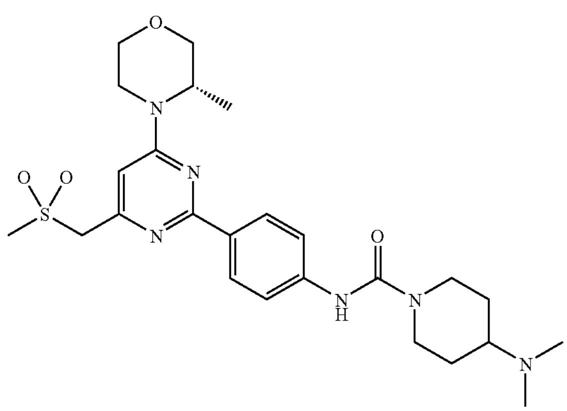 | 4-dimethylamino-N-[4-[4-[(3S)-3-methylmorpholin-4-yl]-6-(methylsulfonylmethyl)pyrimidin-2-yl]phenyl]piperidine-1-carboxamide | 518 | 1.6 |

Test (a): Example (45) 0.66 μM; Example (45a) 0.63 μM; Example (45b) 0.12 μM; Example (45c) 0.082 μM; Example (45d) 0.56 μM; Example (45e) 0.56 μM; Example (45f) 1.6 μM; Example (45g) 0.041 μM; Example (45h) 0.14 μM; Example (45i) 3 μM; Example (45j) 0.72 μM; Example (45k) 0.049 μM; Example (45l) 1.1 μM; Example (45m) 0.17 μM; Example (45n) 0.63 μM; Example (45o) 0.9 μM; Example (45p) 0.92 μM; Example (45q) 0.032 μM; Example (45r) 0.41 μM; Example (45s) 0.3 μM; Example (45t) 0.082 μM; Example (45u) 0.42 μM; Example (45v) 1.2 μM; Example (45w) 0.74 μM; Example (45x) 1.1 μM; Example (45y) 1.2 μM; Example (45z) 1 μM; Example (45aa) 0.83 μM; Example (45ab) 0.39 μM.

The preparation of phenyl N-[4-[4-(methylsulfonylmethyl)-6-morpholin-4-yl-pyrimidin-2-yl]phenyl]carbamate and phenyl N-[4-[4-[(3S)-3-methylmorpholin-4-yl]-6-(methylsulfonylmethyl)pyrimidin-2-yl]phenyl]carbamate were described earlier.

EXAMPLE 46

3-Methyl-1-[5-[4-[(3S)-3-methylmorpholin-4-yl]-6-(methylsulfonylmethyl)pyrimidin-2-yl]-1,3-thiazol-2-yl]urea

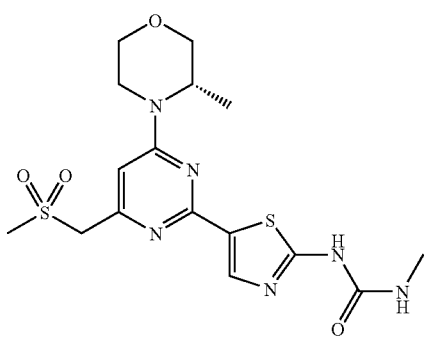

A mixture of phenyl N-[5-[4-[(3S)-3-methylmorpholin-4-yl]-6-(methylsulfonylmethyl)pyrimidin-2-yl]-1,3-thiazol-2-yl]carbamate (100 mg, 0.2 mmol), methylamine (1 mmol), and triethylamine (0.085 mL, 0.6 mmol) in NMP (2 mL), was heated at 70° C. for 2 hours. The material was purified by prep HPLC to give the desired material as a white solid (27 mg).

LCMS Spectrum: MH+ 427, Retention Time 1.44 min

The following compounds were prepared in an analogous fashion.

| Example | Structure | NAME | LCMS MH+ | Retention Time (min) |
|---------|-----------|------|----------|----------------------|
| 46a | 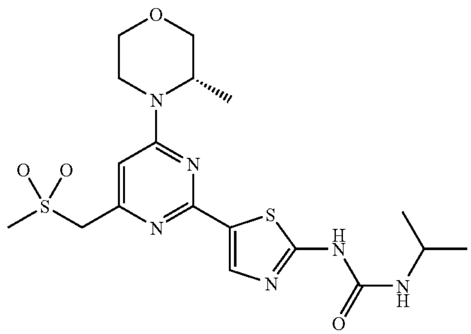 | 1-[5-[4-[(3S)-3-methylmorpholin-4-yl]-6-(methylsulfonylmethyl)pyrimidin-2-yl]-1,3-thiazol-2-yl]-3-propan-2-yl-urea | 455 | 1.84 |
| 46b | 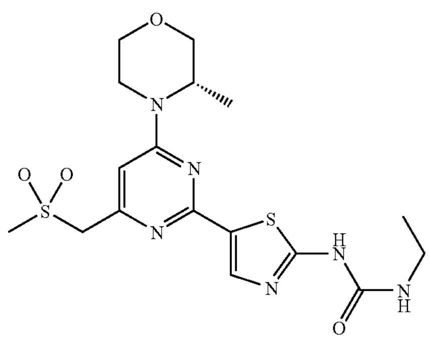 | 1-ethyl-3-[5-[4-[(3S)-3-methylmorpholin-4-yl]-6-(methylsulfonylmethyl)pyrimidin-2-yl]-1,3-thiazol-2-yl]urea | 441 | 1.48 |
| 46c | 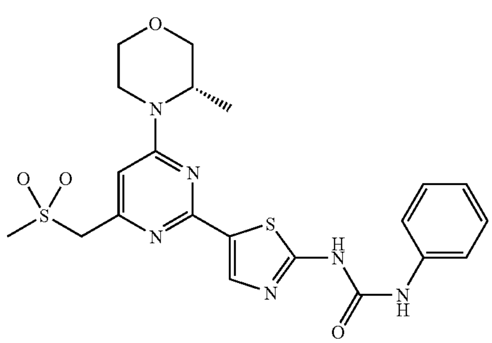 | 1-[5-[4-[(3S)-3-methylmorpholin-4-yl]-6-(methylsulfonylmethyl)pyrimidin-2-yl]-1,3-thiazol-2-yl]-3-phenyl-urea | 489 | 1.86 |
| 46d | 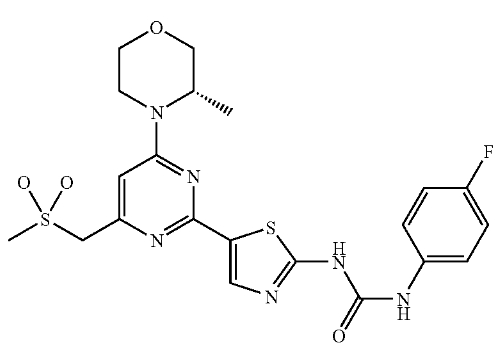 | 3-(4-fluorophenyl)-1-[5-[4-[(3S)-3-methylmorpholin-4-yl]-6-(methylsulfonylmethyl)pyrimidin-2-yl]-1,3-thiazol-2-yl]urea | 507 | 1.88 |

-continued

| Example | Structure | NAME | LCMS MH+ | Retention Time (min) |
|---|---|---|---|---|
| 46e | 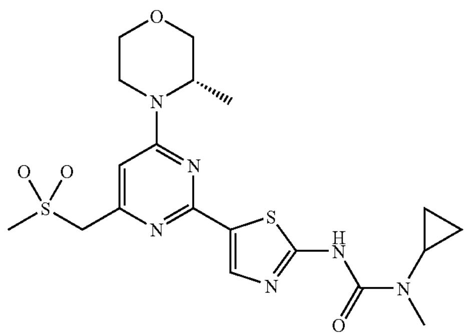 | 1-cyclopropyl-1-methyl-3-[5-[4-[(3S)-3-methylmorpholin-4-yl]-6-(methylsulfonylmethyl)pyrimidin-2-yl]-1,3-thiazol-2-yl]urea | 467 | 1.69 |
| 46f | 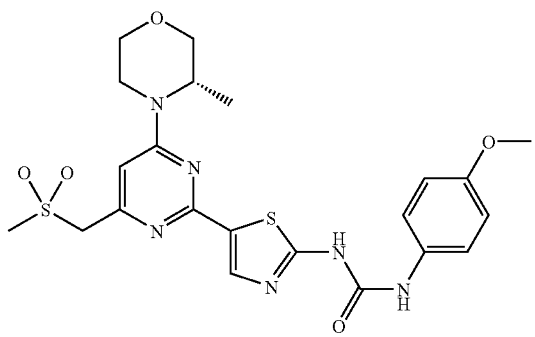 | 3-(4-methoxyphenyl)-1-[5-[4-[(3S)-3-methylmorpholin-4-yl]-6-(methylsulfonylmethyl)pyrimidin-2-yl]-1,3-thiazol-2-yl]urea | 519 | 1.82 |
| 46g | 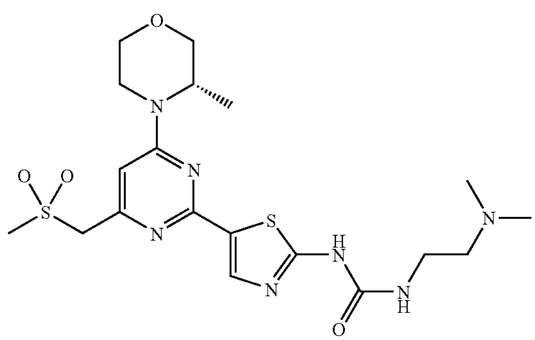 | 3-(2-dimethylaminoethyl)-1-[5-[4-[(3S)-3-methylmorpholin-4-yl]-6-(methylsulfonylmethyl)pyrimidin-2-yl]-1,3-thiazol-2-yl]urea | 484 | 1.39 |
| 46h | 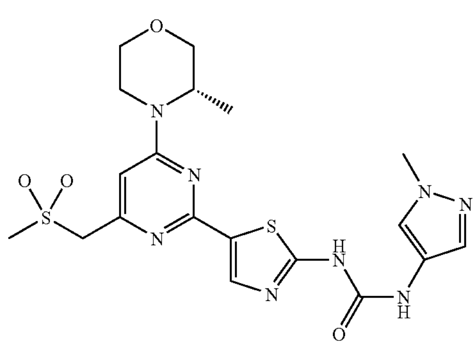 | 1-[5-[4-[(3S)-3-methylmorpholin-4-yl]-6-(methylsulfonylmethyl)pyrimidin-2-yl]-1,3-thiazol-2-yl]-3-(1-methylpyrazol-4-yl)urea | 493 | 1.25 |

| Example | Structure | NAME | LCMS MH+ | Retention Time (min) |
|---|---|---|---|---|
| 46i | 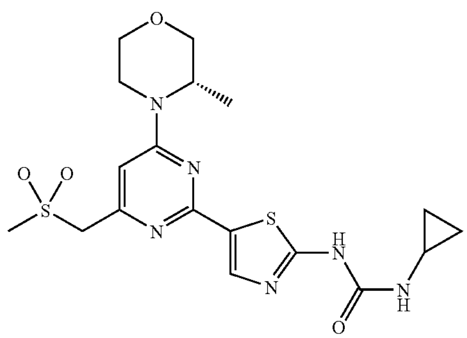 | 3-cyclopropyl-1-[5-[4-[(3S)-3-methylmorpholin-4-yl]-6-(methylsulfonylmethyl)pyrimidin-2-yl]-1,3-thiazol-2-yl]urea | 453 | 1.59 |

Test (a): Example (46) 0.14 μM; Example (46a) 0.35 μM; Example (46b) 0.0061 μM; Example (46c) 0.45 μM; Example (46d) 0.85 μM; Example (46e) 0.71 μM; Example (46f) 1.2 μM; Example (46g) 0.73 μM; Example (46h) 0.063 μM; Example (46i) 0.097 μM.

The preparation of phenyl N-[5-[4-[(3S)-3-methylmorpholin-4-yl]-6-(methylsulfonylmethyl)pyrimidin-2-yl]-1,3-thiazol-2-yl]carbamate is described below.

Phenyl N-[5-[4-[(3S)-3-methylmorpholin-4-yl]-6-(methylsulfonylmethyl)pyrimidin-2-yl]-1,3-thiazol-2-yl]carbamate

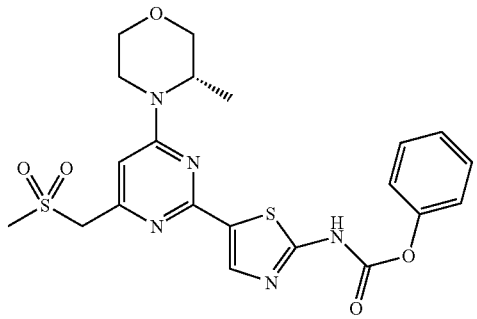

A solution of 5-[4-[(3S)-3-methylmorpholin-4-yl]-6-(methylsulfonylmethyl)pyrimidin-2-yl]-1,3-thiazol-2-amine (1 g, 2.71 mmol), sodium hydrogen carbonate (342 mg), and phenyl chloroformate (0.511 mL) in dioxane was stirred at RT for 2 hours then concentrated in vacuo. The residue was partitioned between DCM and water and the organic layer dried over sodium sulphate and evaporated to give a foam. The foam was triturated with a mixture of hexane and diethyl ether to give the desired material as a white solid (1.1 g).

LCMS Spectrum MH+ 490, retention time 2.17, method monitor acid.

5-[4-[(3S)-3-Methylmorpholin-4-yl]-6-(methylsulfonylmethyl)pyrimidin-2-yl]-1,3-thiazol-2-amine

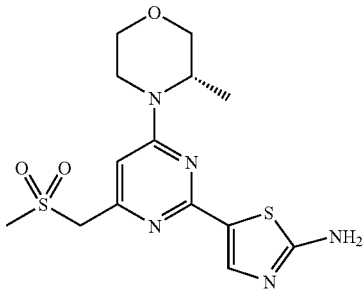

A solution of tert-butyl N-[5-[4-[(3S)-3-methylmorpholin-4-yl]-6-(methylsulfonylmethyl)pyrimidin-2-yl]-1,3-thiazol-2-yl]-N-[(2-methylpropan-2-yl)oxycarbonyl]carbamate (1.7 g, 2.9 mmol) and TFA (8 mL) in DCM (15 mL) was stirred at RT for 16 hours. The solvent was removed under reduced pressure and the residue made basic with aqueous ammonia solution. The product was extracted with ethyl acetate, the organics dried over sodium sulphate, filtered and evaporated to give the desired material as a white solid (1 g).

NMR Spectrum: $^1$H NMR (400.13 MHz, DMSO-$d_6$) δ 1.16-1.22 (3H, m), 3.13-3.18 (1H, m), 3.19 (3H, s), 3.43-3.50 (1H, m), 3.60-3.63 (1H, m), 3.75 (1H, d), 3.94-3.97 (1H, dd), 4.04 (1H, d), 4.37 (1H, s), 4.40 (2H, s), 5.75 (1H, s), 6.64 (1H, s), 7.40 (2H, s), 7.73 (1H, s)

LCMS Spectrum; MH+ 370, retention time 1.38 mins, method monitor base.

tert-Butyl N-[5-[4-[(3S)-3-methylmorpholin-4-yl]-6-(methylsulfonylmethyl)pyrimidin-2-yl]-1,3-thiazol-2-yl]-N-[(2-methylpropan-2-yl)oxycarbonyl]carbamate

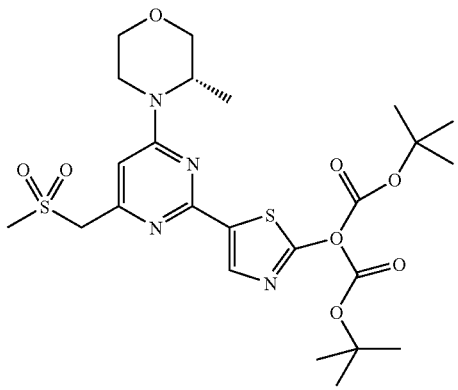

A mixture of tert-butyl N-[(2-methylpropan-2-yl)oxycarbonyl]-N-(5-tributylstannyl-1,3-thiazol-2-yl)carbamate (3 g, 5.1 mmol), 2-chloro-4-[(3S)-3-methylmorpholin-4-yl]-6-(methylsulfonylmethyl)pyrimidine (1 g, 3.2 mmol) and palladium tetrakis (triphenylphosphine) (50 mg), in toluene (10 mL) was heated at 105° C. for 2 hours under nitrogen. The mixture was chromatographed on silica to give the desired material (1.7 g).

NMR Spectrum: $^1$H NMR (400.13 MHz, DMSO-d$_6$) δ 1.20 (3H, d), 1.53 (9H, s), 3.18 (3H, s), 3.55 (1H, t), 3.62 (1H, d), 3.75 (1H, d), 3.98 (1H, d), 4.10 (1H, s), 3.90 (1H, s), 3.98 (2H, s), 6.80 (1H, s), 8.18 (1H, s)

LCMS Spectrum; MH+ 570, retention time 2.89 mins, method monitor base.

tert-Butyl N-[(2-methylpropan-2-yl)oxycarbonyl]-N-(5-tributylstannyl-1,3-thiazol-2-yl)carbamate

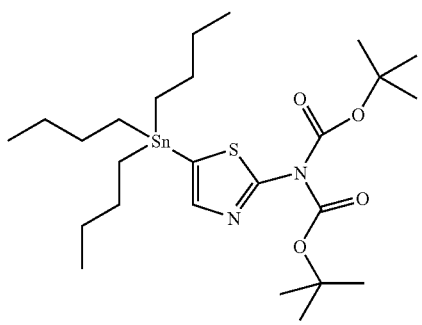

n-Butyl lithium (1.6M in hexanes, 30 mL, 0.48 mol), was added to diisopropylamine (6.7 mL, 0.48 mol) in THF (480 mL) at 0° C. The mixture was stirred at 0° C. for 30 mins then cooled to −78° C. tert-Butyl N-[(2-methylpropan-2-yl)oxycarbonyl]-N-(1,3-thiazol-2-yl)carbamate (12 g, 0.05 mol) was added and solution stirred for 30 minutes. Tributyltin chloride (16.3 mL) was added and solution stirred for 30 minutes before allowing to warm to RT. The reaction was quenched with a saturated aqueous solution of ammonium chloride (20 mL) and the product extracted with ethyl acetate. The organics were dried over sodium sulphate, concentrated in vacuo and chromatographed on silica, eluting with 5-15% ethyl acetate in hexane, to give the desired material as a clear oil (9 g).

NMR Spectrum: $^1$H NMR (400.13 MHz, DMSO-d$_6$) δ 1.49 (18H, s), 7.50 (1H, d), 7.55 (1H, d)

tert-Butyl N-[(2-methylpropan-2-yl)oxycarbonyl]-N-(1,3-thiazol-2-yl)carbamate

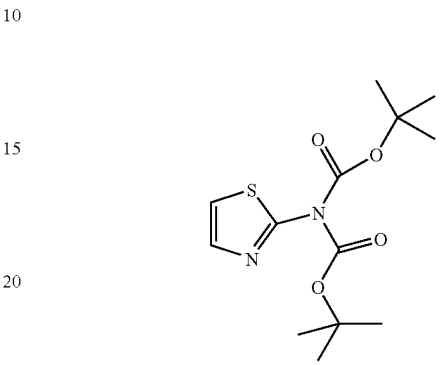

A solution of 2-aminothiazole (5 g, 0.05 mol), (2-methylpropan-2-yl)oxycarbonyl tert-butyl carbonate (27.8 g, 0.15 mol) and DMAP (100 mg) in THF (100 mL) was stirred at reflux overnight. The mixture was allowed to cool and concentrated in vacuo. The residue was chromatographed on silica, eluting with 8% ethyl acetate in hexane, to give the desired material as a white solid (12 g).

NMR Spectrum: $^1$H NMR (400.13 MHz, DMSO-d$_6$) δ 1.49 (18H, s), 7.50 (1H, d), 7.55 (1H, d)

LCMS Spectrum MH-299, retention time 2.6 mins, method monitor base

EXAMPLE 47

3-Methyl-1-[5-[4-[(3S)-3-methylmorpholin-4-yl]-6-(2-methylsulfonylpropan-2-yl)pyrimidin-2-yl]-1,3-thiazol-2-yl]urea

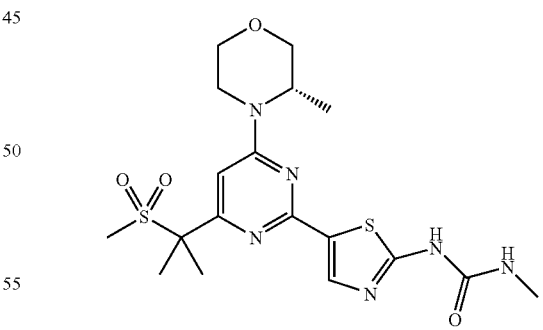

A solution of phenyl N-[5-[4-[(3S)-3-methylmorpholin-4-yl]-6-(2-methylsulfonylpropan-2-yl)pyrimidin-2-yl]-1,3-thiazol-2-yl]carbamate (200 mg, 0.39 mmol), methyl amine (1.5 mmol) and triethylamine (0.163 mL, 1.16 mmol) in NMP (3 mL) was heated at 70° C. for 2 hours. The mixture was chromatographed on silica, eluting with 0-5% methanol in ethyl acetate to give the desired material.

NMR Spectrum: $^1$H NMR (400.13 MHz, DMSO-d$_6$) δ 1.22 (3H, d), 1.70 (6H, s), 3.19 (3H, s), 3.20 (1H, dd), 3.45

(1H, dd), 3.62 (1H, d), 3.75 (1H, d), 3.96 (1H, d), 4.18 (1H, d), 4.52 (1H, s), 6.40 (1H, s), 6.65 (1H, s), 8.09 (1H, s), 10.70 (1H, s)

LCMS Spectrum; MH+ 455, retention time 1.78 mins.

The following compounds were prepared in an analogous fashion.

Example 47a: $^1$H NMR (400.13 MHz, DMSO-$d_6$) δ 0.45 (2H, q), 0.68 (2H, q), 1.20 (3H, d), 1.70 (6H, s), 3.05 (3H, s), 3.20 (1H, dd), 3.48 (1H, dd), 3.62 (1H, d), 3.75 (1H, d), 3.98 (1H, dd), 4.18 (1H, d), 4.55 (1H, s), 6.68 (1H, s), 6.75 (1H, s), 8.05 (1H, s), 11.0 (1H, s).

| Example | Structure | NAME | LCMS MH+ | Retention Time (min) |
|---|---|---|---|---|
| 47a | 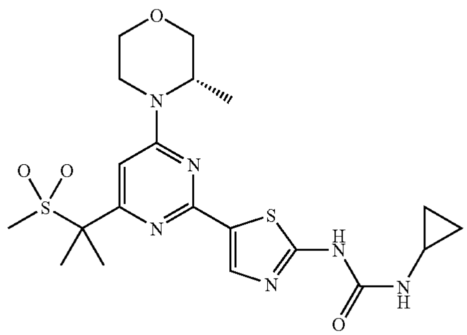 | 3-cyclopropyl-1-[5-[4-[(3S)-3-methylmorpholin-4-yl]-6-(2-methylsulfonylpropan-2-yl)pyrimidin-2-yl]-1,3-thiazol-2-yl]urea | 481 | 1.94 |
| 47b | 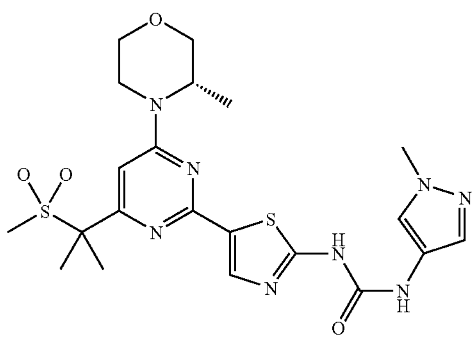 | 1-[5-[4-[(3S)-3-methylmorpholin-4-yl]-6-(2-methylsulfonylpropan-2-yl)pyrimidin-2-yl]-1,3-thiazol-2-yl]-3-(1-methylpyrazol-4-yl)urea | 521 | 1.62 |
| 47c | 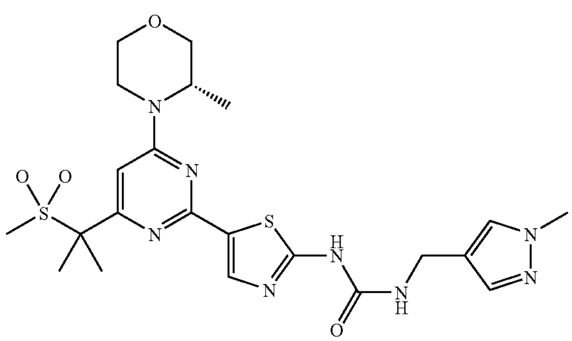 | 1-[5-[4-[(3S)-3-methylmorpholin-4-yl]-6-(2-methylsulfonylpropan-2-yl)pyrimidin-2-yl]-1,3-thiazol-2-yl]-3-[(1-methylpyrazol-4-yl)methyl]urea | 535 | 1.81 |
| 47d | 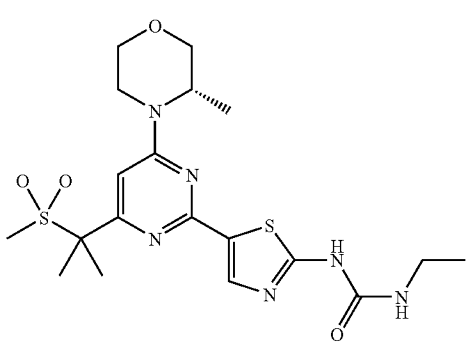 | 1-ethyl-3-[5-[4-[(3S)-3-methylmorpholin-4-yl]-6-(2-methylsulfonylpropan-2-yl)pyrimidin-2-yl]-1,3-thiazol-2-yl]urea | 469 | 1.95 |

Example 47b: $^1$H NMR (400.13 MHz, DMSO-d$_6$) δ 1.20 (3H, d), 1.70 (6H, s), 3.03 (3H, s), 3.20 (1H, dd), 3.48 (1H, dd), 3.65 (1H, d), 3.70-3.80 (4H, m), 3.99 (1H, dd), 4.15 (1H, d), 4.53 (1H, s), 6.70 (1H, s), 7.42 (1H, s), 7.82 (1H, s), 8.10 (1H, s), 8.72 (1H, s), 10.75 (1H, s)

Example 47c: $^1$H NMR (400.13 MHz, DMSO-d$_6$) δ 1.20 (3H, d), 1.70 (6H, s), 2.68 (3H, s), 3.05 (3H, s), 3.18 (1H, dd), 3.48 (1H, dd), 3.62 (1H, d), 3.75 (1H, d), 3.98 (1H, d), 4.05 (1H, q), 4.18 (2H, s), 4.51 (1H, s), 6.68 (1H, s), 6.78 (1H, s), 7.35 (1H, s), 7.62 (1H, s), 8.09 (1H, s), 10.60 (1H, s).

Test (a): Example (47) 0.26 µM; Example (47a) 1.2 µM; Example (47b) 0.41 µM; Example (47c) 1.4 µM; Example (47d) 0.97 µM.

The preparation of phenyl N-[5-[4-[(3S)-3-methylmorpholin-4-yl]-6-(2-methylsulfonylpropan-2-yl)pyrimidin-2-yl]-1,3-thiazol-2-yl]carbamate is described below.

Phenyl N-[5-[4-[(3S)-3-methylmorpholin-4-yl]-6-(2-methylsulfonylpropan-2-yl)pyrimidin-2-yl]-1,3-thiazol-2-yl]carbamate

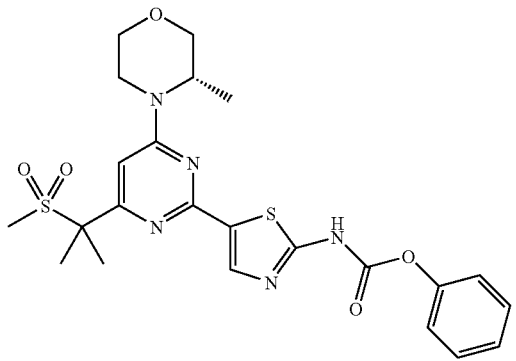

A mixture of 5-[4-[(3S)-3-methylmorpholin-4-yl]-6-(2-methylsulfonylpropan-2-yl)pyrimidin-2-yl]-1,3-thiazol-2-amine (1.05 g, 2.6 mmol), phenyl chloroformate (618 mg, 3.9 mmol) and sodium hydrogen carbonate (311 mg, 3.9 mmol) in dioxane (10 mL) was stirred at RT for 2 hours then diluted with ethyl acetate and washed with water (150 mL) and brine (100 mL). The organics were dried over magnesium sulphate and concentrated in vacuo. The residue was recrystallised from diethyl ether and hexane to give the desired product as a beige solid (1 g).

5-[4-[(3S)-3-Methylmorpholin-4-yl]-6-(2-methylsulfonylpropan-2-yl)pyrimidin-2-yl]-1,3-thiazol-2-amine

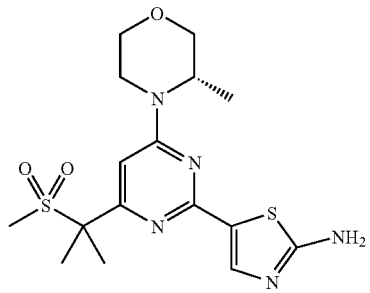

A mixture of 2-chloro-4-[(3S)-3-methylmorpholin-4-yl]-6-(2-methylsulfonylpropan-2-yl)pyrimidine (1.2 g, 3.6 mmol), tert-butyl N-[(2-methylpropan-2-yl)oxycarbonyl]-N-(5-tributylstannyl-1,3-thiazol-2-yl)carbamate (3.1 g, 5.2 mmol), and palladium tetrakis (triphenylphosphine) (200 mg) in toluene (30 mL) was heated at 110° C. under a nitrogen atmosphere overnight. The mixture was diluted with ethyl acetate and washed with water. The organics were dried over magnesium sulphate, filtered and evaporated. The residue was dissolved in DCM (50 mL) and trifluoroacetic acid (15 mL) added. After allowing to stir for 2 hours the mixture was evaporated and water added. The mixture was made basic with aqueous ammonia solution and extracted with ethyl acetate. The organics were dried over magnesium sulphate, filtered and evaporated to a solid. The residue was triturated with a mixture of diethyl ether and hexane to give the desired material (1.05 g).

NMR Spectrum: $^1$H NMR (400.13 MHz, DMSO-d$_6$) δ 1.18 (3H, d), 1.65 (6H, s), 3.0 (3H, s), 3.15 (3H, dd), 3.45 (1H, dd), 3.60 (1H, dd), 3.71 (1H, d), 3.95 (1H, dd), 4.10 (1H, d), 4.50 (1H, S), 6.60 (1H, s), 7.35 (2H, s), 7.75 (1H, s).

LCMS Spectrum; MH+ 398 retention time 1.76 mins, method monitor base

The preparation of 2-chloro-4-[(3S)-3-methylmorpholin-4-yl]-6-(2-methylsulfonylpropan-2-yl)pyrimidine and tert-butyl N-[(2-methylpropan-2-yl)oxycarbonyl]-N-(5-tributylstannyl-1,3-thiazol-2-yl)carbamate was described earlier.

EXAMPLE 48

3-Cyclobutyl-1-[4-[4-[(3S)-3-methylmorpholin-4-yl]-6-(pyridin-4-ylsulfonylmethyl)pyrimidin-2-yl]phenyl]urea

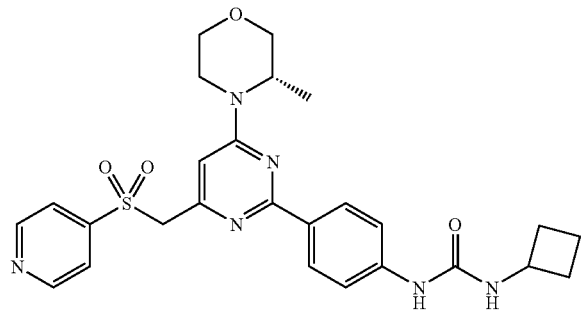

Cyclobutylamine (0.074 mL, 0.87 mmol) was added to a solution of phenyl N-[4-[4-[(3S)-3-methylmorpholin-4-yl]-6-(pyridin-4-ylsulfonylmethyl)pyrimidin-2-yl]phenyl]carbamate (0.095 g, 0.17 mmol) and triethylamine (0.073 mL, 0.52 mmol) in DMF (3 mL) then warmed to 50° C. under nitrogen. The resulting solution was stirred at 50° C. for 2 hours. The solvent was removed in vacuo and the crude product purified by prep HPLC to give the desired material as a white solid (0.089 g).

NMR Spectrum: $^1$H NMR (400.13 MHz, DMSO-d$_6$) δ 1.20-1.22 (3H, d), 1.59-1.66 (2H, m), 1.82-1.92 (2H, m), 2.18-2.25 (2H, m), 3.15-3.22 (1H, td), 3.45-3.52 (1H, td), 3.62-3.65 (1H, td), 3.75-3.78 (1H, d), 3.96-3.99 (1H, dd), 4.09-4.17 (2H, m), 4.39 (1H, bs), 4.87 (2H, s), 6.52-6.54 (1H, d), 6.71 (1H, s), 7.33-7.35 (2H, d), 7.64-7.67 (2H, d), 7.80-7.82 (2H, q), 8.61 (1H, s), 8.90-8.91 (2H, q).

LCMS Spectrum: MH+ 523 retention time 1.96 min.

The following compounds were prepared in an analogous fashion from phenyl N-[4-[4-[(3S)-3-methylmorpholin-4-yl]-6-(pyridin-4-ylsulfonylmethyl)pyrimidin-2-yl]phenyl]carbamate and the appropriate amine.

| Example | Structure | NAME | LCMS MH+ | Retention time (min) |
|---|---|---|---|---|
| 48a | 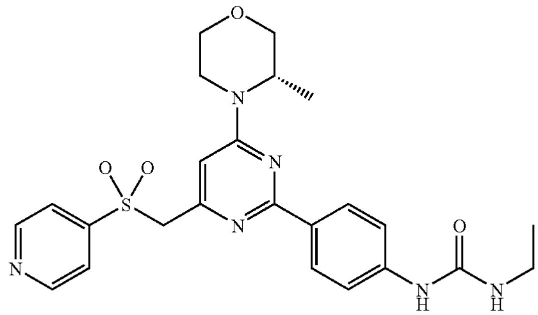 | 3-ethyl-1-[4-[4-[(3S)-3-methylmorpholin-4-yl]-6-(pyridin-4-ylsulfonylmethyl)pyrimidin-2-yl]phenyl]urea | 497 | 1.74 |
| 48b | 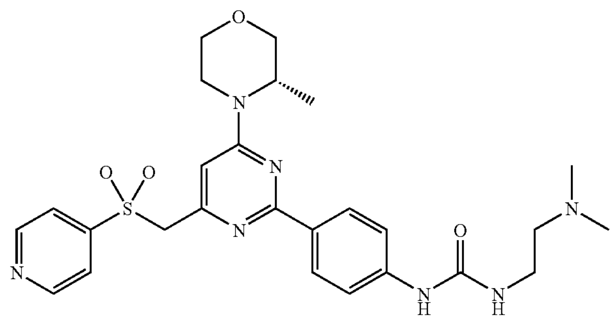 | 3-(2-dimethylaminoethyl)-1-[4-[4-[(3S)-3-methylmorpholin-4-yl]-6-(pyridin-4-ylsulfonylmethyl)pyrimidin-2-yl]phenyl]urea | 540 | 1.83 |

Example 48a: $^1$H NMR (400.13 MHz, DMSO-$d_6$) δ 1.05-1.09 (3H, t), 1.20-1.22 (3H, d), 3.09-3.16 (2H, m), 3.16-3.22 (1H, td), 3.45-3.52 (1H, td), 3.62-3.65 (1H, dd), 3.75-3.78 (1H, d), 3.96-3.99 (1H, dd), 4.10-4.14 (1H, d), 4.39 (1H, bs), 4.88 (2H, s), 6.14-6.17 (1H, t), 6.71 (1H, s), 7.35-7.37 (2H, d), 7.65-7.67 (2H, d), 7.81-7.82 (2H, d), 8.64 (1H, s), 8.90-8.91 (2H, d).

Example 48b: $^1$H NMR (400.13 MHz, DMSO-$d_6$) δ 1.20-1.21 (3H, d), 2.41 (2H, bs), 2.74 (3H, s), 2.90 (3H, s), 3.15-3.23 (1H, td), 3.2-3.4 (2H, m), 3.45-3.51 (1H, td), 3.61-3.65 (1H, dd), 3.75-3.78 (1H, d), 3.96-3.99 (1H, dd), 4.10-4.13 (1H, d), 4.39 (1H, bs), 4.87 (2H, s), 6.25 (1H, t), 6.72 (1H, s), 7.35-7.37 (2H, d), 7.65-7.67 (2H, d), 7.81-7.82 (2H, q), 7.96 (1H, s), 8.89-8.91 (2H, d).

Test (c): Example (48) 0.038 µM; Example (48a) 0.25 µM.

The preparation of phenyl N-[4-[4-[(3S)-3-methylmorpholin-4-yl]-6-(pyridin-4-ylsulfonylmethyl)pyrimidin-2-yl]phenyl]carbamate is described below.

Phenyl N-[4-[4-[(3S)-3-methylmorpholin-4-yl]-6-(pyridin-4-ylsulfonylmethyl)pyrimidin-2-yl]phenyl]carbamate

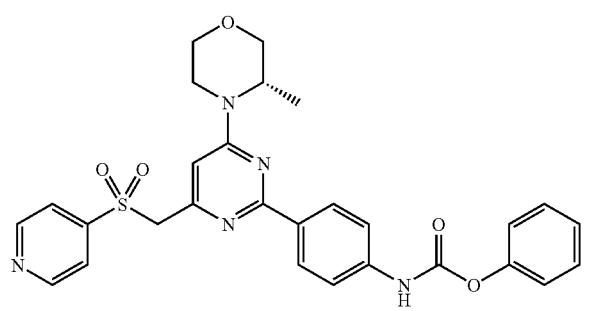

Phenyl chloroformate (0.029 mL, 0.23 mmol) was added to a solution of 4-[4-[(3S)-3-methylmorpholin-4-yl]-6-(pyridin-4-ylsulfonylmethyl)pyrimidin-2-yl]aniline (0.097 g, 0.23 mmol) and sodium bicarbonate (0.029 g, 0.34 mmol) in dioxane at RT. The resulting slurry was stirred at RT for 2 hours. Additional phenyl chloroformate (2×0.005 mL) was added to drive the reaction to completion. Water was then added to the reaction and the solid filtered, and dried in a vacuum oven to give the desired material as an off-white solid (0.098 g).

NMR Spectrum: $^1$H NMR (400.13 MHz, DMSO-$d_6$) δ 1.21-1.23 (3H, d), 3.16-3.24 (1H, td), 3.46-3.52 (1H, td), 3.62-3.66 (1H, dd), 3.76-3.79 (1H, d), 3.96-4.00 (1H, dd), 4.13-4.16 (1H, bd), 4.41 (1H, bs), 4.90 (2H, s), 6.76 (s, 1H), 7.23-7.31 (3H, m), 7.43-7.51 (4H, m), 7.74-7.77 (2H, m), 7.81-7.83 (2H, dd), 8.90-8.92 (2H, dd), 10.39 (1H, s).

LCMS Spectrum: MH+ 546 retention time 2.35 min.

4-[4-[(3S)-3-Methylmorpholin-4-yl]-6-(pyridin-4-ylsulfonylmethyl)pyrimidin-2-yl]aniline

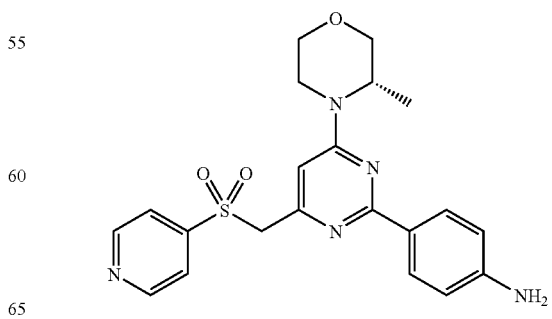

trans-Dichlorobis(triphenylphosphine)palladium (II) (0.039 g, 0.06 mmol) was added to a mixture of 2-chloro-4-[(3S)-3-methylmorpholin-4-yl]-6-(pyridin-4-ylsulfonylmethyl)pyrimidine (0.411 g, 1.11 mmol), 4-(4,4,5,5-Tetramethyl-1,3,2-dioxaborolan-2-yl)aniline (0.366 g, 1.67 mmol) and sodium carbonate (0.233 mL, 5.56 mmol) in 18% DMF in a mixture of 7:3:2 DME:water:ethanol (100 mL) at RT under nitrogen. The resulting solution was stirred at 90° C. for 5 hours. The reaction was cooled and diluted with ethyl acetate and water. The reaction mixture was extracted with ethyl acetate and the combined organics dried ($MgSO_4$), filtered and evaporated. The crude product was chromatographed on silica, eluting with 0-5% methanol in DCM, to give the desired material as a white solid (0.453 g).

NMR Spectrum: $^1$H NMR (400.13 MHz, DMSO-$d_6$) δ 1.19-1.20 (3H, d), 3.12-3.19 (1H, td), 3.44-3.50 (1H, td), 3.61-3.64 (1H, dd), 3.74-3.77 (1H, d), 3.95-3.98 (1H, dd), 4.07-4.11 (1H, d), 4.37 (1H, bs), 4.83 (2H, s), 5.50-5.52 (2H, d), 6.45-6.47 (2H, d), 6.60 (1H, s), 7.48-7.50 (2H, d), 7.80-7.81 (2H, q), 8.89-8.90 (2H, q).

LCMS Spectrum: MH+ 426 retention time 1.80 min.

2-Chloro-4-[(3S)-3-methylmorpholin-4-yl]-6-(pyridin-4-ylsulfonylmethyl)pyrimidine

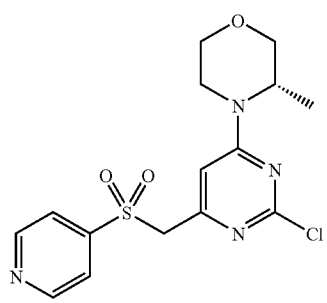

A solution of hydrogen peroxide (1.799 mL, 58.19 mmol) was added dropwise to a stirred solution of 2-chloro-4-[(3S)-3-methylmorpholin-4-yl]-6-(pyridin-4-ylsulfanylmethyl)pyrimidine (0.980 g, 2.91 mmol), sodium tungstate dihydrate (0.005 mL, 0.06 mmol) and 2N sulfuric acid (0.075 mL) in dioxane (200 mL) at 55° C., over a period of 5 minutes under air. The resulting solution was stirred at 55° C. for 3 hours. Water (200 mL) was added and the reaction was cooled, the solids filtered, washed with water and dried in the vacuum oven at 50° C. overnight to give the desired material as a white solid (0.580 g). Additional material was obtained by extracting the aqueous layer with DCM. The extracts were dried ($MgSO_4$), filtered, evaporated and chromatographed on silica, eluting with 0-3% methanol in DCM, to give a further portion of the desired material (0.144 g).

NMR Spectrum: $^1$H NMR (400.13 MHz, DMSO-$d_6$) δ 1.17-1.19 (3H, d), 3.14-3.22 (1H, td), 3.40-3.47 (1H, td), 3.56-3.60 (1H, dd), 3.71-3.74 (1H, d), 3.90 (1H, bs), 3.91-3.95 (1H, dd), 4.20 (1H, bs), 4.79 (2H, s), 6.79 (1H, s), 7.77-7.79 (2H, q), 8.92-8.93 (2H, q).

LCMS Spectrum: MH+ 369 retention time 1.39 min.

2-Chloro-4-[(3S)-3-methylmorpholin-4-yl]-6-(pyridin-4-ylsulfanylmethyl)pyrimidine

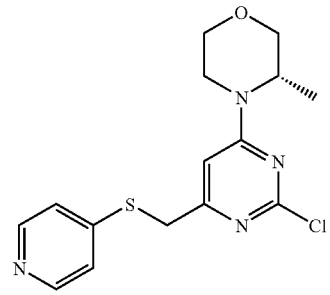

4-Mercaptopyridine (0.752 g, 6.77 mmol) was added to 2-chloro-4-(iodomethyl)-6-[(3S)-3-methylmorpholin-4-yl]pyrimidine (1.596 g, 4.51 mmol) in acetonitrile (100 mL) at RT under air. DBU (0.3 mL, 2.01 mmol) was then added and the resulting solution was stirred at RT for 2 minutes. The solvent was removed and DCM was added. The reaction mixture was washed sequentially with water, the organic layer dried ($MgSO_4$), filtered and evaporated. The crude product was chromatographed on silica, eluting with 0-2% methanol in DCM. Impure fractions were further chromatographed on silica, eluting with 0-4.5% methanol in DCM and combined with the initial pure fractions to give the desired material as a yellow gum (0.980 g).

NMR Spectrum: $^1$H NMR (400.13 MHz, DMSO-$d_6$) δ 1.14-1.16 (3H, d), 3.11-3.18 (1H, td), 3.37-3.44 (1H, td), 3.53-3.57 (1H, dd), 3.64-3.67 (1H, d), 3.86-3.90 (2H, dd), 4.01 (2H, s), 4.14 (1H, bs), 6.43 (1H, s), 7.04-7.06 (2H, d), 8.29-8.30 (2H, d).

LCMS Spectrum: MH+ 337 retention time 1.62 min.

2-Chloro-4-(iodomethyl)-6-[(3S)-3-methylmorpholin-4-yl]pyrimidine

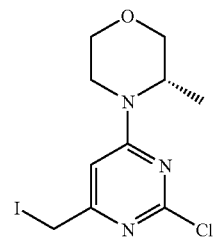

Sodium iodide (1.006 ml, 24.61 mmol) was added to 2-chloro-4-[(3S)-3-methylmorpholin-4-yl]-6-(methylsulfonyloxymethyl)pyrimidine (1.584 g, 4.92 mmol) in DCM at RT. The resulting solution was refluxed at 40° C. for 18 hours. The reaction mixture was diluted with DCM and washed with water. The organic layer was dried ($MgSO_4$), filtered and evaporated to afford the desired product (1.596 g).

353

NMR Spectrum: $^1$H NMR (400.13 MHz, CDCl$_3$) δ 1.27-1.28 (3H, d), 3.20-3.27 (1H, td), 3.46-3.53 (1H, td), 3.62-3.65 (1H, dd), 3.72-3.75 (1H, d), 3.93-3.97 (2H, dd), 4.17 (2H, s), 4.26 (1H, bs), 6.41 (1H, s).

LCMS Spectrum: MH+ 354 retention time 1.85 min.

2-Chloro-4-[(3S)-3-methylmorpholin-4-yl]-6-(methylsulfonyloxymethyl)pyrimidine

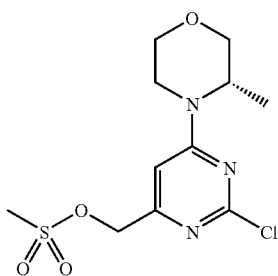

Methanesulfonyl chloride (0.488 mL, 6.31 mmol) was added dropwise to [2-chloro-6-[(3S)-3-methylmorpholin-4-yl]pyrimidin-4-yl]methanol (1.025 g, 4.21 mmol), and triethylamine (0.880 mL, 6.31 mmol) in DCM at 0° C. over a period of 2 minutes. The resulting solution was allowed to gradually warm up to RT over a period of 2 hours. The reaction mixture was diluted with DCM (50 mL), and washed with water. The organic layer was dried (MgSO$_4$), filtered and evaporated to afford the desired material (1.584 g) which was used without further purification.

LCMS Spectrum: MH+ 322 retention time 1.60 min.

The preparation of [2-chloro-6-[(3S)-3-methylmorpholin-4-yl]pyrimidin-4-yl]methanol was described earlier.

354

EXAMPLE 49

3-Cyclopropyl-1-[4-[4-[(cyclopropylamino)methyl]-6-[(3S)-3-methylmorpholin-4-yl]pyrimidin-2-yl]phenyl]urea

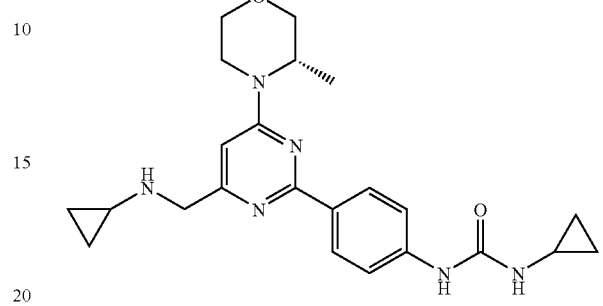

3-Cyclopropyl-1-[4-[4-[(3S)-3-methylmorpholin-4-yl]-6-(methylsulfonyloxymethyl)pyrimidin-2-yl]phenyl]urea (107 mg, 0.23 mmol) was dissolved in DCM (5 mL) and added to cyclopropylamine (1.16 mmol). Triethylamine (0.162 mL, 1.16 mmol) was added to the solution and stirred at RT for 18 hours. The reaction was evaporated to dryness and purified by prep-HPLC (basic) to give the desired material as a white solid (27 mg).

NMR Spectrum: $^1$H NMR (400.13 MHz, DMSO-d$_6$) δ 0.29-0.31 (2H, m), 0.34-0.44 (4H, m), 0.62-0.67 (2H, m), 1.21-1.27 (3H, m), 2.13-2.17 (1H, m), 2.53-2.58 (1H, m), 3.14-3.21 (1H, m), 3.45-3.52 (1H, m), 3.62-3.65 (1H, m), 3.71 (2H, d), 3.75 (1H, s), 3.95-3.99 (1H, m), 4.14-4.17 (1H, m), 4.49-4.51 (1H, m), 6.46 (1H, d), 6.65 (1H, s), 7.47-7.50 (2H, m), 8.21-8.23 (2H, m), 8.55 (1H, s).

Mass Spectrum; M+H$^+$ 423.

The following compounds were made in an analogous fashion from 3-cyclopropyl-1-[4-[4-[(3S)-3-methylmorpholin-4-yl]-6-(methylsulfonyloxymethyl)pyrimidin-2-yl]phenyl]urea and the appropriate amine.

| Example | Structure | NAME | LCMS MH+ |
|---|---|---|---|
| 49a | 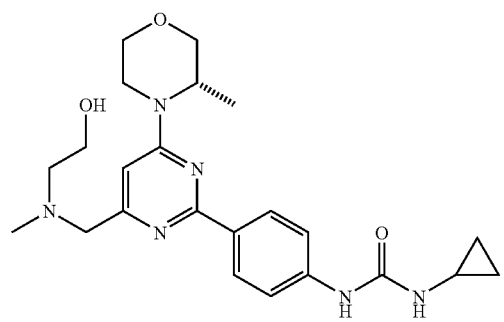 | 3-cyclopropyl-1-[4-[4-[(2-hydroxyethyl-methyl-amino)methyl]-6-[(3S)-3-methylmorpholin-4-yl]pyrimidin-2-yl]phenyl]urea | 441 |

-continued

| Example | Structure | NAME | LCMS MH+ |
|---|---|---|---|
| 49b | 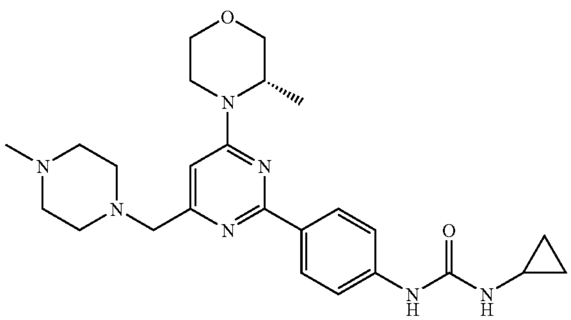 | 3-cyclopropyl-1-[4-[4-[(3S)-3-methylmorpholin-4-yl]-6-[(4-methylpiperazin-1-yl)methyl]pyrimidin-2-yl]phenyl]urea | 466 |
| 49c | 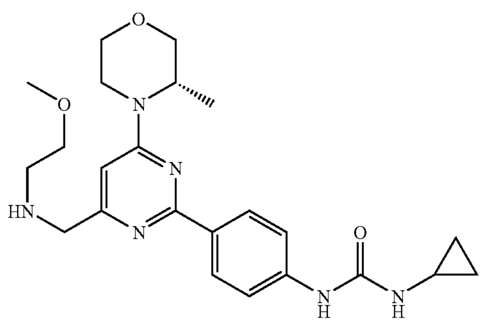 | 3-cyclopropyl-1-[4-[4-[(2-methoxyethylamino)methyl]-6-[(3S)-3-methylmorpholin-4-yl]pyrimidin-2-yl]phenyl]urea | 441 |
| 49d | 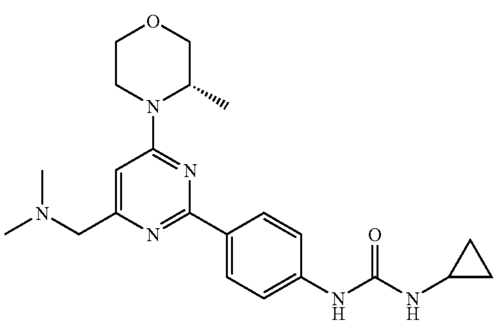 | 3-cyclopropyl-1-[4-[4-(dimethylaminomethyl)-6-[(3S)-3-methylmorpholin-4-yl]pyrimidin-2-yl]phenyl]urea | 411 |
| 49e | 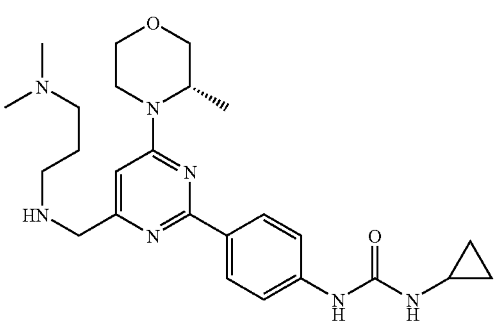 | 3-cyclopropyl-1-[4-[4-[(3-dimethylaminopropylamino)methyl]-6-[(3S)-3-methylmorpholin-4-yl]pyrimidin-2-yl]phenyl]urea | 468 |

-continued

| Example | Structure | NAME | LCMS MH+ |
|---|---|---|---|
| 49f | 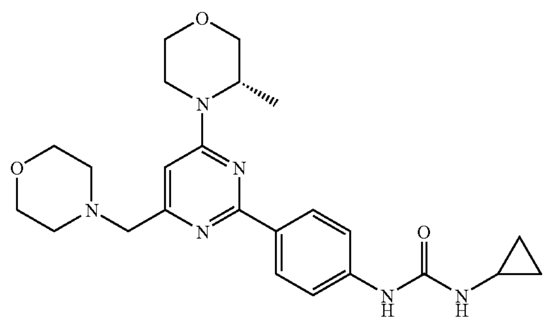 | 3-cyclopropyl-1-[4-[4-[(3S)-3-methylmorpholin-4-yl]-6-(morpholin-4-ylmethyl)pyrimidin-2-yl]phenyl]urea | 453 |
| 49g | 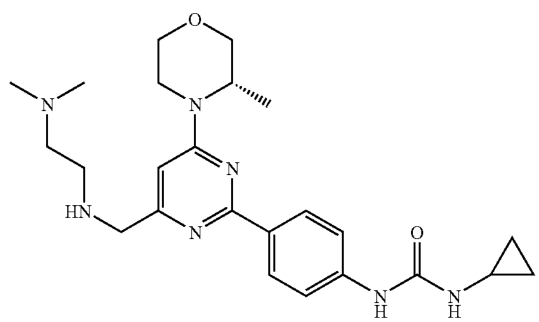 | 3-cyclopropyl-1-[4-[4-[(2-dimethylaminoethylamino)methyl]-6-[(3S)-3-methylmorpholin-4-yl]pyrimidin-2-yl]phenyl]urea | 454 |
| 49h | 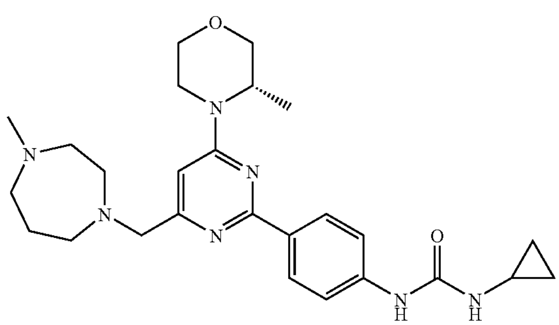 | 3-cyclopropyl-1-[4-[4-[(4-methyl-1,4-diazepan-1-yl)methyl]-6-[(3S)-3-methylmorpholin-4-yl]pyrimidin-2-yl]phenyl]urea | 480 |
| 49i | 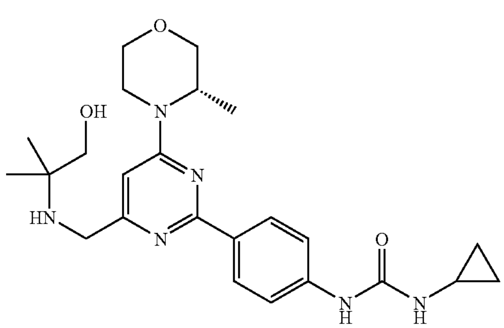 | 3-cyclopropyl-1-[4-[4-[[(1-hydroxy-2-methyl-propan-2-yl)amino]methyl]-6-[(3S)-3-methylmorpholin-4-yl]pyrimidin-2-yl]phenyl]urea | 455 |

| Example | Structure | NAME | LCMS MH+ |
|---|---|---|---|
| 49j | 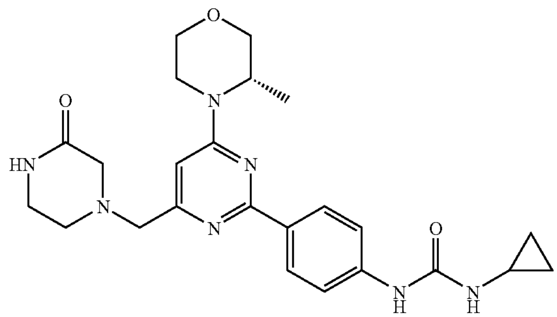 | 3-cyclopropyl-1-[4-[4-[(3S)-3-methylmorpholin-4-yl]-6-[(3-oxopiperazin-1-yl)methyl]pyrimidin-2-yl]phenyl]urea | 456 |
| 49k | 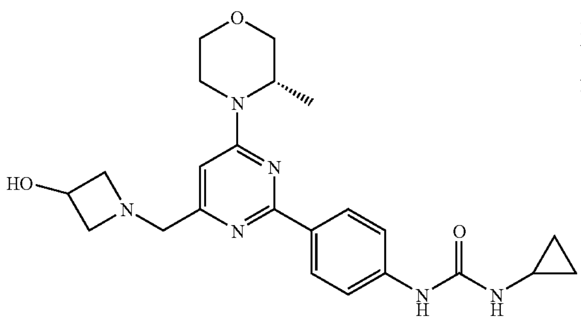 | 3-cyclopropyl-1-[4-[4-[(3-hydroxyazetidin-1-yl)methyl]-6-[(3S)-3-methylmorpholin-4-yl]pyrimidin-2-yl]phenyl]urea | 439 |
| 49l | 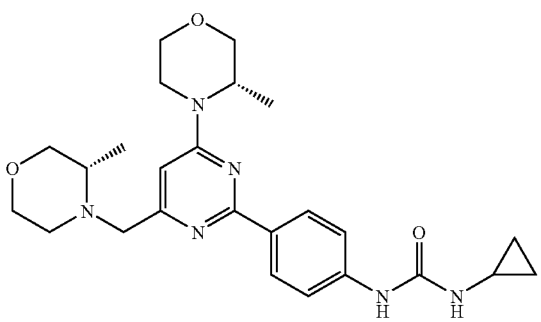 | 3-cyclopropyl-1-[4-[4-[(3S)-3-methylmorpholin-4-yl]-6-[[(3S)-3-methylmorpholin-4-yl]methyl]pyrimidin-2-yl]phenyl]urea | 467 |

Example 49a: $^1$H NMR (400.13 MHz, DMSO-d$_6$) δ 0.40-0.44 (2H, m), 0.62-0.67 (2H, m), 1.21-1.27 (3H, m), 2.30 (3H, s), 2.53-2.58 (1H, m), 3.14-3.21 (1H, m), 3.46-3.58 (7H, m), 3.62-3.66 (1H, m), 3.76 (1H, d), 3.95-3.99 (1H, m), 4.15-4.18 (1H, m), 4.45 (1H, t), 4.48 (1H, s), 6.42 (1H, d), 6.73 (1H, s), 7.47-7.49 (2H, m), 8.19-8.21 (2H, m), 8.50 (1H, s).

Example 49b: $^1$H NMR (400.13 MHz, DMSO-d$_6$) δ 0.40-0.44 (2H, m), 0.62-0.67 (2H, m), 1.21 (3H, d), 2.17 (3H, s), 2.30-2.37 (8H, m), 2.53-2.58 (1H, m), 3.14-3.21 (1H, m), 3.47-3.50 (3H, m), 3.63-3.66 (1H, m), 3.76 (1H, d), 3.95-3.99 (1H, m), 4.12-4.15 (1H, m), 4.45-4.47 (1H, m), 6.43 (1H, d), 6.61 (1H, s), 7.46-7.50 (2H, m), 8.19-8.21 (2H, m), 8.51 (1H, Example 49c: $^1$H NMR (400.13 MHz, DMSO-d$_6$) δ 0.40-0.44 (2H, m), 0.62-0.67 (2H, m), 1.21-1.26 (3H, m), 3.14-3.22 (1H, m), 3.26 (3H, s), 3.39-3.49 (5H, m), 3.62-3.66 (2H, m), 3.67 (2H, s), 3.76 (1H, d), 3.95-3.99 (1H, m), 4.16 (1H, d), 4.48 (1H, s), 6.54 (1H, s), 6.66 (1H, s), 7.50 (2H, d), 8.19 (2H, q), 8.62 (1H, s).

Example 49d: $^1$H NMR (400.13 MHz, DMSO-d$_6$) δ 0.40-0.44 (2H, m), 0.62-0.67 (2H, m), 1.21-1.22 (3H, m), 2.25 (6H, s), 2.52-2.57 (1H, m), 3.17 (1H, d), 3.42 (2H, s), 3.46-3.50 (1H, m), 3.62-3.66 (1H, m), 3.75 (1H, d), 3.95-3.98 (1H, m), 4.14-4.18 (1H, m), 4.46-4.48 (1H, m), 6.44 (1H, d), 6.61 (1H, s), 7.47-7.50 (2H, m), 8.19-8.22 (2H, m), 8.53 (1H, s).

Example 49e: no spectrum

Example 49f: $^1$H NMR (400.13 MHz, DMSO-d$_6$) δ 0.40-0.44 (2H, m), 0.62-0.67 (2H, m), 1.21 (3H, d), 2.52-2.57 (1H, m), 3.14-3.21 (1H, m), 3.49 (2H, s), 3.50 (2H, t), 3.63 (7H, m), 3.66 (1H, d), 3.76 (1H, d), 3.95-3.99 (1H, m), 4.13-4.16 (1H, m), 4.49 (1H, d), 6.42 (1H, d), 6.64 (1H, s), 7.47-7.49 (2H, m), 8.19-8.21 (2H, m), 8.51 (1H, s).

Example 49g: $^1$H NMR (400.13 MHz, DMSO-d$_6$) δ 0.40-0.44 (2H, m), 0.62-0.67 (2H, m), 1.22 (3H, d), 2.13 (6H, s), 2.32-2.35 (2H, m), 2.52-2.57 (1H, m), 2.62 (2H, t), 3.14-3.22 (1H, m), 3.45-3.52 (1H, m), 3.62-3.66 (1H, m), 3.67 (3H, s), 3.76 (1H, d), 3.95-3.99 (1H, m), 4.14-4.18 (1H, m), 4.49 (1H, s), 6.42 (1H, d), 6.65 (1H, s), 7.48 (2H, d), 8.22 (2H, d), 8.50 (1H, s).

Example 49h: $^1$H NMR (400.13 MHz, DMSO-d$_6$) δ 0.40-0.44 (2H, m), 0.62-0.67 (2H, m), 1.24 (3H, d), 1.46 (1H, d), 1.73-1.77 (2H, m), 2.27 (4H, s), 2.37 (1H, d), 2.43 (1H, s), 2.56-2.61 (2H, m), 2.73-2.76 (3H, m), 3.14-3.21 (1H, m), 3.47-3.53 (1H, m), 3.59-3.68 (3H, m), 3.77 (1H, d), 3.96-4.00

(1H, m), 4.14-4.17 (1H, m), 4.45 (1H, s), 6.43 (1H, d), 6.65 (1H, s), 7.47-7.49 (2H, m), 8.19-8.21 (2H, m), 8.51 (1H, s)

Example 49i: $^1$H NMR (400.13 MHz, DMSO-d$_6$) δ 0.40-0.44 (2H, m), 0.62-0.67 (2H, m), 1.01 (6H, s), 1.21-1.27 (3H, m), 1.36 (1H, t), 2.07 (1H, t), 2.52-2.57 (1H, m), 3.15-3.21 (1H, m), 3.23 (2H, d), 3.45-3.52 (1H, m), 3.62-3.65 (3H, m), 3.76 (1H, d), 3.95-3.99 (1H, m), 4.12-4.16 (1H, m), 4.50-4.52 (1H, m), 6.49 (1H, s), 6.69 (1H, s), 7.47-7.50 (2H, m), 8.16-8.22 (2H, m), 8.56 (1H, s), Example 49j: $^1$H NMR (400.13 MHz, DMSO-d$_6$) δ 0.40-0.44 (2H, m), 0.62-0.67 (2H, m), 1.21-1.27 (3H, m), 2.53-2.58 (1H, m), 2.68 (2H, q), 3.09 (2H, s), 3.18 (1H, t), 3.20 (2H, t), 3.46-3.53 (1H, m), 3.57 (2H, s), 3.62-3.66 (1H, m), 3.75 (1H, d), 3.95-3.99 (1H, m), 4.15-4.18 (1H, m), 4.48-4.51 (1H, m), 6.44 (1H, d), 6.63 (1H, s), 7.48-7.50 (2H, m), 7.74 (1H, s), 8.19-8.22 (2H, m), 8.53 (1H, s), Test (a): Example (49) 0.033 μM; Example (49a) 0.15 μM; Example (49b) 0.014 μM; Example (49c) 0.04 μM; Example (49e) 0.032 μM; Example (49f) 0.2 μM; Example (49g0 0.087 μM; Example (49h) 0.18 μM; Example (49i) 0.016 μM; Example (49k) 0.014 μM; Example (49l) 1.6 μM.

Test (c): Example (49d) 0.62 μM; Example (49j) 0.13 μM.

The preparation of 3-cyclopropyl-1-[4-[4-[(3S)-3-methyl-morpholin-4-yl]-6-(methylsulfonyloxymethyl)pyrimidin-2-yl]phenyl]urea was described earlier.

EXAMPLE 50

3-Cyclopropyl-1-[4-[4-[(1,1-dioxo-1,4-thiazinan-4-yl)methyl]-6-[(3S)-3-methylmorpholin-4-yl]pyrimidin-2-yl]phenyl]urea

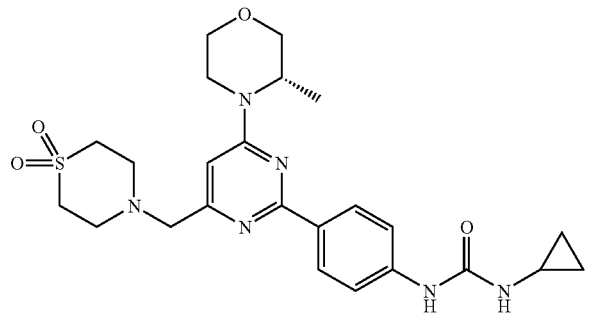

3-Cyclopropyl-1-[4-[4-[(3S)-3-methylmorpholin-4-yl]-6-(methylsulfonyloxymethyl)pyrimidin-2-yl]phenyl]urea (107 mg, 0.23 mmol) was dissolved in DCM (5 mL) and added to thiomorpholine (1.16 mmol). Triethylamine (0.162 mL, 1.16 mmol) was added to the solution and stirred at RT for 18 hours. The reaction was evaporated to dryness and dissolved in a 1,4-Dioxane (4 mL) water (1 mL) mixture. Meta-Chloroperbenzoic acid (100 mg, 0.58 mmol) and sodium permanganate (110 mg, 0.69 mmol) were added in single portions to the solution and stirred at RT for 1 hour. The crude solution was loaded onto a SCX-2 column, removed with 7N ammonia in methanol and evaporated to dryness. The solid was purified by prep-HPLC (basic) to give the desired material as a white solid (11 mg).

NMR Spectrum: $^1$H NMR (400.13 MHz, DMSO-d$_6$) δ 0.40-0.44 (2H, m), 0.62-0.67 (2H, m), 1.22 (3H, d), 2.53-2.58 (1H, m), 3.00 (1H, s), 3.02 (3H, t), 3.15-3.22 (5H, m), 3.50 (1H, d), 3.63-3.67 (1H, m), 3.70 (2H, s), 3.77 (1H, d), 3.96-3.99 (1H, m), 4.18 (1H, s), 4.53 (1H, s), 6.42 (1H, d), 6.70 (1H, s), 7.47-7.50 (2H, m), 8.19-8.21 (2H, m), 8.50 (1H, s).

Mass Spectrum; M+H$^+$ 501.

Test (a): 0.0016 μM.

The preparation of 3-cyclopropyl-1-[4-[4-[(3S)-3-methyl-morpholin-4-yl]-6-(methylsulfonyloxymethyl)pyrimidin-2-yl]phenyl]urea was described earlier.

EXAMPLE 51

1-[4-[4-(Hydroxymethyl)-6-[(3S)-3-methylmorpholin-4-yl]pyrimidin-2-yl]phenyl]-3-[(1-methylpyrazol-4-yl)methyl]urea

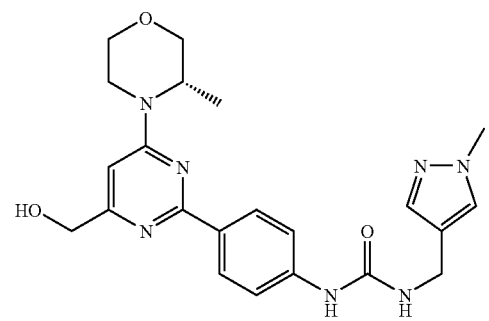

[2-Chloro-6-[(3S)-3-methylmorpholin-4-yl]pyrimidin-4-yl]methanol (1.00 g, 4.10 mmol) was added to 3-[(1-methylpyrazol-4-yl)methyl]-1-[4-(4,4,5,5-tetramethyl-1,3,2-dioxaborolan-2-yl)phenyl]urea (2.193 g, 6.16 mmol) and sodium carbonate (8.21 mL, 16.41 mmol) in 18% DMF in DME:EtOH:Water 7:2:3 (18 mL) and the solution was degassed for 5 minutes. Dichlorobis(triphenylphosphine)palladium(II) (0.144 g, 0.21 mmol) was added to the mixture. The resulting solution was stirred at 85° C. for 18 hours. The reaction was allowed to cool and neutralised with concentrated hydrochloric acid. The crude product was purified by ion exchange chromatography, using an SCX-2 (50 g) column then further purified by flash silica chromatography, elution gradient 0 to 7% methanol in DCM, to give the desired material as a white solid (963 mg).

NMR Spectrum: $^1$H NMR (400.13 MHz, DMSO-d$_6$) δ 1.23 (3H, d), 3.19-3.23 (1H, m), 3.46-3.52 (1H, m), 3.62-3.66 (1H, m), 3.78 (1H, d), 3.79 (3H, s), 3.96-3.99 (1H, m), 4.13 (3H, d), 4.45-4.50 (3H, m), 5.38 (1H, t), 6.39 (1H, t), 6.66 (1H, s), 7.35 (1H, s), 7.45-7.49 (2H, m), 7.59 (1H, s), 8.19-8.21 (2H, m), 8.64 (1H, s), m/z LCMS Spectrum: MH+ 438, retention time 1.37 minutes The preparations of [2-chloro-6-[(3S)-3-methylmorpholin-4-yl]pyrimidin-4-yl]methanol (1.00 g, 4.10 mmol) and 3-[(1-methylpyrazol-4-yl)methyl]-1-[4-(4,4,5,5-tetramethyl-1,3,2-dioxaborolan-2-yl)phenyl]urea were described earlier.

EXAMPLE 52

1-[4-[4-[(3S)-3-Methylmorpholin-4-yl]-6-[(4-methylpiperazin-1-yl)methyl]pyrimidin-2-yl]phenyl]-3-[(1-methylpyrazol-4-yl)methyl]urea

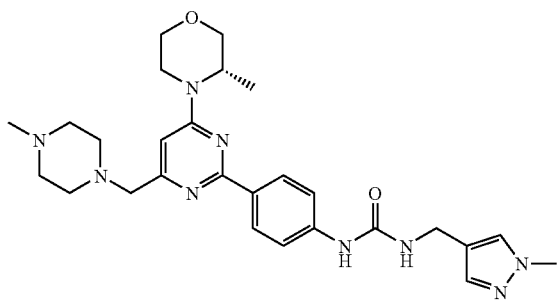

1-Methylpiperazine (0.067 mL, 0.60 mmol) was added to a solution of triethylamine (0.084 mL, 0.60 mmol) and 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea (155 mg, 0.30 mmol) in DCM (5 mL) at RT under nitrogen. The resulting solution was stirred at RT for 18 hours. The reaction mixture was evaporated. The crude product was purified by preparative HPLC using decreasingly polar mixtures of water (containing 1% NH3) and MeCN as eluents, to give the desired material as a white solid (65 mg).

NMR Spectrum: $^1$H NMR (400.13 MHz, DMSO-d$_6$) δ 1.21 (3H, d), 2.17 (3H, s), 2.35 (8H, s), 3.14-3.21 (1H, m), 3.47-3.50 (3H, m), 3.62-3.66 (1H, m), 3.77 (1H, s), 3.79 (3H, s), 3.95-3.99 (1H, m), 4.13 (3H, d), 4.46 (1H, d), 6.42 (1H, t), 6.61 (1H, s), 7.35 (1H, s), 7.47 (2H, d), 7.59 (1H, s), 8.20 (2H, d), 8.66 (1H, s).

LCMS Spectrum: MH+ 520, retention time 1.49 minutes.

The following compounds were prepared in an analogous fashion from 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea and the appropriate amine.

| Example | Structure | NAME | LCMS MH+ | Retention time (mins) |
|---|---|---|---|---|
| 52a | 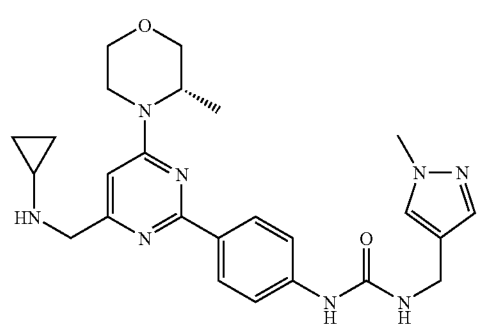 | 1-[4-[4-[(cyclopropylamino)methyl]-6-[(3S)-3-methylmorpholin-4-yl]pyrimidin-2-yl]phenyl]-3-[(1-methylpyrazol-4-yl)methyl]urea | 477 | 1.66 |
| 52b | 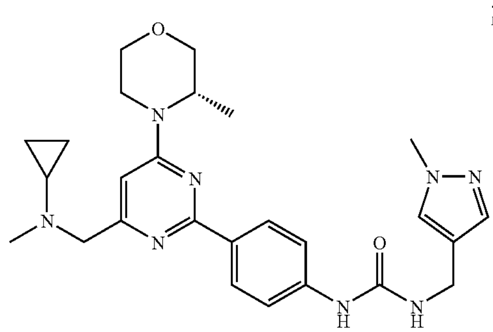 | 1-[4-[4-[(cyclopropyl-methyl-amino)methyl]-6-[(3S)-3-methylmorpholin-4-yl]pyrimidin-2-yl]phenyl]-3-[(1-methylpyrazol-4-yl)methyl]urea | 491 | 1.89 |

Example 52a: ¹H NMR (400.13 MHz, DMSO-$d_6$) δ 0.28-0.33 (2H, m), 0.37-0.39 (1H, m), 1.21-1.26 (3H, m), 1.36 (1H, t), 2.13-2.17 (1H, m), 2.82 (1H, s), 3.14-3.21 (1H, m), 3.43-3.51 (1H, m), 3.62-3.65 (1H, m), 3.71 (2H, d), 3.77-3.79 (4H, m), 3.95-3.99 (1H, m), 4.12-4.17 (3H, m), 4.50 (1H, d), 6.55 (1H, s), 6.64 (1H, s), 7.35 (1H, s), 7.48 (2H, d), 7.59 (1H, s), 8.17-8.23 (2H, m), 8.79 (1H, s).

Example 52b: ¹H NMR (400.13 MHz, DMSO-$d_6$) δ 0.40 (2H, t), 0.44-0.49 (2H, m), 1.20 (3H, d), 1.89-1.94 (1H, m), 2.33 (3H, s), 3.16-3.20 (2H, m), 3.45-3.52 (1H, m), 3.65 (3H, d), 3.79 (3H, s), 3.94-3.98 (1H, m), 4.13 (3H, d), 4.46 (1H, s), 6.40 (1H, t), 6.52 (1H, s), 7.35 (1H, s), 7.46-7.49 (2H, m), 7.59 (1H, s), 8.21 (2H, d), 8.64 (1H, s).

Test (a): Example (52) 1.4 µM; Example (52a) 0.33 µM; Example (52b) 0.57 µM.

The preparation of 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea is described below 1-[4-[4-[(3S)-3-Methylmorpholin-4-yl]-6-(methylsulfonyloxymethyl)pyrimidin-2-yl]phenyl]-3-[(1-methylpyrazol-4-yl)methyl]urea

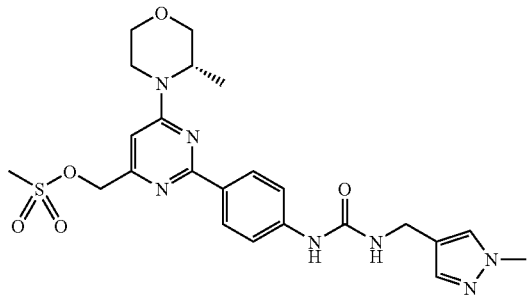

Methanesulfonyl chloride (0.246 mL, 3.15 mmol) was added dropwise over a period of 10 minutes to a solution of triethylamine (0.440 mL, 3.15 mmol) and 1-[4-[4-(hydroxymethyl)-6-[(3S)-3-methylmorpholin-4-yl]pyrimidin-2-yl]phenyl]-3-[(1-methylpyrazol-4-yl)methyl]urea (920 mg, 2.10 mmol) in DCM (30 mL) at 0° C. under nitrogen. The resulting solution was stirred at 20° C. for 45 minutes. The reaction mixture was washed with water (10 mL). The organic layer was dried ($MgSO_4$), filtered and evaporated to afford the desired material which was used without further purification.

LCMS Spectrum: MH+ 516, retention time 1.72 min.

The preparation of -[4-[4-(hydroxymethyl)-6-[(3S)-3-methylmorpholin-4-yl]pyrimidin-2-yl]phenyl]-3-[(1-methylpyrazol-4-yl)methyl]urea was described earlier.

EXAMPLE 53

N-[2-[[6-[(3S)-3-methylmorpholin-4-yl]-2-[4-[(1-methylpyrazol-4-yl)methylcarbamoylamino]phenyl]pyrimidin-4-yl]methylsulfonyl]ethyl]acetamide

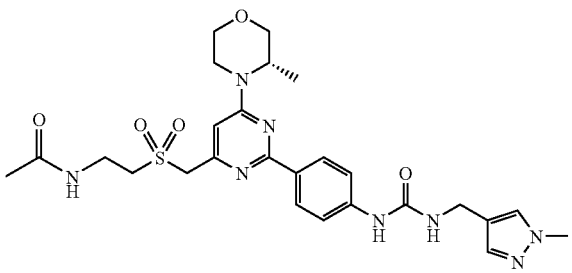

meta-Chloroperbenzoic acid (156 mg, 0.90 mmol) dissolved in Dioxane (2 mL), and sodium permanganate monohydrate (192 mg, 1.20 mmol) dissolved in water (1 mL) were added dropwise to N-[2-[[6-[(3S)-3-methylmorpholin-4-yl]-2-[4-[(1-methylpyrazol-4-yl)methylcarbamoylamino]phenyl]pyrimidin-4-yl]methylsulfanyl]ethyl]acetamide (162 mg, 0.30 mmol) in dioxane (6 mL) and water (2 mL) at RT under nitrogen. The resulting solution was stirred at RT for 1 hour. The crude product was purified by ion exchange chromatography, using an SCX column. The desired product was eluted from the column using 7M ammonia in methanol and pure fractions were evaporated to dryness. The crude product was purified by preparative HPLC using decreasingly polar mixtures of water (containing 1% NH3) and MeCN as eluents, to give the desired material as a white solid (61 mg).

NMR Spectrum: ¹H NMR (400.13 MHz, DMSO-$d_6$) δ 1.24 (3H, d), 1.83 (3H, s), 3.18 (1H, m), 3.50-3.58 (6H, m), 3.66-3.67 (1H, m), 3.76 (1H, s), 3.80 (3H, s), 3.97 (1H, s), 4.13 (2H, d), 4.51 (3H, m), 6.40 (1H, d), 6.78 (1H, s), 7.35 (1H, s), 7.48-7.51 (2H, m), 7.59 (1H, s), 8.15 (1H, s), 8.21 (2H, d), 8.69 (1H, s).

LCMS Spectrum: MH+ 571, retention time 1.42 min.

The following compounds were prepared in an analogous fashion from the appropriate sulphides.

| Example | Structure | NAME | LCMS MH+ | Retention time (mins) |
|---|---|---|---|---|
| 53a | 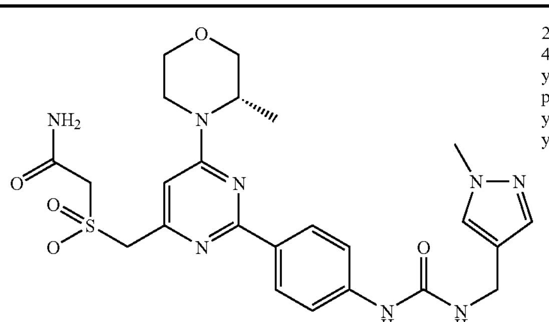 | 2-[[6-[(3S)-3-methylmorpholin-4-yl]-2-[4-[(1-methylpyrazol-4-yl)methylcarbamoylamino]phenyl]pyrimidin-4-yl]pyrimidin-4-yl]methylsulfonyl]acetamide | 543 | 1.40 |

| Example | Structure | NAME | LCMS MH+ | Retention time (mins) |
|---|---|---|---|---|
| 53b | 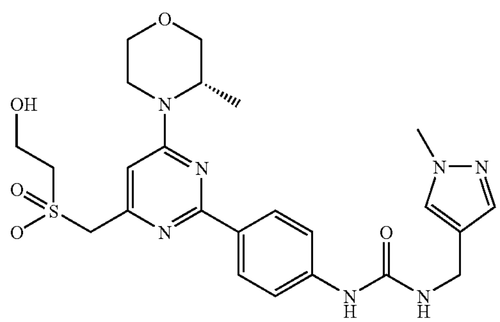 | 1-[4-[4-(2-hydroxyethylsulfonylmethyl)-6-[(3S)-3-methylmorpholin-4-yl]pyrimidin-2-yl]phenyl]-3-[(1-methylpyrazol-4-yl)methyl]urea | 530 | 1.43 |
| 52c | 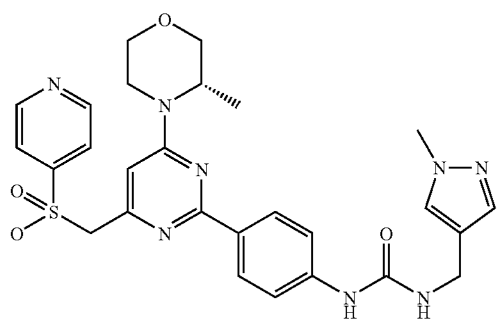 | 1-[4-[4-[(3S)-3-methylmorpholin-4-yl]-6-(pyridin-4-ylsulfonylmethyl)pyrimidin-2-yl]phenyl]-3-[(1-methylpyrazol-4-yl)methyl]urea | 563 | 1.63 |

Example 53a: $^1$H NMR (400.13 MHz, DMSO-d$_6$) δ 1.24 (3H, d), 3.19-3.25 (1H, m), 3.47-3.53 (1H, m), 3.63-3.67 (1H, m), 3.76 (1H, s), 3.79 (3H, s), 3.97-4.00 (1H, m), 4.13 (3H, d), 4.27 (2H, s), 4.48 (1H, s), 4.67 (2H, s), 6.42 (1H, t), 6.76 (1H, s), 7.35 (1H, s), 7.48-7.52 (3H, m), 7.59 (1H, s), 7.79 (1H, s), 8.20 (2H, d), 8.69 (1H, s).

Example 53b: $^1$H NMR (400.13 MHz, DMSO-d$_6$) δ 1.24 (3H, d), 3.22 (1H, d), 3.51 (3H, t), 3.63-3.67 (1H, m), 3.80 (4H, s), 3.92 (2H, q), 3.97-4.01 (1H, m), 4.13 (3H, d), 4.50 (3H, s), 5.18 (1H, t), 6.42 (1H, t), 6.76 (1H, s), 7.35 (1H, s), 7.49-7.51 (2H, m), 7.59 (1H, s), 8.22 (2H, d), 8.68 (1H, s).

Example 53c: $^1$H NMR (400.13 MHz, DMSO-d$_6$) δ 1.20-1.26 (3H, m), 3.15-3.22 (1H, m), 3.45-3.52 (1H, m), 3.61-3.65 (1H, m), 3.78 (1H, s), 3.80 (3H, s), 3.95-3.99 (1H, m), 4.12 (3H, d), 4.39 (1H, s), 4.87 (2H, s), 6.39 (1H, t), 6.71 (1H, s), 7.34-7.39 (3H, m), 7.59 (1H, s), 7.66 (2H, d), 7.81-7.82 (2H, m), 8.64 (1H, s), 8.90-8.91 (2H, m).

Test (a): Example (53) 0.64 μM; Example (53a) 0.6 μM; Example (53c) 0.03 μM.

Test (c): Example (53b) 3 μM.

The preparation of N-[2-[[6-[(3S)-3-methylmorpholin-4-yl]-2-[4-[(1-methylpyrazol-4-yl)methylcarbamoylamino]phenyl]pyrimidin-4-yl]methylsulfanyl]ethyl]acetamide is described below.

N-[2-[[6-[(3S)-3-Methylmorpholin-4-yl]-2-[4-[(1-methylpyrazol-4-yl)methylcarbamoylamino]phenyl]pyrimidin-4-yl]methylsulfanyl]ethyl]acetamide

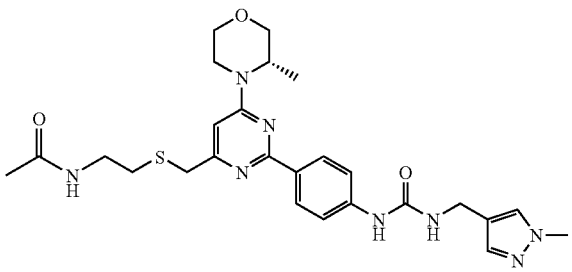

N-Acetylcysteamine (0.056 mL, 0.53 mmol) was added to DBU (0.091 mL, 0.60 mmol) and 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea (155 mg, 0.30 mmol) in acetonitrile (4 mL) under nitrogen. The resulting solution was stirred at RT for 5 hours. The reaction mixture was evaporated to give the desired material which was used without further purification.

LCMS Spectrum: MH+ 539, retention time 1.66 min.

The following sulphides were prepared in an analogous fashion from 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea and the appropriate thiol.

| Structure | NAME |
|---|---|
| 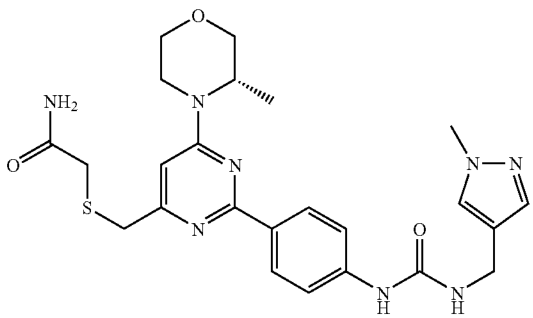 | 2-[[6-[(3S)-3-methylmorpholin-4-yl]-2-[4-[(1-methylpyrazol-4-yl)methylcarbamoylamino]phenyl]pyrimidin-4-yl]methylsulfanyl]acetamide |
| 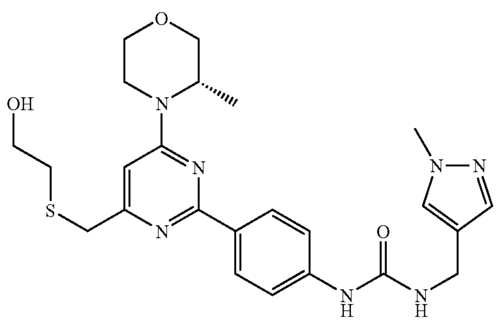 | 1-[4-[4-(2-hydroxyethylsulfanylmethyl)-6-[(3S)-3-methylmorpholin-4-yl]pyrimidin-2-yl]phenyl]-3-[(1-methylpyrazol-4-yl)methyl]urea |
| 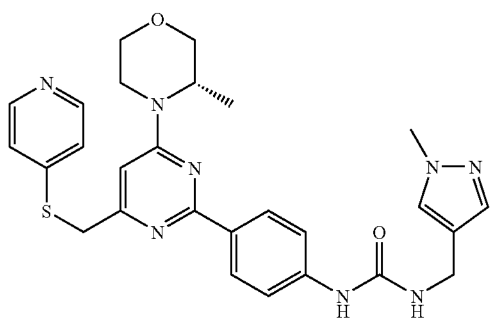 | 1-[4-[4-[(3S)-3-methylmorpholin-4-yl]-6-(pyridin-4-ylsulfanylmethyl)pyrimidin-2-yl]phenyl]-3-[(1-methylpyrazol-4-yl)methyl]urea |

The preparation of 1-[4-[4-[(3S)-3-methylmorpholin-4-yl]-6-(methylsulfonyloxymethyl)pyrimidin-2-yl]phenyl]-3-[(1-methylpyrazol-4-yl)methyl]urea was described earlier.

EXAMPLE 54

3-Cyclopropyl-1-[4-[4-(methoxymethyl)-6-[(3S)-3-methylmorpholin-4-yl]pyrimidin-2-yl]phenyl]urea

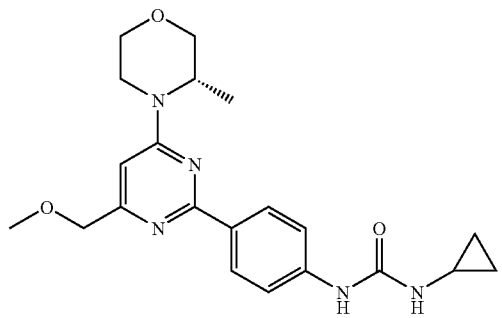

3-Cyclopropyl-1-[4-[4-[(3S)-3-methylmorpholin-4-yl]-6-(methylsulfonyloxymethyl)pyrimidin-2-yl]phenyl]urea (75 mg, 0.16 mmol) and potassium carbonate (90 mg, 0.65 mmol) were suspended in methanol (3 mL) and sealed into a microwave tube. The reaction was heated to 100° C. for 10 minutes in the microwave reactor and cooled to RT. The crude product was purified by ion exchange chromatography, using an SCX column. The desired product was eluted from the column using 7M ammonia in methanol. The crude product was further purified by preparative HPLC using decreasingly polar mixtures of water (containing 1% NH3) and MeCN as eluents, to give the desired material as a white solid (15 mg).

NMR Spectrum: $^1$H NMR (400.13 MHz, DMSO-$d_6$) δ 0.40-0.44 (2H, m), 0.62-0.67 (2H, m), 1.22 (3H, d), 2.54-2.58 (1H, m), 3.18-3.23 (1H, m), 3.40 (3H, s), 3.45-3.52 (1H, m), 3.62-3.66 (1H, m), 3.75 (1H, d), 3.95-3.98 (1H, m), 4.16-4.19 (1H, m), 4.39 (2H, s), 4.50 (1H, s), 6.42 (1H, d), 6.57 (1H, s), 7.47-7.50 (2H, m), 8.19-8.21 (2H, m), 8.51 (1H, s).

LCMS Spectrum: MH+ 398, retention time 1.86 min.

Test (c): 0.11 µM

The preparation of 3-cyclopropyl-1-[4-[4-[(3S)-3-methyl-morpholin-4-yl]-6-(methylsulfonyloxymethyl)pyrimidin-2-yl]phenyl]urea was described earlier.

EXAMPLE 55

3-Cyclopropyl-1-[4-[4-(cyclopropylsulfonylmethyl)-6-[(3S)-3-methylmorpholin-4-yl]pyrimidin-2-yl]phenyl]urea

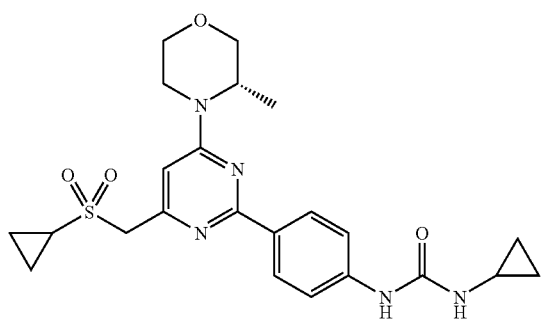

[4-(3-Cyclopropylureido)phenyl]boronic acid, pinacol ester (80 mg, 0.26 mmol), sodium carbonate (1.055 mL, 2.11 mmol), dichlorobis(triphenylphosphine)palladium(II) (14.8 mg, 0.02 mmol) and 2-chloro-4-(cyclopropylsulfonylmethyl)-6-[(3S)-3-methylmorpholin-4-yl]pyrimidine (70 mg, 0.21 mmol) were suspended in 18% DMF in DME:Ethanol:Water 7:2:3 mixture (4 mL) and sealed into a microwave tube. The reaction was heated to 100° C. for 10 minutes in the microwave reactor and cooled to RT. The crude product was purified by ion exchange chromatography, using an SCX column. The desired product was eluted from the column using 7M ammonia in methanol. The crude product was further purified by preparative HPLC using decreasingly polar mixtures of water (containing 1% NH3) and MeCN as eluents, to give the desired material as a colourless gum (33.0 mg).

NMR Spectrum: $^1$H NMR (400.13 MHz, DMSO-$d_6$) δ 0.41-0.43 (2H, m), 0.64-0.66 (2H, m), 0.98-1.01 (2H, m), 1.04-1.08 (2H, m), 1.24 (3H, d), 2.56 (1H, s), 2.86 (1H, d), 3.18 (1H, d), 3.50 (1H, d), 3.67 (1H, d), 3.76-3.79 (1H, m), 4.50 (2H, s), 6.43 (1H, d), 6.77 (1H, s), 7.49-7.51 (2H, m), 7.55-7.57 (1H, m), 7.60-7.65 (2H, m), 8.21-8.23 (2H, m), 8.53 (1H, s).

LCMS Spectrum: MH+ 472, retention time 1.80 min.
Test (a): 0.062 μM.

The preparation of 2-chloro-4-(cyclopropylsulfonylmethyl)-6-[(3S)-3-methylmorpholin-4-yl]pyrimidine is described below.

2-Chloro-4-(cyclopropylsulfonylmethyl)-6-[(3S)-3-methylmorpholin-4-yl]pyrimidine

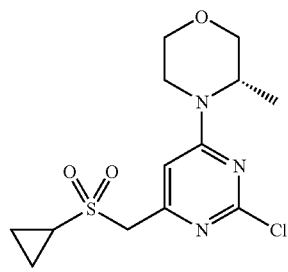

Cyclopropanesulfinic acid, sodium salt (381 mg, 2.97 mmol) was added in one portion to 2-chloro-4-(iodomethyl)-6-[(3S)-3-methylmorpholin-4-yl]pyrimidine (700 mg, 1.98 mmol) in acetonitrile (20 mL) at RT. The resulting suspension was stirred at 90° C. for 3 hours. The reaction mixture was evaporated to dryness and redissolved in DCM (50 mL), and washed with water (50 mL). The organic layer was dried (MgSO$_4$), filtered and evaporated to afford crude product. The crude product was purified by flash silica chromatography, elution gradient 0 to 40% ethyl acetate in DCM, to give the desired material as a white solid (458 mg).

NMR Spectrum: $^1$H NMR (400.13 MHz, DMSO-$d_6$) δ 0.95-0.98 (2H, m), 1.02-1.06 (2H, m), 1.18-1.23 (3H, m), 2.77-2.83 (1H, m), 3.19-3.25 (1H, m), 3.42-3.49 (1H, m), 3.58-3.62 (1H, m), 3.73 (1H, d), 3.92-3.96 (2H, m), 4.30 (1H, s), 4.48 (2H, s), 6.92 (1H, s).

LCMS Spectrum: MH+ 332, retention time 1.68 min.

The preparation of 2-chloro-4-(iodomethyl)-6-[(3S)-3-methylmorpholin-4-yl]pyrimidine was described earlier.

EXAMPLE 56

3-Cyclopropyl-1-[4-[4-(2-cyclopropylsulfonylpropan-2-yl)-6-[(3S)-3-methylmorpholin-4-yl]pyrimidin-2-yl]phenyl]urea

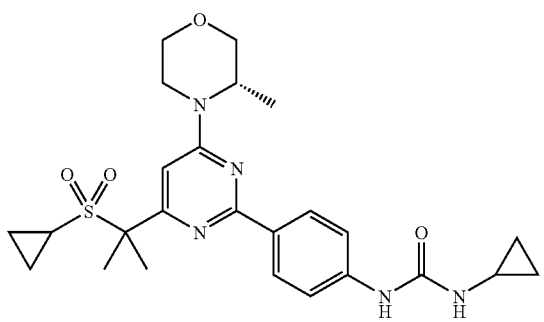

[4-(3-Cyclopropylureido)phenyl]boronic acid, pinacol ester (199 mg, 0.66 mmol), 2-chloro-4-(2-cyclopropylsulfonylpropan-2-yl)-6-[(3S)-3-methylmorpholin-4-yl]pyrimidine (190 mg, 0.53 mmol), sodium carbonate (1.320 mL, 2.64 mmol) and dichlorobis(triphenylphosphine)palladium(II) (37.1 mg, 0.05 mmol) were suspended in 18% DMF in a DME:Water:EtOH 7:3:2 solution (4 mL) and sealed into a microwave tube. The reaction was heated to 100° C. for 20 minutes in the microwave reactor and cooled to RT. The crude product was purified by ion exchange chromatography, using an SCX column. The desired product was eluted from the column using 7M ammonia in methanol and pure fractions were evaporated to dryness. The crude product was further purified by preparative HPLC using decreasingly polar mixtures of water (containing 1% NH3) and MeCN as eluents, to give the desired material as a white solid (85 mg).

NMR Spectrum: $^1$H NMR (400.13 MHz, DMSO-$d_6$) δ 0.40-0.44 (2H, m), 0.62-0.67 (2H, m), 0.78-0.83 (1H, m), 0.81 (1H, d), 0.95 (2H, d), 1.23 (3H, d), 1.81 (6H, d), 2.56 (1H, q), 2.73-2.77 (1H, m), 3.20-3.24 (1H, m), 3.48-3.53 (1H, m), 3.63-3.67 (1H, m), 3.77 (1H, d), 3.96-4.00 (1H, m), 4.20-4.23 (1H, m), 4.57-4.59 (1H, m), 6.42 (1H, d), 6.77 (1H, s), 7.49-7.51 (2H, m), 8.23-8.25 (2H, m), 8.52 (1H, s).

LCMS Spectrum: MH+ 500, retention time 2.04 min.

Test (a): 2.4 μM.

The preparation of 2-chloro-4-(2-cyclopropylsulfonylpropan-2-yl)-6-[(3S)-3-methylmorpholin-4-yl]pyrimidine is described below.

2-Chloro-4-(2-cyclopropylsulfonylpropan-2-yl)-6-[(3S)-3-methylmorpholin-4-yl]pyrimidine

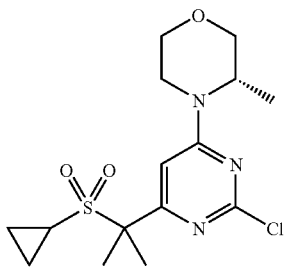

Iodomethane (0.033 mL, 0.53 mmol) was added to sodium tert-butoxide (50.7 mg, 0.53 mmol) and 2-chloro-4-(cyclopropylsulfonylmethyl)-6-[(3S)-3-methylmorpholin-4-yl]pyrimidine (175 mg, 0.53 mmol) in DMF (2 mL) at −10° C. The resulting thick suspension was stirred at RT for 15 minutes to ease the stirring. Iodomethane (0.033 mL, 0.53 mmol) and sodium tert-butoxide (50.7 mg, 0.53 mmol) were again added to the reaction and the resulting suspension stirred at RT for 15 minutes. The reaction mixture was diluted with DCM (20 mL) and washed with water (20 mL). The organic layer was dried (MgSO$_4$), filtered and evaporated to afford the desired material (153 mg).

LCMS Spectrum: MH+ 360, retention time 2.13 min.

The preparation of 2-chloro-4-(cyclopropylsulfonylmethyl)-6-[(3S)-3-methylmorpholin-4-yl]pyrimidine was described earlier.

EXAMPLE 57

1-[4-[4-(2-Cyclopropylsulfonylpropan-2-yl)-6-[(3S)-3-methylmorpholin-4-yl]pyrimidin-2-yl]phenyl]-3-methyl-urea

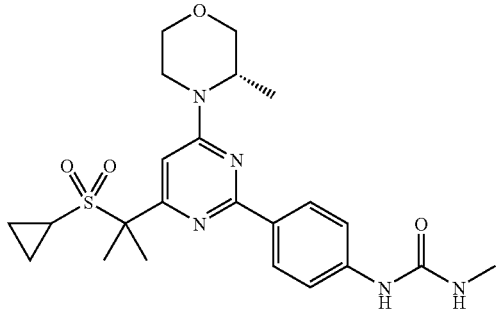

Methylamine (0.699 mL, 1.40 mmol) was added to phenyl N-[4-[4-(2-cyclopropylsulfonylpropan-2-yl)-6-[(3S)-3-methylmorpholin-4-yl]pyrimidin-2-yl]phenyl]carbamate (150 mg, 0.28 mmol) and triethylamine (0.117 mL, 0.84 mmol) in DMF (2 mL). The resulting solution was stirred at 40° C. for 2 hours. The crude product was purified by preparative HPLC using decreasingly polar mixtures of water (containing 1% NH3) and MeCN as eluents, to give the desired material as a white solid (74.0 mg).

NMR Spectrum: $^1$H NMR (400.13 MHz, DMSO-$d_6$) δ 0.77-0.85 (2H, m), 0.91-0.98 (2H, m), 1.22-1.23 (3H, m), 1.81 (6H, d), 2.67 (3H, t), 2.72-2.78 (1H, m), 3.20-3.24 (1H, m), 3.47-3.54 (1H, m), 3.63-3.67 (1H, m), 3.77 (1H, d), 3.96-4.00 (1H, m), 4.20-4.23 (1H, m), 4.57-4.59 (1H, m), 6.06 (1H, q), 6.77 (1H, s), 7.48-7.52 (2H, m), 8.22-8.25 (2H, m), 8.72 (1H, s).

LCMS Spectrum: MH+ 474, retention time 1.92 min.

Test (c): Example (57) 0.25 μM; Example (57a) 0.064 μM; Example (57b) 0.089 μM; Example (57c) 0.36 μM; Example (57d) 0.84 μM; Example (57e) 0.38 μM; Example (57f) 0.72 μM; Example (57g) 0.095 μM; Example (57h) 0.066 μM; Example (57i) 0.27 μM; Example (57j) 0.07 μM; Example (57k) 0.34 μM; Example (57l) 0.088 μM.

The following compounds were made in an analogous fashion from either phenyl N-[4-[4-(2-cyclopropylsulfonylpropan-2-yl)-6-[(3S)-3-methylmorpholin-4-yl]pyrimidin-2-yl]phenyl]carbamate or phenyl N-[4-[4-(cyclopropylsulfonylmethyl)-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 57a | 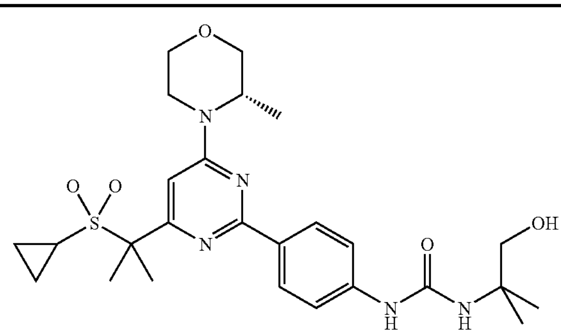 | 1-[4-[4-(2-cyclopropylsulfonylpropan-2-yl)-6-[(3S)-3-methylmorpholin-4-yl]pyrimidin-2-yl]phenyl]-3-(1-hydroxy-2-methyl-propan-2-yl)urea | 532 | 2.03 |

-continued

| Example | Structure | NAME | LCMS MH+ | Retention time (min) |
|---|---|---|---|---|
| 57b | 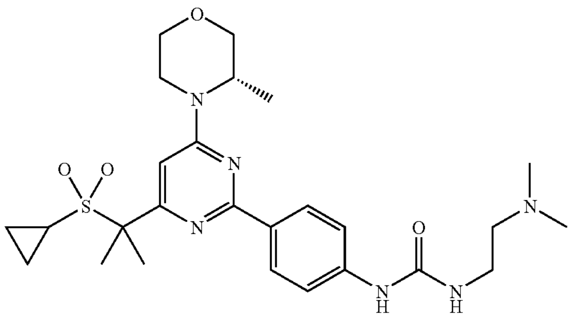 | 1-[4-[4-(2-cyclopropylsulfonylpropan-2-yl)-6-[(3S)-3-methylmorpholin-4-yl]pyrimidin-2-yl]phenyl]-3-(2-dimethylaminoethyl)urea | 531 | 2.00 |
| 57c | 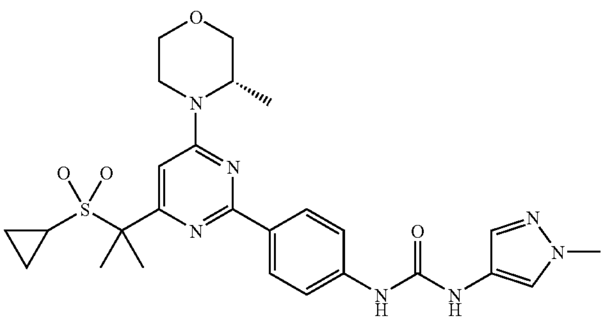 | 1-[4-[4-(2-cyclopropylsulfonylpropan-2-yl)-6-[(3S)-3-methylmorpholin-4-yl]pyrimidin-2-yl]phenyl]-3-(1-methylpyrazol-4-yl)urea | 540 | 1.93 |
| 57d | 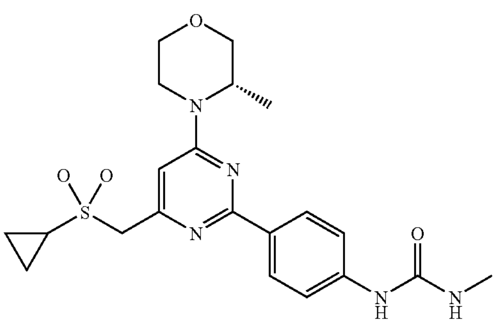 | 1-[4-[4-(cyclopropylsulfonylmethyl)-6-[(3S)-3-methylmorpholin-4-yl]pyrimidin-2-yl]phenyl]-3-methyl-urea | 446 | 1.56 |
| 57e | 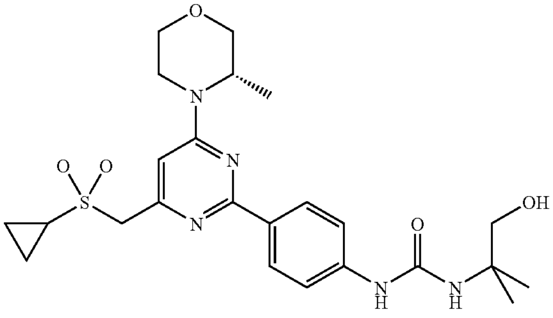 | 1-[4-[4-(cyclopropylsulfonylmethyl)-6-[(3S)-3-methylmorpholin-4-yl]pyrimidin-2-yl]phenyl]-3-(1-hydroxy-2-methyl-propan-2-yl)urea | 504 | 1.70 |

| Example | Structure | NAME | LCMS MH+ | Retention time (min) |
|---|---|---|---|---|
| 57f | 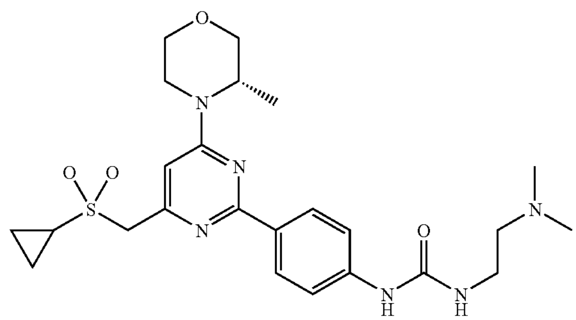 | 1-[4-[4-(cyclopropylsulfonylmethyl)-6-[(3S)-3-methylmorpholin-4-yl]pyrimidin-2-yl]phenyl]-3-(2-dimethylaminoethyl)urea | 503 | 1.66 |
| 57g | 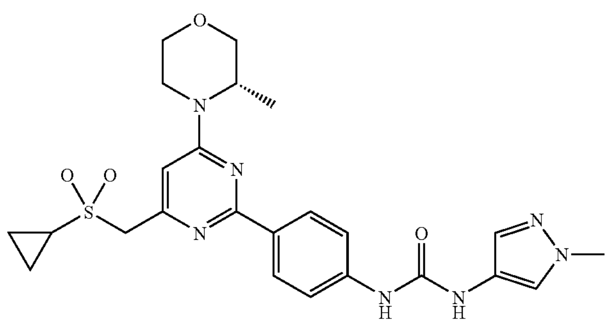 | 1-[4-[4-(cyclopropylsulfonylmethyl)-6-[(3S)-3-methylmorpholin-4-yl]pyrimidin-2-yl]phenyl]-3-(1-methylpyrazol-4-yl)urea | 512 | 1.63 |
| 57h | 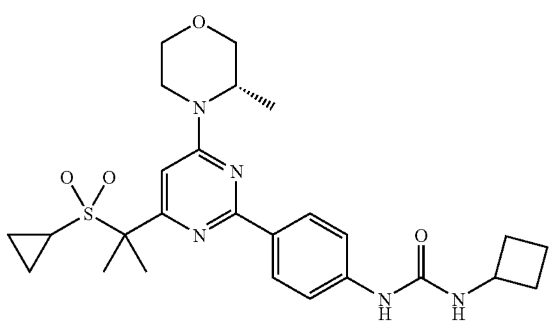 | 3-cyclobutyl-1-[4-[4-(2-cyclopropylsulfonylpropan-2-yl)-6-[(3S)-3-methylmorpholin-4-yl]pyrimidin-2-yl]phenyl]urea | 514 | 2.28 |
| 57i | 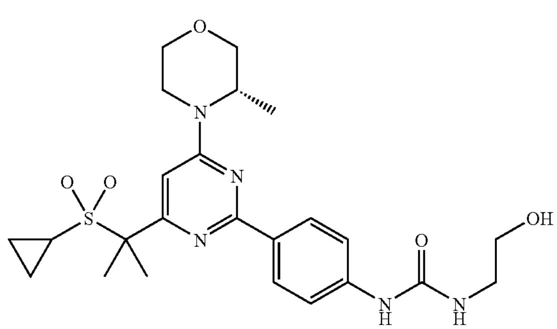 | 1-[4-[4-(2-cyclopropylsulfonylpropan-2-yl)-6-[(3S)-3-methylmorpholin-4-yl]pyrimidin-2-yl]phenyl]-3-(2-hydroxyethyl)urea | 504 | 1.72 |

-continued

| Example | Structure | NAME | LCMS MH+ | Retention time (min) |
|---|---|---|---|---|
| 57j | 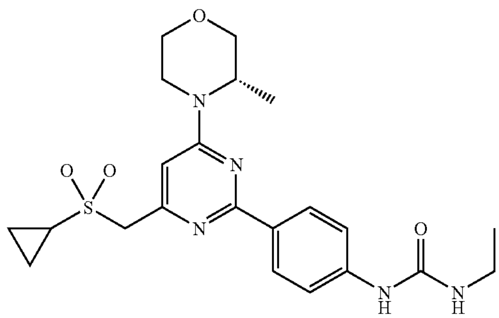 | 1-[4-[4-(cyclopropylsulfonylmethyl)-6-[(3S)-3-methylmorpholin-4-yl]pyrimidin-2-yl]phenyl]-3-ethyl-urea | 460 | 1.71 |
| 57k | 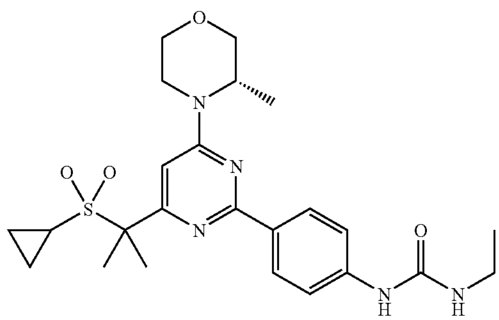 | 1-[4-[4-(2-cyclopropylsulfonylpropan-2-yl)-6-[(3S)-3-methylmorpholin-4-yl]pyrimidin-2-yl]phenyl]-3-ethyl-urea | 488 | 2.04 |
| 57l | 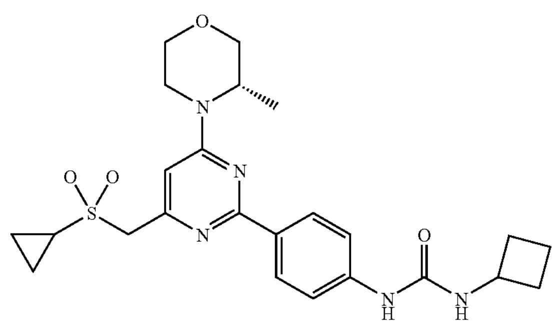 | 3-cyclobutyl-1-[4-[4-(cyclopropylsulfonylmethyl)-6-[(3S)-3-methylmorpholin-4-yl]pyrimidin-2-yl]phenyl]urea | 486 | 1.96 |

Example 57a: $^1$H NMR (400.13 MHz, DMSO-d$_6$) δ 0.79-0.83 (2H, m), 0.94-0.97 (2H, m), 1.22 (3H, d), 1.24 (6H, s), 1.81 (6H, d), 2.74-2.78 (1H, m), 3.21 (1H, t), 3.39 (2H, d), 3.50 (1H, d), 3.63-3.67 (1H, m), 3.77 (1H, d), 3.96-4.00 (1H, m), 4.20-4.23 (1H, m), 4.56-4.59 (1H, m), 4.95 (1H, t), 6.00 (1H, s), 6.76 (1H, s), 7.44-7.46 (2H, m), 8.22 (2H, d), 8.72 (1H, s).

Example 57b: $^1$H NMR (400.13 MHz, DMSO-d$_6$) δ 0.79-0.84 (2H, m), 0.95 (2H, d), 1.23 (3H, d), 1.81 (6H, d), 2.18 (6H, s), 2.34 (2H, t), 2.73-2.77 (1H, m), 3.17-3.23 (3H, m), 3.47-3.54 (1H, m), 3.63-3.67 (1H, m), 3.77 (1H, d), 3.96-4.00 (1H, m), 4.19-4.23 (1H, m), 4.58 (1H, d), 6.15 (1H, t), 6.77 (1H, s), 7.47-7.50 (2H, m), 8.22-8.24 (2H, m), 8.88 (1H, s).

Example 57c: $^1$H NMR (400.13 MHz, DMSO-d$_6$) δ 0.81-0.83 (2H, m), 0.96 (2H, d), 1.22-1.24 (3H, m), 1.82 (6H, d), 2.73-2.77 (1H, m), 3.21-3.25 (1H, m), 3.47-3.51 (1H, m), 3.64-3.68 (1H, m), 3.76 (1H, s), 3.79 (3H, s), 3.97-4.00 (1H, m), 4.22 (1H, d), 4.57-4.60 (1H, m), 6.78 (1H, s), 7.38 (1H, d), 7.53-7.56 (2H, m), 7.76 (1H, s), 8.27 (2H, d), 8.38 (1H, s), 8.82 (1H, s)

Example 57d: $^1$H NMR (400.13 MHz, DMSO-d$_6$) δ 0.97-1.01 (2H, m), 1.03-1.09 (2H, m), 1.23-1.25 (3H, m), 2.67 (3H, t), 2.83-2.90 (1H, m), 3.18 (1H, m), 3.47-3.54 (1H, m), 3.64-3.67 (1H, m), 3.78 (1H, d), 3.97-4.01 (1H, m), 4.20 (1H, d), 4.50 (3H, m), 6.06 (1H, q), 6.77 (1H, s), 7.48-7.51 (2H, m), 8.20-8.23 (2H, m), 8.72 (1H, s).

Example 57e: $^1$H NMR (400.13 MHz, DMSO-d$_6$) δ 0.98-1.01 (2H, m), 1.05-1.09 (2H, m), 1.23 (3H, d), 1.25 (6H, s), 2.85-2.89 (1H, m), 3.18 (1H, d), 3.39 (2H, d), 3.47-3.51 (1H, m), 3.64-3.67 (1H, m), 3.78 (1H, d), 3.97-4.01 (1H, m), 4.15-4.18 (1H, m), 4.47 (1H, s), 4.50 (2H, s), 4.95 (1H, t), 6.00 (1H, s), 6.77 (1H, s), 7.43-7.47 (2H, m), 8.21 (2H, d), 8.72 (1H, s).

Example 57f: $^1$H NMR (400.13 MHz, DMSO-d$_6$) δ 0.99-1.01 (2H, m), 1.05-1.08 (2H, m), 1.24 (3H, d), 2.18 (6H, s), 2.34 (2H, t), 2.86 (1H, d), 3.17 (1H, d), 3.20 (2H, m), 3.51 (1H, s), 3.66-3.67 (1H, m), 3.76-3.79 (1H, m), 4.02 (1H, d), 4.20 (1H, d), 4.50 (3H, m), 6.15 (1H, s), 6.77 (1H, s), 7.47-7.49 (2H, m), 8.20-8.23 (2H, m), 8.88 (1H, s).

Example 57g: $^1$H NMR (400.13 MHz, DMSO-d$_6$) δ 0.99-1.02 (2H, m), 1.04-1.10 (2H, m), 1.25 (3H, d), 2.85-2.89 (1H, m), 3.18 (2H, m), 3.48-3.51 (1H, m), 3.64-3.68 (1H, m), 3.77 (1H, s), 3.79 (3H, s), 3.97-4.01 (1H, m), 4.48 (1H, s), 4.51

(2H, s), 6.78 (1H, d), 7.38-7.39 (1H, m), 7.53-7.55 (2H, m), 7.76 (1H, s), 8.24-8.27 (2H, m), 8.38 (1H, s), 8.82 (1H, s).

Example 57h: $^1$H NMR (400.13 MHz, DMSO-d$_6$) δ 0.77-0.84 (2H, m), 0.91-0.96 (2H, m), 1.22-1.23 (3H, m), 1.59-1.64 (2H, m), 1.80 (6H, s), 1.81-1.85 (2H, m), 2.17-2.25 (2H, m), 2.73-2.77 (1H, m), 3.16-3.24 (1H, m), 3.47-3.53 (1H, m), 3.63-3.67 (1H, m), 3.77 (1H, d), 3.96-4.00 (1H, m), 4.11 (1H, m), 4.19 (1H, m), 4.56-4.59 (1H, m), 6.46 (1H, d), 6.77 (1H, s), 7.46-7.49 (2H, m), 8.24 (2H, d), 8.55 (1H, s).

Example 57i: $^1$H NMR (400.13 MHz, DMSO-d$_6$) δ 0.77-0.83 (2H, m), 0.94 (2H, t), 1.23 (3H, d), 1.81 (6H, d), 2.73-2.77 (1H, m), 3.18 (2H, d), 3.20-3.24 (1H, m), 3.46 (2H, q), 3.48-3.53 (1H, m), 3.63-3.67 (1H, m), 3.77 (1H, d), 3.96-4.00 (1H, m), 4.21 (1H, d), 4.58 (1H, d), 4.72 (1H, t), 6.25 (1H, t), 6.75 (1H, d), 7.47-7.50 (2H, m), 8.23-8.25 (2H, m), 8.79 (1H, s).

Example 57j: $^1$H NMR (400.13 MHz, DMSO-d$_6$) δ 0.97-1.01 (2H, m), 1.03-1.10 (2H, m), 1.04-1.09 (3H, m), 1.23-1.25 (3H, m), 2.85-2.89 (1H, m), 3.09-3.16 (2H, m), 3.21-3.25 (1H, m), 3.47-3.54 (1H, m), 3.64-3.67 (1H, m), 3.78 (1H, d), 3.97-4.01 (1H, m), 4.15 (1H, d), 4.50 (3H, m), 6.16 (1H, t), 6.77 (1H, s), 7.47-7.50 (2H, m), 8.20-8.23 (2H, m), 8.65 (1H, s).

Example 57k: $^1$H NMR (400.13 MHz, DMSO-d$_6$) δ 0.78-0.83 (2H, m), 0.95 (2H, d), 1.07 (3H, t), 1.23 (3H, d), 1.81 (6H, d), 2.75 (1H, d), 3.15 (2H, d), 3.18 (1H, s), 3.50 (1H, d), 3.63-3.67 (1H, m), 3.77 (1H, d), 3.96-4.00 (1H, m), 4.19-4.23 (1H, m), 4.58 (1H, d), 6.16 (1H, t), 6.74-6.77 (1H, m), 7.48-7.50 (2H, m), 8.23 (2H, d), 8.65 (1H, s).

Example 57l: $^1$H NMR (400.13 MHz, DMSO-d$_6$) δ 0.97-1.03 (2H, m), 1.03-1.09 (2H, m), 1.23-1.25 (3H, m), 1.57-1.66 (2H, m), 1.83-1.88 (2H, m), 2.17-2.24 (2H, m), 2.83-2.88 (1H, m), 3.21-3.25 (1H, m), 3.47-3.54 (1H, m), 3.63-3.67 (1H, m), 3.78 (1H, d), 3.97-4.00 (1H, m), 4.14 (2H, m), 4.50 (3H, m), 6.45 (1H, d), 6.77 (1H, s), 7.45-7.49 (2H, m), 8.20-8.23 (2H, m), 8.55 (1H, s).

The preparation of phenyl N-[4-[4-(2-cyclopropylsulfonylpropan-2-yl)-6-[(3S)-3-methylmorpholin-4-yl]pyrimidin-2-yl]phenyl]carbamate is described below.

Phenyl N-[4-[4-(2-cyclopropylsulfonylpropan-2-yl)-6-[(3S)-3-methylmorpholin-4-yl]pyrimidin-2-yl]phenyl]carbamate

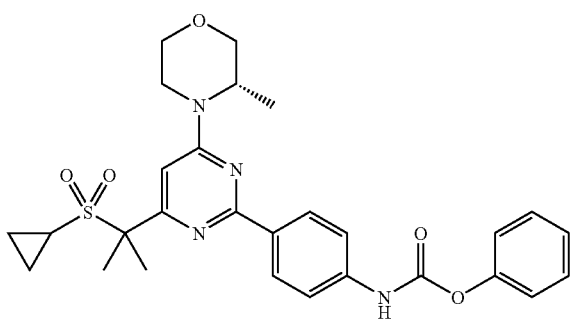

Phenyl chloroformate (0.215 mL, 1.71 mmol) was added dropwise to 4-[4-(2-cyclopropylsulfonylpropan-2-yl)-6-[(3S)-3-methylmorpholin-4-yl]pyrimidin-2-yl]aniline (712 mg, 1.71 mmol) and sodium bicarbonate (215 mg, 2.56 mmol) in dioxane (15 mL) under nitrogen. The resulting suspension was stirred at RT for 2 hours. The reaction mixture was evaporated to dryness and redissolved in ethyl acetate (100 mL) and washed with water (100 mL). The organic layer was dried (MgSO$_4$), filtered and evaporated to give the desired material (983 mg).

NMR Spectrum: $^1$H NMR (400.13 MHz, DMSO-d$_6$) δ 0.77-0.84 (2H, m), 0.95 (2H, t), 1.23 (3H, s), 1.82 (6H, d), 2.74-2.78 (1H, m), 3.18-3.25 (1H, m), 3.47-3.54 (1H, m), 3.64-3.67 (1H, m), 3.77 (1H, d), 3.96-4.00 (1H, m), 4.23 (1H, d), 4.59 (1H, s), 6.80 (1H, s), 7.22-7.30 (3H, m), 7.40-7.48 (2H, m), 7.55-7.64 (2H, m), 8.35 (2H, d), 10.42 (1H, s).

LCMS Spectrum: MH+ 537, retention time 2.87 min.

4-[4-(2-Cyclopropylsulfonylpropan-2-yl)-6-[(3S)-3-methylmorpholin-4-yl]pyrimidin-2-yl]aniline

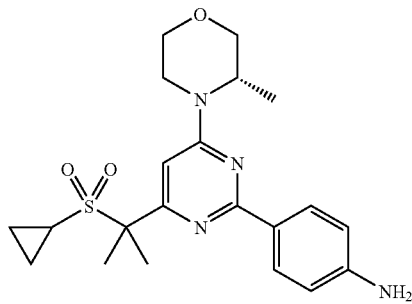

Dichlorobis(triphenylphosphine)palladium(II) (96 mg, 0.14 mmol) was added to (4-aminophenyl)boronic acid pinacol ester (747 mg, 3.41 mmol), 2-chloro-4-(2-cyclopropylsulfonylpropan-2-yl)-6-[(3S)-3-methylmorpholin-4-yl]pyrimidine (982 mg, 2.73 mmol) and sodium carbonate (6.82 mL, 13.64 mmol) in 18% DMF in DME:water:ethanol 7:3:2 (20 mL). The resulting solution was stirred at 80° C. for 16 hours. The crude product was purified by ion exchange chromatography, using an SCX column. The desired product was eluted from the column using 7M ammonia in methanol. The crude product was further purified by flash silica chromatography, elution gradient 0 to 2.5% methanol in DCM, to give the desired material as a yellow crystalline solid (712 mg).

NMR Spectrum: $^1$H NMR (400.13 MHz, DMSO-d$_6$) δ 0.79-0.83 (2H, m), 0.94-0.96 (2H, s), 1.21 (3H, d), 1.79 (6H, d), 2.74 (1H, m), 3.17 (1H, d), 3.49 (1H, d), 3.62-3.66 (1H, m), 3.76 (1H, d), 3.95-3.99 (1H, m), 4.16-4.19 (1H, m), 4.54 (1H, d), 5.51-5.53 (2H, m), 6.59 (2H, t), 6.67 (1H, s), 8.07 (2H, d).

LCMS Spectrum: MH+ 417, retention time 2.22 min.

The preparation of 2-chloro-4-(2-cyclopropylsulfonylpropan-2-yl)-6-[(3S)-3-methylmorpholin-4-yl]pyrimidine was described earlier.

The preparation of phenyl N-[4-[4-(cyclopropylsulfonylmethyl)-6-[(3S)-3-methylmorpholin-4-yl]pyrimidin-2-yl]phenyl]carbamate is described below.

383

Phenyl N-[4-[4-(cyclopropylsulfonylmethyl)-6-[(3S)-3-methylmorpholin-4-yl]pyrimidin-2-yl]phenyl]carbamate

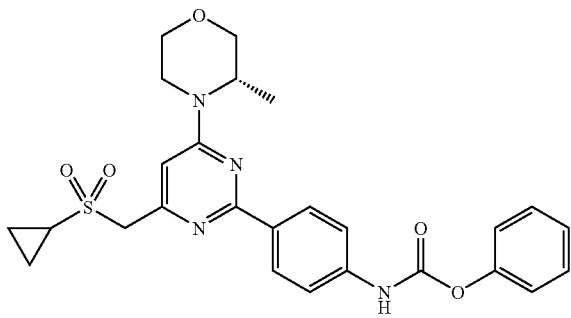

Phenyl chloroformate (0.315 mL, 2.50 mmol) was added dropwise to 4-[4-(cyclopropylsulfonylmethyl)-6-[(3S)-3-methylmorpholin-4-yl]pyrimidin-2-yl]aniline (972 mg, 2.50 mmol) and sodium bicarbonate (315 mg, 3.75 mmol) in dioxane (20 mL). The resulting suspension was stirred at RT for 2 hours. The reaction mixture was evaporated to dryness and redissolved in ethyl acetate (100 mL) and washed with water (100 mL). The organic layer was dried (MgSO$_4$), filtered and evaporated to afford the desired material (1.35 g).

NMR Spectrum: $^1$H NMR (400.13 MHz, DMSO-d$_6$) δ 0.98-1.03 (2H, m), 1.06-1.10 (2H, m), 1.26 (3H, d), 2.86-2.93 (1H, m), 3.48-3.52 (1H, m), 3.58 (1H, s), 3.64-3.68 (1H, m), 3.77-3.80 (1H, m), 3.98-4.06 (1H, m), 4.17 (1H, d), 4.50 (1H, s), 4.56 (2H, s), 6.86 (1H, s), 7.24-7.29 (3H, m), 7.43-7.47 (2H, m), 7.65 (2H, d), 8.31 (2H, d), 10.47 (1H, s).

LCMS Spectrum: MH+ 509, retention time 2.29 min.

4-[4-(Cyclopropylsulfonylmethyl)-6-[(3S)-3-methylmorpholin-4-yl]pyrimidin-2-yl]aniline

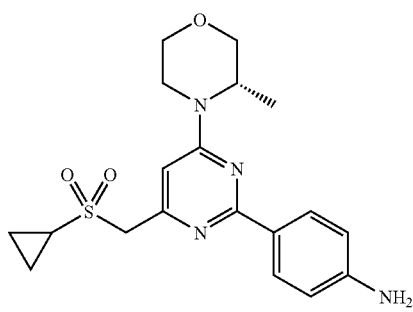

Dichlorobis(triphenylphosphine)palladium(II) (96 mg, 0.14 mmol) was added to (4-aminophenyl)boronic acid pinacol ester (747 mg, 3.41 mmol), 2-chloro-4-(cyclopropylsulfonylmethyl)-6-[(3S)-3-methylmorpholin-4-yl]pyrimidine (905 mg, 2.73 mmol) and sodium carbonate (6.82 mL, 13.64 mmol) in 18% DMF in DME:water:ethanol 7:3:2 (20 mL). The resulting solution was stirred at 80° C. for 6 hours. The crude reaction was purified by ion exchange chromatography, using an SCX column. The desired product was eluted from the column using 7M ammonia in methanol. The crude product was further purified by flash silica chromatography, elution gradient 0 to 2.5% methanol in DCM, to give the desired material as a yellow solid (972 mg).

NMR Spectrum: $^1$H NMR (400.13 MHz, DMSO-d$_6$) δ 0.97-1.02 (2H, m), 1.03-1.10 (2H, m), 1.23 (3H, d), 2.81-2.87 (TH, m), 3.15-3.22 (1H, m), 3.46-3.52 (1H, m), 3.62-3.66 (1H, m), 3.77 (1H, d), 3.96-3.99 (1H, m), 4.12-4.15 (1H, m), 4.45 (3H, s), 5.53 (2H, d), 6.58-6.61 (2H, m), 6.66 (1H, s), 8.03-8.07 (2H, m).

LCMS Spectrum: MH+ 389, retention time 1.82.

The preparation of 2-chloro-4-(cyclopropylsulfonylmethyl)-6-[(3S)-3-methylmorpholin-4-yl]pyrimidine was described earlier.

EXAMPLE 58

3-Methyl-1-[4-[4-[(3S)-3-methylmorpholin-4-yl]-6-(2-pyridin-4-ylsulfonylpropan-2-yl)pyrimidin-2-yl]phenyl]urea

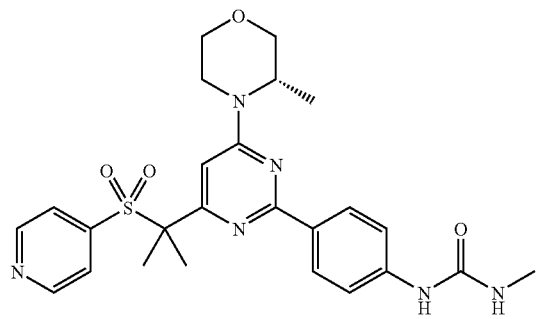

Methylamine (2M solution in THF) (0.55 mL, 1.10 mmol) was added to phenyl N-[4-[4-[(3S)-3-methylmorpholin-4-yl]-6-(2-pyridin-4-ylsulfonylpropan-2-yl)pyrimidin-2-yl]phenyl]carbamate (125 mg, 0.22 mmol) and triethylamine (0.092 mL, 0.66 mmol) in DMF (4 mL). The resulting solution was stirred at 50° C. overnight. The crude product was purified by preparative HPLC using decreasingly polar mixtures of water (containing 1% NH3) and acetonitrile as eluents, to give the desired material as a white solid (91 mg).

NMR Spectrum: $^1$H NMR (400.13 MHz, DMSO-d$_6$) δ 1.22-1.23 (3H, d), 1.82-1.83 (6H, d), 2.66-2.67 (3H, d), 3.15-3.23 (1H, td), 3.47-3.53 (1H, td), 3.63-3.53 (1H, dd), 3.76-3.79 (1H, d), 3.96-4.00 (1H, dd), 4.18-4.21 (1H, d), 4.57 (1H, bs), 6.03-6.07 (1H, q), 6.71 (1H, s), 7.35-7.37 (2H, d), 7.47-7.48 (2H, q), 7.65-7.68 (2H, d), 8.70 (1H, s), 8.74-8.75 (2H, q).

LCMS Spectrum: MH+ 511, retention time 2.03 min.

The following compounds were made in an analogous fashion from phenyl N-[4-[4-[(3S)-3-methylmorpholin-4-yl]-6-(2-pyridin-4-ylsulfonylpropan-2-yl)pyrimidin-2-yl]phenyl]carbamate and the appropriate amine.

| Example | Structure | NAME | LCMS MH+ | Retention time (min) |
|---|---|---|---|---|
| 58a | 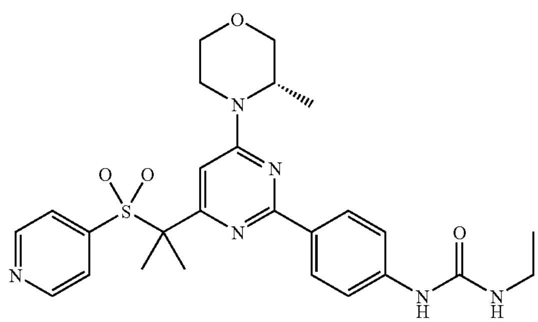 | 3-ethyl-1-[4-[4-[(3S)-3-methylmorpholin-4-yl]-6-(2-pyridin-4-ylsulfonylpropan-2-yl)pyrimidin-2-yl]phenyl]urea | 525 | 2.17 |
| 58b | 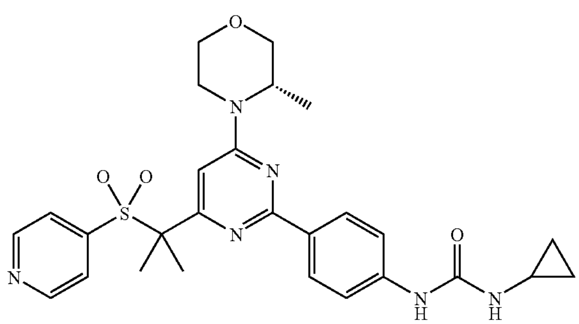 | 3-cyclopropyl-1-[4-[4-[(3S)-3-methylmorpholin-4-yl]-6-(2-pyridin-4-ylsulfonylpropan-2-yl)pyrimidin-2-yl]phenyl]urea | 537 | 2.19 |
| 58c | 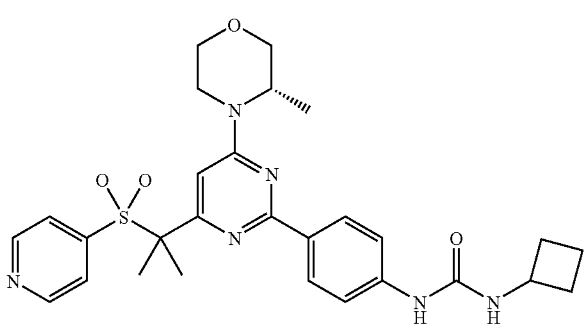 | 3-cyclobutyl-1-[4-[4-[(3S)-3-methylmorpholin-4-yl]-6-(2-pyridin-4-ylsulfonylpropan-2-yl)pyrimidin-2-yl]phenyl]urea | 551 | 2.39 |
| 58d | 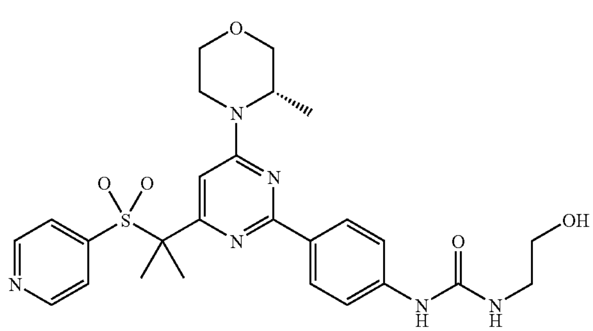 | 3-(2-hydroxyethyl)-1-[4-[4-[(3S)-3-methylmorpholin-4-yl]-6-(2-pyridin-4-ylsulfonylpropan-2-yl)pyrimidin-2-yl]phenyl]urea | 541 | 1.90 |

| Example | Structure | NAME | LCMS MH+ | Retention time (min) |
|---|---|---|---|---|
| 58e | 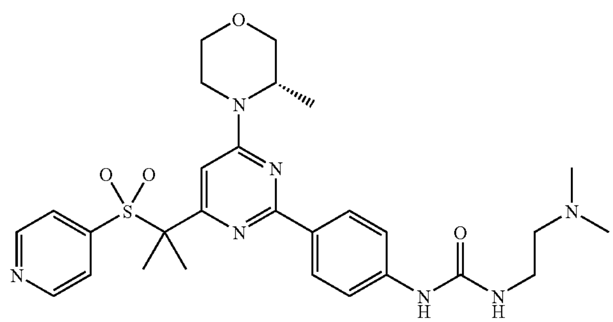 | 3-(2-dimethylaminoethyl)-1-[4-[4-[(3S)-3-methylmorpholin-4-yl]-6-(2-pyridin-4-ylsulfonylpropan-2-yl)pyrimidin-2-yl]phenyl]urea | 568 | 2.36 |

Example 58a: ¹H NMR (400.13 MHz, DMSO-d₆) δ 1.05-1.09 (3H, t), 1.22-1.23 (3H, d), 1.82-1.83 (6H, d), 3.09-3.22 (3H, m), 3.47-3.53 (1H, td), 3.63-3.67 (1H, dd), 3.76-3.79 (1H, d), 3.96-3.99 (1H, dd), 4.18-4.22 (1H, d), 4.57 (1H, bs), 6.13-6.15 (1H, t), 6.71 (1H, s), 7.34-7.36 (2H, d), 7.47-7.48 (2H, q), 7.65-7.68 (2H, d), 8.62 (1H, s), 8.74-8.75 (2H, q).

Example 58b: ¹H NMR (400.13 MHz, DMSO-d₆) δ 0.40-0.44 (2H, m), 0.63-0.68 (2H, m), 1.22-1.23 (3H, d), 1.82-1.83 (6H, d), 2.54-2.59 (1H, m), 3.15-3.23 (1H, td), 3.47-3.53 (1H, td), 3.63-3.67 (1H, dd), 3.76-3.79 (1H, d), 3.96-4.00 (1H, dd), 4.18-4.21 (1H, d), 4.57 (1H, bs), 6.41-6.42 (1H, d), 6.72 (1H, s), 7.35-7.38 (2H, d), 7.47-7.48 (2H, q), 7.66-7.68 (2H, d), 8.50 (1H, s), 8.74-8.75 (2H, q).

Example 58c: ¹H NMR (400.13 MHz, DMSO-d₆) δ 1.22-1.23 (3H, d), 1.58-1.66 (2H, m), 1.82-1.83 (6H, d), 1.83-1.89 (2H, m), 2.18-2.25 (2H, m), 3.15-3.22 (1H, td), 3.47-3.53 (1H, td), 3.63-3.67 (1H, dd), 3.76-3.79 (1H, d), 3.96-4.00 (1H, dd), 4.11-4.21 (2H, m), 4.57 (1H, bs), 6.43-6.45 (1H, d), 6.72 (1H, s), 7.32-7.34 (2H, d), 7.46-7.48 (2H, q), 7.65-7.68 (2H, d), 8.83 (1H, s), 8.74-8.75 (2H, q).

Example 58d: ¹H NMR (400.13 MHz, DMSO-d₆) δ 1.22-1.23 (3H, d), 1.82-1.83 (6H, d), δ 3.16-3.23 (3H, m), 3.44-3.48 (2H, q), 3.48-3.53 (1H, td), 3.63-3.67 (1H, dd), 3.76-3.79 (1H, d), 3.96-4.00 (1H, dd), 4.18-4.22 (1H, d), 4.56 (1H, bs), 4.71-4.74 (1H, t), 6.22-6.25 (1H, t), 6.72 (1H, s), 7.33-7.36 (2H, d), 7.47-7.48 (2H, q), 7.66-7.68 (2H, d), 8.74-8.75 (2H, q), 8.77 (1H, s).

Example 58e: ¹H NMR (400.13 MHz, DMSO-d₆) δ 1.22-123 (3H, d), 1.82-1.83 (6H, d), 2.19 (6H, s), 2.32-2.36 (2H, t), 3.15-3.22 (3H, m), 3.47-3.53 (1H, td), 3.63-3.67 (1H, dd), 3.76-3.79 (1H, d), 3.96-4.00 (1H, dd), 4.18-4.21 (1H, d), 4.56 (1H, bs), 6.13-6.15 (1H, t), 6.72 (1H, s), 7.33-7.35 (2H, d), 7.47-7.48 (2H, q), 7.66-7.68 (2H, d), 8.74-8.75 (2H, q), 8.85 (1H, s).

The preparation of phenyl N-[4-[4-[(3S)-3-methylmorpholin-4-yl]-6-(2-pyridin-4-ylsulfonylpropan-2-yl)pyrimidin-2-yl]phenyl]carbamate is described below.

Phenyl N-[4-[4-[(3S)-3-methylmorpholin-4-yl]-6-(2-pyridin-4-ylsulfonylpropan-2-yl)pyrimidin-2-yl]phenyl]carbamate

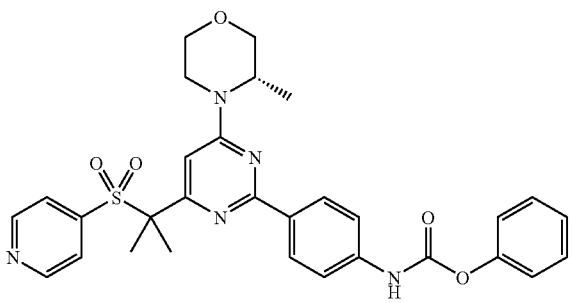

Phenyl chloroformate (0.177 mL, 1.41 mmol) was added to 4-[4-[(3S)-3-methylmorpholin-4-yl]-6-(2-pyridin-4-ylsulfonylpropan-2-yl)pyrimidin-2-yl]aniline (0.640 g, 1.41 mmol) and sodium bicarbonate (0.178 g, 2.12 mmol) in dioxane (175 mL) at RT under air. The resulting slurry was stirred at RT for 2 hours. Two more portions of phenyl chloroformate (2×0.005 mL) were added and the reaction allowed to stir at RT. Water was then added to the reaction and the solids were filtered and dried in a vacuum oven at 55° C. overnight to give the desired material as a tan solid (0.758 g).

NMR Spectrum: ¹H NMR (400.13 MHz, DMSO-d₆) δ 1.23-1.24 (3H, d), 1.83-1.84 (6H, d), 3.17-3.24 (1H, td), 3.48-3.53 (1H, td), 3.64-3.67 (1H, dd), 3.76-3.79 (1H, d), 3.97-4.00 (1H, dd), 4.21-4.24 (1H, d), 4.59 (1H, bs), 6.76 (1H, s), 7.24-7.31 (3H, m), 7.43-7.50 (6H, m), 7.75-7.78 (2H, d), 8.74-8.76 (2H, d), 10.39 (1H, s).

LCMS Spectrum: MH+ 572, retention time 2.82 min.

4-[4-[(3S)-3-Methylmorpholin-4-yl]-6-(2-pyridin-4-ylsulfonylpropan-2-yl)pyrimidin-2-yl]aniline

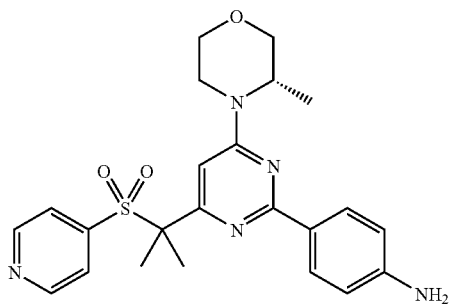

trans-Dichlorobis (triphenylphosphine)palladium (II) (0.050 g, 0.07 mmol) was added to 2-chloro-4-[(3S)-3-methylmorpholin-4-yl]-6-(2-pyridin-4-ylsulfonylpropan-2-yl)pyrimidine (0.560 g, 1.41 mmol), 4-(4,4,5,5-tetramethyl-1,3,2-dioxaborolan-2-yl)aniline (0.464 g, 2.12 mmol) and sodium carbonate (3.53 mL, 7.05 mmol) in 18% DMF in a mixture of DME:water:ethanol (7:3:2) (30 mL) at RT under nitrogen. The resulting solution was stirred at 80° C. for 5 hours. The reaction was allowed to cool and partitioned between ethyl acetate and water. The aqueous layer was extracted with ethyl acetate twice and the combined organics dried (MgSO$_4$), filtered and evaporated to afford the desired material (0.640 g) which was used without further purification.

LCMS Spectrum: MH+ 454, retention time 2.18 min.

2-Chloro-4-[(3S)-3-methylmorpholin-4-yl]-6-(2-pyridin-4-ylsulfonylpropan-2-yl)pyrimidine

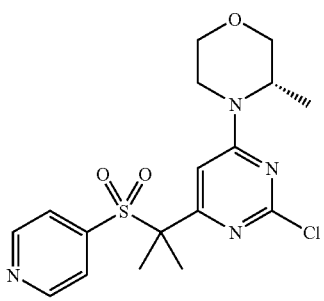

Iodomethane (0.164 mL, 2.63 mmol) was added to 2-chloro-4-[(3S)-3-methylmorpholin-4-yl]-6-(pyridin-4-ylsulfonylmethyl)pyrimidine (0.970 g, 2.63 mmol) and sodium tert-butoxide (0.253 g, 2.63 mmol) in DMF (15 mL) at 0° C. under air. Additional sodium tert-butoxide (0.253 g, 2.63 mmol) and iodomethane (0.164 mL, 2.63 mmol) were added and the resulting solution stirred at 0° C. for 1 hour. The solution was allowed to slowly warm up to RT. Water and ethyl acetate were added and the solution was separated. The aqueous layer was extracted with ethyl acetate twice and the combined organics dried (MgSO$_4$), filtered and evaporated on to silica. The crude product was chromatographed on silica, eluting with 0-60% ethyl acetate in DCM, to give the desired material as a yellow oil which solidified on standing (0.56 g).

NMR Spectrum: $^1$H NMR (400.13 MHz, CDCl$_3$) δ 1.27-1.29 (3H, d), 1.71-1.72 (6H, d), 3.22-3.29 (1H, td), 3.48-3.54 (1H, td), 3.64-3.67 (1H, dd), 3.73-3.76 (1H, d), 3.95-3.98 (2H, dd), 4.29 (1H, bs), 6.63 (1H, s), 7.39-7.41 (2H, dd), 8.78-8.79 (2H, dd).

LCMS Spectrum: MH+ 397, retention time 1.73 min.

The preparation of 2-chloro-4-[(3S)-3-methylmorpholin-4-yl]-6-(pyridin-4-ylsulfonylmethyl)pyrimidine was described earlier.

EXAMPLE 59

3-Ethyl-1-[4-[4-(2-hydroxyethylsulfonylmethyl)-6-[(3S)-3-methylmorpholin-4-yl]pyrimidin-2-yl]phenyl]urea

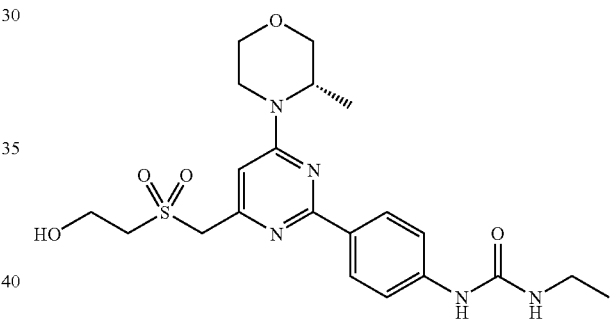

Phenyl N-[4-[4-(2-hydroxyethylsulfonylmethyl)-6-[(3S)-3-methylmorpholin-4-yl]pyrimidin-2-yl]phenyl]carbamate (0.073 g, 0.14 mmol), ethylamine (0.70 mmol) and triethylamine (0.42 mmol) were combined and heated at 50° C. under an atmosphere of air overnight. The crude product was purified by preparative HPLC using decreasingly polar mixtures of water (containing 1% NH$_3$) and MeCN as eluents to give the desired material as a white solid (0.047 g).

NMR Spectrum: $^1$H NMR (400.13 MHz, DMSO-d$_6$) δ 1.06-1.09 (3H, t), 1.24-1.25 (3H, d), 3.10-3.17 (2H, m), 3.19-3.26 (1H, td), 3.47-3.53 (3H, m), 3.64-3.67 (1H, dd), 3.77-3.80 (1H, d), 3.90-3.94 (2H, q), 3.97-4.01 (1H, dd), 4.15-4.19 (1H, d), 4.48 (1H, bs), 4.50 (2H, s), 5.17-5.20 (1H, t), 6.15-6.18 (1H, t), 6.76 (1H, s), 7.49-7.51 (2H, d), 8.20-8.23 (2H, d), 8.66 (1H, s).

LCMS Spectrum: MH+ 464, retention time 1.62 min.

The following compounds were prepared in an analogous fashion from phenyl N-[4-[4-(2-hydroxyethylsulfonylmethyl)-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 59a | 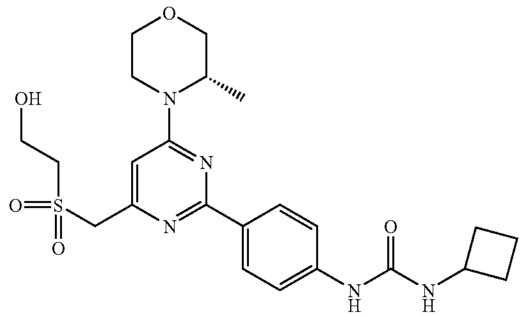 | 3-cyclobutyl-1-[4-[4-(2-hydroxyethylsulfonylmethyl)-6-[(3S)-3-methylmorpholin-4-yl]pyrimidin-2-yl]phenyl]urea | 490 | 1.84 |
| 59b | 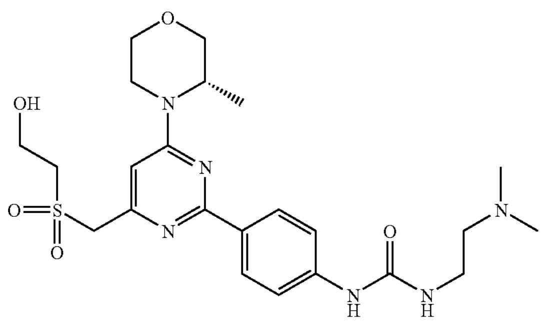 | 3-(2-dimethylaminoethyl)-1-[4-[4-(2-hydroxyethylsulfonylmethyl)-6-[(3S)-3-methylmorpholin-4-yl]pyrimidin-2-yl]phenyl]urea | 507 | 1.61 |

Example 59a: $^1$H NMR (400.13 MHz, DMSO-$d_6$) δ 1.24-1.25 (3H, d), 1.57-1.69 (2H, m), 1.82-1.92 (2H, m), 2.18-2.25 (2H, m), 3.18-3.27 (1H, td), 3.47-3.53 (3H, m), 3.64-3.67 (1H, dd), 3.77-3.79 (1H, d), 3.90-3.94 (2H, q), 3.97-4.01 (1H, dd), 4.10-4.18 (2H, m), 4.47 (1H, bs), 4.50 (2H, s), 5.17-5.20 (1H, t), 6.46-6.48 (1H, d), 6.76 (1H, s), 7.47-7.49 (2H, d), 8.20-8.22 (2H, d), 8.56 (1H, s).

Example 59b: $^1$H NMR (400.13 MHz, DMSO-$d_6$) δ 1.35-1.37 (3H, d), 3.37 (6H, s), 2.56-2.59 (2H, t), 3.31-3.38 (5H, m), 3.49 (2H, s), 3.56-3.63 (1H, td), 3.72-3.76 (1H, dd), 3.82-3.85 (1H, d), 4.03-4.07 (1H, dd), 4.14-4.17 (2H, t), 4.17-4.20 (1H, d), 4.42-4.43 (2H, d), 4.48 (1H, bs), 5.61 (1H, bs), 6.45 (1H, s), 7.46-7.48 (2H, d), 8.19-8.21 (2H, d).

Test (c): Example (59a) 0.037 μM; Example (57b) 0.043 μM.

The preparation of phenyl N-[4-[4-(2-hydroxyethylsulfonylmethyl)-6-[(3S)-3-methylmorpholin-4-yl]pyrimidin-2-yl]phenyl]carbamate is described below.

Phenyl N-[4-[4-(2-hydroxyethylsulfonylmethyl)-6-[(3S)-3-methylmorpholin-4-yl]pyrimidin-2-yl]phenyl]carbamate

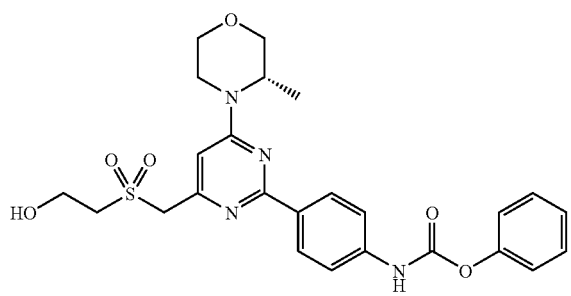

Phenyl chloroformate (0.046 mL, 0.36 mmol) was added to 2-[[2-(4-aminophenyl)-6-[(3S)-3-methylmorpholin-4-yl]pyrimidin-4-yl]methylsulfonyl]ethanol (0.143 g, 0.36 mmol) and sodium bicarbonate (0.046 g, 0.55 mmol) in dioxane (20 mL) at RT under air. The resulting slurry was stirred at RT for 2 hours. Water was added and the mixture extracted with DCM three times. The combined organics were dried (MgSO$_4$), filtered and concentrated in vacuo to give the desired material as a yellow solid (0.228 g).

NMR Spectrum: $^1$H NMR (400.13 MHz, DMSO-$d_6$) δ 1.24-1.26 (3H, d), 3.20-3.26 (1H, td), 3.51-3.54 (3H, m), 3.58 (1H, s), 3.64-3.68 (1H, dd), 3.77-3.80 (1H, d), 3.90-3.95 (2H, m), 3.97-4.01 (1H, dd), 4.18-4.21 (1H, d), 4.48 (1H, bs), 4.52 (2H, s), 5.18-5.20 (1H, t), 6.80 (1H, s), 7.25-7.30 (3H, m), 7.43-7.47 (2H, t), 7.63-7.65 (3H, d), 8.31-8.33 (2H, d), 10.44 (1H, s).

LCMS Spectrum: MH+ 513, retention time 2.28 min.

2-[[2-(4-Aminophenyl)-6-[(3S)-3-methylmorpholin-4-yl]pyrimidin-4-yl]methylsulfonyl]ethanol

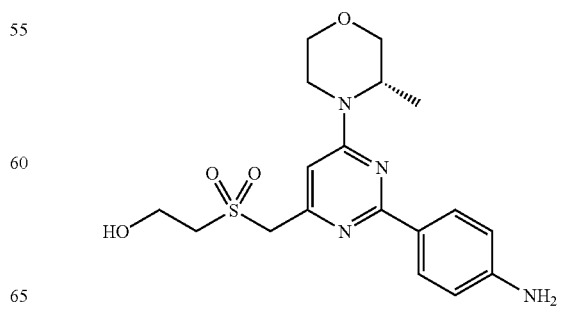

trans-Dichlorobis(triphenylphosphine)palladium (II) (0.013 g, 0.02 mmol) was added to 2-[[2-chloro-6-[(3S)-3-methylmorpholin-4-yl]pyrimidin-4-yl]methylsulfonyl]ethanol (0.122 g, 0.36 mmol), 4-(4,4,5,5-tetramethyl-1,3,2-dioxaborolan-2-yl)aniline (0.119 g, 0.54 mmol) and sodium carbonate (0.908 mL, 1.82 mmol) in 18% DMF in a mixture of DME:water:ethanol (7:3:2) (10 mL) at RT under nitrogen. The resulting solution was stirred at 80° C. for 2 hours. The reaction was cooled and partitioned between ethyl acetate and water. The reaction mixture was extracted with ethyl acetate twice and the combined organics dried (MgSO$_4$) filtered and concentrated in vacuo to give the desired (0.143 g).

LCMS Spectrum: MH+ 393, retention time 1.30 min.

2-[[2-Chloro-6-[(3S)-3-methylmorpholin-4-yl]pyrimidin-4-yl]methylsulfonyl]ethanol

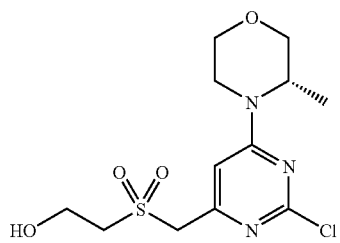

A 30% aqueous solution of hydrogen peroxide (0.225 mL, 7.29 mmol) (was added to a stirred solution of 2-chloro-4-[(3S)-3-methylmorpholin-4-yl]-6-[2-(oxan-2-yloxy)ethylsulfanylmethyl]pyrimidine (0.141 g, 0.36 mmol), sodium tungstate dihydrate (2.4 mg, 0.0073 mmol) in water (0.2 mL) and 2N sulfuric acid (0.011 mL) in 1,4-dioxane (1.4 mL) and methanol (1.4 mL) and warmed to 55° C. under air. The resulting solution was stirred at 55° C. for 4 hours then water (50 mL) added and the reaction cooled. A 10% aqueous solution of sodium metabisulfite was added and then the whole solution extracted with DCM. The organics were dried (MgSO$_4$), filtered and concentrated in vacuo to give the desired material as an opaque oil (0.198 g).

LCMS Spectrum: MH+ 336, retention time 1.18 min.

2-Chloro-4-[(3S)-3-methylmorpholin-4-yl]-6-[2-(oxan-2-yloxy)ethylsulfanylmethyl]pyrimidine

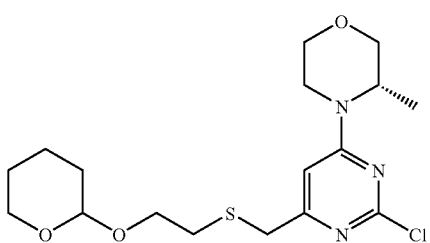

DIPEA (0.211 g, 1.63 mmol) was added dropwise to 2-chloro-4-(iodomethyl)-6-[(3S)-3-methylmorpholin-4-yl]pyrimidine (0.231 g, 0.65 mmol) and 2-(tetrahydro-2H-pyran-2-yloxy)ethanethiol (0.133 g, 0.82 mmol) in acetonitrile at RT under air. The resulting solution was stirred at RT for 1 hour. The solvent was removed and the reaction mixture diluted with DCM and washed with water. The organic layer was dried (MgSO$_4$), filtered and evaporated to afford crude product. The crude product was purified by flash silica chromatography, eluting with 0-2% methanol in DCM, to give the desired material as a colourless oil (0.141 g).

NMR Spectrum: $^1$H NMR (400.13 MHz, CDCl$_3$) δ 1.24-1.26 (3H, d), 1.40-1.55 (4H, m), 1.60-1.67 (1H, m), 1.69-1.77 (1H, m), 2.68-2.71 (2H, t), 3.17-3.24 (1H, td), 3.41-3.47 (2H, m), 3.50-3.58 (1H, m), 3.59 (2H, s), 3.62-3.63 (1H, d), 3.69-3.72 (1H, d), 3.76-3.86 (2H, m), 3.91-3.95 (1H, dd), 3.97 (1H, bs), 4.25 (1H, bs)<4.52-4.54 (1H, t), 6.44 (1H, s).

LCMS Spectrum: m/z (ES+) (M+H)+=386; HPLC tR=2.11 min. MH+ 386, retention time 2.11 min.

The preparation of 2-chloro-4-(iodomethyl)-6-[(3S)-3-methylmorpholin-4-yl]pyrimidine was described earlier.

EXAMPLE 60

3-Cyclobutyl-1-[4-[4-[(3S)-3-methylmorpholin-4-yl]-6-(propan-2-ylsulfonylmethyl)pyrimidin-2-yl]phenyl]urea

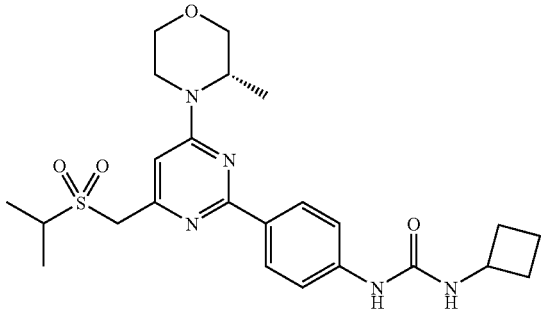

Cyclobutylamine (70 mg, 0.98 mmol) was added to phenyl (4-{4-[(isopropylsulfonyl)methyl]-6-[(3S)-3-methylmorpholin-4-yl]pyrimidin-2-yl}phenyl)carbamate (100 mg, 0.20 mmol) and triethylamine (0.082 mL, 0.59 mmol) in DMF (2 mL). The resulting solution was stirred at 50° C. for 2 hours. The crude product was purified by preparative HPLC using decreasingly polar mixtures of water (containing 1% NH3) and MeCN as eluents, to give the desired material as a white solid (57 mg).

NMR Spectrum: $^1$H NMR (400.132 MHz, DMSO-d$_6$) δ 1.24 (3H, d), 1.35 (3H, d), 1.37 (3H, d), 1.57-1.68 (2H, m), 1.81-1.91 (2H, m), 2.18-2.25 (2H, m), 3.18-3.25 (1H, m), 3.25-3.27 (1H, m), 3.47-3.54 (2H, m), 3.65 (1H, dd), 3.78 (1H, d), 3.99 (1H, dd), 4.11-4.17 (2H, m), 4.46 (2H, s), 6.47 (1H, d), 6.77 (1H, s), 7.48 (2H, d), 8.18 (2H, d), 8.55 (1H, s)

LCMS Spectrum: MH+ 488, retention time 1.99 min.

The following compounds were made in an analogous fashion from either phenyl (4-{4-[(isopropylsulfonyl)methyl]-6-[(3S)-3-methylmorpholin-4-yl]pyrimidin-2-yl}phenyl)carbamate or phenyl N-[4-[4-[(3S)-3-methylmorpholin-4-yl]-6-(2-propan-2-ylsulfonylpropan-2-yl)pyrimidin-2-yl]phenyl]carbamate and the appropriate amine.

| Example | Structure | NAME | LCMS MH+ | Retention time (min) |
|---|---|---|---|---|
| 60a | 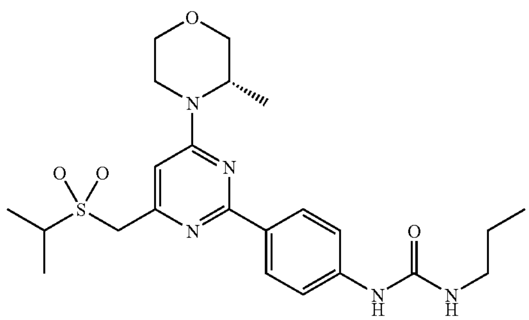 | 3-[4-[4-[(3S)-3-methylmorpholin-4-yl]-6-(propan-2-ylsulfonylmethyl)pyrimidin-2-yl]phenyl]-1-propyl-urea | 476 | 1.91 |
| 60b | 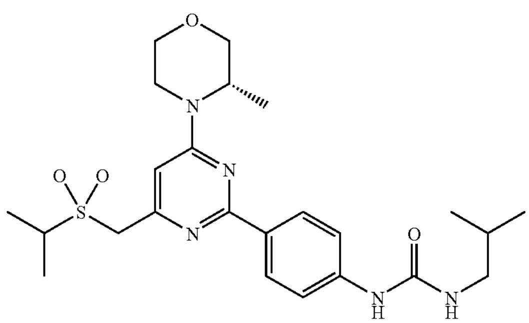 | 1-[4-[4-[(3S)-3-methylmorpholin-4-yl]-6-(propan-2-ylsulfonylmethyl)pyrimidin-2-yl]phenyl]-3-(2-methylpropyl)urea | 490 | 2.10 |
| 60c | 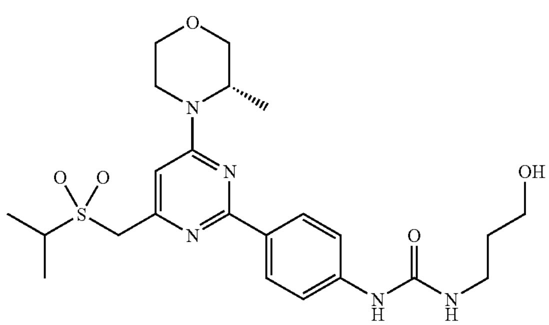 | 3-(3-hydroxypropyl)-1-[4-[4-[(3S)-3-methylmorpholin-4-yl]-6-(propan-2-ylsulfonylmethyl)pyrimidin-2-yl]phenyl]urea | 492 | 1.45 |
| 60d | 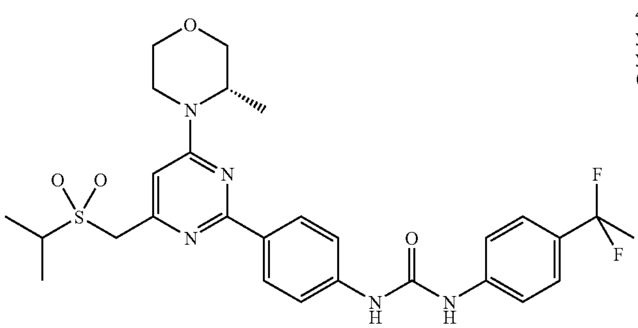 | 1-[4-[4-[(3S)-3-methylmorpholin-4-yl]-6-(propan-2-ylsulfonylmethyl)pyrimidin-2-yl]phenyl]-3-[4-(trifluoromethyl)phenyl]urea | 578 | 2.70 |

-continued

| Example | Structure | NAME | LCMS MH+ | Retention time (min) |
|---|---|---|---|---|
| 60e | 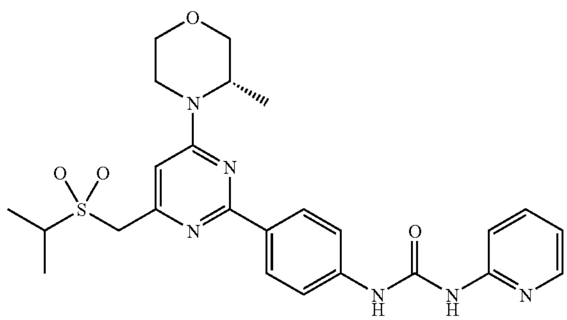 | 1-[4-[4-[(3S)-3-methylmorpholin-4-yl]-6-(propan-2-ylsulfonylmethyl)pyrimidin-2-yl]phenyl]-3-pyridin-2-yl-urea | 511 | 2.16 |
| 60f | 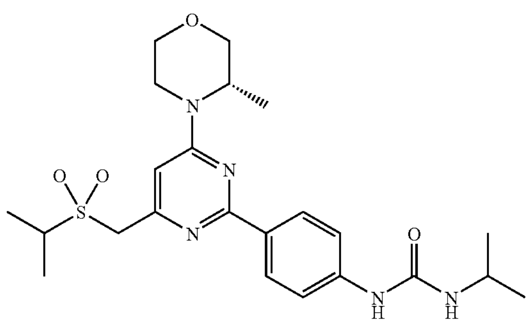 | 1-[4-[4-[(3S)-3-methylmorpholin-4-yl]-6-(propan-2-ylsulfonylmethyl)pyrimidin-2-yl]phenyl]-3-propan-2-yl-urea | 476 | 2.00 |
| 60g | 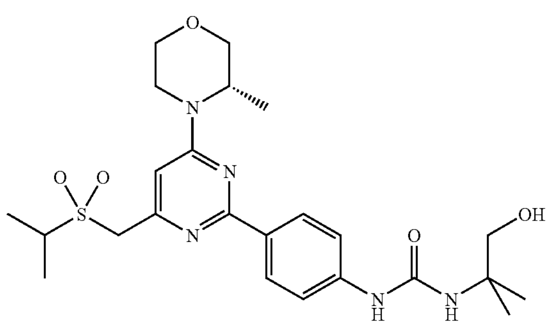 | 3-(1-hydroxy-2-methyl-propan-2-yl)-1-[4-[4-[(3S)-3-methylmorpholin-4-yl]-6-(propan-2-ylsulfonylmethyl)pyrimidin-2-yl]phenyl]urea | 506 | 1.81 |
| 60h | 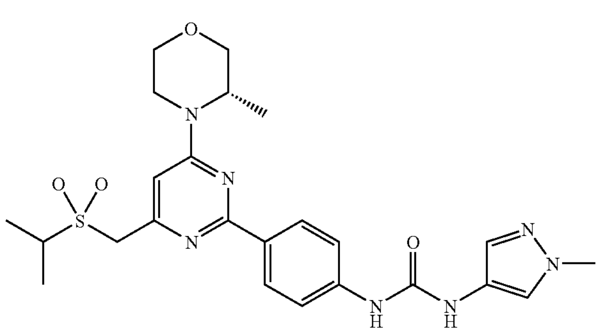 | 1-[4-[4-[(3S)-3-methylmorpholin-4-yl]-6-(propan-2-ylsulfonylmethyl)pyrimidin-2-yl]phenyl]-3-(1-methylpyrazol-4-yl)urea | 514 | 1.71 |

-continued

| Example | Structure | NAME | LCMS MH+ | Retention time (min) |
|---|---|---|---|---|
| 60i | 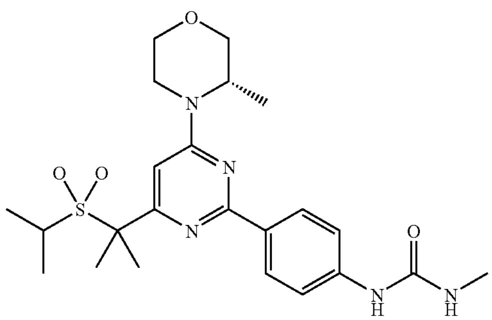 | 3-methyl-1-[4-[4-[(3S)-3-methylmorpholin-4-yl]-6-(2-propan-2-ylsulfonylpropan-2-yl)pyrimidin-2-yl]phenyl]urea | 476 | 1.96 |
| 60j | 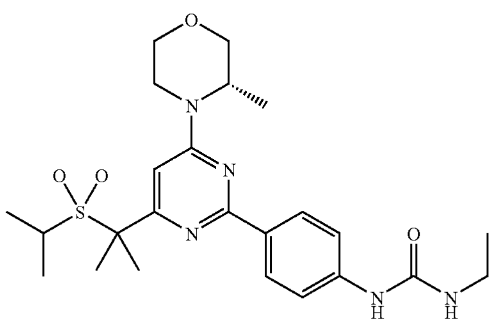 | 1-ethyl-3-[4-[4-[(3S)-3-methylmorpholin-4-yl]-6-(2-propan-2-ylsulfonylpropan-2-yl)pyrimidin-2-yl]phenyl]urea | 490 | 2.14 |
| 60k | 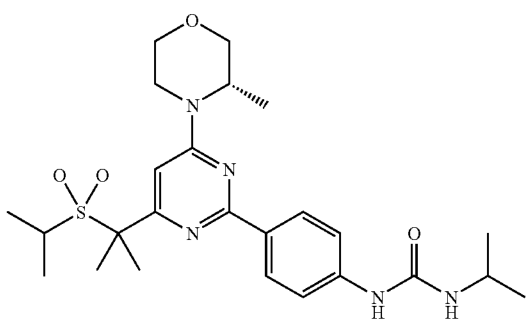 | 1-[4-[4-[(3S)-3-methylmorpholin-4-yl]-6-(2-propan-2-ylsulfonyl-propan-2-yl)pyrimidin-2-yl]phenyl]-3-propan-2-yl-urea | 504 | 2.29 |
| 60l | 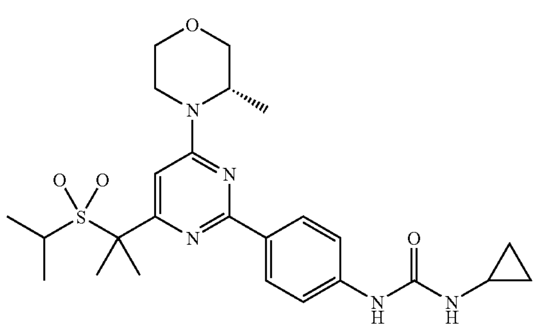 | 3-cyclopropyl-1-[4-[4-[(3S)-3-methylmorpholin-4-yl]-6-(2-propan-2-ylsulfonylpropan-2-yl)pyrimidin-2-yl]phenyl]urea | 502 | 2.12 |

-continued

| Example | Structure | NAME | LCMS MH+ | Retention time (min) |
|---|---|---|---|---|
| 60m | 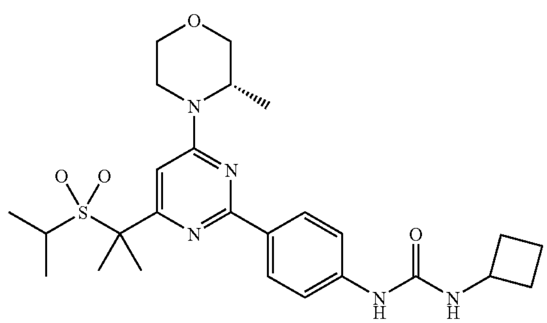 | 3-cyclobutyl-1-[4-[4-[(3S)-3-methylmorpholin-4-yl]-6-(2-propan-2-ylsulfonylpropan-2-yl)pyrimidin-2-yl]phenyl]urea | 516 | 2.34 |
| 60n | 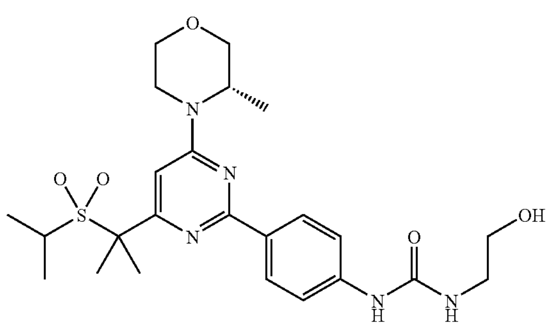 | 3-(2-hydroxyethyl)-1-[4-[4-[(3S)-3-methylmorpholin-4-yl]-6-(2-propan-2-ylsulfonylpropan-2-yl)pyrimidin-2-yl]phenyl]urea | 506 | 1.78 |
| 60o | 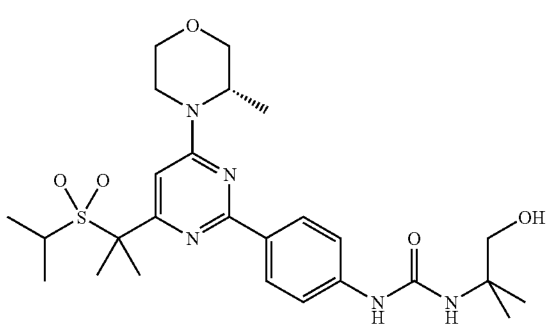 | 3-(1-hydroxy-2-methyl-propan-2-yl)-1-[4-[4-[(3S)-3-methylmorpholin-4-yl]-6-(2-propan-2-ylsulfonylpropan-2-yl)pyrimidin-2-yl]phenyl]urea | 534 | 2.07 |
| 60p | 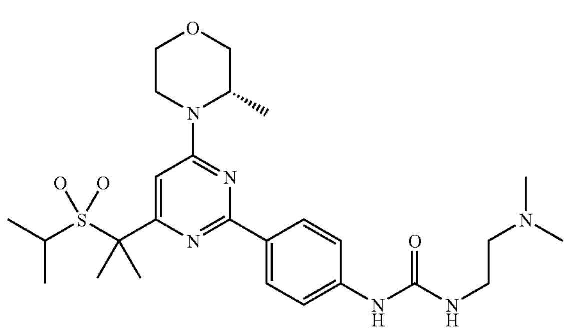 | 3-(2-dimethylaminoethyl)-1-[4-[4-[(3S)-3-methylmorpholin-4-yl]-6-(2-propan-2-ylsulfonylpropan-2-yl)pyrimidin-2-yl]phenyl]urea | 533 | 2.07 |

-continued

| Example | Structure | NAME | LCMS MH+ | Retention time (min) |
|---|---|---|---|---|
| 60q | 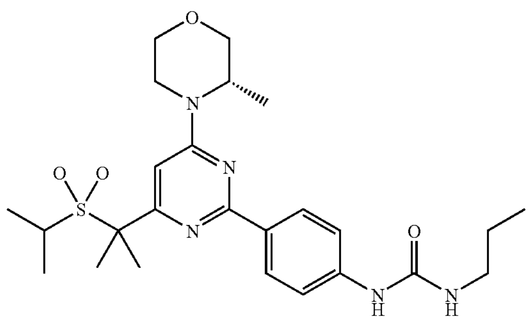 | 3-[4-[4-[(3S)-3-methylmorpholin-4-yl]-6-(2-propan-2-ylsulfonylpropan-2-yl)pyrimidin-2-yl]phenyl]-1-propyl-urea | 504 | 2.26 |
| 60r | 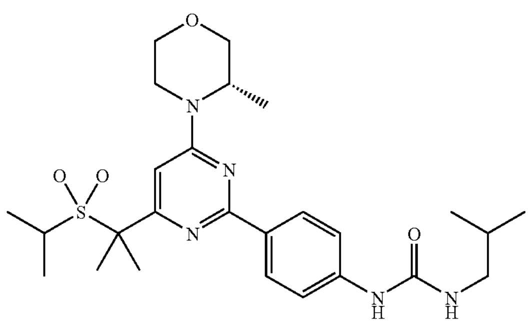 | 1-[4-[4-[(3S)-3-methylmorpholin-4-yl]-6-(2-propan-2-ylsulfonylpropan-2-yl)pyrimidin-2-yl]phenyl]-3-(2-methylpropyl)urea | 518 | 2.43 |
| 60s | 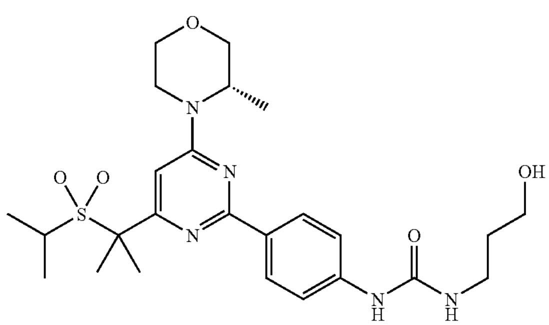 | 3-(3-hydroxypropyl)-1-[4-[4-[(3S)-3-methylmorpholin-4-yl]-6-(2-propan-2-ylsulfonylpropan-2-yl)pyrimidin-2-yl]phenyl]urea | 520 | 1.82 |
| 60t | 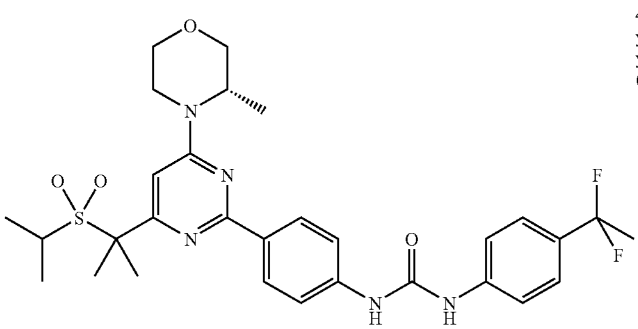 | 1-[4-[4-[(3S)-3-methylmorpholin-4-yl]-6-(2-propan-2-ylsulfonylpropan-2-yl)pyrimidin-2-yl]phenyl]-3-[4-(trifluoromethyl)phenyl]urea | 606 | 2.95 |

-continued

| Example | Structure | NAME | LCMS MH+ | Retention time (min) |
|---|---|---|---|---|
| 60u | 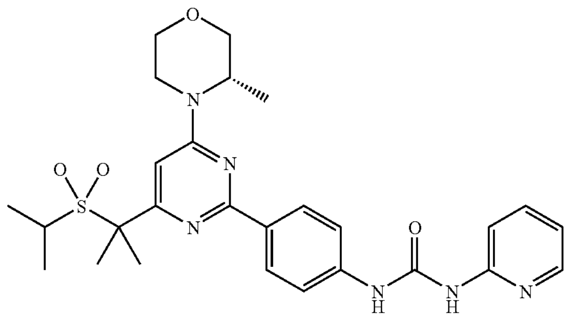 | 1-[4-[4-[(3S)-3-methylmorpholin-4-yl]-6-(2-propan-2-yl]phenyl]-3-pyridin-2-yl-urea | 539 | 2.54 |
| 60v | 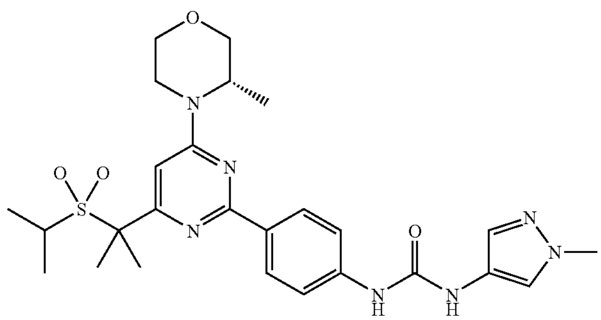 | 1-[4-[4-[(3S)-3-methylmorpholin-4-yl]-6-(2-propan-2-ylsulfonylpropan-2-yl)pyrimidin-2-yl]phenyl]-3-(1-methylpyrazol-4-yl)urea | 542 | 1.97 |

Example 60a: $^1$H NMR (400.132 MHz, DMSO-$d_6$) δ 0.89 (3H, t), 1.25 (3H, d), 1.35 (3H, d), 1.37 (3H, d), 1.43-1.49 (2H, m), 3.04-3.07 (1H, m), 3.21-3.26 (1H, m), 3.47-3.52 (2H, m), 3.64-3.67 (1H, m), 3.67-3.87 (3H, m), 3.98-4.00 (1H, m), 4.20 (1H, d), 4.47 (2H, s), 6.23 (1H, t), 6.79 (1H, s), 7.50 (2H, d), 8.18 (2H, d), 8.66 (1H, s)

Example 60b: $^1$H NMR (400.132 MHz, DMSO-$d_6$) δ 0.89 (6H, d), 1.25 (3H, d), 1.35 (3H, d), 1.37 (3H, d), 1.71 (1H, quintet), 2.95 (2H, t), 3.20-3.27 (1H, m), 3.47-3.54 (3H, m), 3.65 (1H, dd), 3.78 (1H, d), 3.99 (1H, dd), 4.19 (1H, d), 4.47 (2H, s), 6.27 (1H, t), 6.79 (1H, s), 7.50 (2H, d), 8.18 (2H, d), 8.66 (1H, s)

Example 60c: $^1$H NMR (400.132 MHz, DMSO-$d_6$) δ 1.24 (3H, d), 1.35-1.37 (6H, m), 1.60 (2H, quintet), 3.17 (2H, q), 3.21-3.25 (1H, m), 3.45-3.54 (4H, m), 3.63-3.67 (1H, m), 3.78 (1H, d), 3.97-4.00 (1H, m), 4.17 (1H, d), 4.46-4.49 (3H, m), 6.21 (1H, t), 6.77 (1H, s), 7.49 (2H, d), 8.18 (2H, d), 8.70 (1H, s)

Example 60d: $^1$H NMR (400.132 MHz, DMSO-$d_6$) δ 1.25 (3H, d), 1.36 (3H, d), 1.38 (3H, d), 3.20-3.27 (2H, m), 3.48-3.55 (2H, m), 3.66 (1H, dd), 3.79 (1H, d), 4.00 (1H, dd), 4.19 (1H, d), 4.48 (2H, s), 6.80 (1H, s), 7.59 (2H, d), 7.64-7.70 (4H, m), 8.27 (2H, d), 9.04 (1H, s), 9.15 (1H, s)

Example 60e: $^1$H NMR (400.132 MHz, DMSO-$d_6$) δ 1.25 (3H, d), 1.37 (3H, d), 1.38 (3H, d), 3.20-3.24 (1H, m), 3.27 (1H, s), 3.48-3.56 (2H, m), 3.66 (1H, dd), 3.79 (1H, d), 4.00 (1H, dd), 4.19 (1H, d), 4.49 (2H, s), 6.81 (1H, s), 7.02-7.05 (1H, m), 7.55 (1H, d), 7.65 (2H, d), 7.75-7.79 (1H, m), 8.27-8.31 (3H, m), 9.47 (1H, s), 10.63 (1H, s)

Example 60f: $^1$H NMR (400.132 MHz, DMSO-$d_6$) δ 1.11 (6H, d), 1.24 (3H, d), 1.35 (3H, d), 1.37 (3H, d), 3.19-3.25 (2H, m), 3.47-3.54 (2H, m), 3.65 (1H, dd), 3.73-3.82 (2H, m), 3.99 (1H, dd), 4.17 (1H, d), 4.46 (2H, s), 6.07 (1H, d), 6.77 (1H, s), 7.48 (2H, d), 8.18 (2H, d), 8.52 (1H, s)

Example 60g: $^1$H NMR (400.132 MHz, DMSO-$d_6$) δ 1.24 (3H, d), 1.24 (6H, s), 1.35 (3H, d), 1.37 (3H, d), 3.18 (1H, d), 3.22-3.27 (1H, m), 3.39 (1H, d), 3.47-3.55 (2H, m), 3.64-3.66 (1H, m), 3.78 (1H, d), 3.98-4.00 (1H, m), 4.17 (1H, d), 4.46 (2H, s), 4.95 (1H, t), 6.01 (1H, s), 6.77 (1H, s), 7.46 (2H, d), 8.17 (2H, d), 8.73 (1H, s)

Example 60h: $^1$H NMR (400.132 MHz, DMSO-$d_6$) δ 1.25 (3H, d), 1.36 (3H, d), 1.38 (3H, d), 3.18-3.25 (2H, m), 3.48-3.54 (2H, m), 3.66 (1H, dd), 3.78 (1H, d), 3.79 (3H, s), 3.99 (1H, dd), 4.18 (1H, d), 4.47 (2H, s), 6.78 (1H, s), 7.39 (1H, s), 7.55 (2H, d), 7.76 (1H, s), 8.22 (2H, d), 8.40 (1H, s), 8.83 (1H, s)

Example 60i: $^1$H NMR (400.132 MHz, DMSO-$d_6$) δ 1.09 (3H, d), 1.12 (3H, d), 1.22 (3H, d), 1.79 (6H, d), 2.66 (3H, d), 3.16-3.24 (1H, m), 3.50 (1H, dt), 3.65 (1H, dd), 3.70-3.78 (2H, m), 3.98 (1H, dd), 4.22 (1H, d), 4.56 (1H, s), 6.06-6.08 (1H, m), 6.78 (1H, s), 7.51 (2H, d), 8.23 (2H, d), 8.74 (1H, s)

Example 60j: $^1$H NMR (400.132 MHz, DMSO-$d_6$) δ 1.07 (3H, t), 1.09 (3H, d), 1.12 (3H, d), 1.22 (3H, d), 1.79 (6H, d), 3.10-3.15 (2H, m), 3.16-3.24 (1H, m), 3.50 (1H, dt), 3.65 (1H, dd), 3.70-3.78 (2H, m), 3.98 (1H, dd), 4.22 (1H, d), 4.56 (1H, s), 6.16 (1H, t), 6.78 (1H, s), 7.50 (2H, d), 8.23 (2H, d), 8.66 (1H, s)

Example 60k: $^1$H NMR (400.132 MHz, DMSO-$d_6$) δ 1.08-1.13 (12H, m), 1.22 (3H, d), 1.79 (6H, d), 3.18-3.24 (2H, m), 3.50 (1H, dt), 3.65 (1H, dd), 3.70-3.82 (2H, m), 3.98 (1H, dd), 4.22 (1H, d), 4.55 (1H, s), 6.06 (1H, d), 6.78 (1H, s), 7.49 (2H, d), 8.23 (2H, d), 8.53 (1H, s)

Example 60l: $^1$H NMR (400.132 MHz, DMSO-$d_6$) δ 0.33-0.37 (2H, m), 0.56-0.60 (2H, m), 1.02 (3H, d), 1.05 (3H, d), 1.15 (3H, d), 1.73 (6H, d), 2.47-2.52 (1H, m), 3.14 (1H, dt), 3.43 (1H, dt), 3.58 (1H, dd), 3.63-3.72 (2H, m), 3.89-3.92 (1H, m), 4.16 (1H, d), 4.50 (1H, s), 6.36 (1H, d), 6.72 (1H, s), 7.44 (2H, d), 8.16 (2H, d), 8.46 (1H, s)

Example 60m: ¹H NMR (400.132 MHz, DMSO-d₆) δ 1.09 (3H, d), 1.12 (3H, d), 1.22 (3H, d), 1.57-1.66 (2H, m), 1.79 (6H, d), 1.83-1.90 (2H, m), 2.18-2.25 (2H, m), 3.20 (1H, dt), 3.50 (1H, dt), 3.65 (1H, dd), 3.70-3.78 (2H, m), 3.98 (1H, dd), 4.12-4.18 (1H, m), 4.22 (1H, d), 4.55 (1H, s), 6.46 (1H, d), 6.78 (1H, s), 7.48 (2H, d), 8.23 (2H, d), 8.56 (1H, s)

Example 60n: ¹H NMR (400.132 MHz, DMSO-d₆) δ 1.09 (3H, d), 1.12 (3H, d), 1.22 (3H, d), 1.79 (6H, d), 3.16-3.24 (2H, m), 3.44-3.53 (3H, m), 3.65 (1H, dd), 3.70-3.78 (2H, m), 3.98 (1H, dd), 4.22 (1H, d), 4.55 (1H, s), 4.73 (1H, t), 6.26 (1H, t), 6.78 (1H, s), 7.50 (2H, d), 8.24 (2H, s), 8.80 (1H, s)

Example 60o: ¹H NMR (400.132 MHz, DMSO-d₆) δ 1.09 (3H, d), 1.13 (3H, d), 1.22 (3H, d), 1.24 (6H, s), 1.79 (6H, d), 3.17-3.24 (1H, m), 3.39 (2H, d), 3.50 (1H, dt), 3.65 (1H, dd), 3.71-3.78 (2H, m), 3.98 (1H, dd), 4.22 (1H, d), 4.56 (1H, s), 4.95 (1H, t), 6.01 (1H, s), 6.78 (1H, s), 7.46 (2H, d), 8.22 (2H, d), 8.73 (1H, s)

Example 60p: ¹H NMR (400.132 MHz, DMSO-d₆) δ 1.09 (3H, d), 1.12 (3H, d), 1.22 (3H, d), 1.79 (6H, d), 2.18 (6H, s), 2.32-2.35 (2H, m), 3.17-3.22 (3H, m), 3.50 (1H, dt), 3.66 (1H, dd), 3.70-3.78 (2H, m), 3.98 (1H, dd), 4.22 (1H, d), 4.57 (1H, s), 6.16 (1H, t), 6.78 (1H, s), 7.50 (2H, d), 8.23 (2H, d), 8.89 (1H, s)

Example 60q: ¹H NMR (400.132 MHz, DMSO-d₆) δ 0.89 (3H, t), 1.09 (3H, d), 1.12 (3H, d), 1.22 (3H, d), 1.41-1.50 (2H, m), 1.79 (6H, d), 3.04-3.09 (2H, m), 3.18-3.24 (2H, m), 3.50 (1H, dt), 3.65 (1H, dd), 3.70-3.78 (1H, m), 3.98 (1H, dd), 4.22 (1H, d), 4.56 (1H, s), 6.21 (1H, t), 6.78 (1H, s), 7.50 (2H, d), 8.23 (2H, d), 8.65 (1H, s)

Example 60r: ¹H NMR (400.132 MHz, DMSO-d₆) δ 0.89 (6H, d), 1.09 (3H, d), 1.12 (3H, d), 1.22 (3H, d), 1.67-1.74 (1H, m), 1.79 (6H, d), 2.95 (2H, t), 3.22 (1H, dd), 3.50 (1H, dt), 3.65 (1H, dd), 3.70-3.79 (2H, m), 3.98 (1H, dd), 4.22 (1H, d), 4.55 (1H, s), 6.25 (1H, t), 6.78 (1H, s), 7.50 (2H, d), 8.23 (2H, d), 8.64 (1H, s)

Example 60s: ¹H NMR (400.132 MHz, DMSO-d₆) δ 1.09 (3H, d), 1.12 (3H, d), 1.22 (3H, d), 1.60 (2H, quintet), 1.79 (6H, d), 3.15-3.24 (3H, m), 3.45-3.53 (3H, m), 3.65 (1H, dd), 3.70-3.78 (2H, m), 3.98 (1H, dd), 4.22 (1H, d), 4.47 (1H, t), 4.55 (1H, s), 6.21 (1H, t), 6.78 (1H, s), 7.50 (2H, d), 8.23 (2H, d), 8.71 (1H, s)

Example 60t: ¹H NMR (400.132 MHz, DMSO-d₆) δ 1.10 (3H, d), 1.13 (3H, d), 1.23 (3H, d), 1.81 (6H, d), 3.22-3.25 (1H, m), 3.66 (1H, dd), 3.71-3.79 (1H, m), 3.97-4.00 (2H, m), 4.04-4.08 (1H, m), 4.24 (1H, d), 4.57 (1H, s), 6.82 (1H, s), 7.59 (2H, d), 7.64-7.70 (4H, m), 8.31 (2H, d), 9.04 (1H, s), 9.14 (1H, s)

Example 60u: ¹H NMR (400.132 MHz, DMSO-d₆) δ 1.10 (3H, d), 1.14 (3H, d), 1.24 (3H, d), 1.81 (6H, d), 3.18-3.27 (1H, m), 3.51 (1H, dt), 3.66 (1H, ddd), 3.73-3.80 (2H, m), 3.99 (1H, dd), 4.24 (1H, d), 4.57 (1H, s), 6.82 (1H, s), 7.02-7.05 (1H, m), 7.57 (1H, t), 7.65 (2H, d), 7.74-7.79 (1H, m), 8.29-8.33 (3H, m), 9.45 (1H, s), 10.59 (1H, s)

Example 60v: ¹H NMR (400.132 MHz, DMSO-d₆) δ 1.09 (3H, d), 1.13 (3H, d), 1.23 (3H, d), 1.80 (6H, d), 3.18-3.24 (2H, m), 3.51 (1H, dt), 3.64-3.68 (1H, m), 3.71-3.78 (1H, m), 3.79 (3H, s), 3.98 (1H, dd), 4.23 (1H, d), 4.56 (1H, s), 6.80 (1H, s), 7.39 (1H, s), 7.55 (2H, d), 7.76 (1H, s), 8.27 (2H, d), 8.39 (1H, s), 8.84 (1H, s)

Test (c): Example (60) 1.0 μM; Example (60a) 3.3 μM; Example (60b) 1.8 μM; Example (60b) 1.8 μM; Example (60c) 0.77 μM; Example (60d) 0.59 μM; Example (60e) 1.3 μM; Example (60f) 0.87 μM; Example (60g) 0.22 μM; Example (60h) 1.9 μM; Example (60i) 0.12 μM; Example (60j) 0.19 μM; Example (60k) 0.18 μM; Example (60l) 0.064 μM; Example (60m) 0.059 μM; Example (60n) 0.15 μM; Example (60o) 0.086 μM; Example (60p) 0.14 μM; Example (60q) 0.16 μM; Example (60r) 0.21 μM; Example (60s) 0.3 μM; Example (60t) 1.4 μM; Example (60u) 0.16 μM; Example (60v) 0.27 μM.

The preparation of phenyl (4-{4-[(isopropylsulfonyl)methyl]-6-[(3S)-3-methylmorpholin-4-yl]pyrimidin-2-yl}phenyl)carbamate was described earlier.

The preparation of phenyl N-[4-[4-[(3S)-3-methylmorpholin-4-yl]-6-(2-propan-2-ylsulfonylpropan-2-yl)pyrimidin-2-yl]phenyl]carbamate is described below.

Phenyl N-[4-[4-[(3S)-3-methylmorpholin-4-yl]-6-(2-propan-2-ylsulfonylpropan-2-yl)pyrimidin-2-yl]phenyl]carbamate

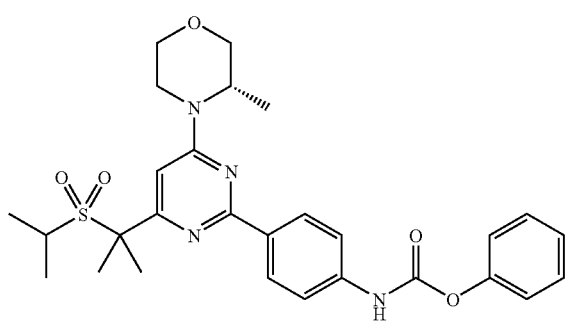

Phenyl chloroformate (0.42 mL, 3.34 mmol) was added dropwise to 4-[4-[(3S)-3-methylmorpholin-4-yl]-6-(2-propan-2-ylsulfonylpropan-2-yl)pyrimidin-2-yl]aniline (1.4 g, 3.34 mmol) and sodium carbonate (0.421 g, 5.02 mmol) in dioxane (20 mL) under nitrogen. The resulting suspension was stirred at RT for 2 hours. The reaction mixture was evaporated to dryness and redissolved in DCM (50 mL) and washed with water (50 mL). The organic layer was dried (MgSO₄), filtered and evaporated to give crude product which was triturated with diethyl ether to give the desired product (1.57 g).

NMR Spectrum: ¹H NMR (400.132 MHz, DMSO-d₆) δ 1.09 (3H, d), 1.12 (3H, d), 1.23 (3H, d), 1.80 (6H, d), 3.17-3.25 (1H, m), 3.47-3.54 (1H, m), 3.66 (1H, dd), 3.72-3.79 (2H, m), 3.97-4.00 (1H, m), 4.24 (1H, d), 4.57 (1H, s), 6.82 (1H, s), 7.25 (3H, d), 7.45 (2H, t), 7.64 (2H, d), 8.34 (2H, d), 10.43 (1H, s)

LCMS Spectrum: MH+ 539, retention time 2.76 min.

4-[4-[(3S)-3-Methylmorpholin-4-yl]-6-(2-propan-2-ylsulfonylpropan-2-yl)pyrimidin-2-yl]aniline

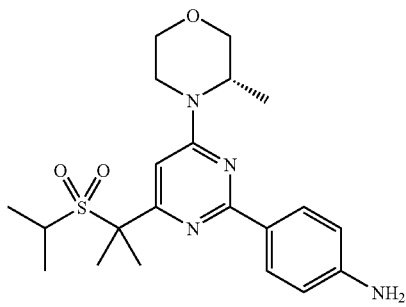

Dichlorobis(triphenylphosphine)palladium(II) (116 mg, 0.17 mmol) was added to 2-chloro-4-[(3S)-3-methylmorpholin-4-yl]-6-(2-propan-2-ylsulfonylpropan-2-yl)pyrimidine (1.2 g, 3.32 mmol), and sodium carbonate (5 mL, 10.00 mmol) in 18% DMF in a mixture of DME:water:ethanol (7:3:2) (20 mL). The resulting solution was stirred at 90° C. for 4 hours.

The reaction mixture was diluted with ethyl acetate (20 mL), and washed with water (2×20 mL). The organic layer was dried (MgSO$_4$), filtered and evaporated to afford crude product.

The crude product was purified by flash silica chromatography, elution gradient 5 to 60% ethyl acetate in isohexane, to give the desired material as a cream solid (1.40 g).

NMR Spectrum: $^1$H NMR (400.132 MHz, DMSO-d$_6$) δ 1.09 (3H, d), 1.12 (3H, d), 1.21 (3H, d), 1.77 (6H, d), 3.13-3.21 (1H, m), 3.46-3.52 (1H, m), 3.62-3.66 (1H, m), 3.69-3.77 (2H, m), 3.97 (1H, dd), 4.19 (1H, d), 4.53 (1H, d), 5.55 (2H, s), 6.61 (2H, d), 6.69 (1H, s), 8.06 (2H, d)

LCMS Spectrum: MH+ 419, retention time 2.11 min.

2-Chloro-4-[(3S)-3-methylmorpholin-4-yl]-6-(2-propan-2-ylsulfonlpropan-2-yl)pyrimidine

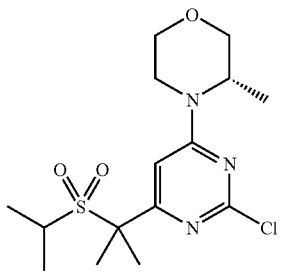

Iodomethane (0.23 mL, 3.75 mmol) was added to sodium tert-butoxide (360 mg, 3.75 mmol) and (3S)-4-{2-Chloro-6-[(isopropylsulfonyl)methyl]pyrimidin-4-yl}-3-methylmorpholine (2.5 g, 7.49 mmol) in DMF (2 mL) at −10° C. The resulting thick suspension was stirred at RT for 15 minutes to ease the stirring. Iodomethane (0.23 mL, 3.75 mmol) and sodium tert-butoxide (360 mg, 3.75 mmol) were again added to the reaction and the resulting suspension stirred at RT for 15 minutes. The reaction mixture was diluted with DCM (20 mL) and washed with water (20 mL). The organic layer was dried (MgSO$_4$), filtered and evaporated to afford crude product. The crude product was purified by flash silica chromatography, elution gradient 0 to 50% ethyl acetate in DCM, to give the desired material as a beige solid (1.20 g).

NMR Spectrum: $^1$H NMR (400.132 MHz, DMSO-d$_6$) δ 1.11 (3H, d), 1.14 (3H, d), 1.20 (3H, d), 1.70 (6H, s), 3.16-3.24 (1H, m), 3.41-3.48 (1H, m), 3.59 (1H, dd), 3.67 (1H, q), 3.72 (1H, d), 3.94 (1H, dd), 4.06 (1H, d), 4.42 (1H, s), 6.91 (1H, s)

LCMS Spectrum: MH+ 362, retention time 2.08 min.

The preparation of (3S)-4-{2-Chloro-6-[(isopropylsulfonyl)methyl]pyrimidin-4-yl}-3-methylmorpholine was described earlier.

EXAMPLE 61

3-Cyclobutyl-1-[4-[4-[(4-fluorophenyl)sulfonylmethyl]-6-[(3S)-3-methylmorpholin-4-yl]pyrimidin-2-yl]phenyl]urea

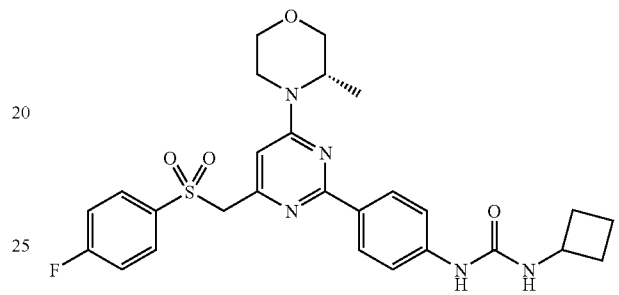

Cyclobutylamine (0.96 mmol) was added to phenyl N-[4-[4-[(4-fluorophenyl)sulfonylmethyl]-6-[(3S)-3-methylmorpholin-4-yl]pyrimidin-2-yl]phenyl]carbamate (120 mg, 0.21 mmol) and triethylamine (0.090 mL, 0.59 mmol) in DMF (2 mL). The resulting solution was stirred at 50° C. for 3 hours. The crude product was purified by preparative HPLC using decreasingly polar mixtures of water (containing 1% NH3) and MeCN as eluents, to give the desired material as a white solid (117 mg).

NMR Spectrum: $^1$H NMR (400.132 MHz, DMSO-d$_6$) δ 1.20 (3H, d), 1.57-1.66 (2H, m), 1.81-1.91 (2H, m), 2.18-2.24 (2H, m), 3.17 (1H, dt), 3.47 (1H, dt), 3.63 (1H, dd), 3.76 (1H, d), 3.97 (1H, dd), 4.08-4.19 (2H, m), 4.38 (1H, s), 4.71 (2H, s), 6.42 (1H, d), 6.64 (1H, s), 7.36 (2H, d), 7.46 (2H, t), 7.78 (2H, d), 7.85-7.89 (2H, m), 8.53 (1H, s)

LCMS Spectrum: MH+ 540, retention time 2.25 min.

The following compounds were made in an analogous fashion from phenyl N-[4-[4-[(4-fluorophenyl)sulfonylmethyl]-6-[(3S)-3-methylmorpholin-4-yl]pyrimidin-2-yl]phenyl]carbamate or phenyl N-[4-[4-[2-(4-fluorophenyl)sulfonylpropan-2-yl]-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 61a | 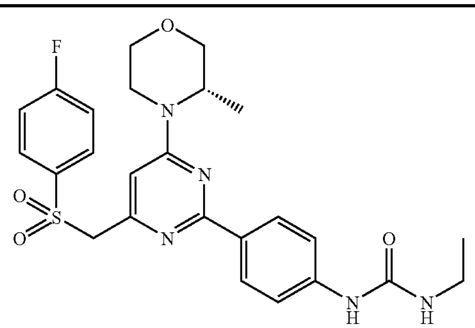 | 1-ethyl-3-[4-[4-[(4-fluorophenyl)sulfonylmethyl]-6-[(3S)-3-methylmorpholin-4-yl]pyrimidin-2-yl]phenyl]urea | 514 | 2.02 |

-continued

| Example | Structure | NAME | LCMS MH+ | Retention time (min) |
|---|---|---|---|---|
| 61b | 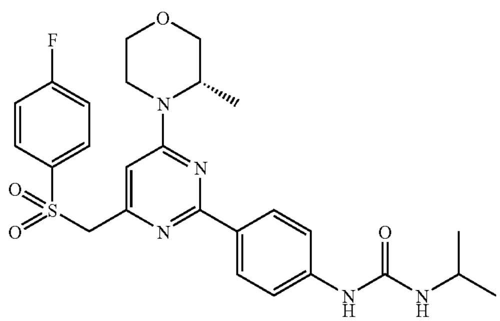 | 1-[4-[4-[(4-fluorophenyl)sulfonylmethyl]-6-[(3S)-3-methylmorpholin-4-yl]pyrimidin-2-yl]phenyl]-3-propan-2-yl-urea | 528 | 2.17 |
| 61c | 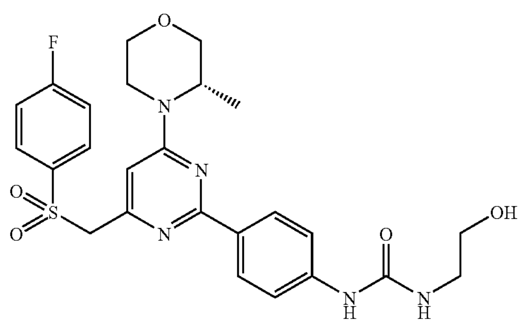 | 1-[4-[4-[(4-fluorophenyl)sulfonylmethyl]-6-[(3S)-3-methylmorpholin-4-yl]pyrimidin-2-yl]phenyl]-3-(2-hydroxyethyl)urea | 530 | 1.72 |
| 61d | 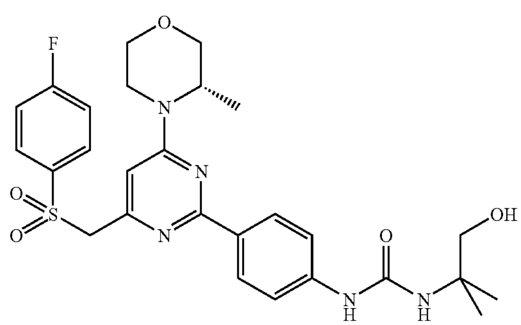 | 1-[4-[4-[(4-fluorophenyl)sulfonylmethyl]-6-[(3S)-3-methylmorpholin-4-yl]pyrimidin-2-yl]phenyl]-3-(1-hydroxy-2-methyl-propan-2-yl)urea | 558 | 1.99 |
| 61e | 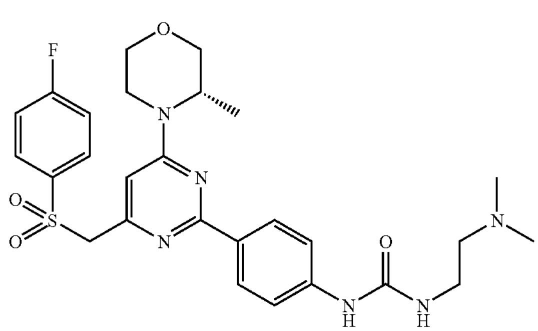 | 3-(2-dimethylaminoethyl)-1-[4-[4-[(4-fluorophenyl)sulfonylmethyl]-6-[(3S)-3-methylmorpholin-4-yl]pyrimidin-2-yl]phenyl]urea | 557 | 1.98 |

-continued

| Example | Structure | NAME | LCMS MH+ | Retention time (min) |
|---|---|---|---|---|
| 61f | 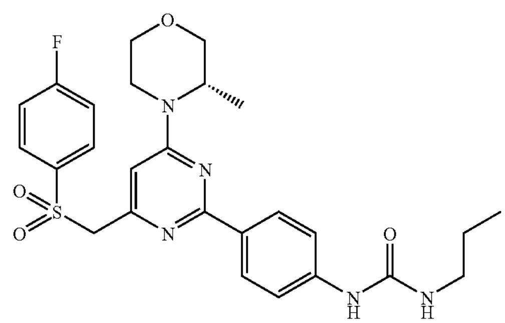 | 3-[4-[4-[(4-fluorophenyl)sulfonylmethyl]-6-[(3S)-3-methylmorpholin-4-yl]pyrimidin-2-yl]phenyl]-1-propyl-urea | 528 | 2.18 |
| 61g | 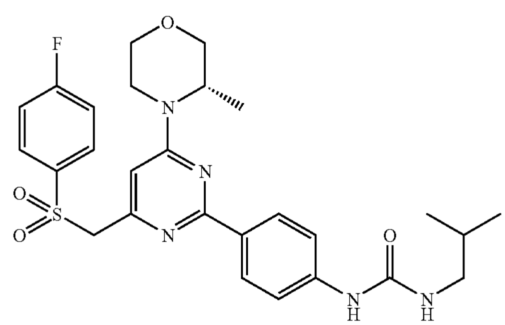 | 1-[4-[4-[(4-fluorophenyl)sulfonylmethyl]-6-[(3S)-3-methylmorpholin-4-yl]pyrimidin-2-yl]phenyl]-3-(2-methylpropyl)urea | 542 | 2.34 |
| 61h | 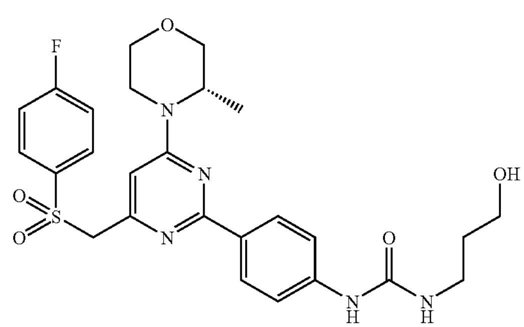 | 1-[4-[4-[(4-fluorophenyl)sulfonylmethyl]-6-[(3S)-3-methylmorpholin-4-yl]pyrimidin-2-yl]phenyl]-3-(3-hydroxypropyl)urea | 544 | 1.76 |
| 61i | 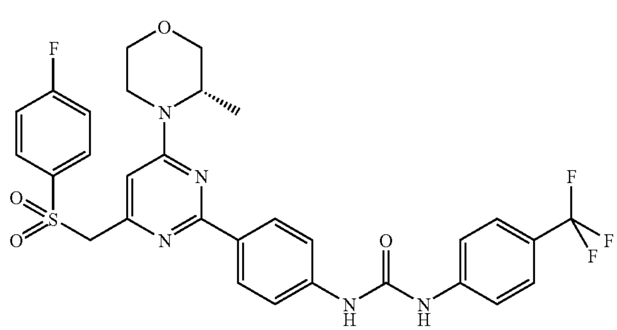 | 1-[4-[4-[(4-fluorophenyl)sulfonylmethyl]-6-[(3S)-3-methylmorpholin-4-yl]pyrimidin-2-yl]phenyl]-3-[4-(trifluoromethyl)phenyl]urea | 630 | 2.82 |

-continued

| Example | Structure | NAME | LCMS MH+ | Retention time (min) |
|---|---|---|---|---|
| 61j | 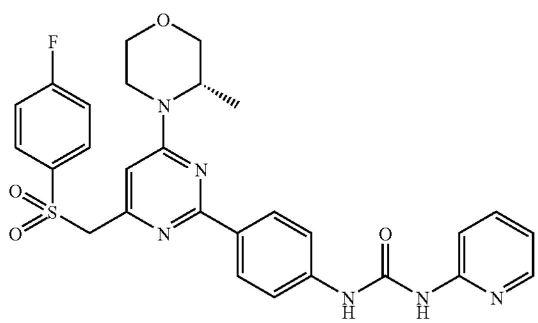 | 1-[4-[4-[(4-fluorophenyl)sulfonylmethyl]-6-[(3S)-3-methylmorpholin-4-yl]pyrimidin-2-yl]phenyl]-3-pyridin-2-yl-urea | 563 | 2.40 |
| 61k | 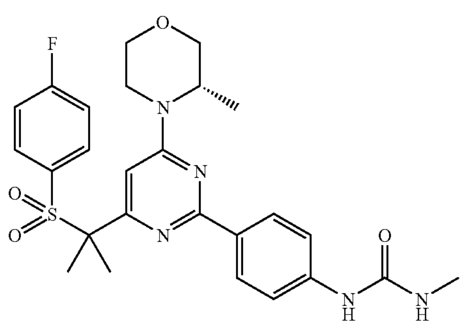 | 1-[4-[4-[2-(4-fluorophenyl)sulfonylpropan-2-yl]-6-[(3S)-3-methylmorpholin-4-yl]pyrimidin-2-yl]phenyl]-3-methyl-urea | 528 | 2.19 |
| 61l | 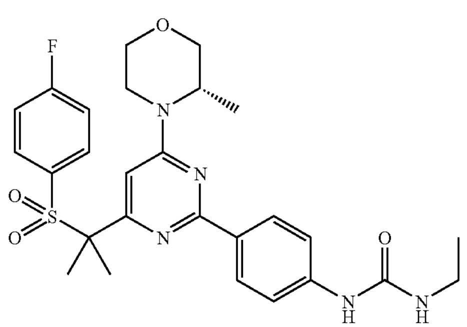 | 1-ethyl-3-[4-[4-[2-(4-fluorophenyl)sulfonylpropan-2-yl]-6-[(3S)-3-methylmorpholin-4-yl]pyrimidin-2-yl]phenyl]urea | 542 | 2.34 |
| 61m | 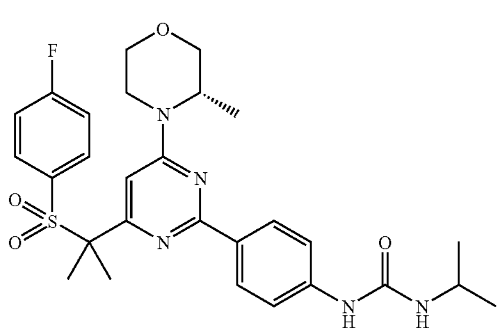 | 1-[4-[4-[2-(4-fluorophenyl)sulfonylpropan-2-yl]-6-[(3S)-3-methylmorpholin-4-yl]pyrimidin-2-yl]phenyl]-3-propan-2-yl-urea | 556 | 2.49 |

| Example | Structure | NAME | LCMS MH+ | Retention time (min) |
|---|---|---|---|---|
| 61n | 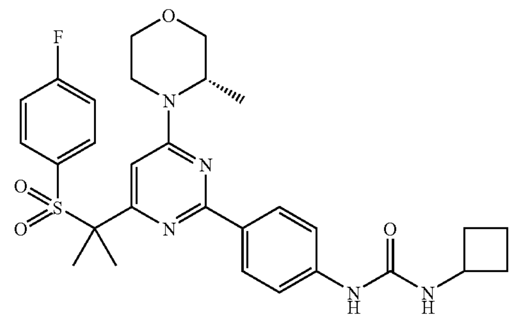 | 3-cyclobutyl-1-[4-[4-[2-(4-fluorophenyl)sulfonylpropan-2-yl]-6-[(3S)-3-methylmorpholin-4-yl]pyrimidin-2-yl]phenyl]urea | 568 | 2.57 |
| 61o | 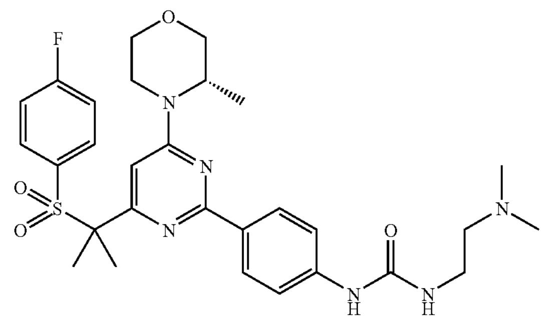 | 3-(2-dimethylaminoethyl)-1-[4-[4-[2-(4-fluorophenyl)sulfonylpropan-2-yl]-6-[(3S)-3-methylmorpholin-4-yl]pyrimidin-2-yl]phenyl]urea | 585 | 1.91 |
| 61p | 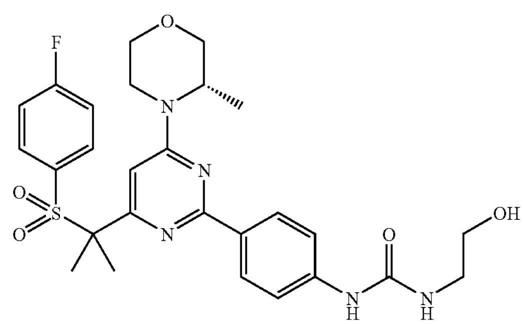 | 1-[4-[4-[2-(4-fluorophenyl)sulfonylpropan-2-yl]-6-[(3S)-3-methylmorpholin-4-yl]pyrimidin-2-yl]phenyl]-3-(2-hydroxyethyl)urea | 558 | 2.01 |
| 61q | 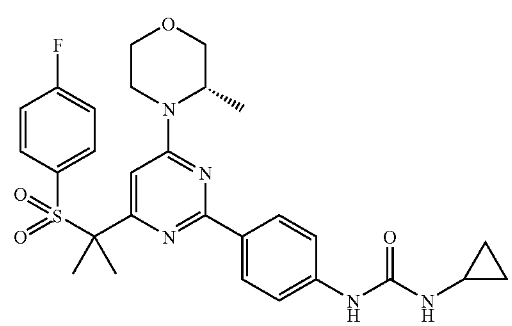 | 3-cyclopropyl-1-[4-[4-[2-(4-fluorophenyl)sulfonylpropan-2-yl]-6-[(3S)-3-methylmorpholin-4-yl]pyrimidin-2-yl]phenyl]urea | 554 | 2.35 |

Example 61a: $^1$H NMR (400.132 MHz, DMSO-$d_6$) δ 1.07 (3H, t), 1.20 (3H, d), 3.09-3.21 (3H, m), 3.49 (1H, dd), 3.63 (1H, dd), 3.76 (1H, d), 3.97 (1H, dd), 4.11 (1H, d), 4.37 (1H, s), 4.71 (2H, s), 6.13 (1H, t), 6.64 (1H, s), 7.38 (2H, d), 7.46 (2H, t), 7.78 (2H, d), 7.85-7.88 (2H, m), 8.64 (1H, s)

Example 61b: $^1$H NMR (400.132 MHz, DMSO-$d_6$) δ 1.11 (6H, d), 1.20 (3H, d), 3.18 (1H, dt), 3.48 (1H, dt), 3.63 (1H, dd), 3.73-3.81 (2H, m), 3.97 (1H, dd), 4.11 (1H, d), 4.38 (1H, s), 4.71 (2H, s), 6.03 (1H, d), 6.64 (1H, s), 7.36 (2H, d), 7.46 (2H, t), 7.79 (2H, d), 7.85-7.89 (2H, m), 8.51 (1H, s)

Example 61c: $^1$H NMR (400.132 MHz, DMSO-$d_6$) δ 1.20 (3H, d), 3.13-3.21 (3H, m), 3.44-3.50 (3H, m), 3.63 (1H, dd), 3.76 (1H, d), 3.97 (1H, dd), 4.11 (1H, d), 4.37 (1H, s), 4.71-4.74 (3H, m), 6.22 (1H, t), 6.64 (1H, s), 7.38 (2H, d), 7.46 (2H, t), 7.79 (2H, d), 7.85-7.89 (2H, m), 8.78 (1H, s)

Example 61d: $^1$H NMR (400.132 MHz, DMSO-$d_6$) δ 1.20 (3H, d), 1.24 (6H, s), 3.14-3.20 (2H, m), 3.39 (1H, d), 3.48

(1H, t), 3.63 (1H, d), 3.76 (1H, d), 3.97 (1H, d), 4.11 (1H, d), 4.37 (1H, s), 4.72 (2H, s), 4.95 (1H, s), 5.98 (1H, s), 6.64 (1H, s), 7.34 (2H, d), 7.46 (2H, t), 7.78 (2H, d), 7.86-7.89 (2H, m), 8.72 (1H, s)

Example 61e: $^1$H NMR (400.132 MHz, DMSO-d$_6$) δ 1.20 (3H, d), 2.18 (6H, s), 2.34 (2H, t), 3.14-3.21 (3H, m), 3.48 (1H, dt), 3.63 (1H, d), 3.76 (1H, d), 3.97 (1H, d), 4.04-4.12 (1H, m), 4.37 (1H, s), 4.71 (2H, s), 6.13 (1H, t), 6.64 (1H, s), 7.37 (2H, d), 7.46 (2H, t), 7.78 (2H, d), 7.85-7.89 (2H, m), 8.86 (1H, s)

Example 61f: $^1$H NMR (400.132 MHz, DMSO-d$_6$) δ 0.89 (3H, t), 1.20 (3H, d), 1.46 (2H, sextet), 3.06 (2H, q), 3.17 (1H, dt), 3.48 (1H, dt), 3.63 (1H, dd), 3.76 (1H, d), 3.97 (1H, dd), 4.11 (1H, d), 4.37 (1H, s), 4.71 (2H, s), 6.17 (1H, t), 6.64 (1H, s), 7.38 (2H, d), 7.46 (2H, t), 7.79 (2H, d), 7.86-7.89 (2H, m), 8.62 (1H, s)

Example 61g: $^1$H NMR (400.132 MHz, DMSO-d$_6$) δ 0.89 (6H, d), 1.20 (3H, d), 1.67-1.72 (1H, m), 2.94 (2H, t), 3.17 (1H, t), 3.48 (1H, t), 3.63 (1H, dd), 3.76 (1H, d), 3.97 (1H, dd), 4.11 (1H, d), 4.38 (1H, s), 4.72 (2H, s), 6.21 (1H, t), 6.65 (1H, s), 7.38 (2H, d), 7.46 (2H, t), 7.79 (2H, d), 7.85-7.89 (2H, m), 8.62 (1H, s)

Example 61h: $^1$H NMR (400.132 MHz, DMSO-d$_6$) δ 1.20 (3H, d), 1.60 (2H, quintet), 3.14-3.21 (3H, m), 3.45-3.51 (3H, m), 3.63 (1H, dd), 3.76 (1H, d), 3.97 (1H, dd), 4.11 (1H, d), 4.38 (1H, s), 4.47 (1H, t), 4.71 (2H, s), 6.17 (1H, t), 6.64 (1H, s), 7.38 (2H, d), 7.46 (2H, t), 7.78 (2H, d), 7.85-7.89 (2H, m), 8.68 (1H, s)

Example 61i: $^1$H NMR (400.132 MHz, DMSO-d$_6$) δ 9.10 (1H, s), 9.02 (1H, s), 7.86-7.89 (4H, m), 7.64-7.70 (4H, m), 7.45-7.49 (4H, m), 6.68 (1H, s), 4.73 (2H, s), 4.39 (1H, s), 4.13 (1H, d), 3.98 (1H, d), 3.77 (1H, d), 3.64 (1H, dd), 3.49 (1H, td), 3.19 (1H, td), 1.21 (3H, d)

Example 61j: $^1$H NMR (400.132 MHz, DMSO-d$_6$) δ 1.21 (3H, d), 3.19 (1H, dt), 3.50 (1H, dt), 3.64 (1H, d), 3.77 (1H, d), 3.98 (1H, d), 4.12 (1H, d), 4.39 (1H, s), 4.74 (2H, s), 6.68 (1H, s), 7.02-7.05 (1H, m), 7.45-7.59 (5H, m), 7.75-7.79 (1H, m), 7.86-7.90 (4H, m), 8.30 (1H, d), 9.42 (1H, s), 10.52 (1H, s)

Example 61k: $^1$H NMR (400.132 MHz, DMSO-d$_6$) δ 1.27 (3H, d), 1.84 (6H, d), 2.71 (3H, d), 3.19-3.26 (1H, m), 3.52-3.57 (1H, m), 3.70 (1H, dd), 3.82 (1H, d), 4.02 (1H, dd), 4.22 (1H, d), 4.59 (1H, s), 6.09-6.10 (1H, m), 6.73 (1H, s), 7.36 (2H, t), 7.44 (2H, d), 7.60-7.63 (2H, m), 7.83 (2H, d), 8.76 (1H, s)

Example 61l: $^1$H NMR (400.132 MHz, DMSO-d$_6$) δ 1.07 (3H, t), 1.22 (3H, d), 1.79 (6H, d), 3.09-3.20 (3H, m), 3.50 (1H, t), 3.65 (1H, d), 3.77 (1H, d), 3.98 (1H, d), 4.17 (1H, d), 4.55 (1H, s), 6.13 (1H, t), 6.68 (1H, s), 7.31 (2H, t), 7.38 (2H, d), 7.54-7.58 (2H, m), 7.78 (2H, d), 8.62 (1H, s)

Example 61m: $^1$H NMR (400.132 MHz, DMSO-d$_6$) δ 1.11 (6H, d), 1.22 (3H, d), 1.79 (6H, d), 3.11-3.20 (1H, m), 3.50 (1H, t), 3.65 (1H, d), 3.75-3.80 (2H, m), 3.98 (1H, d), 4.17 (1H, d), 4.54 (1H, s), 6.03 (1H, d), 6.68 (1H, s), 7.31 (2H, t), 7.36 (2H, d), 7.54-7.58 (2H, m), 7.78 (2H, d), 8.50 (1H, s)

Example 61n: $^1$H NMR (400.132 MHz, DMSO-d$_6$) δ 1.21 (3H, d), 1.57-1.66 (2H, m), 1.78 (6H, d), 1.82-1.91 (2H, m), 2.14-2.25 (2H, m), 3.17 (1H, dt), 3.49 (1H, dt), 3.64 (1H, dd), 3.77 (1H, d), 3.97 (1H, dd), 4.09-4.18 (2H, m), 4.54 (1H, s), 6.43 (1H, d), 6.68 (1H, s), 7.31 (2H, t), 7.36 (2H, d), 7.54-7.58 (2H, m), 7.78 (2H, d), 8.53 (1H, s)

Example 61o: $^1$H NMR (400.132 MHz, DMSO-d$_6$) δ 1.22 (3H, d), 1.79 (6H, d), 2.18 (6H, s), 2.34 (2H, t), 3.13-3.21 (3H, m), 3.50 (1H, t), 3.64 (1H, d), 3.77 (1H, d), 3.98 (1H, d), 4.17 (1H, d), 4.55 (1H, s), 6.14 (1H, t), 6.67 (1H, s), 7.31 (2H, t), 7.37 (2H, d), 7.54-7.58 (2H, m), 7.78 (2H, d), 8.85 (1H, s)

Example 61p: $^1$H NMR (400.132 MHz, DMSO-d$_6$) δ 1.22 (3H, d), 1.79 (6H, d), 3.14-3.21 (3H, m), 3.44-3.53 (3H, m), 3.65 (1H, dd), 3.77 (1H, d), 3.98 (1H, dd), 4.17 (1H, d), 4.55 (1H, s), 4.72 (1H, t), 6.23 (1H, t), 6.68 (1H, s), 7.31 (2H, t), 7.37 (2H, d), 7.54-7.58 (2H, m), 7.78 (2H, d), 8.77 (1H, s)

Example 61q: $^1$H NMR (400.132 MHz, DMSO-d$_6$) δ 0.40-0.44 (2H, m), 0.62-0.67 (2H, m), 1.22 (3H, d), 1.79 (6H, d), 2.54-2.58 (1H, m), 3.17 (1H, dt), 3.49 (1H, dt), 3.65 (1H, dd), 3.77 (1H, d), 3.97 (1H, dd), 4.17 (1H, d), 4.55 (1H, s), 6.40 (1H, d), 6.68 (1H, s), 7.31 (2H, t), 7.39 (2H, d), 7.54-7.58 (2H, m), 7.79 (2H, d), 8.50 (1H, s)

Test (c): Example (61) 0.33 μM; Example (61a) 0.75 μM; Example (61b) 0.038 μM; Example (61c) 0.41 μM; Example (61d) 0.18 μM; Example (61e) 0.12 μM; Example (61g) 0.45 μM; Example (61h) 0.79 μM; Example (61k) 0.12 μM; Example (61l) 0.099 μM; Example (61m) 0.03 μM; Example (61n) 0.038 μM; Example (61o) 0.045 μM; Example (61q) 0.077 μM;

The preparation of phenyl N-[4-[4-[(4-fluorophenyl)sulfonylmethyl]-6-[(3S)-3-methylmorpholin-4-yl]pyrimidin-2-yl]phenyl]carbamate is described below.

Phenyl N-[4-[4-[(4-fluorophenyl)sulfonylmethyl]-6-[(3S)-3-methylmorpholin-4-yl]pyrimidin-2-yl]phenyl]carbamate

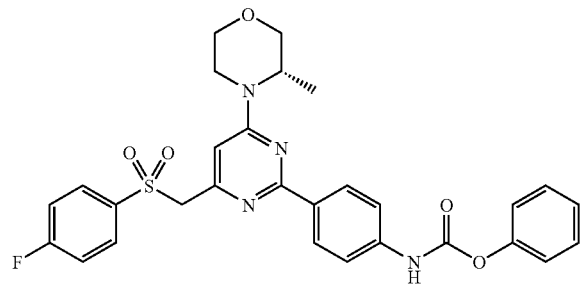

Phenyl chloroformate (0.474 mL, 3.77 mmol) was added dropwise to 4-[4-[(4-fluorophenyl)sulfonylmethyl]-6-[(3S)-3-methylmorpholin-4-yl]pyrimidin-2-yl]aniline (1.67 g, 3.77 mmol) and sodium bicarbonate (476 mg, 5.66 mmol) in dioxane (20 mL) under nitrogen. The resulting suspension was stirred at RT for 2 hours. The reaction mixture was evaporated to dryness and redissolved in DCM (50 mL) and washed with water (50 mL). The organic layer was dried (MgSO$_4$), filtered and evaporated to give crude product which was triturated with diethyl ether to give the desired product (1.90 g).

NMR Spectrum: $^1$H NMR (400.132 MHz, DMSO-d$_6$) δ 1.21 (3H, d), 3.15-3.22 (1H, m), 3.35 (1H, s), 3.45-3.52 (1H, m), 3.63 (1H, dd), 3.77 (1H, d), 3.97 (1H, dd), 4.13 (1H, d), 4.39 (1H, s), 4.73 (2H, s), 6.69 (1H, s), 7.24-7.26 (2H, m), 7.43-7.48 (4H, m), 7.53 (2H, d), 7.86-7.90 (4H, m), 10.39 (1H, s)

LCMS Spectrum: MH+ 563, retention time 2.65 min.

4-[4-[(4-Fluorophenyl)sulfonylmethyl]-6-[(3S)-3-methylmorpholin-4-yl]pyrimidin-2-yl]aniline

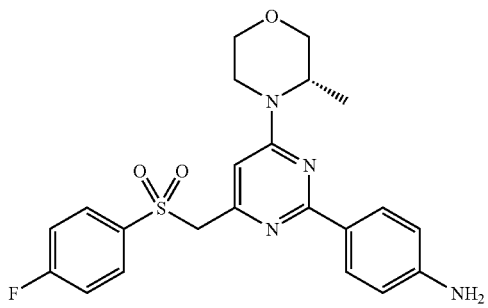

Dichlorobis(triphenylphosphine)palladium(II) (136 mg, 0.19 mmol) was added to 4-(4,4,5,5-tetramethyl-1,3,2-dioxaborolan-2-yl)aniline (1.107 g, 5.05 mmol) and 2-chloro-4-[(4-fluorophenyl)sulfonylmethyl]-6-[(3S)-3-methylmorpholin-4-yl]pyrimidine (1.50 g, 3.89 mmol) and sodium carbonate (5 mL, 10.00 mmol) in 18% DMF in DME:water:ethanol (7:3:2) (20 mL). The resulting solution was stirred at 90° C. for 4 hours. The reaction mixture was diluted with ethyl acetate (20 mL), and washed with water (2×20 mL). The organic layer was dried (MgSO$_4$), filtered and evaporated to afford crude product. The crude product was purified by flash silica chromatography, elution gradient 5 to 60% ethyl acetate in isohexane, to give the desired material as a cream solid (1.670 g).

NMR Spectrum: $^1$H NMR (400.132 MHz, DMSO-d$_6$) δ 1.18 (3H, d), 3.10-3.18 (1H, m), 3.44-3.50 (1H, m), 3.62 (1H, dd), 3.75 (1H, d), 3.96 (1H, dd), 4.07 (1H, d), 4.35 (1H, s), 4.67 (2H, s), 5.52 (2H, s), 6.49 (2H, d), 6.53 (1H, s), 7.45 (2H, t), 7.62 (2H, d), 7.84-7.88 (2H, m)

LCMS Spectrum: MH+ 443, retention time 1.96 min.

2-Chloro-4-[(4-fluorophenyl)sulfonylmethyl]-6-[(3S)-3-methylmorpholin-4-yl]pyrimidine

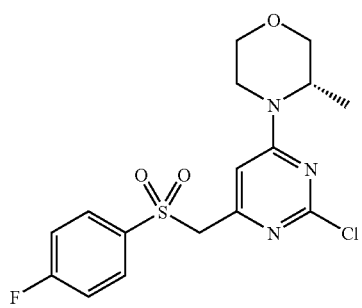

Triethylamine (1.117 ml, 8.01 mmol) was added to 2,4-dichloro-6-[(4-fluorophenyl)sulfonylmethyl]pyrimidine (2.34 g, 7.29 mmol) in DCM (36.4 mL) at 0° C. followed by (3S)-3-methylmorpholine (0.737 g, 7.29 mmol) in DCM (20 mL) over 15 minutes. The reaction was then stirred at RT for 16 hours. The reaction mixture was washed with water (50 mL), the organic layer dried (MgSO$_4$), filtered and evaporated to afford crude product. The crude product was purified by flash silica chromatography, elution gradient 0 to 50% ethyl acetate in DCM, to give the desired material as a beige solid (1.530 g).

NMR Spectrum: $^1$H NMR (400.132 MHz, DMSO-d$_6$) δ 1.17 (3H, d), 3.13-3.20 (1H, m), 3.27-3.28 (1H, m), 3.39-3.46 (1H, m), 3.57 (1H, dd), 3.72 (1H, d), 3.93 (1H, dd), 4.17 (1H, s), 4.65 (2H, s), 6.71 (1H, s), 7.48 (2H, t), 7.83-7.87 (2H, m)

LCMS Spectrum: MH+ 386, retention time 1.94 min.

2,4-Dichloro-6-[(4-fluorophenyl)sulfonylmethyl]pyrimidine

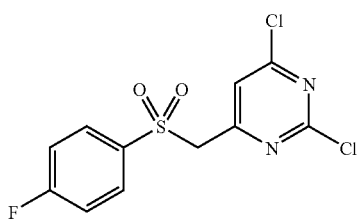

3-Chloroperoxybenzoic acid (3.78 g, 21.89 mmol) was added portionwise to 2,4-dichloro-6-[(4-fluorophenyl)sulfanylmethyl]pyrimidine (2.11 g, 7.30 mmol), in DCM (36.5 mL) and the reaction stirred at RT for 2 hours. The reaction mixture was washed with a saturated aqueous solution of sodium hydrogen carbonate (50 mL) and the organic layer dried (MgSO$_4$), filtered and evaporated to afford desired product (2.35 g).

NMR Spectrum: $^1$H NMR (400.132 MHz, DMSO-d$_6$) δ 4.99 (2H, s), 7.48-7.52 (2H, m), 7.76 (1H, s), 7.85-7.88 (2H, m)

LCMS Spectrum: MH+ 319, retention time 2.01 min.

2,4-Dichloro-6-[(4-fluorophenyl)sulfanylmethyl]pyrimidine

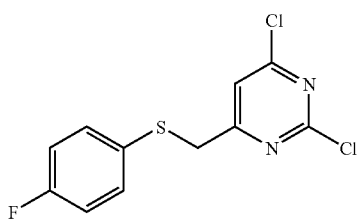

Phosphorus oxychloride (15.2 g, 99.1 mmol) was added to 6-[(4-fluorophenyl)sulfanylmethyl]-1H-pyrimidine-2,4-dione (2.5 g, 9.91 mmol), and the resulting solution was stirred at reflux for 7 hours. The reaction was allowed to cool and the phosphorus oxychloride removed under reduced pressure to give a brown oil. This was dissolved in DCM and ice water (50 mL) added followed by solid sodium bicarbonate (until effervescence stops). The aqueous layer was extracted with DCM (2×50 mL) and the organics dried (MgSO$_4$), filtered and evaporated to afford crude product. The crude product was purified by flash silica chromatography, elution gradient 0 to 40% ethyl acetate in isohexane, to give the desired material as a yellow gum (2.11 g).

NMR Spectrum: $^1$H NMR (400.132 MHz, DMSO-d$_6$) δ 4.21 (2H, s), 7.09-7.14 (2H, m), 7.34-7.38 (2H, m), 7.58 (1H, s)

LCMS Spectrum: M−H+ 287, retention time 2.51 min.

423

6-[(4-Fluorophenyl)sulfanylmethyl]-1H-pyrimidine-2,4-dione

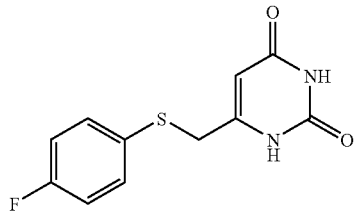

DBU (4.02 mL, 26.91 mmol) was added to 4-fluorobenzenethiol (3.45 g, 26.91 mmol), in DMF (90 mL) at RT. The resulting solution was stirred at 20° C. for 15 minutes. 6-(Chloromethyl)-1H-pyrimidine-2,4-dione (2.88 g, 17.94 mmol) was then added and the reaction stirred for 4 hours. The reaction mixture was concentrated and diluted with DCM (100 mL), and washed with water (100 mL). The aqueous layer was acidified with 2M hydrochloric acid to give a white solid which was filtered and washed with water then dried under vacuum to give desired product (2.5 g).

NMR Spectrum: $^1$H NMR (400.132 MHz, DMSO-$d_6$) δ 3.80 (2H, s), 5.20 (1H, s), 7.18-7.23 (2H, m), 7.45-7.49 (2H, m), 10.90 (1H, s), 10.93 (1H, s)

LCMS Spectrum: M−H-251, retention time 0.80 min.

The preparation of phenyl N-[4-[4-[2-(4-fluorophenyl)sulfonylpropan-2-yl]-6-[(3S)-3-methylmorpholin-4-yl]pyrimidin-2-yl]phenyl]carbamate is described below.

Phenyl N-[4-[4-[2-(4-fluorophenyl)sulfonylpropan-2-yl]-6-[(3S)-3-methylmorpholin-4-yl]pyrimidin-2-yl]phenyl]carbamate

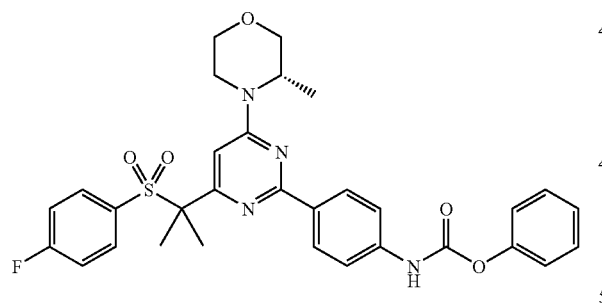

Phenyl chloroformate (0.482 mL, 3.83 mmol) was added dropwise to 4-[4-[2-(4-fluorophenyl)sulfonylpropan-2-yl]-6-[(3S)-3-methylmorpholin-4-yl]pyrimidin-2-yl]aniline (1.8 g, 3.83 mmol) and sodium bicarbonate (0.482 g, 5.74 mmol) in dioxane (20 mL) under nitrogen. The resulting suspension was stirred at RT for 2 hours. The reaction mixture was evaporated to dryness and redissolved in DCM (50 mL) and washed with water (50 mL). The organic layer was dried (MgSO$_4$), filtered and evaporated to give crude product which was triturated with diethyl ether to give the desired material as a white solid (2.26 g).

NMR Spectrum: $^1$H NMR (400.132 MHz, DMSO-$d_6$) δ 1.22 (3H, d), 1.80 (6H, d), 3.18 (1H, dt), 3.50 (1H, dt), 3.65 (1H, dd), 3.77 (1H, d), 3.98 (1H, dd), 4.19 (1H, d), 4.55 (1H, s), 6.72 (1H, s), 7.24-7.33 (5H, m), 7.45 (2H, t), 7.52 (2H, d), 7.55-7.58 (2H, m), 7.88 (2H, d), 10.39 (1H, s)

424

LCMS Spectrum: MH+ 591, retention time 3.10 min.

4-[4-[2-(4-Fluorophenyl)sulfonylpropan-2-yl]-6-[(3S)-3-methylmorpholin-4-yl]pyrimidin-2-yl]aniline

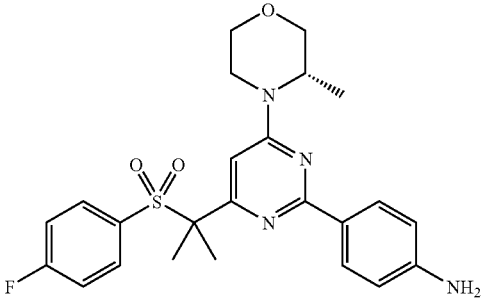

Dichlorobis(triphenylphosphine)palladium(II) (170 mg, 0.24 mmol) was added to 4-(4,4,5,5-tetramethyl-1,3,2-dioxaborolan-2-yl)aniline (1.376 g, 6.28 mmol) and 2-chloro-4-[2-(4-fluorophenyl)sulfonylpropan-2-yl]-6-[(3S)-3-methylmorpholin-4-yl]pyrimidine (2 g, 4.83 mmol), and sodium carbonate (5 mL, 10.00 mmol) in 18% DMF in DME:water:ethanol (7:3:2) (20 mL). The resulting solution was stirred at 90° C. for 4 hours. The reaction mixture was diluted with ethyl acetate (20 mL), and washed with water (2×20 mL1). The organic layer was dried (MgSO$_4$), filtered and evaporated to afford crude product. The crude product was purified by flash silica chromatography, elution gradient 5 to 60% ethyl acetate in isohexane, to give the desired material as a cream solid (1.80 g).

NMR Spectrum: $^1$H NMR (400.132 MHz, DMSO-$d_6$) δ 1.20 (3H, d), 1.76 (6H, d), 3.14 (1H, dt), 3.48 (1H, dt), 3.63 (1H, dd), 3.76 (1H, d), 3.96 (1H, dd), 4.13 (1H, d), 4.51 (1H, d), 5.50 (2H, s), 6.49 (2H, d), 6.58 (1H, s), 7.31 (2H, t), 7.54-7.57 (2H, m), 7.62 (2H, d)

LCMS Spectrum: MH+ 471, retention time 2.57 min.

2-Chloro-4-[2-(4-fluorophenyl)sulfonylpropan-2-yl]-6-[(3S)-3-methylmorpholin-4-yl]pyrimidine

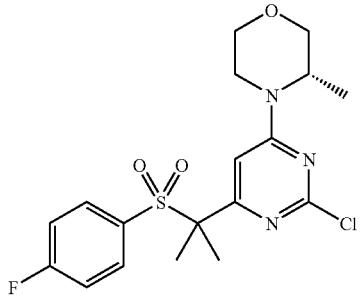

Iodomethane (0.32 mL, 5.20 mmol) was added to sodium tert-butoxide (498 mg, 5.20 mmol) and 2-chloro-4-[(4-fluorophenyl)sulfonylmethyl]-6-[(3S)-3-methylmorpholin-4-yl]pyrimidine (2 g, 5.18 mmol) in DMF (2 mL) at −10° C. The resulting thick suspension was stirred at RT for 15 minutes to ease the stirring. Iodomethane (0.32 mL, 5.20 mmol) and sodium tert-butoxide (498 mg, 5.20 mmol) were again added to the reaction and the resulting suspension stirred at RT for 15 minutes. The reaction mixture was diluted with DCM (20 mL) and washed with water (20 mL). The organic layer was dried (MgSO$_4$), filtered and evaporated to afford crude product. The crude product was purified by flash silica chromatography, elution gradient 0 to 50% ethyl acetate in DCM.

Pure fractions were evaporated to dryness to give the desired product as a white solid (2.00 g).

NMR Spectrum: ¹H NMR (400.132 MHz, DMSO-$d_6$) δ 1.19 (3H, d), 1.67 (6H, d), 3.17 (1H, dt), 3.43 (1H, dt), 3.58 (1H, dd), 3.72 (1H, d), 3.93 (1H, dd), 4.01 (1H, d), 4.38 (1H, s), 6.75 (1H, s), 7.44 (2H, t), 7.58-7.61 (2H, m)

LCMS Spectrum: MH+ 414, retention time 2.35 min.

The preparation of 2-chloro-4-[(4-fluorophenyl)sulfonylmethyl]-6-[(3S)-3-methylmorpholin-4-yl]pyrimidine was described earlier.

EXAMPLE 62

3-Cyclopropyl-1-[4-[4-(2-ethylsulfonylpropan-2-yl)-6-[(3S)-3-methylmorpholin-4-yl]pyrimidin-2-yl]phenyl]urea

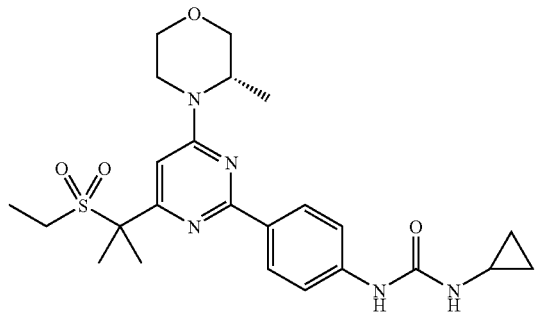

To a solution of phenyl N-[4-[4-(2-ethylsulfonylpropan-2-yl)-6-[(3S)-3-methylmorpholin-4-yl]pyrimidin-2-yl]phenyl]carbamate (150 mg, 0.29 mmol) in DMF (2 mL) was added triethylamine (0.120 mL, 0.86 mmol) followed by cyclopropylamine (0.100 mL, 1.44 mmol) and the reaction heated at 50° C. for 2 hours. The crude product was purified by preparative HPLC using decreasingly polar mixtures of water (containing 1% NH3) and acetonitrile as eluents, to give the desired material as a white solid (85 mg).

NMR Spectrum: ¹H NMR (400.13 MHz, DMSO-$d_6$) δ 0.40-0.44 (2H, m), 0.63-0.67 (2H, m), 1.14 (3H, t), 1.23 (3H, d), 1.79 (6H, s), 2.55 (1H, m), 3.17-3.21 (1H, m), 3.23 (2H, d), 3.46-3.50 (1H, m), 3.63-3.67 (1H, m), 3.77 (1H, d), 3.96-4.00 (1H, m), 4.23 (1H, d), 4.59 (1H, s), 6.43 (1H, d), 6.75 (1H, s), 7.51 (2H, d), 8.23 (2H, d), 8.54 (1H, s).

LCMS Spectrum: MH+ 488, retention time 2.19 min.

The following compounds were made in an analogous fashion from either phenyl N-[4-[4-(2-ethylsulfonylpropan-2-yl)-6-[(3S)-3-methylmorpholin-4-yl]pyrimidin-2-yl]phenyl]carbamate or phenyl N-[4-[4-(ethylsulfonylmethyl)-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 62a | 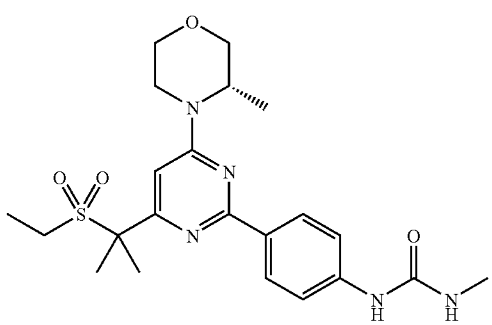 | 1-[4-[4-(2-ethylsulfonylpropan-2-yl)-6-[(3S)-3-methylmorpholin-4-yl]pyrimidin-2-yl]phenyl]-3-methyl-urea | 502 | 2.42 |
| 62b | 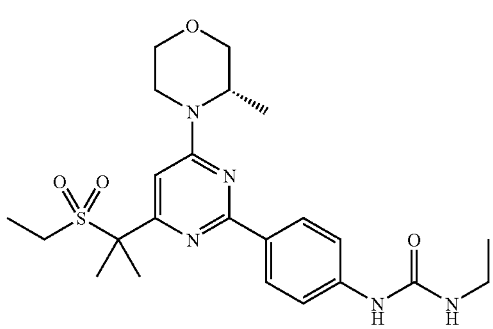 | 1-ethyl-3-[4-[4-(2-ethylsulfonylpropan-2-yl)-6-[(3S)-3-methylmorpholin-4-yl]pyrimidin-2-yl]phenyl]urea | 476 | 2.16 |

-continued

| Example | Structure | NAME | LCMS MH+ | Retention time (min) |
|---|---|---|---|---|
| 62c | 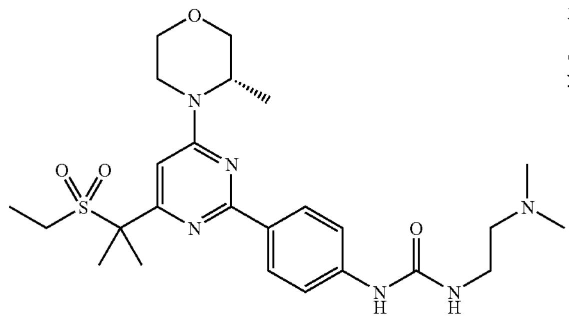 | 3-(2-dimethylaminoethyl)-1-[4-[4-(2-ethylsulfonylpropan-2-yl)-6-[(3S)-3-methylmorpholin-4-yl]pyrimidin-2-yl]phenyl]urea | 519 | 2.10 |
| 62d | 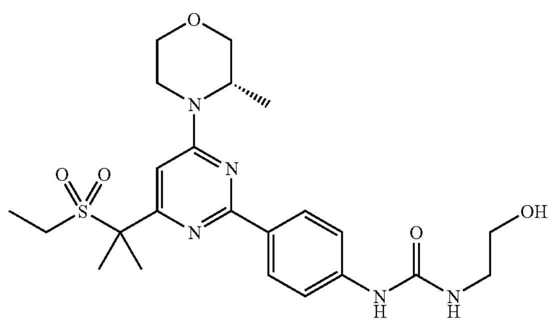 | 1-[4-[4-(2-ethylsulfonylpropan-2-yl)-6-[(3S)-3-methylmorpholin-4-yl]pyrimidin-2-yl]phenyl]-3-(2-hydroxyethyl)urea | 492 | 1.83 |
| 62e | 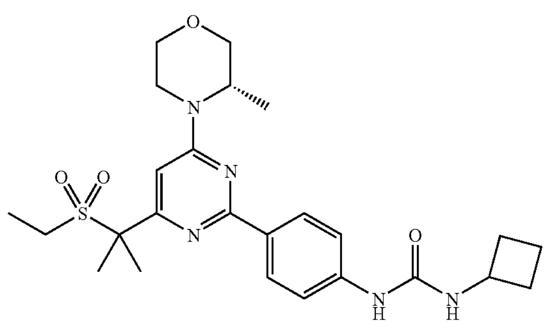 | 3-cyclobutyl-1-[4-[4-(2-ethylsulfonylpropan-2-yl)-6-[(3S)-3-methylmorpholin-4-yl]pyrimidin-2-yl]phenyl]urea | 462 | 2.00 |
| 62f | 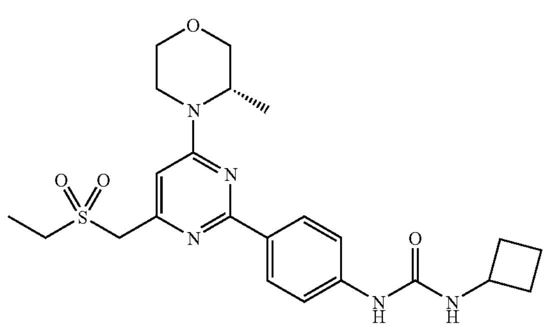 | 3-cyclobutyl-1-[4-[4-(ethylsulfonylmethyl)-6-[(3S)-3-methylmorpholin-4-yl]pyrimidin-2-yl]phenyl]urea | 474 | 2.14 |

| Example | Structure | NAME | LCMS MH+ | Retention time (min) |
|---|---|---|---|---|
| 62g | 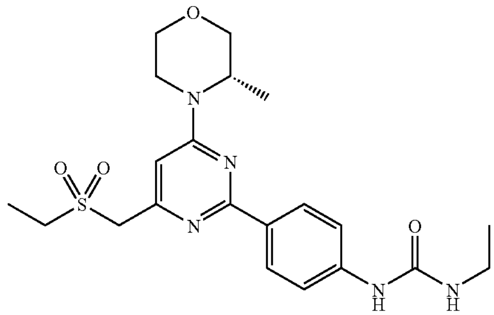 | 1-ethyl-3-[4-[4-(ethylsulfonylmethyl)-6-[(3S)-3-methylmorpholin-4-yl]pyrimidin-2-yl]phenyl]urea | 448 | 1.87 |
| 62h | 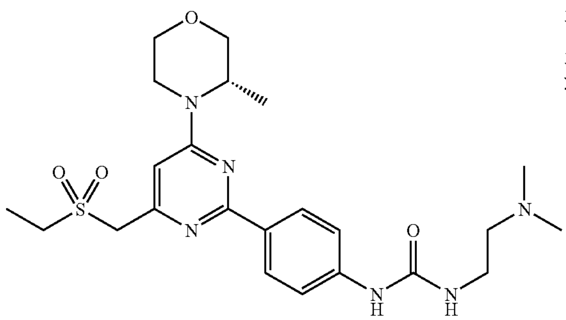 | 3-(2-dimethylaminoethyl)-1-[4-[4-(ethylsulfonylmethyl)-6-[(3S)-3-methylmorpholin-4-yl]pyrimidin-2-yl]phenyl]urea | 491 | 1.83 |

Example 62a: $^1$H NMR (400.13 MHz, DMSO-d$_6$) δ 1.14 (3H, t), 1.23 (3H, d), 1.54-1.68 (2H, m), 1.78 (6H, s), 1.83-1.90 (2H, d), 2.18-2.25 (2H, m), 3.17-3.21 (1H, m), 3.23 (2H, q), 3.46-3.53 (1H, m), 3.63-3.66 (1H, m), 3.77 (1H, d), 3.96-4.00 (1H, m), 4.15 (1H, q), 4.22 (1H, d), 4.59 (1H, s), 6.46 (1H, d), 6.75 (1H, s), 7.48 (2H, d), 8.22 (2H, d), 8.56 (1H, s)

Example 62b: $^1$H NMR (400.13 MHz, DMSO-d$_6$) δ 1.07 (3H, t), 1.14 (3H, t), 1.23 (3H, d), 1.78 (6H, d), 3.09-3.16 (2H, m), 3.18 (1H, m), 3.22 (2H, t), 3.46-3.53 (1H, m), 3.63-3.67 (1H, m), 3.77 (1H, d), 3.96-4.00 (1H, m), 4.23 (1H, d), 4.58 (1H, s), 6.16 (1H, t), 6.75 (1H, d), 7.50 (2H, d), 8.22 (2H, d), 8.66 (1H, s)

Example 62c: $^1$H NMR (400.13 MHz, DMSO-d$_6$) δ 1.07 (3H, t), 1.14 (3H, t), 1.23 (3H, d), 1.78 (6H, d), 3.09-3.16 (2H, m), 3.18 (1H, m), 3.22 (2H, t), 3.46-3.53 (1H, m), 3.63-3.67 (1H, m), 3.77 (1H, d), 3.96-4.00 (1H, m), 4.23 (1H, d), 4.58 (1H, s), 6.16 (1H, t), 6.75 (1H, d), 7.50 (2H, d), 8.22 (2H, d), 8.66 (1H, s)

Example 62d: $^1$H NMR (400.13 MHz, DMSO-d$_6$) δ 1.14 (3H, t), 1.22-1.24 (3H, m), 1.78 (6H, s), 3.17 (1H, t), 3.20-3.22 (2H, s), 3.24 (2H, m), 3.46 (2H, q), 3.48 (1H, m), 3.63-3.66 (1H, m), 3.77 (1H, d), 3.96-4.00 (1H, m), 4.21-4.24 (1H, m), 4.57-4.60 (1H, m), 4.73 (1H, t), 6.25 (1H, t), 6.75 (1H, s), 7.48-7.51 (2H, m), 8.23 (2H, d), 8.80 (1H, s)

Example 62e: $^1$H NMR (400.13 MHz, DMSO-d$_6$) δ 1.14 (3H, t), 1.27 (3H, d), 1.78 (6H, m), 2.68 (3H, d), 3.18 (1H, m), 3.24 (2H, m), 3.46-3.53 (1H, m), 3.63-3.66 (1H, m), 3.77 (1H, d), 3.96-4.00 (1H, m), 4.23 (1H, d), 4.59 (1H, s), 6.07 (1H, t), 6.75 (1H, s), 7.51 (2H, d), 8.22 (2H, d), 8.74 (1H, s)

Example 62f: $^1$H NMR (400.13 MHz, DMSO-d$_6$) δ 1.23-1.25 (3H, m), 1.35 (3H, t), 1.59-1.66 (2H, m), 1.83-1.86 (2H, m), 2.19-2.23 (2H, m), 3.18 (1H, m), 3.33 (2H, m), 3.47-3.50 (1H, m), 3.66 (1H, d), 3.76-3.79 (1H, m), 3.96 (1H, d), 4.14 (2H, d), 4.45 (3H, m), 6.47 (1H, d), 6.78 (1H, s), 7.47-7.49 (2H, m), 8.18-8.20 (2H, m), 8.56 (1H, s)

Example 62g: $^1$H NMR (400.13 MHz, DMSO-d$_6$) δ 1.07 (3H, t), 1.24 (3H, d), 1.35 (3H, t), 3.09-3.16 (2H, m), 3.21-3.26 (1H, m), 3.33 (2H, d), 3.47-3.53 (1H, m), 3.63-3.67 (1H, m), 3.78 (1H, d), 3.97-4.01 (1H, m), 4.14 (1H, d), 4.45 (3H, s), 6.17 (1H, t), 6.77 (1H, s), 7.48-7.51 (2H, m), 8.18-8.20 (2H, m), 8.66 (1H, s)

Example 62h: $^1$H NMR (400.13 MHz, DMSO-d$_6$) δ 1.23-1.25 (3H, m), 1.35 (3H, t), 2.18 (6H, s), 2.34 (2H, t), 3.20 (3H, q), 3.33 (2H, d), 3.47-3.53 (1H, m), 3.63-3.67 (1H, m), 3.78 (1H, d), 3.97-4.01 (1H, m), 4.14 (1H, d), 4.45 (3H, s), 6.16 (1H, t), 6.77 (1H, s), 7.47-7.51 (2H, m), 8.18-8.20 (2H, m), 8.89 (1H, s)

The preparation of phenyl N-[4-[4-(2-ethylsulfonylpropan-2-yl)-6-[(3S)-3-methylmorpholin-4-yl]pyrimidin-2-yl]phenyl]carbamate is described below.

Phenyl N-[4-[4-(2-ethylsulfonylpropan-2-yl)-6-[(3S)-3-methylmorpholin-4-yl]pyrimidin-2-yl]phenyl]carbamate

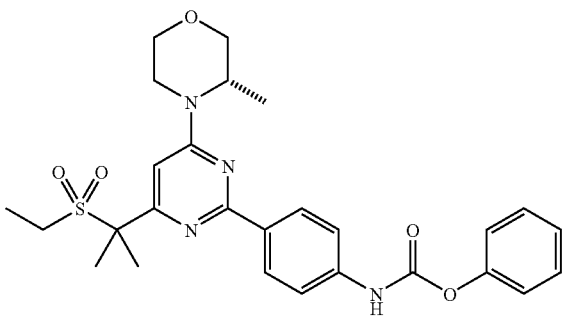

Phenyl chloroformate (0.373 mL, 2.97 mmol) was added dropwise to 4-[4-(2-ethylsulfonylpropan-2-yl)-6-[(3S)-3-methylmorpholin-4-yl]pyrimidin-2-yl]aniline (1.20 g, 2.97 mmol) and sodium bicarbonate (0.374 g, 4.45 mmol) in dioxane (25 mL) under nitrogen. The resulting suspension was stirred at RT for 2 hours. The reaction mixture was evaporated to dryness and partitioned between ethyl acetate (150 mL) and water (150 mL). The organic layer was dried (MgSO$_4$), filtered and evaporated to give the desired material as a white solid (1.40 g).

NMR Spectrum: $^1$H NMR (400.13 MHz, DMSO-d$_6$) δ 1.14 (3H, t), 1.24 (3H, d), 1.79 (6H, d), 3.24 (3H, q), 3.47-3.54 (1H, m), 3.63-3.67 (1H, m), 3.77 (1H, d), 3.96-4.00 (1H, m), 4.24 (1H, d), 4.60 (1H, s), 6.74-6.79 (2H, m), 7.24-7.27 (2H, m), 7.43-7.47 (2H, m), 7.61-7.64 (2H, m), 8.33 (2H, d), 10.43 (1H, s)

LCMS Spectrum: MH+ 525, retention time 2.84 min.

4-[4-(2-Ethylsulfonylpropan-2-yl)-6-[(3S)-3-methylmorpholin-4-yl]pyrimidin-2-yl]aniline

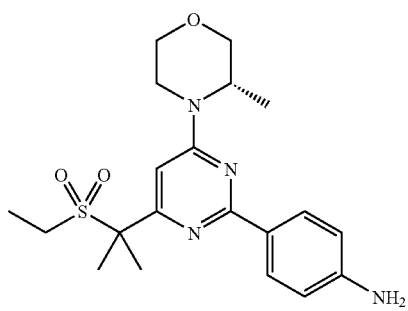

Dichlorobis(triphenylphosphine)palladium(II) (0.360 g, 0.51 mmol) was added to a degassed solution of 2-chloro-4-(2-ethylsulfonylpropan-2-yl)-6-[(3S)-3-methylmorpholin-4-yl]pyrimidine (1.784 g, 5.13 mmol), 4-(4,4,5,5-tetramethyl-1,3,2-dioxaborolan-2-yl)aniline (1.404 g, 6.41 mmol) and sodium carbonate (12.82 mL, 25.64 mmol) in a mixture of 18% DMF in DME:water:ethanol (7:3:2) (25 mL). The resulting solution was stirred at 85° C. for 2 hours. The reaction mixture was concentrated and partitioned between DCM (150 mL), and water (100 mL) and the organics washed with brine (100 mL), dried (MgSO$_4$), filtered and evaporated to afford crude product. The crude product was purified by flash silica chromatography, elution gradient 0 to 2.5% methanol in DCM, to give the desired material as a brown solid (1.20 g).

NMR Spectrum: $^1$H NMR (400.13 MHz, DMSO-d$_6$) δ 1.13 (3H, t), 1.21 (3H, d), 1.76 (6H, d), 3.14-3.18 (1H, m), 3.23 (2H, q), 3.45-3.52 (1H, m), 3.62-3.65 (1H, m), 3.76 (1H, d), 3.95-3.99 (1H, m), 4.17-4.21 (1H, m), 4.54-4.56 (1H, m), 5.54 (2H, d), 6.61 (1H, d), 6.62 (2H, t), 8.06 (2H, d)

LCMS Spectrum: MH+ 405, retention time 2.14 min.

2-Chloro-4-(2-ethylsulfonylpropan-2-yl)-6-[(3S)-3-methylmorpholin-4-yl]pyrimidine

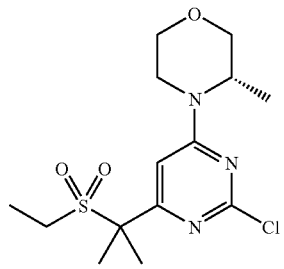

Iodomethane (0.321 mL, 5.13 mmol) was added to sodium tert-butoxide (0.493 g, 5.13 mmol) and 2-chloro-4-(ethylsulfonylmethyl)-6-[(3S)-3-methylmorpholin-4-yl]pyrimidine (1.64 g, 5.13 mmol) in DMF (75 mL) at −5° C. The solution was stirred at −5° C. for 15 minutes. Further iodomethane (0.321 mL, 5.13 mmol) and sodium tert-butoxide (0.493 g, 5.13 mmol) were added and the reaction stirred at −5° C. for 15 minutes. The reaction mixture was diluted with DCM (200 mL) and washed with water (2×100 mL) and brine (100 mL). The organics were dried (MgSO$_4$), filtered and evaporated to give the desired material as a brown solid (1.784 g).

NMR Spectrum: $^1$H NMR (400.13 MHz, DMSO-d$_6$) δ 1.16 (3H, t), 1.21 (3H, d), 1.69 (6H, s), 3.15-3.19 (2H, m), 3.14-3.24 (1H, m), 3.41-3.48 (1H, m), 3.57-3.61 (1H, m), 3.72 (1H, d), 3.92-3.95 (1H, m), 4.05-4.44 (2H, m), 6.87 (1H, s)

LCMS Spectrum: MH+ 348, retention time 1.79 min.

2-Chloro-4-(ethylsulfonylmethyl)-6-[(3S)-3-methylmorpholin-4-yl]pyrimidine

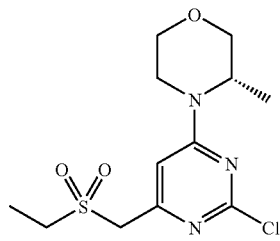

Ethane sulfinic acid sodium salt (3.94 g, 33.94 mmol) was added in one portion to 2-chloro-4-(iodomethyl)-6-[(3S)-3-methylmorpholin-4-yl]pyrimidine (12.0 g, 33.94 mmol) in acetonitrile (250 mL) at RT. The resulting suspension was stirred at 80° C. for 16 hours. The reaction mixture was evaporated to dryness and the residue partitioned between DCM (250 mL) and water (200 mL). The organic layer was dried (MgSO$_4$), filtered and evaporated to afford crude product. The crude product was purified by flash silica chromatography, elution gradient 0 to 40% ethyl acetate in DCM, to give the desired material as a yellow solid (5.94 g).

NMR Spectrum: $^1$H NMR (400.13 MHz, DMSO-d$_6$) δ 1.23 (3H, m), 1.28 (3H, t), 3.22 (2H, d), 3.32 (1H, s), 3.42-3.49 (1H, m), 3.58-3.62 (1H, m), 3.73 (1H, d), 3.92-3.96 (2H, m), 4.25-4.31 (1H, m), 4.43 (2H, s), 6.92 (1H, s)

LCMS Spectrum: MH+ 320, retention time 1.46 min.

The preparation of 2-chloro-4-(iodomethyl)-6-[(3S)-3-methylmorpholin-4-yl]pyrimidine was described earlier.

The preparation of phenyl N-[4-[4-(ethylsulfonylmethyl)-6-[(3S)-3-methylmorpholin-4-yl]pyrimidin-2-yl]phenyl] carbamate is described below.

Phenyl N-[4-[4-(ethylsulfonylmethyl)-6-[(3S)-3-methylmorpholin-4-yl]pyrimidin-2-yl]phenyl]carbamate

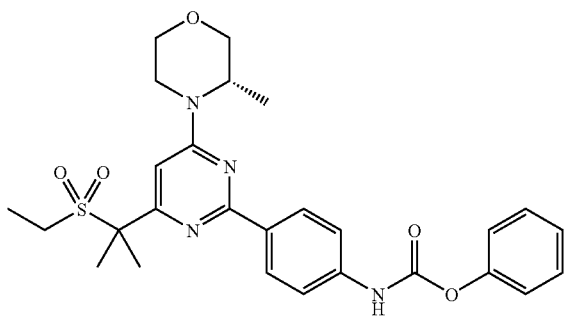

Phenyl chloroformate (0.207 mL, 1.65 mmol) was added dropwise to 4-[4-(ethylsulfonylmethyl)-6-[(3S)-3-methylmorpholin-4-yl]pyrimidin-2-yl]aniline (620 mg, 1.65 mmol) and sodium bicarbonate (208 mg, 2.47 mmol) in dioxane (15 mL) under nitrogen. The resulting suspension was stirred at RT for 2 hours. The reaction mixture was evaporated to dryness and the residue partitioned between ethyl acetate (200 mL) and water (200 mL). The organic layer was dried (MgSO$_4$), filtered and evaporated to give the desired material as a white solid (885 mg).

NMR Spectrum: $^1$H NMR (400.13 MHz, DMSO-d$_6$) δ 1.21-1.29 (3H, m), 1.35 (3H, t), 3.20-3.28 (2H, m), 3.47-3.54 (2H, m), 3.64-3.68 (1H, m), 3.78 (1H, d), 3.97-4.01 (1H, m), 4.20 (1H, d), 4.48 (3H, s), 6.83 (1H, s), 7.24-7.30 (3H, m), 7.42-7.48 (2H, m), 7.64 (2H, d), 8.28-8.30 (2H, m), 10.45 (1H, s)

LCMS Spectrum: MH+ 497, retention time 2.57 min.

4-[4-(Ethylsulfonylmethyl)-6-[(3S)-3-methylmorpholin-4-yl]pyrimidin-2-yl]aniline

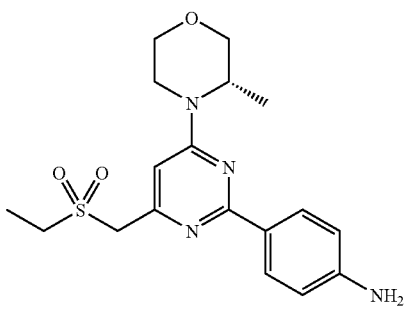

Dichlorobis(triphenylphosphine)palladium(II) (0.162 g, 0.23 mmol) was added to a degassed solution of 2-chloro-4-(ethylsulfonylmethyl)-6-[(3S)-3-methylmorpholin-4-yl]pyrimidine (0.74 g, 2.31 mmol), 4-(4,4,5,5-tetramethyl-1,3,2-dioxaborolan-2-yl)aniline (0.634 g, 2.89 mmol) and sodium carbonate (5.78 mL, 11.57 mmol) in a mixture of 18% DMF in DME:water:ethanol (7:3:2) (20 mL). The resulting solution was stirred at 85° C. for 30 minutes. The reaction mixture was concentrated and diluted with DCM (100 mL) then washed with water (100 mL). The organic layer was dried (MgSO$_4$), filtered and evaporated to afford crude product. The crude product was purified by flash silica chromatography, elution gradient 0 to 2.5% methanol in DCM. The material obtained was further purified using an SCX column, eluting with 7M ammonia in methanol, to give the desired material as a yellow solid (0.62 g).

NMR Spectrum: $^1$H NMR (400.13 MHz, DMSO-d$_6$) δ 1.23 (3H, d), 1.34 (3H, t), 3.16-3.19 (1H, m), 3.32 (2H, m), 3.45-3.52 (1H, m), 3.62-3.66 (1H, m), 3.77 (1H, d), 3.96-3.99 (1H, m), 4.12 (1H, s), 4.42 (3H, d), 5.56 (2H, s), 6.59-6.62 (2H, m), 6.67 (1H, s), 8.01-8.04 (2H, m)

LCMS Spectrum: MH+ 377, retention time 1.83 min.

The preparation of 2-chloro-4-(ethylsulfonylmethyl)-6-[(3S)-3-methylmorpholin-4-yl]pyrimidine was described earlier.

EXAMPLE 63

3-Cyclopropyl-1-[4-[4-[(3S)-3-methylmorpholin-4-yl]-6-(morpholine-4-carbonyl)pyrimidin-2-yl]phenyl]urea

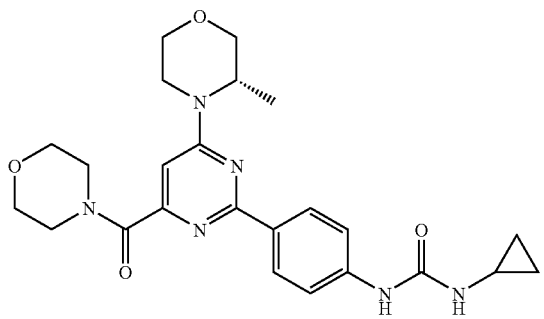

2-[4-(Cyclopropylcarbamoylamino)phenyl]-6-[(3S)-3-methylmorpholin-4-yl]pyrimidine-4-carboxylic acid (100 mg, 0.25 mmol) was added to morpholine (0.066 mL, 0.75 mmol), DIPEA (0.132 mL, 0.75 mmol) and HATU (144 mg, 0.38 mmol) in dry DMF (3 mL) at RT over a period of 30 minutes under nitrogen. The resulting solution was stirred at RT for 3 hours and the crude product purified by preparative HPLC using decreasingly polar mixtures of water (containing 1% NH3) and acetonitrile as eluents, to give the desired material as a white solid (98 mg).

NMR Spectrum: $^1$H NMR (400 MHz, DMSO-d$_6$) δ 0.40-0.44 (2H, m), 0.63-0.68 (2H, m), 1.23-1.25 (3H, d), 2.54-2.59 (1H, m), 3.18-3.27 (1H, m), 3.46-3.49 (3H, m), 3.60-3.69 (7H, m), 3.74-3.77 (1H, d), 3.95-3.99 (1H, dd), 4.21-4.24 (1H, d), 4.56 (1H, s), 6.43-6.44 (1H, d), 6.77 (1H, s), 7.50-7.52 (2H, d), 8.18-8.20 (2H, d), 8.54 (1H, s)

LCMS Spectrum: MH+ 467, retention time 1.69 min

The following compounds were prepared in an analogous fashion from 2-[4-(cyclopropylcarbamoylamino)phenyl]-6-[(3S)-3-methylmorpholin-4-yl]pyrimidine-4-carboxylic acid using the appropriate amine.

| Example | Structure | NAME | LCMS MH+ | Retention time (min) |
|---|---|---|---|---|
| 63a | 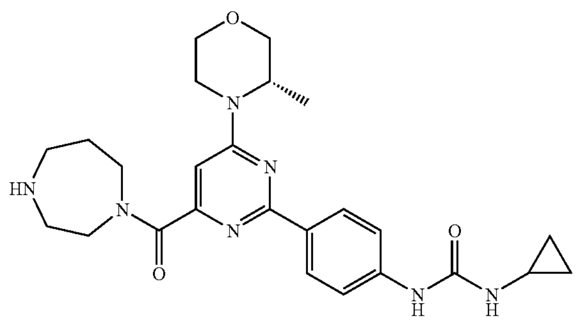 | 3-cyclopropyl-1-[4-[4-(1,4-diazepane-1-carbonyl)-6-[(3S)-3-methylmorpholin-4-yl]pyrimidin-2-yl]phenyl]urea | 479 | 1.6 |
| 63b | 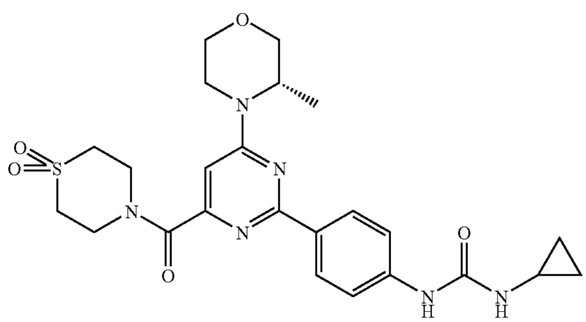 | 3-cyclopropyl-1-[4-[4-(1,1-dioxo1,4-thiazinane-4-carbonyl)-6-[(3S)-3-methylmorpholin-4-yl]pyrimidin-2-yl]phenyl]urea | 514 | 1.74 |
| 63c | 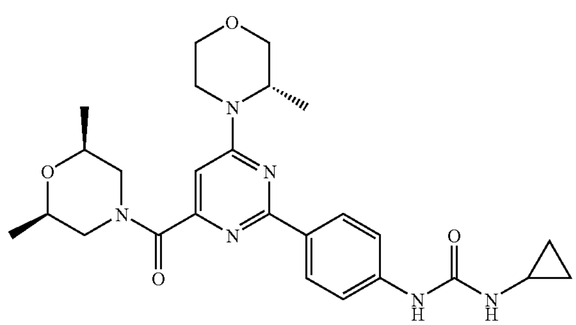 | 3-cyclopropyl-1-[4-[4-[(2R,6S)-2,6-dimethylmorpholine-4-carbonyl]-6-[(3S)-3-methylmorpholin-4-yl]pyrimidin-2-yl]phenyl]urea | 494 | 1.93 |
| 63d | 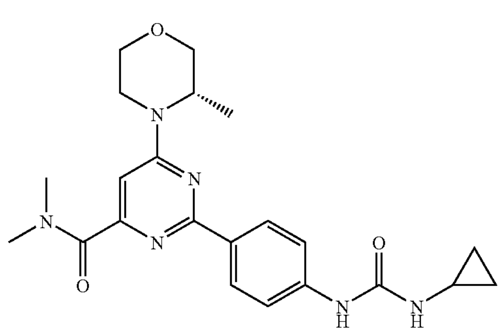 | 2-[4-(cyclopropylcarbamoylamino)phenyl]-N,N-dimethyl-6-[(3S)-3-methylmorpholin-4-yl]pyrimidine-4-carboxamide | 424 | 1.69 |

-continued

| Example | Structure | NAME | LCMS MH+ | Retention time (min) |
|---|---|---|---|---|
| 63e | 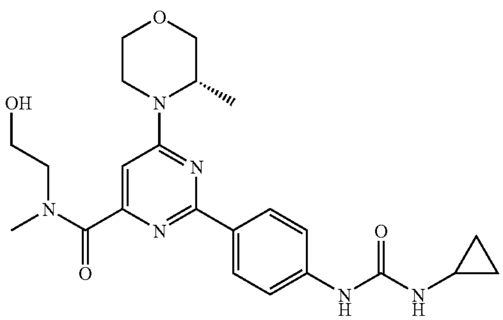 | 2-[4-(cyclopropylcarbamoylamino)phenyl]-N-(2-hydroxyethyl)-N-methyl-6-[(3S)-3-methylmorpholin-4-yl]pyrimidine-4-carboxamide | 455 | 1.53 |
| 63f | 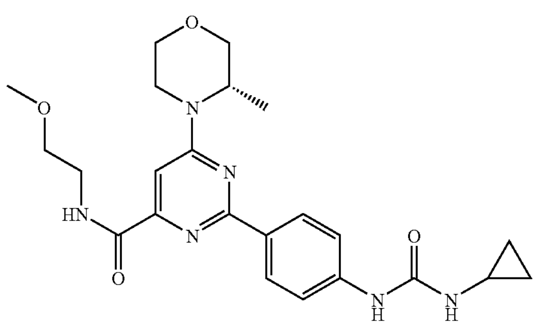 | 2-[4-(cyclopropylcarbamoylamino)phenyl]-N-(2-methoxyethyl)-6-[(3S)-3-methylmorpholin-4-yl]pyrimidine-4-carboxamide | 455 | 1.92 |
| 63g | 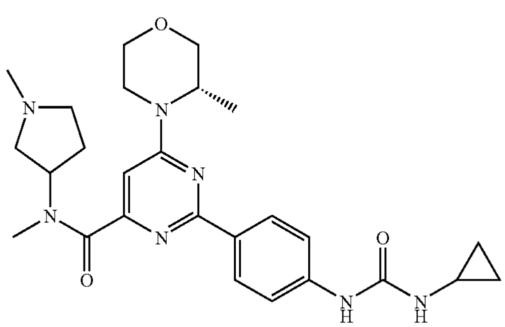 | 2-[4-(cyclopropylcarbamoylamino)phenyl]-N-methyl-6-[(3S)-3-methylmorpholin-4-yl]-N-(1-methylpyrrolidin-3-yl)pyrimidine-4-carboxamide | 494 | 1.72 |
| 63h | 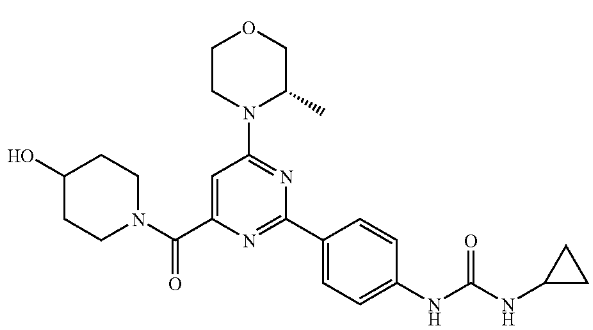 | 3-cyclopropyl-1-[4-[4-(4-hydroxypiperidine-1-carbonyl)-6-[(3S)-3-methylmorpholin-4-yl]pyrimidin-2-yl]phenyl]urea | 481 | 1.54 |

-continued

| Example | Structure | NAME | LCMS MH+ | Retention time (min) |
|---|---|---|---|---|
| 63i | 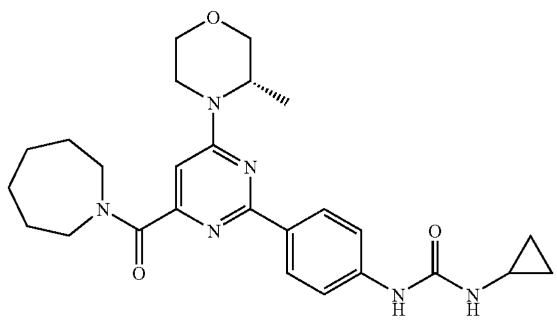 | 1-[4-[4-(azepane-1-carbonyl)-6-[(3S)-3-methylmorpholin-4-yl]pyrimidin-2-yl]phenyl]-3-cyclopropyl-urea | 479 | 2.15 |
| 63j | 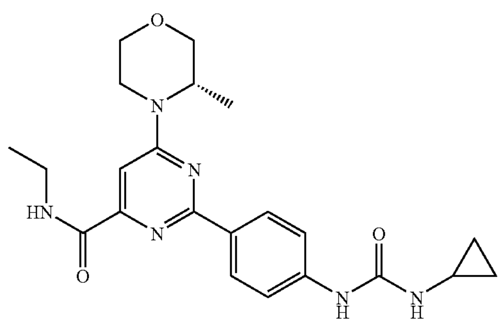 | 2-[4-(cyclopropylcarbamoylamino)phenyl]-N-ethyl-6-[(3S)-3-methylmorpholin-4-yl]pyrimidine-4-carboxamide | 425 | 2.00 |
| 63k | 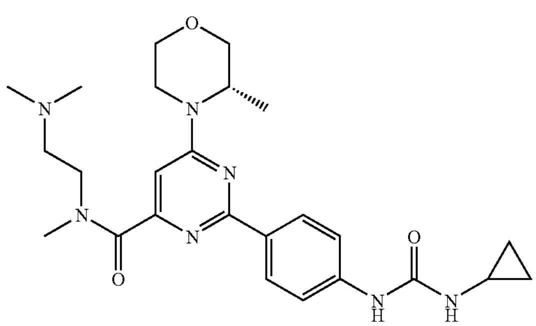 | 2-[4-(cyclopropylcarbamoylamino)phenyl]-N-(2-dimethylaminoethyl)-N-methyl-6-[(3S)-3-methylmorpholin-4-yl]pyrimidine-4-carboxamide | 482 | 1.68 |
| 63l | 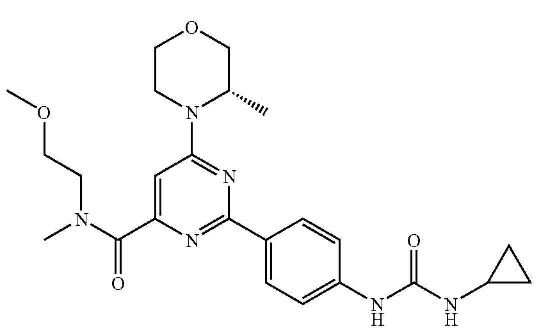 | 2-[4-(cyclopropylcarbamoylamino)phenyl]-N-(2-methoxyethyl)-N-methyl-6-[(3S)-3-methylmorpholin-4-yl]pyrimidine-4-carboxamide | 469 | 1.77 |

-continued

| Example | Structure | NAME | LCMS MH+ | Retention time (min) |
|---|---|---|---|---|
| 63m | 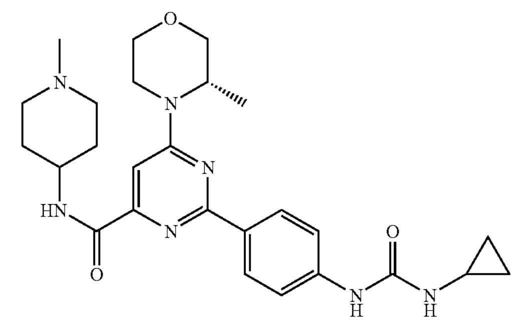 | 2-[4-(cyclopropylcarbamoylamino)phenyl]-6-[(3S)-3-methylmorpholin-4-yl]-N-(1-methyl-4-piperidyl)pyrimidine-4-carboxamide | 494 | 1.93 |
| 63n | 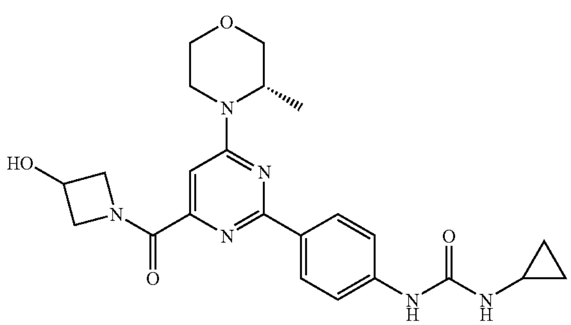 | 3-cyclopropyl-1-[4-[4-(3-hydroxyazetidine-1-carbonyl)-6-[(3S)-3-methylmorpholin-4-yl]pyrimidin-2-yl]phenyl]urea | 453 | 1.62 |
| 63o | 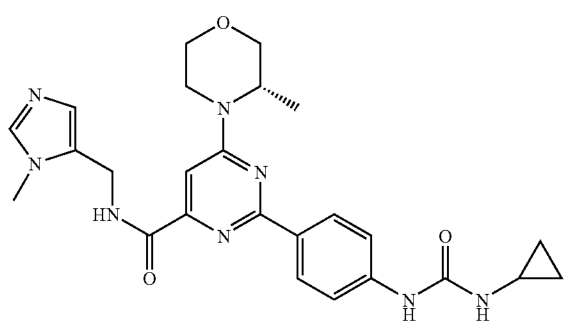 | 2-[4-(cyclopropylcarbamoylamino)phenyl]-N-[(3-methylimidazol-4-yl)methyl]-6-[(3S)-3-methylmorpholin-4-yl]pyrimidine-4-carboxamide | 491 | 1.79 |
| 63p | 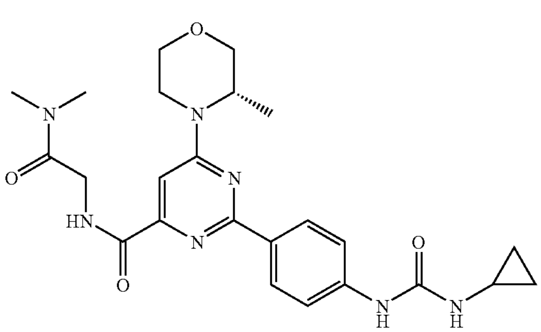 | 2-[4-(cyclopropylcarbamoylamino)phenyl]-N-(dimethylcarbamoylmethyl)-6-[(3S)-3-methylmorpholin-4-yl]pyrimidine-4-carboxamide | 482 | 1.80 |

-continued

| Example | Structure | NAME | LCMS MH+ | Retention time (min) |
|---|---|---|---|---|
| 63q | 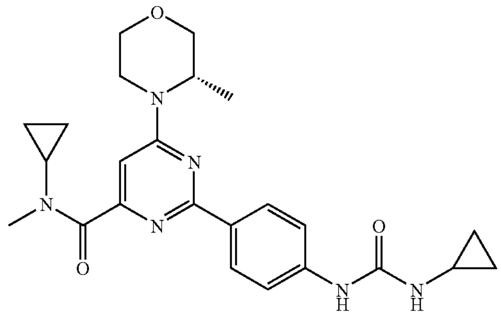 | N-cyclopropyl-2-[4-(cyclopropylcarbamoylamino)phenyl]-N-methyl-6-[(3S)-3-methylmorpholin-4-yl]pyrimidine-4-carboxamide | 451 | 1.85 |
| 63r | 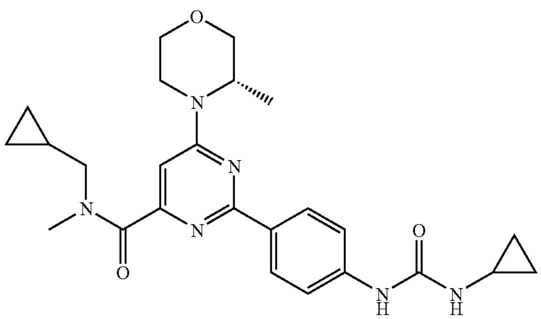 | 2-[4-(cyclopropylcarbamoylamino)phenyl]-N-(cyclopropylmethyl)-N-methyl-6-[(3S)-3-methylmorpholin-4-yl]pyrimidine-4-carboxamide | 465 | 2.02 |
| 63s | 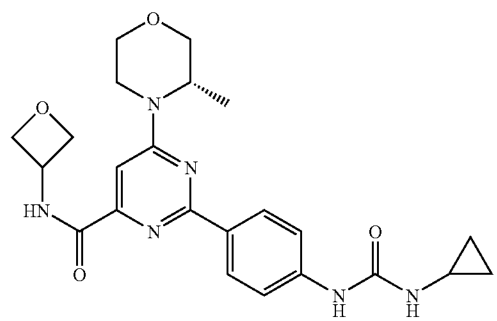 | 2-[4-(cyclopropylcarbamoylamino)phenyl]-6-[(3S)-3-methylmorpholin-4-yl]-N-(oxetan-3-yl)pyrimidine-4-carboxamide | 453 | 1.84 |

Example 63a: $^1$H NMR (400 MHz, CDCl$_3$) δ 0.68-0.68 (2H, d), 0.86-0.87 (2H, d), 1.34-1.35 (3H, d), 1.86-1.90 (1H, m), 1.94-2.02 (1H, m), 2.62-2.64 (1H, t), 2.99-3.04 (2H, m), 3.06-3.11 (2H, m), 3.30-3.37 (1H, td), 3.56-3.59 (1H, d), 3.63-3.68 (3H, m), 3.72-3.75 (1H, d), 3.78-3.84 (3H, m), 4.02-4.06 (1H, dd), 4.15-4.18 (1H, d), 4.49 (1H, s), 4.98-4.99 (1H, d), 6.62-6.64 (1H, d), 7.07-7.08 (1H, d), 7.48-7.50 (2H, d), 8.30-8.33 (2H, m)

Example 63b: $^1$H NMR (400 MHz, DMSO-d$_6$) δ 0.40-0.44 (2H, m), 0.63-0.67 (2H, m), 1.23-1.24 (3H, d), 1.64-1.70 (2H, m), 1.75-1.80 (2H, m), 2.54-2.58 (1H, m), 3.2-3.21 (1H, d), 3.36-3.44 (2H, dt), 3.46-3.53 (1H, m), 3.57-3.60 (1H, q), 3.62-3.65 (2H, m), 3.74-3.77 (1H, d), 3.95-3.98 (1H, dd), 4.21-4.24 (1H, d), 4.54 (1H, s), 6.43-6.44 (1H, d), 6.70-6.71 (1H, d), 7.49-7.51 (2H, d), 8.18-8.20 (2H, d), 8.45 (1H, s)

Example 63c: $^1$H NMR (400 MHz, CDCl$_3$) δ 0.68-0.72 (2H, m), 0.86-0.90 (2H, m), 1.13-1.15 (3H, dd), 1.27-1.29 (3H, d), 1.35-1.37 (3H, d), 2.54-2.61 (1H, t), 2.62-2.66 (1H, m), 2.82-2.91 (1H, m), 3.31-3.39 (1H, td), 3.57-3.63 (1H, td), 3.73-3.76 (3H, m), 3.82-3.85 (1H, d), 4.03-4.07 (1H, dd), 4.11-4.18 (2H, m), 4.51 (1H, s), 4.56-4.60 (1H, dd), 4.96 (1H, s), 6.69 (1H, s), 7.069 (1H, s), 7.51-7.53 (2H, d), 8.31-8.33 (2H, d), Example 63d: $^1$H NMR (400 MHz, DMSO-d$_6$) δ 0.42-0.44 (2H, m), 0.63-0.68 (2H, m), 1.23-1.25 (3H, d), 2.54-2.59 (1H, m), 2.99-3.01 (6H, d), 3.46-3.53 (1H, td), 3.62-3.66 (1H, dd), 3.74-3.77 (1H, d), 3.95-3.99 (1H, dd), 4.21-4.24 (1H, d), 4.55 (1H, s), 6.43-6.44 (1H, d), 6.71 (1H, s), 7.49-7.51 (2H, d), 8.19-8.21 (2H, d), 8.54 (1H, s)

Example 63e: $^1$H NMR (400 MHz, DMSO-d$_6$) δ 0.41-0.44 (2H, m), 0.63-0.67 (2H, m), 1.23-1.25 (3H, d), 2.32-2.34 (1H, m), 2.54-2.61 (1H, m), 3.03 (3H, s), 3.18-3.25 (1H, td), 3.36-3.41 (1H, q), 3.49-3.50 (1H, d), 3.52-3.54 (1H, d), 3.57 (1H, s), 3.63-3.66 (1H, dd), 3.74-3.77 (1H, d), 3.95-3.99 (1H, dd), 4.21-4.23 (1H, d), 4.52 (1H, s), 4.74 (1H, s), 6.45-6.46 (1H, d), 6.70 (1H, s), 7.50-7.52 (2H, d), 8.17-8.20 (2H, m), 8.56 (1H, s)

Example 63f: $^1$H NMR (400 MHz, DMSO-d$_6$) δ 0.41-0.45 (2H, m), 0.63-0.68 (2H, m), 1.24-1.26 (3H, d), 2.33-2.35 (1H, m), 2.67-2.69 (1H, m), 2.70 (1H, s), 2.74 (2H, s), 2.90 (3H, s), 3.49-3.53 (2H, m), 3.63-3.67 (1H, dd), 3.76-3.78 (1H, d), 3.96-4.00 (1H, dd), 4.35 (1H, s), 4.56-4.58 (1H, d), 6.43-6.44 (1H, d), 7.13 (1H, s), 7.52-7.54 (2H, d), 7.96 (1H, s), 8.38-8.40 (2H, d), 8.57 (1H, s)

Example 63g: $^1$H NMR (400 MHz, DMSO-$d_6$) δ 0.41-0.44 (2H, m), 0.63-0.68 (2H, m), 1.23-1.25 (3H, d), 2.20 (2H, s), 2.27 (1H, s), 2.33-2.35 (2H, m), 2.67-2.69 (3H, m), 2.74 (1H, s), 2.90-2.91 (2H, d), 2.97 (2H, s), 3.17-3.21 (1H, m), 3.47-3.52 (1H, m), 3.63-3.66 (1H, dd), 3.74-3.77 (1H, d), 3.96-3.98 (1H, dd), 4.22-4.24 (1H, d), 4.32-4.34 (1H, d), 4.56 (1H, s), 6.43-6.45 (1H, m), 6.69-6.70 (1H, d), 7.49-7.53 (2H, dd), 8.19-8.21 (2H, dd), 8.54 (1H, s), Example 63h: $^1$H NMR (400 MHz, DMSO-$d_6$) δ 0.40-0.44 (2H, m), 0.63-0.67 (2H, m), 1.23-1.24 (3H, d), 1.43 (2H, s), 1.74-1.84 (2H, d), 2.53-2.57 (1H, m), 3.14-3.18 (1H, m), 3.21-2.24 (2H, m), 3.46-3.52 (1H, td), 3.56 (1H, m), 3.62-3.66 (1H, dd), 3.74-3.77 (2H, d), 3.95-3.98 (1H, dd), 4.00-4.04 (1H, m), 4.21 (1H, d), 4.55 (1H, s), 4.77-4.78 (1H, d), 6.43-6.44 (1H, d), 6.71 (1H, s), 7.49-7.52 (2H, d), 8.18-8.20 (2H, d), 8.54 (1H, s)

Example 63i: $^1$H NMR (400 MHz, DMSO-$d_6$) δ 0.40-0.44 (2H, m), 0.63-0.68 (2H, m), 1.23-1.24 (3H, d), 1.60-1.61 (4H, d), 1.74-1.75 (4H, d), 2.67-2.69 (1H, m), 3.17-3.25 (1H, m), 3.37-3.40 (1H, t) 3.56-3.59 (1H, t), 3.62-3.65 (1H, dd), 3.74-3.77 (1H, d), 3.94-3.99 (1H, dd), 4.22-4.24 (1H, d), 4.54 (1H, s), 6.43-6.44 (1H, d), 6.69 (1H, s), 7.49-7.51 (2H, d), 8.18-2.20 (2H, d), 8.53 (1H, s)

Example 63j: $^1$H NMR (400 MHz, DMSO-$d_6$) δ 0.41-0.45 (2H, m), 0.63-0.68 (2H, m), 1.15-1.19 (3H, t), 1.24-1.26 (3H, d), 2.56-2.60 (1H, m), 3.25-3.26 (1H, m), 3.33-3.42 (2H, m), 3.47-3.53 (1H, td), 3.64-3.67 (1H, dd), 3.75-3.78 (1H, d), 3.96-4.00 (1H, dd), 4.35-4.27 (1H, d), 4.57 (1H, s), 6.43-6.44 (1H, d), 7.13 (1H, s), 7.52-7.54 (2H, d), 8.40-8.42 (2H, d), 8.57 (1H, s) 8.91-8.93 (1H, t)

Example 63k: $^1$H NMR (400 MHz, DMSO-$d_6$) δ 0.41-0.44 (2H, m), 0.63-0.68 (2H, m), 1.22-1.25 (3H, m), 2.01 (2H, s), 2.24 (2H, s), 2.55-2.58 (1H, m), 2.99-3.01 (3H, d), 3.27 (3H, s), 3.35-3.39 (3H, m), 3.46-3.49 (1H, dd), 3.52-3.56 (1H, td), 3.62-3.66 (1H, dd), 3.74-3.77 (1H, d), 3.96-3.98 (1H, d), 4.21-4.24 (1H, d), 4.55 (1H, s), 6.43-6.44 (1H, d), 6.68-6.70 (1H, d), 7.50-7.52 (2H, d), 8.20-8.22 (2H, d), 8.54 (1H, s)

Example 63l: $^1$H NMR (400 MHz, DMSO-$d_6$) δ 0.41-0.44 (2H, m), 0.63-0.68 (2H, m), 1.23-1.25 (3H, d), 2.55-2.58 (1H, m), 3.02 (3H, s), 3.19 (2H, s), 3.24-3.25 (1H, m), 3.46-3.47 (1H, d), 3.49-3.54 (1H, m), 3.59-3.60 (1H, d), 3.61-3.66 (1H, dd), 3.74-3.78 (1H, d), 3.95-3.98 (1H, dd), 4.21-4.22 (1H, d), 4.51 (1H, s), 6.44 (1H, s), 6.69-6.71 (1H, d), 7.50-7.52 (2H, d), 8.18-8.20 (2H, d), 8.55 (1H, s)

Example 63m: $^1$H NMR (400 MHz, DMSO-$d_6$) δ 0.41-0.45 (2H, m), 0.63-0.68 (2H, m), 1.24-1.25 (3H, d), 1.74-1.78 (4H, m), 1.97-2.04 (3H, m), 2.55-2.61 (1H, m), 2.76-2.79 (2H, d), 3.21-3.26 (1H, m), 3.27 (1H, s), 3.47-3.53 (1H, td), 3.63-3.67 (1H, dd), 3.73-3.78 (2H, d), 3.80-3.84 (1H, m), 3.96-4.00 (1H, dd), 4.24-4.27 (1H, d), 4.58 (1H, s), 6.44-6.45 (1H, d), 7.12 (1H, s), 7.52-7.54 (2H, d), 8.38-8.40 (2H, d), 8.51-8.54 (1H, d), 8.57 (1H, s)

Example 63n: $^1$H NMR (400 MHz, DMSO-$d_6$) δ 0.41-0.44 (2H, m), 0.63-0.68 (2H, m), 1.23-1.25 (3H, d), 2.56-2.59 (1H, m), 3.19-3.23 (1H, dd), 3.46-3.53 (1H, td), 3.62-3.66 (1H, dd), 3.75-3.78 (1H, d), 3.80-3.84 (1H, m), 3.96-3.99 (1H, dd), 4.23 (1H, s), 4.26-4.31 (1H, qd), 4.42-4.47 (1H, m), 4.53-4.58 (2H, m), 4.88-4.94 (1H, m), 5.72-5.73 (1H, d), 6.44-6.45 (1H, d), 7.04 (1H, s), 7.52-7.54 (2H, d), 8.20-8.23 (2H, d), 8.56 (1H, s)

Example 63o: $^1$H NMR (400 MHz, DMSO-$d_6$) δ 0.40-0.44 (2H, m), 0.63-0.68 (2H, m), 1.24-1.26 (3H, d), 2.55-2.59 (1H, m), 3.21-3.25 (1H, m), 3.47-3.53 (1H, td), 3.63-3.64 (1H, d), 3.66 (3H, s), 3.75-3.78 (1H, d), 3.96-4.00 (1H, dd), 4.24-4.28 (1H, d), 4.52-4.54 (2H, d), 4.58 (1H, s), 6.42-6.44 (1H, d), 6.65 (1H, s), 7.15 (1H, s), 7.50-7.51 (1H, t), 7.52-7.53 (2H, d), 8.38-8.40 (2H, d), 8.56 (1H, s)

Example 63p: $^1$H NMR (400 MHz, DMSO-$d_6$) δ 0.41-0.45 (2H, m), 0.63-0.68 (2H, m), 1.25-1.27 (3H, d), 2.56-2.59 (1H, m), 2.91 (3H, s), 3.03 (3H, s), 3.20-3.24 (1H, m), 2.48-3.54 (1H, td), 3.64-3.68 (1H, dd), 3.76-3.79 (1H, d), 3.97-4.00 (1H, dd), 4.18-4.20 (2H, d), 4.26 (1H, d), 4.59 (1H, s), 6.46-6.47 (1H, d), 7.14 (1H, s), 7.54-7.56 (2H, d), 8.34-8.36 (2H, d), 8.59 (1H, s), 8.99-9.02 (1H, t)

Example 63q: $^1$H NMR (400 MHz, DMSO-$d_6$) δ 0.40-0.44 (2H, m), 0.49-0.53 (4H, m), 0.63-0.67 (2H, m), 1.22-1.24 (3H, d), 2.55-2.61 (2H, m), 2.87-2.88 (1H, d), 2.93 (2.95 (1H, m), 3.17-3.25 (1H, td), 3.27 (1H, s), 3.47-3.54 (1H, td), 3.62-3.67 (1H, dd), 3.75-3.78 (1H, d), 3.94-3.98 (1H, dd), 4.21-4.24 (1H, d), 4.52 (1H, s), 6.42-6.43 (1H, d), 6.73 (1H, s), 7.49-7.51 (2H, d), 8.19-8.22 (2H, d), 8.53 (1H, s)

Example 63r: $^1$H NMR (400 MHz, DMSO-$d_6$) δ 0.14-0.18 (1H, m), 0.30-0.34 (1H, m), 0.40-0.43 (2H, m), 0.44-0.48 (1H, dq), 0.51-0.56 (1H, dq), 0.63-0.67 (2H, m), 1.06-1.10 (1H, m), 1.22-1.25 (3H, m), 2.54-2.59 (1H, m), 3.03-3.06 (3H, d), 3.16-3.19 (1H, m), 3.20-3.25 (1H, m), 3.35-3.37 (1H, m), 3.46-3.53 (1H, td), 3.62-3.66 (1H, dd), 3.74-3.77 (1H, d), 3.95-3.98 (1H, dd), 4.22-4.24 (1H, d), 4.55 (1H, s) 6.44-6.45 (1H, d), 6.70-6.71 (1H, d), 7.49-7.59 (2H, dd), 8.18-8.21 (2H, dd), 8.54-8.55 (1H, d)

Example 63s: $^1$H NMR (400 MHz, DMSO-$d_6$) δ 0.41-0.45 (2H, m), 0.64-0.68 (2H, m), 1.24-1.25 (3H, d), 2.55-2.60 (1H, m), 3.17-3.25 (1H, m), 3.47-3.54 (1H, td), 3.63-3.67 (1H, dd), 3.75-3.78 (1H, d), 3.96-4.00 (1H, dd), 4.25-4.27 (1H, d), 4.57 (1H, s), 4.74-4.80 (4H, m), 5.04-5.13 (1H, m), 6.44-6.45 (1H, d), 7.11 (1H, s), 7.53-7.55 (2H, d), 8.46-8.48 (2H, d), 8.58 (1H, s), 9.38-9.40 (1H, d)

Test (c): Example (63) 0.41 μM; Example (63a) 0.092 μM; Example (63b) 0.5 μM; Example (63c) 0.26 μM.

The preparation of 2-[4-(cyclopropylcarbamoylamino) phenyl]-6-[(3S)-3-methylmorpholin-4-yl]pyrimidine-4-carboxylic acid was described earlier.

EXAMPLE 64

1-[4-[4-(2-Cyclopentylsulfonylpropan-2-yl)-6-[(3S)-3-methylmorpholin-4-yl]pyrimidin-2-yl]phenyl]-3-cyclopropyl-urea

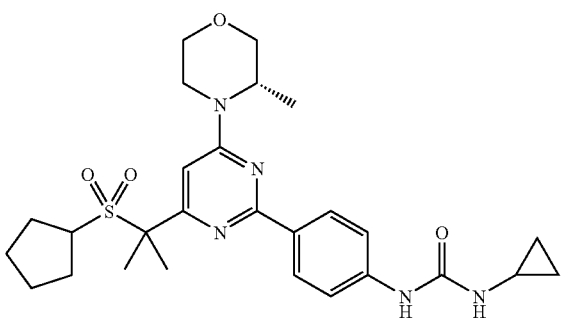

Triethylamine (0.175 mL, 1.25 mmol) was added to a mixture of phenyl N-[4-[4-(2-cyclopentylsulfonylpropan-2-yl)-6-[(3S)-3-methylmorpholin-4-yl]pyrimidin-2-yl]phenyl] carbamate (200 mg, 0.31 mmol) and cyclopropylamine (1.25 mmol) in NMP (2 mL) and heated at 75° C. for 6 hours. The reaction mixture was purified by preparative HPLC using decreasingly polar mixtures of water (containing 1% NH3) and acetonitrile as eluents, to give the desired material as a solid (136 mg).

NMR Spectrum: $^1$H NMR (400.132 MHz, DMSO-$d_6$) δ 0.39-0.44 (2H, m), 0.63-0.67 (2H, m), 1.22 (3H, d), 1.40-1.48 (4H, m), 1.52-1.59 (4H, m), 1.70-1.80 (6H, m), 3.16-3.24 (1H, m), 3.46-3.54 (1H, m), 3.65 (1H, d), 3.77 (1H, d), 3.91-4.01 (2H, m), 4.23 (1H, d), 4.60 (1H, s), 6.44 (1H, d), 6.77 (1H, s), 7.51 (2H, d), 8.24 (2H, d), 8.55 (1H, s)

LCMS Spectrum: MH+ 528, retention time 2.43 min

The following compounds were made in an analogous fashion from either phenyl N-[4-[4-(2-cyclopentylsulfonyl-propan-2-yl)-6-[(3S)-3-methylmorpholin-4-yl]pyrimidin-2-yl]phenyl]carbamate or phenyl N-[4-[4-(cyclopentylsulfonylmethyl)-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 64a | 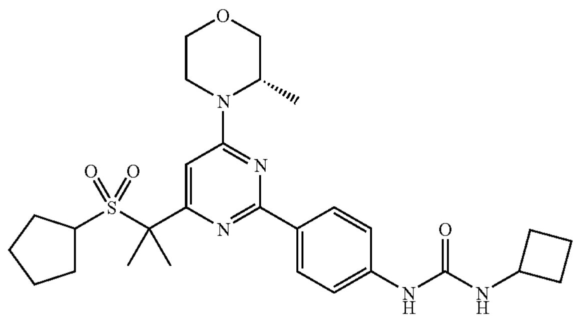 | 3-cyclobutyl-1-[4-[4-(2-cyclopentylsulfonylpropan-2-yl)-6-[(3S)-3-methylmorpholin-4-yl]pyrimidin-2-yl]phenyl]urea | 542 | 2.7 |
| 64b | 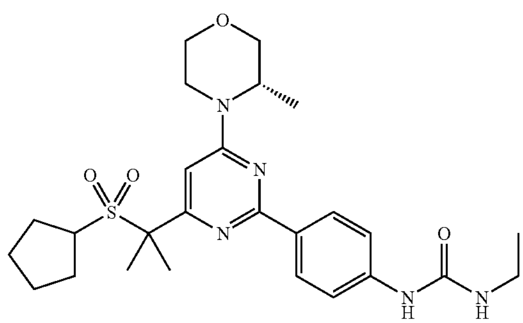 | 1-[4-[4-(2-cyclopentylsulfonylpropan-2-yl)-6-[(3S)-3-methylmorpholin-4-yl]pyrimidin-2-yl]phenyl]-3-ethyl-urea | 516 | 2.42 |
| 64c | 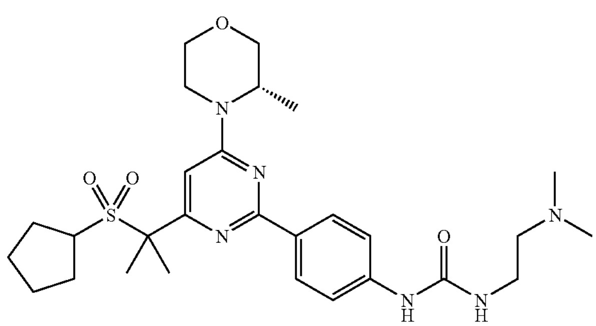 | 1-[4-[4-(2-cyclopentylsulfonylpropan-2-yl)-6-[(3S)-3-methylmorpholin-4-yl]pyrimidin-2-yl]phenyl]-3-(2-dimethylaminoethyl)urea | 559 | 2.35 |
| 64d | 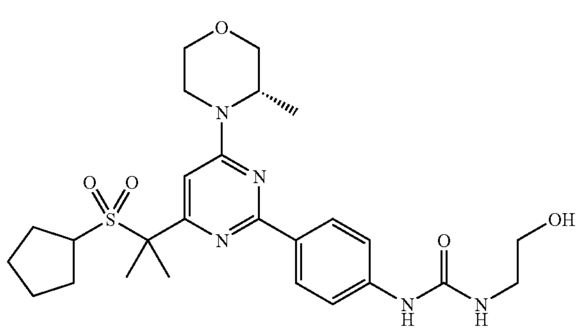 | 1-[4-[4-(2-cyclopentylsulfonylpropan-2-yl)-6-[(3S)-3-methylmorpholin-4-yl]pyrimidin-2-yl]phenyl]-3-(2-hydroxyethyl)urea | 532 | 2.04 |

| Example | Structure | NAME | LCMS MH+ | Retention time (min) |
|---|---|---|---|---|
| 64e | 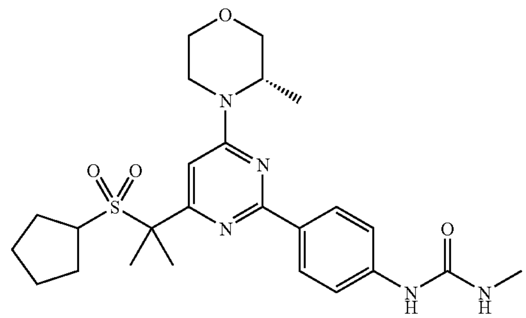 | 1-[4-[4-(2-cyclopentylsulfonylpropan-2-yl)-6-[(3S)-3-methylmorpholin-4-yl]pyrimidin-2-yl]phenyl]-3-methyl-urea | 502 | 2.26 |
| 64f | 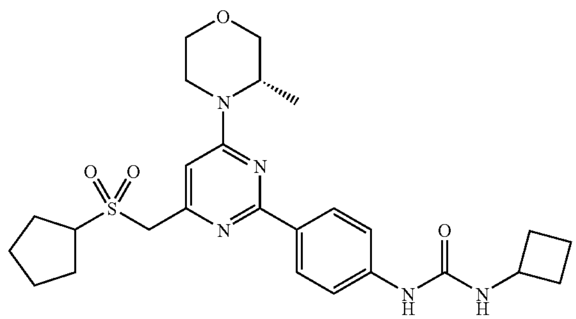 | 3-cyclobutyl-1-[4-[4-(cyclopentylsulfonylmethyl)-6-[(3S)-3-methylmorpholin-4-yl]pyrimidin-2-yl]phenyl]urea | 514 | 2.36 |
| 64g | 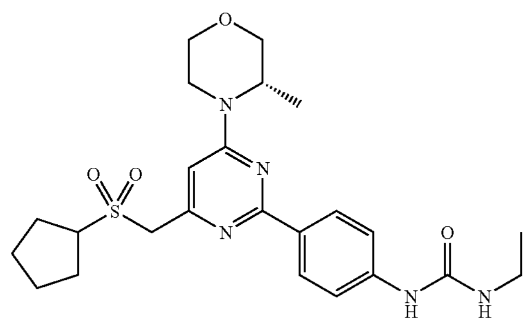 | 1-[4-[4-(cyclopentylsulfonylmethyl)-6-[(3S)-3-methylmorpholin-4-yl]pyrimidin-2-yl]phenyl]-3-ethyl-urea | 488 | 2.13 |
| 64h | 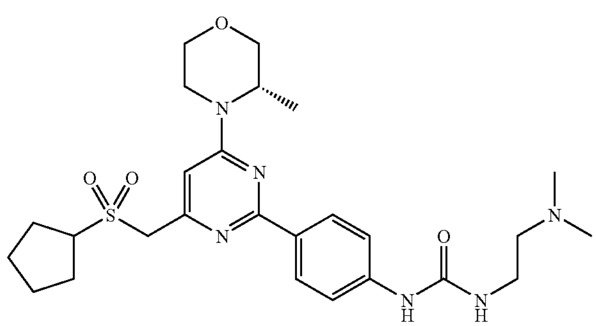 | 1-[4-[4-(cyclopentylsulfonylmethyl)-6-[(3S)-3-methylmorpholin-4-yl]pyrimidin-2-yl]phenyl]-3-(2-dimethylaminoethyl)urea | 531 | 2.08 |

Example 64a: $^1$H NMR (400.132 MHz, DMSO-d$_6$) δ 1.22 (3H, d), 1.39-1.68 (10H, m), 1.69-1.80 (6H, m), 1.86 (2H, q), 2.17-2.25 (2H, m), 3.16-3.24 (1H, m), 3.46-3.55 (1H, m), 3.65 (1H, dd), 3.77 (1H, d), 3.95 (1H, quintet), 4.14 (1H, q), 4.22 (1H, d), 4.60 (1H, s), 6.46 (1H, d), 6.78 (1H, s), 7.48 (2H, d), 8.23 (2H, d), 8.57 (1H, s)

Example 64b: $^1$H NMR (400.132 MHz, DMSO-d$_6$) δ 1.07 (3H, t), 1.22 (3H, d), 1.41-1.48 (4H, m), 1.51-1.57 (4H, m), 1.70-1.79 (6H, m), 3.12 (2H, q), 3.16-3.24 (1H, m), 3.50 (1H, dd), 3.65 (1H, d), 3.77 (1H, d), 3.91-4.00 (2H, m), 4.22 (1H, d), 4.60 (1H, s), 6.17 (1H, t), 6.77 (1H, s), 7.49 (2H, d), 8.22 (2H, d), 8.67 (1H, s)

Example 64c: $^1$H NMR (400.132 MHz, DMSO-d$_6$) δ 1.22 (3H, d), 1.41-1.48 (4H, m), 1.52-1.58 (4H, m), 1.69-1.79 (6H, m), 2.19 (6H, s), 2.33 (2H, t), 3.16-3.24 (3H, m), 3.50 (1H, td), 3.65 (1H, dd), 3.77 (1H, d), 3.90-4.01 (2H, m), 4.22 (1H, d), 4.59 (1H, s), 6.15 (1H, t), 6.78 (1H, s), 7.49 (2H, d), 8.23 (2H, d), 8.90 (1H, s)

Example 64d: ¹H NMR (400.132 MHz, DMSO-d₆) δ 1.22 (3H, d), 1.41-1.47 (4H, m), 1.50-1.58 (4H, m), 1.70-1.79 (6H, m), 3.15-3.24 (3H, m), 3.44-3.54 (3H, m), 3.65 (1H, dd), 3.77 (1H, d), 3.91-4.00 (2H, m), 4.22 (1H, d), 4.60 (1H, s), 4.73 (1H, t), 6.26 (1H, t), 6.77 (1H, s), 7.49 (2H, d), 8.23 (2H, d), 8.82 (1H, s)

Example 64e: ¹H NMR (400.132 MHz, DMSO-d₆) δ 1.22 (3H, d), 1.41-1.49 (4H, m), 1.51-1.58 (4H, m), 1.68-1.81 (6H, m), 2.67 (3H, d), 3.16-3.24 (1H, m), 3.50 (1H, td), 3.65 (1H, dd), 3.77 (1H, d), 3.91-4.00 (2H, m), 4.22 (1H, d), 4.60 (1H, s), 6.07 (1H, t), 6.77 (1H, s), 7.50 (2H, d), 8.23 (2H, d), 8.75 (1H, s)

Example 64f: ¹H NMR (400.132 MHz, DMSO-d₆) δ 1.24 (3H, d), 1.57-1.74 (6H, m), 1.82-1.90 (2H, m), 1.93-2.07 (4H, m), 2.17-2.25 (2H, m), 3.16-3.27 (1H, m), 3.50 (1H, td), 3.65 (1H, dd), 3.73-3.83 (1H, m), 3.99 (1H, dd), 4.10-4.20 (2H, m), 4.45 (2H, s), 4.49 (1H, s), 6.47 (1H, d), 6.79 (1H, s), 7.47 (2H, d), 8.19 (2H, d), 8.56 (1H, s)

Example 64g: ¹H NMR (400.132 MHz, DMSO-d₆) δ 1.07 (3H, t), 1.24 (3H, d), 1.60-1.74 (4H, m), 1.89-2.06 (4H, m), 3.09-3.16 (2H, m), 3.18-3.26 (1H, m), 3.46-3.54 (1H, m), 3.65 (1H, dd), 3.75-3.83 (2H, m), 3.99 (1H, dd), 4.17 (1H, d), 4.43 (2H, s), 4.49 (1H, s), 6.16 (1H, t), 6.79 (1H, s), 7.49 (2H, d), 8.19 (2H, d), 8.66 (1H, s)

Example 64h: ¹H NMR (400.132 MHz, DMSO-d₆) δ 1.24 (3H, d), 1.60-1.74 (4H, m), 1.91-2.07 (4H, m), 2.19 (6H, s), 2.34 (2H, t), 3.16-3.22 (3H, m), 3.50 (2H, td), 3.65 (2H, dd), 3.74-3.83 (2H, m), 3.99 (2H, dd), 4.16 (1H, d), 4.44 (2H, s), 4.51 (1H, s), 6.17 (1H, t), 6.78 (1H, s), 7.49 (2H, d), 8.19 (2H, d), 8.89 (1H, s)

The preparation of phenyl N-[4-[4-(2-cyclopentylsulfonylpropan-2-yl)-6-[(3S)-3-methylmorpholin-4-yl]pyrimidin-2-yl]phenyl]carbamate is described below.

Phenyl N-[4-[4-(2-cyclopentylsulfonylpropan-2-yl)-6-[(3S)-3-methylmorpholin-4-yl]pyrimidin-2-yl]phenyl]carbamate

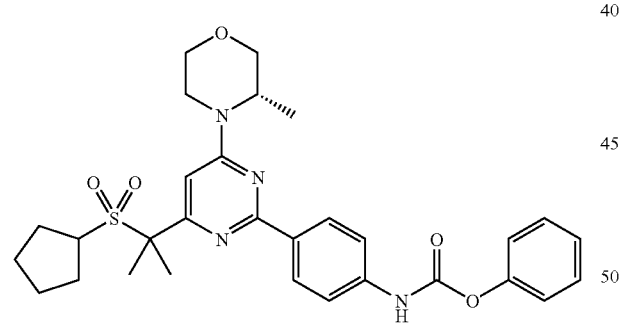

Phenyl chloroformate (0.635 mL, 5.06 mmol) was added to 4-[4-(2-cyclopentylsulfonylpropan-2-yl)-6-[(3S)-3-methylmorpholin-4-yl]pyrimidin-2-yl]aniline (1.5 g, 3.37 mmol) and sodium hydrogen carbonate (0.425 g, 5.06 mmol) in dioxane (20 mL) at 5° C. under nitrogen. The resulting mixture was stirred at RT for 2 hours. The reaction mixture was diluted with ethyl acetate (200 mL), and washed with water (125 mL). The organic layer was dried (MgSO₄), filtered and evaporated to afford crude product which was triturated with a mixture of diethyl ether and isohexane to give the desired material as a white solid (1.30 g).

NMR Spectrum: ¹H NMR (400.132 MHz, DMSO-d₆) δ 1.23 (3H, d), 1.41-1.47 (2H, m), 1.50-1.57 (2H, m), 1.69-1.78 (4H, m), 1.79 (6H, d), 3.21 (1H, td), 3.51 (1H, td), 3.65 (1H, dd), 3.77 (1H, d), 3.92-4.01 (2H, m), 4.24 (1H, d), 4.62 (1H, s), 6.82 (1H, s), 7.23-7.31 (3H, m), 7.42-7.48 (2H, m), 7.64 (2H, d), 8.34 (2H, d), 10.45 (1H, s)

LCMS Spectrum: MH+ 565, retention time 3.0 mins

4-[4-(2-Cyclopentylsulfonylpropan-2-yl)-6-[(3S)-3-methylmorpholin-4-yl]pyrimidin-2-yl]aniline

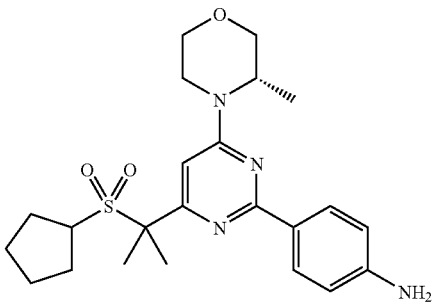

Bis(triphenylphosphine)palladium(II) chloride (200 mg, 0.28 mmol) was added to 2-chloro-4-(2-cyclopentylsulfonyl-propan-2-yl)-6-[(3S)-3-methylmorpholin-4-yl]pyrimidine (1.66 g, 4.28 mmol), 4-(4,4,5,5-tetramethyl-1,3,2-dioxaborolan-2-yl)aniline (1.406 g, 6.42 mmol) and sodium carbonate (10 mL, 20.00 mmol) in a mixture of ethanol (5 mL), DMF (10 mL), water (7 mL) and DME (25 mL) at RT. The resulting mixture was degassed then stirred at 95° C. for 18 hours. The reaction mixture was allowed to cool and diluted with ethyl acetate (200 mL) then washed with water (2×150 mL), and brine (150 mL). The organic layer was dried (Na₂SO₄), filtered and evaporated to afford crude product. The crude product was purified by flash silica chromatography, elution gradient 10 to 60% ethyl acetate in isohexane, and the residue obtained was triturated with a mixture of diethyl ether and isohexane to give the desired material as a pale pink solid (1.52 g).

NMR Spectrum: ¹H NMR (400.132 MHz, DMSO-d₆) δ 1.21 (3H, d), 1.41-1.50 (2H, m), 1.52-1.60 (2H, m), 1.69-1.80 (10H, m), 3.17 (1H, td), 3.49 (1H, td), 3.64 (1H, dd), 3.76 (1H, d), 3.90-3.99 (2H, m), 4.18 (1H, d), 4.56 (1H, s), 5.57 (2H, s), 6.61 (2H, d), 6.68 (1H, s), 8.06 (2H, d)

LCMS Spectrum: MH+ 445, retention time 2.42 mins

2-Chloro-4-(2-cyclopentylsulfonylpropan-2-yl)-6-[(3S)-3-methylmorpholin-4-yl]pyrimidine

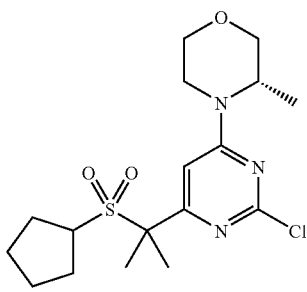

Sodium tert-butoxide (5.56 mmol) was added to a solution of 2-chloro-4-(cyclopentylsulfonylmethyl)-6-[(3S)-3-methylmorpholin-4-yl]pyrimidine (2 g, 5.56 mmol) in DMF (10 mL) at −5° C., followed by dropwise addition of iodomethane (0.365 mL) at −5° C. Additional sodium tert-butoxide (5.56 mmol) and iodomethane (0.365 mL) were added and the reaction stirred at −5° C. overnight. The reaction mixture was diluted with ethyl acetate (250 mL), and washed with water (2×150 mL). The organic layer was dried (MgSO$_4$), filtered and evaporated to afford crude product which was triturated with a mixture of diethyl ether and isohexane to give the desired material as a cream solid (1.66 g).

NMR Spectrum: $^1$H NMR (400.132 MHz, DMSO-d$_6$) δ 1.20 (4H, d), 1.46-1.61 (6H, m), 1.69-1.84 (12H, m), 1.70 (9H, s), 3.20 (3H, td), 3.45 (1H, td), 3.60 (1H, dd), 3.75 (1H, s), 3.85 (2H, q), 3.96 (1H, d), 4.06 (1H, d), 4.46 (1H, s), 6.90 (1H, s)

LCMS Spectrum: MH+ 388, retention time 2.47 mins

2-Chloro-4-(cyclopentylsulfonylmethyl)-6-[(3S)-3-methylmorpholin-4-yl]pyrimidine

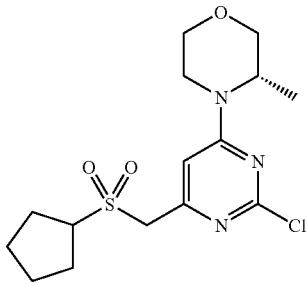

Hydrogen peroxide (19.54 mL, 632 mmol) was added to 2-chloro-4-(cyclopentylsulfanylmethyl)-6-[(3S)-3-methylmorpholin-4-yl]pyrimidine (10.36 g, 31.60 mmol), sodium tungstate dihydrate (0.208 g, 0.63 mmol) (dissolved in minimum quantity of water) and 2M sulphuric acid solution (0.177 mL) in dioxane (100 mL) at 55° C. under air. The resulting solution was stirred at 55° C. for 2 hours. The reaction mixture was diluted with ethyl acetate (100 mL), and washed with water then a 10% aqueous solution of sodium metabisulfite. The organic layer was dried (MgSO$_4$), filtered and evaporated to afford crude product. The crude product was purified by flash silica chromatography, elution gradient 5 to 70% ethyl acetate in isohexane, to give the desired material as a colourless gum (9.7 g).

NMR Spectrum: $^1$H NMR (400.132 MHz, DMSO-d$_6$) δ 1.22 (3H, d), 1.64 (4H, m), 1.95 (4H, m), 3.24 (1H, m), 3.45 (1H, td), 3.60 (1H, dd), 3.71 (1H, m), 3.95 (2H, m), 4.35 (1H, s), 4.40 (2H, s), 6.91 (1H, s)

Mass Spectrum: MH+ 360

2-Chloro-4-(cyclopentylsulfanylmethyl)-6-[(3S)-3-methylmorpholin-4-yl]pyrimidine

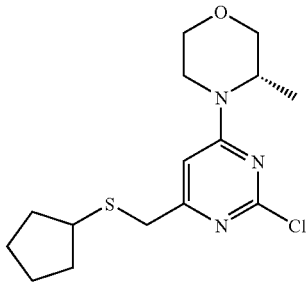

DIPEA (9.62 mL, 55.57 mmol) was added to cyclopentanethiol (5.93 mL, 55.57 mmol), in DMF (80 mL) at RT under nitrogen. The resulting solution was stirred at RT for 20 minutes. 2-Chloro-4-(iodomethyl)-6-[(3S)-3-methylmorpholin-4-yl]pyrimidine (13.1 g, 37.05 mmol) was added to the reaction and stirred for 2 hours at RT. The reaction mixture was diluted with ethyl acetate (500 mL), and washed with water (2×200 mL). The organic layer was dried (MgSO$_4$), filtered and evaporated to afford crude product. The crude product was purified by flash silica chromatography, elution gradient 0 to 30% ethyl acetate in isohexane, to give the desired material as a colourless gum (11.13 g).

NMR Spectrum: $^1$H NMR (400.132 MHz, DMSO-d$_6$) δ 1.20 (3H, d), 1.43 (2H, m), 1.53 (2H, m), 1.65 (2H, m), 1.94 (2H, m), 3.16 (2H, m), 3.44 (1H, td), 3.71 (1H, d), 3.95 (2H, m), 4.35 (1H, s), 6.79 (1H, s)

Mass Spectrum: MH+ 328

The preparation of 2-chloro-4-(iodomethyl)-6-[(3S)-3-methylmorpholin-4-yl]pyrimidine was described earlier The preparation of phenyl N-[4-[4-(cyclopentylsulfonylmethyl)-6-[(3S)-3-methylmorpholin-4-yl]pyrimidin-2-yl]phenyl]carbamate is described below Phenyl N-[4-[4-(cyclopentylsulfonylmethyl)-6-[(3S)-3-methylmorpholin-4-yl]pyrimidin-2-yl]phenyl]carbamate

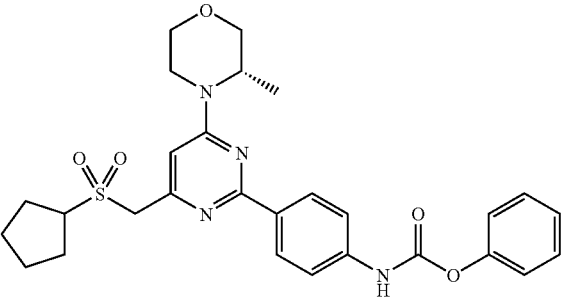

Phenyl chloroformate (0.759 mL, 6.05 mmol) was added to 4-[4-(cyclopentylsulfonylmethyl)-6-[(3S)-3-methylmorpholin-4-yl]pyrimidin-2-yl]aniline (1.68 g, 4.03 mmol) and sodium hydrogen carbonate (0.508 g, 6.05 mmol) in dioxane (20 mL) at 5° C. under nitrogen. The resulting mixture was stirred at RT for 2 hours. The reaction mixture was diluted with ethyl acetate (200 mL), and washed with water (125 mL). The organic layer was dried (MgSO$_4$), filtered and evaporated to afford crude product which was triturated with a mixture of diethyl ether and isohexane to give the desired material as a white solid (2.10 g).

NMR Spectrum: $^1$H NMR (400.132 MHz, DMSO-d$_6$) δ 1.25 (3H, d), 1.57-1.76 (4H, m), 1.93-2.08 (4H, m), 3.24 (1H, td), 3.47-3.54 (1H, m), 3.66 (1H, dd), 3.75-3.84 (2H, m), 3.99 (1H, dd), 4.20 (1H, d), 4.47 (2H, s), 4.52 (1H, s), 6.84 (1H, s), 7.24-7.31 (3H, m), 7.42-7.48 (2H, m), 7.64 (2H, d), 8.29 (2H, d), 10.47 (1H, s)

LCMS Spectrum: MH+ 537, retention time 2.75 mins

4-[4-(Cyclopentylsulfonylmethyl)-6-[(3S)-3-methyl-morpholin-4-yl]pyrimidin-2-yl]aniline

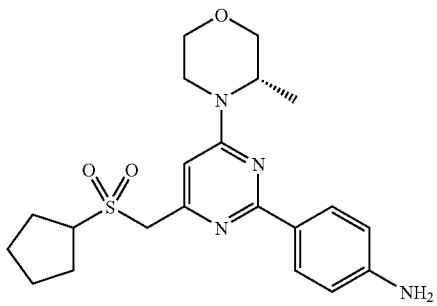

Bis(triphenylphosphine)palladium(II) chloride (118 mg, 0.17 mmol) was added to 2-chloro-4-(cyclopentylsulfonylmethyl)-6-[(3S)-3-methylmorpholin-4-yl]pyrimidine (1.67 g, 4.64 mmol), 4-(4,4,5,5-tetramethyl-1,3,2-dioxaborolan-2-yl)aniline (1.525 g, 6.96 mmol) and sodium carbonate (10 mL, 20.00 mmol) in a mixture of ethanol (6 mL), DMF (10 mL), water (6 mL) and DME (20 mL) at RT. The resulting mixture was degassed then stirred at 95° C. for 18 hours. The reaction mixture was diluted with ethyl acetate (400 mL), and washed with water (2×150 mL). The organic layer was dried (MgSO$_4$), filtered and evaporated to afford crude product. The crude product was purified by flash silica chromatography, elution gradient 10 to 60% ethyl acetate in isohexane, to give the desired material as a cream crystalline solid (1.680 g).

NMR Spectrum: $^1$H NMR (400.132 MHz, DMSO-d$_6$) δ 1.22 (3H, d), 1.58-1.73 (4H, m), 1.93-2.06 (4H, m), 3.19 (1H, td), 3.49 (1H, td), 3.64 (1H, dd), 3.74-3.82 (2H, m), 3.97 (1H, dd), 4.14 (1H, d), 4.39 (2H, s), 4.47 (1H, s), 5.57 (2H, s), 6.60 (2H, d), 6.67 (1H, s), 8.03 (2H, d)

LCMS Spectrum: MH+ 417, retention time 2.09 mins

The preparation of 2-chloro-4-(cyclopentylsulfonylmethyl)-6-[(3S)-3-methylmorpholin-4-yl]pyrimidine was described earlier.

EXAMPLE 65

3-Cyclopropyl-1-[4-[4-[(3S)-3-methylmorpholin-4-yl]-6-[2-[2-(trifluoromethyl)phenyl]sulfonylpropan-2-yl]pyrimidin-2-yl]phenyl]urea

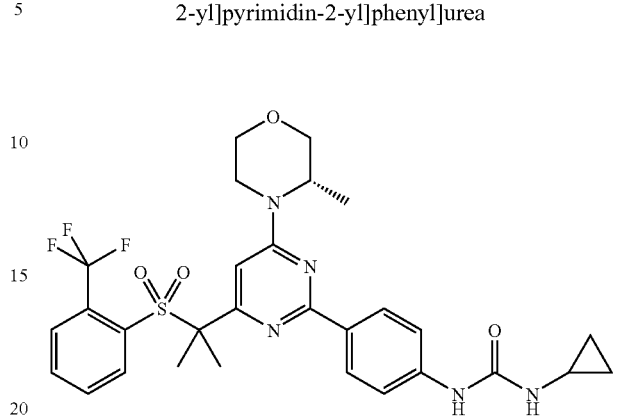

Triethylamine (0.197 mL, 1.40 mmol) was added to a mixture of phenyl N-[4-[4-[(3S)-3-methylmorpholin-4-yl]-6-[2-[2-(trifluoromethyl)phenyl]sulfonylpropan-2-yl]pyrimidin-2-yl]phenyl]carbamate (200 mg, 0.35 mmol) and cyclopropylamine (1.40 mmol) in NMP (2 mL) and heated at 75° C. for 6 hours. The reaction mixture was purified by preparative HPLC using decreasingly polar mixtures of water (containing 1% NH3) and acetonitrile as eluents, to give the desired material as a solid (163 mg).

NMR Spectrum: $^1$H NMR (400.132 MHz, DMSO-d$_6$) δ 0.40-0.43 (2H, m), 0.63-0.66 (2H, m), 1.20 (3H, d), 1.84 (6H, d), 3.11-3.19 (1H, m), 3.49 (1H, dd), 3.64 (1H, dd), 3.76 (1H, d), 3.97 (1H, d), 4.13 (1H, d), 4.62 (1H, s), 6.41 (1H, d), 6.67 (1H, s), 7.32 (2H, d), 7.59 (2H, d), 7.78 (1H, d), 7.82-7.91 (2H, m), 7.97 (1H, d), 8.48 (1H, s)

LCMS Spectrum: MH+ 604, retention time 2.59 min

The following compounds were made in an analogous fashion from either phenyl N-[4-[4-[(3S)-3-methylmorpholin-4-yl]-6-[2-[2-(trifluoromethyl)phenyl]sulfonylpropan-2-yl]pyrimidin-2-yl]phenyl]carbamate or phenyl N-[4-[4-[(3S)-3-methylmorpholin-4-yl]-6-[[2-(trifluoromethyl)phenyl]sulfonylmethyl]pyrimidin-2-yl]phenyl]carbamate and the appropriate amine.

| Example | Structure | NAME | LCMS MH+ | Retention time (min) |
|---|---|---|---|---|
| 65a | (structure shown) | 3-cyclobutyl-1-[4-[4-[(3S)-3-methylmorpholin-4-yl]-6-[2-[2-(trifluoromethyl)phenyl]sulfonylpropan-2-yl]pyrimidin-2-yl]phenyl]urea | 618 | 2.83 |

-continued

| Example | Structure | NAME | LCMS MH+ | Retention time (min) |
|---|---|---|---|---|
| 65b | 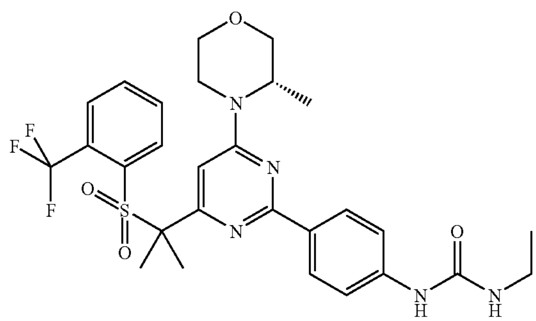 | 3-ethyl-1-[4-[4-[(3S)-3-methylmorpholin-4-yl]-6-[2-[2-(trifluoromethyl)phenyl]sulfonylpropan-2-yl]pyrimidin-2-yl]phenyl]urea | 592 | 2.60 |
| 65c | 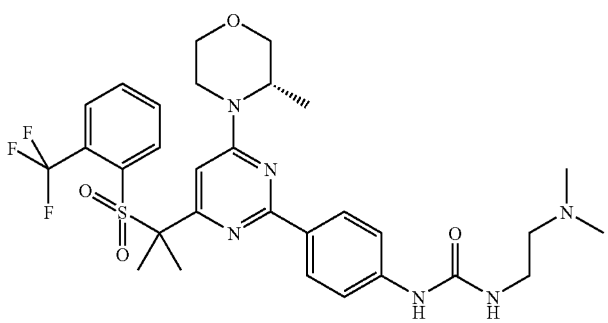 | 3-(2-dimethylaminoethyl)-1-[4-[4-[(3S)-3-methylmorpholin-4-yl]-6-[2-[2-(trifluoromethyl)phenyl]sulfonylpropan-2-yl]pyrimidin-2-yl]phenyl]urea | 635 | 2.53 |
| 65d | 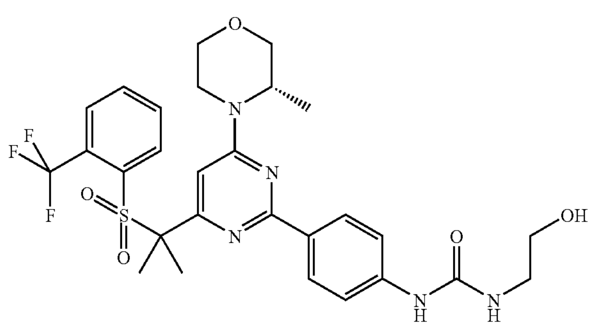 | 3-(2-hydroxyethyl)-1-[4-[4-[(3S)-3-methylmorpholin-4-yl]-6-[2-[2-(trifluoromethyl)phenyl]sulfonylpropan-2-yl]pyrimidin-2-yl]phenyl]urea | 608 | 2.22 |
| 65e | 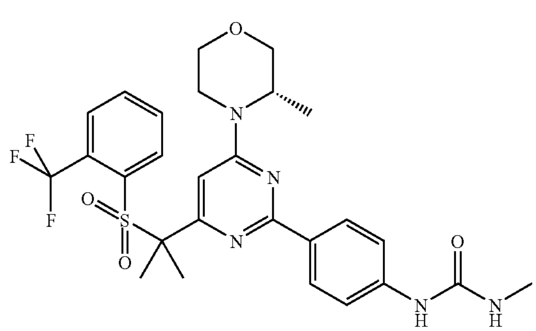 | 3-methyl-1-[4-[4-[(3S)-3-methylmorpholin-4-yl]-6-[2-[2-(trifluoromethyl)phenyl]sulfonylpropan-2-yl]pyrimidin-2-yl]phenyl]urea | 578 | 2.42 |

| Example | Structure | NAME | LCMS MH+ | Retention time (min) |
|---|---|---|---|---|
| 65f | 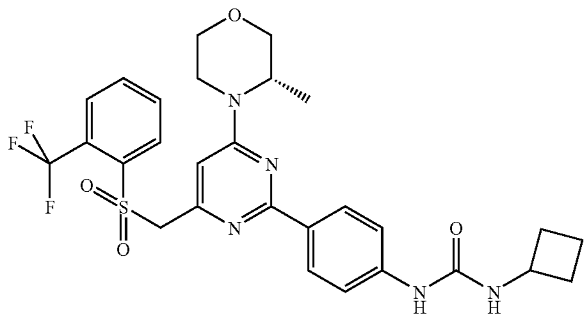 | 3-cyclobutyl-1-[4-[4-[(3S)-3-methylmorpholin-4-yl]-6-[[2-(trifluoromethyl)phenyl]sulfonylmethyl]pyrimidin-2-yl]phenyl]urea | 590 | 2.56 |
| 65g | 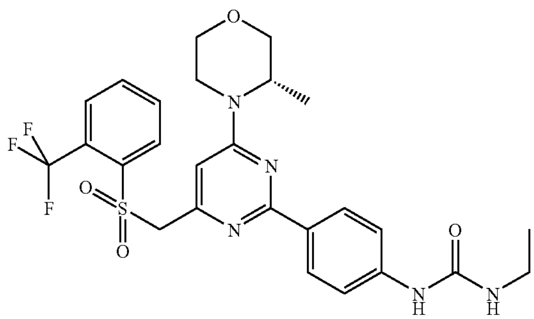 | 3-ethyl-1-[4-[4-[(3S)-3-methylmorpholin-4-yl]-6-[[2-(trifluoromethyl)phenyl]sulfonylmethyl]pyrimidin-2-yl]phenyl]urea | 564 | 2.39 |
| 65h | 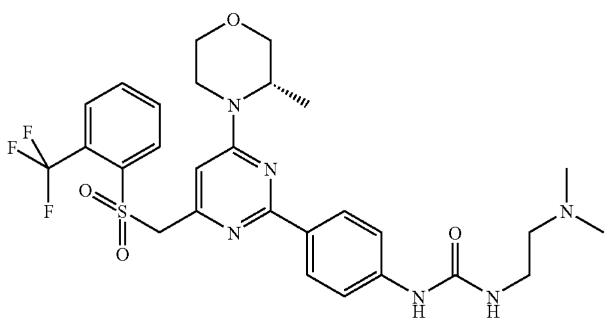 | 3-(2-dimethylaminoethyl)-1-[4-[4-[(3S)-3-methylmorpholin-4-yl]-6-[[2-(trifluoromethyl)phenyl]sulfonylmethyl]pyrimidin-2-yl]phenyl]urea | 607 | 1.32 |

Example 65a: $^1$H NMR (400.132 MHz, DMSO-$d_6$) δ 1.20 (3H, d), 1.57-1.68 (4H, m), 1.84 (6H, d), 2.18-2.25 (2H, m), 3.12-3.18 (1H, m), 3.45-3.53 (1H, m), 3.64 (1H, d), 3.76 (1H, d), 3.97 (1H, d), 4.09-4.18 (2H, m), 4.60 (1H, s), 6.43 (1H, d), 6.66 (1H, s), 7.29 (2H, d), 7.59 (2H, d), 7.78 (1H, d), 7.82-7.91 (2H, m), 7.97 (1H, d), 8.50 (1H, s)

Example 65b: $^1$H NMR (400.132 MHz, DMSO-$d_6$) δ 1.06 (3H, t), 1.20 (3H, d), 1.82 (6H, d), 3.08-3.19 (2H, m), 3.49 (1H, dd), 3.64 (1H, dd), 3.77 (1H, d), 3.94-3.99 (1H, m), 4.12 (1H, d), 4.62 (1H, s), 6.14 (1H, t), 6.68 (1H, s), 7.30 (2H, d), 7.59 (2H, d), 7.77-7.80 (1H, m), 7.82-7.91 (2H, m), 7.97 (1H, d), 8.60 (1H, s)

Example 65c: $^1$H NMR (400.132 MHz, DMSO-$d_6$) δ 1.20 (3H, d), 1.84 (6H, d), 2.20 (6H, s), 2.34 (2H, t), 3.09-3.21 (3H, m), 3.49 (1H, td), 3.64 (1H, dd), 3.76 (1H, d), 3.97 (1H, dd), 4.12 (1H, d), 4.61 (1H, s), 6.14 (1H, t), 6.67 (1H, s), 7.30 (2H, d), 7.59 (2H, d), 7.78 (2H, d), 7.82-7.91 (2H, m), 7.97 (2H, d), 8.83 (1H, s)

Example 65d: $^1$H NMR (400.132 MHz, DMSO-$d_6$) δ 1.19 (3H, d), 1.85 (6H, d), 3.11-3.20 (3H, m), 3.43-3.53 (3H, m), 3.64 (1H, dd), 3.76 (1H, d), 3.97 (1H, dd), 4.13 (1H, d), 4.60 (1H, s), 4.72 (1H, t), 6.23 (1H, t), 6.67 (1H, s), 7.30 (2H, d), 7.59 (2H, d), 7.78 (1H, dd), 7.82-7.91 (2H, m), 7.95-7.99 (1H, m), 8.74 (1H, s)

Example 65e: $^1$H NMR (400.132 MHz, DMSO-$d_6$) δ 1.20 (3H, d), 1.84 (6H, d), 2.66 (3H, d), 3.15 (1H, td), 3.49 (1H, td), 3.64 (1H, dd), 3.77 (1H, d), 3.97 (1H, dd), 4.12 (1H, d), 4.61 (1H, s), 6.02-6.07 (1H, m), 6.66 (1H, s), 7.31 (2H, d), 7.59 (2H, d), 7.76-7.80 (1H, m), 7.82-7.91 (2H, m), 7.95-7.99 (1H, m), 8.67 (1H, s)

Example 65f: $^1$H NMR (400.132 MHz, DMSO-$d_6$) δ 1.10 (3H, t), 1.20 (3H, d), 1.58-1.67 (2H, m), 1.81-1.92 (2H, m), 2.16-2.25 (2H, m), 3.12-3.22 (1H, m), 3.44-3.52 (1H, m), 3.63 (1H, d), 3.97 (1H, d), 4.06-4.17 (2H, m), 4.44 (1H, s), 4.77 (2H, s), 6.45 (1H, d), 6.71 (1H, s), 7.33 (2H, d), 7.71 (2H, d), 7.76-7.82 (1H, m), 7.87-7.93 (2H, m), 8.09 (1H, d), 8.52 (1H, s)

Example 65g: $^1$H NMR (400.132 MHz, DMSO-$d_6$) δ 1.07 (3H, t), 1.21 (3H, d), 3.08-3.22 (3H, m), 3.48 (1H, td), 3.64 (1H, dd), 3.77 (1H, d), 3.97 (1H, d), 4.11 (1H, d), 4.44 (1H, s), 4.78 (2H, s), 6.15 (1H, t), 6.70 (1H, s), 7.35 (2H, d), 7.72 (2H, d), 7.79 (1H, t), 7.87-7.93 (2H, m), 8.08 (1H, d), 8.61 (1H, s)

Example 65h: ¹H NMR (400.132 MHz, DMSO-d₆) δ 1.21 (3H, d), 2.19 (6H, s), 2.33 (2H, t), 3.13-3.22 (3H, m), 3.44-3.53 (1H, m), 3.64 (1H, dd), 3.76 (1H, d), 3.97 (1H, dd), 4.10 (1H, d), 4.44 (1H, s), 4.76 (2H, s), 6.14 (1H, t), 6.70 (1H, s), 7.34 (2H, d), 7.71 (2H, d), 7.79 (1H, t), 7.87-7.92 (2H, m), 8.08 (1H, d), 8.84 (1H, s)

The preparation of phenyl N-[4-[4-[(3S)-3-methylmorpholin-4-yl]-6-[2-[2-(trifluoromethyl)phenyl]sulfonylpropan-2-yl]pyrimidin-2-yl]phenyl]carbamate is described below.

Phenyl N-[4-[4-[(3S)-3-methylmorpholin-4-yl]-6-[2-[2-(trifluoromethyl)phenyl]sulfonylpropan-2-yl]pyrimidin-2-yl]phenyl]carbamate

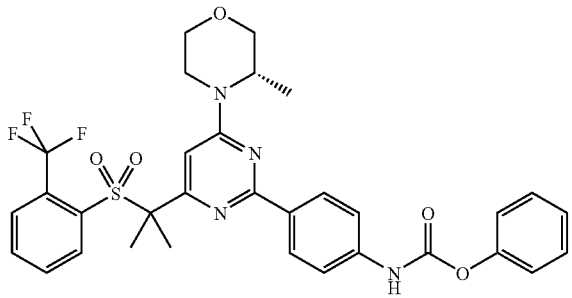

Phenyl chloroformate (0.542 mL, 4.32 mmol) was added to 4-[4-[(3S)-3-methylmorpholin-4-yl]-6-[2-[2-(trifluoromethyl)phenyl]sulfonylpropan-2-yl]pyrimidin-2-yl]aniline line (1.5 g, 2.88 mmol) and sodium hydrogen carbonate (0.363 g, 4.32 mmol) in dioxane (20 mL) at 5° C. under nitrogen. The resulting mixture was stirred at RT for 2 hours then diluted with ethyl acetate (200 mL), and washed with water (125 mL). The organic layer was dried (MgSO₄), filtered and evaporated to afford crude product which was triturated with a mixture of diethyl ether and isohexane to give the desired material as a white solid (1.38 g).

NMR Spectrum: ¹H NMR (400.132 MHz, DMSO-d₆) δ 1.21 (3H, d), 1.85 (6H, d), 3.16 (1H, td), 3.45-3.54 (1H, m), 3.65 (1H, dd), 3.77 (1H, d), 3.97 (1H, dd), 4.15 (1H, d), 4.63 (1H, s), 6.71 (1H, s), 7.23-7.29 (3H, m), 7.42-7.47 (4H, m), 7.69 (2H, d), 7.78 (1H, d), 7.82-7.92 (2H, m), 7.98 (1H, d), 10.37 (1H, s)

LCMS Spectrum: MH+ 641, retention time 3.08 mins

4-[4-[(3S)-3-Methylmorpholin-4-yl]-6-[2-[2-(trifluoromethyl)phenyl]sulfonylpropan-2-yl]pyrimidin-2-yl]aniline

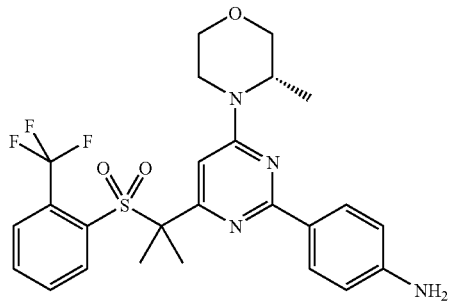

Bis(triphenylphosphine)palladium(II) chloride (200 mg, 0.28 mmol) was added to 2-chloro-4-[(3S)-3-methylmorpholin-4-yl]-6-[2-[2-(trifluoromethyl)phenyl]sulfonylpropan-2-yl]pyrimidine (1.91 g, 4.12 mmol), 4-(4,4,5,5-tetramethyl-1,3,2-dioxaborolan-2-yl)aniline (1.353 g, 6.18 mmol) and sodium carbonate (10 mL, 20.00 mmol) in a mixture of ethanol (5 mL), DMF (10 mL), water (7 mL) and DME (25 mL) at RT. The resulting mixture was degassed then stirred at 95° C. for 18 hours. The reaction mixture was allowed to cool and diluted with ethyl acetate (200 mL), and washed with water (2×200 mL), and brine (100 mL). The organic layer was dried (Na₂SO₄), filtered and evaporated to afford crude product. The crude product was purified by flash silica chromatography, elution gradient 10 to 60% ethyl acetate in isohexane, and the resultant material triturated with a mixture of diethyl ether and isohexane to give the desired material as a white solid (1.50 g).

NMR Spectrum: ¹H NMR (400.132 MHz, DMSO-d₆) δ 1.18 (3H, d), 1.82 (6H, d), 3.12 (1H, td), 3.47 (1H, td), 3.63 (1H, dd), 3.75 (1H, d), 3.95 (1H, dd), 4.08 (1H, d), 4.57 (1H, s), 5.47 (2H, s), 6.42 (2H, d), 6.56 (1H, s), 7.44 (2H, d), 7.78-7.89 (3H, m), 7.92-7.96 (1H, m)

LCMS Spectrum: MH+ 521, retention time 2.56 mins

2-Chloro-4-[(3S)-3-methylmorpholin-4-yl]-6-[2-[2-(trifluoromethyl)phenyl]sulfonylpropan-2-yl]pyrimidine

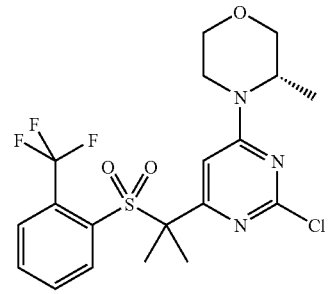

Sodium tert-butoxide (4.59 mmol) was added to a solution of 2-chloro-4-[(3S)-3-methylmorpholin-4-yl]-6-[[2-(trifluoromethyl)phenyl]sulfonylmethyl]pyrimidine (2 g, 4.59 mmol) in DMF (10 mL) at −5° C., followed by dropwise addition of iodomethane (0.030 mL) at −5° C. Additional sodium tert-butoxide (4.59 mmol) and iodomethane (0.030 mL) were added and the reaction stirred at −5° C. for overnight. The organics were removed in vacuo and the residue partitioned between ethyl acetate (200 mL) and water (100 mL). The organic layer was washed with water (100 mL), dried (MgSO₄), filtered and evaporated to afford crude product which was triturated with a mixture of diethyl ether and isohexane to give the desired material as a cream solid (1.91 g).

NMR Spectrum: ¹H NMR (400.132 MHz, DMSO-d₆) δ 1.17 (3H, d), 3.13 (1H, td), 3.41 (1H, td), 3.57 (1H, dd), 3.71 (1H, d), 3.89-3.98 (2H, m), 4.46 (1H, s), 6.72 (1H, s), 7.87-8.02 (4H, m)

463

2-Chloro-4-[(3S)-3-methylmorpholin-4-yl]-6-[[2-(trifluoromethyl)phenyl]sulfonylmethyl]pyrimidine

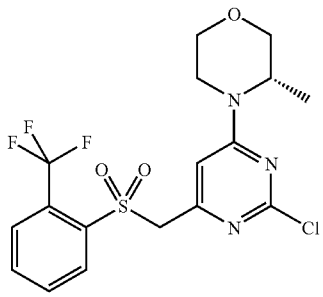

Sodium 2-(trifluoromethyl)benzenesulfinate (10.24 g, 44 mmol) was added to 2-chloro-4-(iodomethyl)-6-[(3S)-3-methylmorpholin-4-yl]pyrimidine (13 g, 36.77 mmol), in acetonitrile (500 mL) at RT under nitrogen. The resulting mixture was stirred at 80° C. for 3 hours. Additional sodium 2-(trifluoromethyl)benzenesulfinate (10.2 g, 44 mmol) was added and reaction heated at 80° C. for 1 hour. The reaction mixture allowed to cool and concentrated in vacuo. The material was dissolved in ethyl acetate (500 mL), and washed with water (200 mL). The organic layer was dried ($MgSO_4$), filtered and evaporated to afford crude product. The crude product was purified by flash silica chromatography, elution gradient 0 to 40% ethyl acetate in isohexane, to give the desired material as an orange/cream solid (9.48 g).

NMR Spectrum: $^1$H NMR (400.132 MHz, DMSO-$d_6$) δ 1.18 (3H, d), 3.17 (1H, td), 3.43 (1H, td), 3.58 (1H, dd), 3.72 (1H, d), 3.93 (2H, m), 4.27 (1H, s), 4.68 (2H, s), 6.79 (1H, s), 7.94 (3H, m), 8.08 (1H, d)

LCMS Spectrum: MH+ 436; retention time 2.35 min.

Sodium 2-(trifluoromethyl)benzenesulfinate

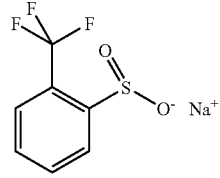

Sodium sulfite (3.92 mL, 81.88 mmol) was dissolved in water and stirred at RT 10 minutes. Sodium bicarbonate (13.74 g, 163.52 mmol) was added and the mixture stirred at 50° C. for 1 hour. 2-(Trifluoromethyl)benzene-1-sulfonyl chloride (12.62 mL, 81.76 mmol) was added dropwise to the reaction mixture which was then stirred at 50° C. for 18 hours. The reaction mixture was evaporated to dryness and the residue suspended in methanol (250 mL) and stirred at RT for 20 minutes. The solid was removed by filtration and the filtrate evaporated to give the desired material (20.00 g).

NMR Spectrum: $^1$H NMR (400.132 MHz, DMSO-$d_6$) δ 7.40 (1H, d), 7.51 (1H, d), 7.64 (1H, d), 8.05 (1H, d)

The preparation of 2-chloro-4-(iodomethyl)-6-[(3S)-3-methylmorpholin-4-yl]pyrimidine was described earlier.

The preparation of phenyl N-[4-[4-[(3S)-3-methylmorpholin-4-yl]-6-[[2-(trifluoromethyl)phenyl]sulfonylmethyl]pyrimidin-2-yl]phenyl]carbamate is described below.

464

Phenyl N-[4-[4-[(3S)-3-methylmorpholin-4-yl]-6-[[2-(trifluoromethyl)phenyl]sulfonylmethyl]pyrimidin-2-yl]phenyl]carbamate

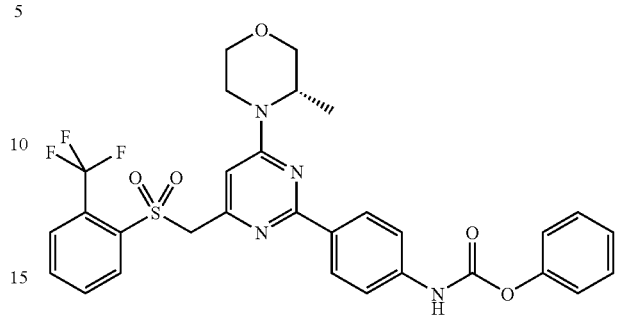

Phenyl chloroformate (0.535 mL, 4.26 mmol) was added to 4-[4-[(3S)-3-methylmorpholin-4-yl]-6-[[2-(trifluoromethyl)phenyl]sulfonylmethyl]pyrimidin-2-yl]aniline (1.4 g, 2.84 mmol) and sodium hydrogen carbonate (0.358 g, 4.26 mmol) in dioxane (20 mL) at 5° C. under nitrogen. The resulting mixture was stirred at RT for 2 hours then the reaction mixture diluted with ethyl acetate (200 mL), and washed with water (125 mL). The organic layer was dried ($MgSO_4$), filtered and evaporated to afford crude product which was triturated with a mixture of diethyl ether and isohexane to give the desired material as a white solid (1.70 g).

NMR Spectrum: $^1$H NMR (400.132 MHz, DMSO-$d_6$) δ 1.22 (3H, d), 3.19 (1H, td), 3.49 (1H, td), 3.64 (1H, dd), 3.77 (1H, d), 3.98 (1H, dd), 4.13 (1H, d), 4.47 (1H, s), 4.79 (2H, s), 6.75 (1H, s), 7.23-7.31 (3H, m), 7.42-7.51 (4H, m), 7.77-7.83 (2H, m), 7.87-7.92 (2H, m), 8.09 (1H, d), 10.39 (1H, s)

LCMS Spectrum: MH+ 613, retention time 2.92 mins

4-[4-[(3S)-3-Methylmorpholin-4-yl]-6-[[2-(trifluoromethyl)phenyl]sulfonylmethyl]pyrimidin-2-yl]aniline

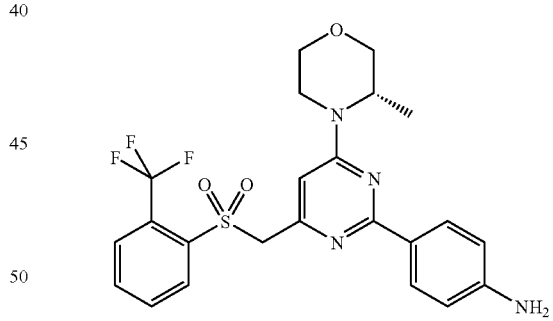

Bis(triphenylphosphine)palladium(II) chloride (300 mg, 0.43 mmol) was added to 2-chloro-4-[(3S)-3-methylmorpholin-4-yl]-6-[[2-(trifluoromethyl)phenyl]sulfonylmethyl]pyrimidine (1.66 g, 3.81 mmol), 4-(4,4,5,5-tetramethyl-1,3,2-dioxaborolan-2-yl)aniline (1.252 g, 5.71 mmol) and sodium carbonate (10 mL, 20.00 mmol) in a mixture of ethanol (6 mL), DMF (10 mL), water (6 mL) and DME (20 mL) at RT. The resulting mixture was degassed then stirred at 95° C. for 18 hours. The reaction mixture was allowed to cool then diluted with ethyl acetate (400 mL), and washed with water (2×200 mL). The organic layer was dried ($MgSO_4$), filtered and evaporated to afford crude product. The crude product was purified by flash silica chromatography, elution gradient 10 to 60% ethyl acetate in isohexane, to give the desired material as a cream crystalline solid (1.40 g).

NMR Spectrum: ¹H NMR (400.132 MHz, DMSO-d₆) δ 1.19 (3H, d), 3.14 (1H, td), 3.47 (1H, td), 3.62 (1H, dd), 3.75 (1H, d), 3.96 (1H, dd), 4.04-4.11 (1H, m), 4.41 (1H, s), 4.72 (2H, s), 5.51 (2H, s), 6.47 (2H, d), 6.59 (1H, s), 7.56 (2H, d), 7.76-7.81 (1H, m), 7.86-7.92 (2H, m), 8.07 (1H, d)

LCMS Spectrum: MH+ 493, retention time 2.35 mins

The preparation of 2-chloro-4-[(3S)-3-methylmorpholin-4-yl]-6-[[2-(trifluoromethyl)phenyl]sulfonylmethyl]pyrimidine was described earlier.

EXAMPLE 66

3-Ethyl-1-[4-[4-[(3S)-3-methylmorpholin-4-yl]-6-(tert-butylsulfonylmethyl)pyrimidin-2-yl]phenyl]urea

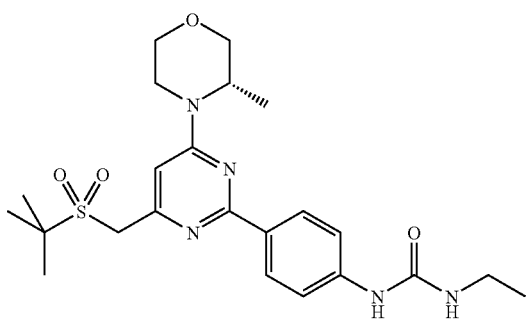

Ethylamine hydrochloride (86.4 mg, 1.03 mmol) was added to phenyl N-[4-[4-[(3S)-3-methylmorpholin-4-yl]-6-(tert-butylsulfonylmethyl)pyrimidin-2-yl]phenyl]carbamate (120 mg, 0.23 mmol) and triethylamine (0.21 mL, 1.49 mmol) in DMF (2 mL). The reaction mixture was allowed to stand at RT for 65 hours. The crude product was purified by preparative HPLC using decreasingly polar mixtures of water (containing 1% NH3) and acetonitrile as eluents, to give the desired material as a colourless solid (79.0 mg).

NMR Spectrum: ¹H NMR (399.9 MHz, DMSO-d₆) δ 1.07 (3H, t), 1.25 (3H, d), 1.39 (9H, s), 3.10-3.25 (3H, m), 3.45-3.54 (1H, m), 3.63-3.69 (1H, m), 3.79 (1H, d), 3.95-4.03 (1H, m), 4.18 (1H, d), 4.46 (3H, s), 6.18 (1H, t), 6.75 (1H, s), 7.50 (2H, m), 8.21 (2H, d), 8.68 (1H, s)

LCMS Spectrum: MH+ 476, retention time 2.04 min.

The following compounds were made in an analogous fashion from either phenyl N-[4-[4-[(3S)-3-methylmorpholin-4-yl]-6-(tert-butylsulfonylmethyl)pyrimidin-2-yl]phenyl]carbamate or phenyl N-[4-[4-[(3S)-3-methylmorpholin-4-yl]-6-(2-tert-butylsulfonylpropan-2-yl)pyrimidin-2-yl]phenyl]carbamate and the appropriate amine.

| Example | Structure | NAME | LCMS MH+ | Retention time (min) |
|---|---|---|---|---|
| 66a | 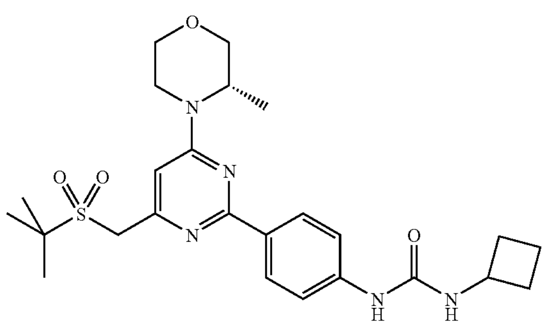 | 3-cyclobutyl-1-[4-[4-[(3S)-3-methylmorpholin-4-yl]-6-(tert-butylsulfonylmethyl)pyrimidin-2-yl]phenyl]urea | 502 | 2.25 |
| 66b | 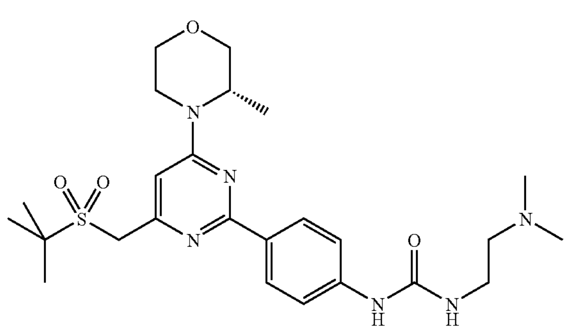 | 3-(2-dimethylaminoethyl)-1-[4-[4-[(3S)-3-methylmorpholin-4-yl]-6-(tert-butylsulfonylmethyl)pyrimidin-2-yl]phenyl]urea | 519 | 1.97 |

-continued

| Example | Structure | NAME | LCMS MH+ | Retention time (min) |
|---|---|---|---|---|
| 66c | 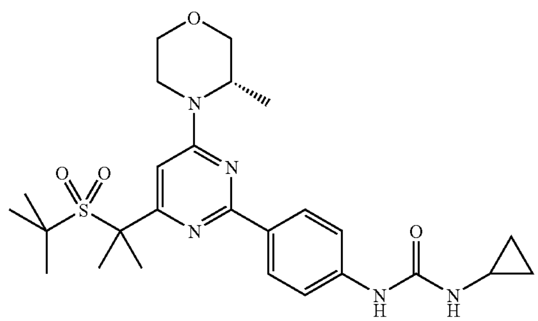 | 3-cyclopropyl-1-[4-[4-[(3S)-3-methylmorpholin-4-yl]-6-(2-tert-butylsulfonylpropan-2-yl)pyrimidin-2-yl]phenyl]urea | 516 | 2.36 |
| 66d | 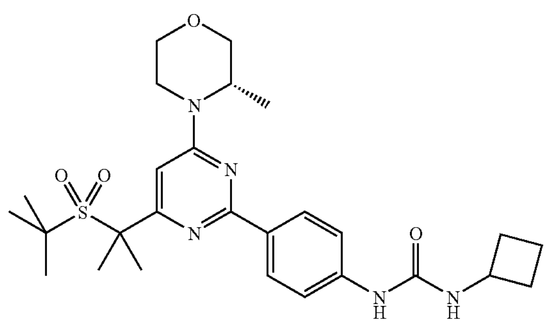 | 3-cyclobutyl-1-[4-[4-[(3S)-3-methylmorpholin-4-yl]-6-(2-tert-butylsulfonylpropan-2-yl)pyrimidin-2-yl]phenyl]urea | 530 | 2.64 |
| 66e | 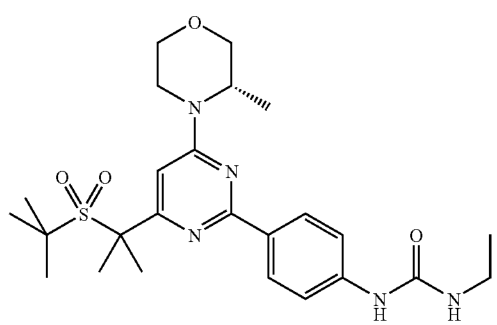 | 3-ethyl-1-[4-[4-[(3S)-3-methylmorpholin-4-yl]-6-(2-tert-butylsulfonylpropan-2-yl)pyrimidin-2-yl]phenyl]urea | 504 | 2.34 |
| 66f | 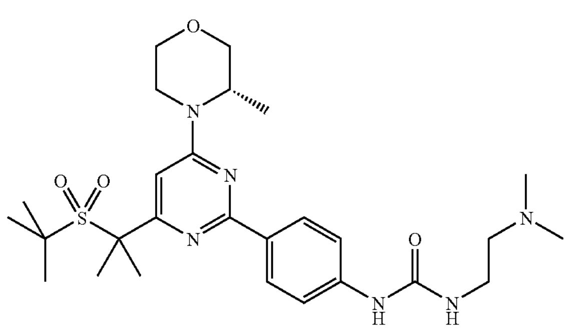 | 3-(2-dimethylaminoethyl)-1-[4-[4-[(3S)-3-methylmorpholin-4-yl]-6-(2-tert-butylsulfonylpropan-2-yl)pyrimidin-2-yl]phenyl]urea | 547 | 2.27 |

-continued

| Example | Structure | NAME | LCMS MH+ | Retention time (min) |
|---|---|---|---|---|
| 66g | 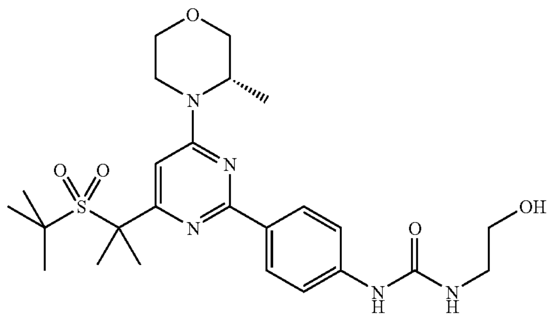 | 3-(2-hydroxyethyl)-1-[4-[4-[(3S)-3-methylmorpholin-4-yl]-6-(2-tert-butylsulfonylpropan-2-yl)pyrimidin-2-yl]phenyl]urea | 520 | 1.98 |
| 66h | 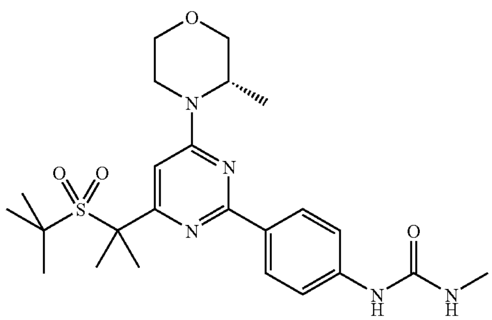 | 3-methyl-1-[4-[4-[(3S)-3-methylmorpholin-4-yl]-6-(2-tert-butylsulfonylpropan-2-yl)pyrimidin-2-yl]phenyl]urea | 490 | 2.27 |

Example 66a: $^1$H NMR (399.9 MHz, DMSO-$d_6$) δ 1.24 (3H, d), 1.39 (9H, s), 1.54-1.69 (2H, m), 1.79-1.92 (2H, m), 2.15-2.27 (2H, m), 3.15-3.25 (1H, m), 3.51 (1H, t), 3.66 (1H, d), 3.78 (1H, d), 3.99 (1H, d), 4.10-4.22 (2H, m), 4.46 (3H, s), 6.46 (1H, d), 6.75 (1H, s), 7.48 (2H, d), 8.21 (2H, d), 8.1 (1H, s)

Example 66b: $^1$H NMR (399.9 MHz, DMSO-$d_6$) δ 1.24-1.25 (3H, m), 1.39 (9H, s), 2.19 (6H, s), 2.34 (2H, t), 3.19-3.25 (1H, m), 3.45-3.56 (1H, m), 3.62-3.68 (1H, m), 3.79 (1H, d), 3.95-4.02 (1H, m), 4.08 (2H, q), 4.18 (1H, d), 4.46 (3H, s), 6.17 (1H, t), 6.75 (1H, s), 7.49 (2H, d), 8.21 (2H, d), 8.90 (1H, s)

Example 66c: $^1$H NMR (399.9 MHz, DMSO-$d_6$) δ 0.41-0.44 (2H, m), 0.63-0.68 (2H, m), 1.15 (9H, s), 1.21 (3H, d), 1.85 (3H, s), 1.88 (3H, s), 2.55-2.59 (1H, m), 3.18 (1H, dt), 3.51 (1H, dt), 3.66 (1H, dd), 3.78 (1H, d), 3.99 (1H, dd), 4.22 (1H, d), 4.51 (1H, br, s), 6.44 (1H, d), 6.88 (1H, s), 7.52 (2H, d), 8.27 (2H, d), 8.55 (1H, s)

Example 66d: $^1$H NMR (399.9 MHz, DMSO-$d_6$) δ 1.15 (9H, s), 1.21 (3H, d), 1.58-1.68 (2H, m), 1.80-1.91 (8H, m), 2.15-2.25 (2H, m), 3.12-3.23 (1H, m), 3.45-3.55 (1H, m), 3.62-3.68 (1H, m), 3.78 (1H, d), 3.94-4.02 (1H, m), 4.08-4.26 (2H, m), 4.51 (1H, br, s), 6.47 (1H, d), 6.88 (1H, s), 7.49 (2H, d), 8.26 (2H, d), 8.58 (1H, s)

Example 66e: $^1$H NMR (399.9 MHz, DMSO-$d_6$) δ 1.07 (3H, t), 1.15 (9H, s), 1.21 (3H, d), 1.85 (3H, s), 1.88 (3H, s), 3.10-3.24 (3H, m), 3.44-3.55 (1H, m), 3.62-3.68 (1H, m), 3.78 (1H, d), 3.94-4.01 (1H, m), 4.22 (1H, d), 4.51 (1H, br, s), 6.17 (1H, t), 6.88 (1H, s), 7.51 (2H, d), 8.26 (2H, d), 8.67 (1H, s)

Example 66f: $^1$H NMR (399.9 MHz, DMSO-$d_6$) δ 1.15 (9H, s), 1.21 (3H, d), 1.85 (3H, s), 1.88 (3H, s), 2.19 (6H, s), 2.35 (2H, t), 3.13-3.23 (3H, m), 3.45-3.54 (1H, m), 3.62-3.68 (1H, m), 3.78 (1H, d), 3.94-4.01 (1H, m), 4.22 (1H, d), 4.52 (1H, br, s), 6.17 (1H, t), 6.88 (1H, s), 7.50 (2H, d), 8.26 (2H, d), 8.91 (1H, s)

Example 66g: $^1$H NMR (399.9 MHz, DMSO-$d_6$) δ 1.15 (9H, s), 1.21 (3H, d), 1.85 (3H, s), 1.88 (3H, s), 3.12-3.22 (3H, m), 3.43-3.54 (3H, m), 3.62-3.68 (1H, m), 3.78 (1H, d), 3.95-4.01 (1H, m), 4.22 (1H, d), 4.51 (1H, br, s), 4.74 (1H, t), 6.27 (1H, t), 6.88 (1H, s), 7.50 (2H, d), 8.27 (2H, d), 8.82 (1H, s)

Example 66h: $^1$H NMR (399.9 MHz, DMSO-$d_6$) δ 1.15 (9H, s), 1.21 (3H, d), 1.85 (3H, s), 1.88 (3H, s), 2.67 (3H, d), 3.14-3.23 (1H, m), 3.46-3.55 (1H, m), 3.63-3.69 (1H, m), 3.78 (1H, d), 3.96-4.02 (1H, m), 4.22 (1H, d), 4.52 (1H, br, s), 6.06-6.12 (1H, m), 6.88 (1H, s), 7.52 (2H, d), 8.26 (2H, d), 8.77 (1H, s)

Test (c): Example (66c) 0.15 µM; Example (66d) 0.16 µM; Example (66e) 0.26 µM; Example (66f) 0.04 µM; Example (66g) 0.3 µM.

The preparation of phenyl N-[4-[4-[(3S)-3-methylmorpholin-4-yl]-6-(2-tert-butylsulfonylpropan-2-yl)pyrimidin-2-yl]phenyl]carbamate is described below.

Phenyl N-[4-[4-[(3S)-3-methylmorpholin-4-yl]-6-(2-tert-butylsulfonylpropan-2-yl)pyrimidin-2-yl]phenyl] carbamate

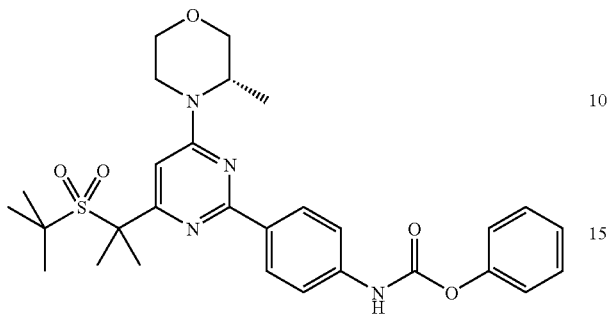

Phenyl chloroformate (0.368 mL, 2.93 mmol) was added to 4-[4-[(3S)-3-methylmorpholin-4-yl]-6-(2-tert-butylsulfonylpropan-2-yl)pyrimidin-2-yl]aniline (1.153 g, 2.67 mmol) and sodium hydrogen carbonate (0.336 g, 4.00 mmol) in dioxane (20 mL) at RT. The resulting slurry was stirred at RT for 2 hours. The reaction mixture was partitioned between ethyl acetate and water. The organic solution was dried (MgSO$_4$), filtered and concentrated under reduced pressure. The residue was chromatographed on silica, eluting with 20%-70% ethyl acetate in isohexane, to give the desired material as a near colourless solid (1.42 g).

NMR Spectrum: $^1$H NMR (400.13 MHz, CDCl$_3$) δ 1.25 (9H, s), 1.32 (3H, d), 1.95 (3H, s), 1.97 (3H, s), 3.31 (1H, dt), 3.61 (1H, dt), 3.76 (1H, dd), 3.83 (1H, d), 4.05 (1H, dd), 4.18 (1H, d), 4.47 (1H, br), 6.88 (1H, s), 7.10 (1H, br, s), 7.20-7.27 (3H, m), 7.41 (2H, t), 7.55 (2H, d), 8.43 (2H, d)

LCMS Spectrum: MH+ 553, retention time 3.05 min.

4-[4-[(3S)-3-Methylmorpholin-4-yl]-6-(2-tert-butylsulfonylpropan-2-yl)pyrimidin-2-yl]aniline

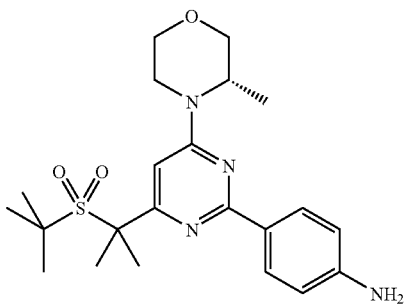

Dichlorobis(triphenylphosphine)-palladium(II) (0.103 g, 0.15 mmol) was added to 2-chloro-4-[(3S)-3-methylmorpholin-4-yl]-6-(2-tert-butylsulfonylpropan-2-yl)pyrimidine (1.10 g, 2.93 mmol), 4-(4,4,5,5-tetramethyl-1,3,2-dioxaborolan-2-yl)aniline (0.833 g, 3.80 mmol) and 2M aqueous sodium carbonate (5.27 mL, 10.53 mmol) in DMF (6 mL), DME (5 mL), ethanol (5 mL) and water (12.5 mL) at RT under nitrogen. The reaction was purged with nitrogen for 15 minutes and the resulting mixture was stirred at 80° C. for 16 hours. The reaction mixture was diluted with ethyl acetate and washed with water. The organic solution was dried (MgSO$_4$), filtered, and concentrated under reduced pressure. The residue was chromatographed on silica, eluting with 25%-100% ethyl acetate in isohexane, to give the desired material as a yellow solid (1.19 g).

NMR Spectrum: $^1$H NMR (400 MHz, CDCl$_3$) δ 1.24 (9H, s), 1.30 (3H, d), 1.93 (3H, s), 1.95 (3H, s), 3.28 (1H, dt), 3.60 (1H, dt), 3.75 (1H, dd), 3.82 (1H, d), 3.90 (2H, s), 4.03 (1H, dd), 4.16 (1H, d), 4.46 (1H, br), 6.72 (2H, d), 6.79 (1H, s), 8.26 (2H, d)

LCMS Spectrum: MH+ 433, retention time 2.42 min.

2-Chloro-4-[(3S)-3-methylmorpholin-4-yl]-6-(2-tert-butylsulfonylpropan-2-yl)pyrimidine

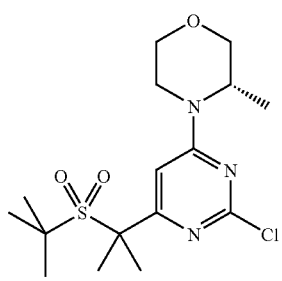

Sodium tert-butoxide (0.345 g, 3.59 mmol) was added to 2-chloro-4-[(3S)-3-methylmorpholin-4-yl]-6-(tert-butylsulfonylmethyl)pyrimidine (1.250 g, 3.59 mmol) in DMF (30 mL) at 0° C. under nitrogen. Iodomethane (0.224 mL, 3.59 mmol) was added and the resulting solution was stirred at 0° C. for 15 minutes. Further sodium tert-butoxide (0.345 g, 3.59 mmol) was added followed by iodomethane (0.224 mL, 3.59 mmol) and the resulting solution was stirred at 0° C. for 1 hour. The reaction was diluted with DCM (100 mL) and washed with water (100 mL) and brine (100 mL). The organic layer was dried (MgSO$_4$), filtered and the solvent evaporated to give a gum which slowly crystallised. The crude product was chromatographed on silica, eluting with 0-40% ethyl acetate in DCM, to give the desired material as a colourless solid (1.14 g).

NMR Spectrum: $^1$H NMR (400 MHz, CDCl$_3$) δ 1.28 (9H, s), 1.30 (3H, d), 1.84 (3H, s), 1.86 (3H, s), 3.27 (1H, dt), 3.54 (1H, dt), 3.69 (1H, dd), 3.79 (1H, d), 3.99-4.05 (2H, m), 4.30 (1H, br, s), 6.89 (1H, s).

LCMS Spectrum: MH+ 376, 378, retention time 2.52 min.

2-Chloro-4-[(3S)-3-methylmorpholin-4-yl]-6-(tert-butylsulfonylmethyl)pyrimidine

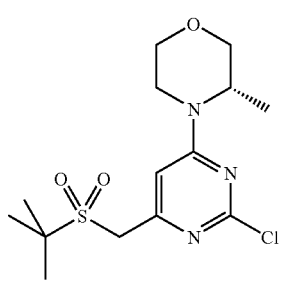

A solution of hydrogen peroxide (9.48 mL, 107.30 mmol) (35% aqueous solution) was added dropwise to a stirred solution of 2-chloro-4-[(3S)-3-methylmorpholin-4-yl]-6-(tert-butylsulfanylmethyl)pyrimidine (9.82 g, 31.1 mmol), sodium tungstate dihydrate (0.205 g, 0.62 mmol) and sulfuric acid (0.6 mL, 1M, 0.6 mmol) in dioxane (80 mL). The mixture was heated at 55° C. under air for 1 hour. When the reaction was complete, the solution was diluted with water and cooled. A solution of sodium metabisulfite (10% w/v) was added to destroy remaining peroxide. The solution was extracted with DCM, dried (MgSO₄) and filtered to give the desired material as a near colourless gum (9.34 g).

NMR Spectrum: $^1$H NMR (399.9 MHz, CDCl₃) δ 1.33 (3H, d), 1.44 (9H, s), 3.29 (1H, dt), 3.54 (1H, dt), 3.69 (1H, dd), 3.78 (1H, d), 3.97-4.13 (2H, m), 4.21 (2H, s), 4.30 (1H, br, s), 6.71 (1H, s).

LCMS Spectrum: MH+ 348, 350, retention time 1.82 min.

2-Chloro-4-[(3S)-3-methylmorpholin-4-yl]-6-(tert-butylsulfanylmethyl)pyrimidine

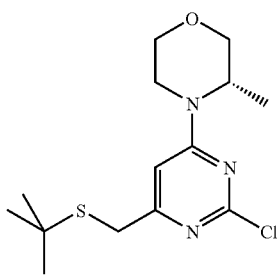

N-Ethyldiisopropylamine (8.61 mL, 49.78 mmol) was added to 2-methyl-2-propanethiol (4.21 mL, 37.33 mmol), in DMF (55 mL) at RT under nitrogen. The resulting solution was stirred at RT for 20 minutes. 2-Chloro-4-(iodomethyl)-6-[(3S)-3-methylmorpholin-4-yl]pyrimidine (11.00 g, 31.11 mmol) was added to the reaction mixture in one portion. The mixture was stirred for 4 hours at RT. The reaction mixture was placed in a water bath at 60° C. for 1.5 hours then partitioned between ethyl acetate and water. The organic layer was washed with additional water and then was dried (MgSO₄), filtered and evaporated to afford the desired material as a yellow gum (10.02 g).

NMR Spectrum: $^1$H NMR (399.9 MHz, CDCl3) δ 1.31 (3H, d), 1.34 (9H, s), 3.27 (1H, dt), 3.54 (1H, dt), 3.66-3.71 (3H, m), 3.78 (1H, d), 3.97-4.07 (2H, m), 4.31 (1H, br, s), 6.56 (1H, s)

LCMS Spectrum: MH+ 316, 318, retention time 2.61 min.

The preparation of 2-chloro-4-(iodomethyl)-6-[(3S)-3-methylmorpholin-4-yl]pyrimidine was described earlier.

The preparation of phenyl N-[4-[4-[(3S)-3-methylmorpholin-4-yl]-6-(tert-butylsulfonylmethyl)pyrimidin-2-yl]phenyl]carbamate is described below.

Phenyl N-[4-[4-[(3S)-3-methylmorpholin-4-yl]-6-(tert-butylsulfonylmethyl)pyrimidin-2-yl]phenyl] carbamate

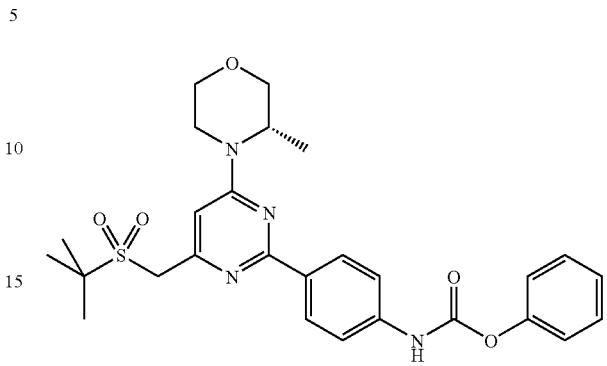

Phenyl chloroformate (0.227 mL, 1.81 mmol) was added to 4-[4-[(3S)-3-methylmorpholin-4-yl]-6-(tert-butylsulfonylmethyl)pyrimidin-2-yl]aniline (665 mg, 1.64 mmol) and sodium hydrogen carbonate (207 mg, 2.47 mmol) in dioxane (12 mL). The resulting slurry was stirred at RT for 1 hour. The mixture was partitioned between ethyl acetate and water. The organic solution was dried (MgSO₄) and concentrated under reduced pressure. The residue was chromatographed on silica, eluting with 25%-80% ethyl acetate in isohexane, to give the desired material as a yellow dry film (860 mg).

NMR Spectrum: $^1$H NMR (400 MHz, CDCl₃) δ 1.34 (3H, d), 1.44 (9H, s), 3.32 (1H, dt), 3.60 (1H, dt), 3.75 (1H, dd), 3.82 (1H, d), 4.04 (1H, dd), 4.20 (1H, d), 4.34 (2H, s), 4.46 (1H, br), 6.68 (1H, s), 7.10 (1H, s), 7.19-7.27 (3H, m), 7.40 (2H, t), 7.53 (2H, d), 8.37 (2H, d)

LCMS Spectrum: MH+ 525, retention time 2.69 min.

4-[4-[(3S)-3-Methylmorpholin-4-yl]-6-(tert-butylsulfonylmethyl)pyrimidin-2-yl]aniline

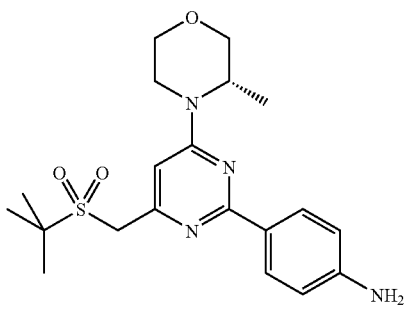

Dichlorobis(triphenylphosphine)-palladium(II) (63 mg, 0.09 mmol) was added to 2-chloro-4-[(3S)-3-methylmorpholin-4-yl]-6-(tert-butylsulfonylmethyl)pyrimidine (626 mg, 1.8 mmol), 4-(4,4,5,5-tetramethyl-1,3,2-dioxaborolan-2-yl) aniline (513 mg, 2.34 mmol) and 2M aqueous sodium carbonate (3.24 mL, 6.48 mmol) in DMF (3.75 mL), DME (5 mL), ethanol (5 mL) and water (12.5 mL) at RT under nitrogen. The reaction mixture was purged with nitrogen for 15 minutes and the resulting mixture was stirred at 80° C. for 16 hours. The mixture was partitioned between ethyl acetate and water. The organic solution was dried (MgSO₄), filtered, and concentrated under reduced pressure. The residue was chromatographed on silica, eluting with 25%-100% ethyl acetate in isohexane, to give the desired material as a yellow solid (681 mg).

NMR Spectrum: ¹H NMR (400 MHz, CDCl₃) δ 1.32 (3H, d), 1.43 (9H, s), 3.30 (1H, m), 3.60 (1H, m), 3.74 (1H, dd), 3.81 (1H, d), 3.89 (2H, s), 4.03 (1H, dd), 4.18 (1H, d), 4.31 (2H, d), 4.44 (1H, br), 6.61 (1H, s), 6.71 (2H, d), 8.21 (2H, d)

LCMS Spectrum: MH+ 405, retention time 1.98 min.

The preparation of 2-chloro-4-[(3S)-3-methylmorpholin-4-yl]-6-(tert-butylsulfonylmethyl)pyrimidine was described earlier.

EXAMPLE 67

1-[4-[4-[(3,5-Difluorophenyl)sulfonylmethyl]-6-[(3S)-3-methylmorpholin-4-yl]pyrimidin-2-yl]phenyl]-3-ethyl-urea

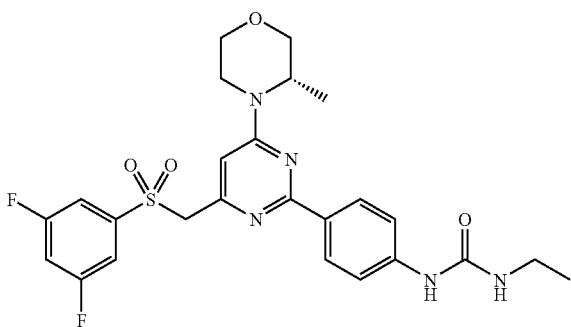

Phenyl N-[4-[4-[(3,5-difluorophenyl)sulfonylmethyl]-6-[(3S)-3-methylmorpholin-4-yl]pyrimidin-2-yl]phenyl]carbamate (120 mg, 0.207 mmol) was added to a mixture of ethylamine hydrochloride (86 mg, 1.03 mmol) and triethylamine (0.2 mL, 1.49 mmol) in DMF (1.5 mL) at RT. The reaction mixture was allowed to stand at RT for 65 hours. The crude product was purified by preparative HPLC using decreasingly polar mixtures of water (containing 1% ammonia) and acetonitrile as eluents, to give the desired material as a colourless solid (19.0 mg).

NMR Spectrum: ¹H NMR (399.9 MHz, DMSO-d₆) δ 1.07 (3H, t), 1.22 (3H, d), 3.09-3.3 (3H, m), 3.44-3.3 (1H, m), 3.61-3.67 (1H, m), 3.78 (1H, d), 3.94-4.01 (1H, m), 4.09-4.18 (1H, m), 4.41 (1H, br, s), 4.87 (2H, s), 6.16 (1H, t), 6.71 (1H, s), 7.40 (2H, d), 7.58-7.64 (2H, m), 7.72-7.83 (3H, m), 8.65 (1H, s).

LCMS Spectrum: MH+ 532, retention time 2.29 min.

The following compounds were made in an analogous fashion from either phenyl N-[4-[4-[(3,5-difluorophenyl)sulfonylmethyl]-6-[(3S)-3-methylmorpholin-4-yl]pyrimidin-2-yl]phenyl]carbamate or phenyl N-[4-[4-[2-(3,5-difluorophenyl)sulfonylpropan-2-yl]-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 67a | 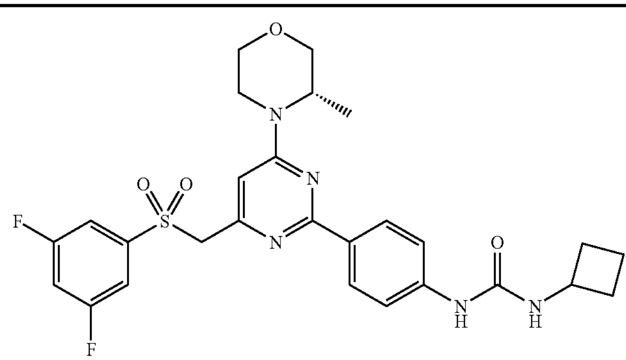 | 3-cyclobutyl-1-[4-[4-[(3,5-difluorophenyl)sulfonylmethyl]-6-[(3S)-3-methylmorpholin-4-yl]pyrimidin-2-yl]phenyl]urea | 558 | 2.51 |
| 67b | 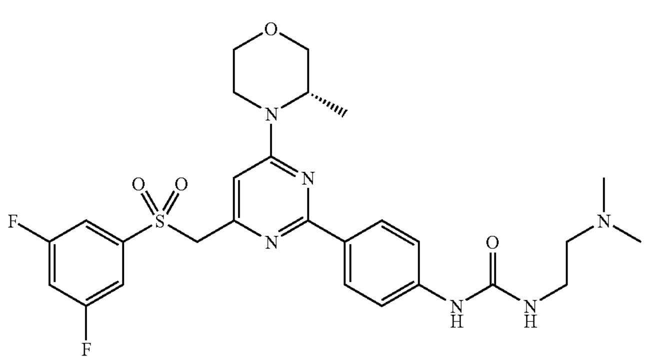 | 1-[4-[4-[(3,5-difluorophenyl)sulfonylmethyl]-6-[(3S)-3-methylmorpholin-4-yl]pyrimidin-2-yl]phenyl]-3-(2-dimethylaminoethyl)urea | 575 | 2.25 |

-continued

| Example | Structure | NAME | LCMS MH+ | Retention time (min) |
|---|---|---|---|---|
| 67c | 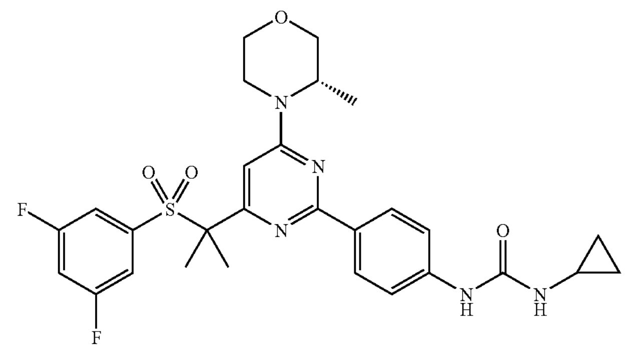 | 3-cyclopropyl-1-[4-[4-[2-(3,5-difluorophenyl)sulfonylpropan-2-yl]-6-[(3S)-3-methylmorpholin-4-yl]pyrimidin-2-yl]phenyl]urea | 572 | 2.60 |
| 67d | 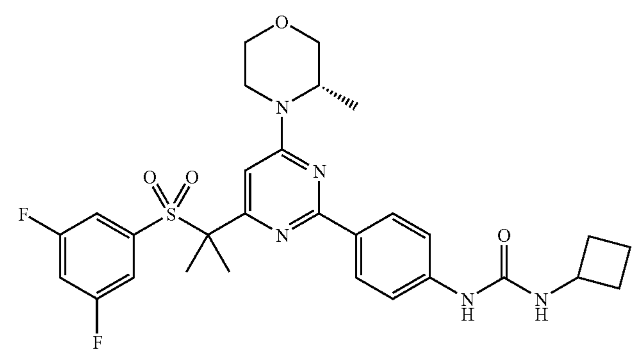 | 3-cyclobutyl-1-[4-[4-[2-(3,5-difluorophenyl)sulfonylpropan-2-yl]-6-[(3S)-3-methylmorpholin-4-yl]pyrimidin-2-yl]phenyl]urea | 586 | 2.81 |
| 67e | 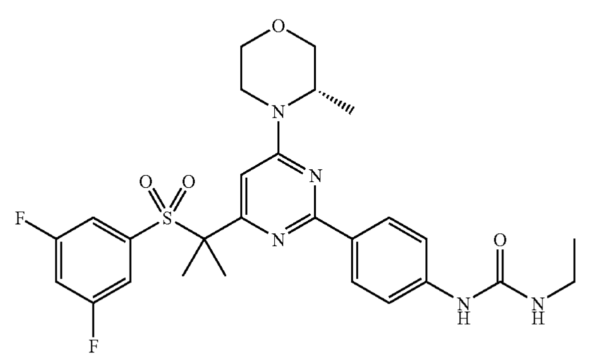 | 3-[4-[4-[2-(3,5-difluorophenyl)sulfonylpropan-2-yl]-6-[(3S)-3-methylmorpholin-4-yl]pyrimidin-2-yl]phenyl]-1-ethyl-urea | 560 | 2.59 |
| 67f | 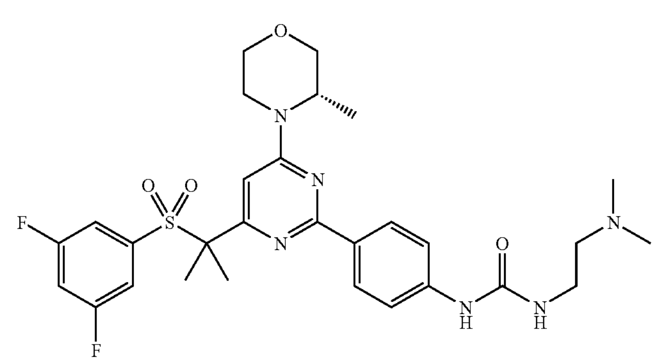 | 1-[4-[4-[2-(3,5-difluorophenyl)sulfonylpropan-2-yl]-6-[(3S)-3-methylmorpholin-4-yl]pyrimidin-2-yl]phenyl]-3-(2-dimethylaminoethyl)urea | 603 | 2.57 |

| Example | Structure | NAME | LCMS MH+ | Retention time (min) |
|---|---|---|---|---|
| 67g | 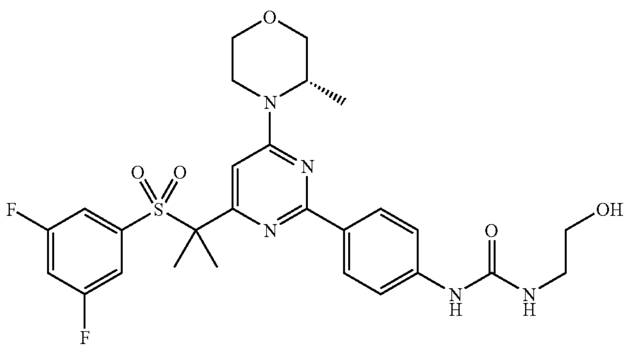 | 1-[4-[4-[2-(3,5-difluorophenyl)sulfonylpropan-2-yl]-6-[(3S)-3-methylmorpholin-4-yl]pyrimidin-2-yl]phenyl]-3-(2-hydroxyethyl)urea | 576 | 2.23 |
| 67h | 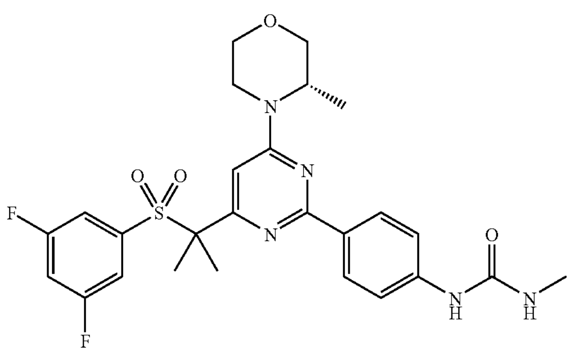 | 1-[4-[4-[2-(3,5-difluorophenyl)sulfonylpropan-2-yl]-6-[(3S)-3-methylmorpholin-4-yl]pyrimidin-2-yl]phenyl]-3-methyl-urea | 546 | 2.44 |

Example 67a: $^1$H NMR (399.9 MHz, DMSO-d$_6$) δ 1.22 (3H, d), 1.56-1.70 (2H, m), 1.80-1.94 (2H, m), 2.15-2.27 (2H, m), 3.14-3.24 (1H, m), 3.44-3.53 (1H, m), 3.61-3.67 (1H, m), 3.77 (1H, d), 3.95-4.02 (1H, m), 4.08-4.20 (2H, m), 4.41 (1H, br, s), 4.87 (2H, s), 6.46 (1H, d), 6.71 (1H, s), 7.38 (2H, d), 7.59-7.64 (2H, m), 7.72-7.83 (3H, m), 8.55 (1H, s).

Example 67b: $^1$H NMR (399.9 MHz, DMSO-d$_6$) δ 1.22 (3H, d), 2.19 (6H, s), 2.34 (2H, t), 3.14-3.23 (3H, m), 3.44-3.54 (1H, m), 3.62-3.66 (1H, m), 3.77 (1H, d), 3.94-4.00 (1H, m), 4.06-4.14 (1H, m), 4.41 (1H, br, s), 4.87 (2H, s), 6.16 (1H, t), 6.71 (1H, s), 7.39 (2H, d), 7.58-7.64 (2H, m), 7.74-7.83 (3H, m), 8.88 (1H, s).

Example 67c: $^1$H NMR (399.9 MHz, DMSO-d$_6$) δ 0.39-0.45 (2H, m), 0.62-0.69 (2H, m), 1.23 (3H, d), 1.82 (6H, s), 2.54-2.60 (1H, m), 3.13-3.22 (1H, m), 3.46-3.54 (1H, m), 3.62-3.68 (1H, m), 3.78 (1H, d), 3.95-4.00 (1H, m), 4.18 (1H, d), 4.59 (1H, br, s), 6.43 (1H, s), 6.71 (1H, s), 7.16-7.23 (2H, d), 7.41 (2H, d), 7.60-7.67 (1H, m), 7.84 (2H, d), 8.53 (1H, s).

Example 67d: $^1$H NMR (399.9 MHz, DMSO-d$_6$) δ 1.22 (3H, d), 1.56-1.69 (2H, m), 1.78-1.92 (8H, m), 2.17-2.26 (2H, m), 3.12-3.22 (1H, m), 3.46-3.53 (1H, m), 3.61-3.68 (1H, m), 3.78 (1H, d), 3.95-4.02 (1H, m), 4.10-4.22 (2H, m), 4.59 (1H, br, s), 6.46 (1H, d), 6.71 (1H, s), 7.15-7.23 (2H, m), 7.38 (2H, d), 7.60-7.68 (1H, m), 7.84 (2H, d), 8.55 (1H, s).

Example 67e: $^1$H NMR (399.9 MHz, DMSO-d$_6$) δ 1.08 (3H, t), 1.23 (3H, d), 1.83 (6H, s), 3.09-3.22 (3H, m), 3.50 (1H, t), 3.66 (1H, d), 3.78 (1H, d), 3.99 (1H, d), 4.19 (1H, d), 4.60 (1H, br, s), 6.16 (1H, s), 6.71 (1H, s), 7.21 (2H, s), 7.41 (2H, d), 7.59-7.69 (1H, m), 7.84 (2H, d), 8.65 (1H, s).

Example 67f: $^1$H NMR (400.13 MHz, DMSO-d$_6$) δ 1.22 (3H, d), 1.80-1.83 (6H, m), 2.18 (6H, s), 2.34 (2H, t), 3.12-3.23 (3H, m), 3.44-3.54 (1H, m), 3.63-3.67 (1H, m), 3.77 (1H, d), 3.94-4.01 (1H, m), 4.18 (1H, d), 4.59 (1H, br, s), 6.15 (1H, t), 6.70 (1H, s), 7.15-7.23 (2H, m), 7.39 (2H, d), 7.59-7.66 (1H, m), 7.84 (2H, d), 8.86 (1H, s).

Example 67g: $^1$H NMR (400.13 MHz, DMSO-d$_6$) δ 1.22 (3H, d), 1.80-1.83 (6H, m), 3.12-3.23 (3H, m), 3.40-3.53 (3H, m), 3.62-3.67 (1H, m), 3.77 (1H, d), 3.95-4.01 (1H, m), 4.18 (1H, d), 4.59 (1H, br, s), 4.73 (1H, t), 6.24 (1H, t), 6.70 (1H, s), 7.16-7.23 (2H, m), 7.39 (2H, d), 7.59-7.66 (1H, m), 7.84 (2H, d), 8.78 (1H, s).

Example 67h: $^1$H NMR (400.13 MHz, DMSO-d$_6$) δ 1.22 (3H, d), 1.82 (6H, s), 2.66 (3H, d), 3.12-3.22 (1H, m), 3.44-3.54 (1H, m), 3.60-3.68 (1H, m), 3.77 (1H, d), 3.93-4.00 (1H, m), 4.18 (1H, d), 4.58 (1H, br, s), 6.03-6.09 (1H, m), 6.70 (1H, s), 7.14-7.23 (2H, m), 7.40 (2H, d), 7.63 (1H, t), 7.83 (2H, d), 8.71 (1H, s).

The preparation of phenyl N-[4-[4-[2-(3,5-difluorophenyl)sulfonylpropan-2-yl]-6-[(3S)-3-methylmorpholin-4-yl]pyrimidin-2-yl]phenyl]carbamate is described below.

Phenyl N-[4-[4-[2-(3,5-difluorophenyl)sulfonylpropan-2-yl]-6-[(3S)-3-methylmorpholin-4-yl]pyrimidin-2-yl]phenyl]carbamate

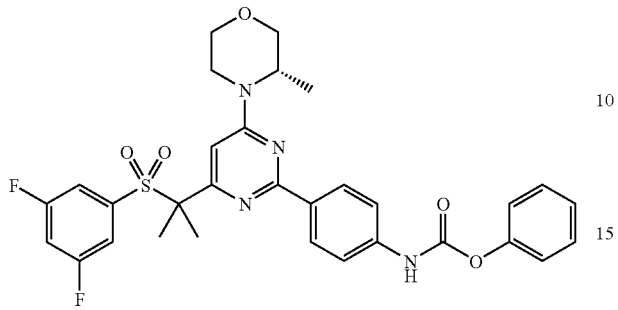

Phenyl chloroformate (0.413 mL, 3.29 mmol) was added to 4-[4-[2-(3,5-difluorophenyl)sulfonylpropan-2-yl]-6-[(3S)-3-methylmorpholin-4-yl]pyrimidin-2-yl]aniline (1.46 g, 2.99 mmol) and sodium hydrogen carbonate (0.377 g, 4.48 mmol) in dioxane (25 mL). The resulting slurry was stirred at RT for 1 hour. The mixture was partitioned between ethyl acetate and water. The organic solution was dried (MgSO$_4$), filtered, and concentrated under reduced pressure. The residue was chromatographed on silica, eluting with 25%-80% ethyl acetate in isohexane, to give a colourless gum. This material was triturated with diethyl ether to give the desired material as a colourless crystalline solid (1.808 g).

NMR Spectrum: $^1$H NMR (399.9 MHz, CDCl$_3$) δ 1.36 (3H, d), 1.89 (6H, s), 3.34 (1H, dt), 3.63 (1H, dt), 3.79 (1H, dd), 3.86 (1H, d), 4.08 (1H, dd), 4.14 (1H, d), 4.48-4.58 (1H, m), 6.66 (1H, s), 6.88-6.95 (1H, m), 7.04 (1H, s), 7.08-7.13 (2H, m), 7.19-7.28 (3H, m), 7.38-7.44 (4H, m), 7.98 (2H, d).

LCMS Spectrum: MH+ 609, retention time 3.26 min.

4-[4-[2-(3,5-Difluorophenyl)sulfonylpropan-2-yl]-6-[(3S)-3-methylmorpholin-4-yl]pyrimidin-2-yl]aniline

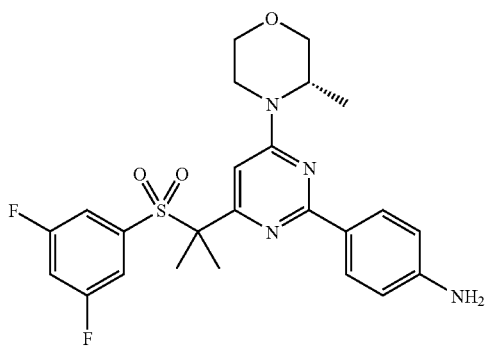

A stream of nitrogen was passed through a mixture of 2-chloro-4-[2-(3,5-difluorophenyl)sulfonylpropan-2-yl]-6-[(3S)-3-methylmorpholin-4-yl]pyrimidine (1.4 g, 3.24 mmol), 4-(4,4,5,5-tetramethyl-1,3,2-dioxaborolan-2-yl)aniline (0.923 g, 4.21 mmol) and 2M aqueous sodium carbonate (5.83 mL, 11.67 mmol) in DMF (6 mL), DME (5 mL), ethanol (5 mL) and water (12.5 mL) at RT. The reaction mixture was treated with dichlorobis(triphenylphosphine)palladium(II) (0.114 g, 0.16 mmol) and was stirred at 80° C. for 1 hour. The reaction mixture was diluted with ethyl acetate and washed with water. The organic solution was dried (MgSO$_4$) and concentrated under reduced pressure. The residue was chromatographed on silica, eluting with 25%-60% ethyl acetate in isohexane, to give the desired material as a pale yellow solid (1.496 g).

NMR Spectrum: $^1$H NMR (400 MHz, CDCl$_3$) δ 1.34 (3H, d), 1.88 (6H, s), 3.32 (1H, dt), 3.63 (1H, dt), 3.77 (1H, dd), 3.82 (1H, s), 3.86 (2H, s), 4.05 (1H, dd), 4.12 (1H, d), 4.46-4.54 (1H, m), 6.57-6.62 (3H, m), 6.88-6.93 (1H, m), 7.08-7.12 (2H, m), 7.82 (2H, d).

LCMS Spectrum: MH+ 489, retention time 2.77 min.

2-Chloro-4-[2-(3,5-difluorophenyl)sulfonylpropan-2-yl]-6-[(3S)-3-methylmorpholin-4-yl]pyrimidine

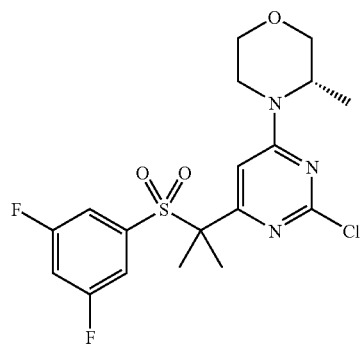

Sodium tert-butoxide (0.336 g, 3.49 mmol) was added to 2-chloro-4-[(3,5-difluorophenyl)sulfonylmethyl]-6-[(3S)-3-methylmorpholin-4-yl]pyrimidine (1.41 g, 3.49 mmol) in DMF (30 mL) at 0° C. under nitrogen. Iodomethane (0.217 mL, 3.49 mmol) was added and the resulting solution was stirred at 0° C. for 15 minutes. Sodium tert-butoxide (0.336 g, 3.49 mmol) was added followed by iodomethane (0.217 mL, 3.49 mmol) and the resulting solution was stirred at 0° C. for 1 hour. The reaction was poured into water (100 mL). The resulting precipitate was isolated by filtration and dried in vacuo, to give the desired product as a colourless solid (1.434 g).

NMR Spectrum: $^1$H NMR (399.9 MHz, CDCl$_3$) δ 1.34 (3H, d), 1.77 (6H, s), 3.32 (1H, dt), 3.58 (1H, dt), 3.72 (1H, dd), 3.81 (1H, d), 3.97-4.05 (2H, m), 4.36 (1H, br, s), 6.69 (1H, s), 7.07-7.16 (3H, m).

LCMS Spectrum: MH+ 432, 434, retention time 2.78 min.

2-Chloro-4-[(3,5-difluorophenyl)sulfonylmethyl]-6-[(3S)-3-methylmorpholin-4-yl]pyrimidine

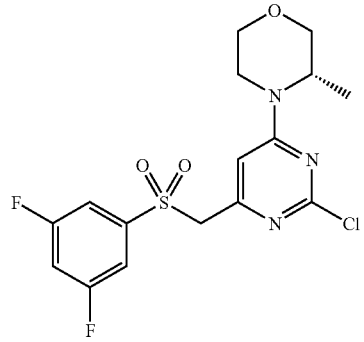

A solution of sodium tungstate dihydrate (199 mg, 0.60 mmol) in water (2 mL) was added to a stirred solution of 2-chloro-4-[(3,5-difluorophenyl)sulfanylmethyl]-6-[(3S)-3-methylmorpholin-4-yl]pyrimidine (11.23 g, 30.2 mmol) and 2M sulfuric acid (0.302 mL, 0.60 mmol) in dioxane (40 mL). Hydrogen peroxide (3.22 mL, 104.19 mmol) was added and the mixture was stirred at RT overnight. A precipitate was collected by filtration and dried in vacuo. The filtrate was partitioned between ethyl acetate and water. The organic solution was dried (MgSO$_4$) and concentrated under reduced pressure. The residue was chromatographed on silica, eluting with 5%-20% ethyl acetate in DCM, and the product obtained combined with the precipitated material to give the desired material as a near colourless solid (11.27 g).

NMR Spectrum: $^1$H NMR (400 MHz, CDCl$_3$) δ 1.34 (3H, s), 3.31 (1H, dt), 3.56 (1H, dt), 3.71 (1H, dd), 3.80 (1H, d), 3.98-4.10 (2H, m), 4.31 (2H, s), 6.55 (1H, s), 7.12 (1H, tt), 7.30-7.36 (2H, m).

LCMS Spectrum: MH+ 404,406, retention time 2.32 min.

2-Chloro-4-[(3,5-difluorophenyl)sulfanylmethyl]-6-[(3S)-3-methylmorpholin-4-yl]pyrimidine

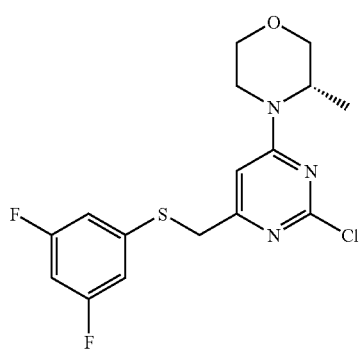

DIPEA (8.07 mL, 46.67 mmol) was added to 3,5-difluorobenzenethiol (5.00 g, 34.22 mmol), in DMF (55 mL) at RT under nitrogen. The resulting solution was stirred at RT for 20 minutes. 2-Chloro-4-(iodomethyl)-6-[(3S)-3-methylmorpholin-4-yl]pyrimidine (11.00 g, 31.11 mmol) was added to the reaction mixture in one portion. The mixture was stirred for 4 hours at RT. The reaction mixture was heated in a water bath at 60° C. for 1.5 hours before being partitioned between ethyl acetate and water. The organic solution was washed with further water, dried (MgSO$_4$), filtered and evaporated to afford the desired material as a gum (12.24 g).

NMR Spectrum: $^1$H NMR (399.9 MHz, CDCl$_3$) δ 1.27 (3H, d), 3.24 (1H, dt), 3.52 (1H, dt), 3.66 (1H, dd), 3.76 (1H, d), 3.96-4.04 (4H, m), 4.21 (1H, br, s), 6.41 (1H, s), 6.59-6.66 (1H, m), 6.80-6.86 (2H, m).

LCMS Spectrum: MH+ 372, 374, retention time 2.66 min.

The preparation of 2-chloro-4-(iodomethyl)-6-[(3S)-3-methylmorpholin-4-yl]pyrimidine was described earlier.

The preparation of phenyl N-[4-[4-[(3,5-difluorophenyl)sulfonylmethyl]-6-[(3S)-3-methylmorpholin-4-yl]pyrimidin-2-yl]phenyl]carbamate is described below.

Phenyl N-[4-[4-[(3,5-difluorophenyl)sulfonylmethyl]-6-[(3S)-3-methylmorpholin-4-yl]pyrimidin-2-yl]phenyl]carbamate

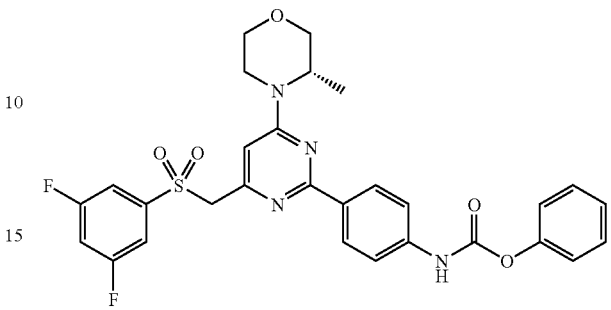

Phenyl chloroformate (0.208 mL, 1.66 mmol) was added to 4-[4-[(3,5-difluorophenyl)sulfonylmethyl]-6-[(3S)-3-methylmorpholin-4-yl]pyrimidin-2-yl]aniline (693 mg, 1.50 mmol) and sodium hydrogen carbonate (190 mg, 2.26 mmol) in dioxane (10 mL). The resulting slurry was stirred at RT for 1 hour. The mixture was partitioned between ethyl acetate and water. The organic solution was dried (MgSO$_4$) and concentrated under reduced pressure. The residue was chromatographed on silica, eluting with 25%-80% ethyl acetate in isohexane, to give the desired product as a yellow dry film (827 mg).

NMR Spectrum: $^1$H NMR (399.9 MHz, CDCl$_3$) δ 1.35 (3H, d), 3.33 (1H, dt), 3.61 (1H, dt), 3.76 (1H, dd), 3.83 (1H, d), 4.16 (1H, d), 4.38-4.48 (3H, m), 6.48 (1H, s), 6.98-7.08 (2H, m), 7.19-7.28 (4H, m), 7.32-7.47 (5H, m), 8.02 (2H, d).

LCMS Spectrum: MH+ 581, retention time 2.91 min.

4-[4-[(3,5-Difluorophenyl)sulfonylmethyl]-6-[(3S)-3-methylmorpholin-4-yl]pyrimidin-2-yl]aniline

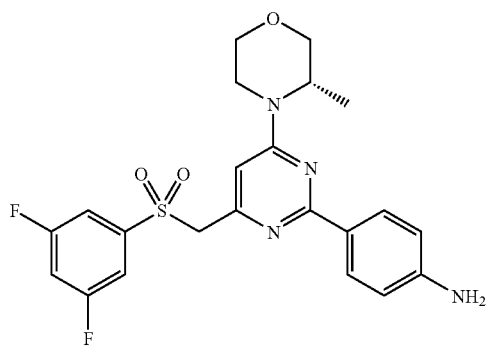

A stream of nitrogen was passed through 2-chloro-4-[(3,5-difluorophenyl)sulfonylmethyl]-6-[(3S)-3-methylmorpholin-4-yl]pyrimidine (0.727 g, 1.8 mmol), 4-(4,4,5,5-tetramethyl-1,3,2-dioxaborolan-2-yl)aniline (0.513 g, 2.34 mmol) and 2M aqueous sodium carbonate (3.24 mL, 6.48 mmol) in DMF (3.75 mL), DME (5 mL), ethanol (5 mL) and water (12.5 mL) for 15 minutes. The reaction mixture was treated with dichlorobis(triphenylphosphine)palladium(II) (0.063 g, 0.09 mmol) and the mixture was stirred at 80° C. for 16 hours. The mixture was partitioned between ethyl acetate and water. The organic solution was dried (MgSO$_4$) and concentrated under reduced pressure. The residue was chromatographed on silica, eluting with 25%-60% ethyl acetate in isohexane, to give the desired product as a yellow solid (0.735 g).

NMR Spectrum: ¹H NMR (400 MHz, CDCl₃) δ 1.33 (3H, t), 3.31 (1H, dt), 3.60 (1H, dt), 3.75 (1H, dd), 3.80-3.93 (3H, m), 4.01-4.08 (1H, dd), 4.15 (1H, d), 4.40 (3H, s), 6.40 (1H, s), 6.62 (2H, d), 7.01 (1H, tt), 7.32-7.38 (2H, m), 7.85 (2H, d).

LCMS Spectrum: MH+ 461, retention time 2.46 min.

The preparation of 2-chloro-4-[(3,5-difluorophenyl)sulfonylmethyl]-6-[(3S)-3-methylmorpholin-4-yl]pyrimidine was described earlier.

EXAMPLE 68

1-[4-[4-(2-Cyclohexylsulfonylpropan-2-yl)-6-[(3S)-3-methylmorpholin-4-yl]pyrimidin-2-yl]phenyl]-3-cyclopropyl-urea

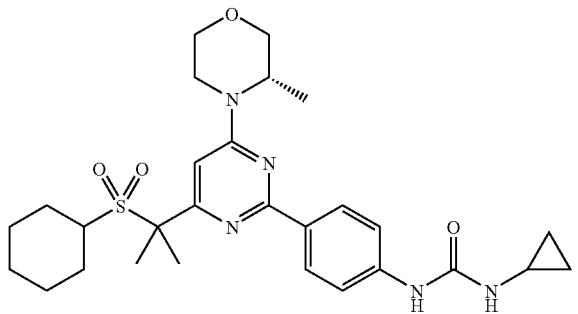

To a solution of cyclopropylamine (53 mg, 0.93 mmol) in DMF (2 mL) was added triethylamine (0.09 mL, 0.64 mmol) followed by phenyl N-[4-[4-(2-cyclohexylsulfonylpropan-2-yl)-6-[(3S)-3-methylmorpholin-4-yl]pyrimidin-2-yl]phenyl]carbamate (118 mg, 0.20 mmol). The resultant mixture was heated to 50° C. and stirred for 2 hours. The reaction mixture was cooled and diluted with further DMF (1 mL) before purifying crude reaction mixture by preparative HPLC, using decreasingly polar mixtures of water (containing 1% aq. ammonia solution) and acetonitrile as eluents, to give the desired material as a white solid (75 mg).

NMR Spectrum: ¹H NMR (400.132 MHz, DMSO-d₆) δ 0.40-0.44 (2H, m), 0.63-0.67 (2H, m), 1.00-1.19 (3H, m), 1.22 (3H, d), 1.24-1.37 (2H, m), 1.47-1.53 (1H, m), 1.64-1.82 (10H, m), 2.53-2.59 (1H, m), 3.20 (1H, td), 3.50 (1H, td), 3.65 (1H, dd), 3.71-3.78 (2H, m), 3.98 (1H, dd), 4.23 (1H, d), 4.56-4.62 (1H, m), 6.44 (1H, d), 6.75 (1H, s), 7.52 (2H, d), 8.25 (2H, d), 8.55 (1H, s).

LCMS Spectrum: MH+ 542, retention time 2.37 min.

The following compounds were made in an analogous fashion from either phenyl N-[4-[4-(2-cyclohexylsulfonylpropan-2-yl)-6-[(3S)-3-methylmorpholin-4-yl]pyrimidin-2-yl]phenyl]carbamate or phenyl N-[4-[4-(cyclohexylsulfonylmethyl)-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 68a | 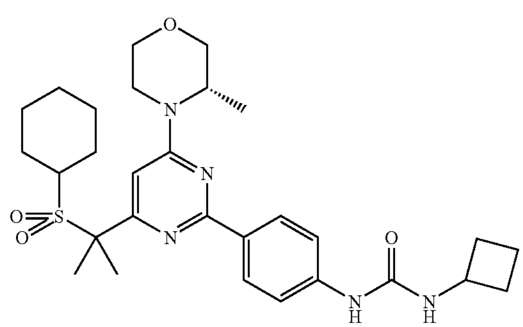 | 3-cyclobutyl-1-[4-[4-(2-cyclohexylsulfonylpropan-2-yl)-6-[(3S)-3-methylmorpholin-4-yl]pyrimidin-2-yl]phenyl]urea | 556 | 2.59 |
| 68b | 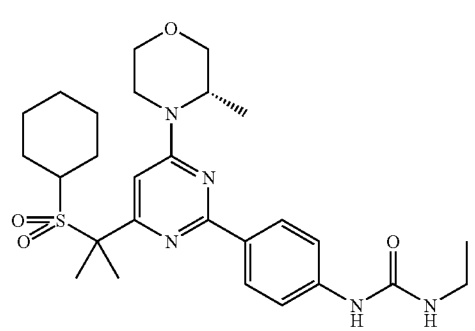 | 3-[4-[4-(2-cyclohexylsulfonylpropan-2-yl)-6-[(3S)-3-methylmorpholin-4-yl]pyrimidin-2-yl]phenyl]-1-ethyl-urea | 530 | 2.35 |

-continued

| Example | Structure | NAME | LCMS MH+ | Retention time (min) |
|---|---|---|---|---|
| 68c | 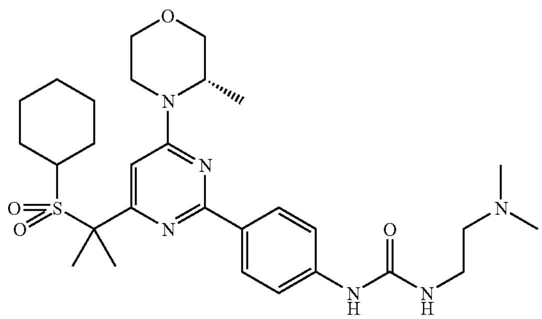 | 1-[4-[4-(2-cyclohexylsulfonylpropan-2-yl)-6-[(3S)-3-methylmorpholin-4-yl]pyrimidin-2-yl]phenyl]-3-(2-dimethylaminoethyl)urea | 573 | 2.26 |
| 68d | 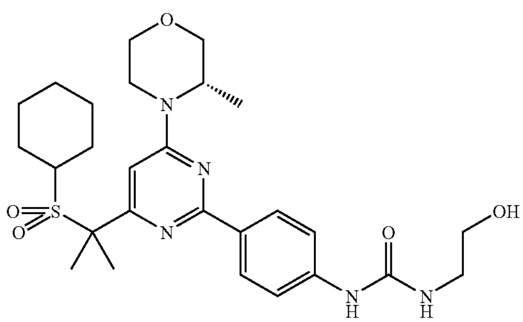 | 1-[4-[4-(2-cyclohexylsulfonylpropan-2-yl)-6-[(3S)-3-methylmorpholin-4-yl]pyrimidin-2-yl]phenyl]-3-(2-hydroxyethyl)urea | 546 | 1.99 |
| 68e | 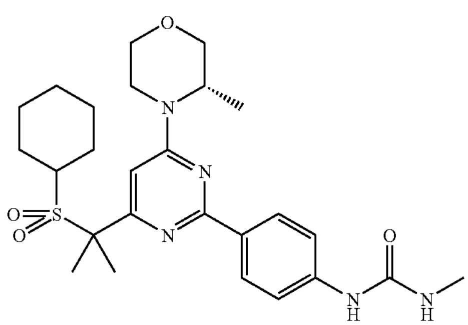 | 1-[4-[4-(2-cyclohexylsulfonylpropan-2-yl)-6-[(3S)-3-methylmorpholin-4-yl]pyrimidin-2-yl]phenyl]-3-methyl-urea | 516 | 2.19 |
| 68f | 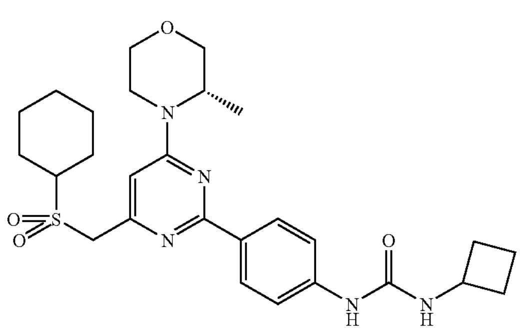 | 3-cyclobutyl-1-[4-[4-(cyclohexylsulfonylmethyl)-6-[(3S)-methylmorpholin-4-yl]pyrimidin-2-yl]phenyl]urea | 529 | 2.57 |

-continued

| Example | Structure | NAME | LCMS MH+ | Retention time (min) |
|---|---|---|---|---|
| 68g | 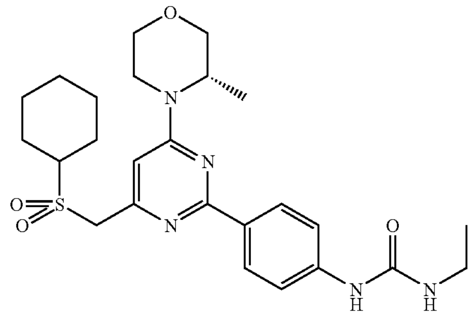 | 3-[4-[4-(cyclohexylsulfonylmethyl)-6-[(3S)-3-methylmorpholin-4-yl]pyrimidin-2-yl]phenyl]-1-ethyl-urea | 503 | 2.32 |
| 68h | 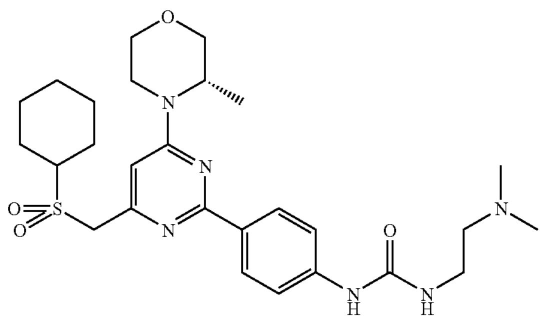 | 1-[4-[4-(cyclohexylsulfonylmethyl)-6-[(3S)-3-methylmorpholin-4-yl]pyrimidin-2-yl]phenyl]-3-(2-dimethylaminoethyl)urea | 545 | 2.25 |

Example 68a: $^1$H NMR (400.132 MHz, DMSO-d$_6$) δ 1.02-1.18 (3H, m), 1.22 (3H, d), 1.25-1.35 (2H, m), 1.47-1.53 (1H, m), 1.57-1.91 (14H, m), 2.18-2.25 (2H, m), 3.20 (1H, td), 3.50 (1H, td), 3.65 (1H, dd), 3.70-3.78 (2H, m), 3.98 (1H, dd), 4.11-4.26 (2H, m), 4.55-4.61 (1H, m), 6.48 (1H, d), 6.75 (1H, s), 7.49 (2H, d), 8.24 (2H, d), 8.58 (1H, s).

Example 68b: $^1$H NMR (400.132 MHz, DMSO-d$_6$) δ 0.99-1.17 (6H, m), 1.22 (3H, d), 1.25-1.36 (2H, m), 1.47-1.53 (1H, m), 1.64-1.84 (10H, m), 3.10-3.16 (2H, m), 3.20 (1H, td), 3.50 (1H, td), 3.65 (1H, dd), 3.71-3.78 (2H, m), 3.98 (1H, dd), 4.23 (1H, d), 4.55-4.62 (1H, m), 6.17 (1H, t), 6.75 (1H, s), 7.51 (2H, d), 8.25 (2H, d), 8.68 (1H, s).

Example 68c: $^1$H NMR (400.132 MHz, DMSO-d$_6$) δ 0.99-1.19 (3H, m), 1.22 (3H, d), 1.25-1.37 (2H, m), 1.48-1.53 (1H, m), 1.64-1.84 (10H, m), 2.18 (6H, s), 2.34 (2H, t), 3.17-3.24 (3H, m), 3.50 (1H, td), 3.65 (1H, dd), 3.70-3.78 (2H, m), 3.98 (1H, dd), 4.23 (1H, d), 4.56-4.62 (1H, m), 6.17 (1H, t), 6.75 (1H, s), 7.50 (2H, d), 8.25 (2H, d), 8.91 (1H, s).

Example 68d: $^1$H NMR (400.132 MHz, DMSO-d$_6$) δ 0.99-1.18 (3H, m), 1.22 (3H, d), 1.25-1.37 (2H, m), 1.47-1.53 (1H, m), 1.63-1.84 (10H, m), 3.16-3.24 (3H, m), 3.44-3.53 (3H, m), 3.65 (1H, dd), 3.70-3.78 (2H, m), 3.98 (1H, dd), 4.23 (1H, d), 4.56-4.63 (1H, m), 4.73 (1H, t), 6.26 (1H, t), 6.75 (1H, s), 7.50 (2H, d), 8.25 (2H, d), 8.82 (1H, s).

Example 68e: $^1$H NMR (400.132 MHz, DMSO-d$_6$) δ 1.00-1.18 (3H, m), 1.22 (3H, d), 1.25-1.36 (2H, m), 1.47-1.52 (1H, m), 1.64-1.84 (10H, m), 2.66 (3H, d), 3.20 (1H, td), 3.50 (1H, td), 3.65 (1H, dd), 3.71-3.78 (2H, m), 3.98 (1H, dd), 4.23 (1H, d), 4.56-4.61 (1H, m), 6.08 (1H, q), 6.75 (1H, s), 7.52 (2H, d), 8.25 (2H, d), 8.76 (1H, s).

Example 68f: $^1$H NMR (400.132 MHz, DMSO-d$_6$) δ 1.18-1.31 (6H, m), 1.41-1.49 (2H, m), 1.57-1.69 (3H, m), 1.82-1.92 (4H, m), 2.18-2.28 (4H, m), 3.22 (1H, td), 3.34 (1H, tt), 3.50 (1H, td), 3.65 (1H, dd), 3.78 (1H, d), 3.99 (1H, dd), 4.09-4.22 (2H, m), 4.40-4.51 (3H, m), 6.48 (1H, d), 6.77 (1H, d), 7.48 (2H, d), 8.19 (2H, d), 8.58 (1H, s).

Example 68g: $^1$H NMR (400.132 MHz, DMSO-d$_6$) δ 1.07 (3H, t), 1.15-1.33 (6H, m), 1.39-1.50 (2H, m), 1.65-1.71 (1H, m), 1.86-1.92 (2H, m), 2.21-2.28 (2H, m), 3.09-3.16 (2H, m), 3.22 (1H, td), 3.34 (1H, tt), 3.50 (1H, td), 3.65 (1H, dd), 3.78 (1H, d), 3.99 (1H, dd), 4.13-4.21 (1H, m), 4.40-4.51 (3H, m), 6.18 (1H, t), 6.77 (1H, s), 7.50 (2H, d), 8.20 (2H, d), 8.68 (1H, s).

Example 68h: $^1$H NMR (400.132 MHz, DMSO-d$_6$) δ 1.16-1.33 (6H, m), 1.39-1.50 (2H, m), 1.65-1.71 (1H, m), 1.86-1.92 (2H, m), 2.18 (6H, s), 2.21-2.27 (2H, m), 2.34 (2H, t), 3.17-3.26 (3H, m), 3.34 (1H, tt), 3.50 (1H, td), 3.65 (1H, dd), 3.78 (1H, d), 3.99 (1H, dd), 4.14-4.21 (1H, m), 4.40-4.51 (3H, m), 6.18 (1H, t), 6.77 (1H, s), 7.49 (2H, d), 8.20 (2H, d), 8.90 (1H, s).

The preparation of phenyl N-[4-[4-(2-cyclohexylsulfonyl-propan-2-yl)-6-[(3S)-3-methylmorpholin-4-yl]pyrimidin-2-yl]phenyl]carbamate is described below.

Phenyl N-[4-[4-(2-cyclohexylsulfonylpropan-2-yl)-6-[(3S)-3-methylmorpholin-4-yl]pyrimidin-2-yl] phenyl]carbamate

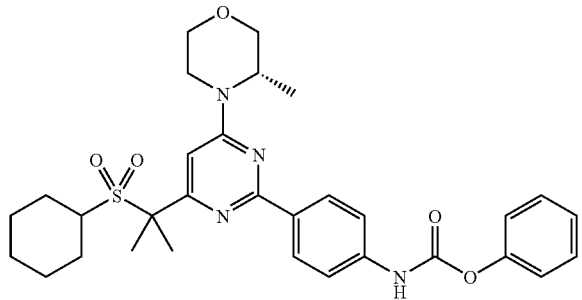

To a solution of 4-[4-(2-cyclohexylsulfonylpropan-2-yl)-6-[(3S)-3-methylmorpholin-4-yl]pyrimidin-2-yl]aniline (1.1 g, 2.40 mmol) in 1,4-dioxane (12 mL) was added sodium bicarbonate (0.302 g, 3.60 mmol). Phenyl chloroformate (0.316 mL, 2.52 mmol) was then added dropwise and the resulting mixture was stirred at RT for 3 hours. The resulting mixture was evaporated to dryness and the residue partitioned between water (10 mL) and DCM (10 mL). The organic layer was separated and evaporated to dryness. The residue was triturated with diethyl ether to give the desired material as a solid (1.328 g).

NMR Spectrum: $^1$H NMR (400.132 MHz, DMSO-$d_6$) δ 0.99-1.18 (3H, m), 1.20-1.37 (5H, m), 1.46-1.52 (1H, m), 1.63-1.83 (10H, m), 3.21 (1H, td), 3.51 (1H, td), 3.65 (1H, dd), 3.69-3.79 (3H, m), 3.98 (1H, dd), 4.21-4.28 (1H, m), 4.56-4.64 (1H, m), 7.24-7.30 (3H, m), 7.45 (2H, t), 7.65 (2H, d), 8.36 (2H, d), 10.43 (1H, s).

LCMS Spectrum: MH+ 579, retention time 3.11 min.

4-[4-(2-Cyclohexylsulfonylpropan-2-yl)-6-[(3S)-3-methylmorpholin-4-yl]pyrimidin-2-yl]aniline

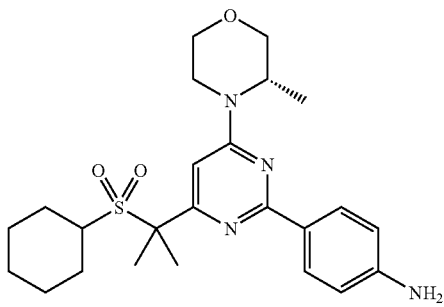

A mixture of 2-chloro-4-(2-cyclohexylsulfonylpropan-2-yl)-6-[(3S)-3-methylmorpholin-4-yl]pyrimidine (1.18 g, 2.94 mmol), 2M aqueous sodium carbonate solution (5.5 mL, 11.00 mmol) and 4-(4,4,5,5-tetramethyl-1,3,2-dioxaborolan-2-yl)aniline (0.907 g, 4.14 mmol) in a mixture of DMF (5 mL), water (12.50 mL), ethanol (5.00 mL) and DME (5.00 mL) was purged with nitrogen for 10 minutes before being treated with bis(triphenylphosphine)palladium(II) chloride (0.111 g, 0.16 mmol). The stirred mixture was heated to 80° C. and stirred under nitrogen for 2.5 hours. The reaction mixture was cooled and treated with ethyl acetate (50 mL) and water (50 mL). The organic layer was separated and the aqueous re-extracted with ethyl acetate (2×30 mL). The combined organics were washed with brine, dried (MgSO$_4$) and evaporated to afford the crude product, which was purified by flash silica chromatography, elution gradient 25 to 75% ethyl acetate in isohexane, to give the desired material (1.130 g).

NMR Spectrum: $^1$H NMR (400.132 MHz, DMSO-$d_6$) δ 0.99-1.23 (6H, m), 1.25-1.36 (2H, m), 1.47-1.53 (1H, m), 1.65-1.83 (10H, m), 3.18 (1H, td), 3.49 (1H, td), 3.64 (1H, dd), 3.73-3.81 (2H, m), 3.97 (1H, dd), 4.19 (1H, d), 4.52-4.58 (1H, m), 5.54-5.57 (2H, m), 6.62 (2H, d), 6.64 (1H, s), 8.08 (2H, d).

LCMS Spectrum: MH+ 459, retention time 2.56 min.

2-Chloro-4-(2-cyclohexylsulfonylpropan-2-yl)-6-[(3S)-3-methylmorpholin-4-yl]pyrimidine

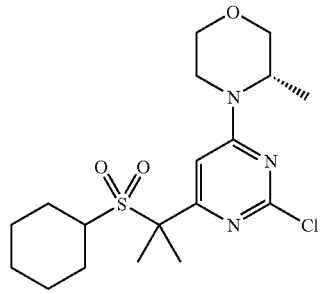

A cooled (ice/water bath) solution of 2-chloro-4-(cyclohexylsulfonylmethyl)-6-[(3S)-3-methylmorpholin-4-yl]pyrimidine (1.26 g, 3.37 mmol) in DMF (16 mL) was treated with sodium tert-butoxide (0.324 g, 3.37 mmol). The mixture was stirred at 0° C. for 5 minutes. Iodomethane (0.210 mL, 3.37 mmol) was then added and mixture stirred at 0° C. for a further 10 minutes. Further sodium tert-butoxide (0.324 g, 3.37 mmol) was then added and stirring continued for a further 5 minutes before addition of more iodomethane (0.210 mL, 3.37 mmol). The resultant mixture was stirred at 0° C. for a further 15 minutes. The cooling bath was then removed and reaction allowed to warm, with stirring to RT. Water (75 mL) was added to reaction mixture and resultant precipitate collected by suction filtration, washed with more water (40 mL) and dried to afford the desired material (1.180 g).

NMR Spectrum: $^1$H NMR (400.132 MHz, DMSO-$d_6$) δ 1.04-1.15 (1H, m), 1.19-1.37 (7H, m), 1.54-1.60 (1H, m), 1.69 (6H, s), 1.70-1.80 (4H, m), 3.17-3.25 (1H, m), 3.45 (1H, td), 3.52-3.62 (2H, m), 3.72 (1H, d), 3.94 (1H, dd), 4.07 (1H, d), 4.39-4.48 (1H, m), 6.89 (1H, s).

LCMS Spectrum: MH+ 402, retention time 2.72 min.

2-Chloro-4-(cyclohexylsulfonylmethyl)-6-[(3S)-3-methylmorpholin-4-yl]pyrimidine

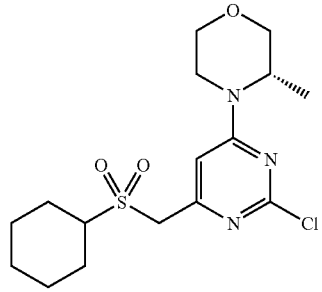

To a cooled (ice/water bath) solution of 2,4-dichloro-6-(cyclohexylsulfonylmethyl)pyrimidine (1.65 g, 5.34 mmol) in DCM (25 mL) was added triethylamine (0.820 mL, 5.88 mmol). The resulting solution was treated, dropwise over 8 minutes, with a solution of (3S)-3-methylmorpholine (609 mg, 6.02 mmol) in DCM (5 mL). The mixture was stirred at 6° C. for 30 minutes. The cooling bath was then removed and reaction mixture left to stir overnight. Water (25 mL) was then added and reaction mixture stirred for 5 minutes. The organic layer was then separated, dried (MgSO$_4$) and evaporated to give a crude brown oil, which was purified by flash silica chromatography, elution gradient 25 to 75% ethyl acetate in isohexane, to give the desired material (1.440 g).

NMR Spectrum: $^1$H NMR (400.132 MHz, DMSO-d$_6$) δ 1.15-1.45 (8H, m), 1.63-1.68 (1H, m), 1.81-1.87 (2H, m), 2.11-2.17 (2H, m), 3.15-3.25 (2H, m), 3.45 (1H, td), 3.60 (1H, dd), 3.73 (1H, d), 3.92-4.01 (2H, m), 4.30 (1H, br s), 4.39 (2H, s), 6.90 (1H, s).

LCMS Spectrum: MH+ 374, retention time 2.24 min.

2,4-Dichloro-6-(cyclohexylsulfonylmethyl)pyrimidine

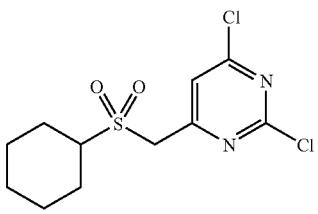

To a stirred solution of 2,4-dichloro-6-(cyclohexylsulfanylmethyl)pyrimidine (1.53 g, 5.52 mmol) in DCM (28 mL) was added, portionwise, 3-chloroperoxybenzoic acid (3.09 g, 13.80 mmol) over a period of 20 minutes under nitrogen, so as to control temperature below 28° C. The resulting suspension was stirred at RT for 3 hours then saturated aqueous sodium hydrogen carbonate solution (40 mL) added and the reaction mixture stirred for 5 minutes. The organic layer was then separated, dried (MgSO$_4$) and evaporated to dryness. The resultant solid was redissolved in DCM (40 mL) and saturated aqueous sodium hydrogen carbonate solution (40 mL) added. The mixture was stirred for 15 minutes before separating organic layer, drying over (MgSO$_4$) and evaporating to afford the desired material (1.650 g).

NMR Spectrum: $^1$H NMR (400.132 MHz, DMSO-d$_6$) δ 1.12-1.46 (5H, m), 1.61-1.69 (1H, m), 1.80-1.88 (2H, m), 2.10-2.17 (2H, m), 3.22 (1H, tt), 4.73 (2H, s), 7.85 (1H, s).

LCMS Spectrum: M−H-307, retention time 2.26 min.

2,4-Dichloro-6-(cyclohexylsulfanylmethyl)pyrimidine

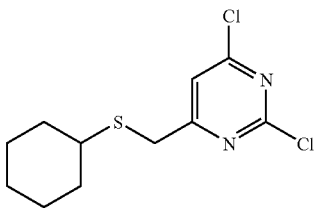

A suspension of 6-(cyclohexylsulfanylmethyl)-1H-pyrimidine-2,4-dione (3.6 g, 14.98 mmol) in phosphorus oxychloride (15 mL, 160.93 mmol) was warmed to 100° C., over a period of 15 minutes. The resulting dark orange solution was stirred at 100° C. for 7 hours. The reaction mixture was then cooled before evaporating to a viscous brown oil which was partitioned between DCM (20 mL) and iced water (20 mL). Solid sodium hydrogen carbonate was then added carefully and portionwise, over 30 minutes so as to control effervescence. Further aliquots of water (30 mL) and DCM were added during addition. Once effervescence had ceased and pH had been adjusted to 8, mixture was transferred to a separating funnel and organic layer separated. The aqueous layer was re-extracted with DCM (2×50 mL) and the combined organic layers washed with brine (100 mL), dried (MgSO$_4$) and evaporated to afford crude product, which was purified by flash silica chromatography, elution gradient 10 to 40% ethyl acetate in isohexane, to give the desired material (1.60 g).

NMR Spectrum: $^1$H NMR (400.132 MHz, DMSO-d$_6$) δ 1.18-1.31 (5H, m), 1.51-1.58 (1H, m), 1.63-1.71 (2H, m), 1.86-1.93 (2H, m), 2.70-2.77 (1H, m), 3.85 (2H, s), 7.81 (1H, s).

LCMS Spectrum: M−H-275, retention time 3.04 min.

6-(Cyclohexylsulfanylmethyl)-1H-pyrimidine-2,4-dione

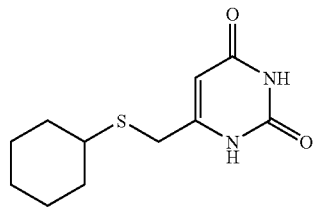

A solution of cyclohexanethiol (10 mL, 81.74 mmol) in DMF (150 mL) was treated with 1,8-diazabicyclo[5.4.0]undec-7-ene (14 mL, 93.80 mmol). The resulting solution was stirred at RT for 20 minutes. 6-(chloromethyl)pyrimidine-2,4(1H,3H)-dione (10 g, 62.28 mmol) was then added, portionwise, over a period of 30 minutes, under nitrogen, so as to maintain the internal temperature below 35° C. The resulting solution was stirred at RT overnight. The reaction mixture was then evaporated to dryness and the residue was partitioned between DCM (100 mL) and water (150 mL). On mixing a precipitate formed, this was removed by suction filtration, and dried under vacuum, at 55° C. for 2 hours to afford the desired material (6.45 g). Additional desired material (3.62 g) was obtained by adjusting the filtrate to pH2 by the dropwise addition of 2M hydrochloric acid and removing the precipitate, washing the precipitate with water (100 mL) and drying in a vacuum oven.

NMR Spectrum: $^1$H NMR (400.132 MHz, DMSO-d$_6$) δ 1.16-1.34 (5H, m), 1.51-1.58 (1H, m), 1.63-1.72 (2H, m), 1.87-1.96 (2H, m), 2.65-2.72 (1H, m), 3.41 (2H, s), 5.49 (1H, s), 10.75-10.96 (2H, m).

LCMS Spectrum: MH+ 241, retention time 0.99 min.

The preparation of phenyl N-[4-[4-(cyclohexylsulfonylmethyl)-6-[(3S)-3-methylmorpholin-4-yl]pyrimidin-2-yl]phenyl]carbamate is described below.

Phenyl N-[4-[4-(cyclohexylsulfonylmethyl)-6-[(3S)-3-methylmorpholin-4-yl]pyrimidin-2-yl]phenyl]carbamate

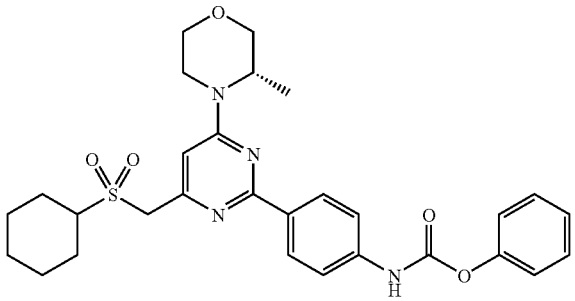

Sodium bicarbonate (113 mg, 1.35 mmol) was added to a solution of 4-[4-(cyclohexylsulfonylmethyl)-6-[(3S)-3-methylmorpholin-4-yl]pyrimidin-2-yl]aniline (370 mg, 0.86 mmol) in 1,4-dioxane (5 mL). Phenyl chloroformate (0.124 mL, 0.99 mmol) was added dropwise and the resultant mixture was stirred at RT for 5 hours. The resulting mixture was evaporated to dryness and the residue partitioned between DCM (5 mL) and water (5 mL). The organic layer was separated and evaporated to dryness. The crude residue was triturated with diethyl ether to give the desired material (429 mg).

NMR Spectrum: $^1$H NMR (400.132 MHz, DMSO-d$_6$) δ 1.16-1.33 (6H, m), 1.40-1.50 (2H, m), 1.64-1.70 (1H, m), 1.85-1.92 (2H, m), 2.21-2.28 (2H, m), 3.19-3.36 (2H, m), 3.50 (1H, td), 3.65 (1H, dd), 3.78 (1H, d), 3.99 (1H, dd), 4.16-4.23 (1H, m), 4.43-4.52 (3H, m), 6.81 (1H, s), 7.24-7.30 (3H, m), 7.43-7.47 (2H, m), 7.63 (2H, d), 8.30 (2H, d), 10.44 (1H, s).

LCMS Spectrum: MH+ 551, retention time 2.88 min.

4-[4-(Cyclohexylsulfonylmethyl)-6-[(3S)-3-methylmorpholin-4-yl]pyrimidin-2-yl]aniline

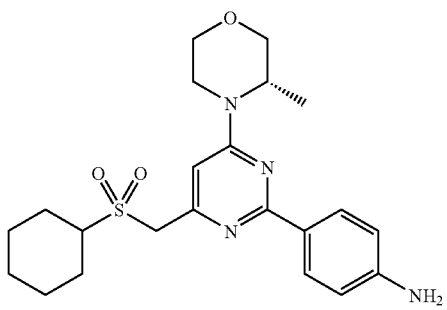

A mixture of 2-chloro-4-(cyclohexylsulfonylmethyl)-6-[(3S)-3-methylmorpholin-4-yl]pyrimidine (437 mg, 1.17 mmol), 4-(4,4,5,5-tetramethyl-1,3,2-dioxaborolan-2-yl)aniline (381 mg, 1.74 mmol) and 2M aqueous sodium carbonate solution (0.60 mL, 1.20 mmol) in a mixture of DMF (2 mL), ethanol (2 mL), water (5 mL) and DME (2 mL) was purged with nitrogen for 5 minutes before addition of bis(triphenylphosphine)palladium(II) chloride (41.0 mg, 0.06 mmol). The reaction mixture was heated to 80° C., under nitrogen, and stirred for 3.5 hours. The reaction mixture was cooled and partitioned between ethyl acetate (25 mL) and water (30 mL). The organic layer was separated and aqueous re-extracted with ethyl acetate (2×25 mL). The combined organic extracts were washed with saturated brine (50 mL), dried (MgSO$_4$), filtered and evaporated to afford crude product, which was purified by flash silica chromatography, elution gradient 25 to 75% ethyl acetate in isohexane, to give the desired material (402 mg).

NMR Spectrum: $^1$H NMR (400.132 MHz, DMSO-d$_6$) δ 1.16-1.32 (6H, m), 1.38-1.50 (2H, m), 1.64-1.70 (1H, m), 1.85-1.92 (2H, m), 2.20-2.27 (2H, m), 3.19 (1H, td), 3.31-3.40 (1H, m), 3.48 (1H, td), 3.64 (1H, dd), 3.77 (1H, d), 3.97 (1H, dd), 4.10-4.18 (1H, m), 4.38 (2H, s), 4.40-4.48 (1H, m), 5.57 (2H, s), 6.61 (2H, d), 6.66 (1H, s), 8.04 (2H, d).

LCMS Spectrum: MH+ 431, retention time 2.33 min.

The preparation of 2-chloro-4-(cyclohexylsulfonylmethyl)-6-[(3S)-3-methylmorpholin-4-yl]pyrimidine was described earlier.

EXAMPLE 69

3-Cyclopropyl-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea

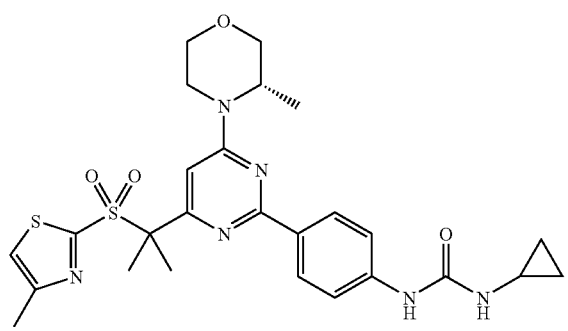

To cyclopropylamine (53 mg, 0.93 mmol) was added a solution of phenyl N-[4-[4-[(3S)-3-methylmorpholin-4-yl]-6-[2-[(4-methyl-1,3-thiazol-2-yl)sulfonyl]propan-2-yl]pyrimidin-2-yl]phenyl]carbamate (54 mg, 0.09 mmol) in DMA (2 mL) and triethylamine (0.045 mL, 0.32 mmol). The resultant mixture was heated to 50° C. for 16 hours. The reaction mixture was cooled and poured into water (30 mL). The resultant precipitate was collected by suction filtration and dried under suction to afford the crude product, which was purified by flash silica chromatography, elution gradient 25 to 75% ethyl acetate in isohexane. Product containing fractions were evaporated to dryness, triturated with isohexane/diethyl ether and dried under vacuum, at 50° C., for 1 hour to afford the desired material as a white solid (38 mg).

NMR Spectrum: $^1$H NMR (400.132 MHz, DMSO-d$_6$) δ 0.40-0.44 (2H, m), 0.63-0.67 (2H, m), 1.21 (3H, d), 1.92 (6H, s), 2.42 (3H, s), 2.53-2.59 (1H, m), 3.16 (1H, td), 3.49 (1H, td), 3.64 (1H, dd), 3.77 (1H, d), 3.97 (1H, dd), 4.13-4.20 (1H, m), 4.52-4.58 (1H, m), 6.40-6.42 (1H, m), 6.69 (1H, s), 7.42 (2H, d), 7.68 (1H, d), 7.87 (2H, d), 8.51 (1H, s)

LCMS Spectrum: MH+ 557, retention time 2.33 min.

The following compounds were made in an analogous fashion from either phenyl N-[4-[4-[(3S)-3-methylmorpholin-4-yl]-6-[2-[(4-methyl-1,3-thiazol-2-yl)sulfonyl]propan-2-yl]pyrimidin-2-yl]phenyl]carbamate or phenyl N-[4-[4-[(3S)-3-methylmorpholin-4-yl]-6-[(4-methyl-1,3-thiazol-2-yl)sulfonylmethyl]pyrimidin-2-yl]phenyl]carbamate and the appropriate amine.

| Example | Structure | NAME | LCMS MH+ | Retention time (min) |
|---|---|---|---|---|
| 69a | 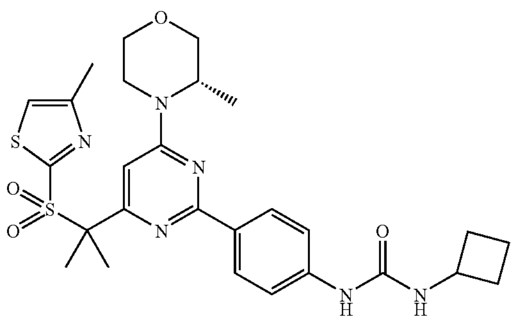 | 3-cyclobutyl-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea | 571 | 2.53 |
| 69b | 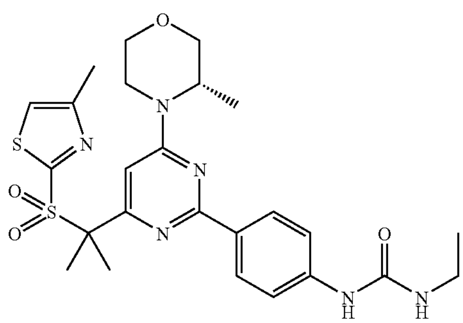 | 3-ethyl-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea | 545 | 2.3 |
| 69c | 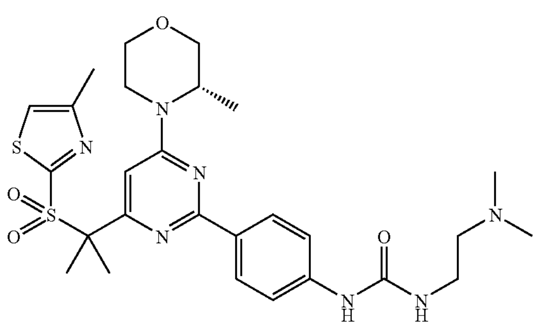 | 3-(2-dimethylaminoethyl)-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea | 588 | 2.44 |
| 69d | 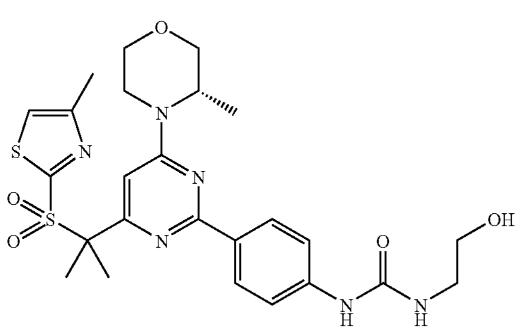 | 3-(2-hydroxyethyl)-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea | 561 | 1.99 |

| Example | Structure | NAME | LCMS MH+ | Retention time (min) |
|---|---|---|---|---|
| 69e | 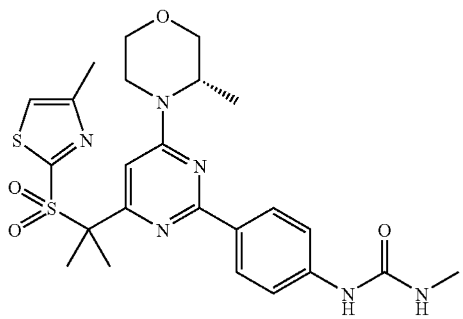 | 3-methyl-1-[4-[4-[(3S)-3-methylmorpholin-4-yl]-6-[2-[(4-methyl-1,3-thiazol-2-yl)sulfonyl]propan-2-yl]pyrimidin-2-yl]phenyl]urea | 531 | 2.15 |
| 69f | 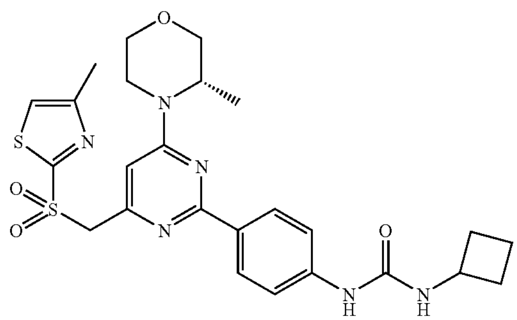 | 3-cyclobutyl-1-[4-[4-[(3S)-3-methylmorpholin-4-yl]-6-[(4-methyl-1,3-thiazol-2-yl)sulfonylmethyl]pyrimidin-2-yl]phenyl]urea | 543 | 2.28 |
| 69g | 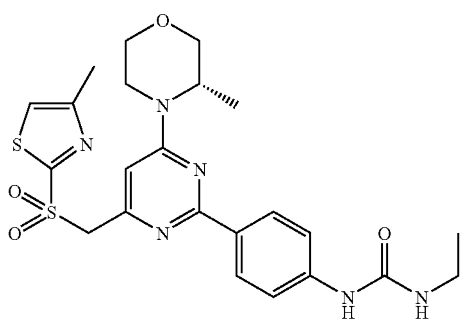 | 3-ethyl-1-[4-[4-[(3S)-3-methylmorpholin-4-yl]-6-[(4-methyl-1,3-thiazol-2-yl)sulfonylmethyl]pyrimidin-2-yl]phenyl]urea | 517 | 2.04 |
| 69h | 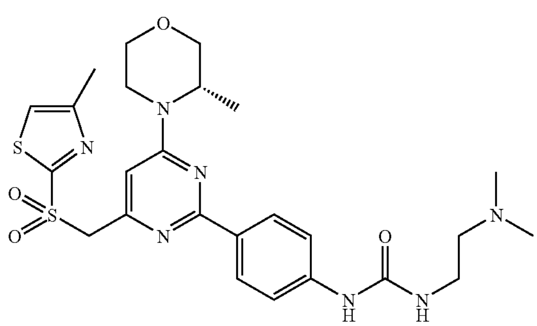 | 3-(2-dimethylaminoethyl)-1-[4-[4-[(3S)-3-methylmorpholin-4-yl]-6-[(4-methyl-1,3-thiazol-2-yl)sulfonylmethyl]pyrimidin-2-yl]phenyl]urea | 560 | 2.14 |

Example 69a: ¹H NMR (400.132 MHz, DMSO-d₆) δ 1.21 (3H, d), 1.57-1.68 (2H, m), 1.80-1.92 (2H, m), 1.92 (6H, s), 2.18-2.25 (2H, m), 2.41-2.42 (3H, m), 3.16 (1H, td), 3.49 (1H, td), 3.64 (1H, dd), 3.76 (1H, d), 3.97 (1H, dd), 4.11-4.19 (2H, m), 4.51-4.58 (1H, m), 6.44 (1H, d), 6.69 (1H, s), 7.39 (2H, d), 7.68 (1H, d), 7.87 (2H, d), 8.53 (1H, s).

Example 69b: ¹H NMR (400.132 MHz, DMSO-d₆) δ 1.07 (3H, t), 1.21 (3H, d), 1.92 (6H, s), 2.41-2.42 (3H, m), 3.09-3.20 (3H, m), 3.49 (1H, td), 3.64 (1H, dd), 3.77 (1H, d), 3.97 (1H, dd), 4.14-4.19 (1H, m), 4.52-4.58 (1H, m), 6.14 (1H, t), 6.69 (1H, s), 7.41 (2H, d), 7.68 (1H, d), 7.87 (2H, d), 8.63 (1H, s).

Example 69c: ¹H NMR (400.132 MHz, DMSO-d₆) δ 1.21 (3H, d), 1.92 (6H, s), 2.20 (6H, s), 2.33-2.40 (2H, m), 2.42 (3H, s), 3.12-3.22 (3H, m), 3.49 (1H, td), 3.64 (1H, dd), 3.76 (1H, d), 3.97 (1H, dd), 4.16 (1H, d), 4.51-4.57 (1H, m), 6.15 (1H, t), 6.69 (1H, s), 7.40 (2H, d), 7.68 (1H, s), 7.87 (2H, d), 8.87 (1H, s).

Example 69d: ¹H NMR (400.132 MHz, DMSO-d$_6$) δ 1.21 (3H, d), 1.92 (6H, s), 2.41 (3H, s), 3.13-3.21 (3H, m), 3.44-3.52 (3H, m), 3.64 (1H, dd), 3.77 (1H, d), 3.97 (1H, dd), 4.13-4.19 (1H, m), 4.52-4.57 (1H, m), 4.72 (1H, t), 6.24 (1H, t), 6.69 (1H, s), 7.40 (2H, d), 7.68 (1H, s), 7.87 (2H, d), 8.78 (1H, s).

Example 69e: ¹H NMR (400.132 MHz, DMSO-d$_6$) δ 1.21 (3H, d), 1.92 (6H, s), 2.41-2.42 (3H, m), 2.66 (3H, d), 3.12-3.20 (1H, m), 3.49 (1H, td), 3.64 (1H, dd), 3.76 (1H, d), 3.97 (1H, dd), 4.13-4.19 (1H, m), 4.51-4.57 (1H, m), 6.05 (1H, q), 6.69 (1H, s), 7.42 (2H, d), 7.68 (1H, d), 7.87 (2H, d), 8.72 (1H, s).

Example 69f: No NMR spectrum
Example 69g: No NMR spectrum
Example 69h: No NMR spectrum The preparation of phenyl N-[4-[4-[(3S)-3-methylmorpholin-4-yl]-6-[2-[(4-methyl-1,3-thiazol-2-yl)sulfonyl]propan-2-yl]pyrimidin-2-yl]phenyl]carbamate is described below.

Phenyl N-[4-[4-[(3S)-3-methylmorpholin-4-yl]-6-[2-[(4-methyl-1,3-thiazol-2-yl)sulfonyl]propan-2-yl]pyrimidin-2-yl]phenyl]carbamate

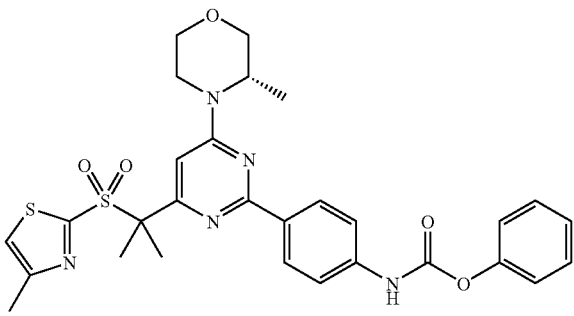

To a solution of 4-[4-[(3S)-3-methylmorpholin-4-yl]-6-[2-[(4-methyl-1,3-thiazol-2-yl)sulfonyl]propan-2-yl]pyrimidin-2-yl]aniline (340 mg, 0.72 mmol) in 1,4-dioxane (4 mL) was added sodium bicarbonate (90 mg, 1.08 mmol). Phenyl chloroformate (0.104 mL, 0.83 mmol) was then added dropwise and the resulting mixture was stirred at RT for 6 hours. Reaction mixture was then evaporated and the residue was partitioned between DCM (5 mL) and water (5 mL). The organic layer was separated and aqueous re-extracted with more DCM (5 mL). The combined organic layers were combined and evaporated to dryness to afford an amber gum, which was taken up in diethyl ether (5 mL) and triturated with sonication. The resultant solid was collected by suction filtration and dried to afford the desired material (334 mg).

NMR Spectrum: ¹H NMR (400.132 MHz, DMSO-d$_6$) δ 1.22 (3H, d), 1.93 (6H, s), 2.41 (3H, s), 3.17 (1H, td), 3.49 (1H, td), 3.64 (1H, dd), 3.77 (1H, d), 3.98 (1H, dd), 4.15-4.22 (1H, m), 4.53-4.59 (1H, m), 6.73 (1H, s), 7.24-7.30 (3H, m), 7.45 (2H, t), 7.55 (2H, d), 7.68 (1H, m), 7.97 (2H, d), 10.39 (1H, s).

LCMS Spectrum: MH+ 594, retention time 2.91 min.

4-[4-[(3S)-3-Methylmorpholin-4-yl]-6-[2-[(4-methyl-1,3-thiazol-2-yl)sulfonyl]propan-2-yl]pyrimidin-2-yl]aniline

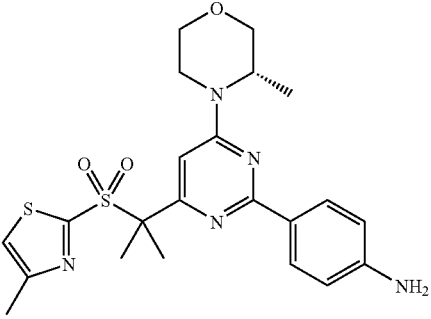

A mixture of 2-chloro-4-[(3S)-3-methylmorpholin-4-yl]-6-[2-[(4-methyl-1,3-thiazol-2-yl)sulfonyl]propan-2-yl]pyrimidine (480 mg, 1.15 mmol), 4-(4,4,5,5-tetramethyl-1,3,2-dioxaborolan-2-yl)aniline (378 mg, 1.73 mmol) and 2M aqueous sodium carbonate solution (2.8 mL, 5.60 mmol) in a mixture of DMF (2 mL), 1,2-dimethoxyethane (2 mL), ethanol (2 mL) and water (5 mL) was purged with nitrogen for 10 minutes prior to addition of bis(triphenylphosphine)palladium(II) chloride (54 mg, 0.08 mmol). The reaction mixture was heated to 85° C. and stirred at that temperature, under nitrogen for 3 hours. The reaction mixture was then cooled and partitioned between ethyl acetate (50 mL) and water (30 mL). The organic layer was separated and the aqueous layer re-extracted with ethyl acetate (25 mL). Combined organic layers were washed with brine (50 mL), dried (MgSO$_4$), filtered and evaporated to afford the crude product, which was purified by flash silica chromatography, elution gradient 25 to 75% ethyl acetate in isohexane, to give the desired material (367 mg).

NMR Spectrum: ¹H NMR (400.132 MHz, DMSO-d$_6$) δ 1.19 (3H, d), 1.90 (6H, s), 2.43 (3H, s), 3.13 (1H, td), 3.48 (1H, td), 3.63 (1H, dd), 3.75 (1H, d), 3.96 (1H, dd), 4.09-4.15 (1H, m), 4.47-4.54 (1H, m), 5.50 (2H, s), 6.52 (1H, d), 6.58 (2H, s), 7.68-7.72 (3H, m).

LCMS Spectrum: MH+ 474, retention time 2.31 min.

2-Chloro-4-[(3S)-3-methylmorpholin-4-yl]-6-[2-[(4-methyl-1,3-thiazol-2-yl)sulfonyl]propan-2-yl]pyrimidine

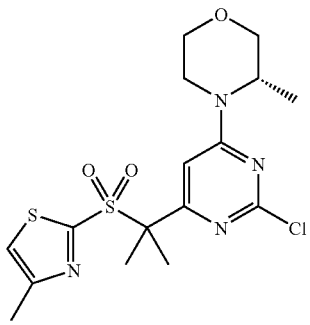

To a cooled (ice/water bath) solution of 2-chloro-4-[(3S)-3-methylmorpholin-4-yl]-6-[(4-methyl-1,3-thiazol-2-yl)sulfonylmethyl]pyrimidine (612 mg, 1.57 mmol) in DMF (8 mL) was added sodium tert-butoxide (157 mg, 1.63 mmol). The mixture was stirred for 5 minutes, under nitrogen, before addition of iodomethane (0.100 mL, 1.61 mmol). The reaction mixture was allowed to stir, in cooling bath, for a further 10 minutes before addition of further sodium tert-butoxide (157 mg, 1.63 mmol). After a further 5 minutes stirring more iodomethane (0.100 mL, 1.61 mmol) was added and reaction mixture stirred, under nitrogen, in cooling bath for 20 minutes. Cooling bath was then removed and stirring continued for a further 2 hours. Water (25 mL) was then added and resultant precipitate collected by filtration, washed with water (50 mL) and dried under vacuum, at 50° C., for 2 hours to afford the desired material (487 mg).

NMR Spectrum: $^1$H NMR (400.132 MHz, DMSO-d$_6$) δ 1.19 (3H, d), 1.79 (6H, d), 2.46 (3H, s), 3.15 (1H, td), 3.43 (1H, td), 3.58 (1H, dd), 3.72 (1H, d), 3.93 (1H, dd), 3.96-4.03 (1H, m), 4.35-4.44 (1H, m), 6.78 (1H, s), 7.89 (1H, s).

LCMS Spectrum: MH+ 417, retention time 2.28 min.

2-Chloro-4-[(3S)-3-methylmorpholin-4-yl]-6-[(4-methyl-1,3-thiazol-2-yl)sulfonylmethyl]pyrimidine

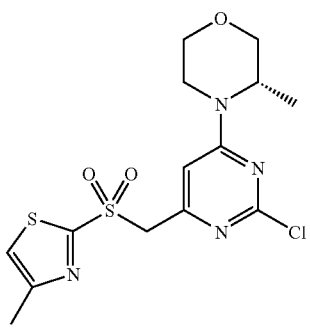

To a cooled (ice/water bath) solution of 2,4-dichloro-6-[(4-methyl-1,3-thiazol-2-yl)sulfonylmethyl]pyrimidine (901 mg, 2.78 mmol) in DCM (12 mL) was added triethylamine (0.45 mL, 3.23 mmol). The resulting solution was treated dropwise, over 3 minutes, with a solution of (3S)-3-methylmorpholine (319 mg, 3.15 mmol) in DCM (2.5 mL). The reaction mixture was stirred, under nitrogen for 24 hours, allowing reaction to warm to RT. Water (20 mL) was added to reaction mixture and stirred for 15 minutes. The organic layer was then separated, dried (MgSO$_4$) and evaporated to give crude product, which was purified by flash silica chromatography, elution gradient 25 to 75% ethyl acetate in isohexane, to give the desired material (615 mg).

NMR Spectrum: $^1$H NMR (400.132 MHz, DMSO-d$_6$) δ 1.18 (3H, d), 2.49 (3H, s), 3.18 (1H, td), 3.43 (1H, td), 3.58 (1H, dd), 3.72 (1H, d), 3.86-3.96 (2H, m), 4.16-4.28 (1H, m), 4.82 (2H, s), 6.80 (1H, s), 7.89 (1H, d).

LCMS Spectrum: MH+ 389, retention time 1.89 min.

2,4-Dichloro-6-[(4-methyl-1,3-thiazol-2-yl)sulfonylmethyl]pyrimidine

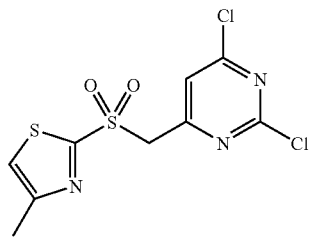

To a cooled (ice/water bath) solution of 2,4-dichloro-6-[(4-methyl-1,3-thiazol-2-yl)sulfanylmethyl]pyrimidine (867 mg, 2.97 mmol) in DCM (15 mL) was added portionwise, over 10 minutes, 3-chloroperoxybenzoic acid (1.42 g, 6.34 mmol). The resulting suspension was stirred in cooling bath for 15 minutes. Cooling bath was then removed and reaction mixture allowed to warm to RT and stirred for 22 hours. The reaction was incomplete and further 3-chloroperoxybenzoic acid (162 mg, 0.72 mmol) was added and the mixture stirred for a further 1 hour. Saturated aqueous sodium bicarbonate solution (20 mL) was added to the reaction mixture and stirred for 30 minutes. The organic layer was separated, dried (MgSO$_4$), filtered and evaporated to afford the desired material (912 mg).

NMR Spectrum: $^1$H NMR (400.132 MHz, DMSO-d$_6$) δ 2.48 (3H, d), 5.19 (2H, s), 7.84 (1H, s), 7.94-7.95 (1H, m).

LCMS Spectrum: M−H−322, retention time 1.47 min.

2,4-Dichloro-6-[(4-methyl-1,3-thiazol-2-yl)sulfanylmethyl]pyrimidine

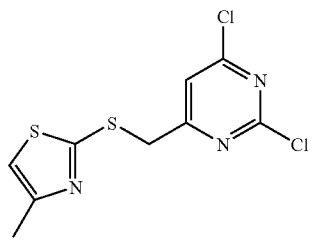

A suspension of 6-[(4-methyl-1,3-thiazol-2-yl)sulfanylmethyl]-1H-pyrimidine-2,4-dione (1.4 g, 5.48 mmol) in phosphorus oxychloride (6 mL, 64.37 mmol) was warmed to 100° C. and stirred for 6 hours. The reaction mixture was cooled before evaporating and the residue was partitioned between DCM (30 mL) and iced water (30 mL). Sodium hydrogen carbonate was then added carefully and portionwise, over 30 minutes, so as to control effervescence. Once effervescence had ceased and pH had been adjusted to 8, mixture was treated with more DCM (30 mL) and water (20 mL), transferred to a separating funnel and organic layer separated. The aqueous layer was re-extracted with further DCM (2×25 mL) and the combined organic extracts washed with brine, dried (MgSO$_4$) and evaporated to dryness to afford the crude product, which was purified by flash silica chromatography, elution gradient 10 to 20% ethyl acetate in isohexane, to give the desired material (0.90 g).

NMR Spectrum: $^1$H NMR (400.132 MHz, DMSO-d$_6$) δ 2.31 (3H, d), 4.55 (2H, s), 7.23-7.24 (1H, m), 7.83 (1H, s).

LCMS Spectrum: MH+ 292, retention time 2.33 min.

6-[(4-Methyl-1,3-thiazol-2-yl)sulfanylmethyl]-1H-pyrimidine-2,4-dione

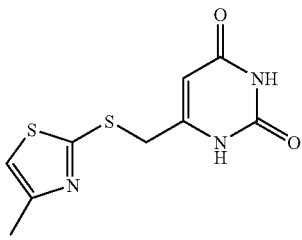

A solution of 4-methylthiazole-2-thiol (1.01 g, 7.70 mmol) in DMF (15 mL) was added 1,8-diazabicyclo[5.4.0]undec-7-ene (1.4 mL, 9.38 mmol). The resulting solution was stirred at RT for 30 minutes. 6-(chloromethyl)pyrimidine-2,4(1H,3H)-dione (1 g, 6.23 mmol) was then added portionwise, over a period of 10 minutes, under nitrogen. The resulting solution was stirred at RT for 19 hours. The reaction mixture was then evaporated to dryness and the residue partitioned between DCM (20 mL) and water (20 mL). A solid precipitated which was collected by suction filtration, washed with water (20 mL) and dried, under vacuum, at 60° C., for 2 hours to afford the desired material (1.07 g, 67%). Additional desired material (0.330 g) was obtained by adjusting the filtrate to pH2 with 2M hydrochloric acid, filtering the precipitate, washing it with water (20 mL) and drying in a vacuum oven.

NMR Spectrum: $^1$H NMR (400.132 MHz, DMSO-$d_6$) δ 2.34 (3H, d), 4.08 (2H, s), 5.43 (1H, s), 7.27 (1H, m), 11.01 (2H, s).

LCMS Spectrum: MH+ 256, retention time 0.53 min.

The preparation of phenyl N-[4-[4-[(3S)-3-methylmorpholin-4-yl]-6-[(4-methyl-1,3-thiazol-2-yl)sulfonylmethyl]pyrimidin-2-yl]phenyl]carbamate is described below.

Phenyl N-[4-[4-[(3S)-3-methylmorpholin-4-yl]-6-[(4-methyl-1,3-thiazol-2-yl)sulfonylmethyl]pyrimidin-2-yl]phenyl]carbamate

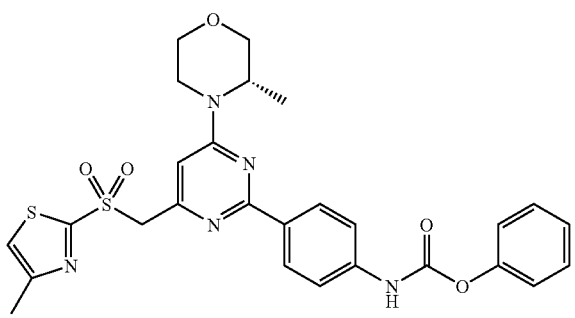

Phenyl chloroformate (0.190 mL, 1.51 mmol) was added to 4-[4-[(3S)-3-methylmorpholin-4-yl]-6-[(4-methyl-1,3-thiazol-2-yl)sulfonylmethyl]pyrimidin-2-yl]aniline (450 mg, 1.01 mmol), sodium hydrogen carbonate (127 mg, 1.51 mmol) in dioxane (10 mL) at 5° C. under nitrogen. The resulting mixture was stirred at RT for 2 hours. The reaction mixture was diluted with ethyl acetate (200 mL), and washed with water (125 mL). The organic layer was dried (MgSO$_4$), filtered and evaporated to afford crude product, which was triturated with a mixture of diethyl ether and isohexane to afford the desired material (360 mg).

NMR Spectrum: $^1$H NMR (400.132 MHz, DMSO-$d_6$) δ 1.22 (3H, d), 2.53 (3H, s) [obscured by DMSO], 3.20 (1H, td), 3.49 (1H, td), 3.64 (1H, dd), 3.77 (1H, d), 3.98 (1H, dd), 4.15 (1H, d), 4.45 (1H, s), 4.93 (2H, s), 6.77 (1H, s), 7.22-7.32 (3H, m), 7.43-7.47 (2H, m), 7.56 (2H, d), 7.84 (1H, s), 7.97 (2H, d), 10.43 (1H, s).

LCMS Spectrum: MH+ 566, retention time 2.66 mins

4-[4-[(3S)-3-Methylmorpholin-4-yl]-6-[(4-methyl-1,3-thiazol-2-yl)sulfonylmethyl]pyrimidin-2-yl]aniline

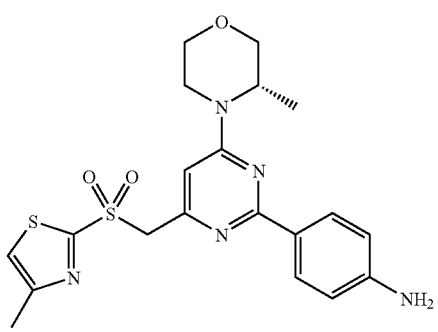

Bis(triphenylphosphine)palladium(II) chloride (54.4 mg, 0.08 mmol) was added to 2-chloro-4-[(3S)-3-methylmorpholin-4-yl]-6-[(4-methyl-1,3-thiazol-2-yl)sulfonylmethyl]pyrimidine (600 mg, 1.55 mmol), 4-(4,4,5,5-tetramethyl-1,3,2-dioxaborolan-2-yl)aniline (510 mg, 2.33 mmol) and sodium carbonate (5 mL, 10.00 mmol) in a mixture of DMF (6 mL), DME (12 mL), ethanol (3 mL) and water (3.5 mL) at RT under nitrogen. The reaction mixture was evacuated and refilled with nitrogen several times and the resulting mixture stirred at 95° C. for 18 hours. The reaction mixture was diluted with ethyl acetate (250 mL), and washed with water (2×150 mL). The organic layer was dried (Na$_2$SO$_4$), filtered and evaporated to afford crude product, which was purified by flash silica chromatography, elution gradient 10 to 70% ethyl acetate in isohexane, to the desired material (450 mg).

NMR Spectrum: $^1$H NMR (400.132 MHz, DMSO-$d_6$) δ 1.19 (3H, d), 2.53 (3H, s), 3.15 (1H, td), 3.47 (1H, td), 3.62 (1H, dd), 3.75 (1H, d), 3.96 (1H, dd), 4.09 (1H, d), 4.40 (1H, s), 4.83 (2H, s), 5.54 (2H, s), 6.52 (2H, d), 6.60 (1H, s), 7.70 (2H, d), 7.81 (1H, s).

LCMS Spectrum: MH+ 446, retention time 2.0 mins

The preparation of 2-chloro-4-[(3S)-3-methylmorpholin-4-yl]-6-[(4-methyl-1,3-thiazol-2-yl)sulfonylmethyl]pyrimidine was described earlier.

EXAMPLE 70

3-Ethyl-1-[4-[4-[(3S)-3-methylmorpholin-4-yl]-6-(2-pyridin-2-ylsulfonylpropan-2-yl)pyrimidin-2-yl]phenyl]urea

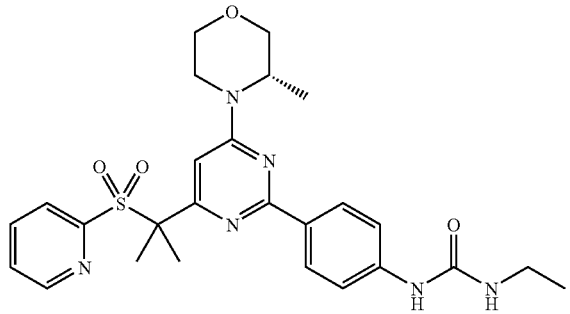

A 2M solution of Ethylamine in methanol (0.471 mL, 0.94 mmol) was added in one portion to phenyl N-[4-[4-[(3S)-3-methylmorpholin-4-yl]-6-(2-pyridin-2-ylsulfonylpropan-2-yl)pyrimidin-2-yl]phenyl]carbamate (120 mg, 0.21 mmol), in DMF (2 mL) at RT under nitrogen. The resulting solution was stirred at RT for 60 minutes. The reaction mixture was evaporated to dryness and the crude product was purified by flash silica chromatography, elution gradient 0 to 7% methanol in DCM, to give the desired material as a white foam (103 mg).

NMR Spectrum: $^1$H NMR (399.902 MHz, DMSO-d$_6$) δ 1.07 (t, 3H), 1.21 (d, 3H), 1.88 (s, 6H), 3.09-3.21 (m, 3H), 3.45-3.53 (m, 1H), 3.61-3.66 (m, 1H), 3.77 (d, 1H), 3.95-4.00 (m, 1H), 4.15 (d, 1H), 4.53 (s, 1H), 6.15 (t, 1H), 6.66 (s, 1H), 7.35 (d, 2H), 7.61-7.66 (m, 2H), 7.71 (d, 2H), 7.88-7.93 (m, 1H), 8.61 (s, 1H), 8.74-8.76 (m, 1H)

LCMS Spectrum: MH+ 525.56, retention time 2.14 min.

The preparation of phenyl N-[4-[4-[(3S)-3-methylmorpholin-4-yl]-6-(2-pyridin-2-ylsulfonylpropan-2-yl)pyrimidin-2-yl]phenyl]carbamate is described below.

Phenyl N-[4-[4-[(3S)-3-methylmorpholin-4-yl]-6-(2-pyridin-2-ylsulfonylpropan-2-yl)pyrimidin-2-yl]phenyl]carbamate

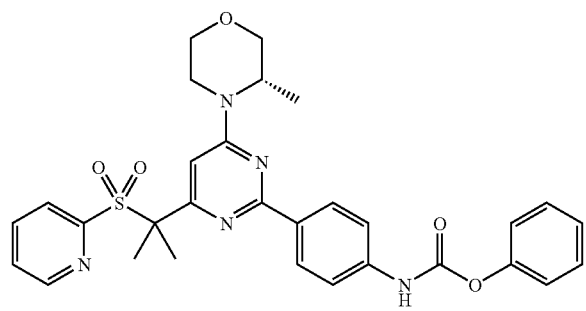

Phenyl chloroformate (0.432 mL, 3.44 mmol) was added to 4-[4-[(3S)-3-methylmorpholin-4-yl]-6-(2-pyridin-2-ylsulfonylpropan-2-yl)pyrimidin-2-yl]aniline (1.3 g, 2.87 mmol) and sodium hydrogen carbonate (0.482 g, 5.73 mmol) in dioxane (20 mL) at RT. The resulting slurry was stirred at RT for 1 hour and then the reaction mixture was partitioned between ethyl acetate and water. The organic solution was dried (MgSO$_4$) and concentrated under reduced pressure. The residue was chromatographed on silica, eluting with 0%-20% ethyl acetate in DCM, to give the desired material as a yellow dry film (1.62 g).

NMR Spectrum: $^1$H NMR (399.902 MHz, CDCl$_3$) δ 1.27 (d, 3H), 1.90 (s, 6H), 3.25 (m, 1H), 3.55 (m, 1H), 3.70 (m, 1H), 4.03 (m, 2H), 4.39-4.46 (m, 1H), 6.60 (s, 1H), 6.93 (s, 1H), 7.12-7.22 (m, 12H), 7.32 (m, 5H), 7.57 (m, 2H), 7.82 (d, 2H).

LCMS Spectrum: MH+ 574.52, retention time 2.85 min. (monitor acidic).

4-[4-[(3S)-3-Methylmorpholin-4-yl]-6-(2-pyridin-2-ylsulfonylpropan-2-yl)pyrimidin-2-yl]aniline

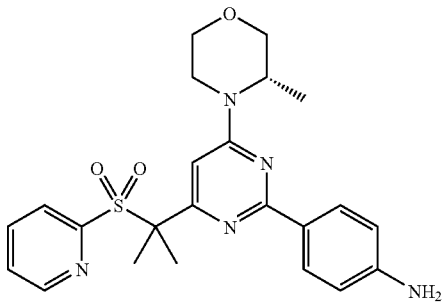

Tetramethyl-1,3,2-dioxaborolan-2-yl)aniline (0.773 g, 3.53 mmol) and 2-chloro-4-[(3S)-3-methylmorpholin-4-yl]-6-(2-pyridin-2-ylsulfonylpropan-2-yl)pyrimidine (1.4 g, 3.53 mmol) were suspended in a mixture of DME (10 mL), ethanol (10.00 mL), DMF (10.00 mL) and water (10 mL) at RT under nitrogen. The mixture was purged with nitrogen and bis(triphenylphosphine)palladium(II) chloride (0.124 g, 0.18 mmol) was added. The resulting suspension was stirred at 80° C. for 90 minutes under an atmosphere of nitrogen. The reaction mixture was concentrated and diluted with ethyl acetate (150 mL), and washed with water (2×150 mL) and saturated brine (100 mL). The organic layer was dried (MgSO$_4$), filtered and evaporated to afford the crude product. The crude product was purified by flash silica chromatography, elution gradient 0 to 40% ethyl acetate in DCM, to give the desired material as a yellow foam (1.210 g).

NMR Spectrum: $^1$H NMR (399.902 MHz, CDCl$_3$) δ 1.25 (d, 3H), 1.89 (s, 6H), 3.22 (m, 1H), 3.54 (m, 1H), 3.66-3.80 (m, 4H), 3.97 (m, 1H), 4.05 (m, 1H), 4.42 (s, 1H), 6.46-6.53 (m, 3H), 7.28 (m, 1H), 7.55 (m, 2H), 7.64 (d, 2H), 8.61 (d, 1H).

LCMS Spectrum: MH+ 454.58, retention time 1.88 min.

2-Chloro-4-[(3S)-3-methylmorpholin-4-yl]-6-(2-pyridin-2-ylsulfonylpropan-2-yl)pyrimidine

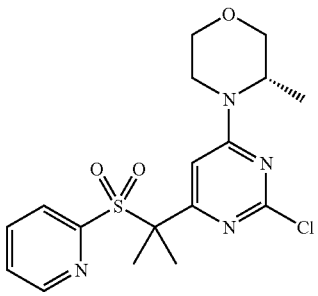

Iodomethane (1.266 mL, 20.33 mmol) was added to a solution of 2-chloro-4-[(3S)-3-methylmorpholin-4-yl]-6-(pyridin-2-ylsulfonylmethyl)pyrimidine (2.5 g, 6.78 mmol) and sodium tert-butoxide (1.954 g, 20.33 mmol) in DMF (50 mL) at 0° C. under nitrogen. The solution was allowed to slowly warm up to RT and stirred at RT for 1 hour. Water and ethyl acetate were added and the solution was shaken and separated. The combined ethyl acetate layers were dried (MgSO$_4$) and filtered. The filtrate was evaporated and the crude product was purified by flash silica chromatography, elution gradient 0 to 60% ethyl acetate in DCM, to give the desired material as a yellow oil which solidified on standing (1.77 g).

NMR Spectrum: $^1$H NMR (399.902 MHz, CDCl$_3$) δ 1.26 (d, 3H), 1.77 (s, 6H), 3.22 (m, 1H), 3.49 (m, 1H), 3.64 (m, 1H), 3.74 (d, TH), 3.89-3.98 (m, 2H), 4.27 (s, 1H), 6.67 (s, 1H), 7.46 (m, 1H), 7.73 (m, 1H), 7.80 (d, TH), 7.82 (m, 1H).

LCMS Spectrum: MH+ 397.38, retention time 2.04 min.

2-Chloro-4-[(3S)-3-methylmorpholin-4-yl]-6-(pyridin-2-ylsulfonylmethyl)pyrimidine

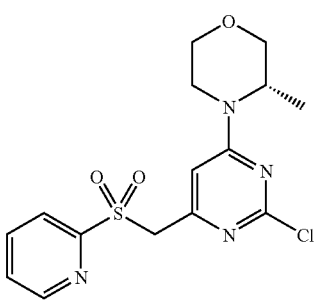

A 35% aqueous solution of hydrogen peroxide (8.26 mL, 93.53 mmol) was added dropwise to a stirred solution of 2-chloro-4-[(3S)-3-methylmorpholin-4-yl]-6-(pyridin-2-ylsulfanylmethyl)pyrimidine (10.5 g, 31.17 mmol), sodium tungstate dihydrate (0.206 g, 0.62 mmol) and 2N Sulfuric acid (0.6 mL) in dioxane (300 mL) and then the solution warmed to 55° C. The solution was stirred at 55° C. for 4 hours. Further hydrogen peroxide (8.26 mL) was added and the mixture stirred at 50° C. for 18 hours. 3-Chloroperoxybenzoic acid (5.38 g, 31.17 mmol) was added and the mixture stirred at RT for 2 hours. The solution was diluted with water (500 mL) and cooled to 20° C. A 10% solution of sodium metabisulfite was added to destroy any remaining peroxide and the solution was extracted with ethyl acetate. The organic layer was dried (MgSO$_4$) and filtered. The crude product was purified by flash silica chromatography, elution gradient 0 to 50% ethyl acetate in DCM, to give the desired material as a yellow gum (10.5 g).

NMR Spectrum: $^1$H NMR (399.902 MHz, CDCl$_3$) δ 1.24 (d, 3H), 3.20 (m, 1H), 3.46 (m, 1H), 3.61 (d, 1H), 3.71 (d, 1H), 3.90-3.98 (m, 2H), 4.21 (s, 1H), 4.51 (s, 2H), 6.50 (s, 1H), 7.51-7.53 (m, 1H), 7.86-7.95 (m, 2H), 8.72-8.74 (m, 1H)

LCMS Spectrum: MH+ 369.37, retention time 1.73 min.

2-Chloro-4-[(3S)-3-methylmorpholin-4-yl]-6-(pyridin-2-ylsulfanylmethyl)pyrimidine

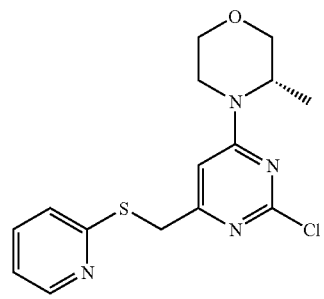

DIPEA (8.77 ml, 50.71 mmol) was added to 2-mercaptopyridine (3.80 g, 34.22 mmol), in DMF (300 mL) at RT in an atmosphere of nitrogen. The resulting solution was stirred at RT for 15 minutes. 2-Chloro-4-(iodomethyl)-6-[(3S)-3-methylmorpholin-4-yl]pyrimidine (11 g, 31.11 mmol) was added portionwise over 5 minutes and the mixture stirred at RT for 3 hours. The reaction mixture was evaporated to dryness and redissolved in DCM (200 mL) and washed sequentially with saturated sodium hydrogen carbonate solution (100 mL) and saturated brine (50 mL). The organic layer was dried (MgSO$_4$), filtered and evaporated to afford crude product. The crude product was purified by flash silica chromatography, elution gradient 0 to 20% ethyl acetate in DCM, to give the desired material as a tan oil (10.50 g). NMR shows the presence of 0.6 eq. of m-chlorobenzoic acid. This material was used in the subsequent step without further purification.

NMR Spectrum: $^1$H NMR (399.902 MHz, CDCl$_3$) δ 1.23 (d, 3H), 3.17-3.25 (m, 1H), 3.46-3.54 (m, 1H), 3.62-3.67 (m, 1H), 3.74 (d, 1H), 3.93-4.01 (m, 2H), 4.20 (s, 1H), 4.29-4.38 (m, 2H), 6.60 (s, 1H), 6.99-7.02 (m, 1H), 7.20 (d, 1H), 7.47-7.51 (m, 1H), 8.40-8.42 (m, 1H).

LCMS Spectrum: MH+ 337.48, retention time 2.19 min.

The preparation of 2-chloro-4-(iodomethyl)-6-[(3S)-3-methylmorpholin-4-yl]pyrimidine was described earlier.

EXAMPLE 71

3-Ethyl-1-[4-[4-[(3S)-3-methylmorpholin-4-yl]-6-(pyridin-2-ylsulfonylmethyl)pyrimidin-2-yl]phenyl]urea

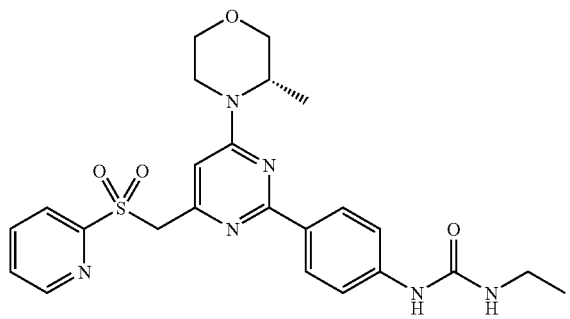

A 2M solution of ethylamine in methanol (0.495 mL, 0.99 mmol) was added in one portion to a solution of phenyl N-[4-[4-[(3S)-3-methylmorpholin-4-yl]-6-(pyridin-2-ylsulfonylmethyl)pyrimidin-2-yl]phenyl]carbamate (120 mg, 0.22 mmol) in DMF (2 mL) at RT under nitrogen. The resulting solution was stirred at RT for 60 minutes. The reaction mixture was evaporated to dryness and the crude product was purified by flash silica chromatography, elution gradient 0 to 7% methanol in DCM, to give the desired material as a white foam (83 mg).

NMR Spectrum: $^1$H NMR (399.902 MHz, DMSO-d$_6$) δ 1.07 (t, 3H), 1.20 (d, 3H), 3.09-3.22 (m, 3H), 3.44-3.52 (m, 1H), 3.61-3.65 (m, 1H), 3.76 (d, 1H), 3.95-4.00 (m, 1H), 4.12 (d, 1H), 4.40 (s, 1H), 4.85 (q, 2H), 6.14 (t, 1H), 6.69 (s, 1H), 7.35 (d, 2H), 7.66 (d, 2H), 7.79-7.82 (m, 1H), 7.90 (d, 1H), 8.08-8.13 (m, 1H), 8.62 (s, 1H), 8.93 (d, 1H).

LCMS Spectrum: MH+ 497.49, retention time 1.66 min.

The preparation of phenyl N-[4-[4-[(3S)-3-methylmorpholin-4-yl]-6-(pyridin-2-ylsulfonylmethyl)pyrimidin-2-yl]phenyl]carbamate is described below.

Phenyl N-[4-[4-[(3S)-3-methylmorpholin-4-yl]-6-(pyridin-2-ylsulfonylmethyl)pyrimidin-2-yl]phenyl]carbamate

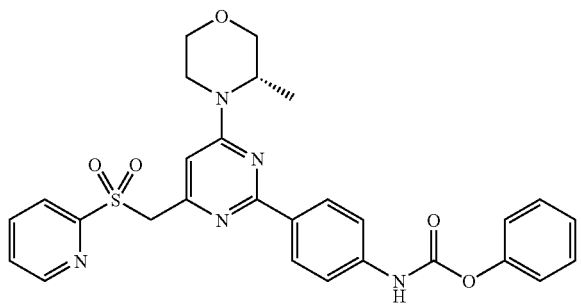

Phenyl chloroformate (0.390 mL, 3.10 mmol) was added to 4-[4-[(3S)-3-methylmorpholin-4-yl]-6-(pyridin-2-ylsulfonylmethyl)pyrimidin-2-yl]aniline (1.1 g, 2.59 mmol) and sodium hydrogen carbonate (0.434 g, 5.17 mmol) in dioxane (25 mL) at RT. The resulting slurry was stirred at RT for 1 hour. The mixture was partitioned between ethyl acetate and water. The organic solution was separated, dried (MgSO$_4$) and concentrated under reduced pressure. The residue was purified by flash silica chromatography using gradient elution 0%-20% ethyl acetate in DCM, to give the desired material as a yellow foam (1.130 g).

NMR Spectrum: $^1$H NMR (399.902 MHz, CDCl$_3$) δ 1.25 (d, 3H), 3.23 (m, 1H), 3.52 (m, 1H), 3.65-3.68 (m, 1H), 3.75 (d, 1H), 3.95-3.99 (m, 1H), 4.05-4.11 (m, 2H), 4.31-4.38 (m, 1H), 4.63 (q, 2H), 6.39 (s, 1H), 6.95 (s, 1H), 7.13 (m, 2H), 7.17-7.21 (m, 1H), 7.34 (m, 4H), 7.48 (m, 1H), 7.75-7.85 (m, 4H), 8.77-8.79 (m, 1H).

LCMS Spectrum: MH+ 546.49, retention time 2.54 min.

4-[4-[(3S)-3-Methylmorpholin-4-yl]-6-(pyridin-2-ylsulfonylmethyl)pyrimidin-2-yl]aniline

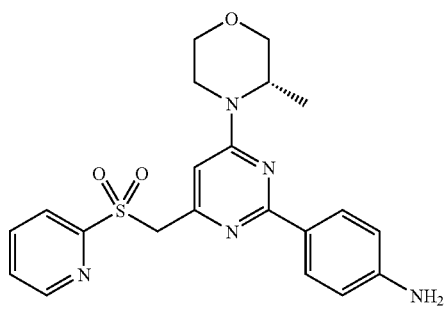

Sodium carbonate (7.32 mL, 14.64 mmol) was added to 4-(4,4,5,5-tetramethyl-1,3,2-dioxaborolan-2-yl)aniline (0.891 g, 4.07 mmol) and 2-chloro-4-[(3S)-3-methylmorpholin-4-yl]-6-(pyridin-2-ylsulfonylmethyl)pyrimidine (1.5 g, 4.07 mmol) in a mixture of DME (10 mL), ethanol (10.00 mL), DMF (10.00 mL) and water (10 mL) at RT under nitrogen. The mixture was purged with nitrogen three times, bis(triphenylphosphine)palladium(II) chloride (0.143 g, 0.20 mmol) was added and the mixture purged with nitrogen again. The resulting suspension was stirred at 80° C. for 90 minutes. The reaction mixture was evaporated to dryness and suspended in ethyl acetate (150 mL), and washed with water (2×150 mL) and saturated brine (100 mL). The organic layer was dried (MgSO$_4$), filtered and evaporated to afford crude product. The crude product was purified by flash silica chromatography, elution gradient 0 to 40% ethyl acetate in DCM, to give the desired material as a yellow foam (1.21 g).

NMR Spectrum: $^1$H NMR (399.902 MHz, CDCl$_3$) δ 1.23 (d, 3H), 3.16-3.24 (m, 1H), 3.47-3.55 (m, 1H), 3.63-3.68 (m, 1H), 3.71-3.80 (m, 3H), 3.92-3.98 (m, 1H), 4.02-4.09 (m, 1H), 4.30-4.37 (m, 1H), 4.59 (q, 2H), 6.32 (s, 1H), 6.48-6.53 (m, 2H), 7.44-7.49 (m, 1H), 7.67 (d, 2H), 7.73-7.83 (m, 2H), 8.77-8.79 (m, 1H).

LCMS Spectrum: MH+ 426.48, retention time 1.24 min. (monitor acidic).

The preparation of 2-chloro-4-[(3S)-3-methylmorpholin-4-yl]-6-(pyridin-2-ylsulfonylmethyl)pyrimidine was described earlier.

EXAMPLE 72

1-[4-[4-[2-(4-Chlorophenyl)sulfonylpropan-2-yl]-6-[(3S)-3-methylmorpholin-4-yl]pyrimidin-2-yl]phenyl]-3-cyclopropyl-urea

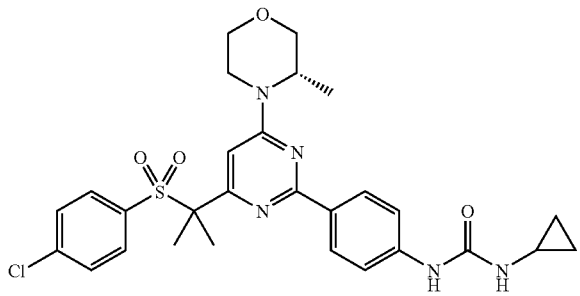

Cyclopropylamine (0.139 mL, 1.98 mmol) was added to phenyl N-[4-[4-[2-(4-chlorophenyl)sulfonylpropan-2-yl]-6-[(3S)-3-methylmorpholin-4-yl]pyrimidin-2-yl]phenyl]carbamate (150 mg, 0.25 mmol) in DMF (2 mL). The resulting solution was stirred at 60° C. for 5 hours. The mixture was evaporated to dryness and the residue was partitioned between ethyl acetate (30 mL) and water (30 mL). The organic layer was washed with water (2×30 mL) and saturated brine (30 mL), dried (MgSO$_4$), filtered and evaporated to dryness. The residue was purified by flash silica chromatography, elution gradient 30 to 60% ethyl acetate in isohexane. Pure fractions were evaporated to dryness and the residue triturated with diethyl ether to give the desired material as a white solid (92 mg).

NMR Spectrum: $^1$H NMR (399.902 MHz, CDCl3) δ 0.70 (2H, s), 0.88 (2H, s), 1.34 (3H, d), 1.86 (6H, s), 2.63 (1H, t), 3.33 (1H, td), 3.63 (1H, td), 3.78 (2H, dd), 3.85 (2H, d), 4.06 (1H, dd), 4.14 (1H, d), 4.49 (1H, d), 4.88 (1H, s), 6.63 (1H, s), 6.93 (1H, s), 7.30 (4H, d), 7.39 (2H, d), 7.47 (2H, d), 7.87 (2H, d).

LCMS Spectrum: MH+ 570, 572, retention time 2.63 min.

The following compounds were made in an analogous fashion from either phenyl N-[4-[4-[2-(4-chlorophenyl)sulfonylpropan-2-yl]-6-[(3S)-3-methylmorpholin-4-yl]pyrimidin-2-yl]phenyl]carbamate or phenyl N-[4-[4-[(4-chlorophenyl)sulfonylmethyl]-6-[(3S)-3-methylmorpholin-4-yl]pyrimidin-2-yl]phenyl]carbamate and the appropriate amine.

| Example | Structure | NAME | LCMS MH+ | Retention time (min) |
|---|---|---|---|---|
| 72a | 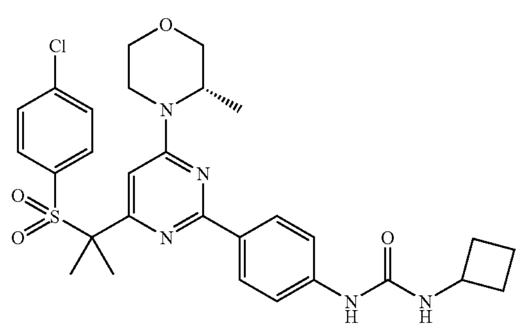 | 1-[4-[4-[2-(4-chlorophenyl)sulfonylpropan-2-yl]-6-[(3S)-3-methylmorpholin-4-yl]pyrimidin-2-yl]phenyl]-3-cyclobutyl-urea | 584, 586 | 2.86 |
| 72b | 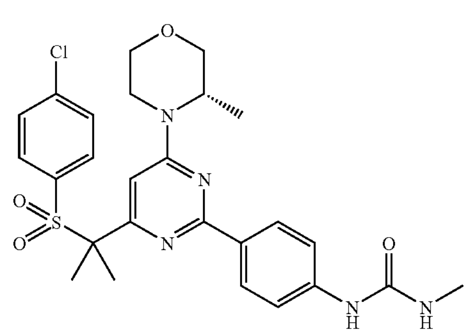 | 1-[4-[4-[2-(4-chlorophenyl)sulfonylpropan-2-yl]-6-[(3S)-3-methylmorpholin-4-yl]pyrimidin-2-yl]phenyl]-3-methyl-urea | 544, 546 | 2.46 |

-continued

| Example | Structure | NAME | LCMS MH+ | Retention time (min) |
|---|---|---|---|---|
| 72c | 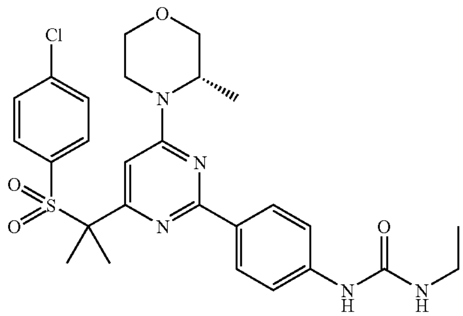 | 1-[4-[4-[2-(4-chlorophenyl)sulfonylpropan-2-yl]-6-[(3S)-3-methylmorpholin-4-yl]pyrimidin-2-yl]phenyl]-3-ethyl-urea | 558, 560 | 2.63 |
| 72d | 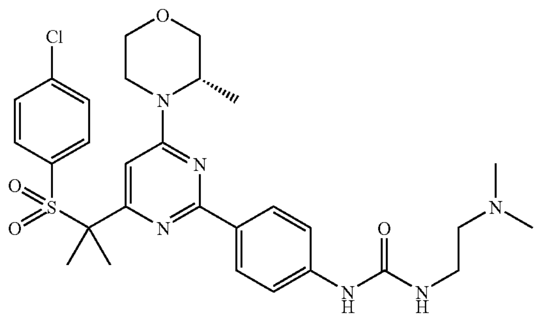 | 1-[4-[4-[2-(4-chlorophenyl)sulfonylpropan-2-yl]-6-[(3S)-3-methylmorpholin-4-yl]pyrimidin-2-yl]phenyl]-3-(2-dimethylaminoethyl)urea | 601, 603 | 2.51 |
| 72e | 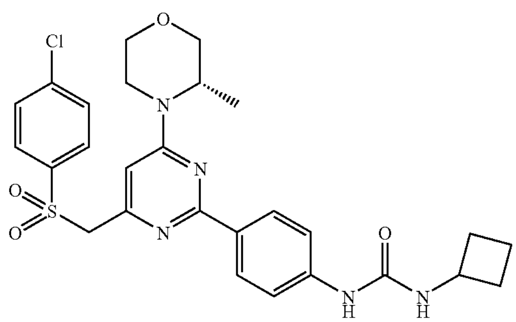 | (S)-1-(4-(4-((4-chlorophenylsulfonyl)methyl)-6-3-methylmorpholino)pyrimidin-2-yl)phenyl)-3-cyclobutylurea | 556, 558 | 2.56 |
| 72f | 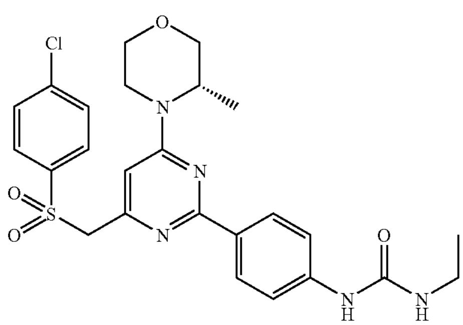 | 1-[4-[4-[(4-chlorophenyl)sulfonylmethyl]-6-[(3S)-3-methylmorpholin-4-yl]pyrimidin-2-yl]phenyl]-3-ethyl-urea | 530, 532 | 2.38 |

Example 72a: $^1$H NMR (399.902 MHz, CDCl$_3$) δ 1.34 (3H, d), 1.72 (2H, m), 1.86 (2H, m), 1.86 (6H, s), 2.39 (2H, m), 3.32 (1H, ddd), 3.63 (1H, ddd), 3.77 (1H, dd), 3.85 (1H, d), 4.06 (1H, dd), 4.14 (1H, d), 4.31 (1H, dtt), 4.49 (1H, br.d), 4.86 (1H, d), 6.29 (1H, s), 6.63 (1H, s), 7.27 (2H, d), 7.29 (2H, d), 7.47 (2H, d), 7.86 (2H, d).

Example 72b: $^1$H NMR (399.902 MHz, CDCl$_3$) δ 1.34 (3H, d), 1.86 (6H, s), 2.86 (3H, s), 3.32 (1H, ddd), 3.62 (1H, ddd), 3.77 (1H, dd), 3.84 (1H, d), 4.06 (1H, dd), 4.13 (1H, d), 4.48 (1H, br.d), 4.81 (1H, q), 6.52 (1H, s), 6.62 (1H, s), 7.28 (2H, d), 7.29 (2H, d), 7.47 (2H, d), 7.87 (2H, d).

Example 72c: $^1$H NMR (399.902 MHz, CDCl$_3$) δ 1.17 (3H, t), 1.34 (3H, d), 1.86 (6H, s), 3.32 (2H, dq), 3.32 (1H, ddd), 3.62 (1H, ddd), 3.77 (1H, dd), 3.84 (1H, d), 4.06 (1H, dd), 4.13 (1H, d), 4.49 (1H, br.d), 4.78 (1H, t), 6.46 (1H, s), 6.62 (1H, s), 7.28 (2H, d), 7.29 (2H, d), 7.47 (2H, d), 7.86 (2H, d).

Example 72d: ¹H NMR (399.90 MHz, CDCl₃) δ 1.34 (3H, d), 1.85 (6H, s), 2.32 (6H, s), 2.53 (2H, t), 3.31 (1H, ddd), 3.33 (2H, dt), 3.62 (1H, ddd), 3.77 (1H, dd), 3.84 (1H, d), 4.06 (1H, dd), 4.14 (1H, d), 4.49 (1H, br.d), 5.29 (1H, br.s), 6.61 (1H, s), 7.29 (2H, d), 7.33 (2H, d), 7.47 (2H, d), 7.83 (2H, d), 8.41 (1H, v.br.s).

Example 72e: ¹H NMR (399.902 MHz, CDCl₃) δ 1.33 (3H, d), 1.71 (2H, m), 1.84 (2H, m), 2.37 (2H, m), 3.30 (1H, ddd), 3.59 (1H, ddd), 3.74 (1H, dd), 3.82 (1H, d), 4.04 (1H, dd), 4.14 (1H, d), 4.30 (2H, dtt), 4.38 (2H, s), 4.39 (1H, d), 4.97 (1H, d), 6.44 (1H, s), 6.49 (1H, s), 7.31 (2H, d), 7.43 (2H, d), 7.70 (2H, d), 7.87 (2H, d).

Example 72f: ¹H NMR (399.902 MHz, CDCl₃) δ 1.17 (3H, t), 1.33 (3H, d), 3.30 (1H, ddd), 3.32 (2H, dq), 3.60 (1H, ddd), 3.74 (1H, dd), 3.83 (1H, d), 4.05 (1H, dd), 4.15 (1H, d), 4.38 (2H, s), 4.42 (1H, br.d), 4.77 (1H, t), 6.44 (1H, s), 6.47 (1H, s), 7.31 (2H, d), 7.43 (2H, d), 7.70 (2H, d), 7.88 (2H, d).

The preparation of phenyl N-[4-[4-[2-(4-chlorophenyl)sulfonylpropan-2-yl]-6-[(3S)-3-methylmorpholin-4-yl]pyrimidin-2-yl]phenyl]carbamate is described below.

Phenyl N-[4-[4-[2-(4-chlorophenyl)sulfonylpropan-2-yl]-6-[(3S)-3-methylmorpholin-4-yl]pyrimidin-2-yl]phenyl]carbamate

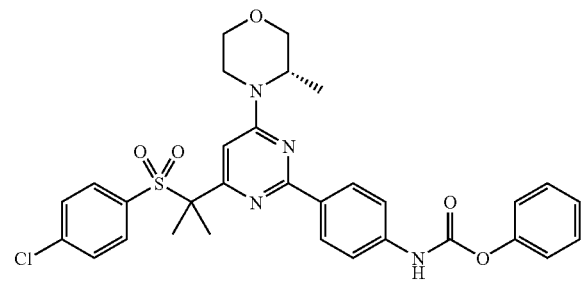

Phenyl chloroformate (0.256 mL, 2.04 mmol) was added dropwise to 4-[4-[2-(4-chlorophenyl)sulfonylpropan-2-yl]-6-[(3S)-3-methylmorpholin-4-yl]pyrimidin-2-yl]aniline (850 mg, 1.85 mmol) and sodium hydrogencarbonate (233 mg, 2.78 mmol) in dioxane (20 mL) at RT. The resulting suspension was stirred at RT for 2 hours. The reaction mixture was diluted with ethyl acetate (100 mL) and washed with water (2×100 mL) and saturated brine (50 mL). The organic layer was dried (MgSO₄), filtered and evaporated. The crude product was purified by flash silica chromatography, elution gradient 30 to 50% ethyl acetate in isohexane. Pure fractions were evaporated to dryness to afford the desired material as a white solid (955 mg).

NMR Spectrum: ¹H NMR (399.902 MHz, CDCl3) δ 1.34 (3H, d), 3.32 (1H, ddd), 3.61 (1H, ddd), 3.75 (1H, dd), 3.84 (1H, d), 4.05 (1H, dd), 4.16 (1H, br.d), 4.38 (2H, s), 4.43 (1H, br.d), 6.46 (1H, s), 7.03 (1H, s), 7.21 (2H, d), 7.25 (1H, dd), 7.40 (2H, d), 7.43 (2H, dd), 7.45 (2H, d), 7.70 (2H, d), 7.92 (2H, d)

LCMS Spectrum: MH+ 579, 581, retention time 2.94 min.

4-[4-[2-(4-Chlorophenyl)sulfonylpropan-2-yl]-6-[(3S)-3-methylmorpholin-4-yl]pyrimidin-2-yl]aniline

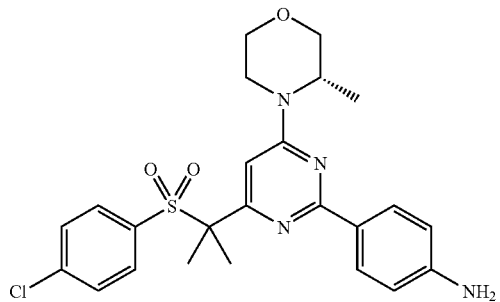

Sodium carbonate (2M in water, 6.69 mL, 13.38 mmol) was added to 4-(4,4,5,5-tetramethyl-1,3,2-dioxaborolan-2-yl)aniline (0.815 g, 3.72 mmol) and 2-chloro-4-[2-(4-chlorophenyl)sulfonylpropan-2-yl]-6-[(3S)-3-methylmorpholin-4-yl]pyrimidine (1.60 g, 3.72 mmol) in a mixture of DME (10 mL), ethanol (10.00 mL), DMF (10.00 mL) and water (20 mL) at RT under nitrogen. The mixture was degassed and purged with nitrogen three times. Bis(triphenylphosphine)palladium(II) chloride (0.130 g, 0.19 mmol) was added and the mixture was degassed and purged with nitrogen a further three times. The resulting suspension was stirred under nitrogen at 80° C. for 90 minutes. The reaction mixture was concentrated and diluted with ethyl acetate (150 mL) and washed with water (2×150 mL) and saturated brine (100 mL). The organic layer was dried (MgSO₄), filtered and evaporated. The crude product was purified by flash silica chromatography, elution gradient 30 to 45% ethyl acetate in isohexane, to give the desired material as a white solid (1.502 g).

NMR Spectrum: ¹H NMR (399.902 MHz, CDCl3) δ 1.33 (3H, d), 1.84 (6H, s), 3.31 (1H, ddd), 3.62 (1H, ddd), 3.77 (1H, dd), 3.84 (1H, d), 3.86 (2H, s), 4.05 (1H, dd), 4.13 (1H, br.d), 4.48 (1H, br.d), 6.57 (1H, s), 6.60 (2H, d), 7.30 (2H, d), 7.47 (2H, d), 7.72 (2H, d).

LCMS Spectrum: MH+ 487, 489, retention time 2.64 min.

2-Chloro-4-[2-(4-chlorophenyl)sulfonylpropan-2-yl]-6-[(3S)-3-methylmorpholin-4-yl]pyrimidine

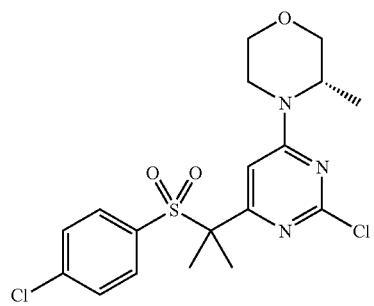

Methyl iodide (0.310 mL, 4.97 mmol) was added dropwise to 2-chloro-4-[(4-chlorophenyl)sulfonylmethyl]-6-[(3S)-3-methylmorpholin-4-yl]pyrimidine (2.00 g, 4.97 mmol) and sodium tert-butoxide (0.478 g, 4.97 mmol) in DMF (50 mL) at 0° C. over a period of 5 minutes under nitrogen. The resulting solution was stirred at 0° C. for 15 minutes. Sodium tert-butoxide (0.478 g, 4.97 mmol) was added at 0° C., followed by methyl iodide (0.310 mL, 4.97 mmol) and the mixture stirred for a further 1 hour at 0° C. The mixture was poured into rapidly stirred water (700 mL); the resulting precipitate was collected by filtration, washed with water and dried in vacuo to give the desired material as a white solid (1.79 g)

NMR Spectrum: $^1$H NMR (399.902 MHz, CDCl3) δ 1.34 (3H, d), 1.74 (6H, s), 3.30 (1H, ddd), 3.57 (1H, ddd), 3.72 (dd, 1H), 3.81 (1H, d), 4.02 (2H, m), 4.33 (1H, br.s), 6.71 (1H, s), 7.45 (2H, d), 7.50 (2H, d).

LCMS Spectrum: MH+ 430, 432, retention time 2.68 min.

2-Chloro-4-[(4-chlorophenyl)sulfonylmethyl]-6-[(3S)-3-methylmorpholin-4-yl]pyrimidine

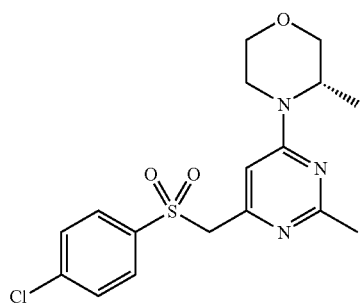

4-Chlorobenzenesulphinic acid sodium salt (5.39 g, 27.15 mmol) was added in one portion to 2-chloro-4-(iodomethyl)-6-[(3S)-3-methylmorpholin-4-yl]pyrimidine (8.00 g, 22.63 mmol) in acetonitrile (400 mL) at RT. The resulting suspension was stirred at 85° C. under reflux for 5 hours. The reaction mixture was concentrated and diluted with DCM (400 mL) and washed with water (400 mL). The organic layer was dried (MgSO$_4$), filtered and evaporated. The crude product was purified by flash silica chromatography, elution gradient 25 to 40% ethyl acetate in isohexane, to give the desired material as a white solid (6.90 g).

NMR Spectrum: $^1$H NMR (399.902 MHz, CDCl3) δ 1.33 (3H, d), 3.30 (1H, ddd), 3.55 (1H, ddd), 3.70 (1H, dd), 3.80 (1H, d), 4.02 (2H, m), 4.28 (1H, br.s), 4.29 (2H, s), 6.55 (1H, s), 7.51 (2H, d), 7.70 (2H, d).

LCMS Spectrum: MH+ 402, 404, retention time 2.26 min.

The preparation of 2-chloro-4-(iodomethyl)-6-[(3S)-3-methylmorpholin-4-yl]pyrimidine was described earlier.

The preparation of phenyl N-[4-[4-[(4-chlorophenyl)sulfonylmethyl]-6-[(3S)-3-methylmorpholin-4-yl]pyrimidin-2-yl]phenyl]carbamate is described below.

Phenyl N-[4-[4-[(4-chlorophenyl)sulfonylmethyl]-6-[(3S)-3-methylmorpholin-4-yl]pyrimidin-2-yl]phenyl]carbamate

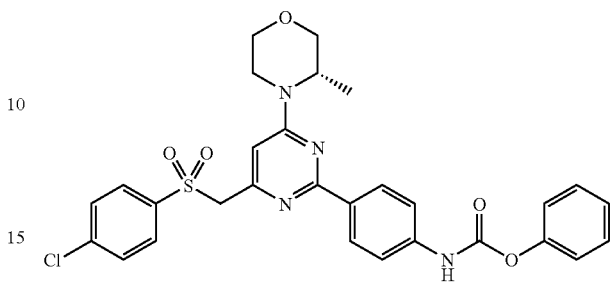

Phenyl chloroformate (0.256 mL, 2.04 mmol) was added dropwise to 4-[4-[(4-chlorophenyl)sulfonylmethyl]-6-[(3S)-3-methylmorpholin-4-yl]pyrimidin-2-yl]aniline (850 mg, 1.85 mmol) and sodium hydrogen carbonate (233 mg, 2.78 mmol) in dioxane (20 mL) at RT. The resulting suspension was stirred at RT for 2 hours. The reaction mixture was diluted with ethyl acetate (100 mL), washed with water (2×100 mL) and saturated brine (50 mL). The organic layer was dried (MgSO$_4$), filtered and evaporated. The crude product was purified by flash silica chromatography, elution gradient 30 to 50% ethyl acetate in isohexane, to give the desired material as a white solid (955 mg).

NMR Spectrum: $^1$H NMR (399.902 MHz, CDCl3) δ 1.34 (3H, d), 3.32 (1H, ddd), 3.61 (1H, ddd), 3.75 (1H, dd), 3.84 (1H, d), 4.05 (1H, dd), 4.16 (1H, br.d), 4.38 (2H, s), 4.43 (1H, br.d), 6.46 (1H, s), 7.03 (1H, s), 7.21 (2H, d), 7.25 (1H, dd), 7.40 (2H, d), 7.43 (2H, dd), 7.45 (2H, d), 7.70 (2H, d), 7.92 (2H, d).

LCMS Spectrum: MH+ 579, 581, retention time 2.94 min.

4-[4-[(4-Chlorophenyl)sulfonylmethyl]-6-[(3S)-3-methylmorpholin-4-yl]pyrimidin-2-yl]aniline

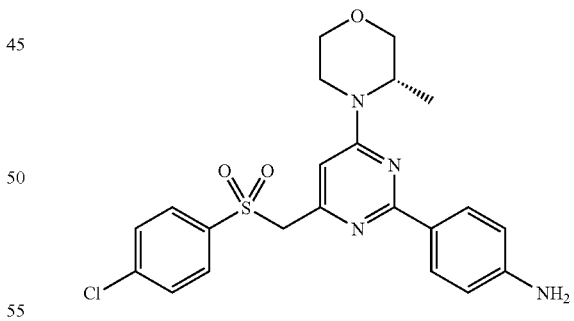

Sodium carbonate (2M in water, 4.47 mL, 8.95 mmol) was added to 4-(4,4,5,5-tetramethyl-1,3,2-dioxaborolan-2-yl)aniline (0.572 g, 2.61 mmol) and 2-chloro-4-[(4-chlorophenyl)sulfonylmethyl]-6-[(3S)-3-methylmorpholin-4-yl]pyrimidine (1.00 g, 2.49 mmol) in a mixture of DME (6.00 mL), DMF (6.00 mL), ethanol (6.00 mL) and water (14.00 mL) at RT. The mixture was degassed and purged with nitrogen three times. Bis(triphenylphosphine)palladium(II) chloride (0.087 g, 0.120 mmol) was added and the mixture was degassed and purged with nitrogen a further three times. The resulting suspension was stirred under nitrogen at 80° C. for 90 minutes. The reaction mixture was concentrated and diluted with ethyl acetate (100 mL) and washed with water (2×100 mL). The organic layer was dried over (MgSO$_4$), filtered and evaporated. The crude product was purified by flash silica chromatography, elution gradient 30 to 60% ethyl acetate in isohexane, to give the desired material as a white solid (0.980 g).

NMR Spectrum: $^1$H NMR (399.902 MHz, CDCl3) δ 1.33 (3H, d), 3.30 (1H, ddd), 3.60 (1H, ddd), 3.74 (1H, dd), 3.82 (1H, d), 3.87 (2H, s), 4.04 (1H, dd), 4.15 (1H, m), 4.36 (2H, s), 4.42 (1H, br.s), 6.39 (1H, s), 6.62 (2H, d), 7.44 (2H, d), 7.69 (2H, d), 7.73 (2H, d).

LCMS Spectrum: MH+ 459, 461, retention time 2.34 min.

The preparation of 2-chloro-4-[(4-chlorophenyl)sulfonyl-methyl]-6-[(3S)-3-methylmorpholin-4-yl]pyrimidine was described earlier.

The invention claimed is:

1. A compound of formula (I)

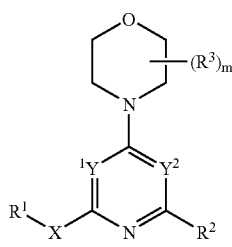

formula (I)

or a pharmaceutically acceptable salt thereof; wherein
m is 0, 1, 2, 3 or 4;
$^1$Y and Y$^2$ are independently N or CR$^8$ provided that one of $^1$Y and Y$^2$ is N and the other is CR$^8$;
X is a linker group selected from —CR$^4$=CR$^5$—, —CR$^4$=CR$^5$CR$^6$R$^7$—, —CR$^6$R$^7$CR$^5$=CR$^4$—, —C≡C—, —C≡CCR$^6$R$^7$—, —CR$^6$R$^7$C≡C—, —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —S(O)$_2$NR$^4$CR$^6$R$^7$—, —C(O)NR$^4$—, —NR$^4$C(O)—, —NR$^4$C(O)NR$^5$—, —S(O)$_2$NR$^4$— and —NR$^4$S(O)$_2$—;
R$^1$ is a group selected from hydrogen, C$_{1-6}$alkyl, C$_{2-6}$alkenyl, C$_{2-6}$alkynyl, carbocyclyl, carbocyclylC$_{1-6}$alkyl, heterocyclyl and heterocyclylC$_{1-6}$alkyl, which group is optionally substituted by one or more substituent group selected from halo, cyano, nitro, R$^9$, —OR$^9$, —SR$^9$, —SOR$^9$, —SO$_2$R$^9$, —COR$^9$, —CO$_2$R$^9$, —CONR$^9$R$^{10}$, —NR$^9$R$^{10}$, —NR$^9$COR$^{10}$, —NR$^9$CO$_2$R$^{10}$, —NR$^9$CONR$^{10}$R$^{15}$, —NR$^9$COCONR$^{10}$R$^{15}$ and —NR$^9$SO$_2$R$^{10}$;
R$^2$ is a group selected from C$_{1-6}$alkyl, carbocyclyl and heterocyclyl which group is substituted by —NR$^{17}$CONR$^{18}$R$^{19}$ and optionally substituted by one or more substituent group independently selected from halo, cyano, nitro, —R$^{11}$, —OR$^{11}$, —SR$^{11}$, —SOR$^{11}$, —SO$_2$R$^{11}$, —COR$^{11}$, —CO$_2$R$^{11}$, —CONR$^{11}$R$^{12}$, —NR$^{11}$R$^{12}$, —NR$^{11}$COR$^{12}$, and —NR$^{11}$COCONR$^{12}$R$^{16}$;
each R$^3$, when present, is independently selected from halo, cyano, nitro, —R$^{13}$, —OR$^{13}$, —SR$^{13}$, —SOR$^{13}$, —SO$_2$R$^{13}$, —COR$^{13}$, —CO$_2$R$^{13}$, —CONR$^{13}$R$^{14}$, —NR$^{13}$R$^{14}$, —NR$^{13}$COR$^{14}$, —NR$^{13}$CO$_2$R$^{14}$ and —NR$^{13}$SO$_2$R$^{14}$;
R$^4$ and R$^5$ are independently hydrogen or C$_{1-6}$alkyl; or R$^1$ and R$^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;
R$^6$ and R$^7$ are independently selected from hydrogen, halo, cyano, nitro and C$_{1-6}$alkyl;
R$^8$ is selected from hydrogen, halo, cyano and C$_{1-6}$alkyl;
R$^9$ and R$^{10}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;
R$^{11}$, R$^{12}$, R$^{17}$ and R$^{18}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;
R$^{13}$, R$^{14}$, R$^{15}$, R$^{16}$ and R$^{19}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl; or
R$^{18}$ and R$^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano $C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

2. The compound, or a pharmaceutically acceptable salt thereof, according to claim 1 wherein the compound of formula (I) is a compound of formula (Ia) or (Ib)

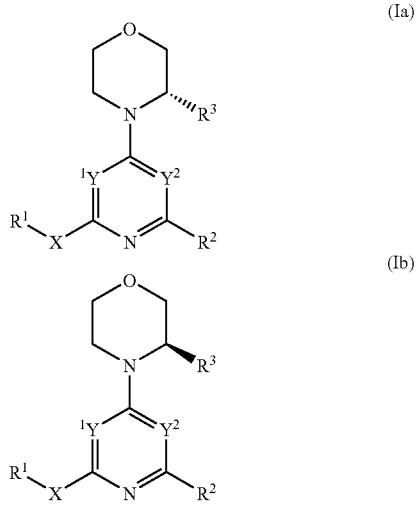

or a pharmaceutically acceptable salt thereof, wherein $R^1$, $R^2$, $R^3$, X, $Y^1$ and $Y^2$ are as defined for the compound of formula (I) as claimed in claim 1.

3. The compound, or a pharmaceutically acceptable salt thereof, according to claim 2 wherein $R^3$ is methyl.

4. The compound, or a pharmaceutically acceptable salt thereof, according to claim 3 wherein $Y^1$ is $CR^8$ and $Y^2$ is N.

5. The compound, or a pharmaceutically acceptable salt thereof, according to claim 4 wherein $Y^1$ is CH and $Y^2$ is N.

6. The compound, or a pharmaceutically acceptable salt thereof, according to claim 5 wherein X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$, —$C(O)NR^4$— and —$NR^4C(O)$—.

7. The compound, or a pharmaceutically acceptable salt thereof, according to claim 6 wherein X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4$—, and —$NR^4C(O)$—.

8. The compound, or a pharmaceutically acceptable salt thereof, according to claim 6 wherein X is a linker group selected from —$NR^4$—$CH_2$—, —$OCH_2$—, —$OCH(CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —$S(O)C(CH_3)_2$—, —$S(O)_2CH_2$—, —$S(O)_2CH(CH_3)$—, —$S(O)_2C(CH_3)_2$—, —$C(O)NR^4$— and —$NR^4C(O)$—.

9. The compound, or a pharmaceutically acceptable salt thereof, according to claim 6 wherein X is —$S(O)_2CH_2$—, —$S(O)_2CH(CH_3)$— or —$S(O)_2C(CH_3)_2$—.

10. The compound, or a pharmaceutically acceptable salt thereof, according to claim 6 wherein X is —$S(O)_2C(CH_3)_2$—.

11. The compound, or a pharmaceutically acceptable salt thereof, according to claim 5 wherein $R^1$ is a group selected from adamantyl, methyl, ethyl, propyl, butyl, isobutyl, tert-butyl, cyclopentyl, cyclohexyl, phenyl, benzyl, oxetanyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —$OR^9$, —$COR^9$, —$CONR^9R^{10}$, —$NR^9R^{10}$ and —$NR^9COR^{10}$.

12. The compound, or a pharmaceutically acceptable salt thereof, according to claim 11 wherein $R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrrolidinyl, pyrazolylethyl, furanylmethyl, oxetanyl, imidazolylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NMe_2$, —$NHCOCH_3$, —$CONH_2$ and —$CONHCH_3$.

13. The compound, or a pharmaceutically acceptable salt thereof, according to claim 11 wherein $R^1$ is a group selected from methyl, ethyl, isopropyl, tert-butyl, cyclopropyl, cyclopentyl, cyclohexyl, —$CH_2CH_2OH$, —$CH_2CH_2OMe$, —$CH_2CH_2NMe_2$, —$CH_2CH_2NC(O)CH_3$, —$CH_2CONH_2$, phenyl, 3,5-difluorophenyl, 4-fluorophenyl, 2-chlorophenyl, 4-chlorophenyl, 2-trifluoromethylphenyl, 2-methoxyphenyl, 2-methylphenyl, 4-acetamidophenyl, 4-aminophenyl, pyridin-4-yl, pyridin-2-yl, oxetan-3-yl, 2-oxopyrrolidin-3-yl, 1-methylimidazol-5-ylmethyl, 1-methylpyrrolidin-3-yl, thiazol-2-yl, 4-methylthiazol-2-yl, and 3-methyl-1,3,4-thiadiazol-2-yl.

14. The compound, or a pharmaceutically acceptable salt thereof, according to claim 11 wherein $R^1$ is a group selected from methyl, isopropyl, cyclopropyl, cyclohexyl, —$CH_2CH_2OH$, —$CH_2CH_2NC(O)CH_3$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrrolidin-3-yl, thiazol-2-yl, 4-methylthiazol-2-yl, and 3-methyl-1,3,4-thiadiazol-2-yl.

15. The compound, or a pharmaceutically acceptable salt thereof, according to claim 11 wherein $R^1$ is methyl, ethyl, isopropyl, tert-butyl, 4-fluorophenyl, 3,5-difluorophenyl, pyridin-4-yl or cyclopropyl.

16. The compound, or a pharmaceutically acceptable salt thereof, according to claim 11 wherein $R^1$ is methyl, ethyl, isopropyl, tert-butyl, 4-fluorophenyl, pyridin-4-yl or cyclopropyl.

17. The compound, or a pharmaceutically acceptable salt thereof, according to claim 5 wherein $R^2$ is selected from 5- or 6-membered carbocyclyl or heterocyclyl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$, and —$NR^{11}COR^{12}$.

18. The compound, or a pharmaceutically acceptable salt thereof, according to claim 17 wherein $R^2$ is selected from a 6-membered aryl and 5- or 6-membered heteroaryl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

19. The compound, or a pharmaceutically acceptable salt thereof, according to claim 17 wherein $R^2$ is selected from phenyl, pyrrolyl, imidazolyl, pyrazolyl, furanyl, thienyl, pyridinyl, pyrimidinyl, pyridazinyl, thiazolyl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

20. The compound, or a pharmaceutically acceptable salt thereof, according to claim 17 wherein $R^2$ is selected from phenyl, pyrrolyl, imidazolyl, pyrazolyl, furanyl, thienyl, pyridinyl, pyrimidinyl, pyridazinyl, thiazolyl which group is substituted by —$NR^{17}CONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

21. The compound, or a pharmaceutically acceptable salt thereof, according to claim 17 wherein $R^2$ is phenyl or pyridyl substituted by —$NR^{17}CONR^{18}R^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$.

22. The compound, or a pharmaceutically acceptable salt thereof, according to claim 17 wherein $R^2$ is

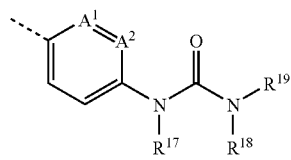

wherein $A^1$ and $A^2$ are selected from CH or N provided that at least one of $A^1$ or $A^2$ is CH.

23. The compound, or a pharmaceutically acceptable salt thereof, according to claim 22 wherein $R^{17}$ is hydrogen.

24. The compound, or a pharmaceutically acceptable salt thereof, according to claim 23 wherein $R^{18}$ is hydrogen.

25. The compound, or a pharmaceutically acceptable salt thereof, according to claim 24 wherein $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy $C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino $C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl ($C_{1-6}$alkyl)amino, carbamoyl, $C_{1-6}$alkylcarbamoyl and bis ($C_{1-6}$alkyl)carbamoyl.

26. The compound, or a pharmaceutically acceptable salt thereof, according to claim 25 wherein $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy $C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino $C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl ($C_{1-6}$alkyl)amino, carbamoyl, $C_{1-6}$alkylcarbamoyl and bis ($C_{1-6}$alkyl)carbamoyl.

27. The compound, or a pharmaceutically acceptable salt thereof, according to claim 25 wherein $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —$CH_2$(cyclopropyl), —$CH_2CH_2NMe_2$, —$CH(CH_3)CH_2OH$, —$C(CH_3)_2CH_2OH$, —$CH_2CH_2OH$, —$CH_2CH_2CH_2OH$, 4-methylphenyl, 4-chlorophenyl, 4-trifluoromethylphenyl, 4-fluorophenyl, 4-methoxyphenyl, 3,4-difluorophenyl, thien-2-yl, —$CH_2$(imidazol-2-yl), —$CH_2$ (imidazol-3-yl), isoxazol-3-yl, 6-oxo-1H-pyridin-2-yl, 5-methylisoxazol-3-yl, 1-methylpyrazol-4-yl, —$CH_2$(1-methylpyrazol-4-yl), 6-methoxypyridin-3-yl, 5-fluoropyridin-2-yl, pyridin-2-yl, pyrimidin-2-yl, and 1H-pyrazol-3-yl.

28. The compound, or a pharmaceutically acceptable salt thereof, according to claim 25 wherein $R^{19}$ is a group selected from methyl, ethyl, propyl, cyclopropyl, cyclobutyl, —$CH_2CH_2OH$, —$CH_2CH_2NMe_2$, —$C(Me)_2CH_2OH$ and 1H-pyrazol-3-yl.

29. The compound, or a pharmaceutically acceptable salt thereof, according to claim 5 wherein X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)$ $NR^5CR^6R^7$—, —$S(O)_2NR^4CR^6R^7$, —$C(O)NR^4$— and —$NR^4C(O)$—;

$R^1$ is a group selected from adamantyl, methyl, ethyl, propyl, butyl, isobutyl, tert-butyl, cyclopentyl, cyclohexyl, phenyl, benzyl, oxetanyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —$OR^9$, —$COR^9$, —$CONR^9R^{10}$, —$NR^9R^{10}$ and —$NR^9COR^{10}$; and $R^2$ is selected from 5- or 6-membered carbocyclyl or heterocyclyl which group is substituted by —$NR^{17}CONR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$.

30. The compound, or a pharmaceutically acceptable salt thereof, according to claim 29 wherein X is a linker group selected from X is a linker group selected from —$NR^4$—$CH_2$—, —$OCH_2$—, —$OCH (CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —S(O)C(CH$_3$)$_2$—, —S(O)$_2$CH$_2$—, —S(O)$_2$CH(CH$_3$)—, —S(O)$_2$C(CH$_3$)$_2$—, —C(O)NR$^4$— and —NR$^4$C(O)—;

R$^1$ is a group selected from methyl, ethyl, isopropyl, tert-butyl, cyclopropyl, cyclopentyl, cyclohexyl, —CH$_2$CH$_2$OH, —CH$_2$CH$_2$OMe, —CH$_2$CH$_2$NMe$_2$, —CH$_2$CH$_2$NC(O)CH$_3$, —CH—CONH$_2$, phenyl, 3,5-difluorophenyl, 4-fluorophenyl, 2-chlorophenyl, 4-chlorophenyl, 2-trifluoromethylphenyl, 2-methoxyphenyl, 2-methylphenyl, 4-acetamidophenyl, 4-aminophenyl, pyridin-4-yl, pyridin-2-yl, oxetan-3-yl, 2-oxopyrrolidin-3-yl, 1-methylimidazol-5-ylmethyl, 1-methylpyrrolidin-3-yl, thiazol-2-yl, 4-methylthiazol-2-yl, and 3-methyl-1,3,4-thiadiazol-2-yl; and R$^2$ is phenyl or pyridyl substituted by —NR$^{17}$CONR$^{18}$R$^{19}$ and optionally substituted by one or more substituent group independently selected from fluoro, methyl, methoxy, hydroxymethyl, cyanomethyl, —CONH$_2$, —CONHCH$_3$ and —CON(CH$_3$)$_2$.

31. The compound, or a pharmaceutically acceptable salt thereof, according to claim 30 wherein X is —S(O)C(CH$_3$)$_2$—;

R$^1$ is a group selected from is methyl, ethyl, isopropyl, tert-butyl, 4-fluorophenyl, 3,5-difluorophenyl, pyridin-4-yl or cyclopropyl; and R$^2$ is

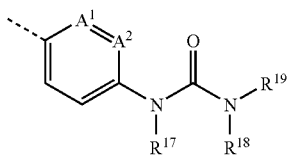

wherein

A$^1$ and A$^2$ are selected from CH or N provided that at least one of A$^1$ or A$^2$ is CH, R$^{17}$ is hydrogen, and R$^{18}$ is hydrogen.

32. The compound, or a pharmaceutically acceptable salt thereof, according to claim 31 wherein R$^{19}$ is hydrogen or a group selected from C$_{1-6}$alkyl, C$_{3-6}$cycloakyl, aryl, heteroaryl, arylC$_{1-6}$alkyl and heteroarylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)amino C$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

33. The compound, or a pharmaceutically acceptable salt thereof, according to claim 32 wherein R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyrazolylmethyl, pyridinyl and pyrimidinyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)amino C$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

34. The compound, or a pharmaceutically acceptable salt thereof, according to claim 33 wherein R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazol-3-yl, 6-oxo-1H-pyridin-2-yl, 5-methylisoxazol-3-yl, 1-methylpyrazol-4-yl, —CH$_2$(1-methylpyrazol-4-yl), 6-methoxypyridin-3-yl, 5-fluoropyridin-2-yl, pyridin-2-yl, pyrimidin-2-yl, and 1H-pyrazol-3-yl.

35. The compound, or a pharmaceutically acceptable salt thereof, according to claim 34 wherein R$^{19}$ is a group selected from methyl, ethyl, propyl, cyclopropyl, cyclobutyl, —CH$_2$CH$_2$OH, —CH$_2$CH$_2$NMe$_2$, —C(Me)$_2$CH$_2$OH and 1H-pyrazol-3-yl.

36. A pharmaceutical composition comprising a compound of formula (I), or a pharmaceutically acceptable salt thereof, as claimed in claim 1 in association with a pharmaceutically acceptable adjuvant, diluent or carrier.

37. A process for the preparation of a pharmaceutical composition comprising a compound of formula (I), or a pharmaceutically acceptable salt thereof, as claimed in claim 1 in association with a pharmaceutically acceptable adjuvant, diluent or carrier which comprises mixing a compound of formula (I), or a pharmaceutically acceptable salt thereof, as defined in claim 1, with a pharmaceutically acceptable adjuvant, diluent or carrier.

38. A method of modulating mTOR activity which comprises administering to a patient in need thereof a therapeutically effective amount of a compound of formula (I), or a pharmaceutically acceptable salt thereof, as claimed in claim 1.

39. A method of treating cancer of the breast in a warm-blooded animal in need of such treatment which comprises administering to said animal an effective amount of a compound of formula (I) or a pharmaceutically acceptable salt as claimed in claim 1.

* * * * *